(12) United States Patent
Moll et al.

(10) Patent No.: US 8,257,303 B2
(45) Date of Patent: *Sep. 4, 2012

(54) ROBOTIC CATHETER SYSTEM AND METHODS

(75) Inventors: Frederic H. Moll, San Francisco, CA (US); Daniel T. Wallace, Santa Cruz, CA (US); Gregory J. Stahler, San Jose, CA (US); David F. Moore, San Carlos, CA (US); Daniel T. Adams, Palo Alto, CA (US); Kenneth M. Martin, Los Gatos, CA (US); Robert G. Younge, Portola Valley, CA (US); Michael R. Zinn, Pleasanton, CA (US); Gunter D. Niemeyer, Mountain View, CA (US); David C. Lundmark, Los Altos, CA (US)

(73) Assignee: Hansen Medical, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/225,324

(22) Filed: Sep. 2, 2011

(65) Prior Publication Data

US 2012/0065467 A1  Mar. 15, 2012

Related U.S. Application Data

(63) Continuation of application No. 11/481,433, filed on Jul. 3, 2006, now Pat. No. 8,052,636.

(60) Provisional application No. 60/695,947, filed on Jul. 1, 2005, provisional application No. 60/698,171, filed on Jul. 11, 2005.

(51) Int. Cl.
*A61M 31/00* (2006.01)

(52) U.S. Cl. ............. 604/95.04; 600/114; 600/146

(58) Field of Classification Search ......... 600/407–411, 600/424, 473, 476, 427, 101, 109, 114, 146, 600/139, 117, 118; 606/130; 604/95.04, 604/164.12, 164.09
See application file for complete search history.

(56) References Cited

U.S. PATENT DOCUMENTS 5,078,714 A   1/1992   Katims
(Continued)

FOREIGN PATENT DOCUMENTS

CA   2285342   9/1999
(Continued)

OTHER PUBLICATIONS

PCT International Search Report for PCT/US2006/026218, Applicant Hansen Medical, Inc., forms PCT/ISA/210 and 220, dated Dec. 12, 2006 (6 pages).

(Continued)

*Primary Examiner* — Sanjay Cattungal
(74) *Attorney, Agent, or Firm* — Vista IP Law Group LLP

(57) ABSTRACT

The apparatus of one embodiment of the present invention is comprised of a flexible sheath instrument, a flexible guide instrument, and a tool. The flexible sheath instrument comprises a first instrument base removably coupleable to an instrument driver and defines a sheath instrument working lumen. The flexible guide instrument comprises a second instrument base removably coupleable to the instrument driver and is threaded through the sheath instrument working lumen. The guide instrument also defines a guide instrument working lumen. The tool is threaded through the guide instrument working lumen. For this embodiment of the apparatus, the sheath instrument and guide instrument are independently controllable relative to each other.

22 Claims, 388 Drawing Sheets

U.S. PATENT DOCUMENTS

| | | | |
|---|---|---|---|
| 5,341,807 A | | 8/1994 | Nardella |
| 5,447,529 A | | 9/1995 | Marchlinski et al. |
| 5,469,857 A | | 11/1995 | Laurent et al. |
| 5,662,108 A | | 9/1997 | Budd et al. |
| 5,673,704 A | | 10/1997 | Marchlinski et al. |
| 5,722,959 A | * | 3/1998 | Bierman ............... 604/174 |
| 5,836,874 A | | 11/1998 | Swanson et al. |
| 5,836,990 A | | 11/1998 | Li |
| 5,845,646 A | * | 12/1998 | Lemelson ............... 128/899 |
| 5,885,277 A | | 3/1999 | Korth |
| 5,891,095 A | | 4/1999 | Eggers et al. |
| 5,935,079 A | | 8/1999 | Swanson et al. |
| 6,004,271 A | * | 12/1999 | Moore ............... 600/445 |
| 6,061,587 A | * | 5/2000 | Kucharczyk et al. ......... 600/411 |
| 6,381,483 B1 | * | 4/2002 | Hareyama et al. ............ 600/407 |
| 6,530,913 B1 | * | 3/2003 | Giba et al. ............... 604/528 |
| 6,544,230 B1 | * | 4/2003 | Flaherty et al. ............ 604/164.12 |
| 6,551,273 B1 | * | 4/2003 | Olson et al. ............ 604/103.03 |
| 6,610,007 B2 | * | 8/2003 | Belson et al. ............... 600/146 |
| 6,669,709 B1 | * | 12/2003 | Cohn et al. ............... 606/167 |
| 6,905,460 B2 | * | 6/2005 | Wang et al. ............... 600/102 |
| 6,949,106 B2 | | 9/2005 | Brock et al. |
| 7,090,683 B2 | | 8/2006 | Brock et al. |
| 7,214,230 B2 | | 5/2007 | Brock et al. |
| 7,276,044 B2 | | 10/2007 | Ferry et al. |
| 7,371,210 B2 | * | 5/2008 | Brock et al. ............... 600/114 |
| 7,404,824 B1 | * | 7/2008 | Webler et al. ............... 623/2.36 |
| 2001/0009976 A1 | * | 7/2001 | Panescu et al. ............... 600/424 |
| 2001/0029366 A1 | * | 10/2001 | Swanson et al. ............... 606/29 |
| 2002/0087169 A1 | * | 7/2002 | Brock et al. ............... 606/139 |
| 2002/0138009 A1 | * | 9/2002 | Brockway et al. ............ 600/485 |
| 2002/0177789 A1 | * | 11/2002 | Ferry et al. ............... 600/585 |
| 2003/0073908 A1 | * | 4/2003 | Desai ............... 600/464 |
| 2003/0074011 A1 | * | 4/2003 | Gilboa et al. ............... 606/130 |
| 2003/0135204 A1 | * | 7/2003 | Lee et al. ............... 606/1 |
| 2004/0176751 A1 | * | 9/2004 | Weitzner et al. ............... 606/1 |
| 2004/0193146 A1 | * | 9/2004 | Lee et al. ............... 606/1 |
| 2004/0220588 A1 | * | 11/2004 | Kermode et al. ............... 606/129 |
| 2005/0159789 A1 | * | 7/2005 | Brockway et al. ............ 607/32 |
| 2005/0182295 A1 | * | 8/2005 | Soper et al. ............... 600/117 |
| 2005/0182330 A1 | * | 8/2005 | Brockway et al. ............ 600/486 |
| 2006/0271036 A1 | * | 11/2006 | Garabedian et al. ............ 606/41 |
| 2007/0038181 A1 | * | 2/2007 | Melamud et al. ............ 604/158 |
| 2007/0060879 A1 | * | 3/2007 | Weitzner et al. ............ 604/95.04 |
| 2008/0300592 A1 | * | 12/2008 | Weitzner et al. ............... 606/41 |
| 2009/0054884 A1 | * | 2/2009 | Farley et al. ............... 606/15 |

FOREIGN PATENT DOCUMENTS

WO    2005087128    9/2005

OTHER PUBLICATIONS

PCT Written Opinion of the International Searching Authority for PCT/US2006/023443, Applicant Hansen Medical, Inc., form PCT/ISA/237, dated Dec. 12, 2006 (7 pages).

* cited by examiner

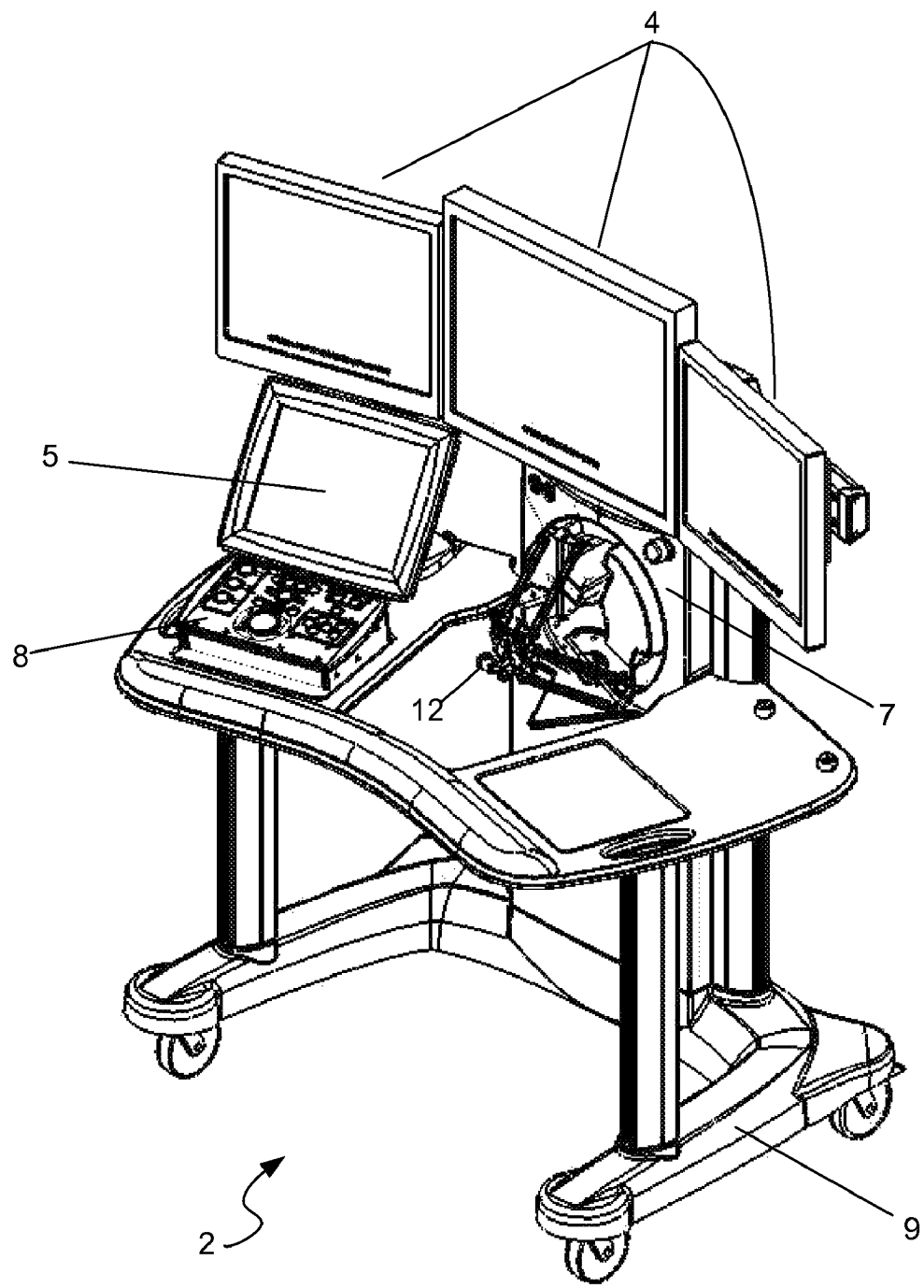
Fig 2.1

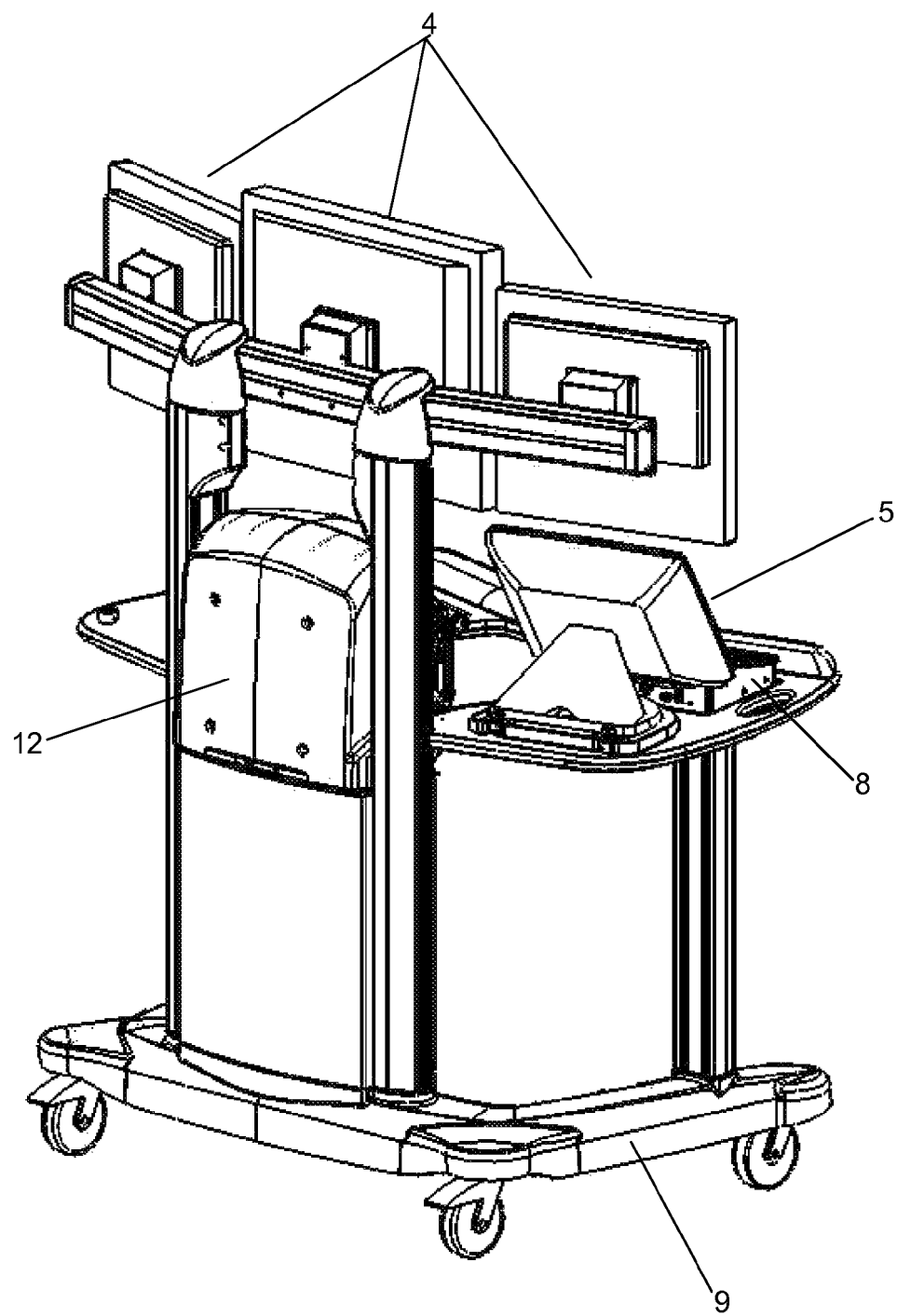
Fig 2.2

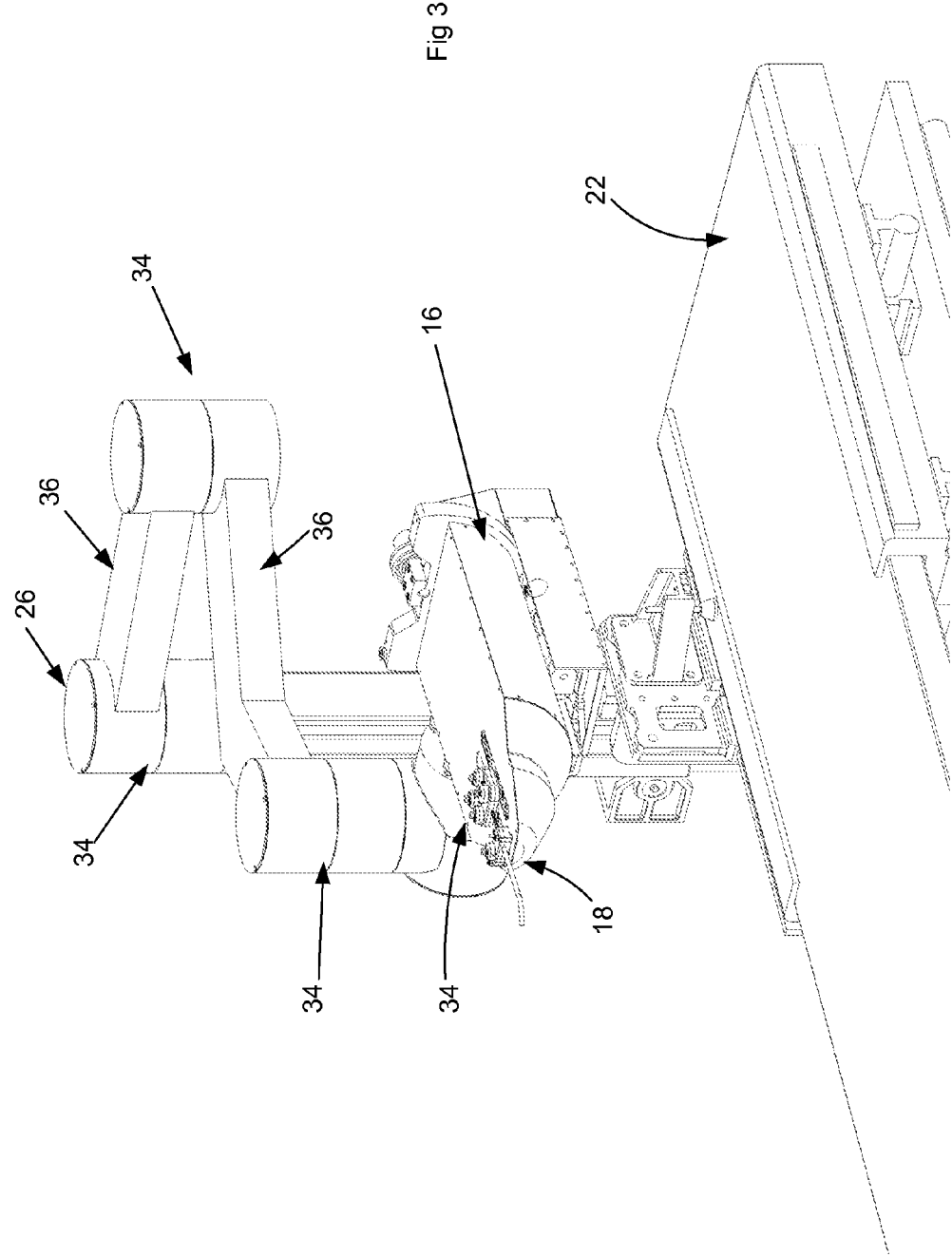

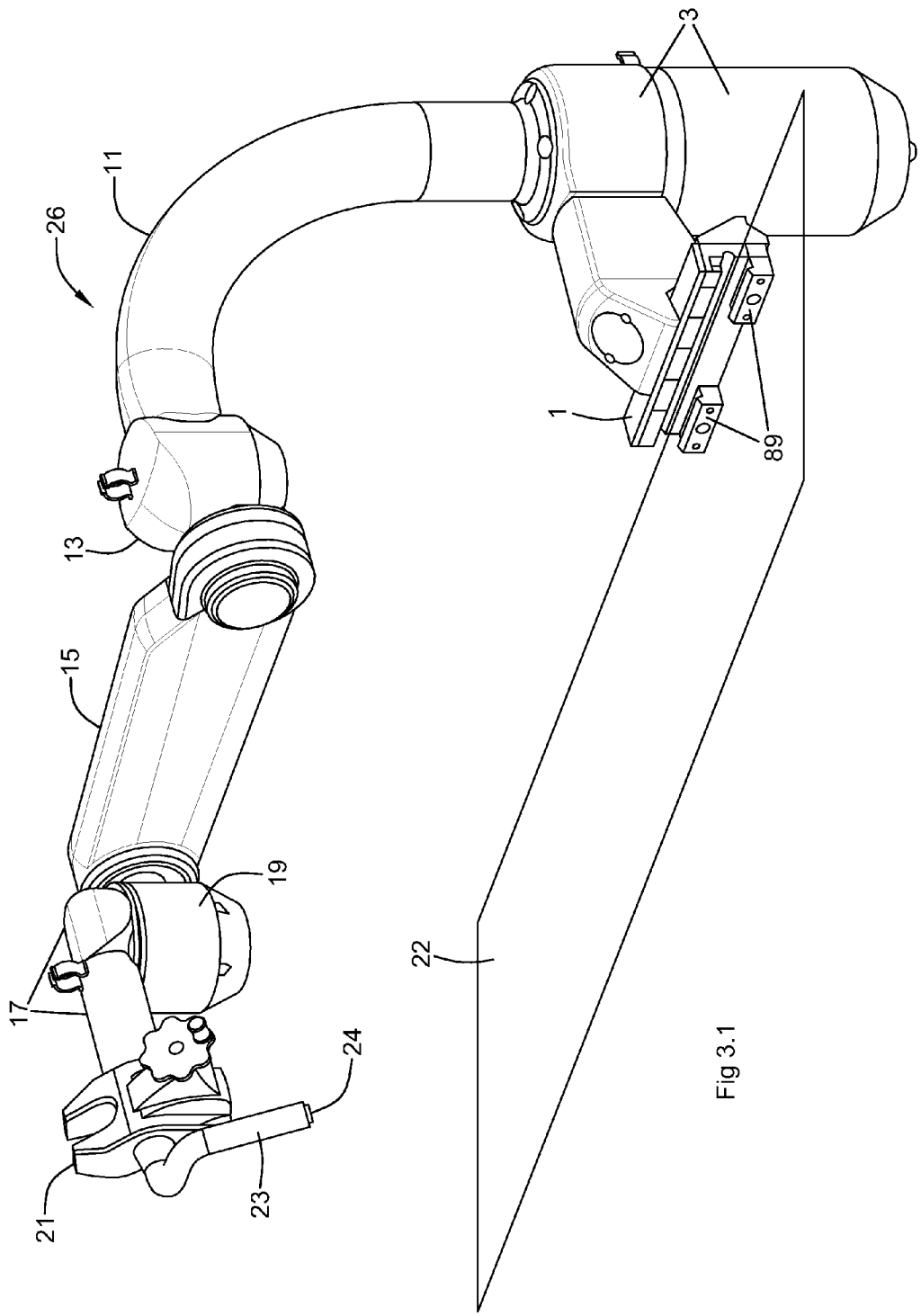
Fig 3.1

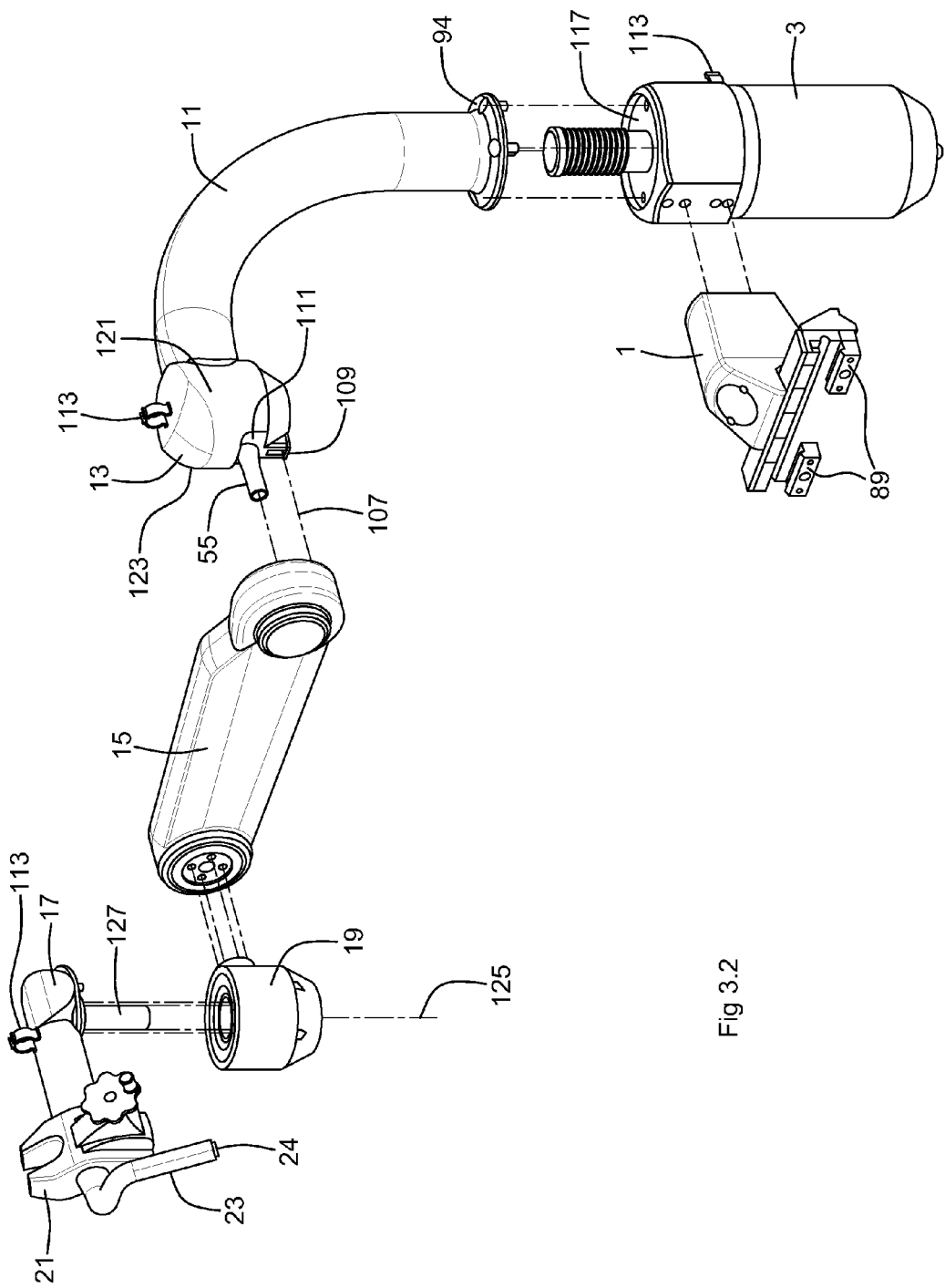
Fig 3.2

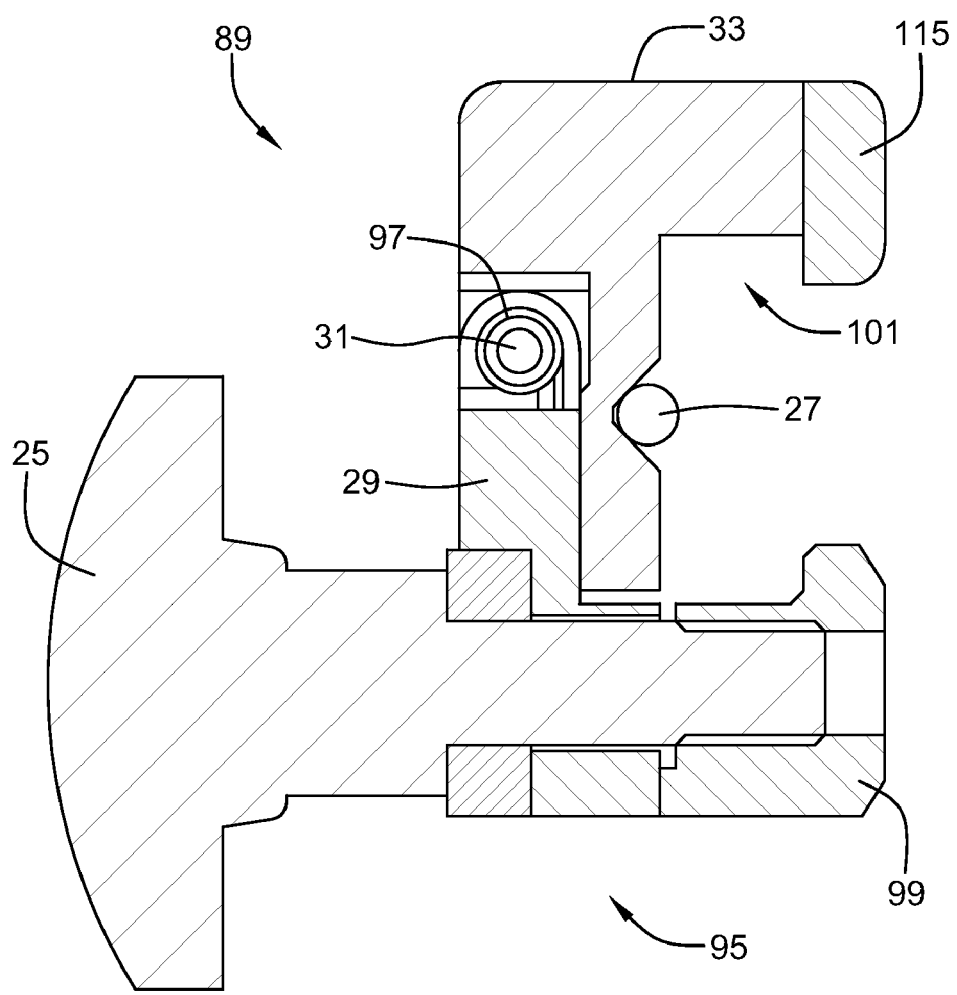
Fig 3.3

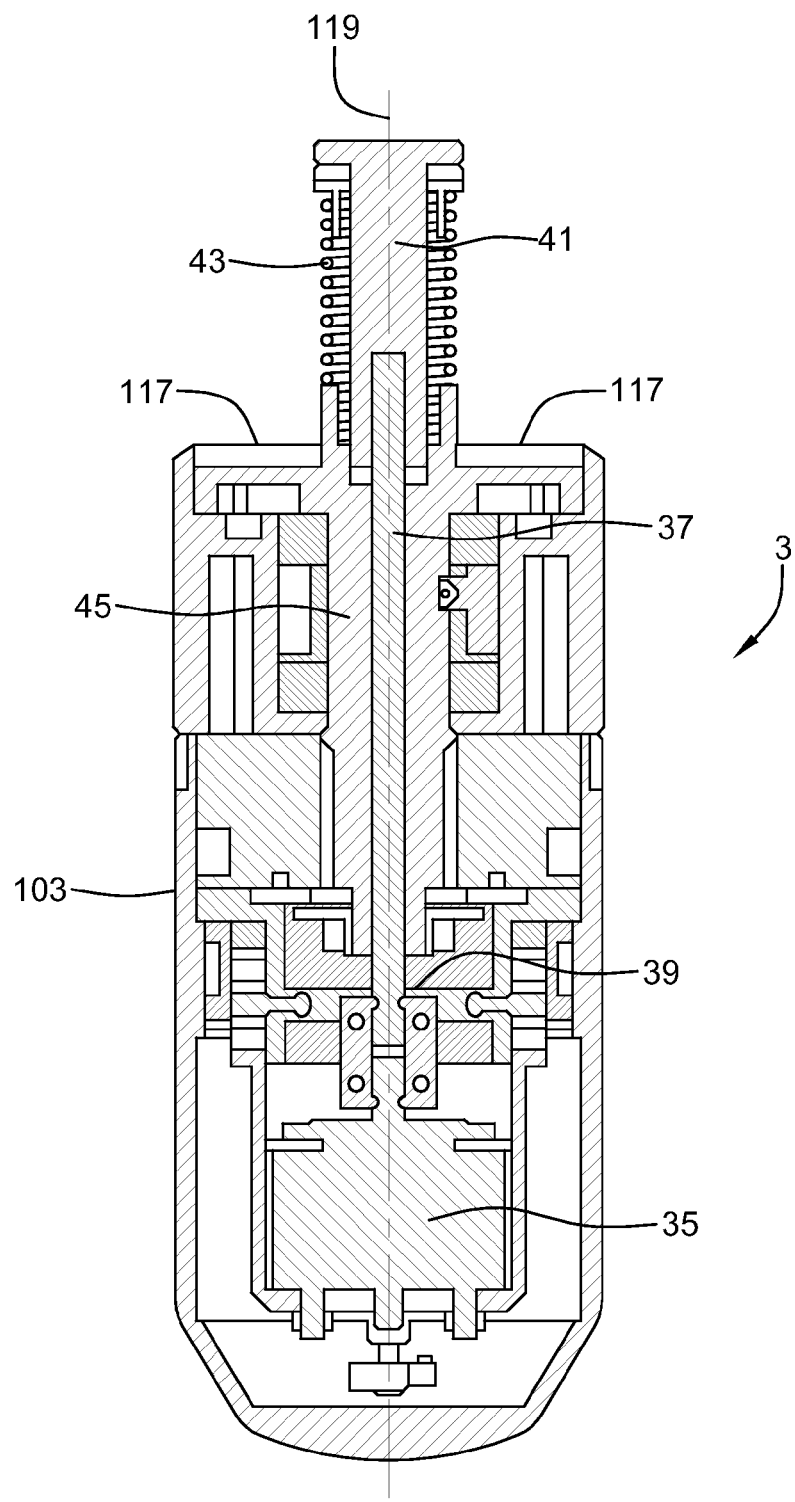
Fig 3.4

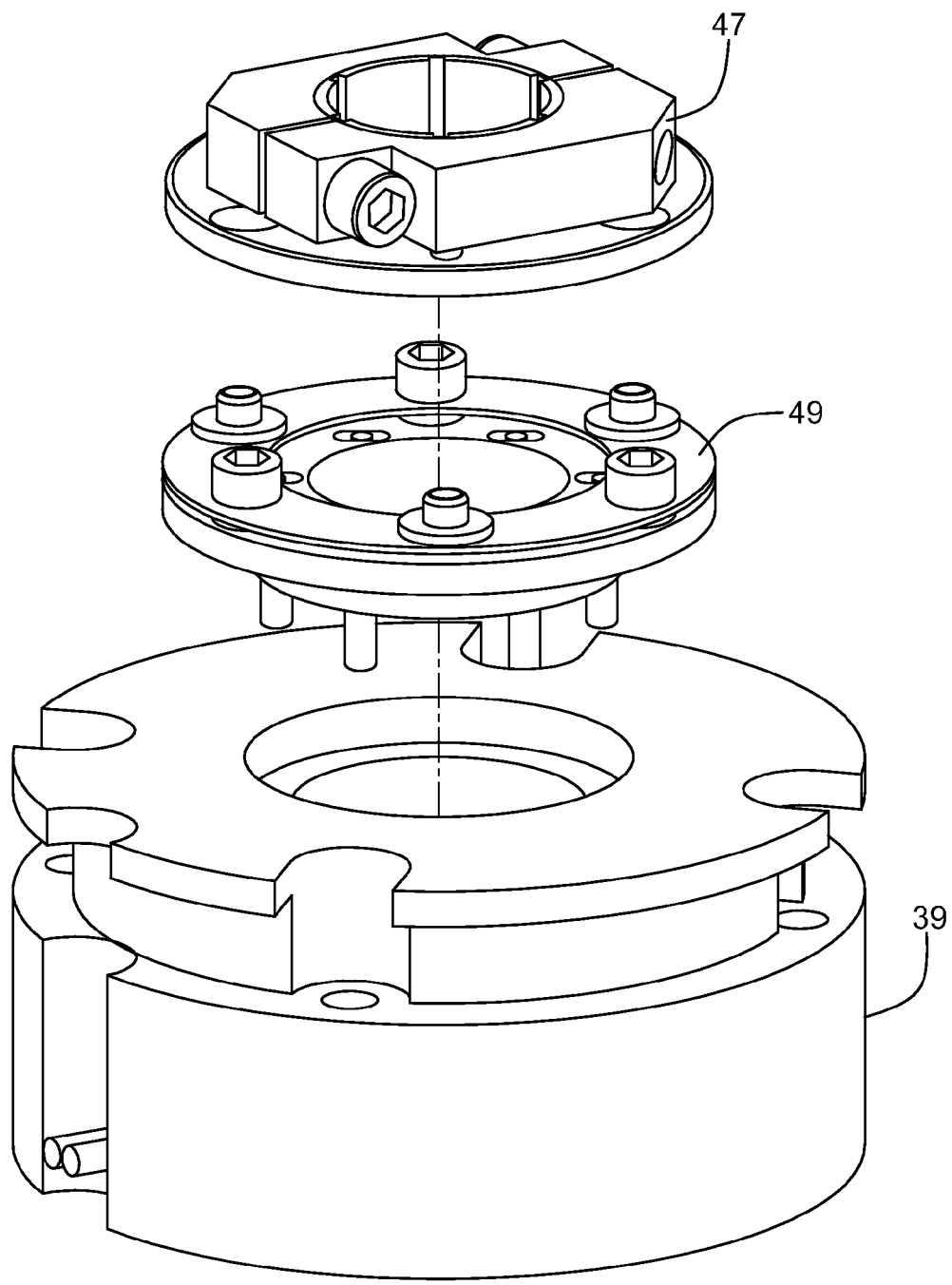
Fig 3.5

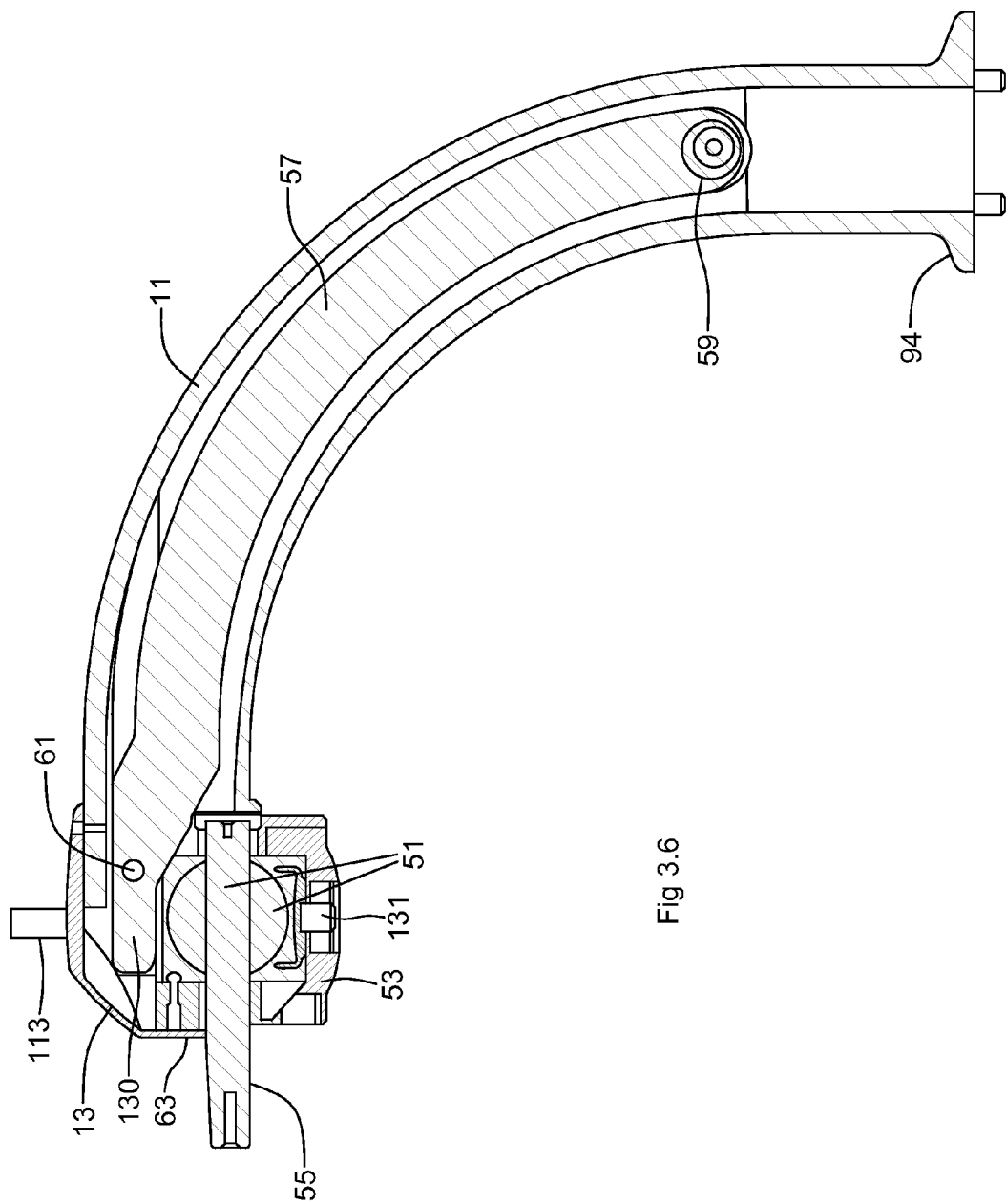
Fig 3.6

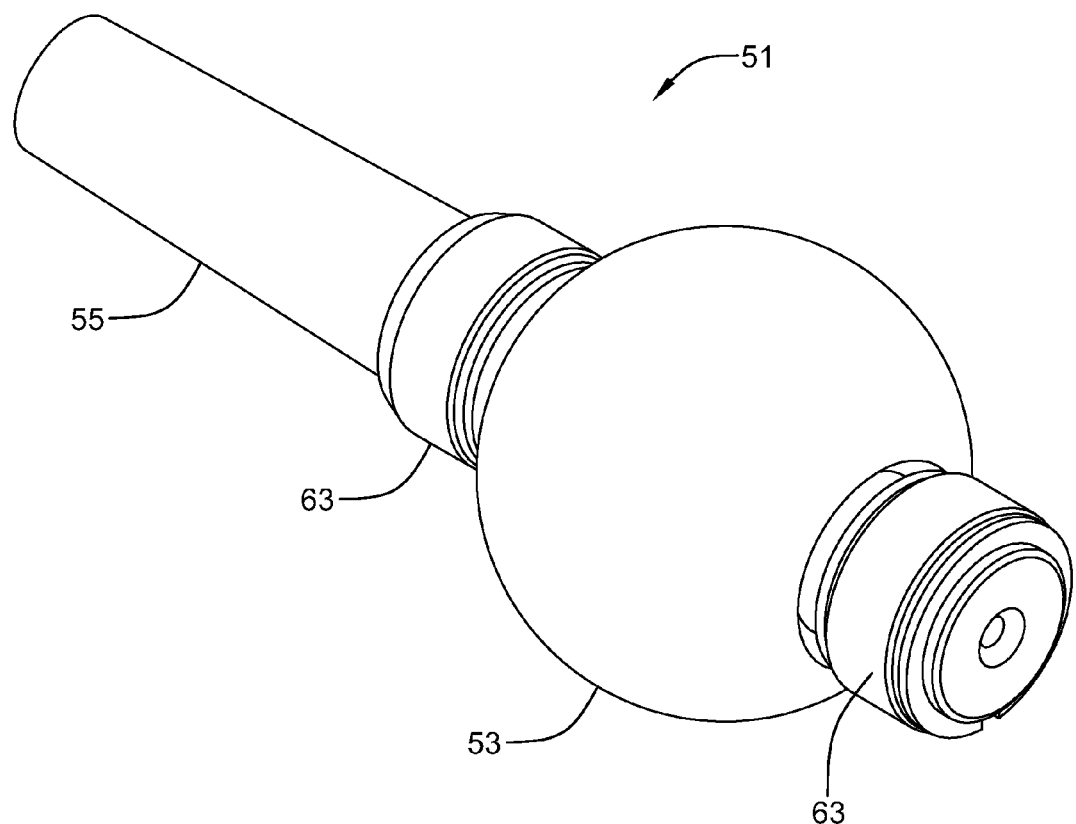
Fig 3.7

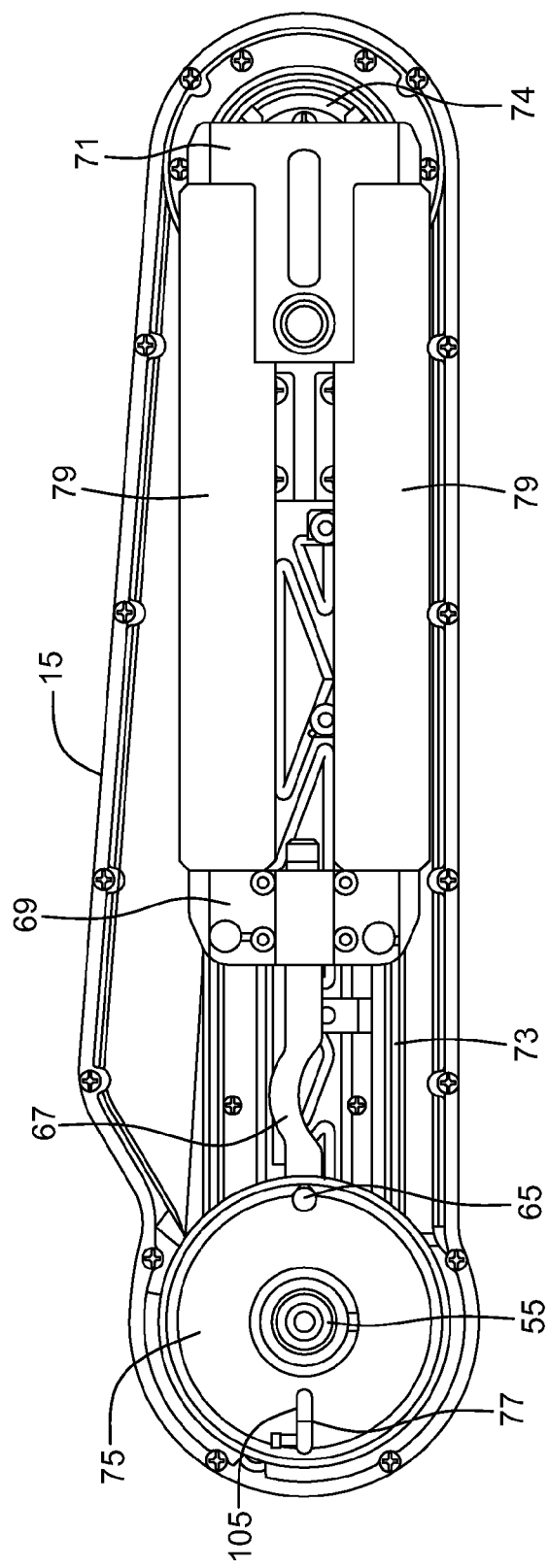
Fig 3.8

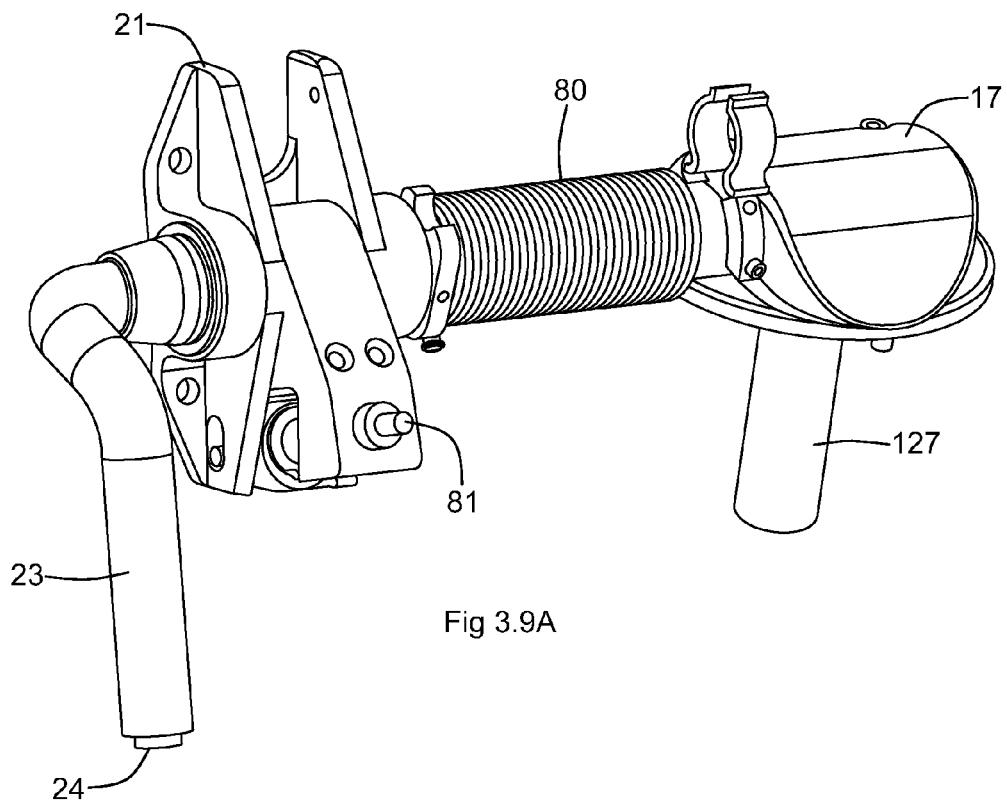
Fig 3.9A
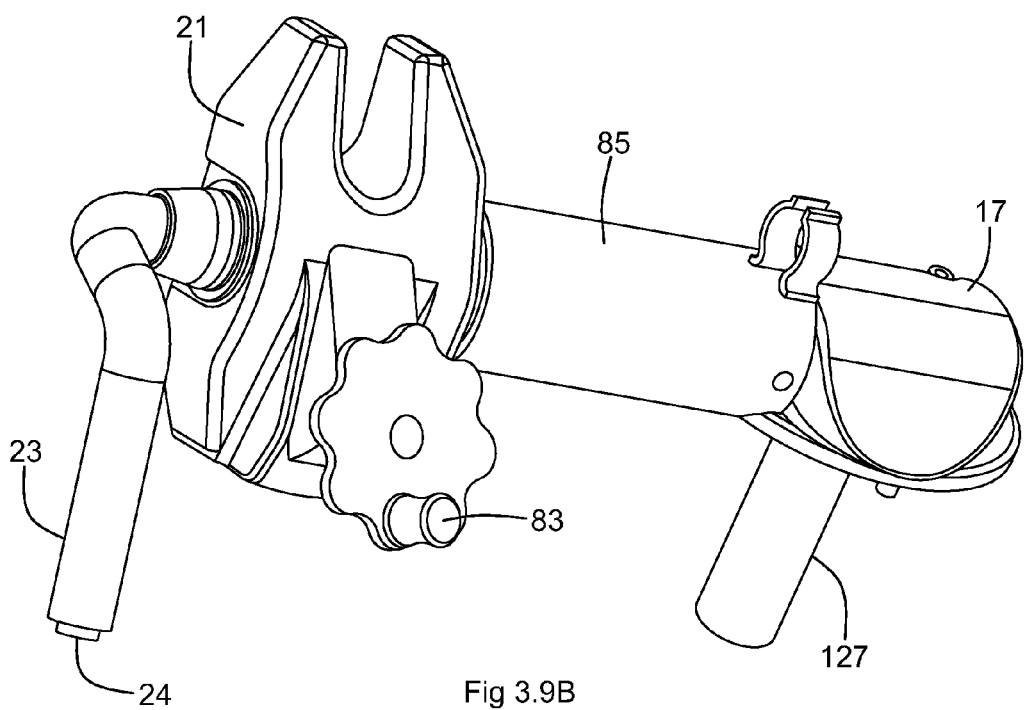
Fig 3.9B

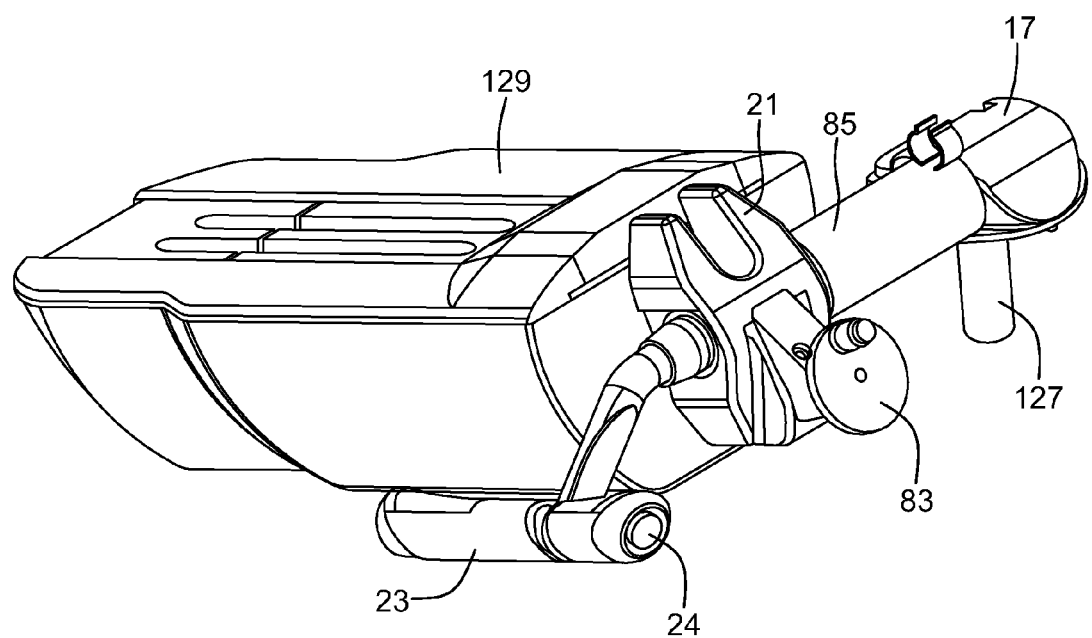
Fig 3.10A

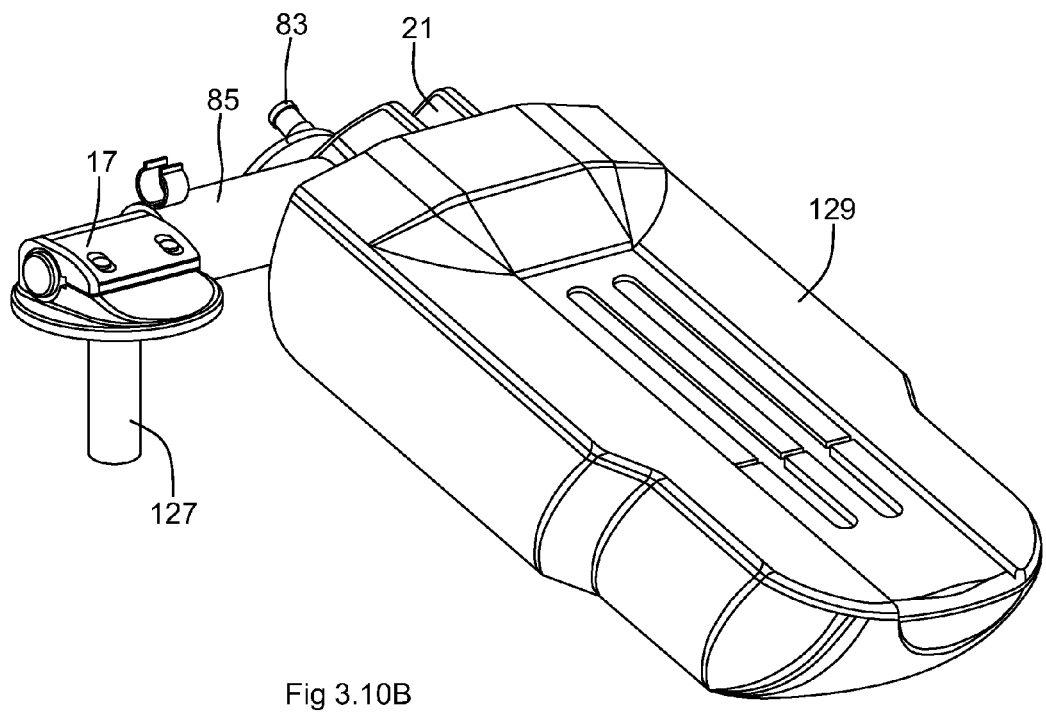
Fig 3.10B

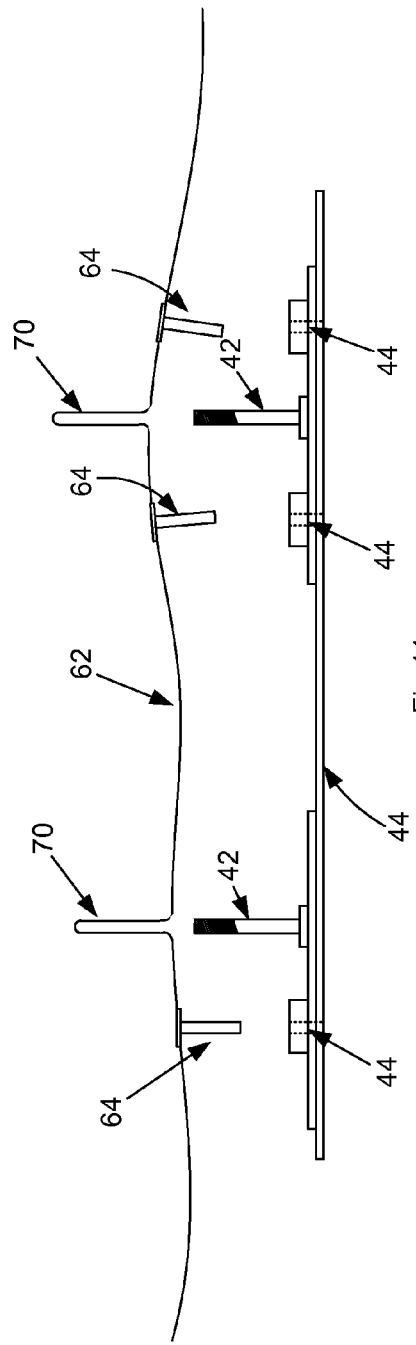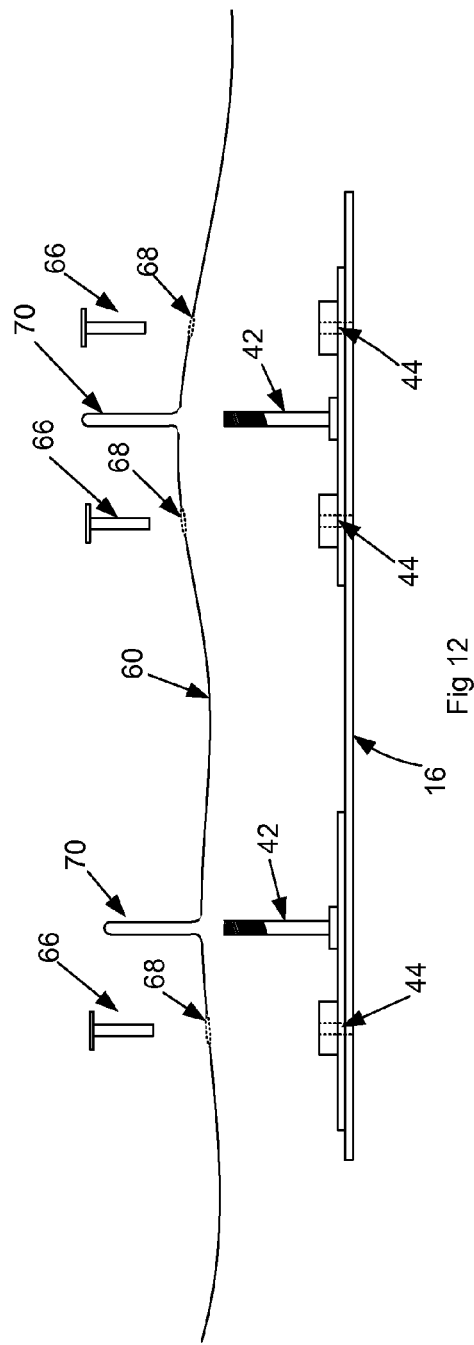

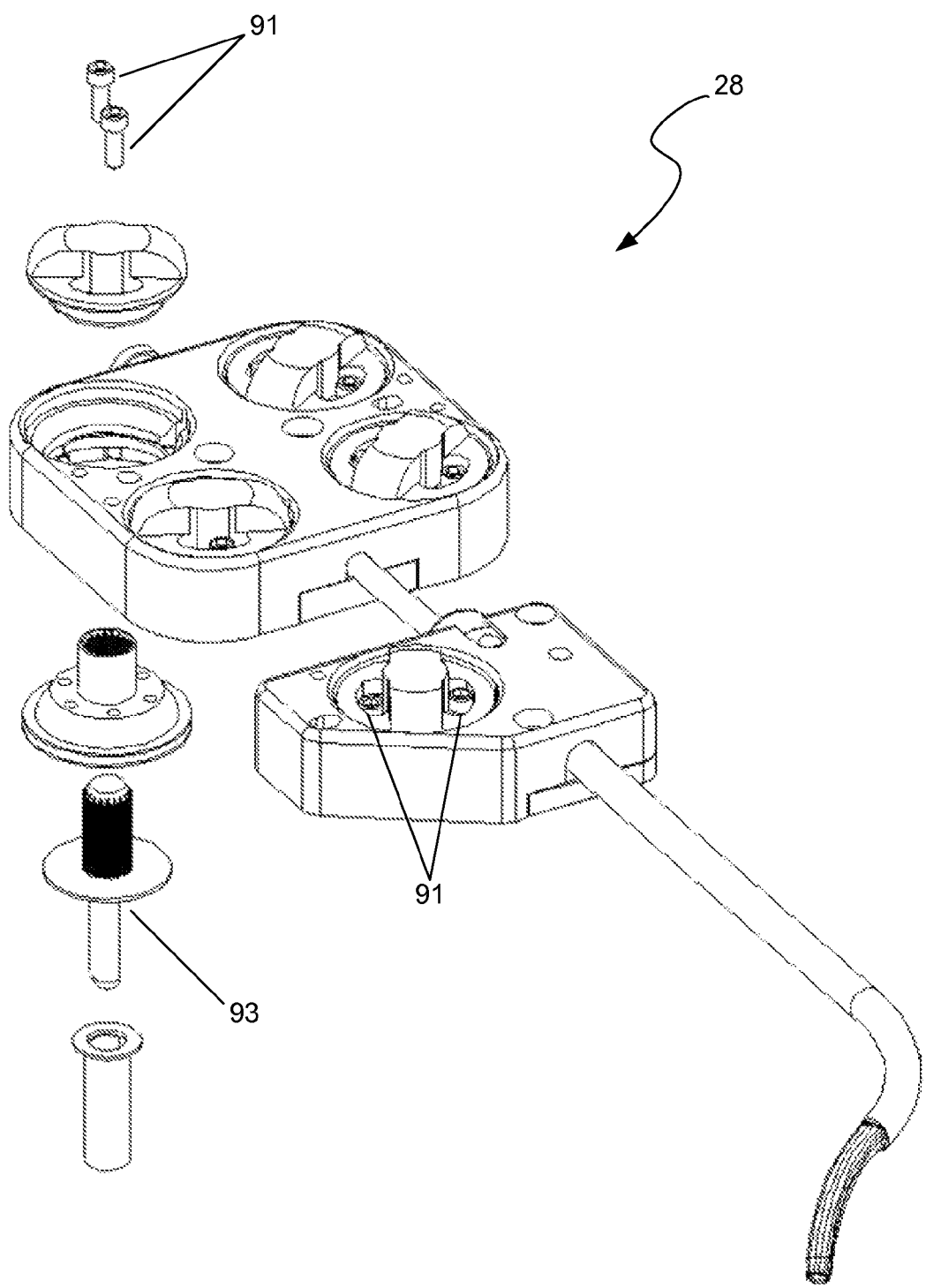
Fig 14.1

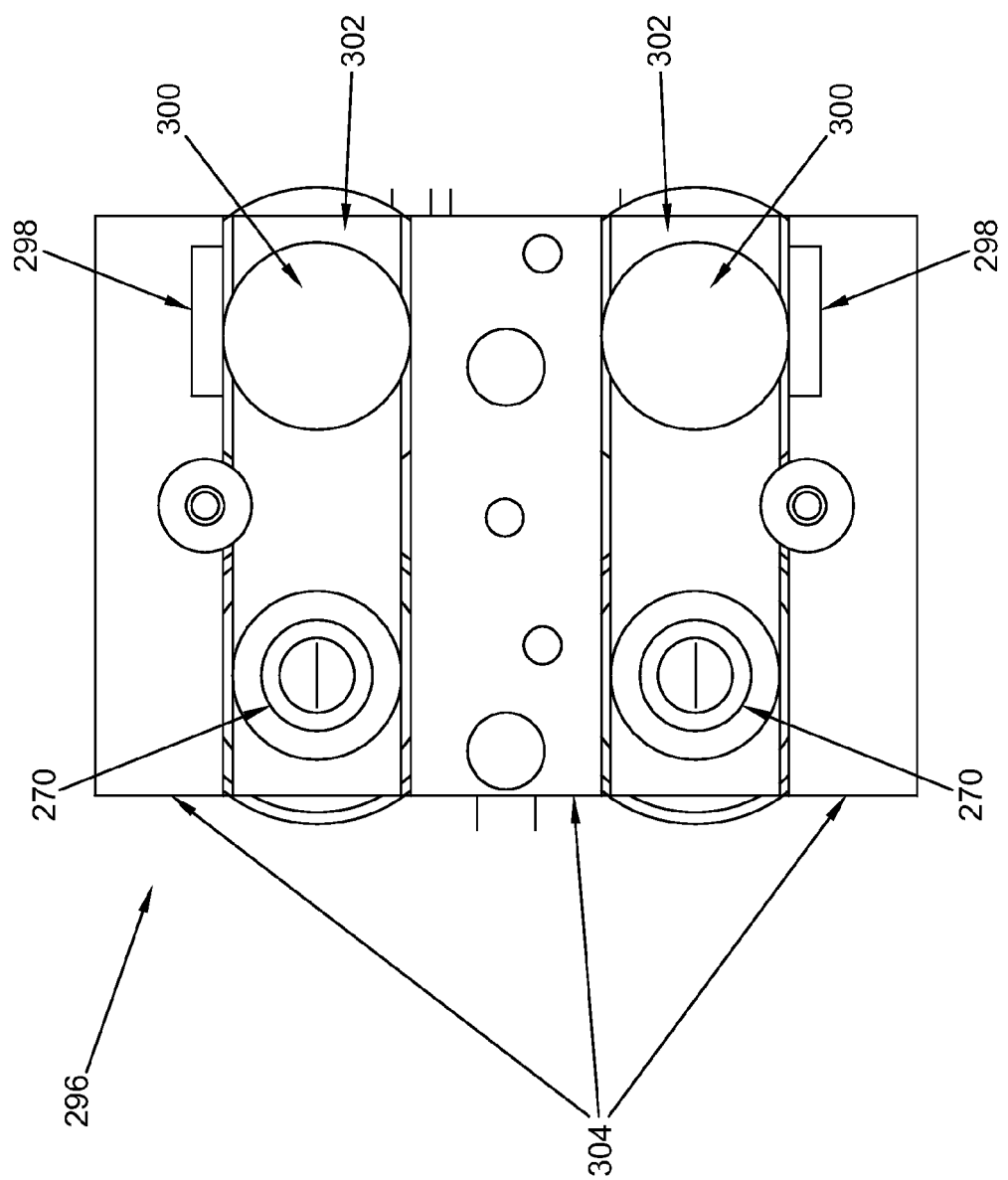

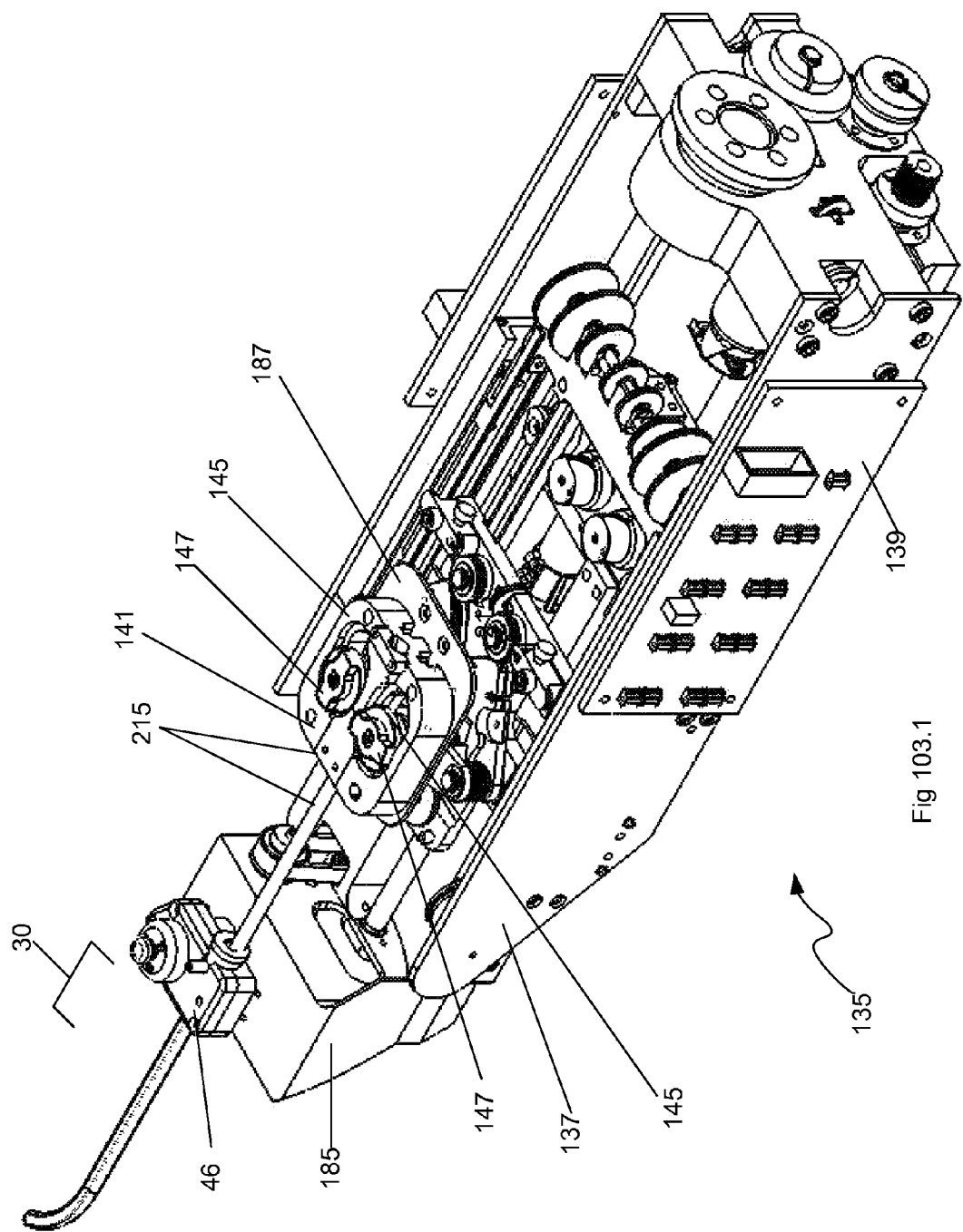
Fig 103.1

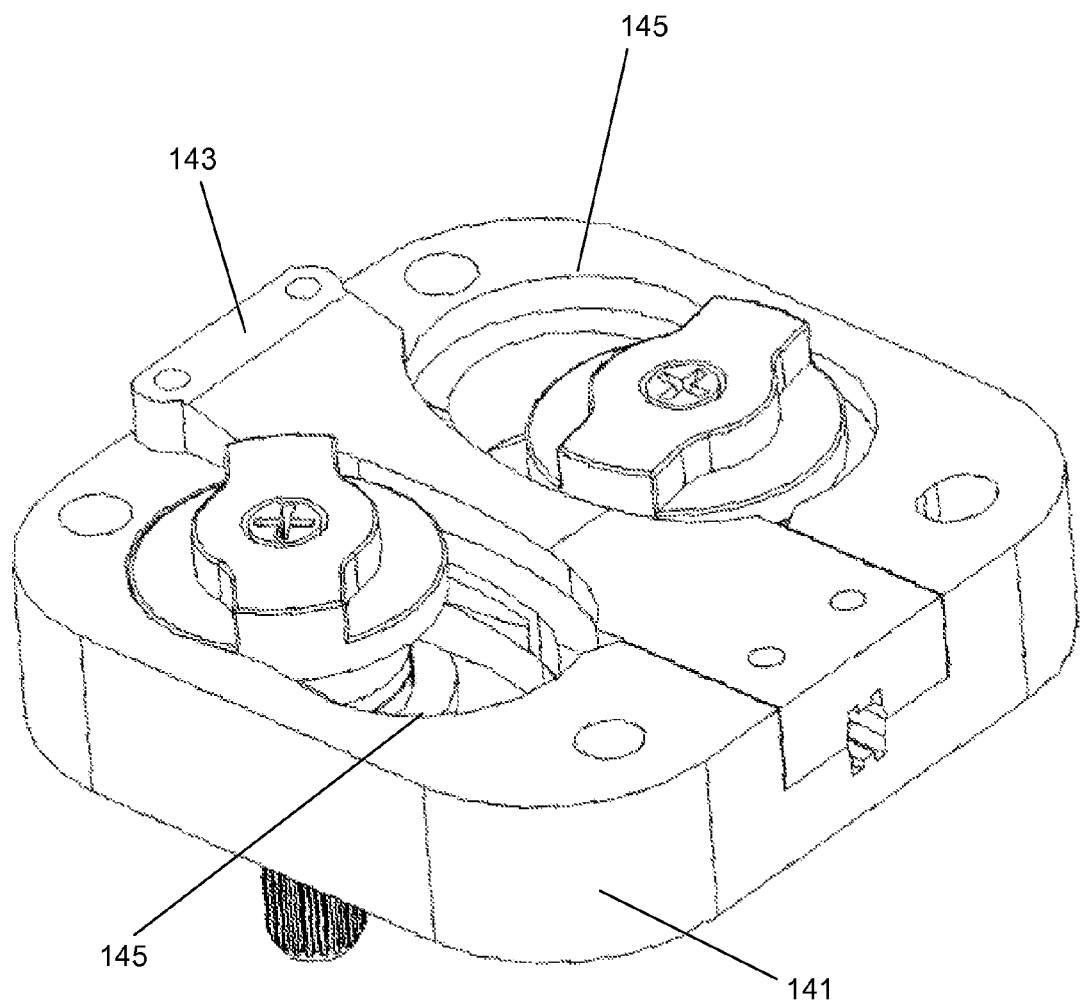
Fig 103.2

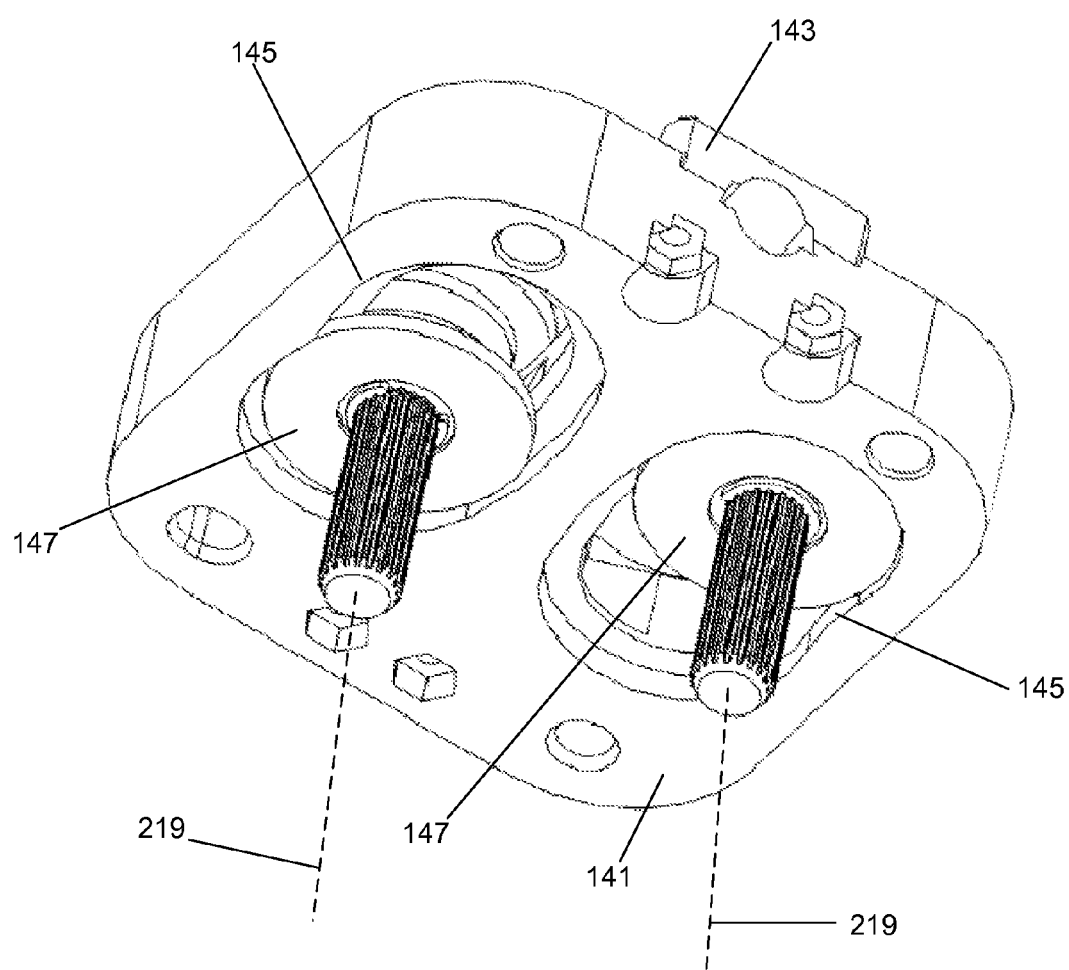
Fig 103.3

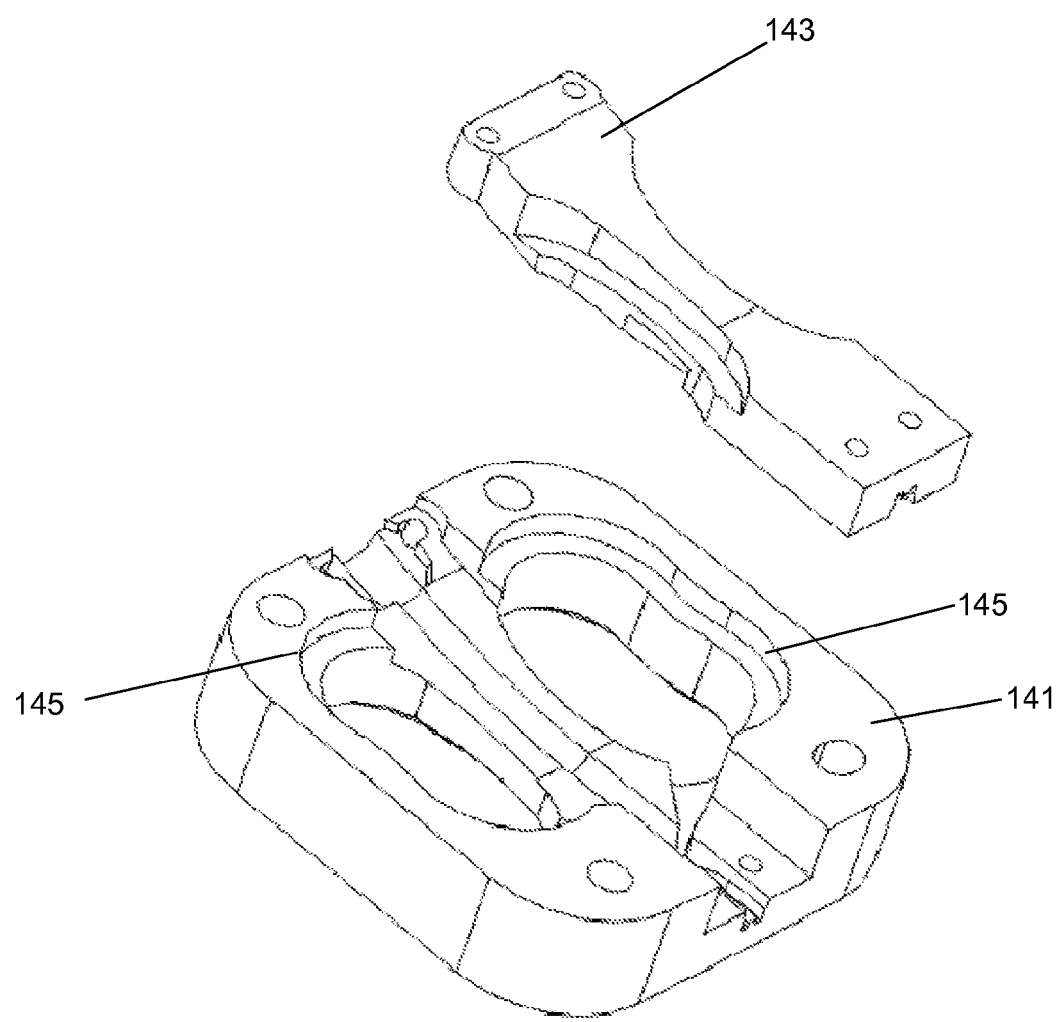
Fig 103.4

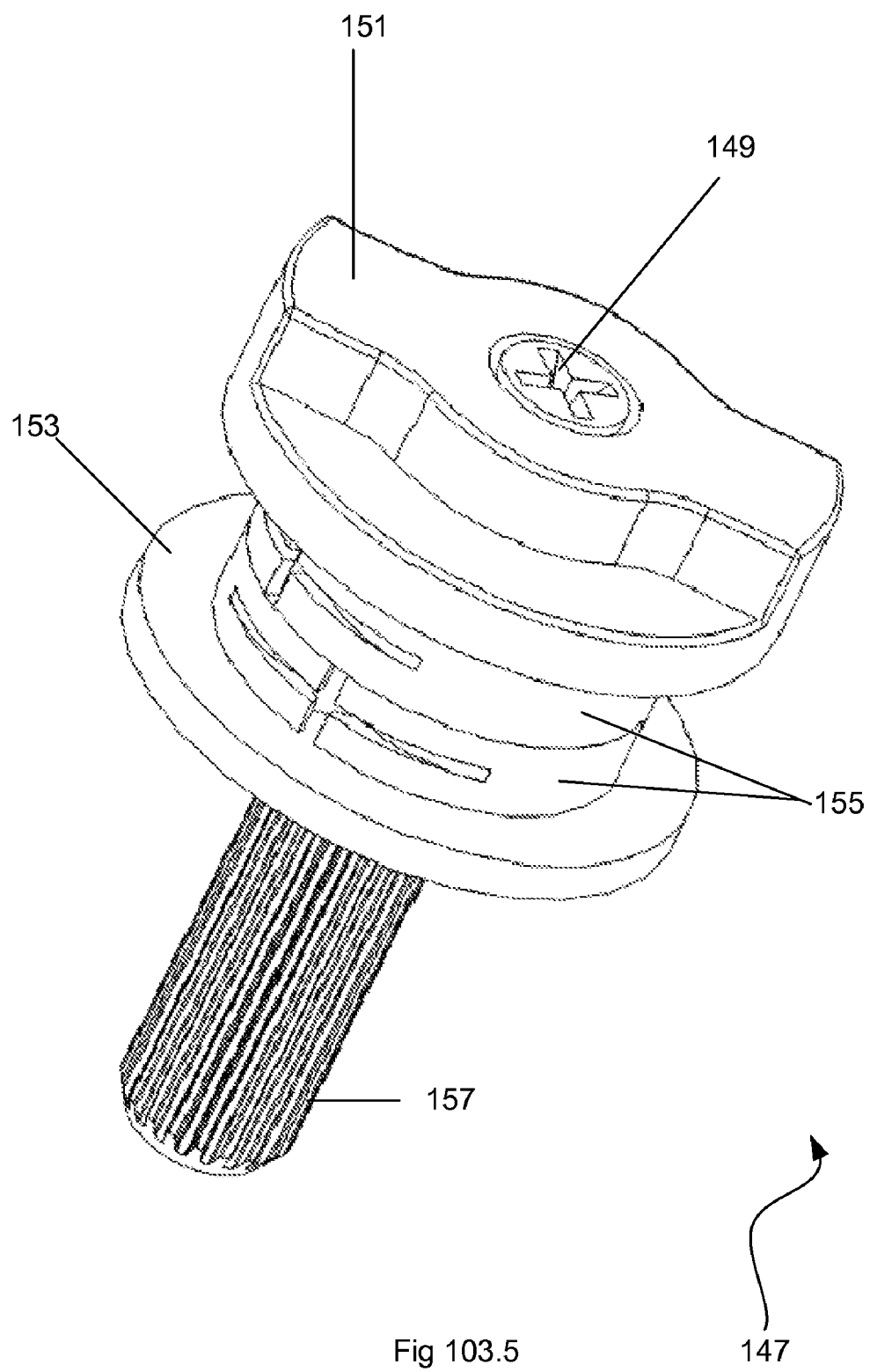
Fig 103.5

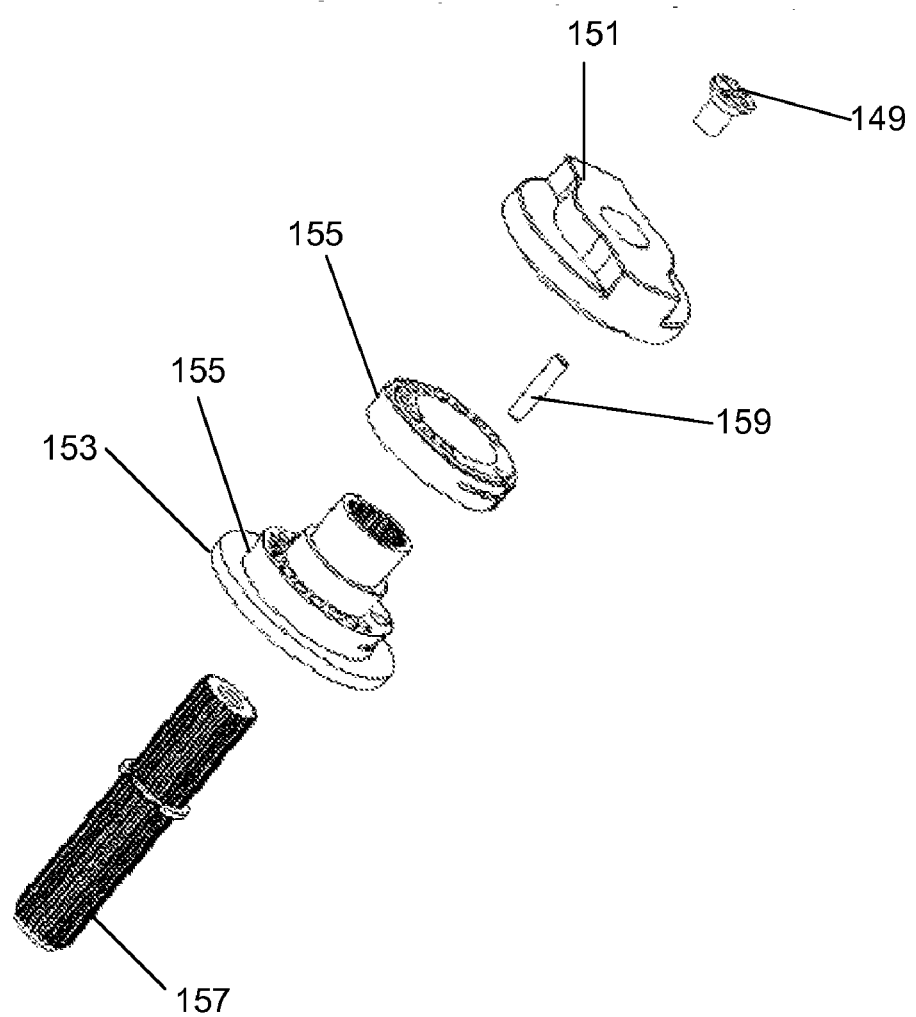
Fig 103.6

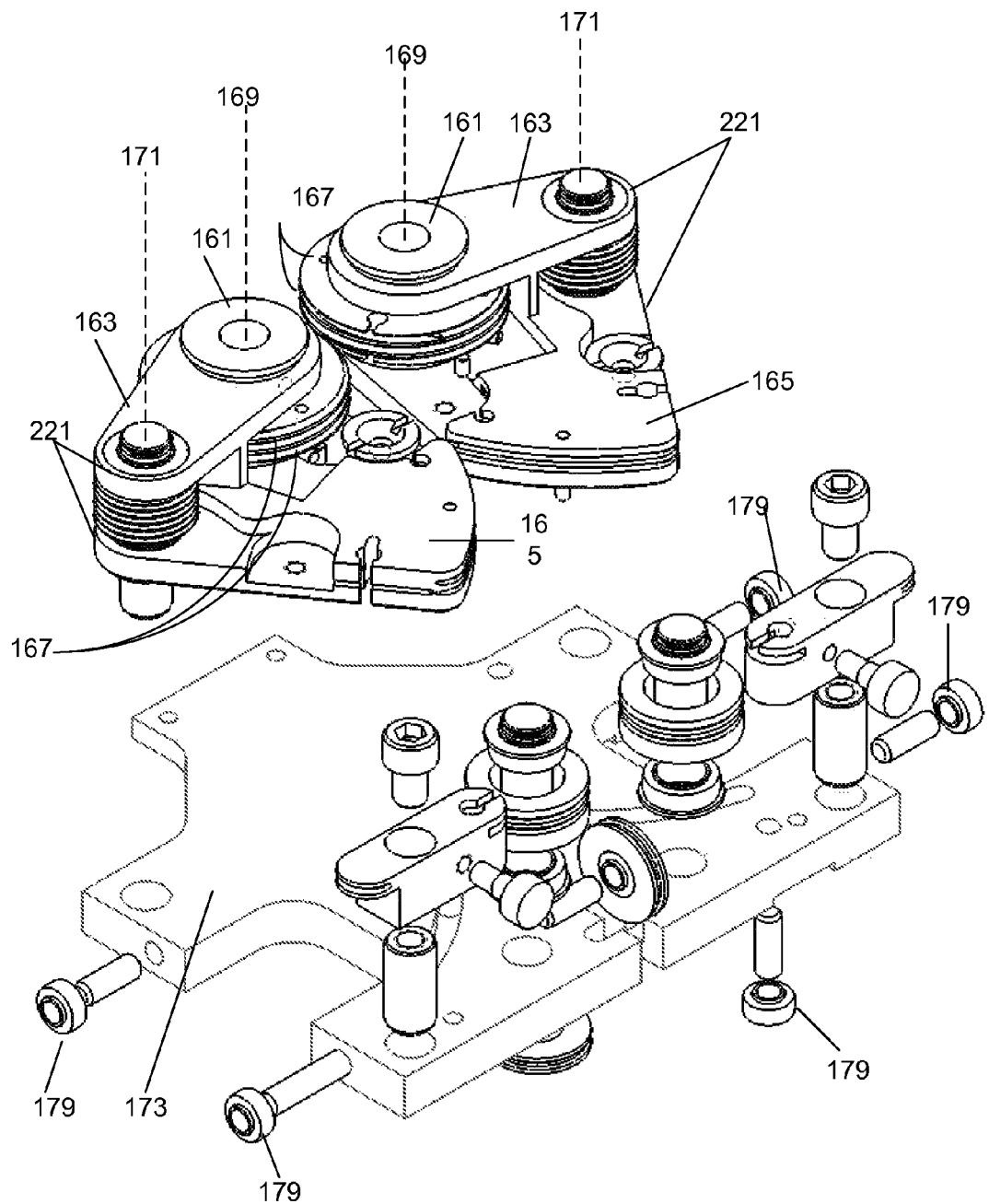
Fig 103.7

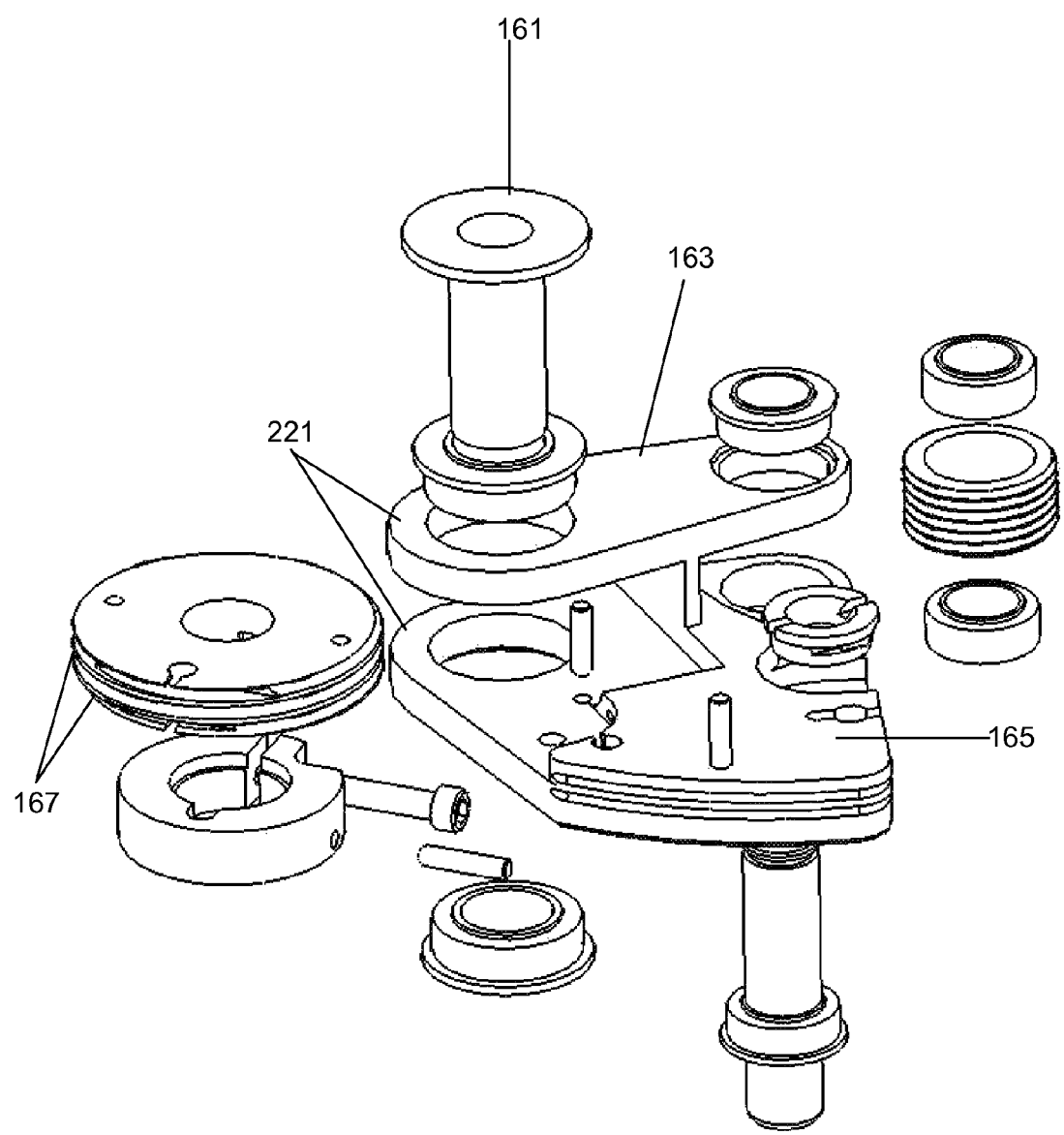
Fig 103.8

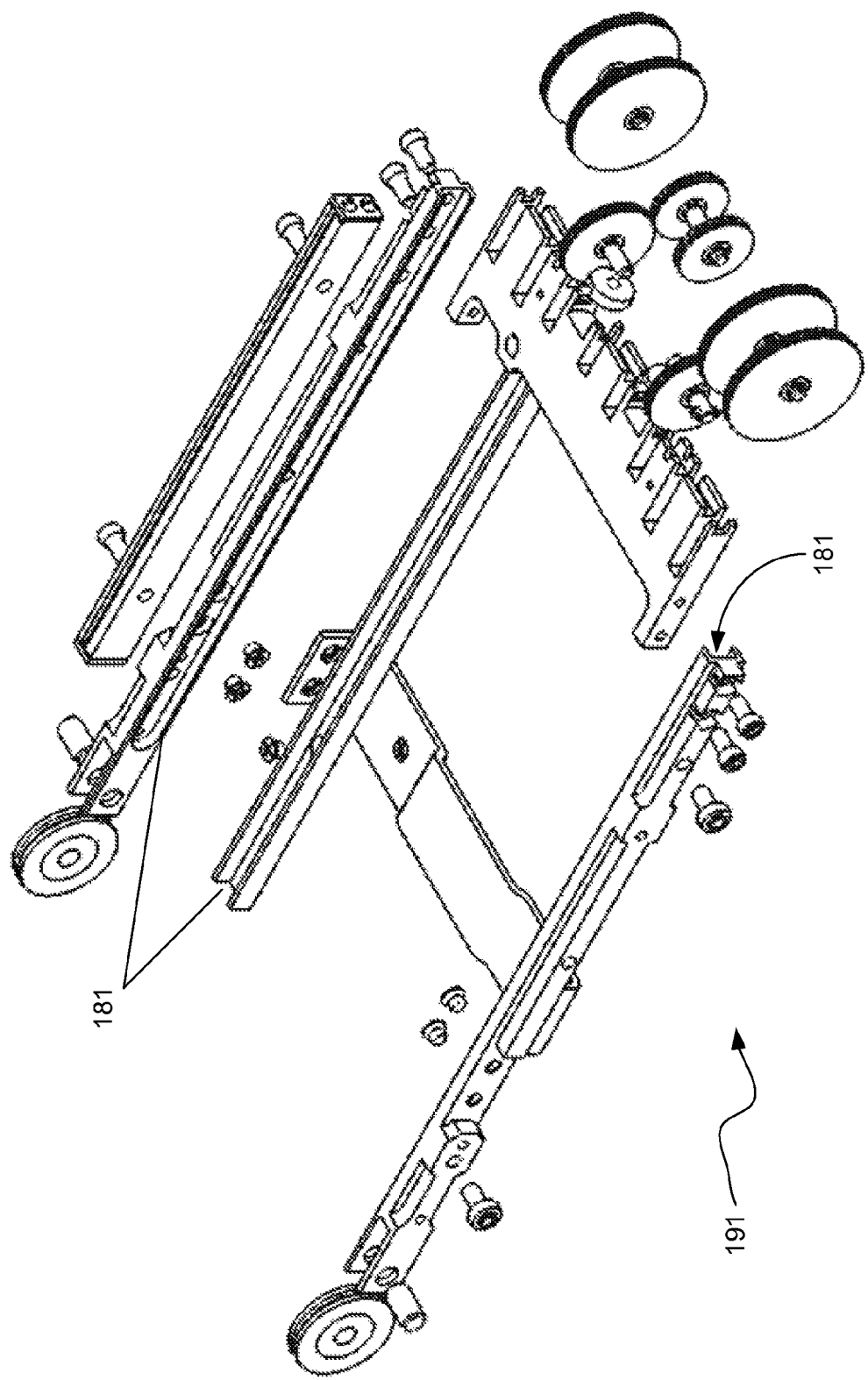
Fig 103.9

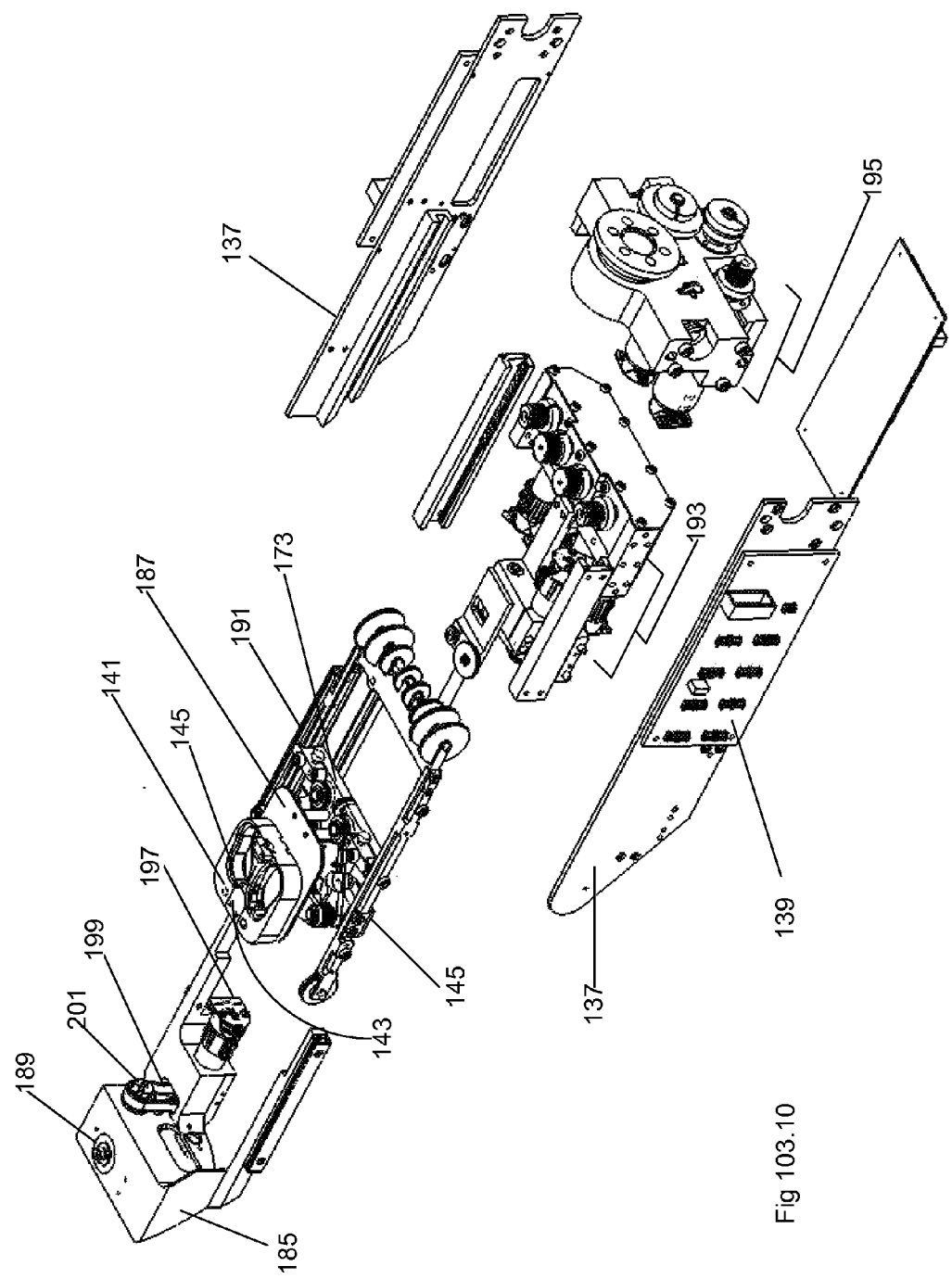
Fig 103.10

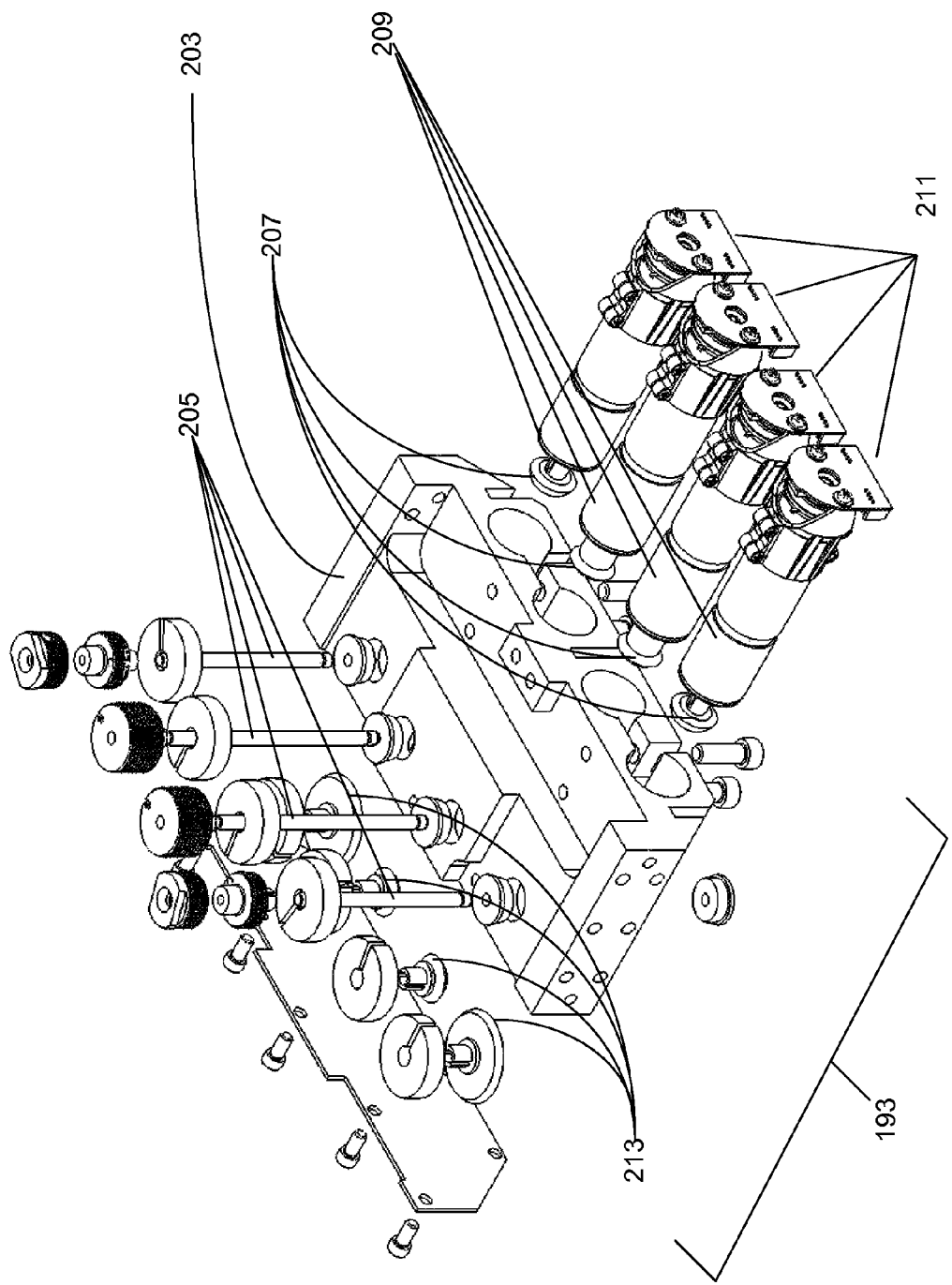
Fig 103.11

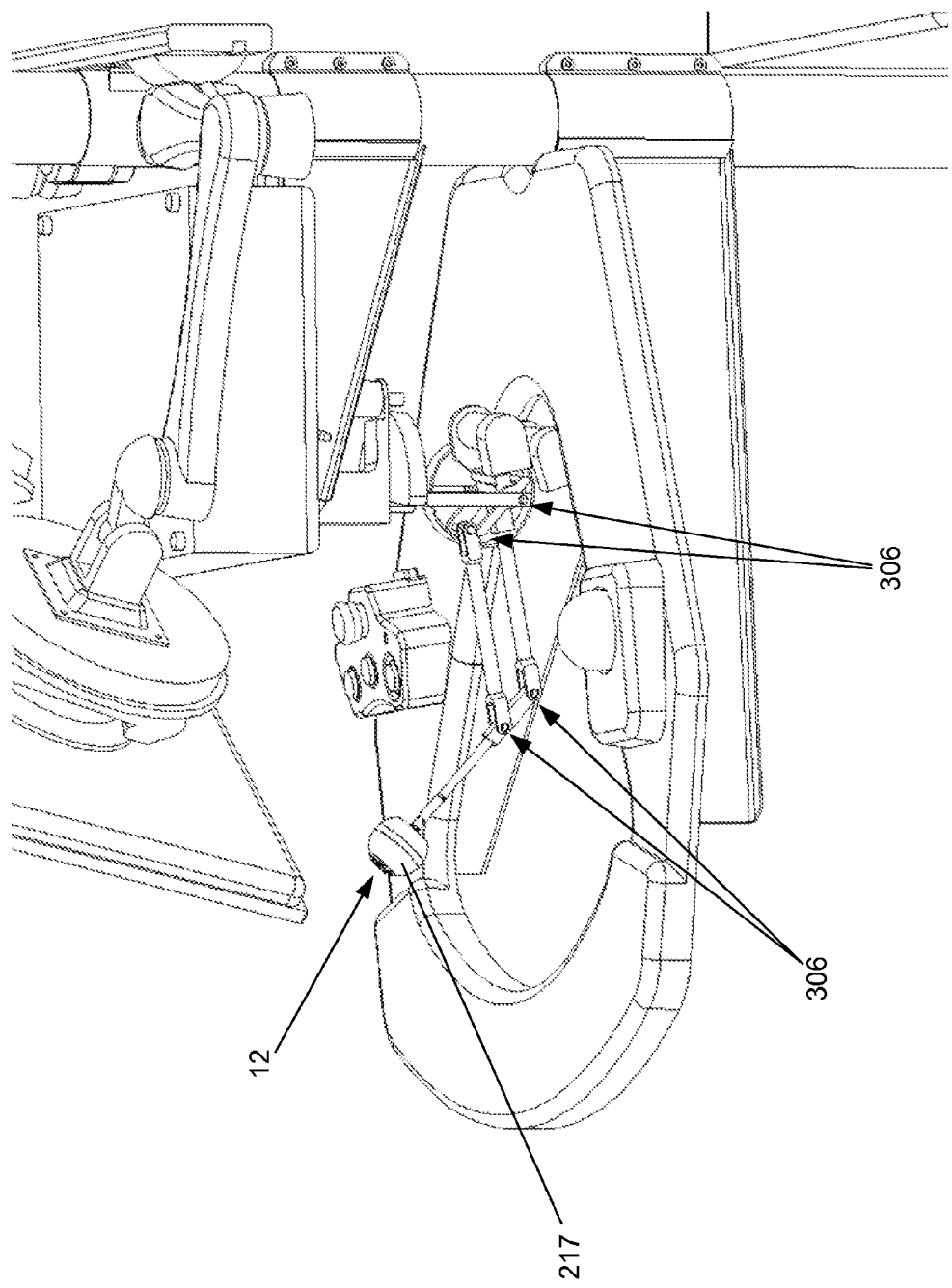

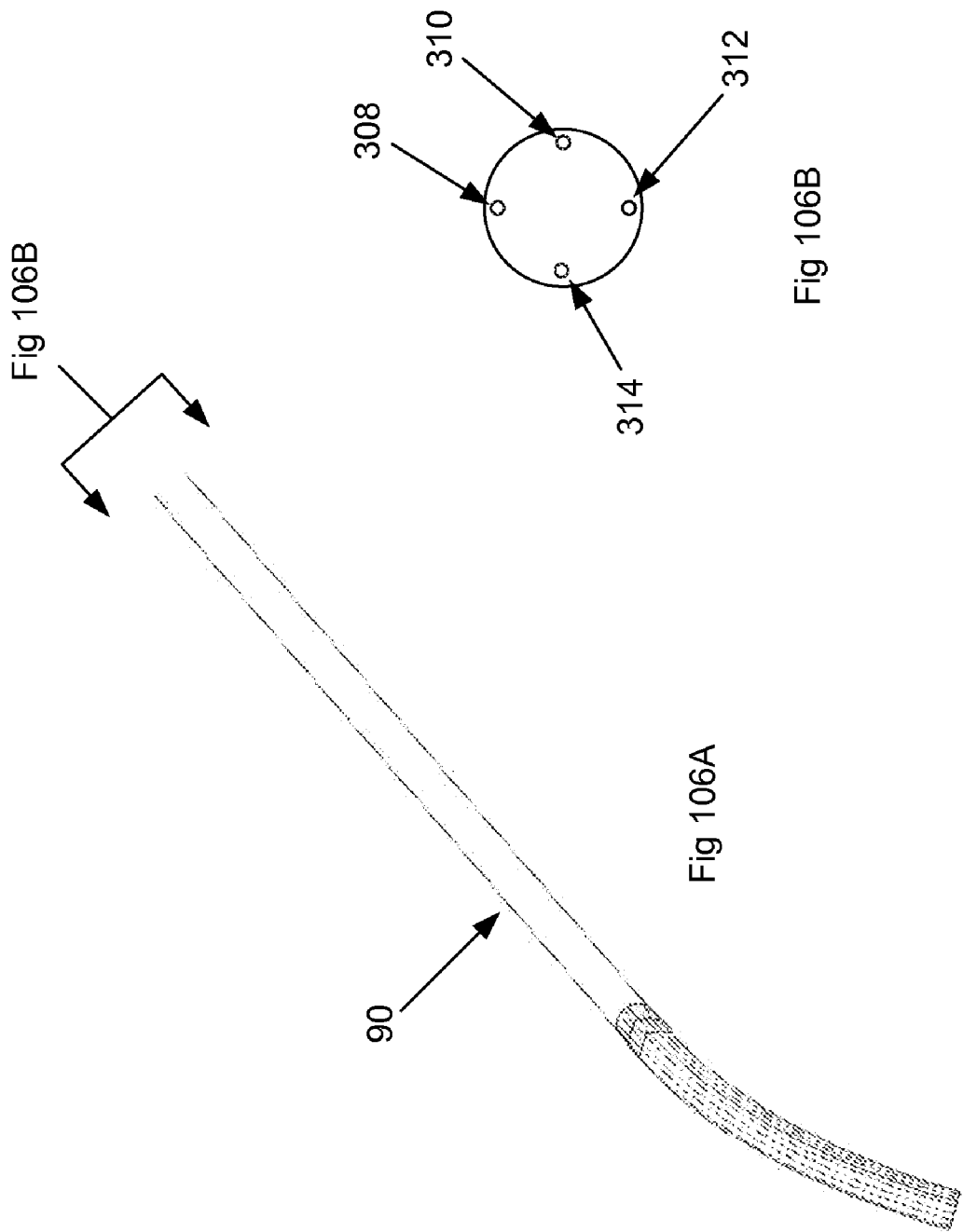

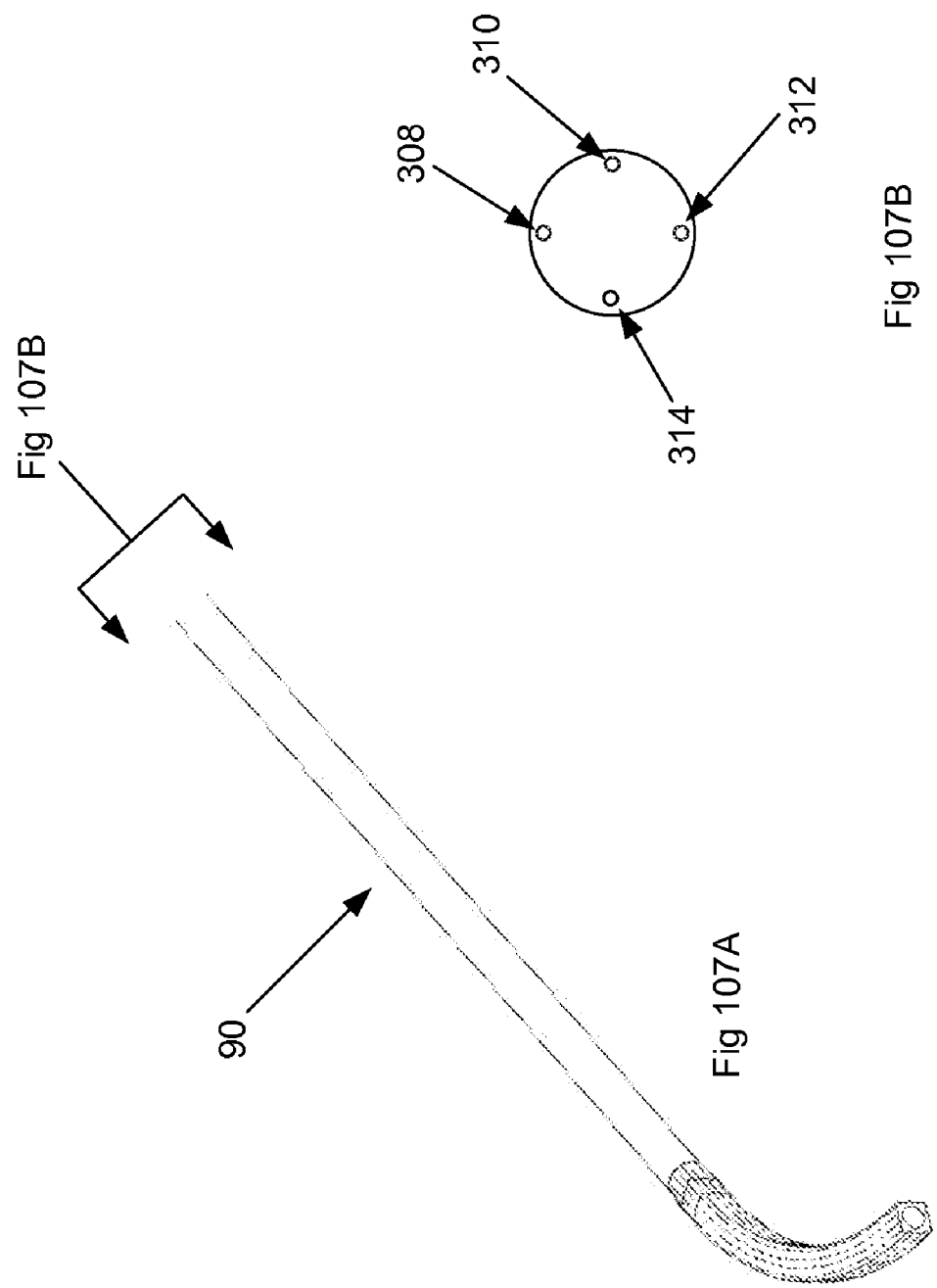

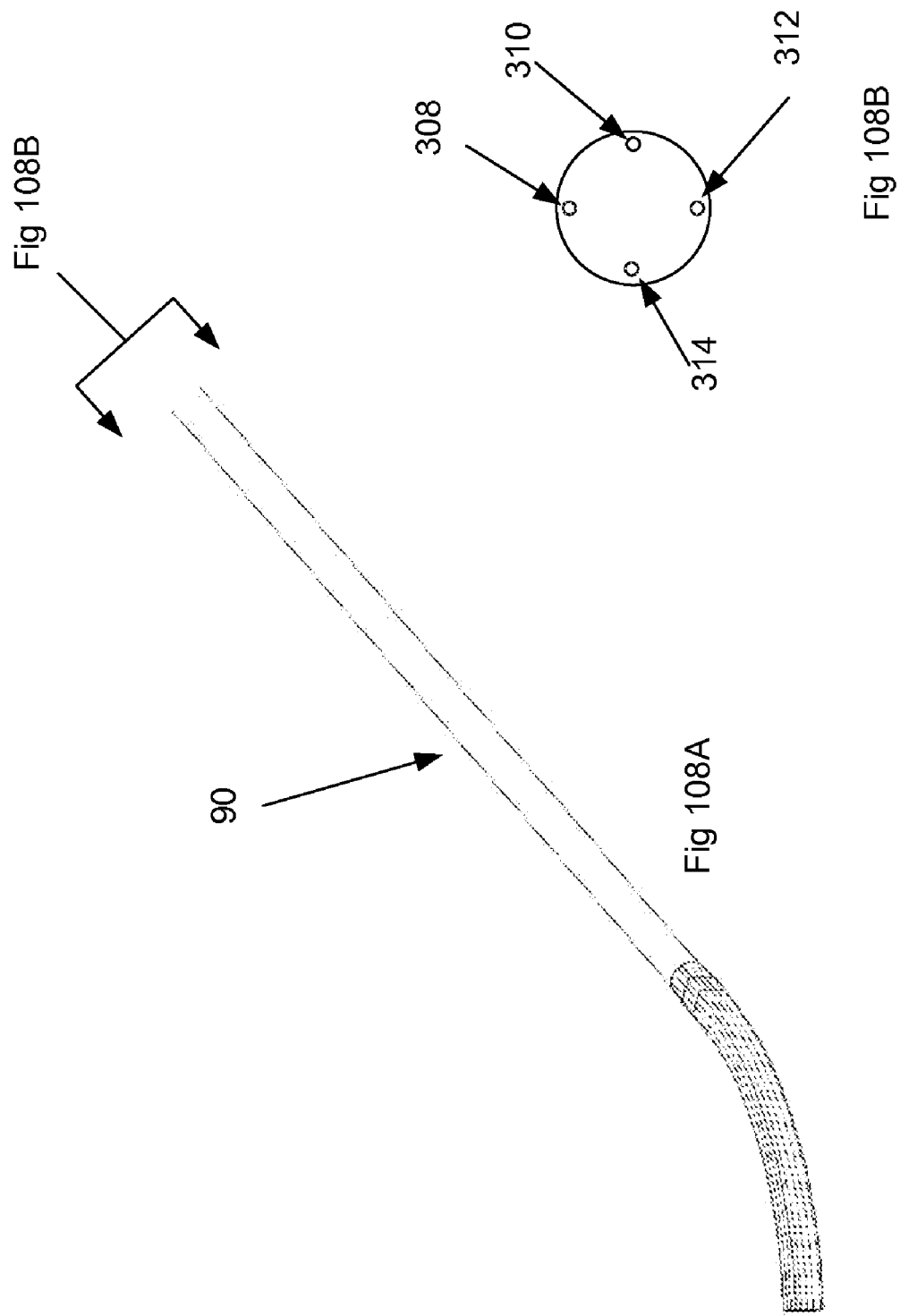

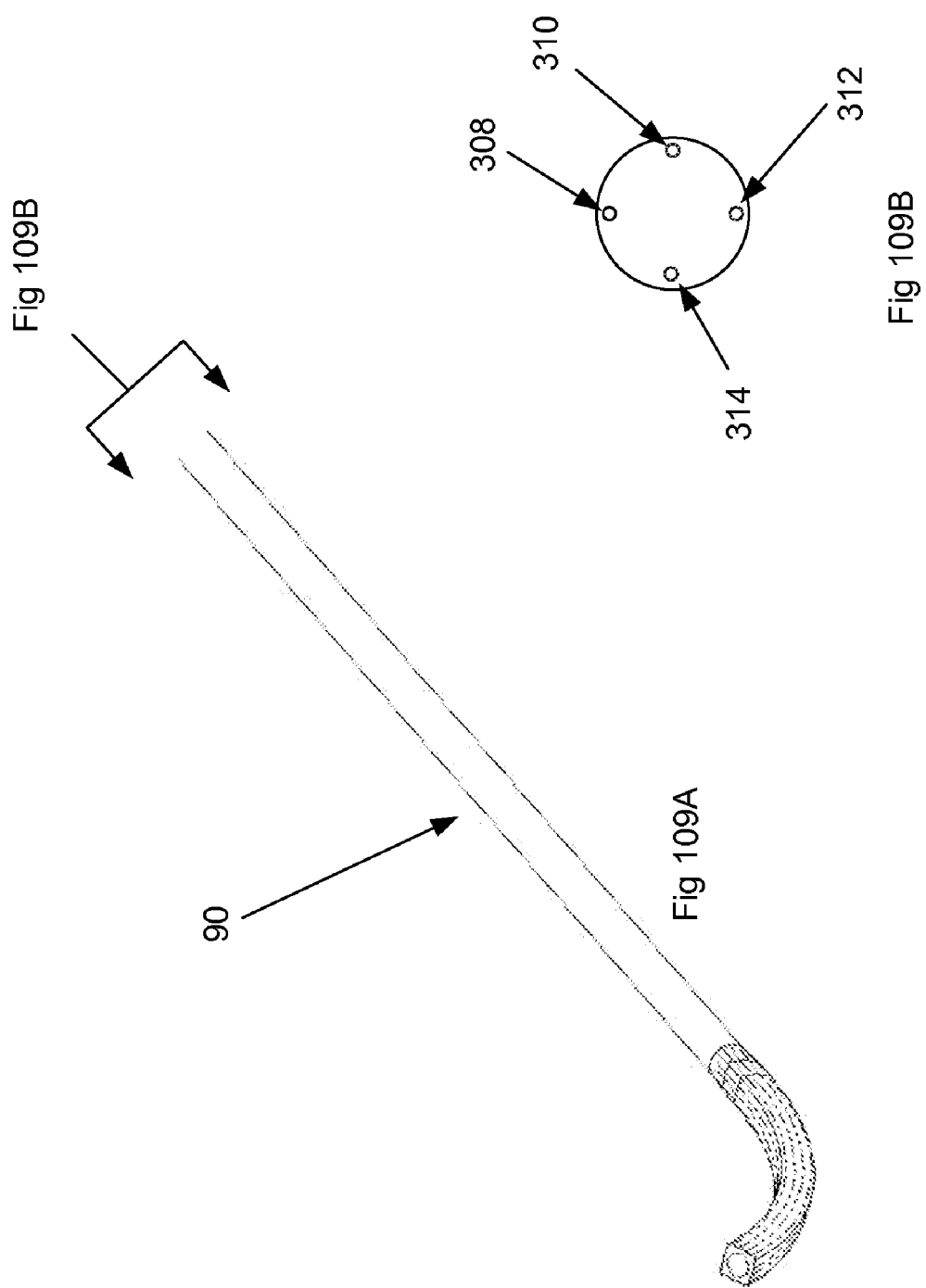

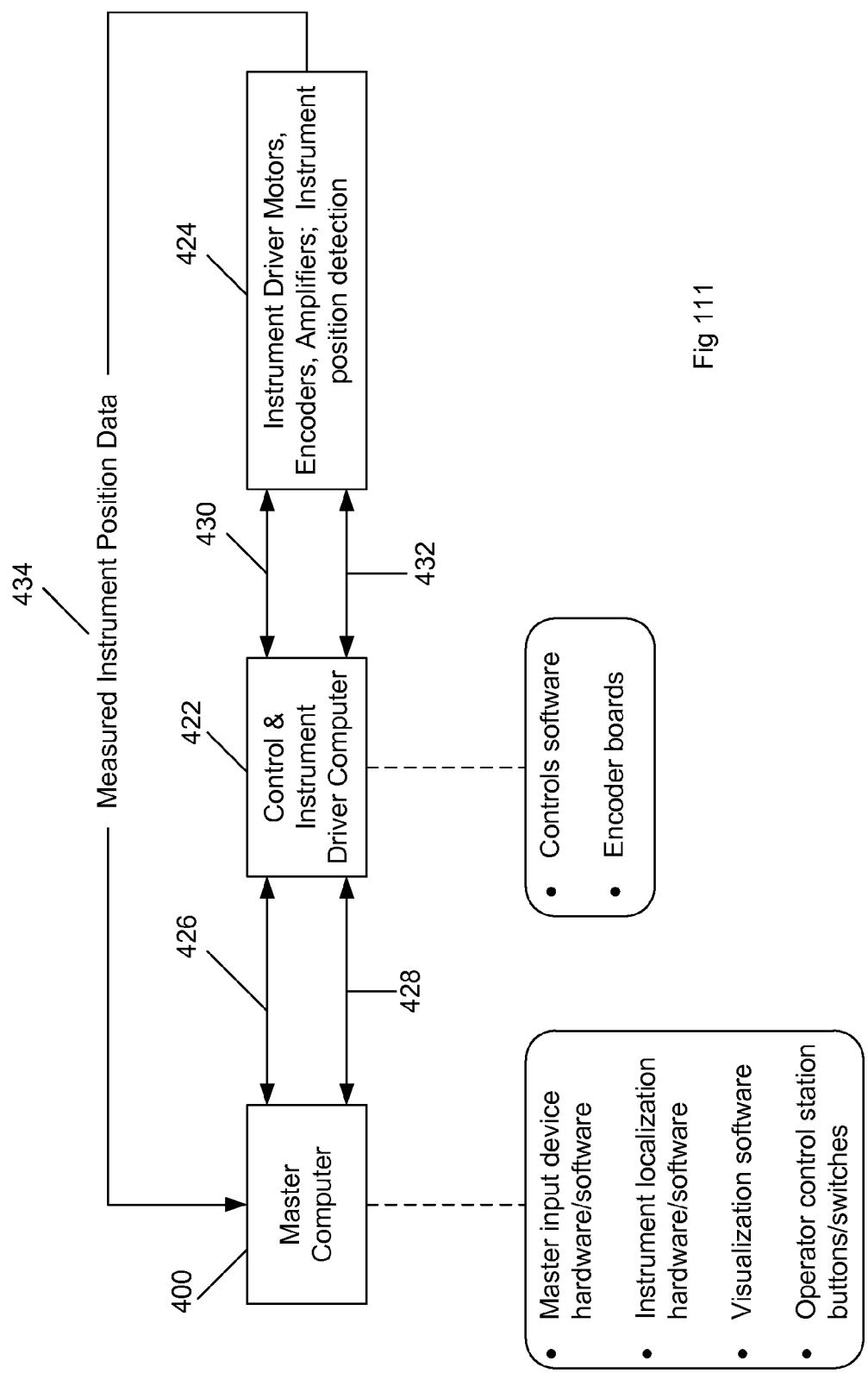

Forward Kinematics:
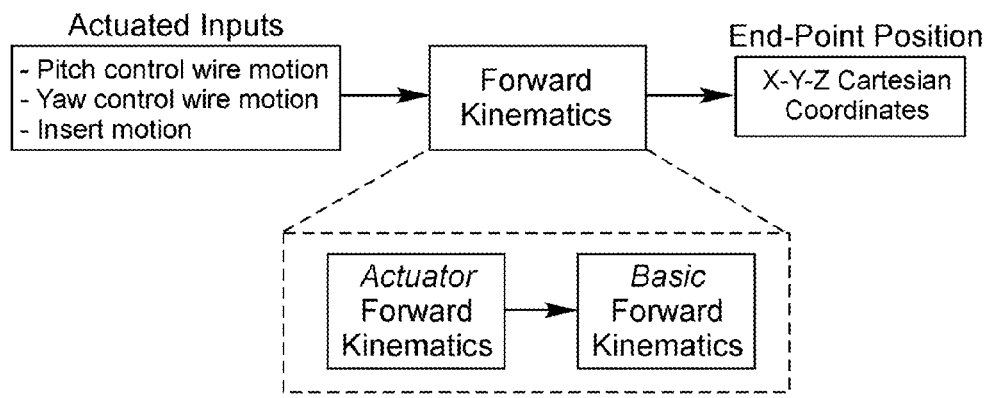
Inverse Kinematics:
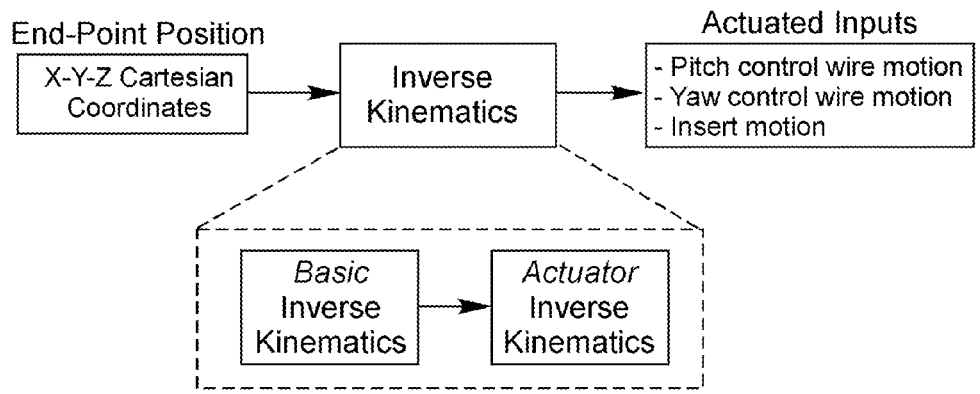
Fig 125

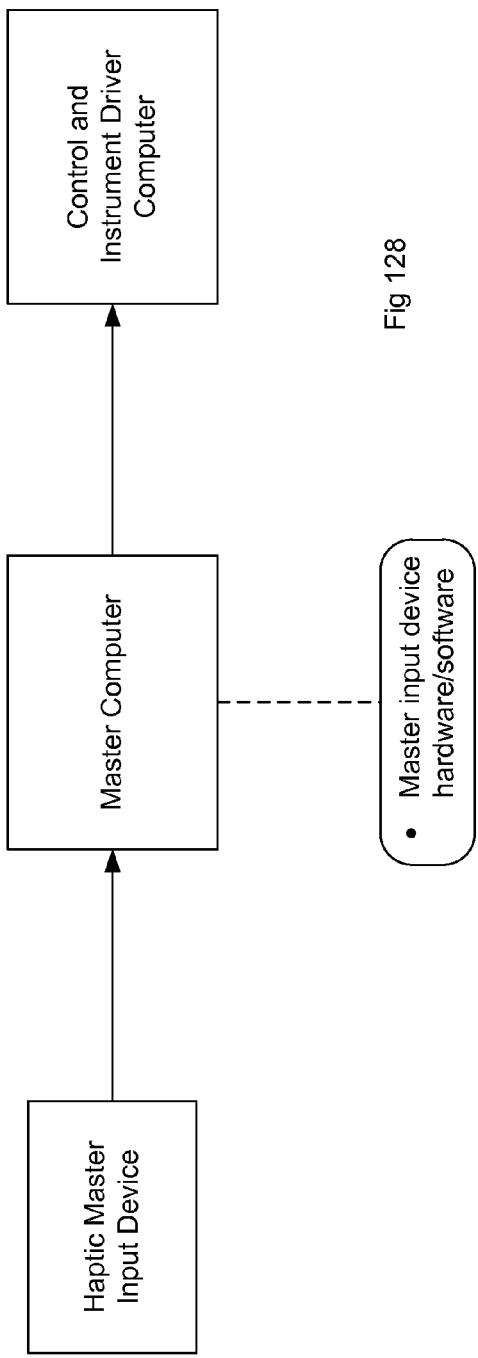
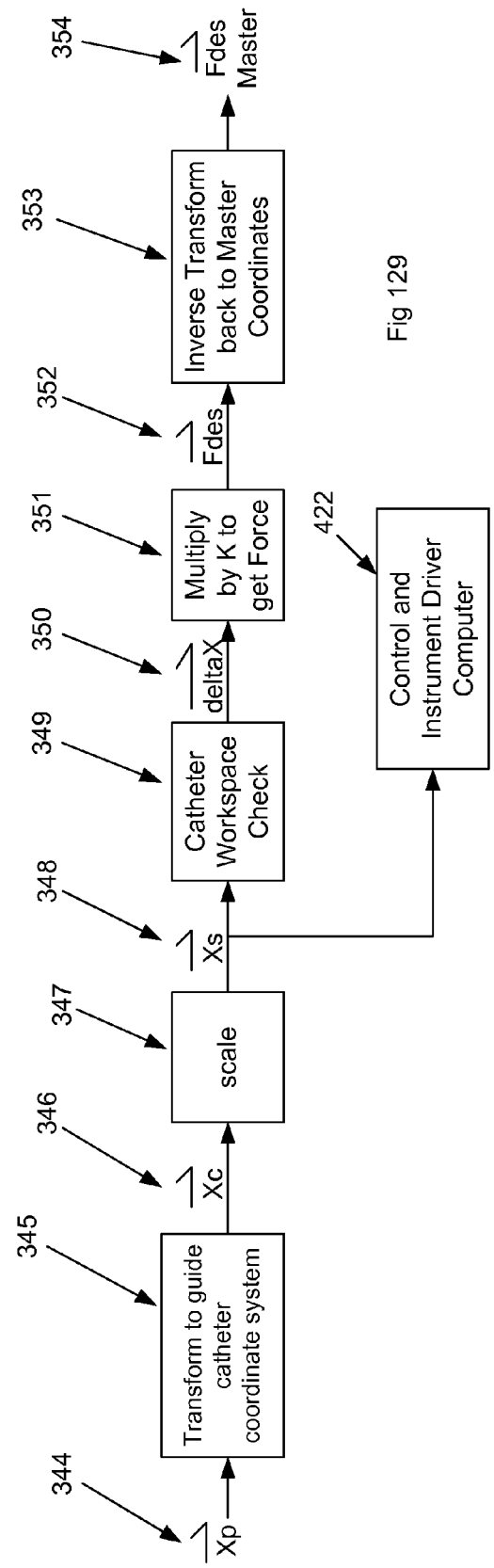

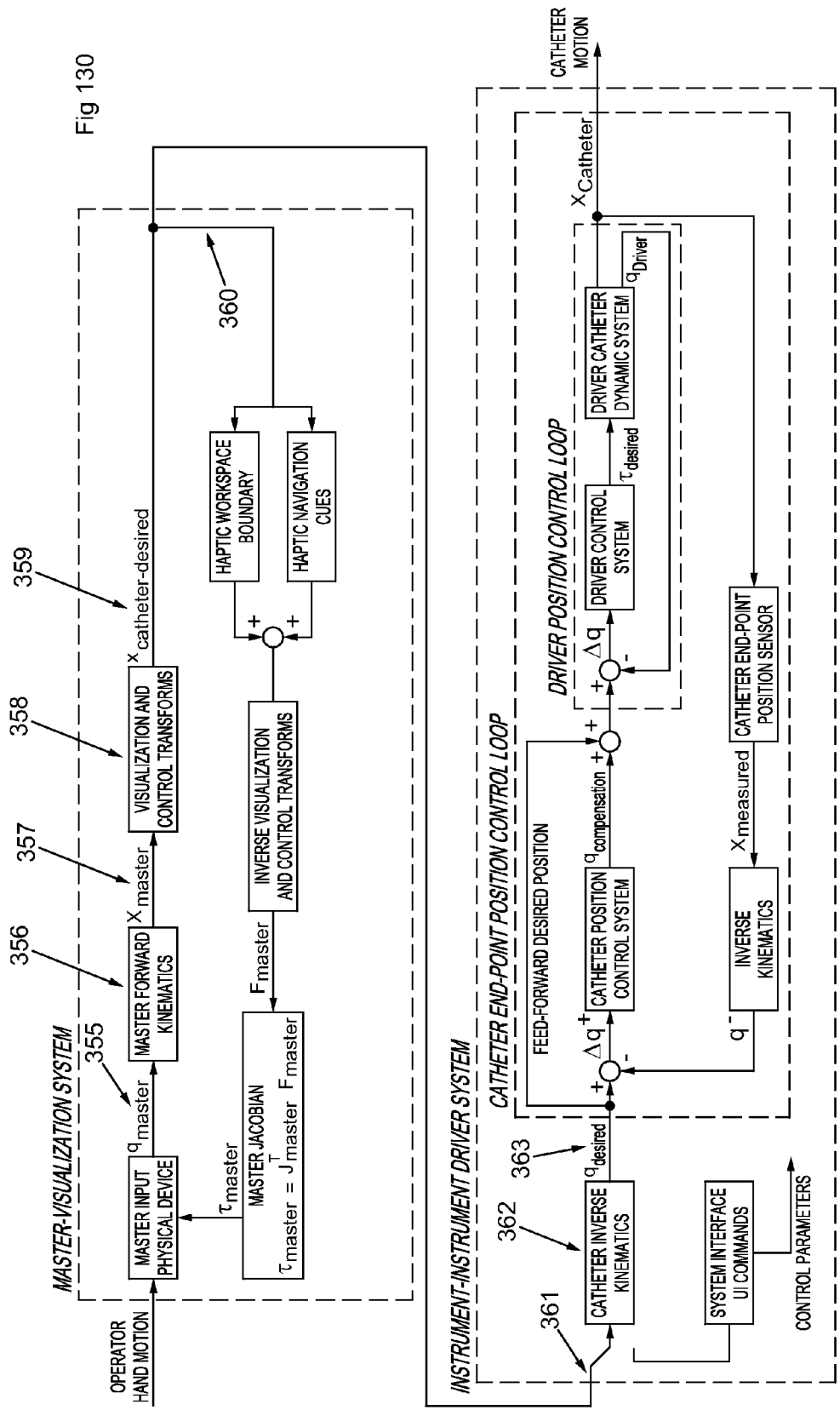

$$\Delta_1 = r_a \ \theta_a - r_T \ \theta_T$$
$$\Delta_2 = r_a \ \theta_a - r_T \ \theta_T$$

364, 365

Desired Tension - 1 DOF:

$$\delta_T = K_T \|\varnothing_a\|$$

Desired Tension - 2 DOF (i.e., pitch & yaw):

$$\begin{pmatrix} \delta_{T_{Pitch}} \\ \delta_{T_{Yaw}} \end{pmatrix} = \begin{bmatrix} K_T & K_{TC} \\ K_{TC} & K_T \end{bmatrix} \cdot \begin{pmatrix} \varnothing_{a_{Pitch}} \\ \varnothing_{a_{Yaw}} \end{pmatrix}$$

Tension coupling   Tension slope

370

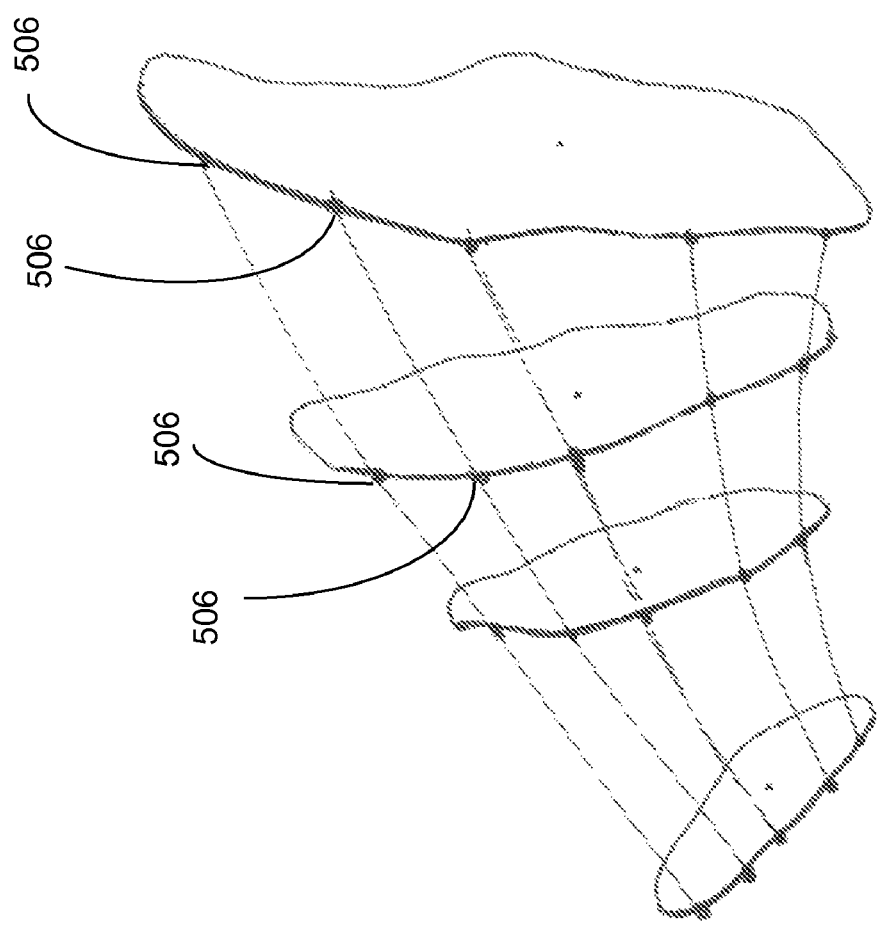

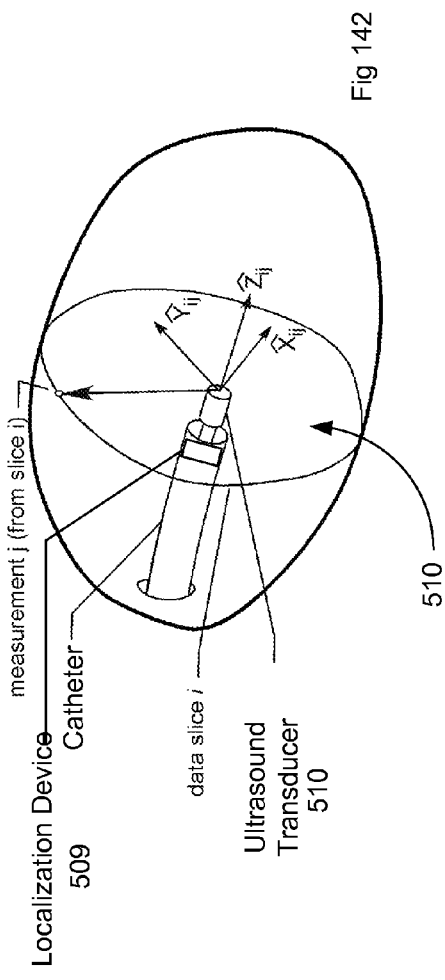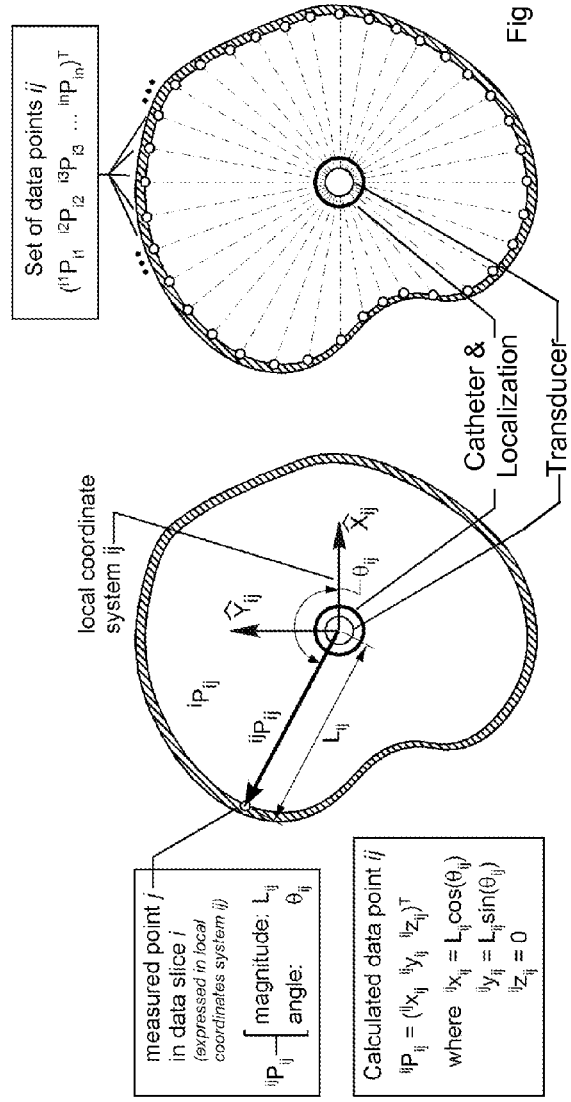

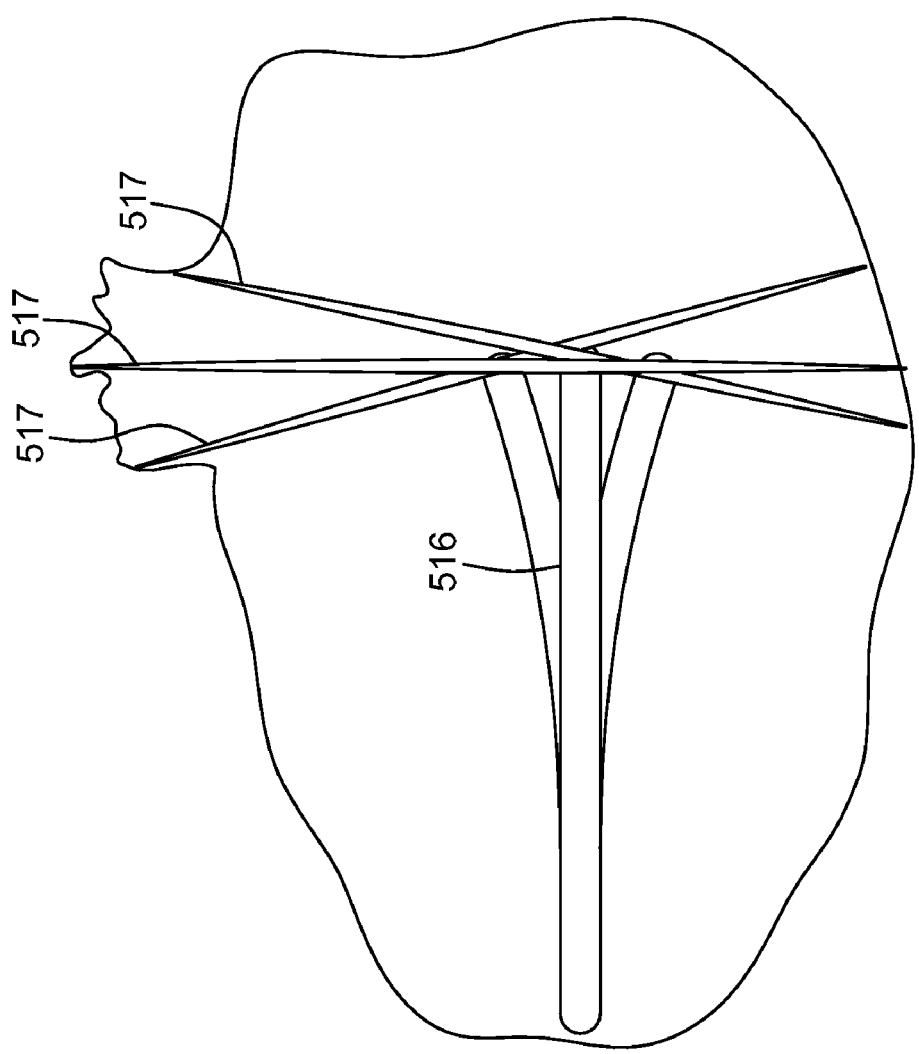

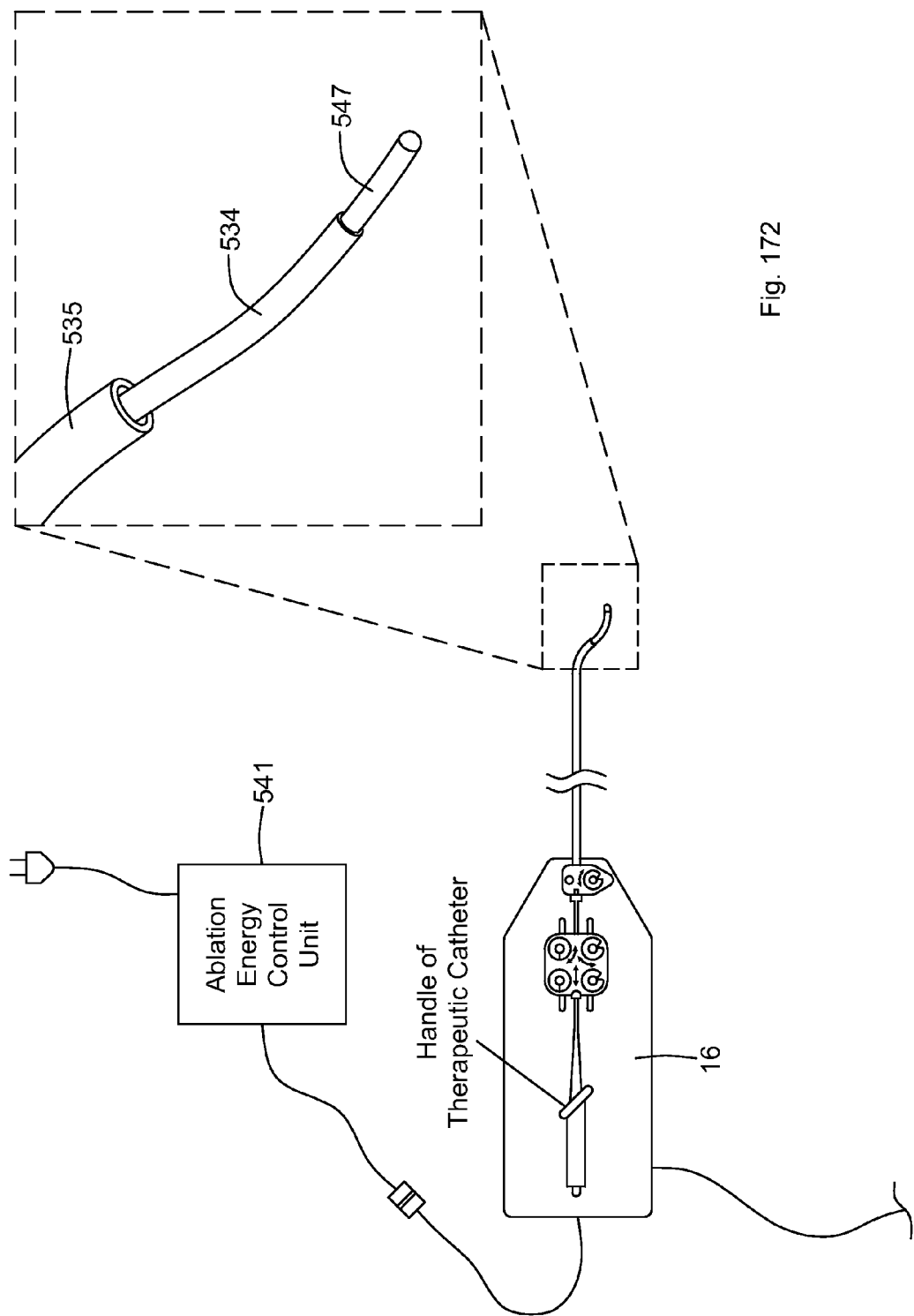

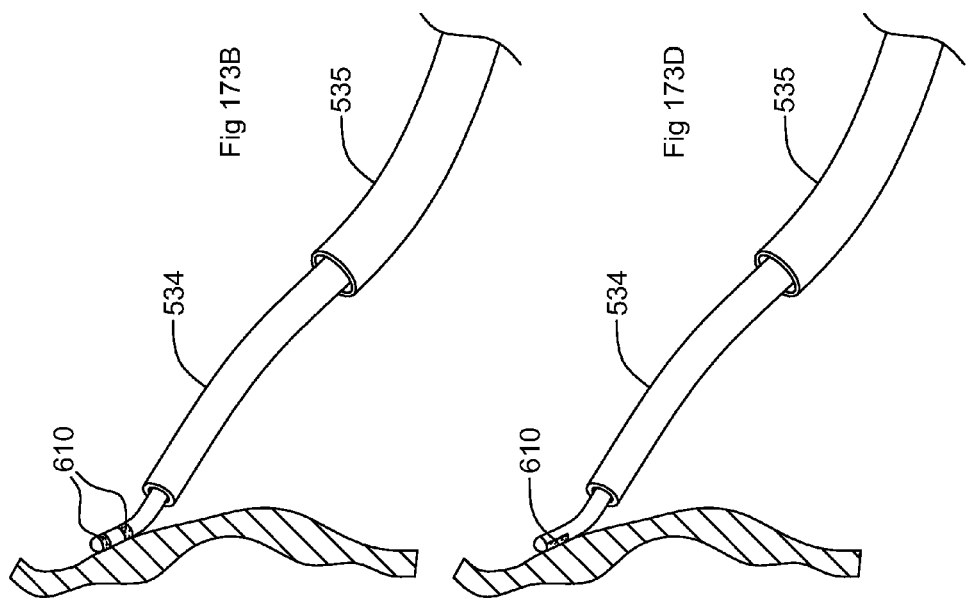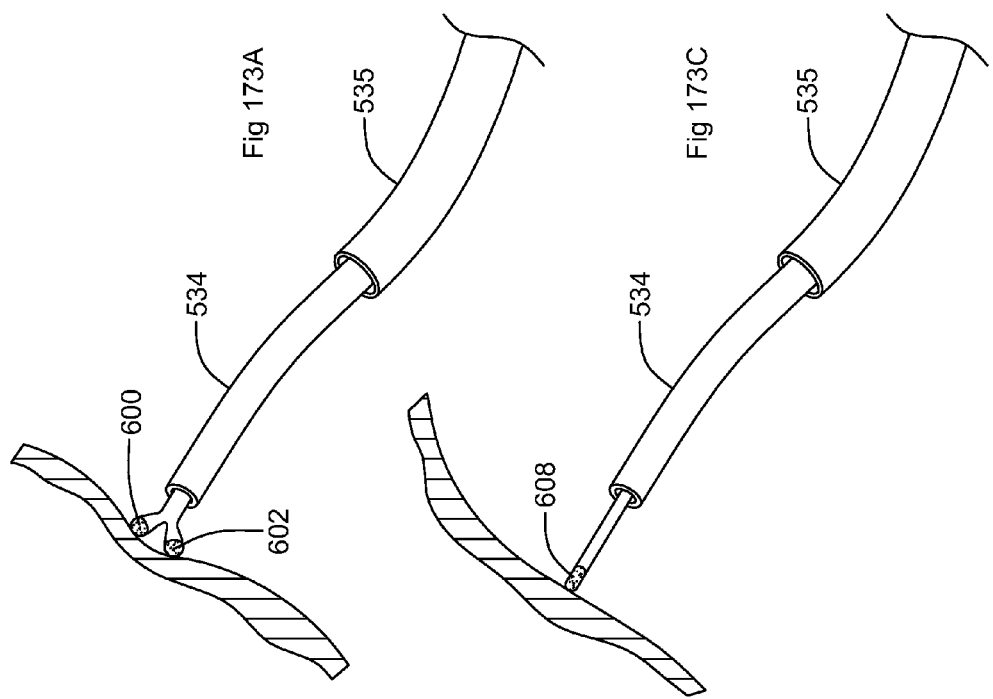

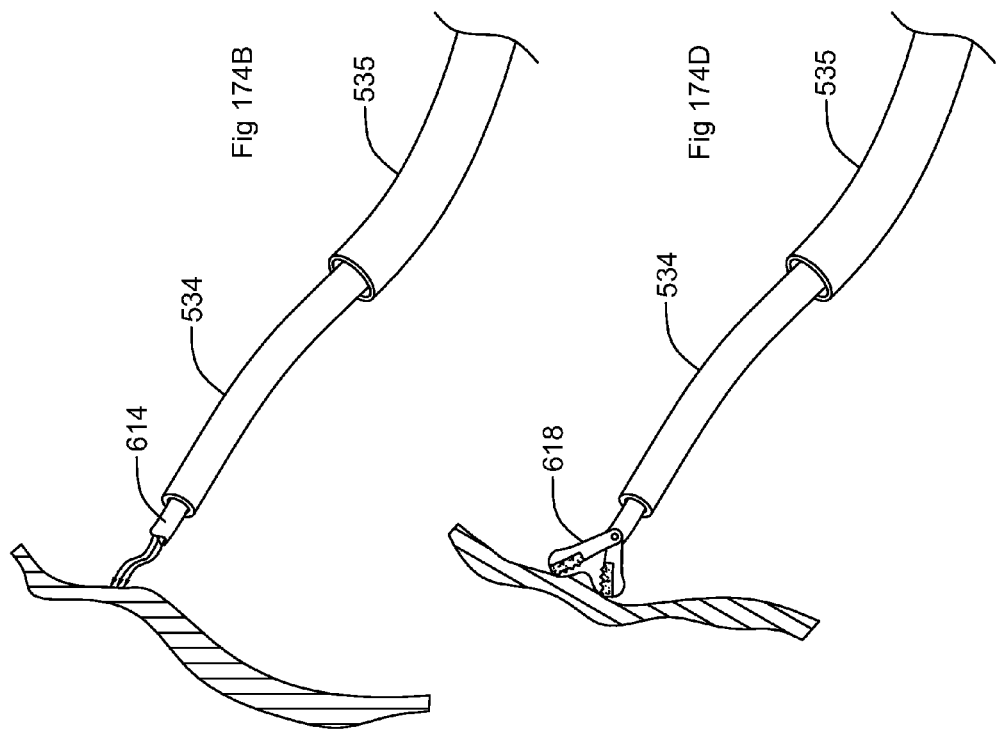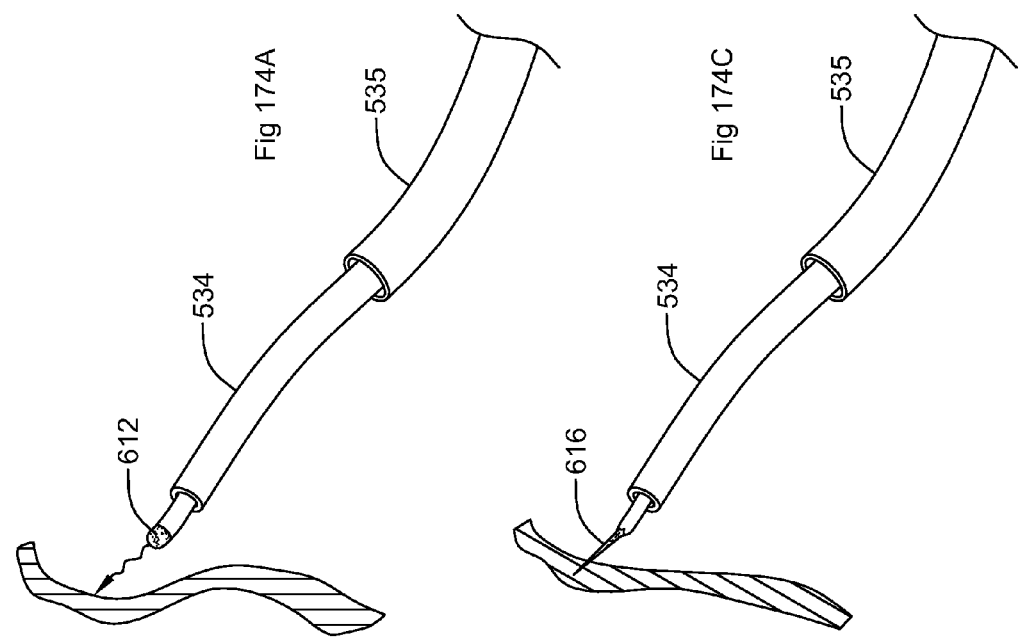

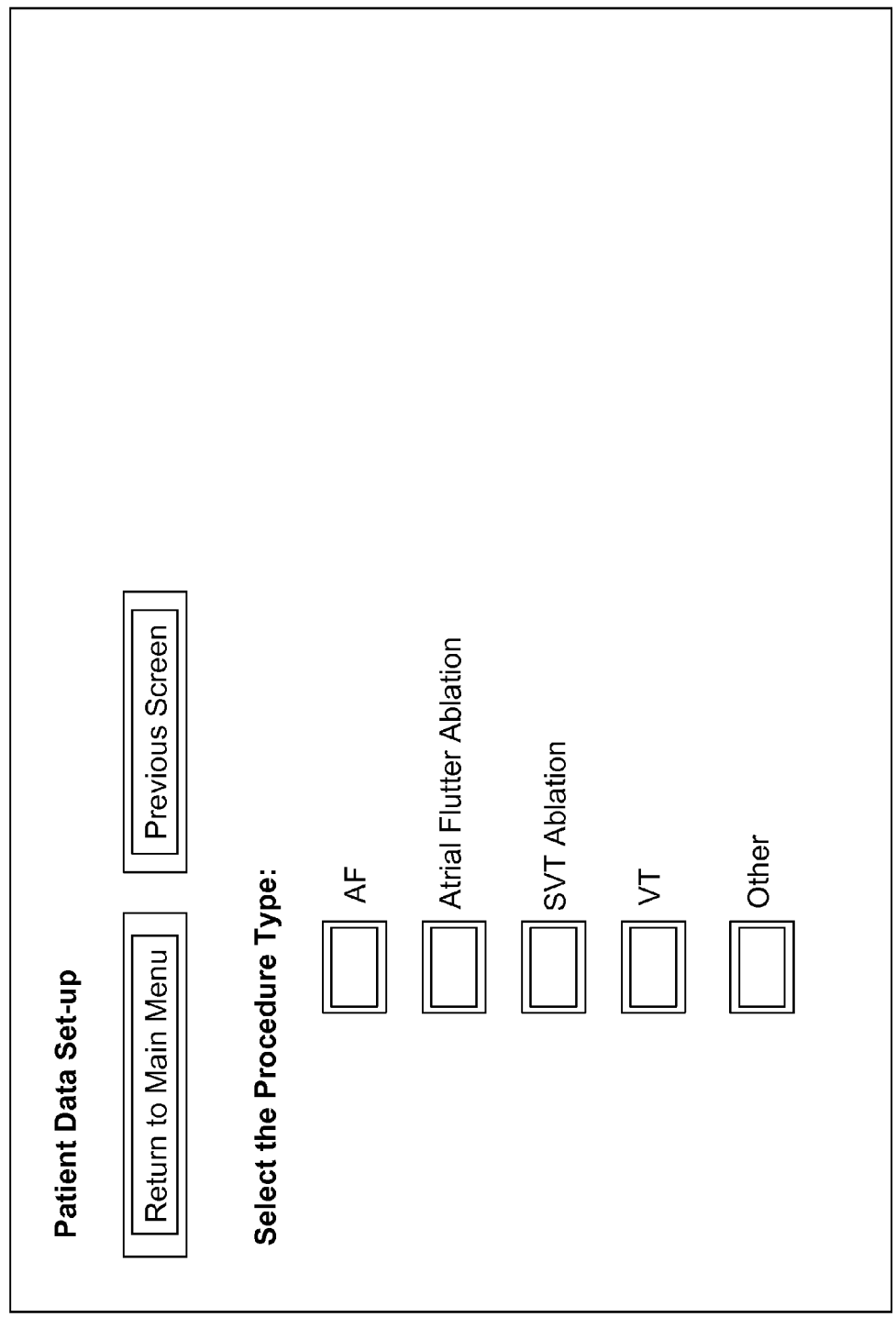

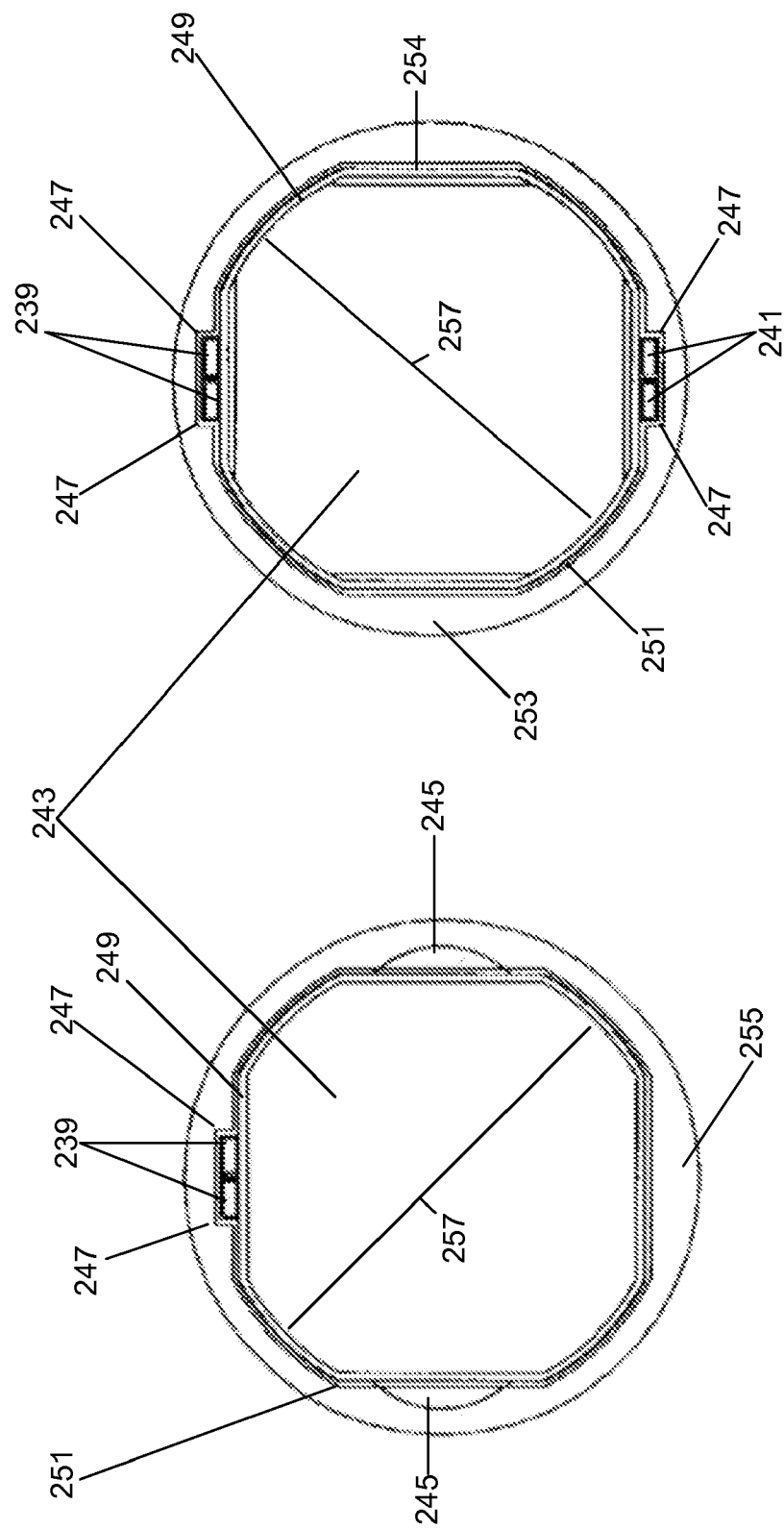

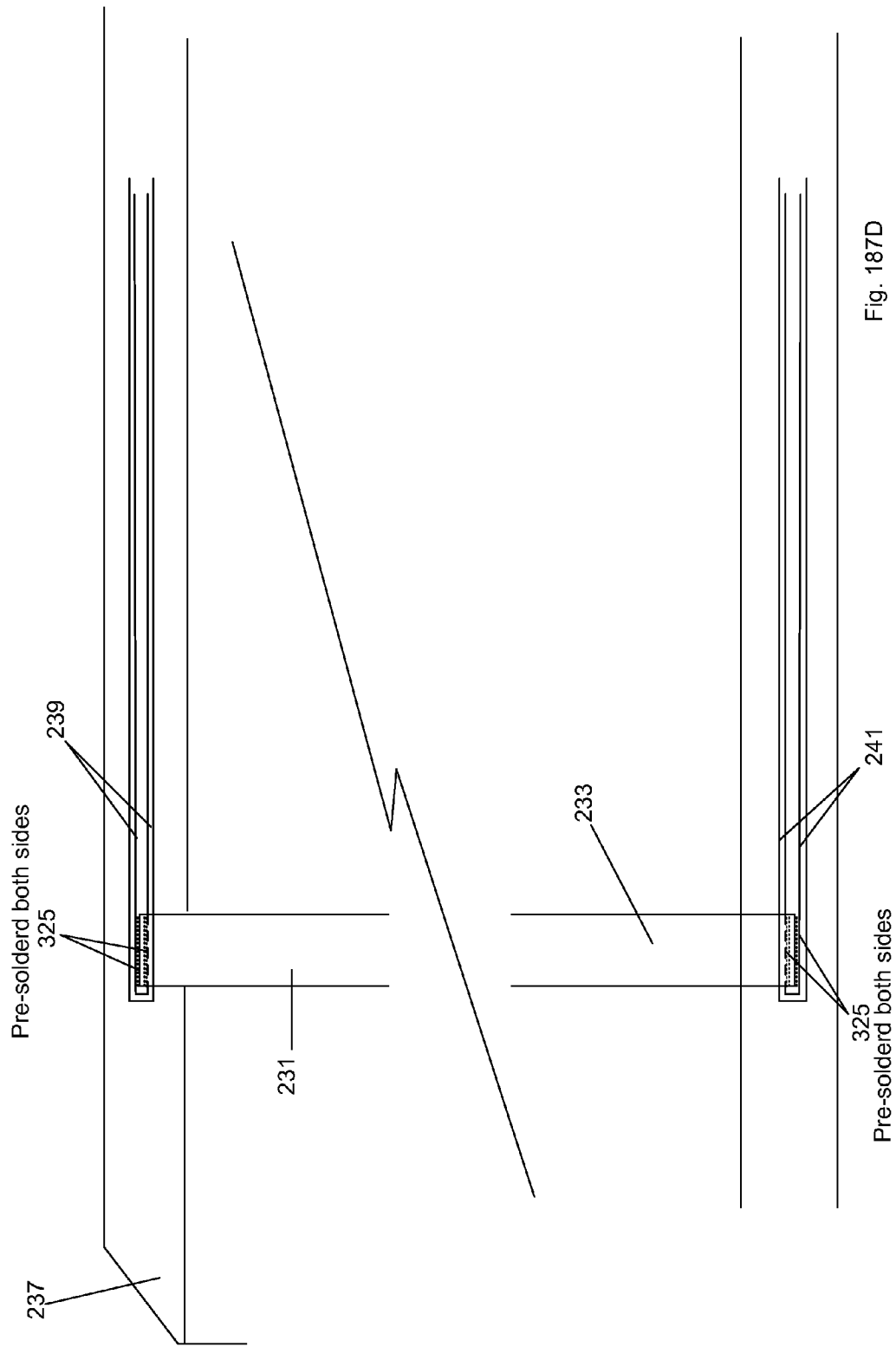

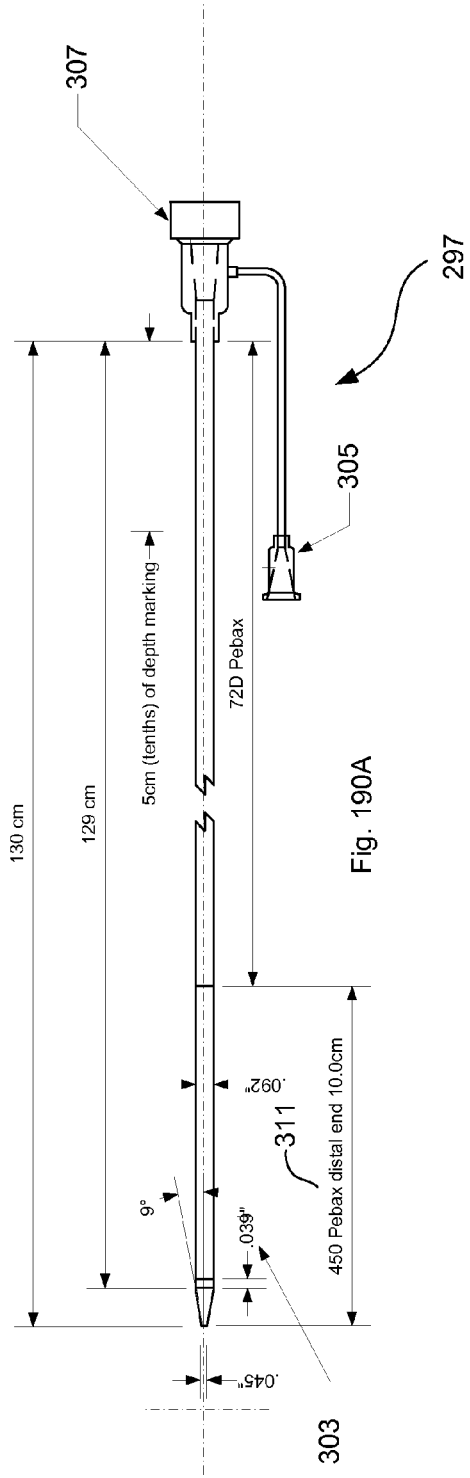
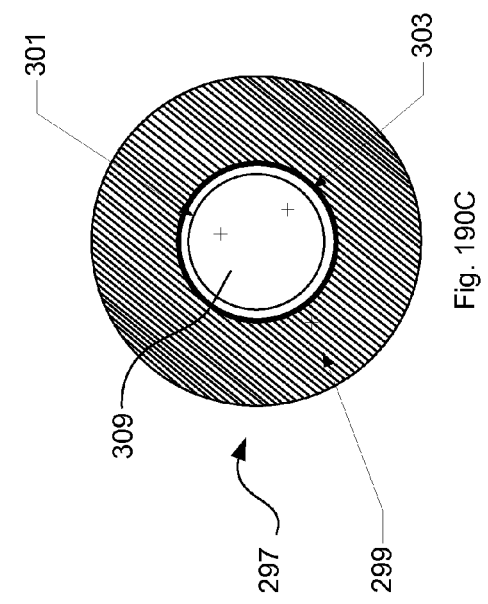
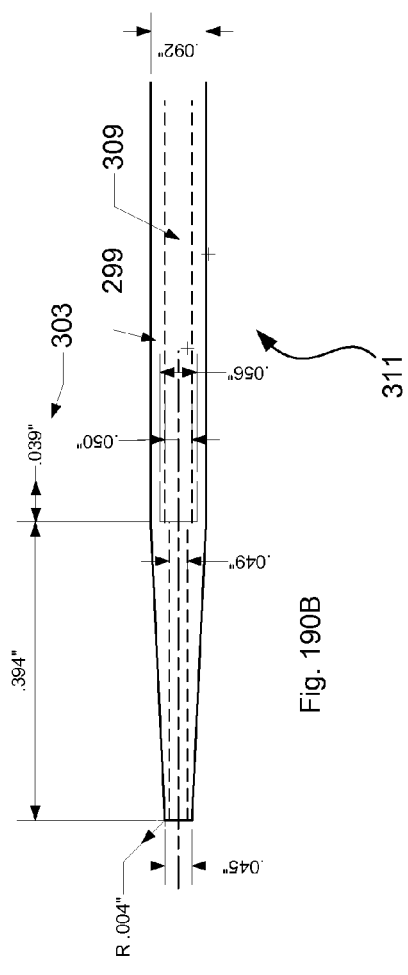
Fig. 190A
Fig. 190B
Fig. 190C

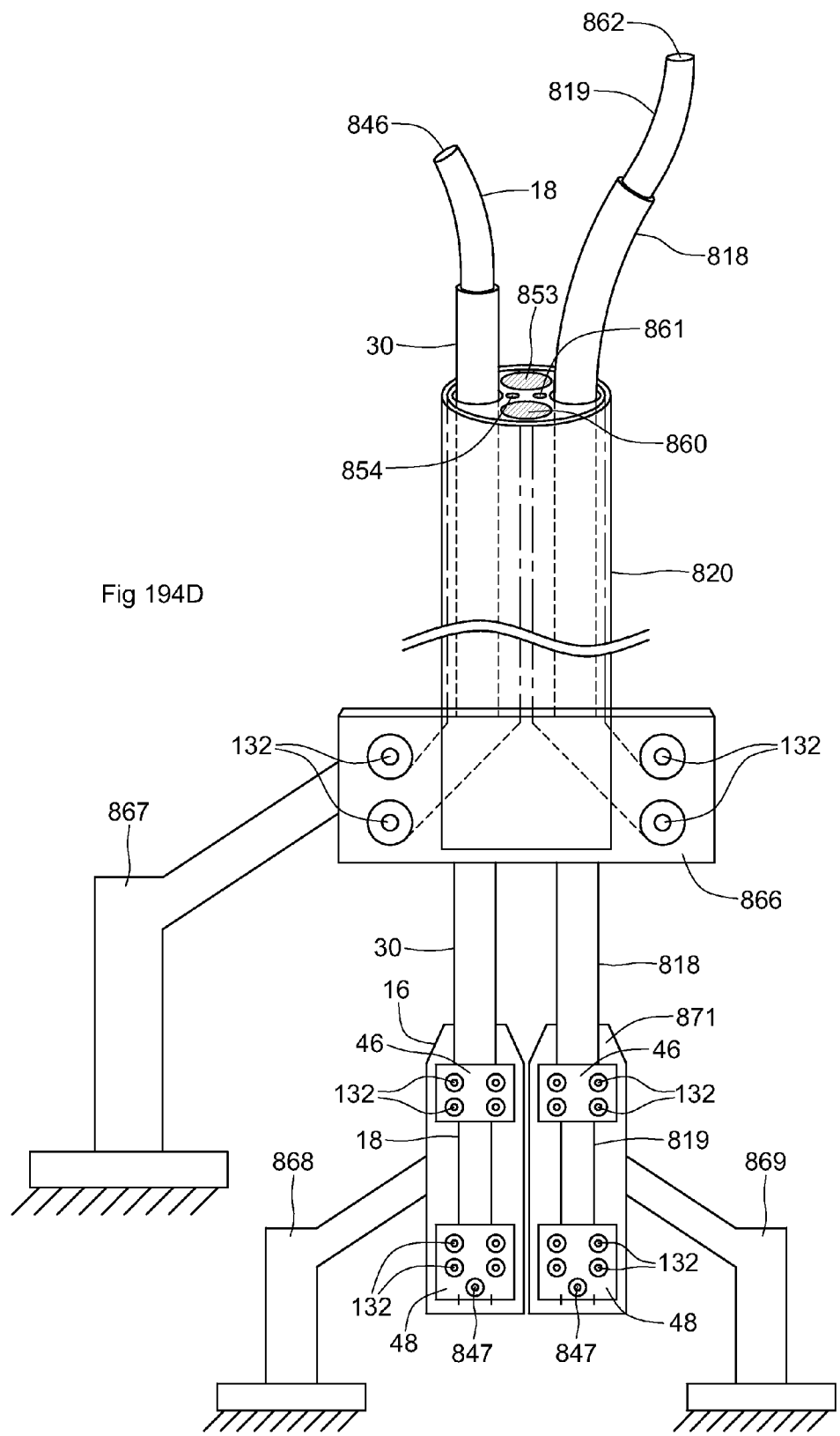

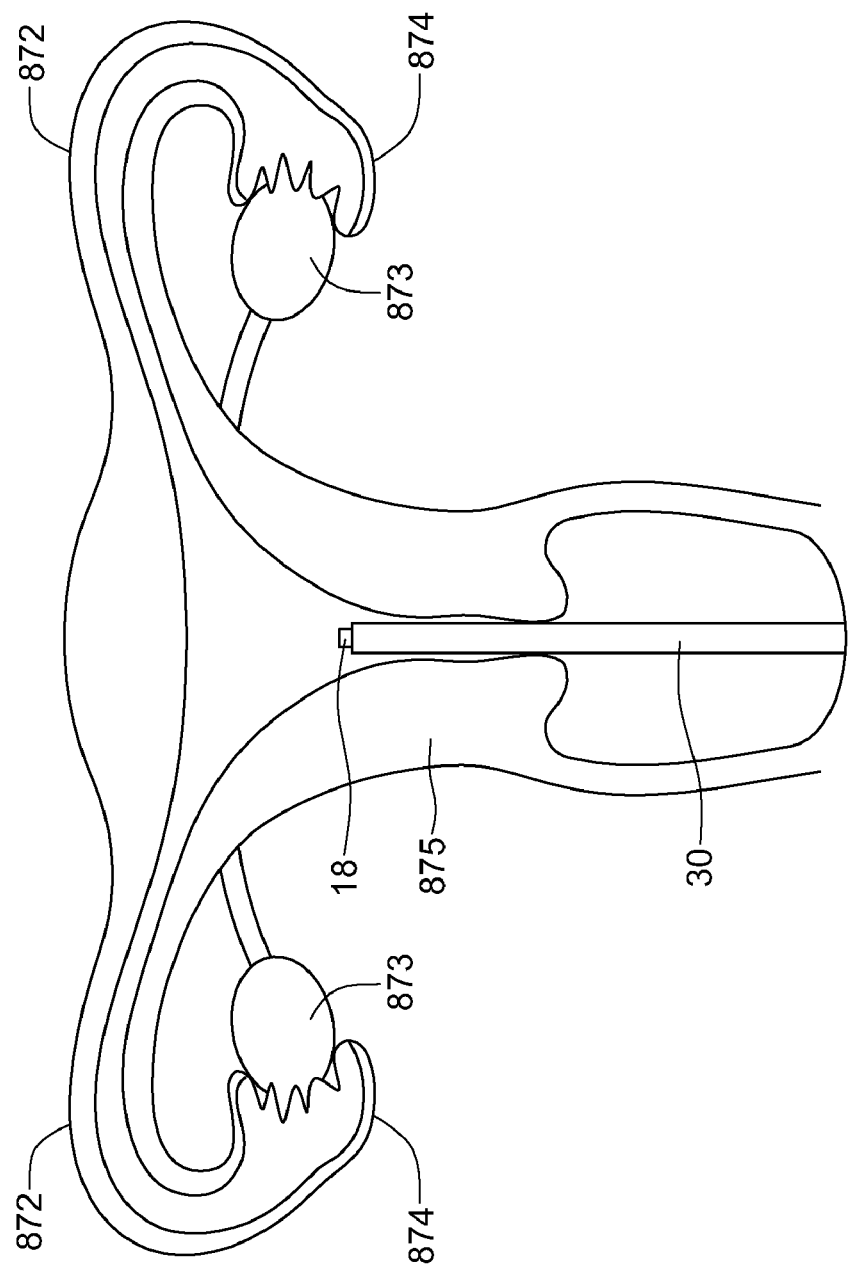

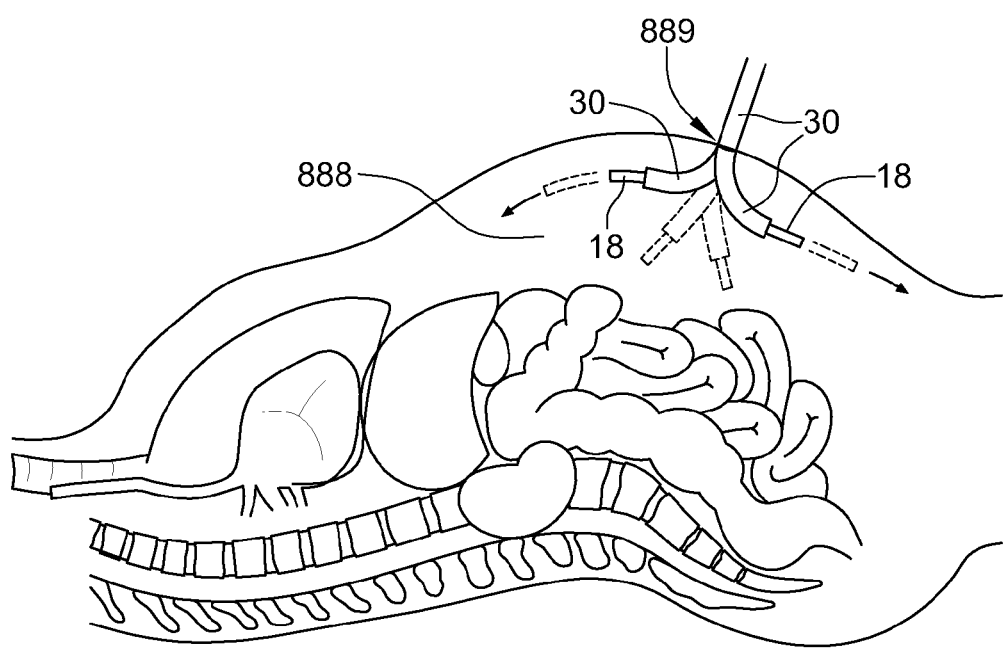
Fig. 203.5A

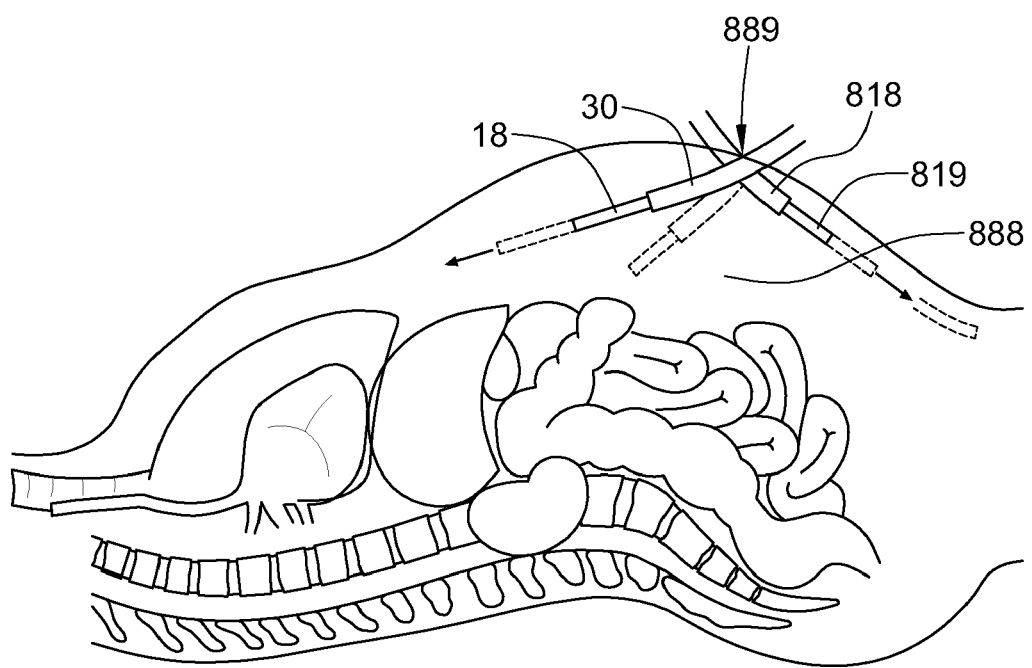
Fig. 203.5B

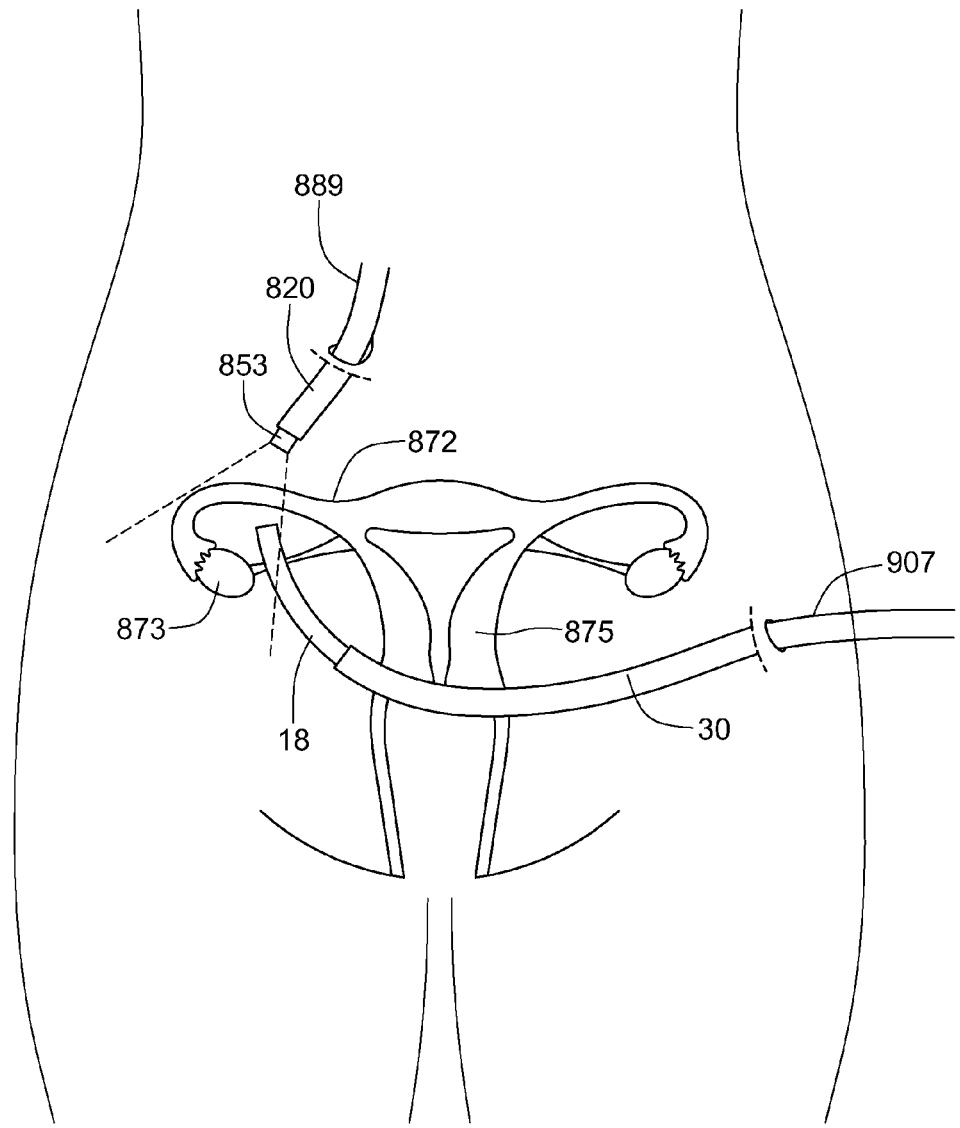
Fig. 204.5A

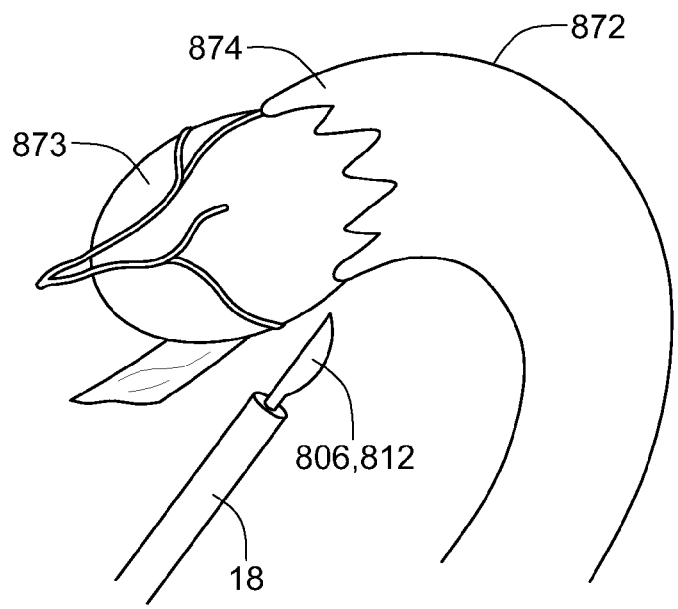
Fig. 204.5B
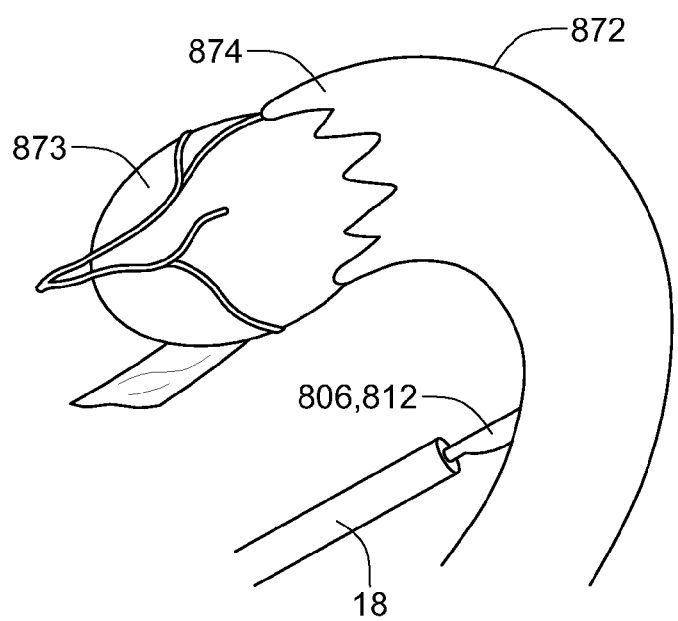
Fig. 204.5C

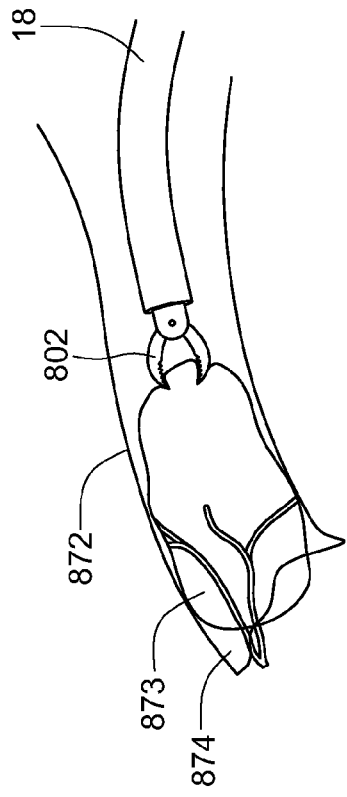
Fig 204.5E
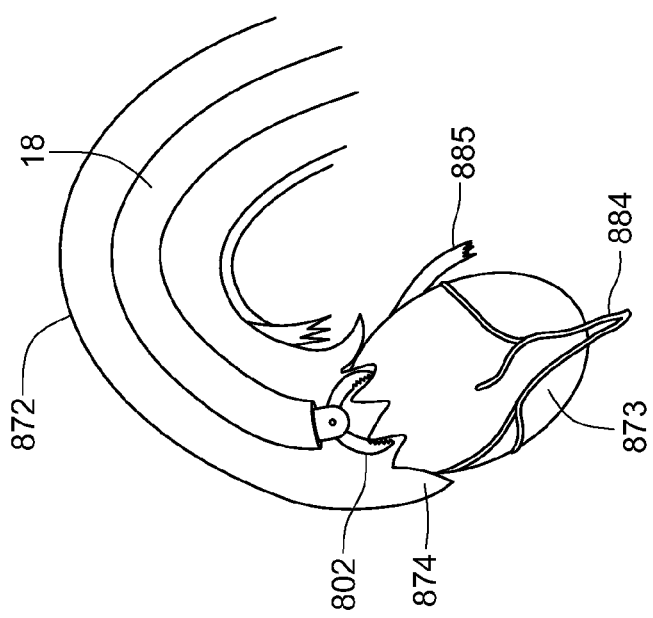
Fig 204.5D

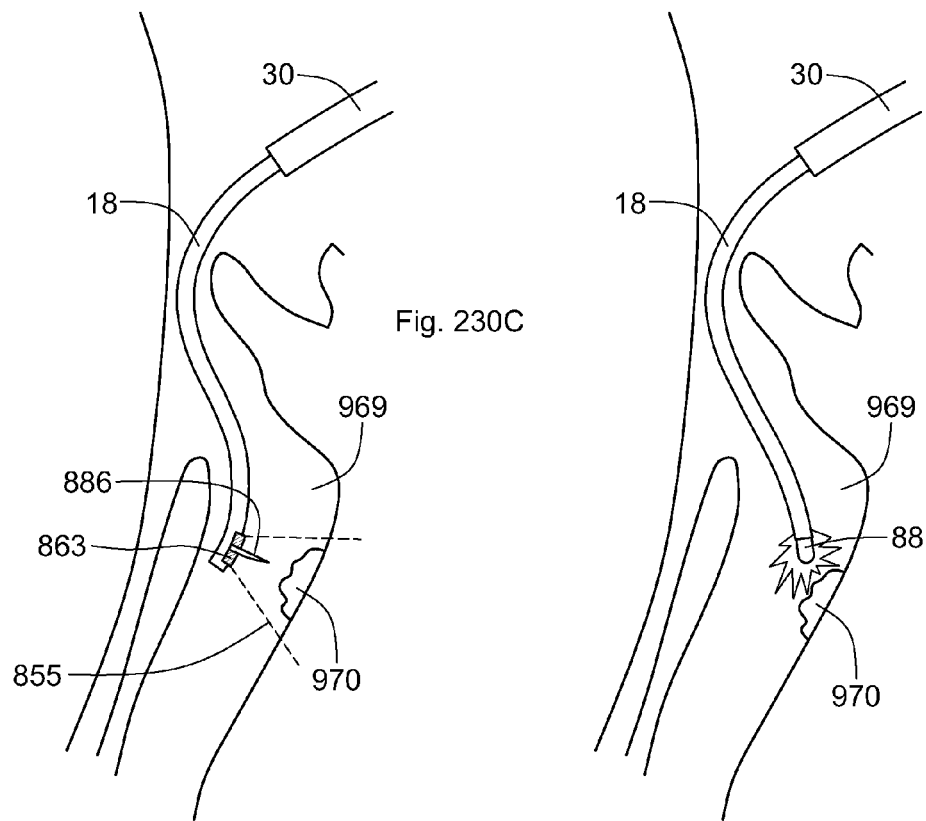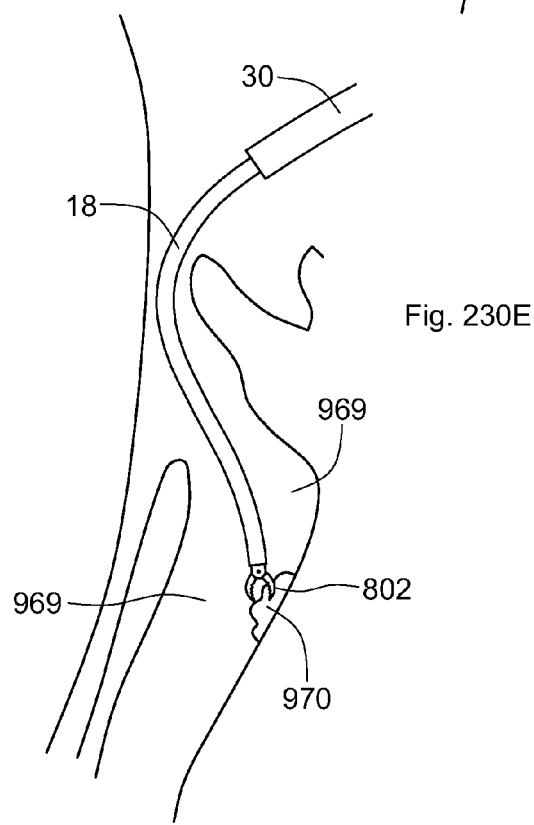

ROBOTIC CATHETER SYSTEM AND METHODS

RELATED APPLICATION DATA

The present application is a continuation of pending U.S. patent application Ser. No. 11/481,433, filed Jul. 3, 2006, which claims the benefit under 35 U.S.C. §119 to U.S. Provisional Patent Application Ser. Nos. 60/695,947, filed Jul. 1, 2005, and 60/698,171, filed Jul. 11, 2005. The foregoing applications, along with U.S. application Ser. No. 11/073,363, filed on Mar. 4, 2005, are hereby incorporated by reference into the present application in their entirety

FIELD OF INVENTION

The invention relates generally to robotically controlled systems, such as telerobotic surgical systems, and more particularly to a robotic catheter system for performing minimally invasive diagnostic and therapeutic procedures.

BACKGROUND

Robotic interventional systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be accessed via naturally-occurring pathways such as blood vessels or other lumens, via surgically-created wounds of minimized size, or both.

BRIEF DESCRIPTION OF THE DRAWINGS

The drawings illustrate the design and utility of illustrated embodiments of the invention, in which similar elements are referred to by common reference numerals, and in which:

FIG. 2.1 illustrates the operator control station of one embodiment;

FIG. 2.2 illustrates a reverse view of the operator control station of FIG. 2.1;

FIG. 3 illustrates a closer view of a support assembly;

FIGS. 3.1-3.10B illustrate various components of the support assembly in accordance to one embodiment;

FIGS. 9-16 illustrate various embodiments of draping schemas;

FIGS. 103.1-103.11 illustrate various aspects of the instrument driver of another embodiment;

FIGS. 106A-109B illustrate the kinematics for a catheter of one embodiment;

FIG. 111 illustrates one embodiment of a controls system flow;

FIG. 125 illustrates the kinematics of one embodiment;

FIG. 128 illustrates a block diagram of system with a master input device;

FIG. 129 illustrates a sample flowchart of transforming a position vector to a haptic signal;

FIG. 130 illustrates a block diagram of a system including haptics capability;

FIGS. 140-148C illustrate various aspects of another embodiment for acquiring and compiling a tissue structure image;

FIGS. 161-172 illustrate a myocardial ablation procedure in accordance with one embodiment of the present invention;

FIGS. 173A-D illustrate electrode configurations for various embodiments;

FIGS. 174A-D illustrate tip options for other embodiments of working instruments;

FIGS. 187A-191C illustrate several embodiments of instruments;

FIGS. 190A-C illustrate one embodiment of a dilator;

FIGS. 191A-C illustrate a needle of one embodiment;

FIGS. 194A, 194B, 194C, and 194D illustrate embodiments of sheath/guide combinations coaxially positioned within larger instruments;

FIGS. 195A-195F illustrate one example of a system of coaxially positioned, steerable guide and sheath instruments being advanced into a uterus during a transvaginal intervention procedure;

FIGS. 203.5A-203.5B illustrate an exemplary system and procedure wherein steerable sheath and guide instruments are inserted into a patient's insufflated cavity through the umbilicus;

FIGS. 204.5A-204.5E illustrate an exemplary laparoscopic oophorectomy system and procedure wherein part of the procedure is conducted through various laparoscopic ports with one embodiment of a robotic catheter platform;

FIGS. 230A-230E illustrate various embodiments of larynx intervention systems and procedures using a flexible, steerable instrument assembly;

DETAILED DESCRIPTION

Figure 1:
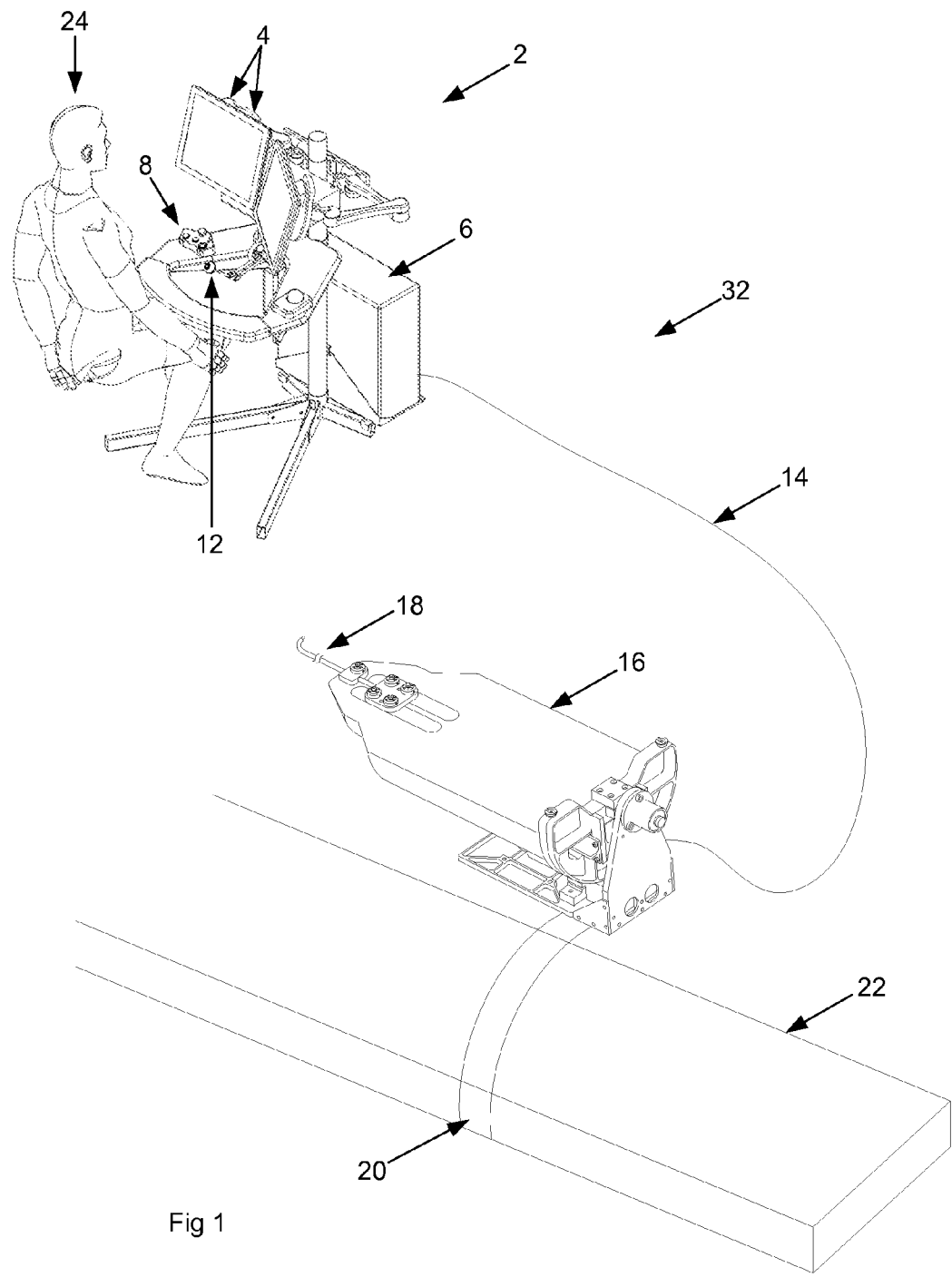
FIG. 1 illustrates one embodiment of a robotic catheter system.

Referring to FIG. 1, one embodiment of a robotic catheter system (32), includes an operator control station (2) located remotely from an operating table (22), to which a instrument driver (16) and instrument (18) are coupled by a instrument driver mounting brace (20). A communication link (14) transfers signals between the operator control station (2) and instrument driver (16). The instrument driver mounting brace (20) of the depicted embodiment is a relatively simple, arcuate-shaped structural member configured to position the instrument driver (16) above a patient (not shown) lying on the table (22).

Figure 2:
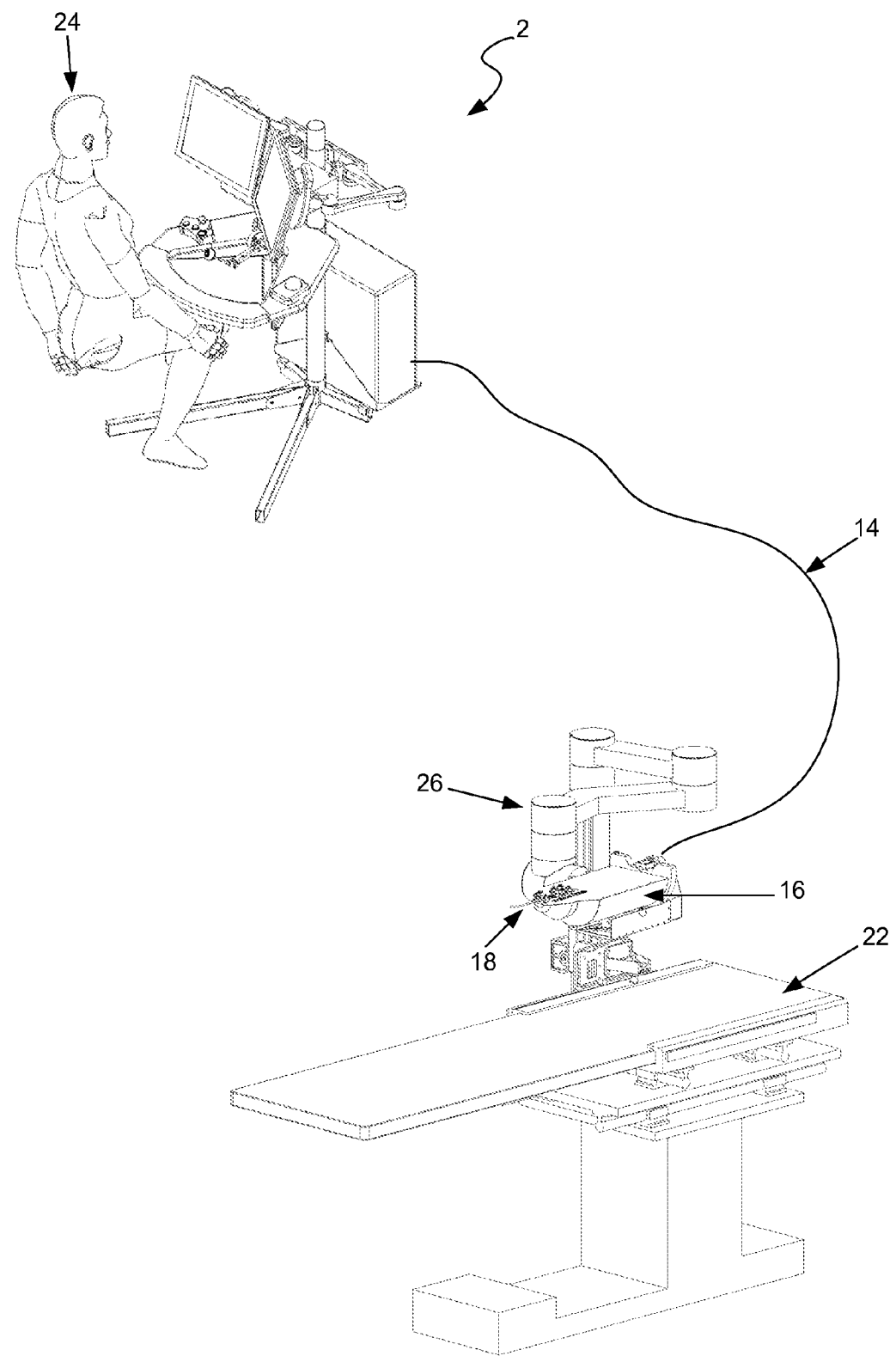
FIG. 2 illustrates another embodiment of a robotic catheter system.

In FIG. 2, another embodiment of a robotic catheter system is depicted, wherein the arcuate-shaped member (20) is replaced by a movable support-arm assembly (26). The support assembly (26) is configured to movably support the instrument driver (16) above the operating table (22) in order to position the instrument driver (16) for convenient access into desired locations relative to a patient (not shown). The support assembly (26) in FIG. 2 is also configured to lock the instrument driver 16 into position once it is positioned.

Referring to FIG. 2.1, a view of another variation of an operator control station (2) is depicted having three displays (4), a touchscreen user interface (5), and a control button console (8). The master input device (12) depicted in the embodiment of FIG. 2.1 is depicted and described in further detail in reference to FIG. 105B. Also depicted in the embodiment of FIG. 2.1 is a device disabling switch (7) configured to disable activity of the instrument temporarily. The cart (9) depicted in FIG. 2.1 is configured for easy movability within the operating room or catheter lab, one advantage of which is location of the operator control station (2) away from radiation sources, thereby decreasing radiation dosage to the operator. FIG. 2.2 depicts a reverse view of the embodiment depicted in FIG. 2.1.

FIG. 3 provides a closer view of the support assembly (26) depicted in the embodiment of FIG. 2.1. The support assembly (26) comprises a series of rigid links (36) coupled by electronically braked joints (34). The joints (34) allow motion of the links (36) when energized by a control system (not shown), but otherwise prevent motion of the links. The control system may be activated by a switch (e.g., a footswitch or thumb switch), or computer interface. In another embodiment, the rigid links (36) may be coupled by mechanically lockable joints, which may be locked and unlocked manually using, for example, locking pins, screws, or clamps. The rigid links (36) preferably comprise a light but strong material, such as high-gage aluminum, shaped to withstand the stresses and strains associated with precisely maintaining a three-dimensional position of the approximately ten pound weight of a typical embodiment of the instrument driver (16) once the position of the link (36) is fixed.

FIGS. 3.1-3.10B depict another embodiment of the support assembly (26). Referring to FIGS. 3.1 and 3.2, in this embodiment, a mechanical operating table interface (1) includes a pair of clamp members (89) to removably attach the support assembly (26) to the operating table (22) (shown in phantom outline). As explained in greater detail in conjunction with FIG. 3.3, the clamp members (89) include a lower clamp toe configured to pivot outwards for ease in engaging a rail (not shown) on an edge of the operating table (22).

The main body of the mechanical interface (1) is fixed to the housing of a solenoid and brake unit (3). A proximal base of an arcuate, vertical extension member (11) is coupled to, and selectively rotatable about a central axis of, the solenoid and brake unit (3). The vertical extension member (11) bends through an angle of approximately 90°, and has a distal end rotatably coupled, via a pan-rotate interface (13), to a first end of a further proximal extension member (15). As explained in greater detail in conjunction with FIG. 3.6, the pan-rotate interface (13) selectively allows extension member (15) to both rotate about an axis of a distal extending shaft (55) (seen in FIG. 3.2), as well as pan laterally along an arc defined by lateral movement of the shaft (55) through a pan slot (111) defined by the housing (121) of the pan-rotate interface (13) in a plane that is preferably parallel to a plane defined by the operating table.

A distal brake unit (19) is coupled to a sprocket comprising the second end of extension member (15), the sprocket being rotatably coupled to the housing of the extension member (15), as described in further detail below. The brake unit (19) is configured for selectively allowing rotation of an instrument driver support shaft (17) relative to the brake unit (19), the support shaft (17) carrying a pivotable instrument driver mounting interface (21) for attaching the instrument driver (not shown). The support shaft (17) further includes a handle portion (23), which has a button (24) for electronically actuating the respective electronic brake and solenoid in unit (3), as well as the distal brake (19), to thereby allow the aforedescribed motions of the various components of the support assembly (26). Cable holder brackets (113) are provided along the exterior of the support shaft (17), pan-rotate interface (13), and solenoid and brake unit (3), respectively, for attaching a power/control cable from the instrument driver (not shown). One a more control cables (not seen) also extend internally within the various components of the support assembly (26) from the distal end button (24) to the distal brake (19) and to the solenoid and brake unit (3).

The support assembly (26) is configured to facilitate easy positioning and repositioning of a remotely controlled instrument driver over the operating table (22). When the button (24) on the handle portion (23) is depressed, the respective electronic brakes and solenoid of the assembly (26) allow the respective interfaces to move freely relative to each other, constrained only by the interface configurations, to allow for repositioning of the handle (23) and associated instrument driver support shaft (17) relative to the operating table (22). When the button (24) is not depressed, the respective brakes prevent any further movement of the support shaft (17), wherein the support assembly (26) is configured to provide a high level of mechanical stability. In one embodiment, upon activation of the solenoid and release of the brakes, the distal brake unit (19) is configured to allow an approximately 135 degree range of motion about the rotational axis (125) of the brake unit (19), the pan-rotate interface (13) is configured to allow an approximately 140 degree range of motion rotation about the rotational axis of the shaft (55) as well as approximately 110 degrees of pan rotational motion through the plane defined by the pan slot (111), and the vertical extension member (11) is configured to allow an approximately 350 degree range of rotational motion relative to the solenoid and brake unit (3), which is configured to be coupled to an operating table.

As shown in FIG. 3.3, the mounting clamps (89) each generally comprise a fixed body portion (33) having a mating surface (101), and upper and lower clamp toe portions (115, 99) configured for attachably coupling to a rail (not shown) disposed on an edge of the operating table (22). The lower clamp toe portion (99) is preferably fastened to the swinging clamp body portion (29), with a threaded locking member (25) used to tighten/loosen the lower clamp toe portion (99) against the rail to secure/release the clamp (89) thereto or therefrom. For ease in loading the assembly (26) onto an operating table rail, the mating surface (101) of the fixed clamp body portion (33) is indented to seat a fulcrum rod (27) that rides against a side of the rail, and the swinging clamp body portions (29) of the clamps (89) may be individually pivoted (95) about the pin member (31) to rotate away from the operating table rail (not shown) to facilitate extending the upper clamp toe member (115) onto the rail with easy access to the mating surface (101). In the depicted embodiment, the swinging clamp toe bodies (29) are spring (97) biased to rotate (95) in this manner until the mating surface (101) has been positioned against the operating table rail (not shown), subsequent to which the swinging clamp toe bodies (29) may be manually rotated about the pin (31) and wound into position interfacing with the operating table rail (not shown) with the threaded locking member (25), as depicted in FIG. 3.3.

Referring to FIG. 3.4, the solenoid and brake unit (3) comprises an outer housing (103) and an inner member (45) that is rotatably mounted within the housing (103). The inner member (45) includes a distal facing surface (117), configured to receive a proximal mounting interface (94) of the vertical extension member (11) (see FIG. 3.2). In this manner, the extension member (11) (see FIG. 3.2) is rotatable about a longitudinal axis (119) of the solenoid and brake unit (3). A brake assembly (39) is biased to prevent rotation of member (45), and thus of extension arm (11), unless electronically actuated to release the member (45). In FIG. 3.5, the brake (39) is depicted, along with a flex-disk interface (49) and a clamp (47), which couples firmly to the rotatable frame member (45). The flex-disk interface (49) allows for some axial movement between the clamp (47) and the brake (39), without significant rotational slop commonly associated with more conventional spline interfaces. Thus, manual rotation of the vertical arm (11) about an axis which may be substantially orthogonal to the operating table (22) (i.e., for positioning an instrument driver (16) mounted on the support shaft (17) relative to a patient positioned on the operating table (22)) is selectively allowed by electronic activation of the brake (39) when the button (24) is depressed into the handle (23).

Referring back to FIG. 3.4, a top end of the solenoid and brake unit (3) includes a plunger (41), that is biased by a set of helical springs (43) to push away from the housing (103) of the solenoid and brake unit (3), into an interior bore of the extension member (11). When a solenoid (35) located in a lower portion of the housing (103) is electronically activated, it pulls a pull-rod (37), which in turn pulls the plunger (41), in a compressive direction against the springs (43), toward the housing (103) of the solenoid and brake unit (3).

As shown in FIG. 3.6, the vertical extension member (11) has a hollow interior to accommodate an arcuate lever (57) configured to compress and lock into place the pan-rotate interface (13) when rotated counterclockwise about a pivot pin (61) within, and relative to, the vertical extension member (11) as the plunger (41) (see FIG. 3.4) is pushed upward away from the housing (103) (see FIG. 3.4) by the spring (43) load. With the plunger (41) pushed upward, the ball (53) is placed into compression between the toe (130) of the arcuate lever (57) and a contoured surface (131) coupled to the base of the pan-rotate interface (13) housing (121). The ball (53), contoured surface (131) and bearings (63) mounted upon the shaft (55) preferably are configured to place substantially all of the applied compressive load upon the ball (53) and not the bearings (63). When the plunger (41) is pulled downward by the activated solenoid (35), the load previously applied by the plunger (41) to the wheelset (59) at the end of the arcuate lever (57) is released and gravity pulls the arcuate lever (57) into clockwise rotation about the pivot pin (61), thus substantially releasing the compressive loads that lock into the place the pan-rotate interface (13) and allowing panning and rotation of the shaft (55). The pan-rotate interface (13) includes a ball (53) and shaft (55) construct (collectively indicated with reference (51)), that, in one embodiment, is configured to provide a 15:1 leverage ratio for loads applied by the plunger (41) at a wheel set (59) housed in the extension member (11) and coupled to the proximal end of the arcuate lever (57).

Referring to FIG. 3.7, the ball/shaft interface (51) comprises bearings (63) to facilitate stable panning rotation, as well as rotation of an associated structure about the longitudinal axis of the shaft (55). The ball (53) preferably is greased to facilitate smooth panning and rotation when not compressibly locked into position. The bearings facilitate lateral panning of the shaft member (55) about a plane formed by the pan-rotate interface (13), which causes the bearings (63) to rotate on a planar annulus about the center of the ball (53). The result is constrained motion in two different degrees of freedom: lateral panning as per the planar annulus and bearing interface, and rotation about the axis of the shaft (55). The bias force of the springs (43) on the plunger (41) extending from the solenoid housing (103) normally lock the ball/shaft interface (51) into place, preventing either panning or rotation motion at the interface. Electronic activation of the solenoid withdraws the pull-rod and, by extension, plunger (41) away from the wheel set (59), thereby unloading the significant compressive forces that otherwise keep the ball (53) locked into place, allowing for panning/rotation.

Referring also back to FIG. 3.2, the shaft (55) protrudes through a horizontal pan slot (111) located in a distal face (123) of the housing (121) covering the pan-rotate interface (13). The pan slot (111) constrains the horizontal panning motion of the shaft (55), and by extension, the proximal extension member (15) in a plane that may be substantially parallel to the operating table within the range of motion defined by the boundaries of the slot (111).

Referring to FIG. 3.8, the shaft (55) is coupled to a proximal sprocket (75) of the horizontal extension member (15) using a conventional interference fit, such as a "number 3 Morse taper." The proximal sprocket (75) is coupled to a distal sprocket (74) by a timing chain (73), so that rotation of the shaft (55) correspondingly rotates both sprockets (74, 75), preferably with a 1:1 ratio of rotational movement, resulting in the same rotational displacement at each of the sprockets. Rotational movement of the proximal sprocket (75), caused by fixing the relative rotational position of the proximal sprocket (75) relative to the distal face 123 of the pan rotate interface (13) housing (121) with a key member (105) fitted into key slots (77, 109) defined by the distal sprocket (74) and pan rotate interface (13) housing (121), causes rotation of a pin (65), which in turn causes tension via a linkage (67), proximal linkage base (71), and distal linkage base (69), respectively, to a set of gas tension springs (79) configured to constrain the rotational motion of the sprockets (74, 75), and thus, of the shaft (55). The position (107) of the key member (105) is depicted in FIG. 3.2. Given this configuration, with the solenoid (35) activated and the pan-rotate interface (13) free to move, the timing chain (73) and sprocket (74, 75) configuration within the horizontal extension member (15) is configured to maintain the relative planar positioning of the most distal hardware of the system relative to the plane of the operating table. This is important because a robotic catheter driver (not shown; see FIGS. 3.10A-B, for example) may be mounted upon the instrument driver interface (21) and pulled around by the handle (23), with the solenoid activated and the brakes released, to rotate about the rotational axis (125) of the distal brake unit (19), to rotate about the axis (119) of the rotatable frame member (45) within the solenoid and brake unit housing (3), to rotate and pan about the pan-rotate interface (13) via connectivity of the horizontal extension member (15), all simultaneously, without substantially changing the planar orientation of the instrument driver interface (21) relative to the plane of the operating table (not shown). In other words, the axis of rotation (125) of the proximal extension (127) of the instrument driver support shaft (17) may be configured to always be oriented perpendicular to the plane of the operating table, by virtue of the timing chain and sprocket interfacing of the extension member (15). When electronically activated, the brake unit (19) allows rotational movement of the support shaft (17) about an axis of the proximal extension (127). When the brake is not electronically activated, such rotational movement of the support shaft (17) is prevented.

Referring to FIGS. 3.9A-B, the instrument driver support shaft (17) comprises an instrument driver mounting interface (21), and a biasing spring (80) configured to at least partially counterbalance the cantilevered load upon the instrument driver interface (21) caused by the weight of an instrument driver mounted upon it. The biasing spring (80) preferably is covered by a spring housing (85). A lead screw (81) is provided and configured to change the pitch of the instrument driver interface (21) relative to the support shaft (17) when a knob (83) is rotated.

Referring to FIGS. 3.10A-B, an instrument driver (16) fitted with a cover (129) is depicted mounted to the instrument driver interface (21). The cover (129) is configured to provide an additional barrier between the instrument driver which is covers and draping, liquids, vapors, and other substances that may be encountered during a procedure. Preferably the cover (129) comprises a polymer or metal material and is made with processes such as stereolithography, injection molding, or machining. Preferably the cover (129) may be snapped or fastened into place around the instrument driver with simple recessed screws, bolts, or other fasteners. Similar covers may be configured to cover instrument bases. As depicted in FIGS. 3.10A-B, the cantilevered mass of the covered instrument driver (16) creates a moment. Torsional loads associated with such moment are counteracted by the spring (not shown in FIGS. 3.10A-B—see biasing spring (80) of FIG. 3.9A) housed within the housing (85). This counteraction is configured to prevent binding of the knob (83) actuated lead screw (81) pitch control of the instrument driver interface (21).

In summary, a support assembly (26), or support structure, is configured to allow for easy repositioning of an instrument driver or other device relative to an operating table when an actuation button is depressed, thereby activating a solenoid and releasing two electronic brakes. The position of an instrument driver then may be easily fine-tuned, for example, or modified quickly and substantially to remove the instrument driver from the immediate area of a patient on an operating table for quick medical intervention with broad physical access. Constraints limit the movement of the instrument driver relative to the operating table—i.e., a pan-rotate interface (13), a horizontal extension member (15) with a rotational position maintaining timing chain (73) for distally-coupled structures, and brake-lockable rotations about two axes of rotation (125, 119) which may be parallel and both perpendicular relative to the plane of the operating table—to provide desirable mechanics. When an actuation button is not depressed and the structures are substantially locked into position relative to each other, with the exception of manually-activated lead screw pitch adjustment of an instrument driver interface (21), the support assembly (26) is configured to provide a robust structural platform upon which an instrument driver or other device may be positioned relative to an operating table.

Figure 4:
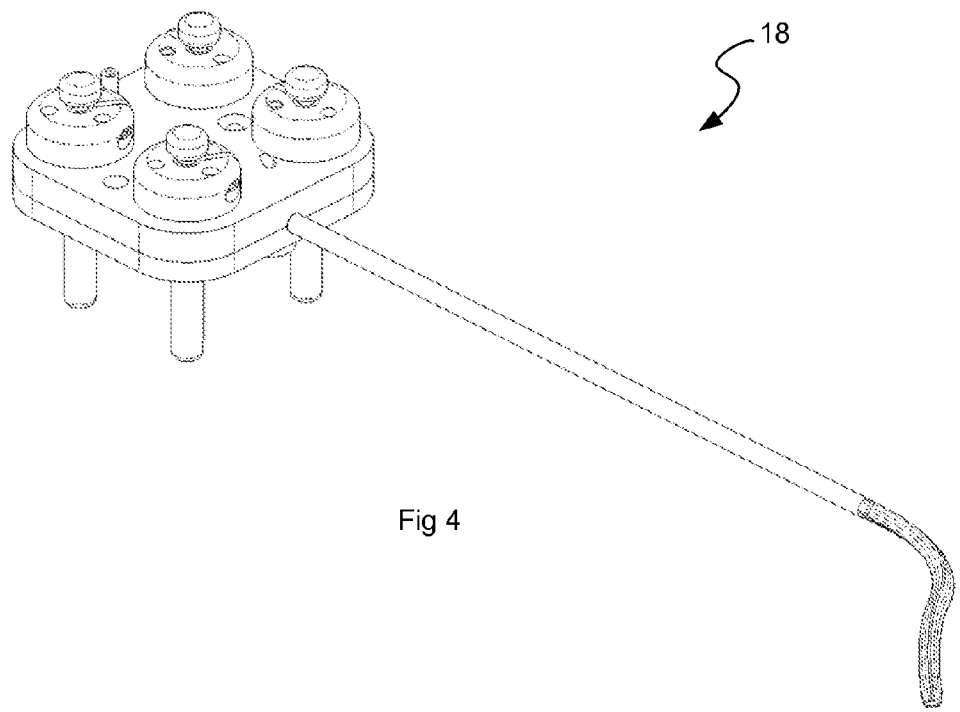
FIG. 4 illustrates an isometric view of an instrument for use with one embodiment of an instrument driver.
Figure 5:
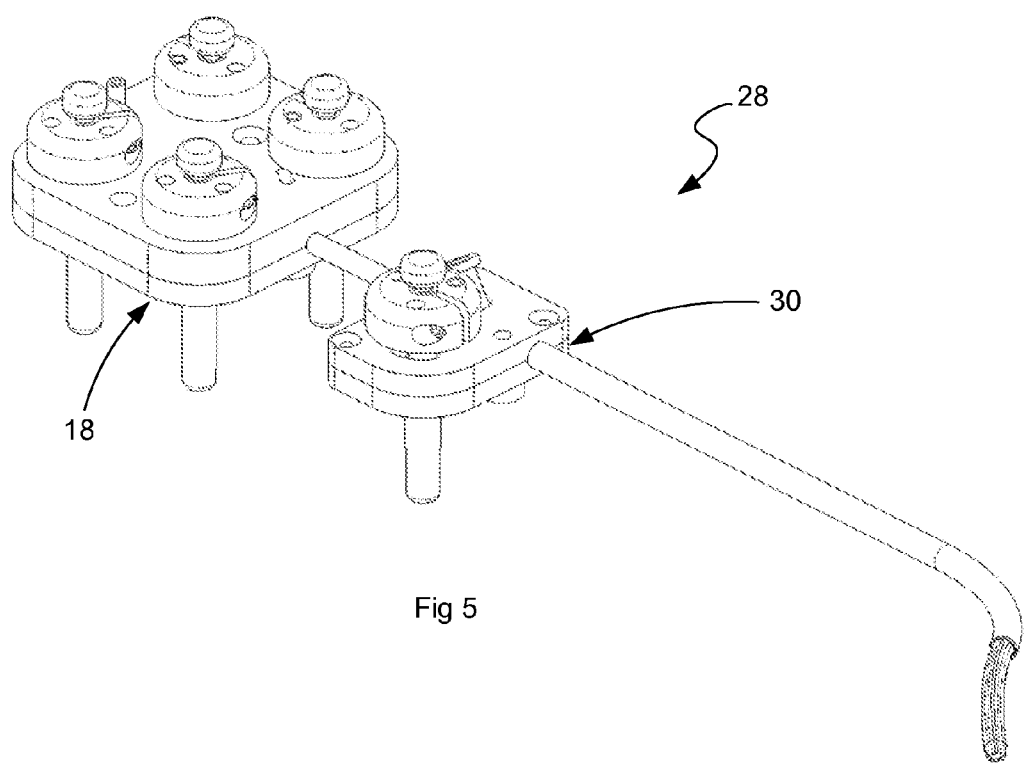
FIG. 5 illustrates an isometric view of two instruments.

FIGS. 4 and 5 depict isometric views of respective embodiments of instruments configured for use with an embodiment of the instrument driver (16), such as that depicted in FIGS. 1-3. FIG. 4 depicts an instrument (18) embodiment without an associated coaxial sheath coupled at its midsection. FIG. 5 depicts a set of two instruments (28), combining an embodiment like that of FIG. 4 with a coaxially coupled and independently controllable sheath instrument (30). To distinguish the non-sheath instrument (18) from the sheath instrument (30) in the context of this disclosure, the "non-sheath" instrument may also be termed the "guide" instrument (18).

Figure 6:
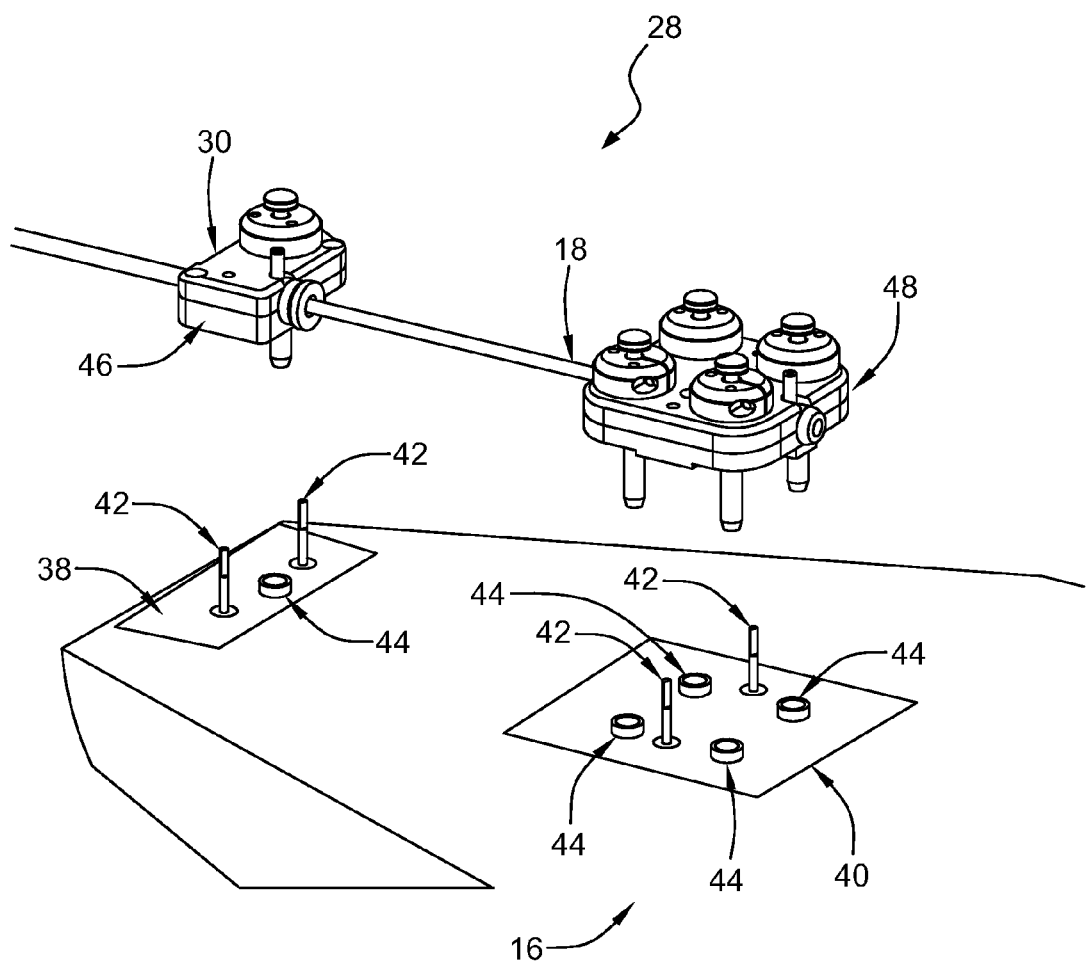
FIG. 6 illustrates an exemplary mounting scheme.

Referring to FIG. 6, a set of instruments (28), such as those in FIG. 5, is depicted adjacent an instrument driver (16) to illustrate an exemplary mounting scheme. The sheath instrument (30) may be coupled to the depicted instrument driver (16) at a sheath instrument interface surface (38) having two mounting pins (42) and one interface socket (44) by sliding the sheath instrument base (46) over the pins (42). Similarly, and preferably simultaneously, the guide instrument base (48) may be positioned upon the guide instrument interface surface (40) by aligning the two mounting pins (42) with alignment holes in the guide instrument base (48). As will be appreciated, further steps may be required to lock the instruments (18, 30) into place upon the instrument driver (16).

Figure 7A:
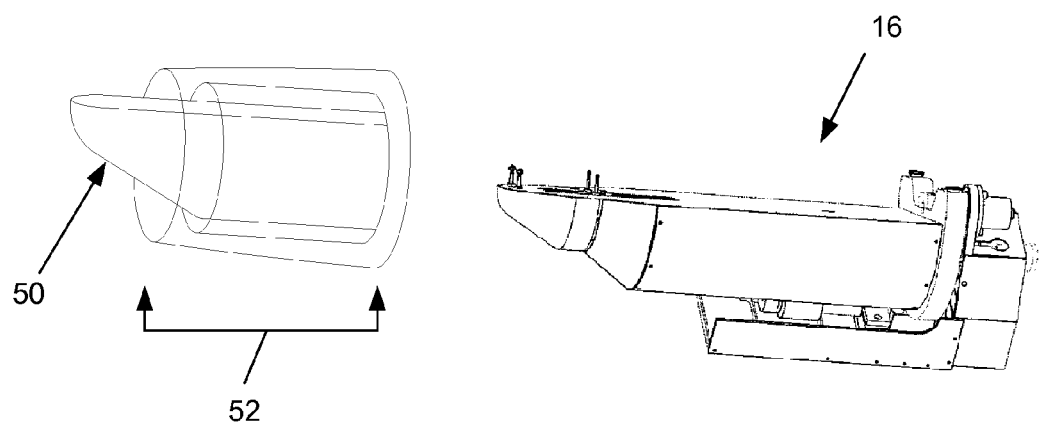
FIGS. 7A-C illustrate draping configurations of one embodiment.
Figure 7B:
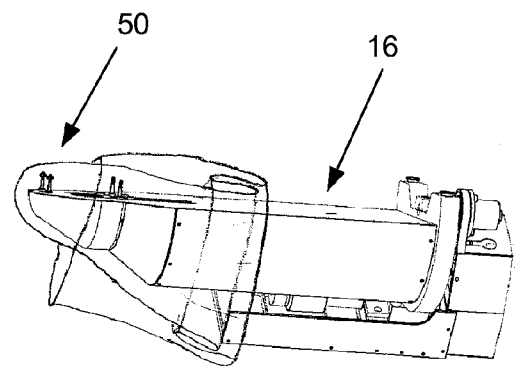
Figure 7C:
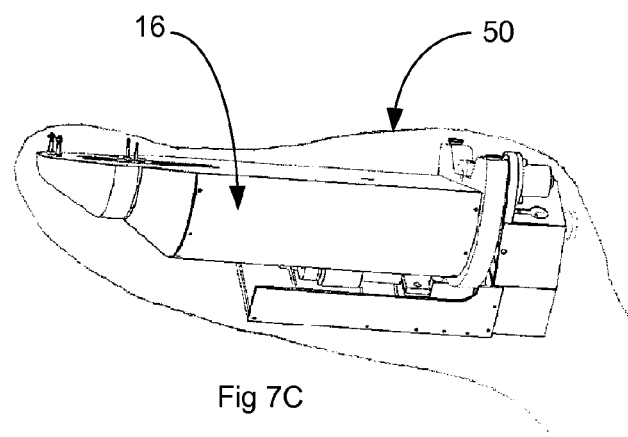

In one embodiment, the instruments (18, 30) are provided for a medical procedure in sterile packaging, while the instrument driver (16) is not necessarily sterile. In accordance with conventional sterile medical procedure, the non-sterile instrument driver (16) must be isolated from the patient by a sterile barrier of some type. Referring to FIGS. 7A-7C, a drape (50) comprising conventional surgical draping material may be folded into a configuration (52) to enable gloved hands of a person (not shown) to slide the drape (50) over the instrument driver (16), from one end to the other without contamination of the sterile side of the drape (50). The drape (50) is then unrolled around the instrument driver (16), as shown in FIGS. 7B-7C.

Figure 8A:
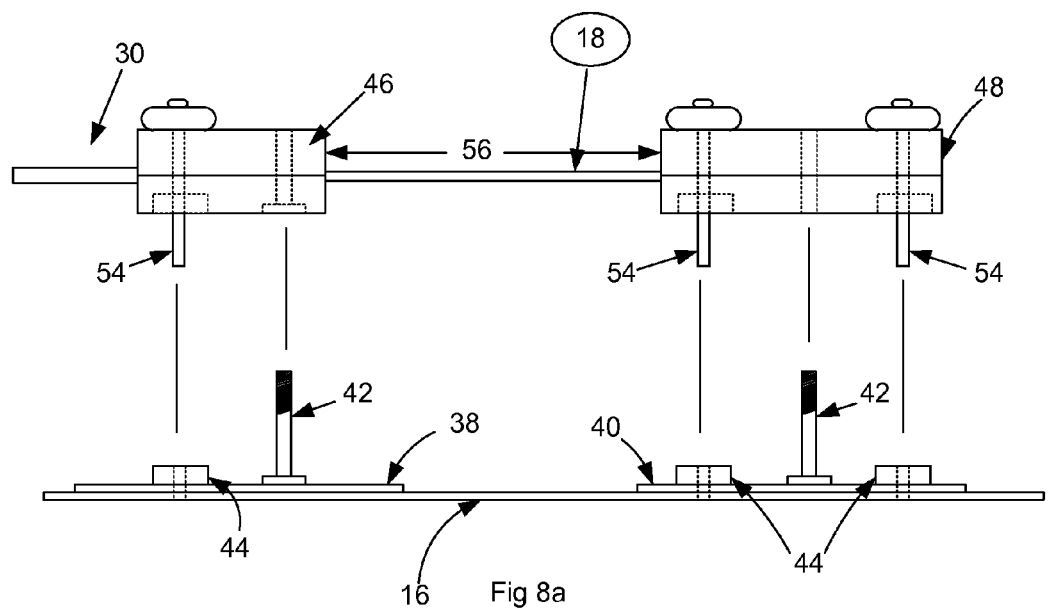
FIGS. 8A-B illustrate providing a sterile barrier in accordance to one embodiment.
Figure 8B:
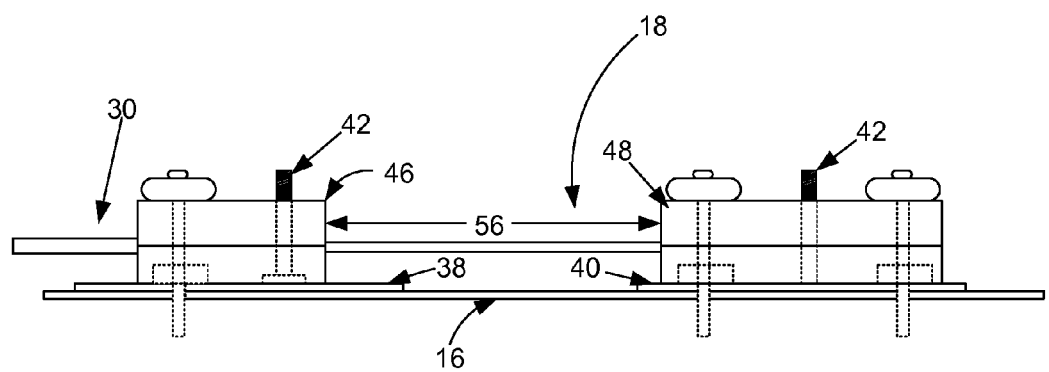

Referring to FIGS. 8A and 8B, the interfacing between instrument driver (16) and instrument bases (46, 48) utilizing alignment pins (42) is depicted to further illustrate the issues associated with providing a sterile barrier between the instruments and driver. In the illustrated embodiment(s), wherein the instrument is a set of two instruments comprising both a sheath instrument (30) and a guide instrument (18), the draping is preferably configured to accommodate relative motion (56) between the two instrument bases (46, 48). Further, the fit between the instrument bases (46, 48) and pertinent alignment pins (42) preferably is not loose and does not allow for relative motion. Similarly, the interface between axels (54) extending from the instruments and sockets (44) comprising the instrument driver (16) preferably is a precision interface.

Figure 9:
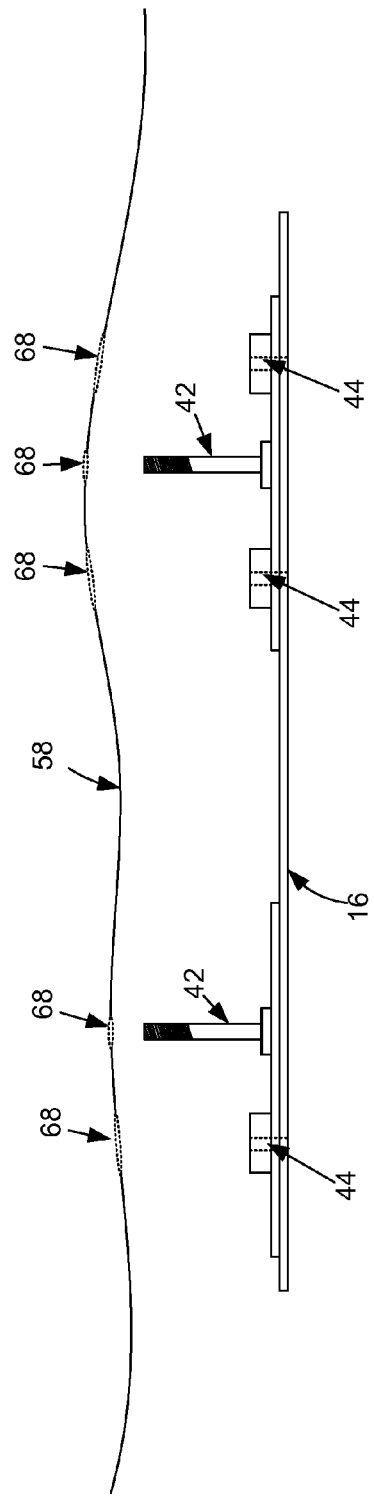

Referring to FIGS. 9-16, various embodiments of suitable draping schemas are depicted. As shown in FIG. 9, a perforated drape (58) may be utilized, wherein perforations (68) are sized to fit the alignment pins (42) and interface sockets (44). The perforated drape (58), preferably made from conventional draping materials, is simply aligned appropriately and pulled down upon the instrument driver (16).

Figure 10:
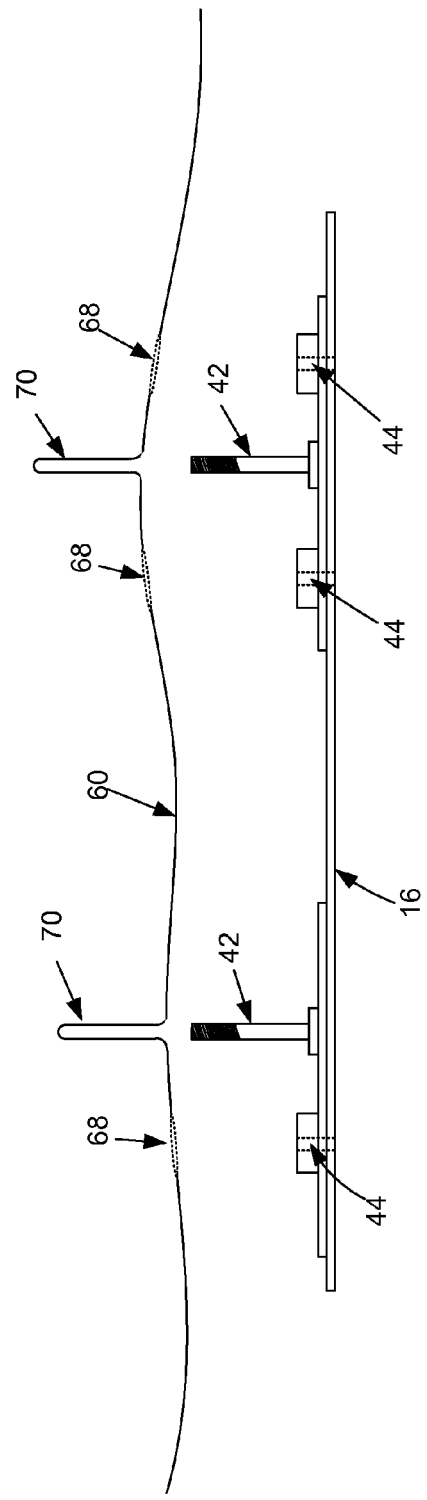

Referring to FIG. 10, a perforated drape with socks (60) may also be utilized. The depicted drape (60) has perforations (68) for the underlying interface sockets (44), but has socks (70), also formed from conventional draping material, which are sized to encapsulate the mounting pins (42) of the instrument driver (16).

Referring to FIG. 11, the depicted drape (62) may comprise "socks" (70) to engage the mounting pins (42), as with the drape in FIG. 10, but also have integrated plastic sleeves (64) rotatably coupled to the surrounding conventional drape material. The integrated plastic sleeves (64) are preferably precisely sized to engage both the interface sockets (44) of the instrument driver (16) and the axels (not shown) of an instrument. The sleeves (64) are preferably constructed of a sterilizable, semi-rigid plastic material, such as polypropylene or polyethylene, which has a relatively low coefficient of friction as compared with conventional drape material. To decrease rotational friction between the integrated plastic sleeves (64) and the surrounding drape material, perforations in the drape material through which the sleeves (64) are to be placed may be circumferentially lined with plastic collars (not shown), comprising a material having a low coefficient of friction relative to that of the integrated plastic sleeves (64).

Figure 13:
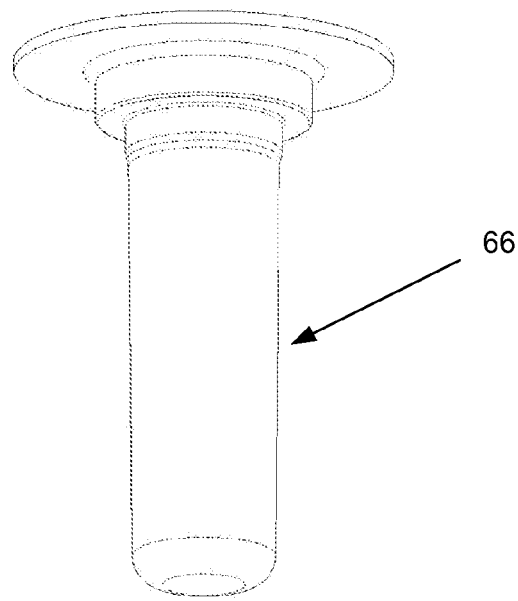
Figure 14:
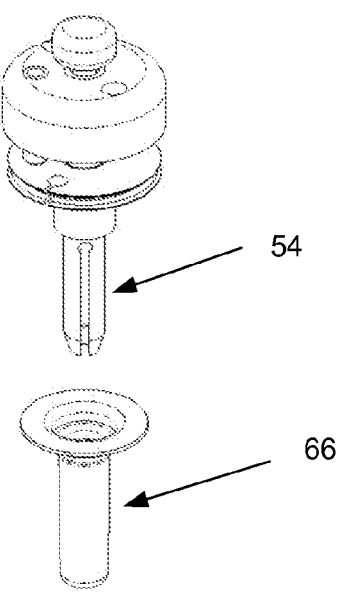

Referring to FIG. 12, an embodiment similar to that of FIG. 11 is depicted, with the exception that removable plastic sleeves (66) are not integrated into the drape, as delivered and unwrapped. Instead, the drape (60) may be delivered with perforations (68), circumferentially lined in one embodiment with plastic collars (not shown), positioned for convenient drop-in positioning of the sleeves (66). FIG. 13 is a close up view of a plastic sleeve (66) suitable, for example, in the embodiment of FIG. 12. The sleeve (66) may also be integrated into the embodiment depicted in FIG. 11. FIG. 14 illustrates that the inside of the sleeve (66) may be fitted to engage an axle (54) extending down from an instrument body.

Referring to FIG. 14.5, an alternative variation of a set of instruments (28) is depicted, wherein all of the parts with the exception of screws (91) and an axle (93) are comprised of polymeric materials such as polycarbonate or Delrin. As depicted in FIG. 14.5, each axle (93) forms a spline interface with the associated control elements pulley which carries an associated tension element.

Figure 15:
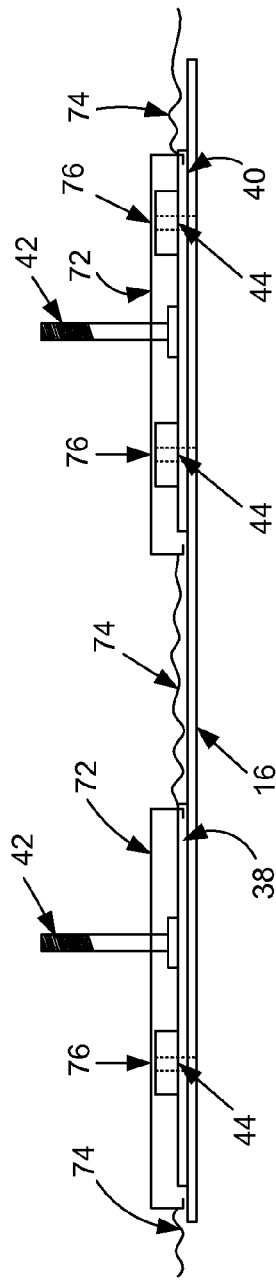

Referring to FIG. 15, another draping embodiment is depicted, wherein two semi-rigid covers or plates (72) are incorporated into a larger piece of conventional draping material. The covers (72) are configured to snap into position upon the sheath instrument interface surface (38) and guide instrument interface surface (40), fit over the mounting pins (42), and provide relatively high-tolerance access to the underlying interface sockets (44), with pre-drilled holes (76) fitted for the pertinent drive axle structures (not shown). Due to the anticipated relative motion between the two instrument interfaces, as previously described with reference to FIGS. 8A and 8B, it may be preferable to have elastic draping material or extra draping material bunched or bellowed in between the two interfaces, as shown in FIG. 15, and similarly applicable to the embodiments of FIGS. 9-14.

Figure 16:
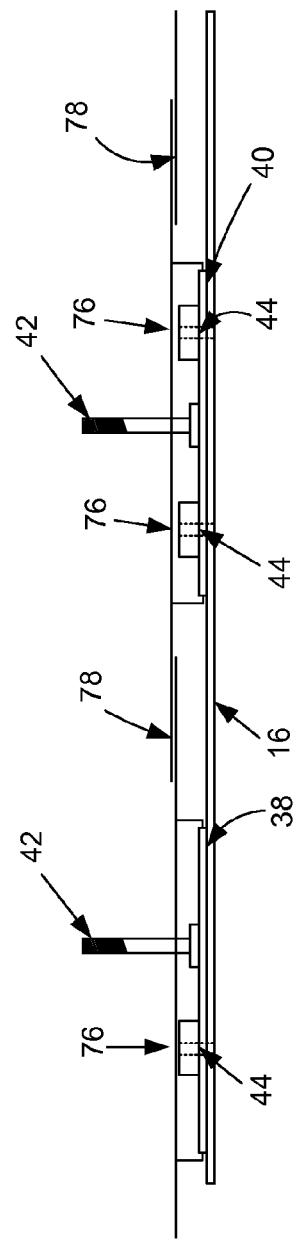

Referring to FIG. 16, another semi-rigid covering embodiment comprises a semi-rigid covering for the entire local surface of the instrument driver (16), without conventional draping in between semi-rigid sub-pieces. To accommodate relative motion, high tolerance overlap sections (78) are provided with sufficient overlap to allow relative motion without friction binding, as well as gapping of sufficient tightness that the sterility of the barrier remains intact. The semi-rigid covers of the embodiments of FIGS. 15 and 16 may be molded or machined from polymeric materials, such as polycarbonate, which are inexpensive, sterilizable, somewhat flexible for manual snap-on installation, and fairly translucent to facilitate installation and troubleshooting.

Figure 17:
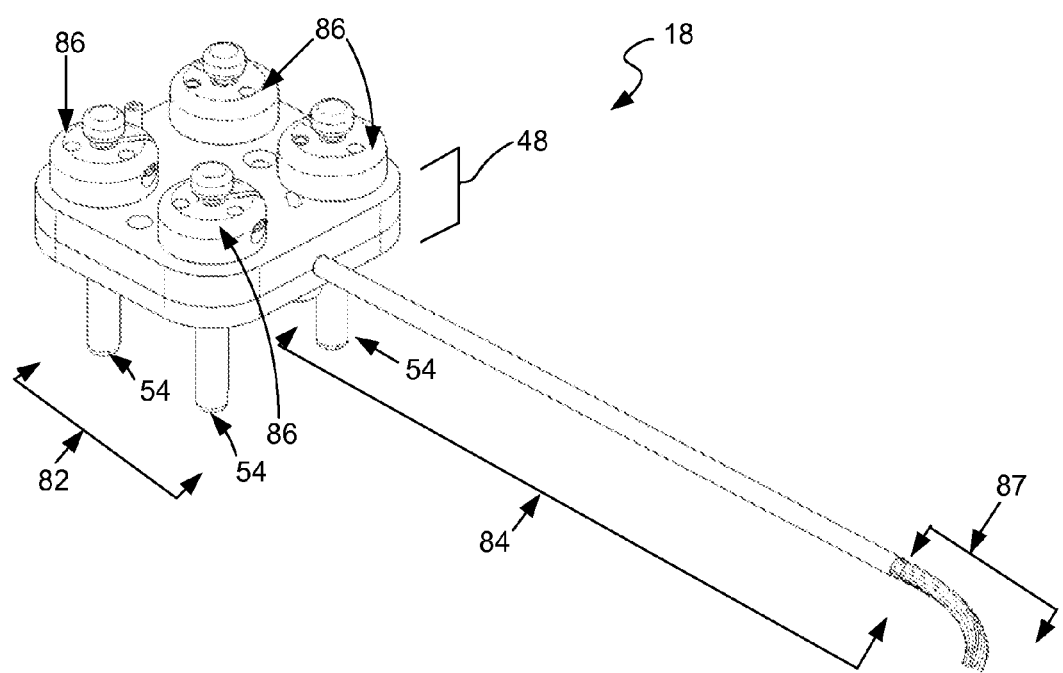
FIG. 17 illustrates an isometric view of an instrument configures for instrument steering.

FIG. 17 is an isometric view of one embodiment of an instrument (18) configured for instrument steering via independent control of four catheter control elements, or four tension elements, such as cables comprising materials, e.g., stainless steel. The proximal portion (82) comprises a guide instrument base (48) and four axles (54) with associated manual adjustment knobs (86). The middle (84) and distal portions (87) comprise a catheter member which extends into the guide instrument base (48) forming part of the proximal portion (82).

Figure 18:
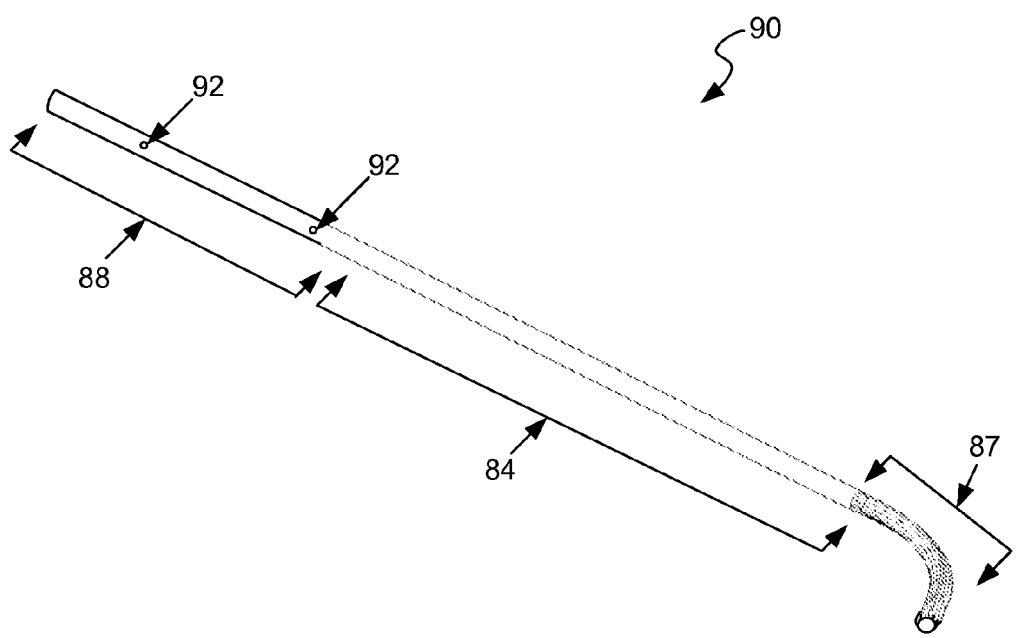
FIG. 18 illustrates one embodiment of a catheter member.

Referring to FIG. 18, a catheter member (90) is depicted having control element apertures (92) through the proximal portion (88) of the catheter member to accommodate control elements (not shown), such as tension cables. The control elements may be disposed along the length of the catheter member (90), and positioned to exit the catheter through the apertures (92) and into association with other structures comprising the proximal portion (82) of the instrument. The proximal (88) and middle (84) portions of the catheter member (90) are shown in a substantially straight configuration, which is preferred for controllability of the more flexible distal portion (87). Indeed, the proximal (88) and middle (84) portions are structurally reinforced and made from stiffer materials to enhance torque transmission and insertability to the distal portion, while also providing enough cantilever bendability to facilitate access to remote tissue locations, such as the chambers of the heart.

Figure 19:
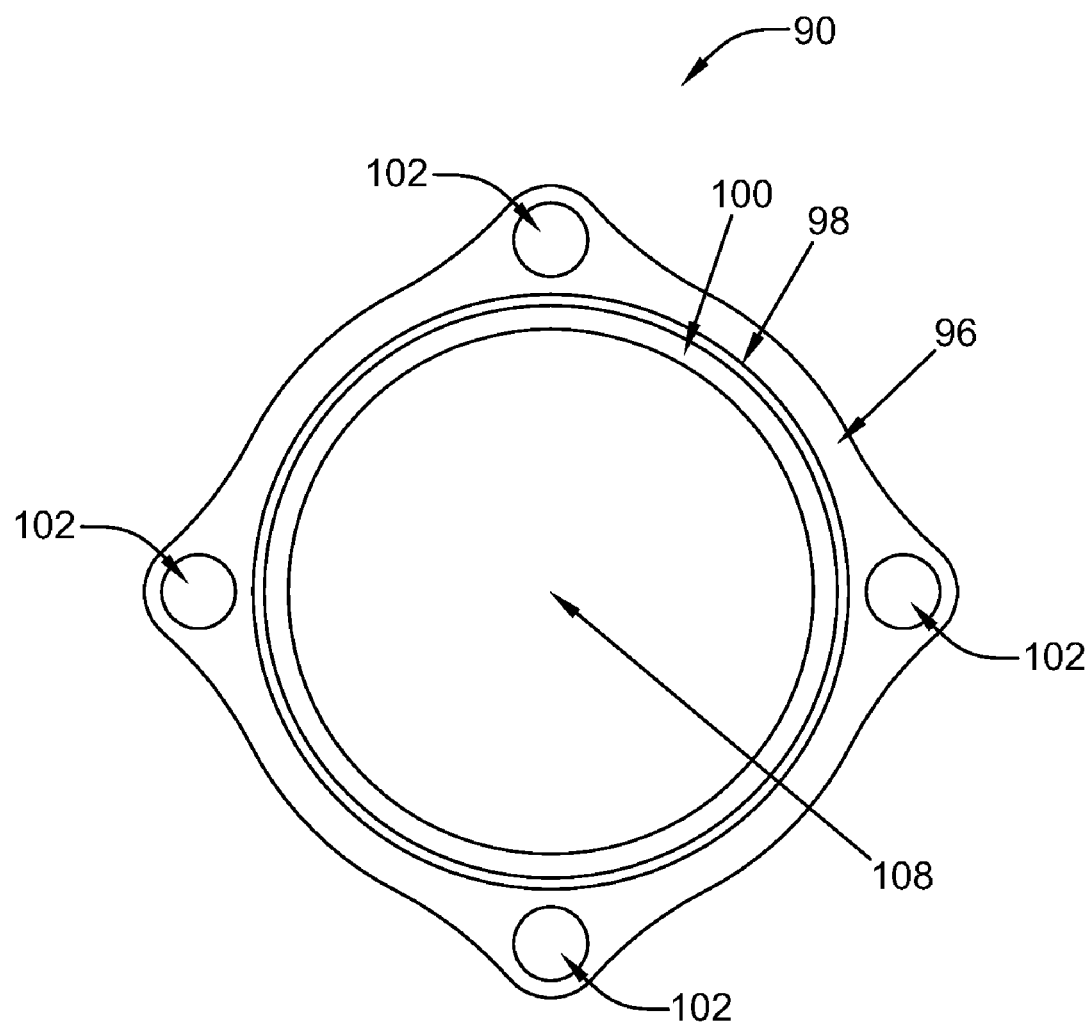
FIG. 19 illustrates a cross sectional view of a catheter member.

FIG. 19 is a cross sectional view of the catheter member (90) at either the proximal (88) or middle (84) portion. At the center of the cross sectional construct is a central (or "working") lumen (108), the geometry of which is selected in accordance with the requisite medical application. For example, in one embodiment it is desired to pass a commercially available ablation catheter having an outer diameter of about 7 French through the working lumen (108), in which case it is preferable to have a working lumen in the range of 7 French in diameter. The catheter member (90) and the robotic catheter system (32) can be sized up or down in accordance with the desired procedure and tools. The proximal portion of the catheter member (90) may be reinforced with a stiffening member such as a braiding layer (98) which is preferably encapsulated on the outside by an outer layer (96) having at least one control element lumen (102) to accommodate a control element, such as a tension cable (not shown), and a low-friction inner layer (100) selected to provide a low-friction surface over the inside of the braiding layer (98). Four extruded lumens (102) are provided in the illustrated embodiment to accommodate four respective control elements (not shown).

Figure 20:
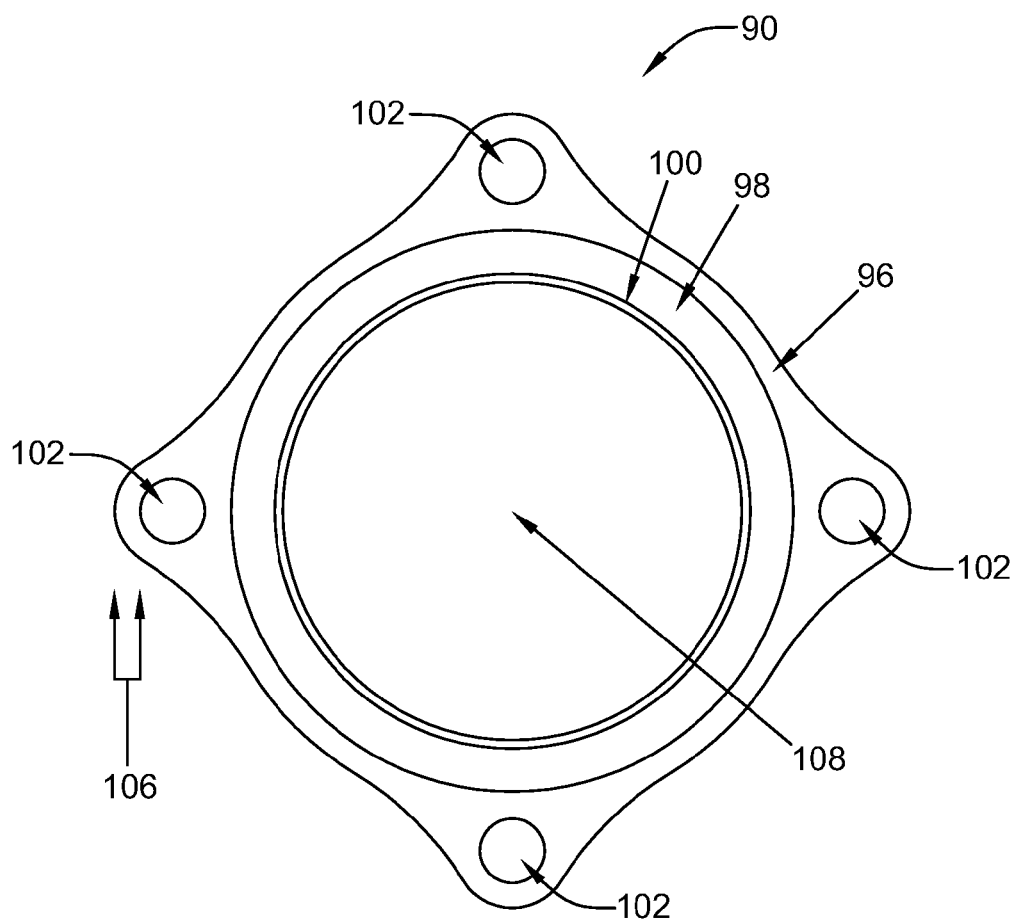
FIG. 20 illustrates a cross sectional view of another embodiment of a catheter member.

To prevent relative rotational motion between the catheter member (90) and other structures which may surround it, the profile of the outer layer adjacent the control element lumens (102) may be increased. The cross section of the embodiment of FIG. 19 has a relatively low surface profile (104) adjacent the control element lumens (102), as compared with the cross section of the embodiment of FIG. 20, which is otherwise similar to that of FIG. 19. Indeed, within the same catheter member, it is preferable to have a more pronounced surface profile distally to interface with surrounding structures and prevent "wind up", or torsional rotation, of the distal and middle portions of the catheter member. With the braiding layer (98) in the middle (84) and proximal (82) portions of the instrument, "wind up" is not as significant an issue, and therefore it is less important to have a pronounced surface profile to interface or "key" with other adjacent structures.

Figure 21:
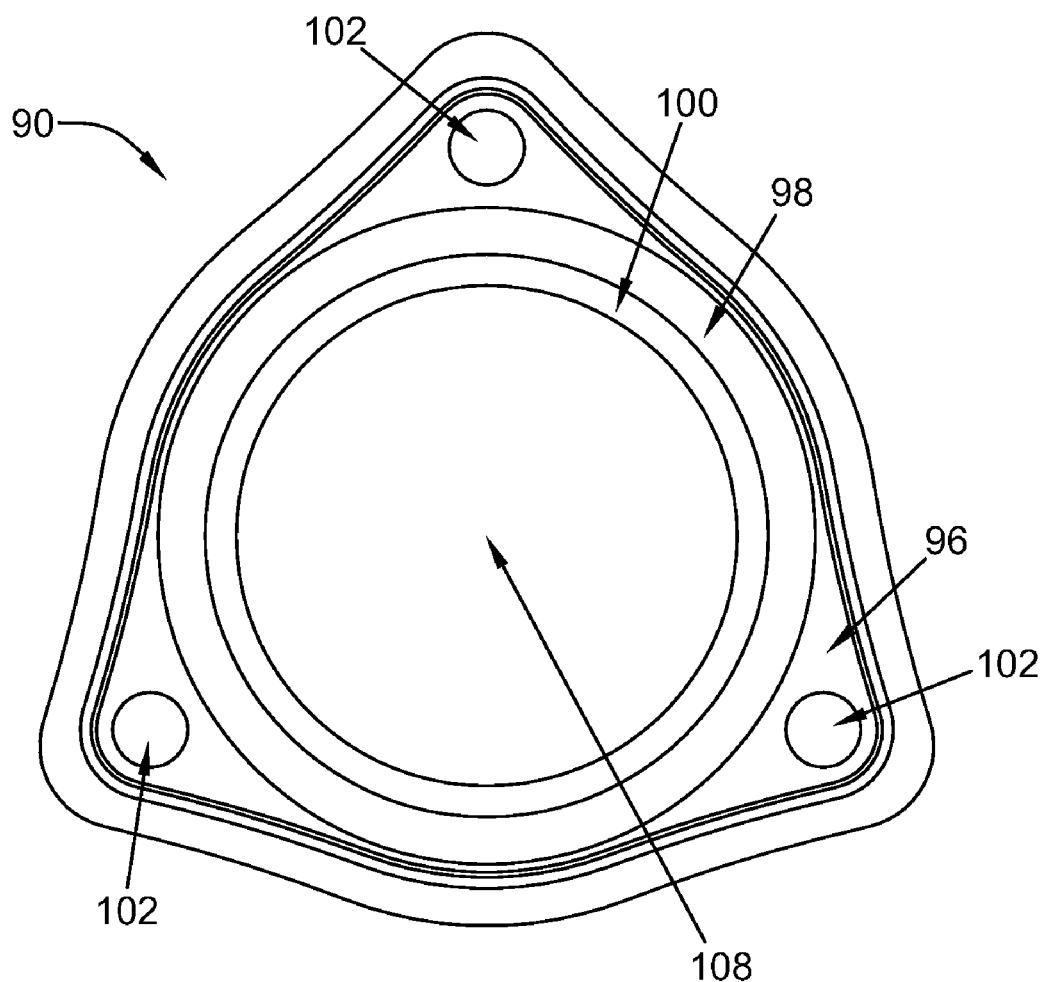
FIG. 21 illustrates one embodiment of a catheter member having three control element lumens.
Figure 22:
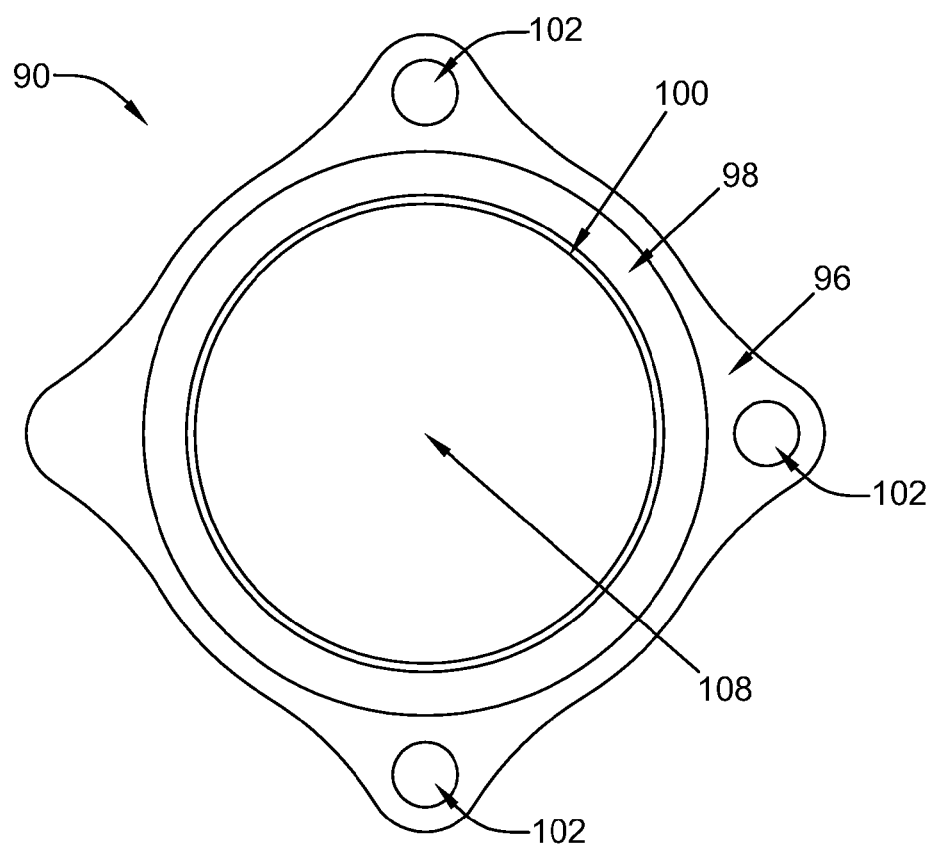
FIGS. 22-24 illustrate embodiments of catheter members having a non-equidistant lumen configurations.
Figure 23:
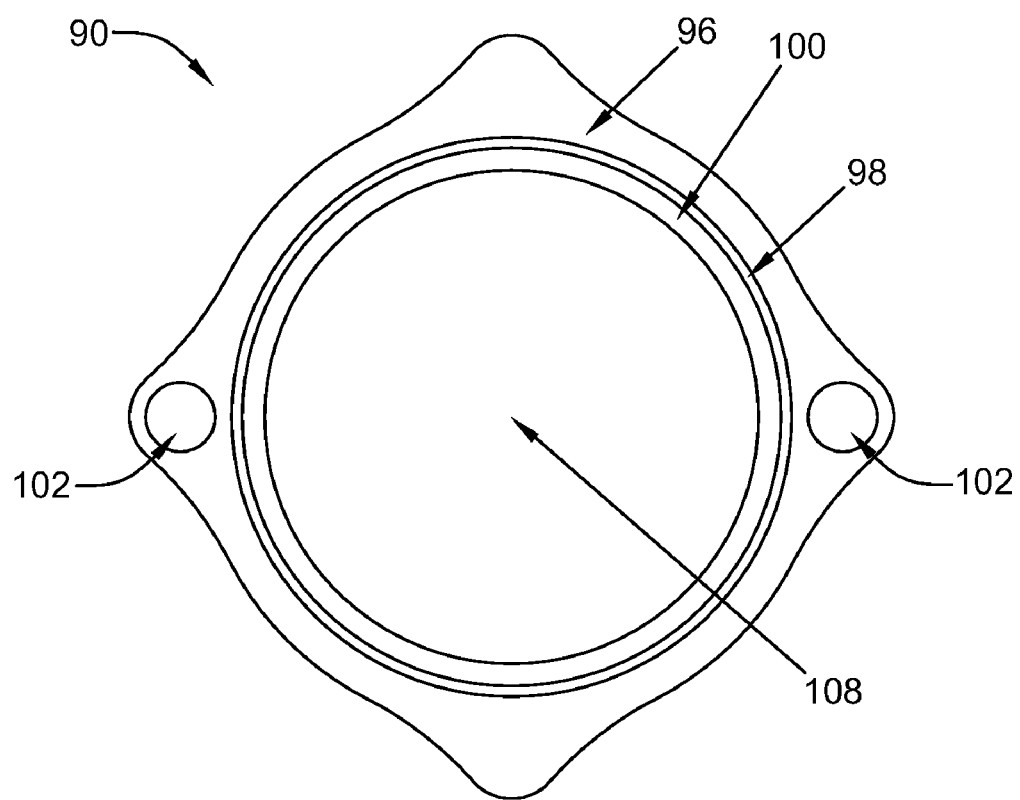
Figure 24:
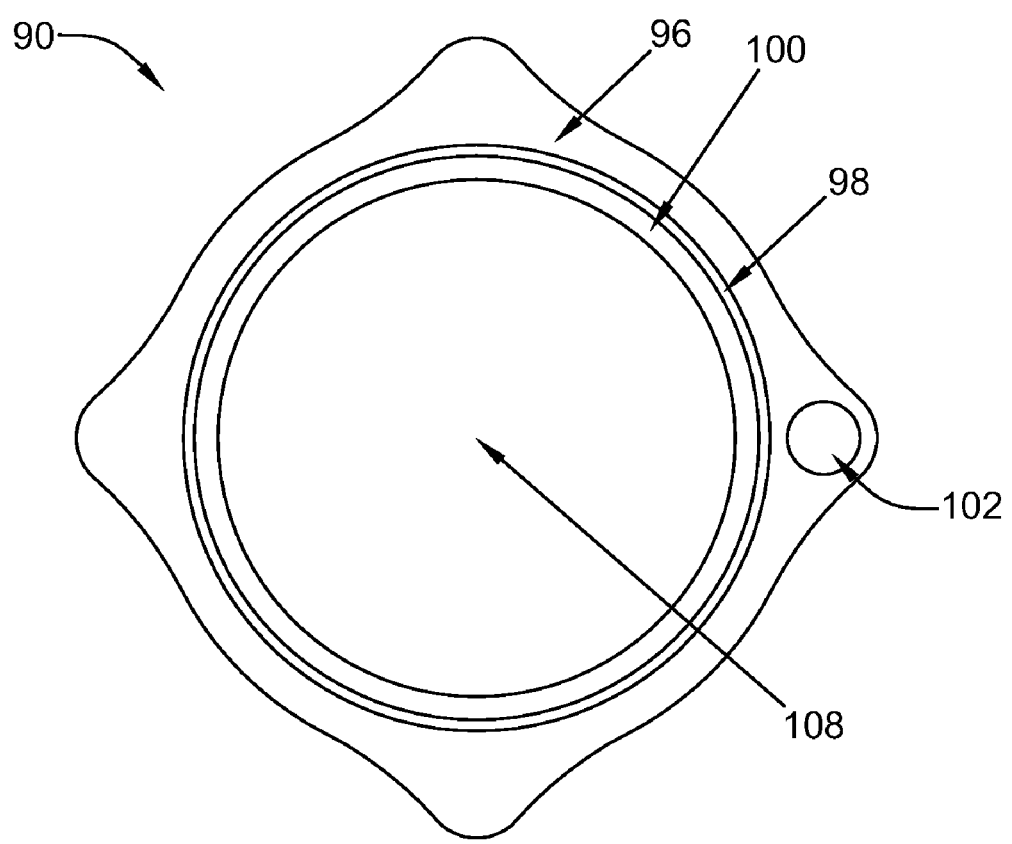

FIG. 21 depicts an embodiment having three control element lumens (102) disposed approximately equidistantly from each other about the perimeter of the catheter member (90) cross section. This embodiment illustrates by way of non-limiting example that the catheter member (90) need not be limited to configurations comprising four control element lumens or four control elements. By way of another example, FIG. 22 illustrates a non-equidistant, three-lumen (102) configuration, with two-lumen (102) and single lumen (102) variations shown in FIGS. 23 and 24, respectively.

Figure 25:
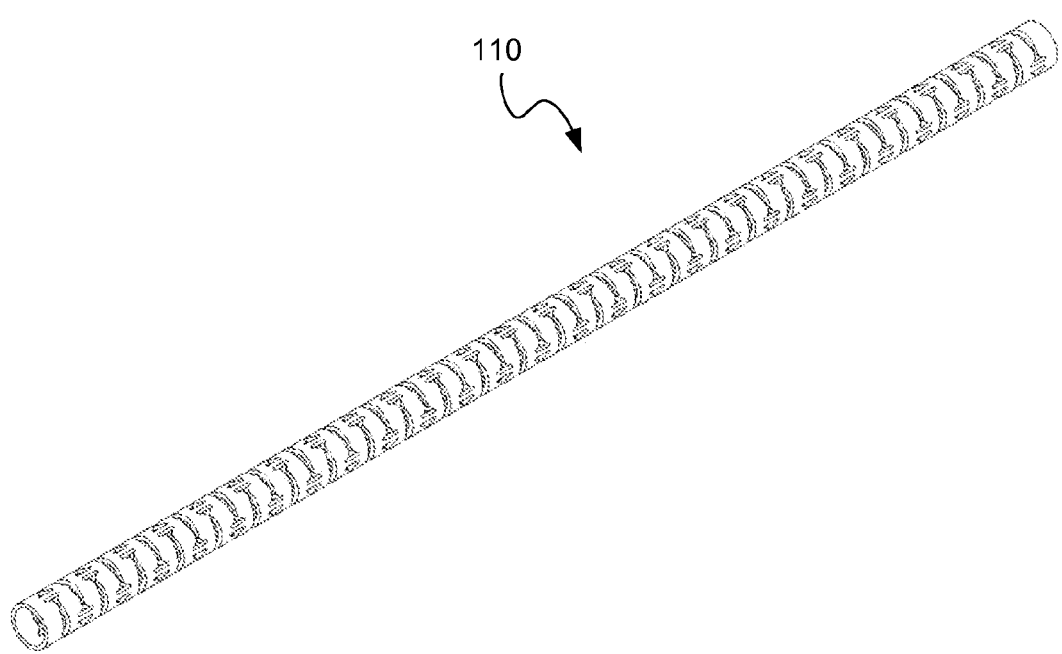
FIGS. 25-27 illustrate various embodiments of a metal spine.
Figure 26:
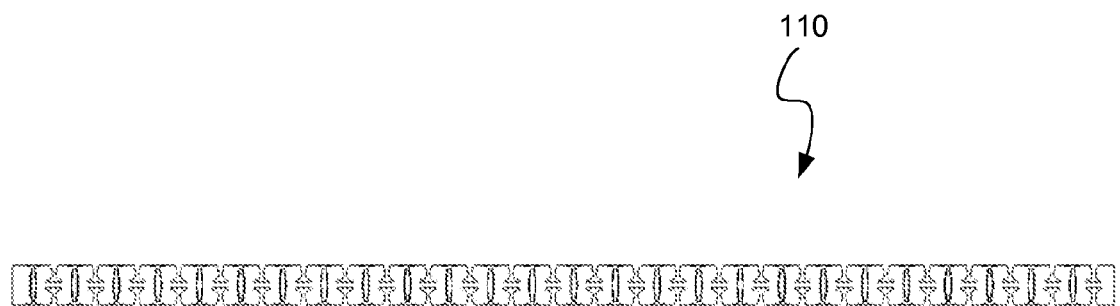
Figure 27:
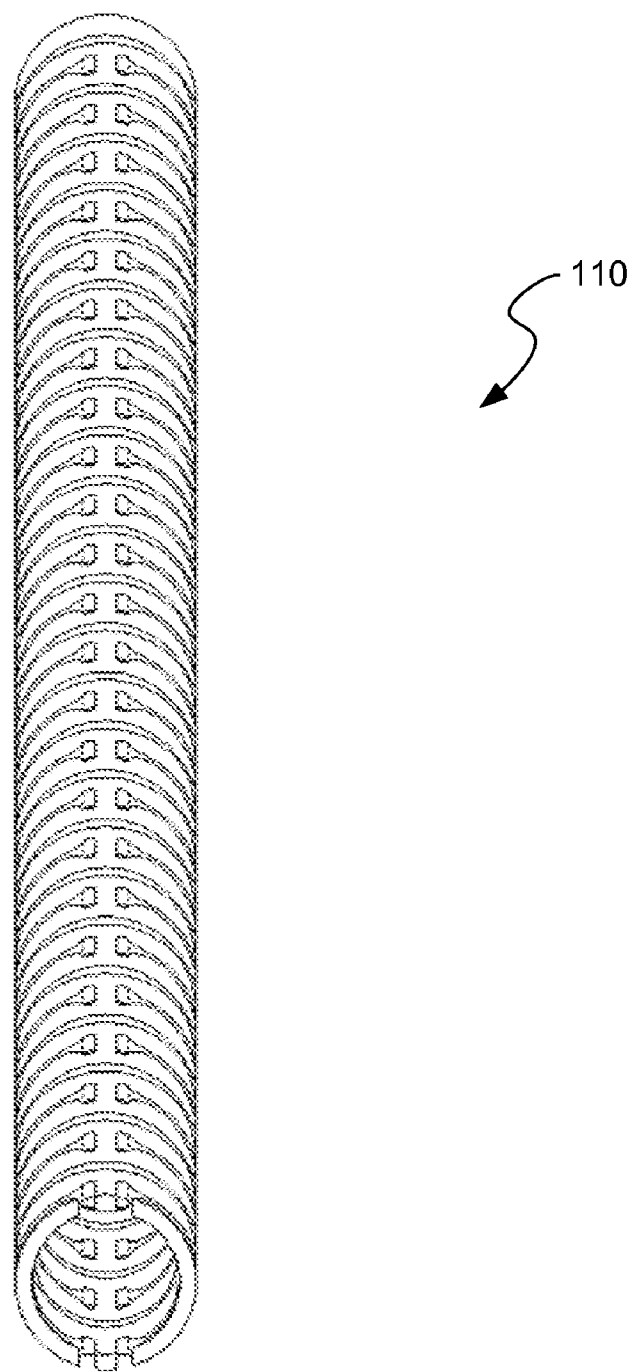
Figure 28:
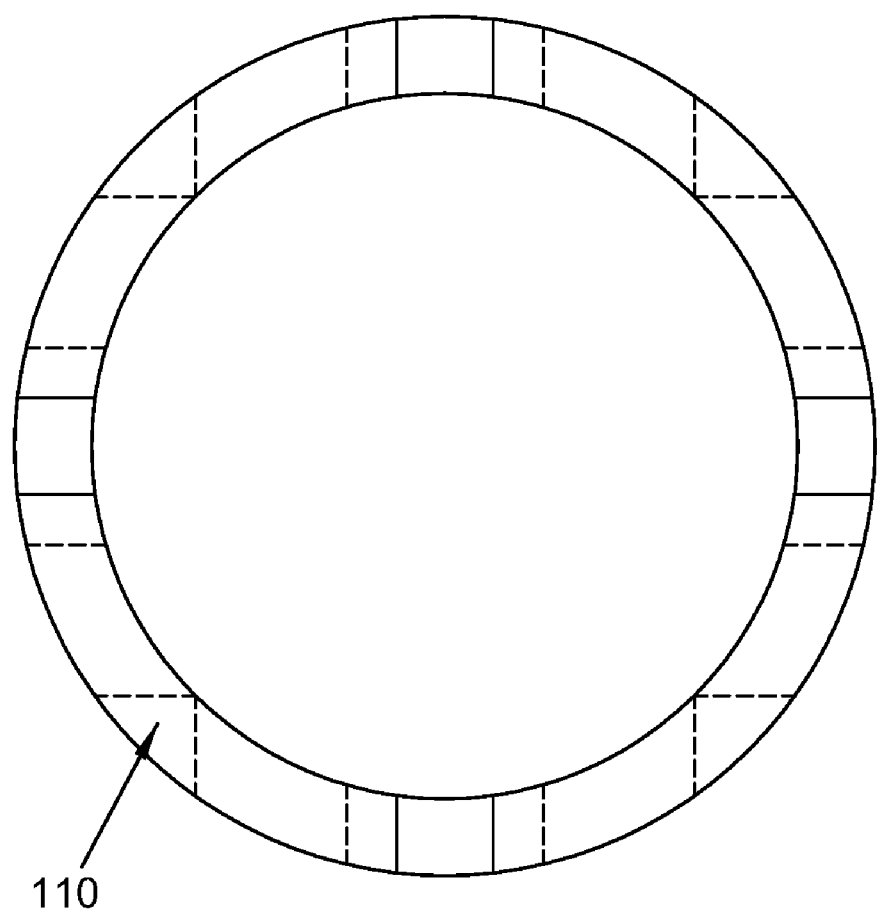
FIG. 28 illustrates a cross sectional view of a metal spine.

To facilitate more dramatic bendability at the distal portion (87) of the catheter member (90), a reinforcing structure other than a braiding layer may be preferred. By way of non-limiting example, FIGS. 25-27 depict a metal spine (110) having a unique stress relief geometry cut into its walls. FIG. 28 depicts a cross section of an embodiment of a metal spine (110) to illustrate that the working lumen may be continued from the proximal (88) and middle (84) portions of the catheter member into the distal portion (87) through the center of the metal spine (110). Indeed, the metal spine preferably has similar inner and outer diameter sizes as the braiding layer (98) in the more proximal portions of the catheter member (90). Depending upon the metal utilized for the metal spine (110), very tight bend radius operation of the distal portion (87) of the catheter member (90) is possible, due in significant part to such a highly bendable reinforcing structure and its associated repeated stress relief pattern. To further enhance the flexibility of the distal portion (87) of the catheter member (90), softer polymeric materials may be utilized in the construct, such as a polyether block amide (Pebax®) resin from Arkema Inc. of Philadelphia, Pa. For example, in one embodiment, the outer layer (96) in the proximal (88) and middle (84) portions of the catheter member (90) may preferably be comprised of a 70 Shore D hardness (durometer hardness value) Pebax® resin, while the distal portion (84) and outer layer (96) may preferably be comprised of a 35 or 40 durometer Pebax® resin.

Figure 29:
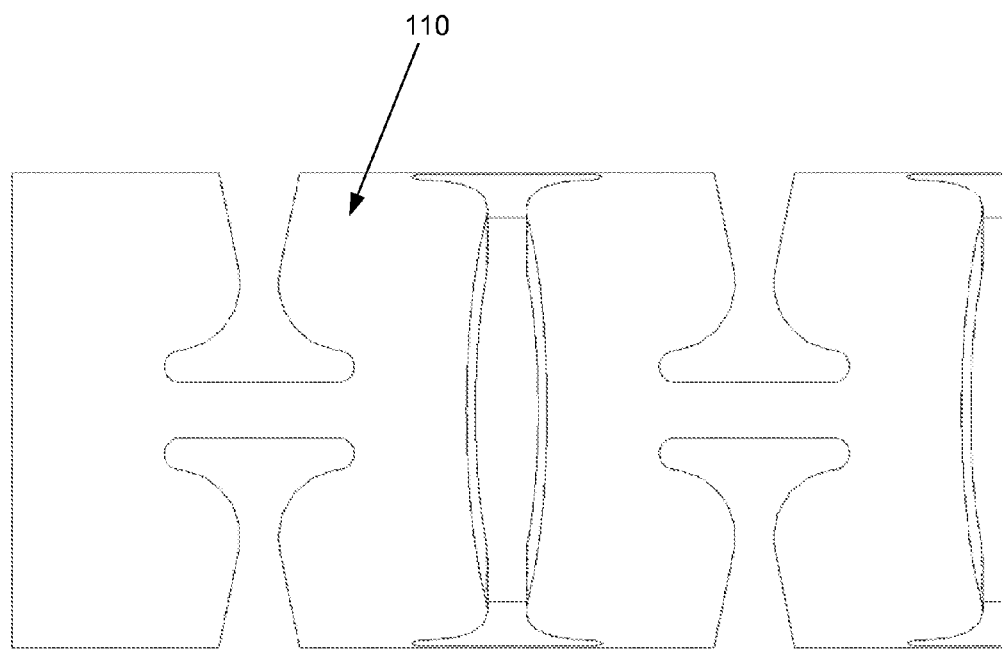
FIGS. 29-30 illustrate a stress relief pattern for the spine of one embodiment.
Figure 30:
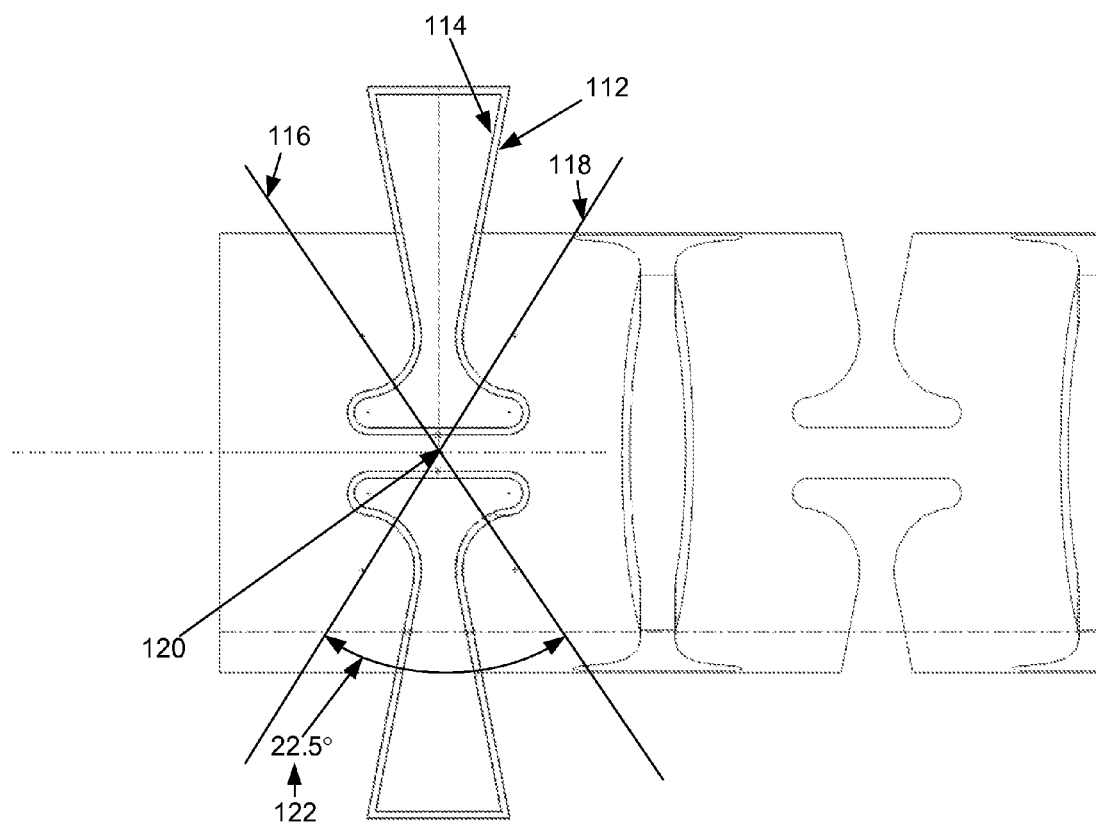

Referring to FIGS. 29 and 30, one embodiment of a stress relief pattern is depicted in close-up view to illustrate that the pattern may be shifted by about ninety degrees with each longitudinal step along the spine (110) to maximize the homogeneity of stress concentration and bending behavior of the overall construct. To further enhance the flexibility of the metal spine, and clean up undesirable geometric discrepancies left behind after laser cutting, the metal spine may be chemically etched and electropolished before incorporation into the catheter member (90). As shown in FIG. 30, chemical etching takes the pattern from the original laser cut positioning (114) to a revised positioning (112) with larger windows in the pattern. In this embodiment, subsequent to chemical etching, the pattern forms a relief angle with sides (116, 118) with an intersection (120) and included angle (122). Preferred metal spine materials include, but are not limited to, stainless steel and nitinol.

Figure 31:
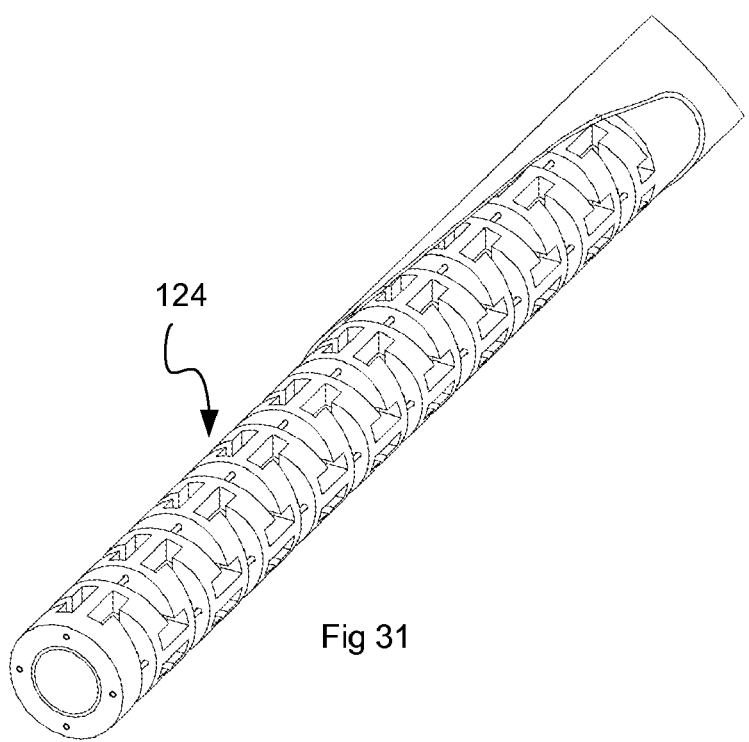
FIGS. 31-32 illustrate a polymeric spine of one embodiment.
Figure 32:
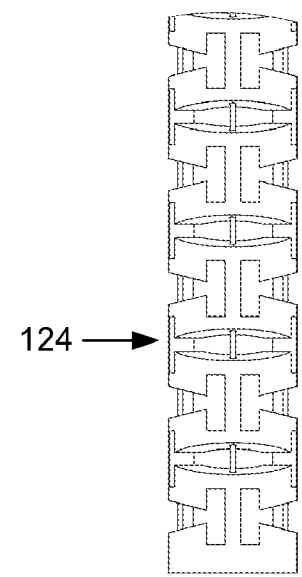

Referring to FIGS. 31 and 32, the distal reinforcing structure may also comprise a polymeric spine (124) similarly configured to homogeneously bend due to a stress relief pattern comprising the tubular wall of the spine (124). In particular, due to the greater fracture toughness of many available polymeric materials, a more squared stress concentrating pattern may be repeated with polymer structures. Further, high-precision structures such as the depicted polymeric spine (124), may be formed using injection molding and/or other techniques less inexpensive than laser cutting and etching. As will be apparent to those skilled in the art, many other distal spine structures for concentrating and relieving stress may also be utilized to provide the requisite tight bend radius functionality distally within the catheter member (90) construct, including but not limited to coils and braids.

Figure 33:
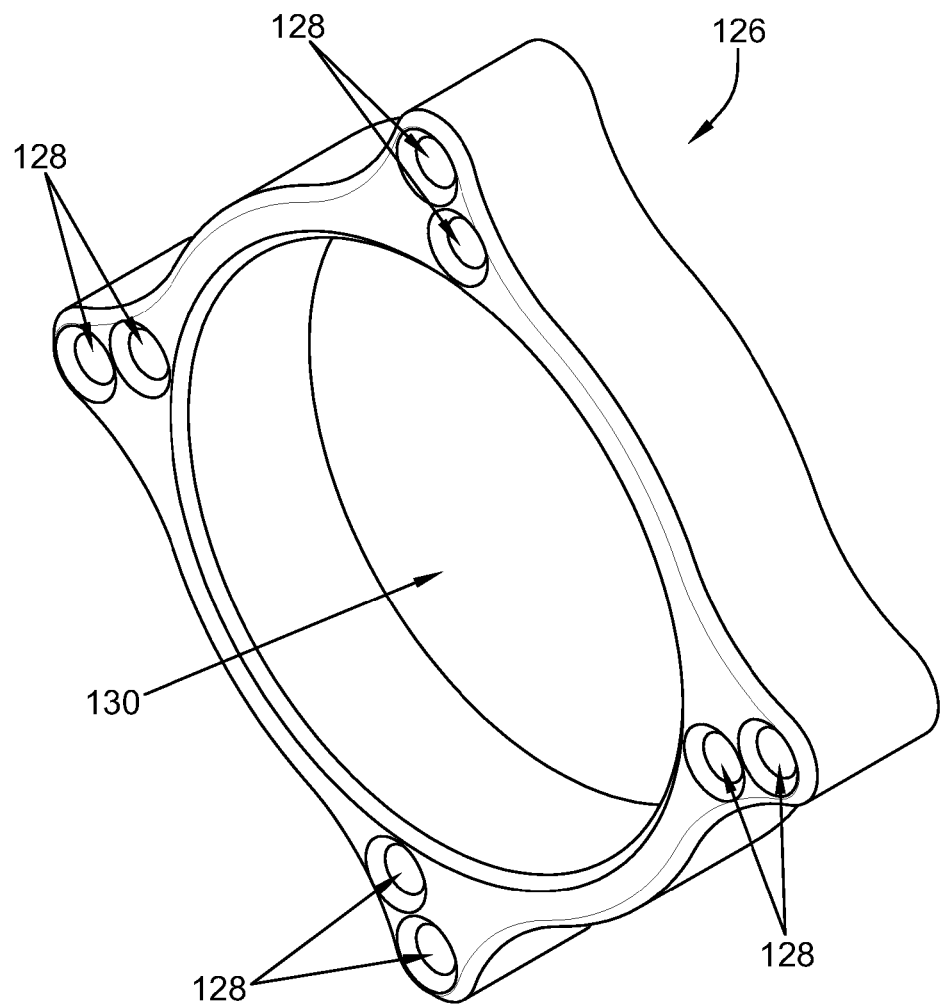
FIGS. 33-34 illustrates one embodiment of a control element anchoring ring.
Figure 34:
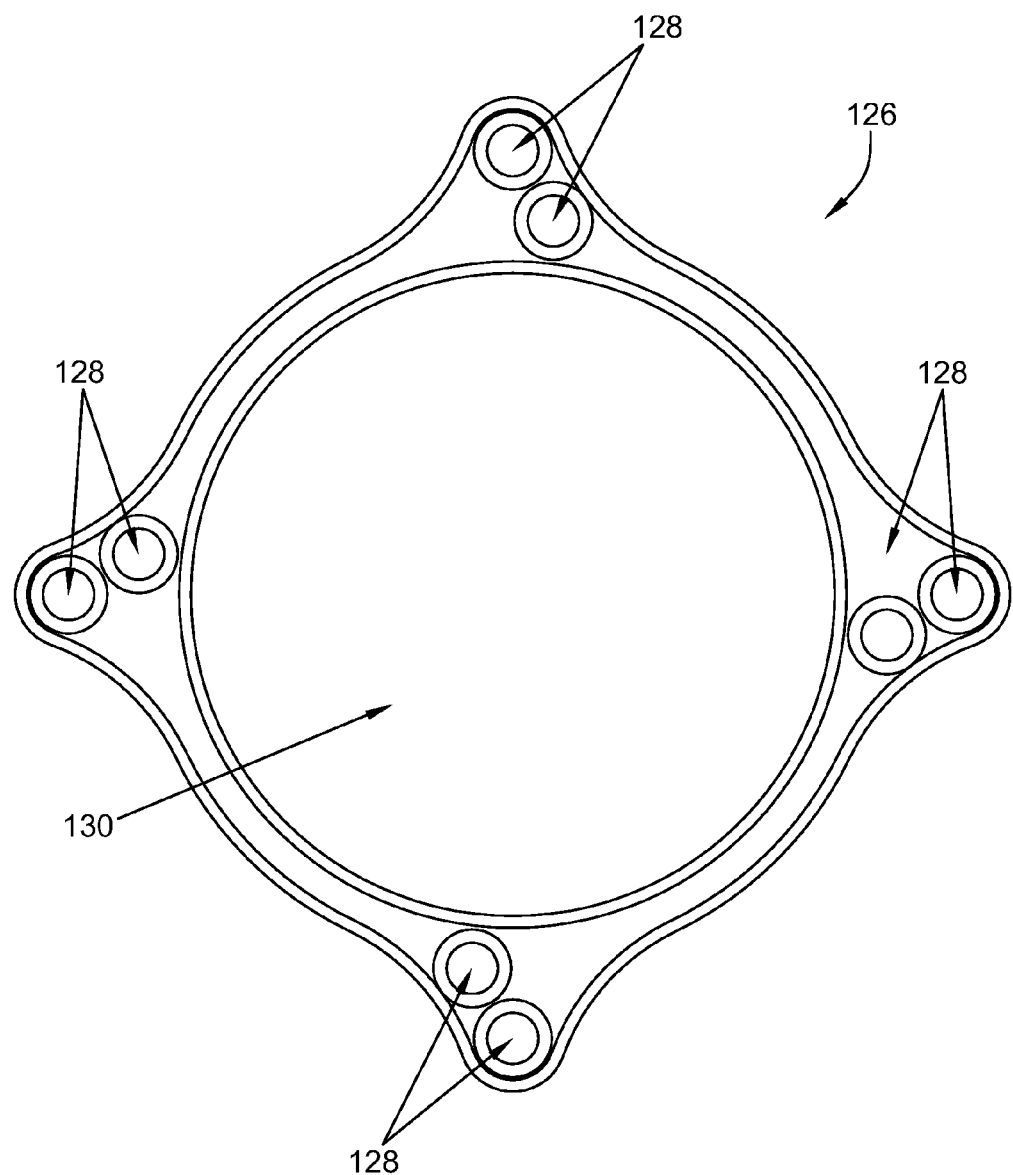

Referring to FIGS. 33 and 34, a control element anchoring ring (126) is depicted having two anchoring lumens (128) for each incoming control element to be anchored at the distal tip of the catheter member (90). The anchoring ring (126) comprises the last rigid construct at the distal tip of the catheter member (90), beyond which only a low durometer polymeric atraumatic distal tip (not shown) extends, as the low friction liner (100) meets the outer layer (96) subsequent to these two layers encapsulating the anchoring ring (126). The anchoring ring (126) is the "anchor" into which the relatively high-tension control elements are fixedly inserted—and is therefore a key to the steerability and controllability of the catheter member (90) regardless of the number of control elements pulling upon it. In one embodiment, tension wire control elements (not shown) insert into the outermost of the anchoring lumens, then bend directly back into the innermost of the anchoring lumens, where they are soldered to the anchoring ring, which comprise machined or gold plated stainless steel for solderability.

Figure 35:
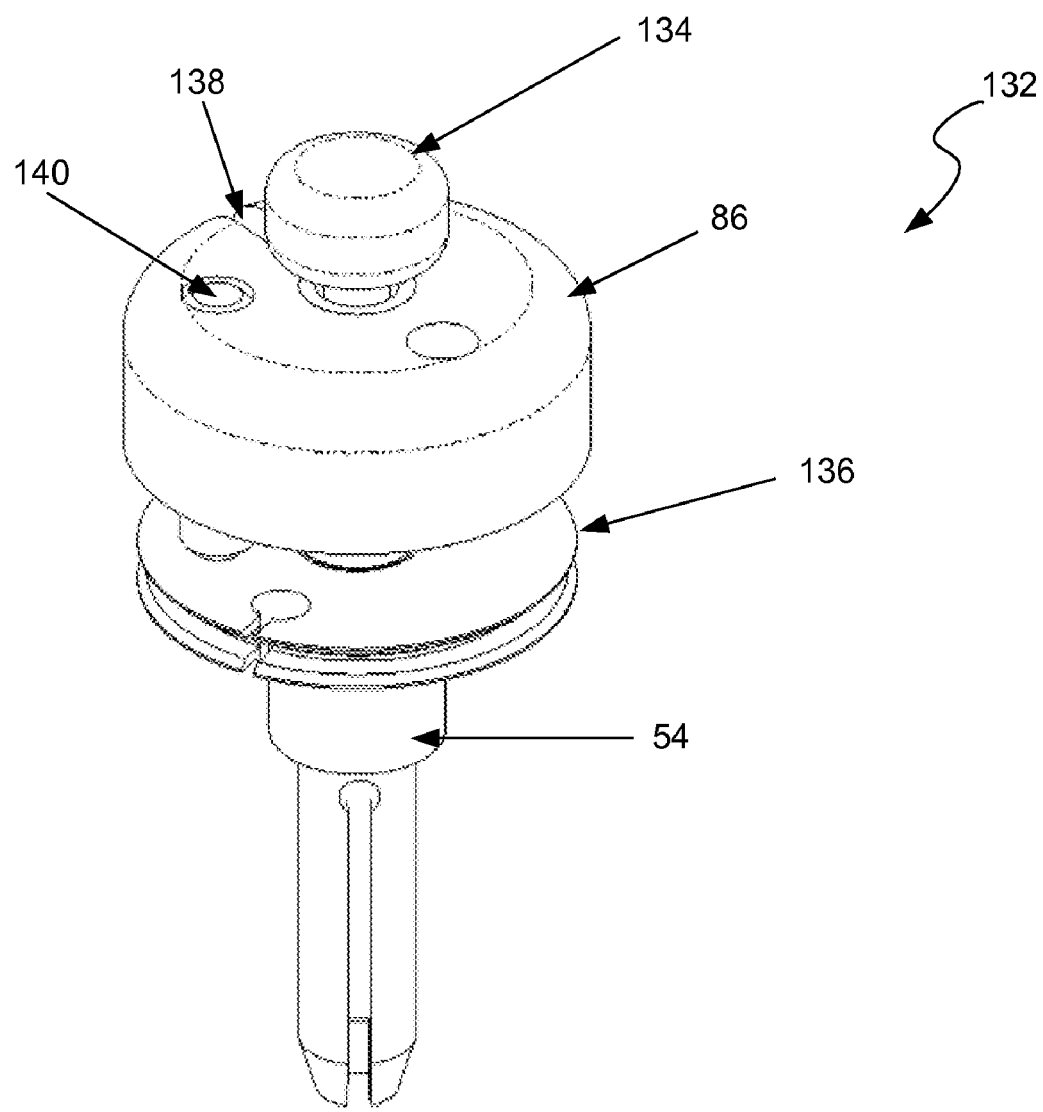
FIGS. 35A-49 illustrate various aspects of an instrument base in accordance to one embodiment.
Figure 35A:
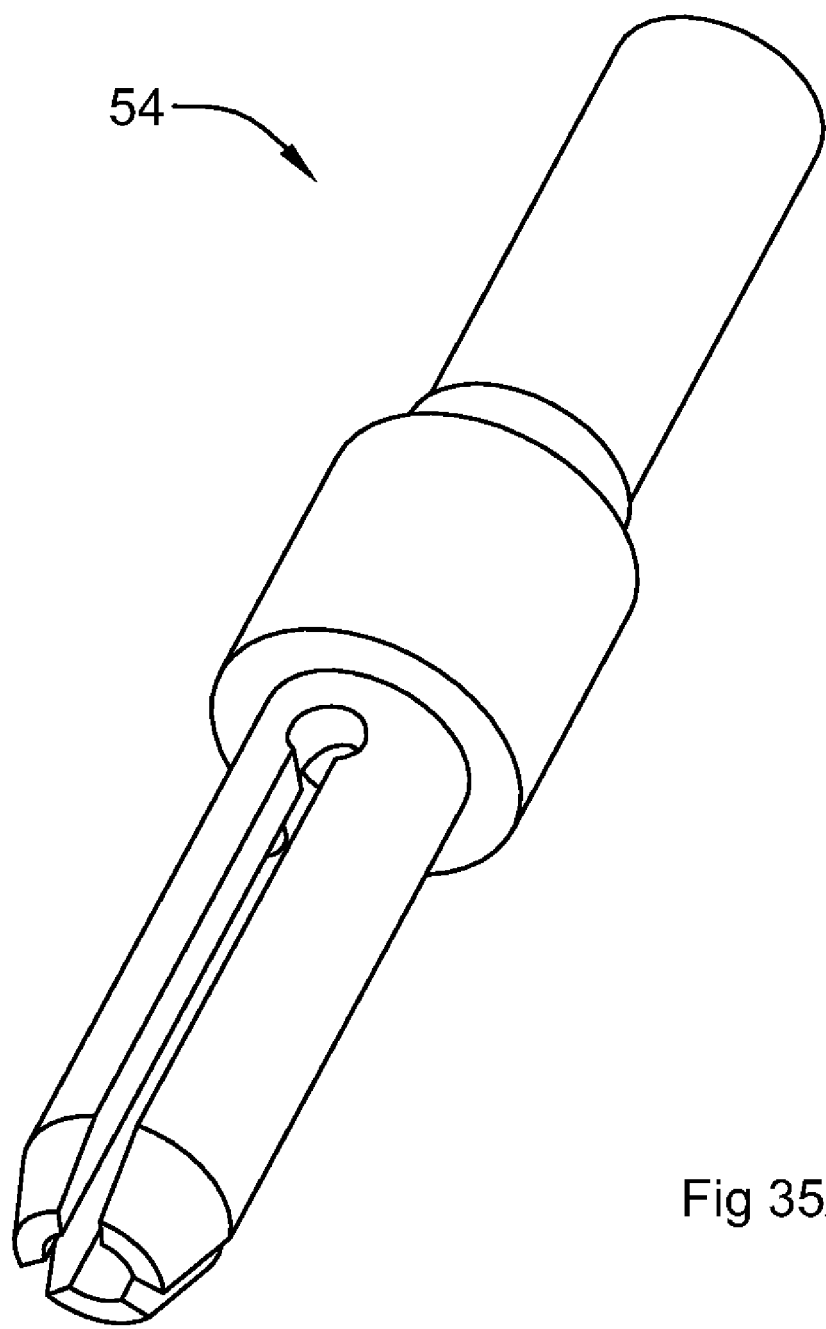
Figure 36:
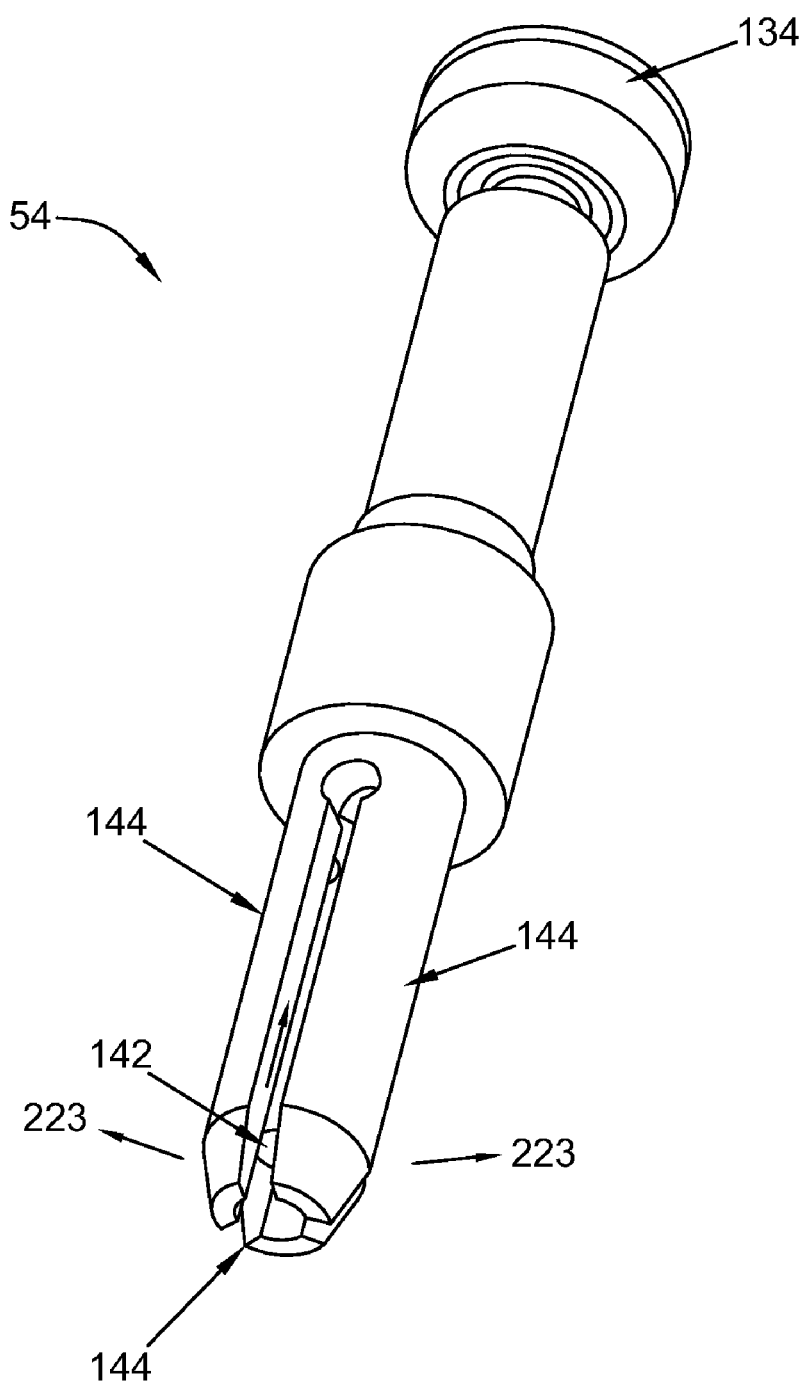

FIGS. 35A-49 depict various aspects of an instrument base at the proximal portion (82) of an instrument (18) similar to that depicted in FIG. 17. Referring to FIG. 35A, a control element interface assembly (132) is depicted, comprising an axle (54), a control element pulley (136), a manual adjustment knob (86), and a drive engagement knob (134). The manual adjustment knob is configured to facilitate manual adjustment of control element tensions during setup of the instrument upon the instrument driver. It is held in place against the axle (54) with a clamp screw (138), and houses a rotation range of motion limitation pin (140) which limits the range of motion of the axle subsequent to setup and tightening of the clamp screw. Referring to FIG. 35B, one embodiment of an axle (54) is depicted in isometric view without other hardware mounted upon it. Referring to FIG. 36, an axle (54) is depicted with a drive engagement knob (134) mounted upon it. The drive engagement knob (134) may take a shape similar to a screw with a long threaded portion configured to extend through the axle to engage a tapered nut (142), as shown. Twisting of the drive engagement knob (134) causes the tapered nut (142) to urge the teeth (144) of the axle outward (223), thereby engaging whatever structures surround the lower portion of the axle, including, but not limited to a instrument driver interface socket (44).

Figure 37:
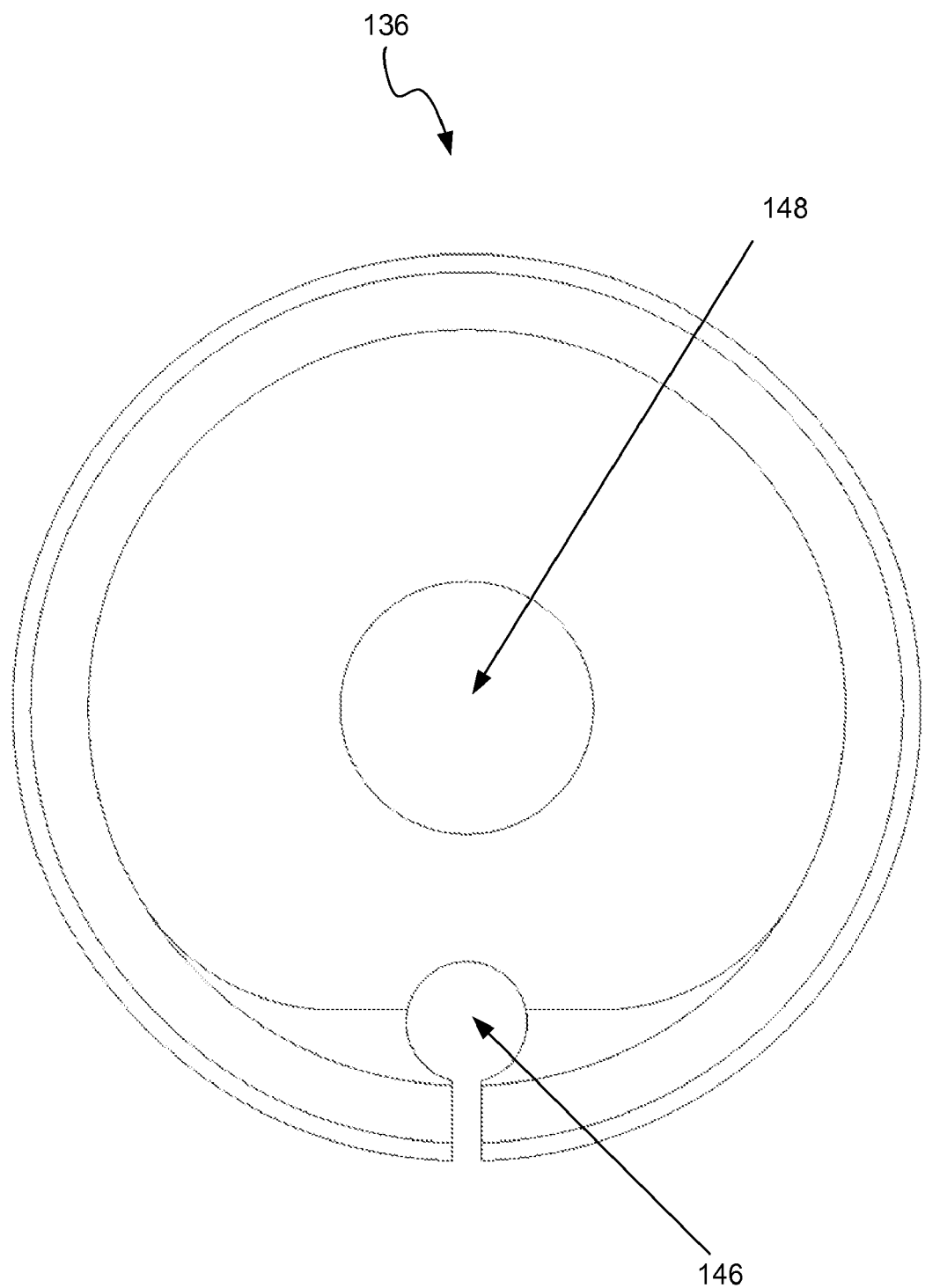
Figure 38:
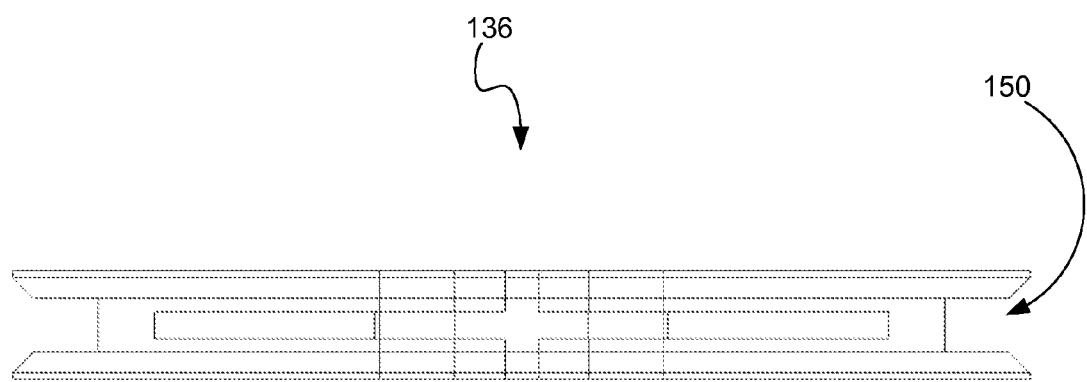

FIGS. 37 and 38 depict respective orthogonal views of one embodiment of a control element pulley (136). The central hole (148) in the pulley (136) is sized for a press fit upon an axle, and the control element termination engagement slot (146) is configured to capture a control element terminator, such as a lead or steel cable terminator, that is pushed into the slot before a control element is wound around the pulley (136) during manufacture or rebuilding. Referring to FIG. 38, the pulley (136) preferably has a flanged shape (150) to facilitate winding and positional maintenance of a control element.

Figure 39:
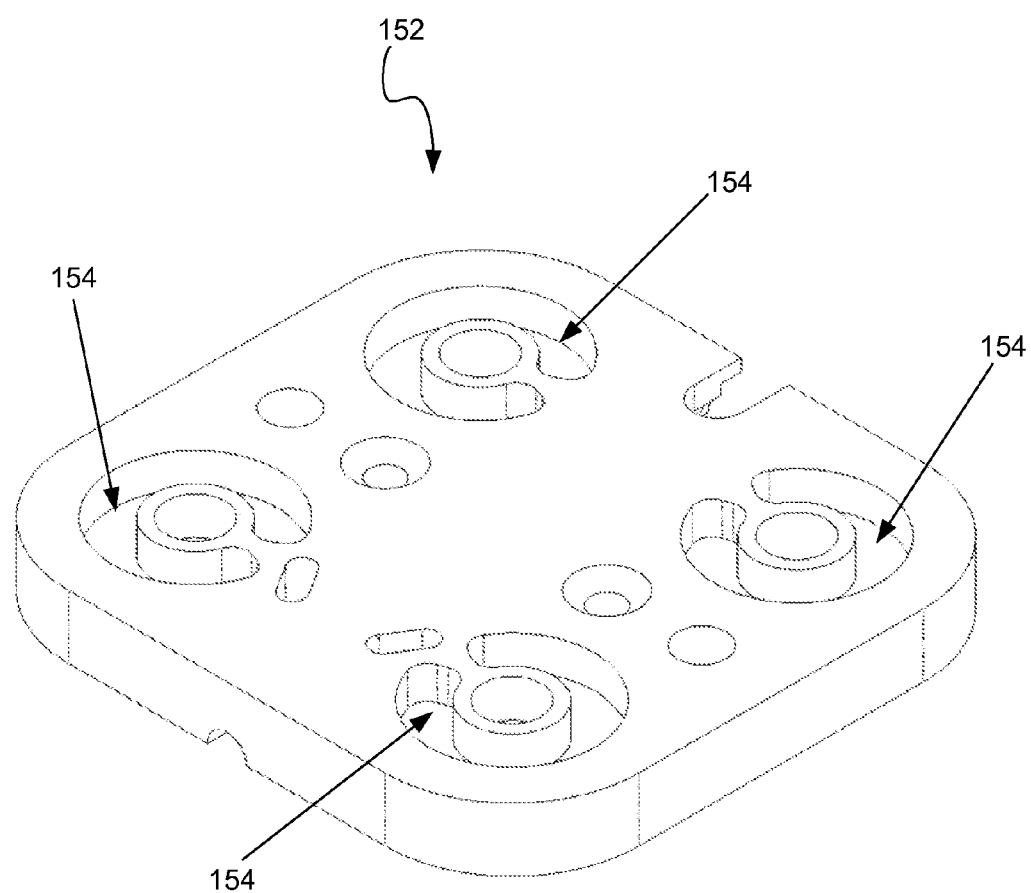
Figure 40:
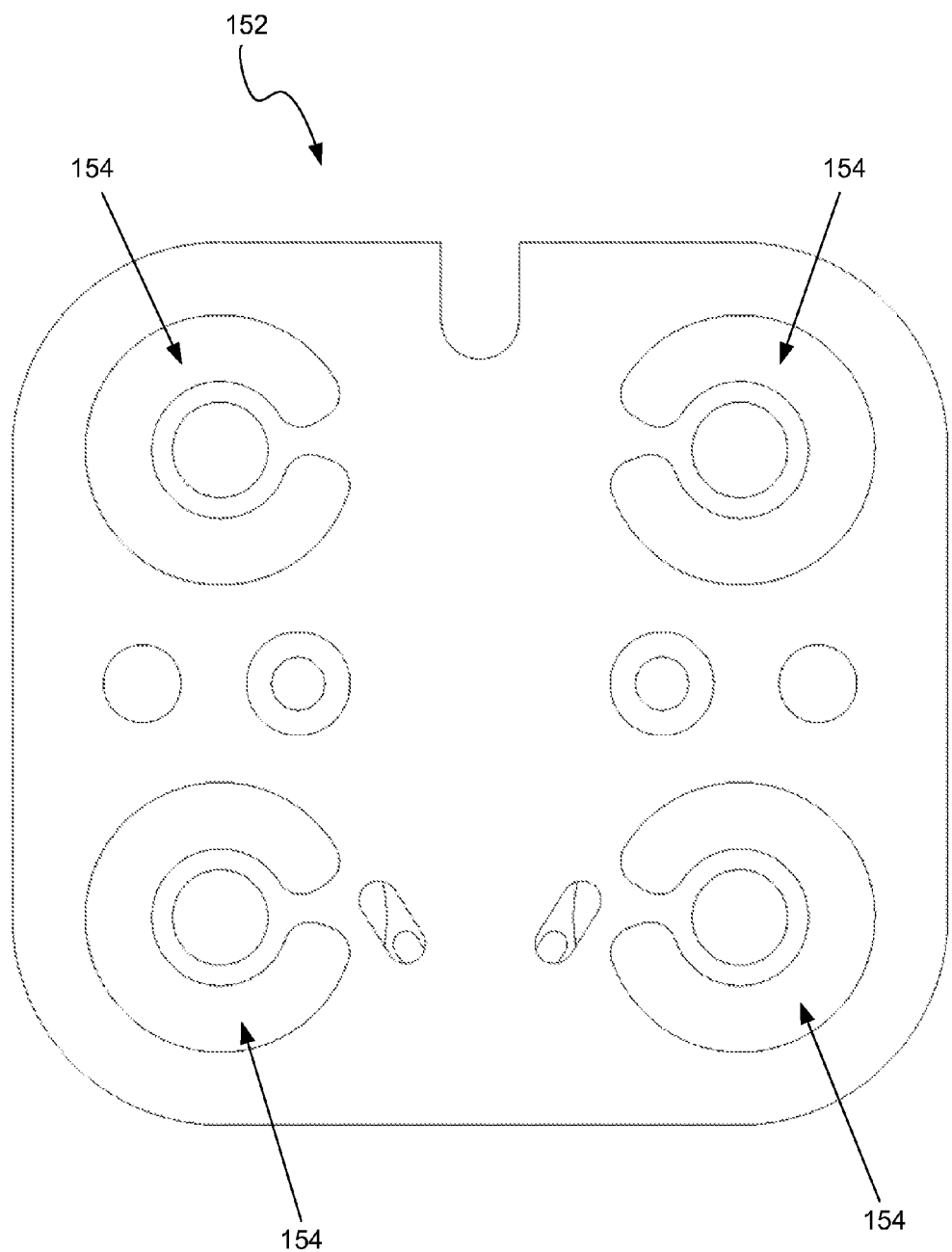
Figure 41:
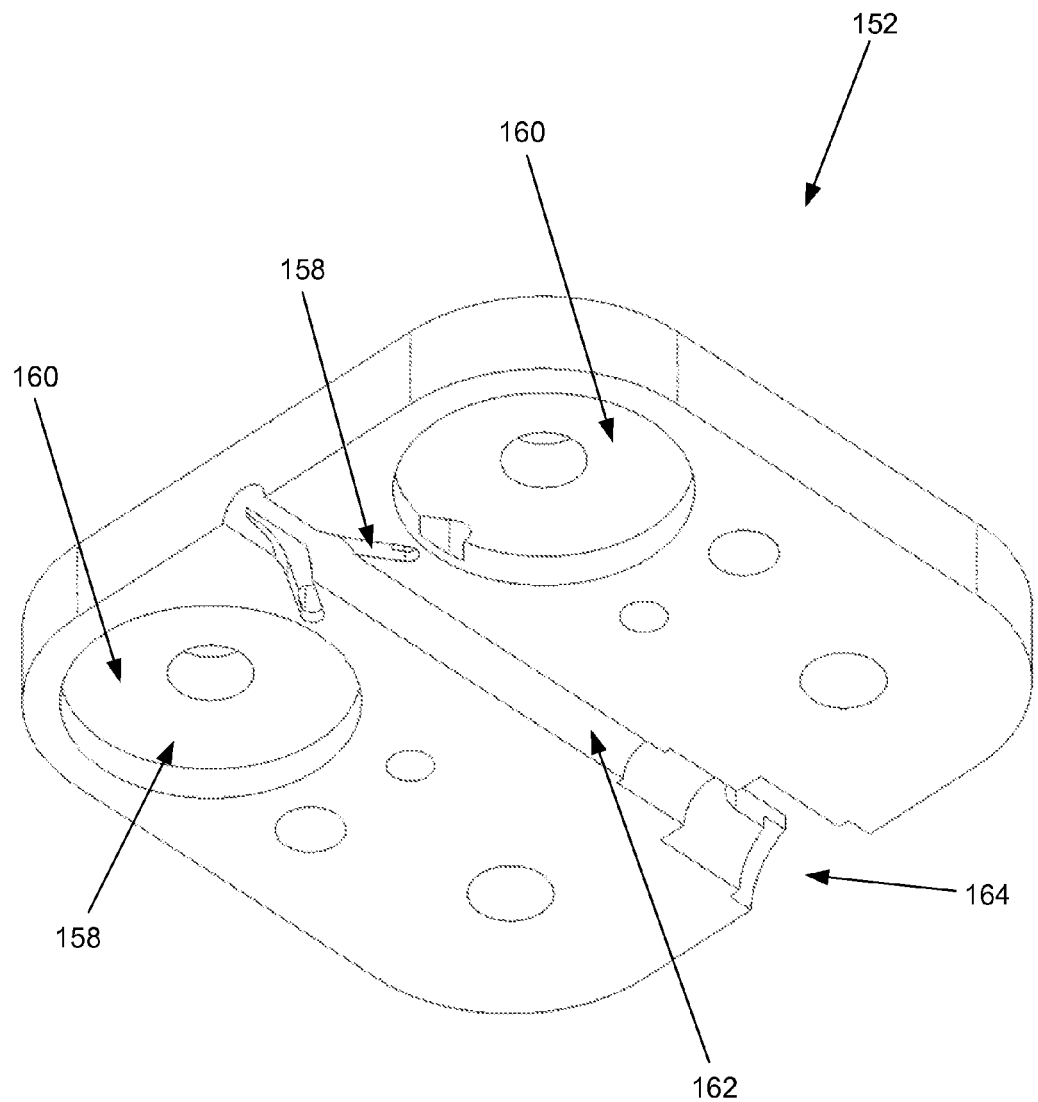
Figure 42:
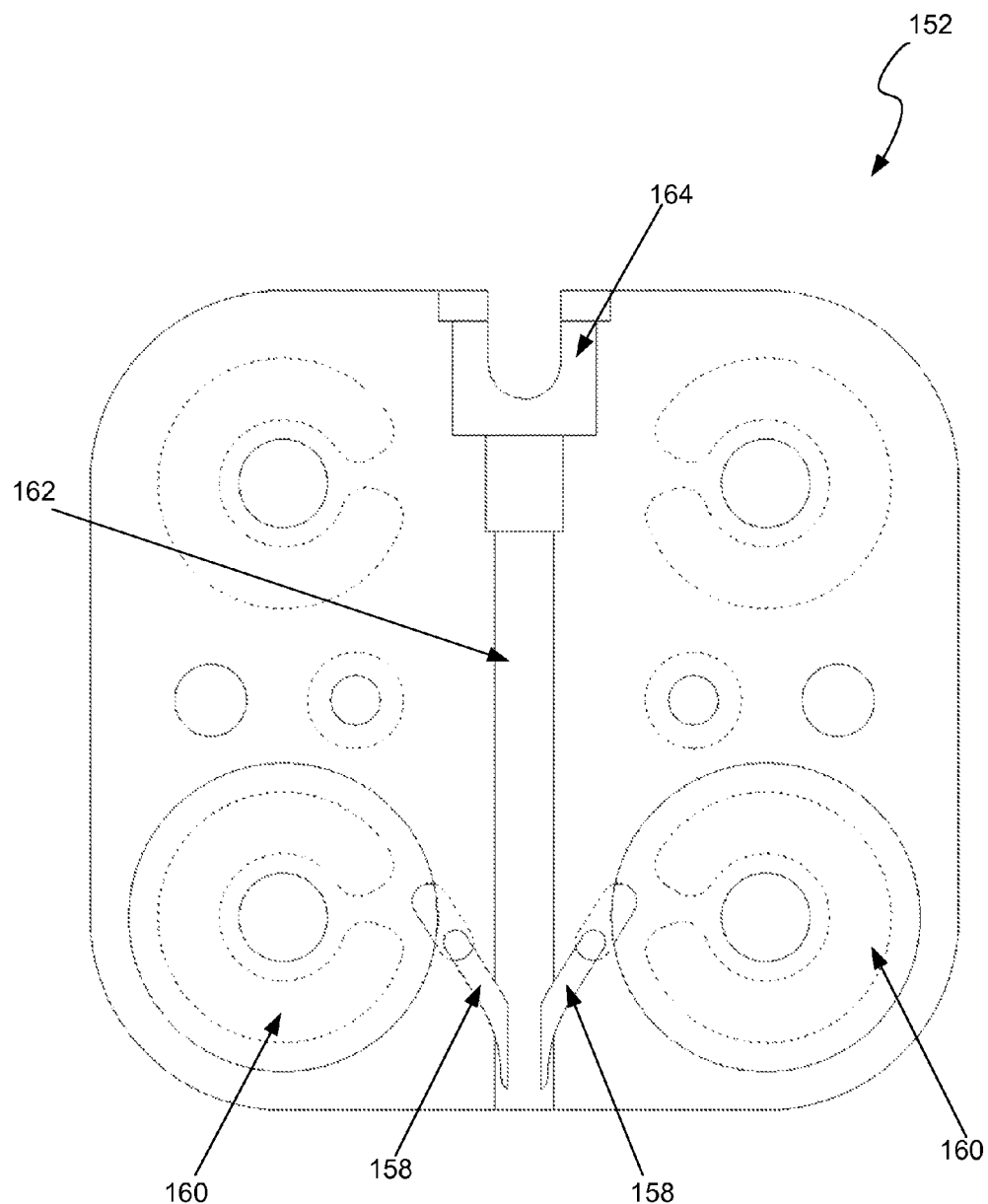

As shown in FIG. 39, the top portion (152) of one embodiment of a guide instrument base (48) comprises slots (154) to interface with the rotation range of motion limitation pins (140), which may be housed within a manual adjustment knob (86). FIG. 40 depicts a top view of the top portion (152). FIG. 41 depicts the same top portion (152), as viewed isometrically from underneath, to demonstrate how two pulleys may be mounted in related to the top portion (152) of the guide instrument base (48). The control element splay tracks (158) are employed to guide control elements (not shown) from apertures in a catheter member into pulleys which may be positioned within the pulley geometry accommodations (160) formed into the top portion (152) of the guide instrument base (48). Also shown in the top portion (152) is a catheter member geometry accommodation (162) and a seal geometry accommodation (164). FIG. 42 depicts an orthogonal view of the structures of FIG. 41 to better illustrate the control element splay track (158) structures positioned to guide control elements (not shown) away from a catheter member and over to a pulley associated with the top portion (152) of the guide instrument base (48).

Figure 43:
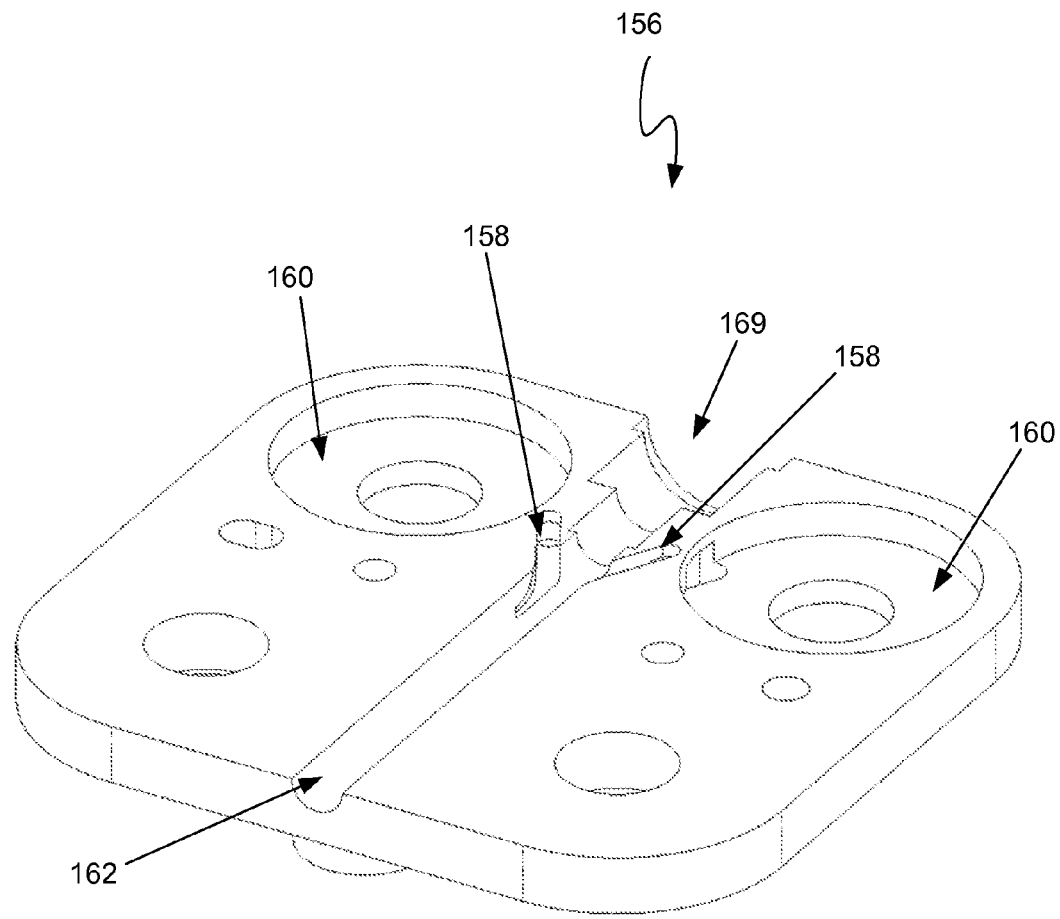
Figure 44:
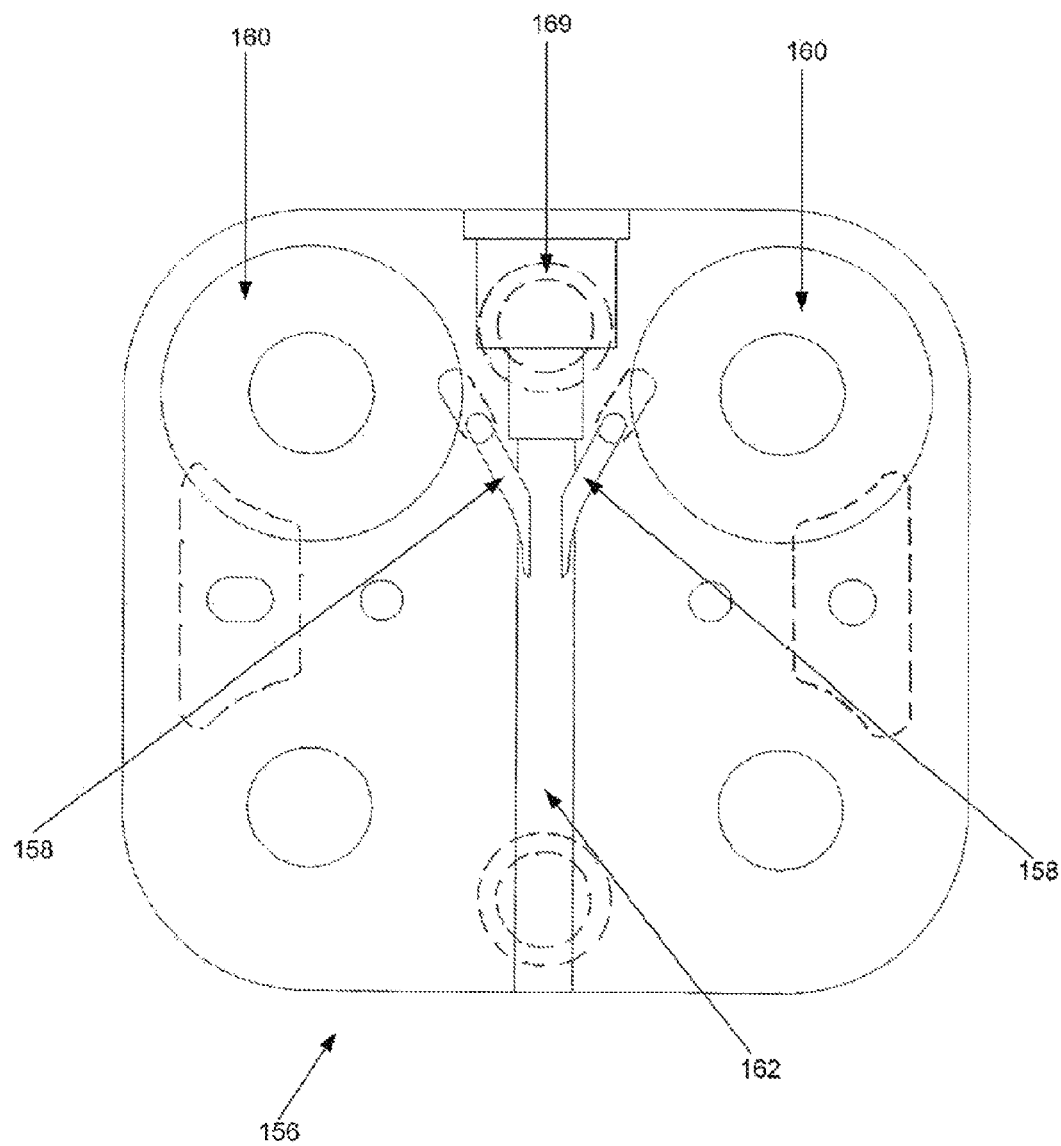
Figure 45:
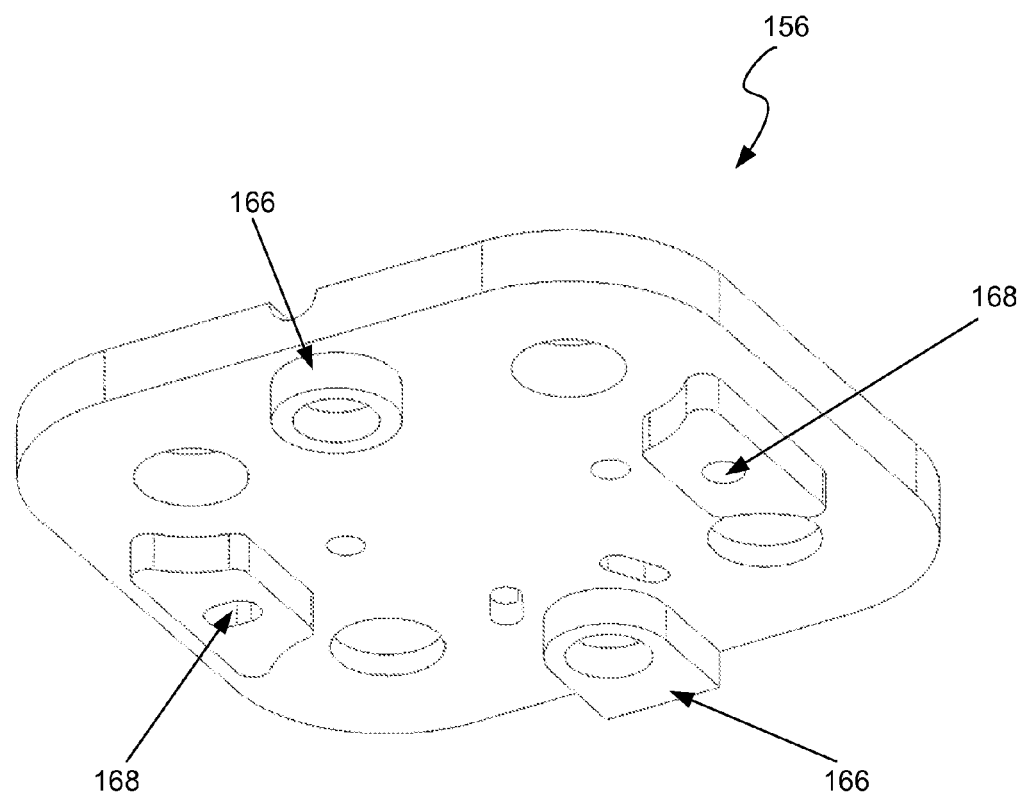
Figure 46:
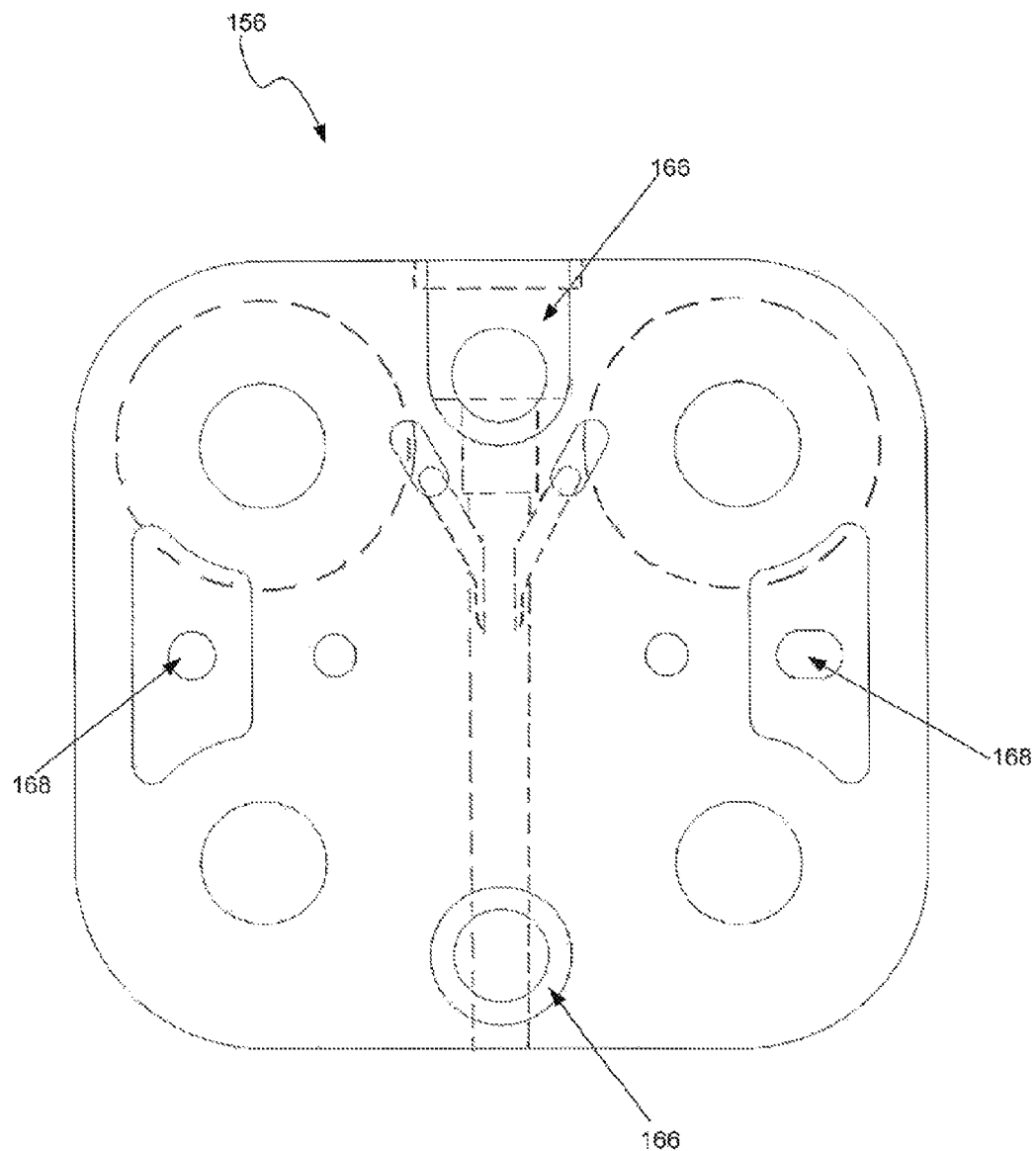

Referring to FIG. 43, a bottom portion (156) of one embodiment of a guide instrument base (48) is configured to interface with a top portion (152) such as that depicted in FIGS. 39-42. The bottom portion (156) has two additional pulley geometry accommodations (160) and associated control element splay tracks (158). The top (152) and bottom (156) portions of the guide instrument base (48) are "sandwiched" together to capture the proximal portion (88) of a catheter member (90), and therefore the bottom portion (156) also has a catheter member geometry accommodation (162) and a seal geometry accommodation (164) formed into it. FIG. 44 depicts an orthogonal view of the structures of FIG. 43 to better illustrate the control element splay track (158) structures positioned to guide control elements (not shown) away from a catheter member and to a pulley associated with the bottom portion (156) of the guide instrument base (48). FIG. 45 depicts an underside isometric view of the same bottom portion (156) shown in FIGS. 43 and 44. The bottom surface may comprise magnets (166) to facilitate mounting of the instrument upon an instrument driver 16. The depicted embodiment also has mounting pin interface holes (168) formed through it to accommodate mounting pins from an instrument driver 16. Further, the bottom surface preferably has a generally asymmetric geometry to ensure that it will only fit an underlying instrument driver snugly in one way. FIG. 46 depicts an orthogonal view of the bottom portion (156) of the guide instrument base (48) embodiment of FIG. 45.

Figure 47:
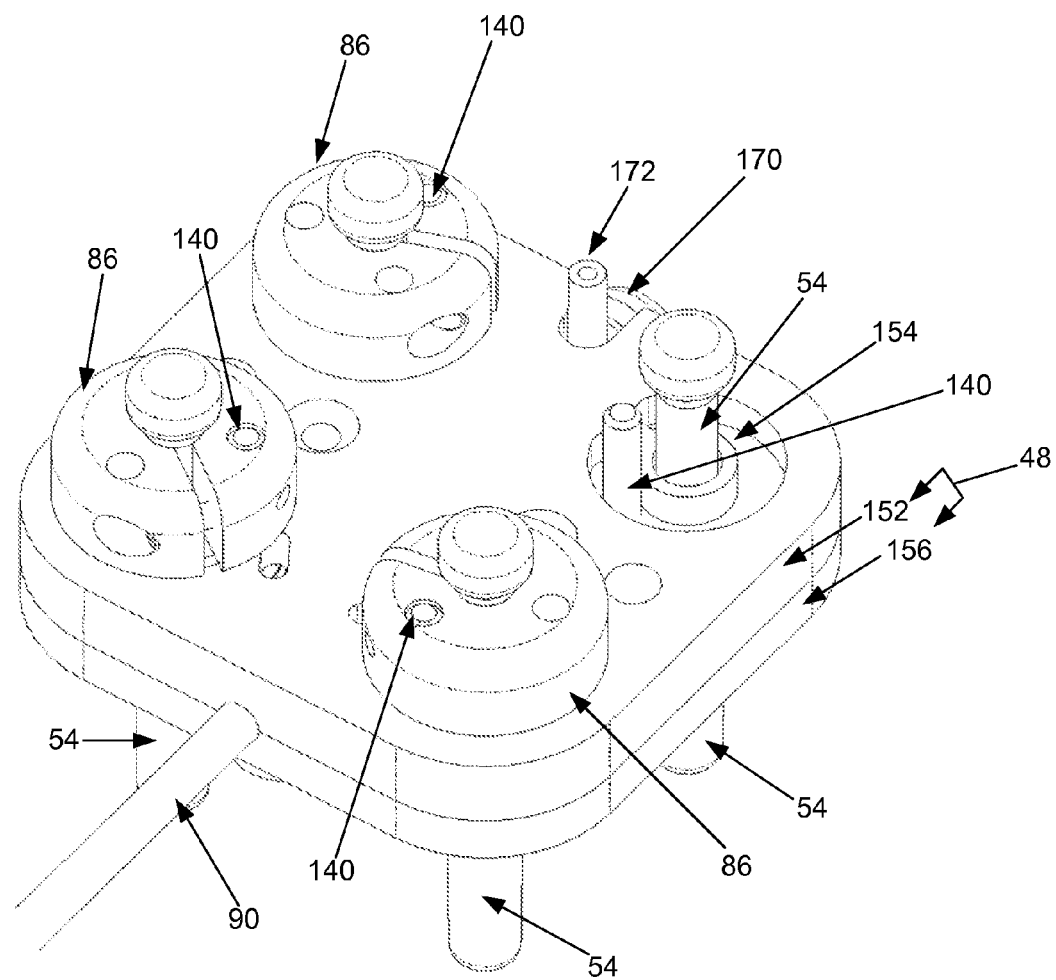
Figure 48:
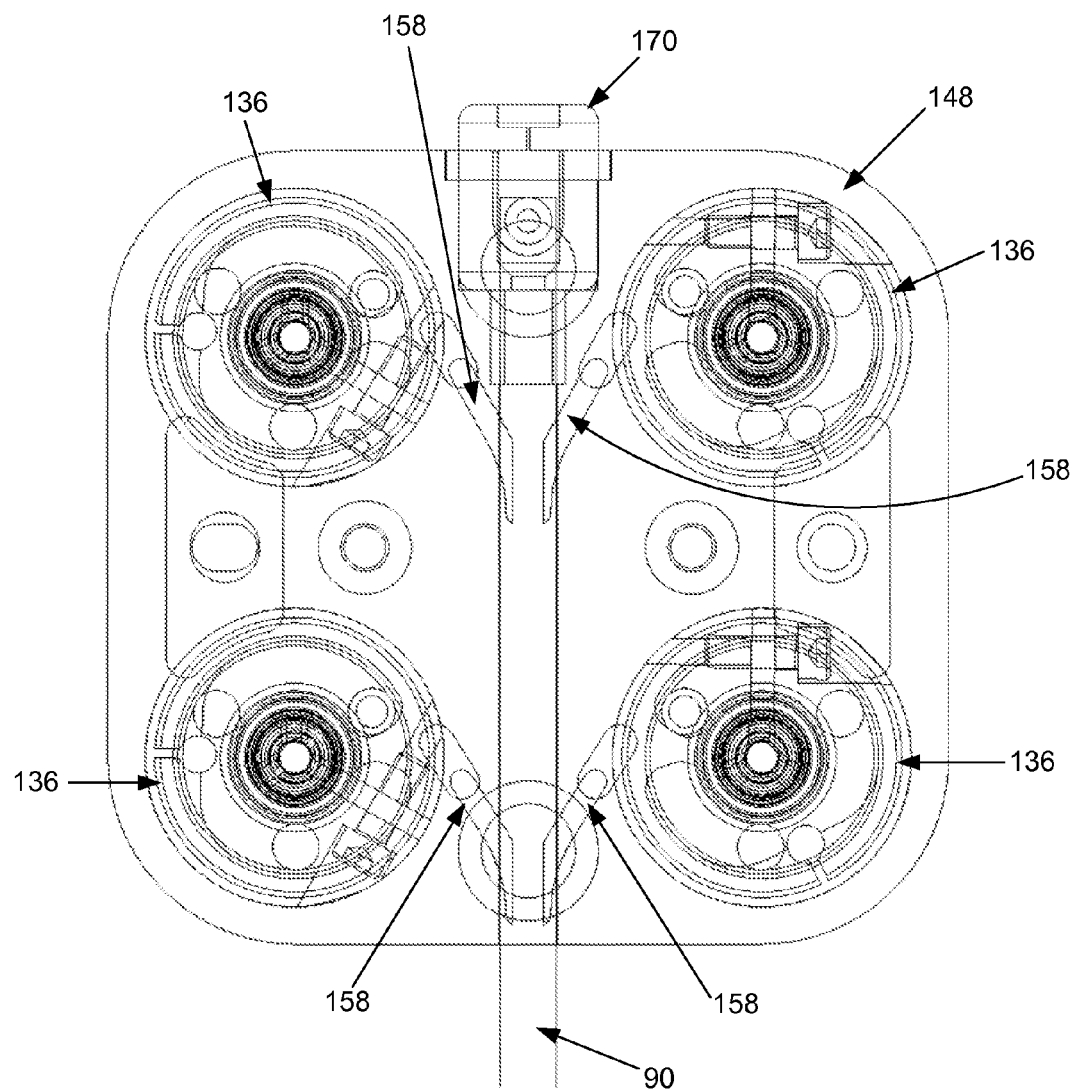
Figure 49:
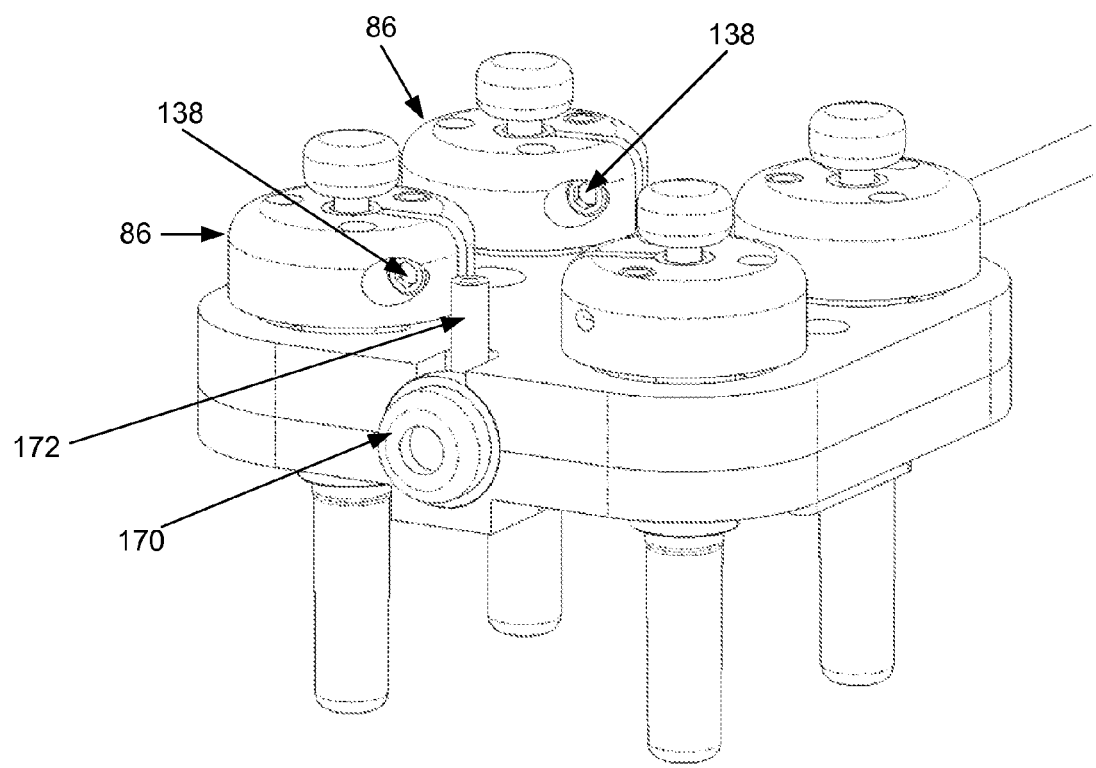

FIG. 47 illustrates one embodiment of a partially assembled instrument proximal end (82), including a top portion (152) and bottom portion (156) of an instrument base (48) interfaced together. The proximal end (82) houses four pulleys (not shown), a catheter member (90), and a seal (170), including and a purging port (172). Three manual adjustment knobs (86) are shown mounted to the guide instrument base (48) by axles (54), which are held in place by pulleys (not visible) mounted upon the axles (54). Rotational range of motion limitation pins (140) interface with the manual adjustment knobs and slots (154) in the guide instrument base (48) top portion (152). One of the four manual adjustment knobs 86 has been omitted from the illustration in FIG. 47 to better illustrate the interaction between the motion limitation pin (140) and slot (154). FIG. 48 shows the locations of the control element pulleys (136) and control element splay tracks (158) within this four-control element embodiment. Control elements (not shown) preferably comprise solid wires made from materials such as stainless steel, which are sized for the anticipated loads and geometric parameters of the particular application. They may be coated with materials such as a Teflon® fluoropolymer resin from DuPont of Wilmington, Del. to reduce friction forces. FIG. 49 illustrates a different isometric view of an instrument base similar to the embodiment of FIG. 47 to better illustrate the seal (170) and purging port (172) positioning, as well as the clamp screws (138) of the manual adjustment knobs (86). The seal (170) preferably comprises a silicon rubber seal configured to accommodate insertion of working members or instruments, such as, e.g., relatively small profile guidewires (e.g., in the range of 0.035" diameter), or relatively larger profile catheters (e.g., of up to 7 French or even larger).

Referring to FIGS. 50-73, other embodiments of instruments are depicted having the respective capabilities to drive two, three, or four control elements with less than four control element interface assemblies (132) as previously discussed. For ease in illustration, many of the same components are utilized in these embodiments. As will be appreciated by those skilled in the art, such component matching is by no means required to accomplish the described functions, and many alternative arrangements are possible within the scope of the inventions disclosed herein.

Figure 50:
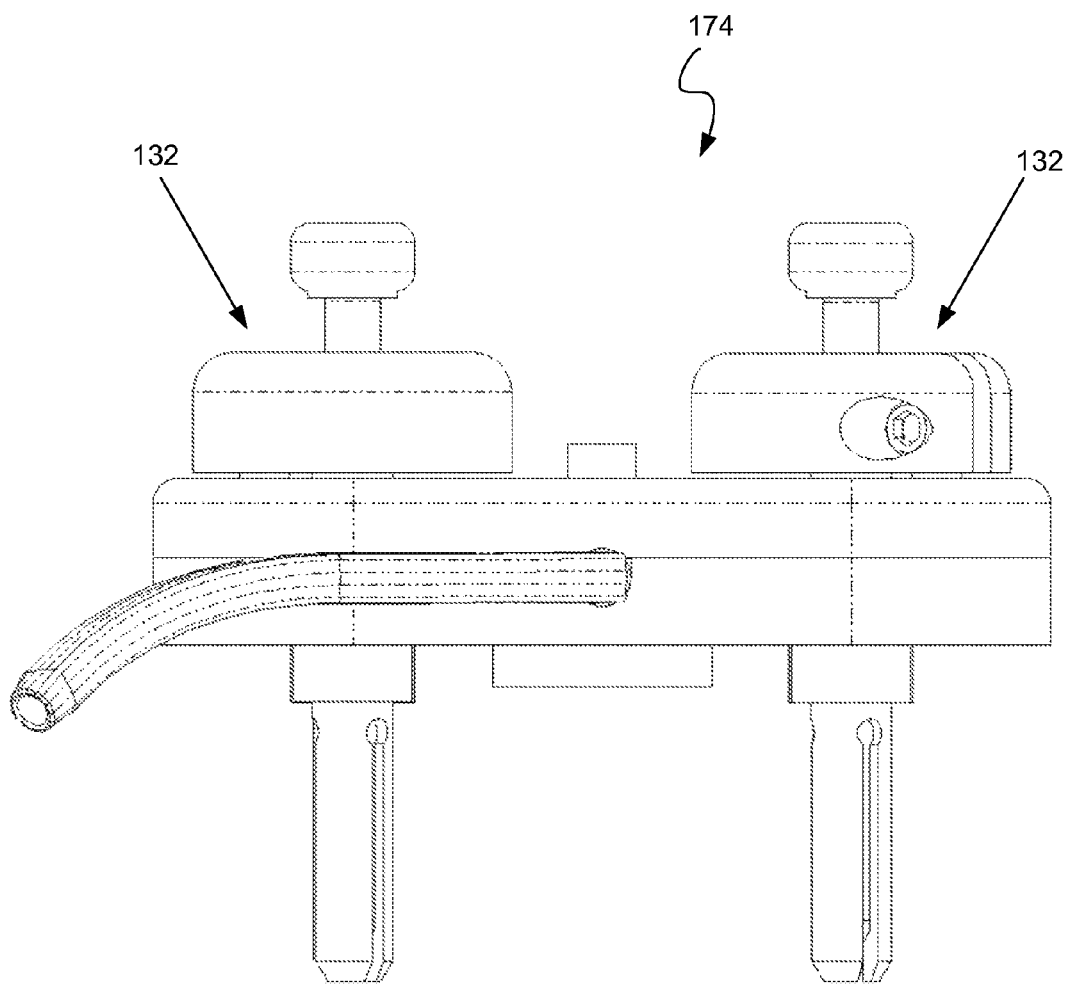
FIGS. 50-73 illustrate alternative embodiments of instruments.
Figure 51:
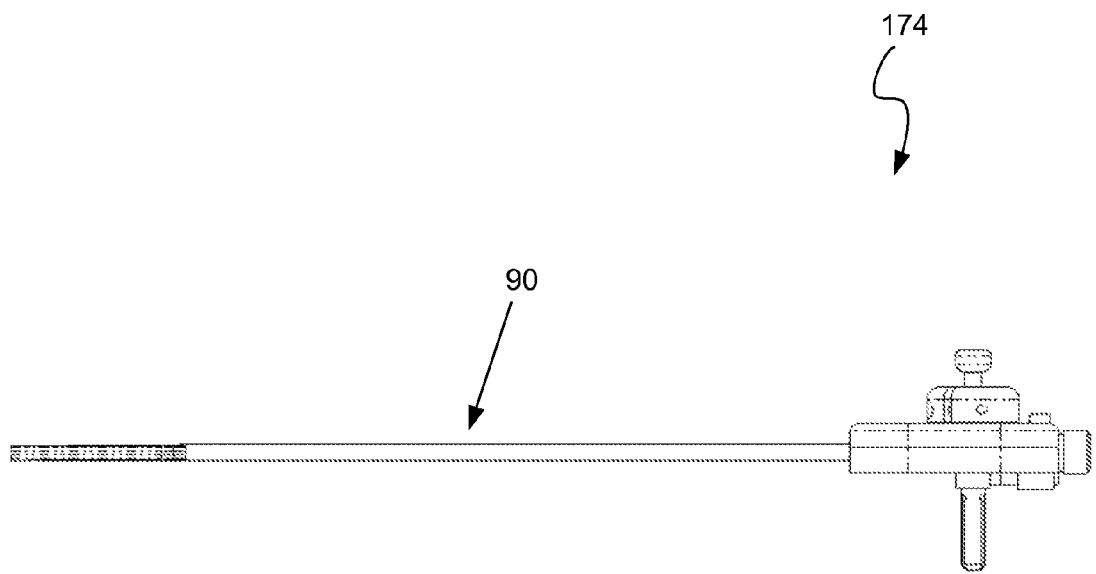
Figure 52:
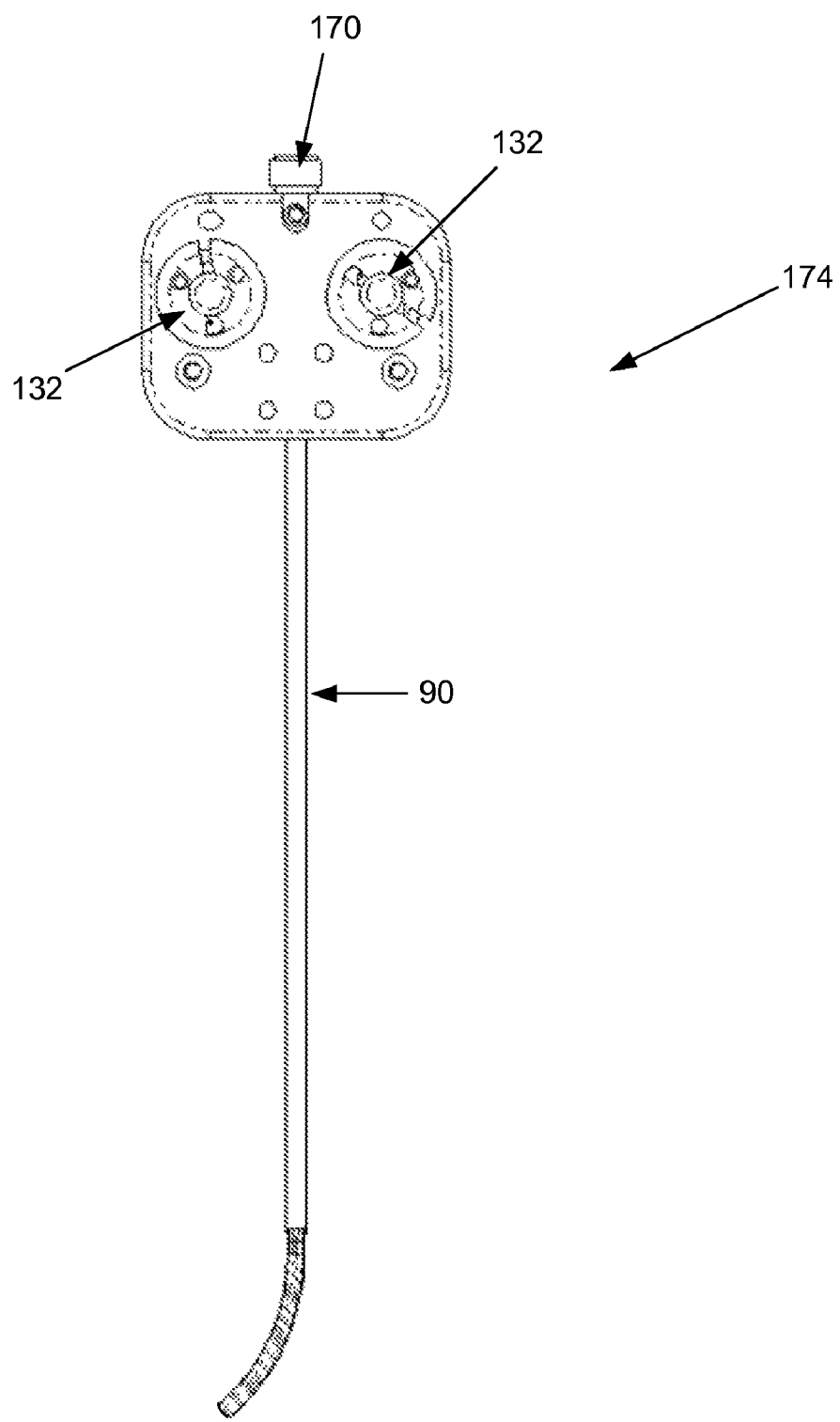
Figure 53:
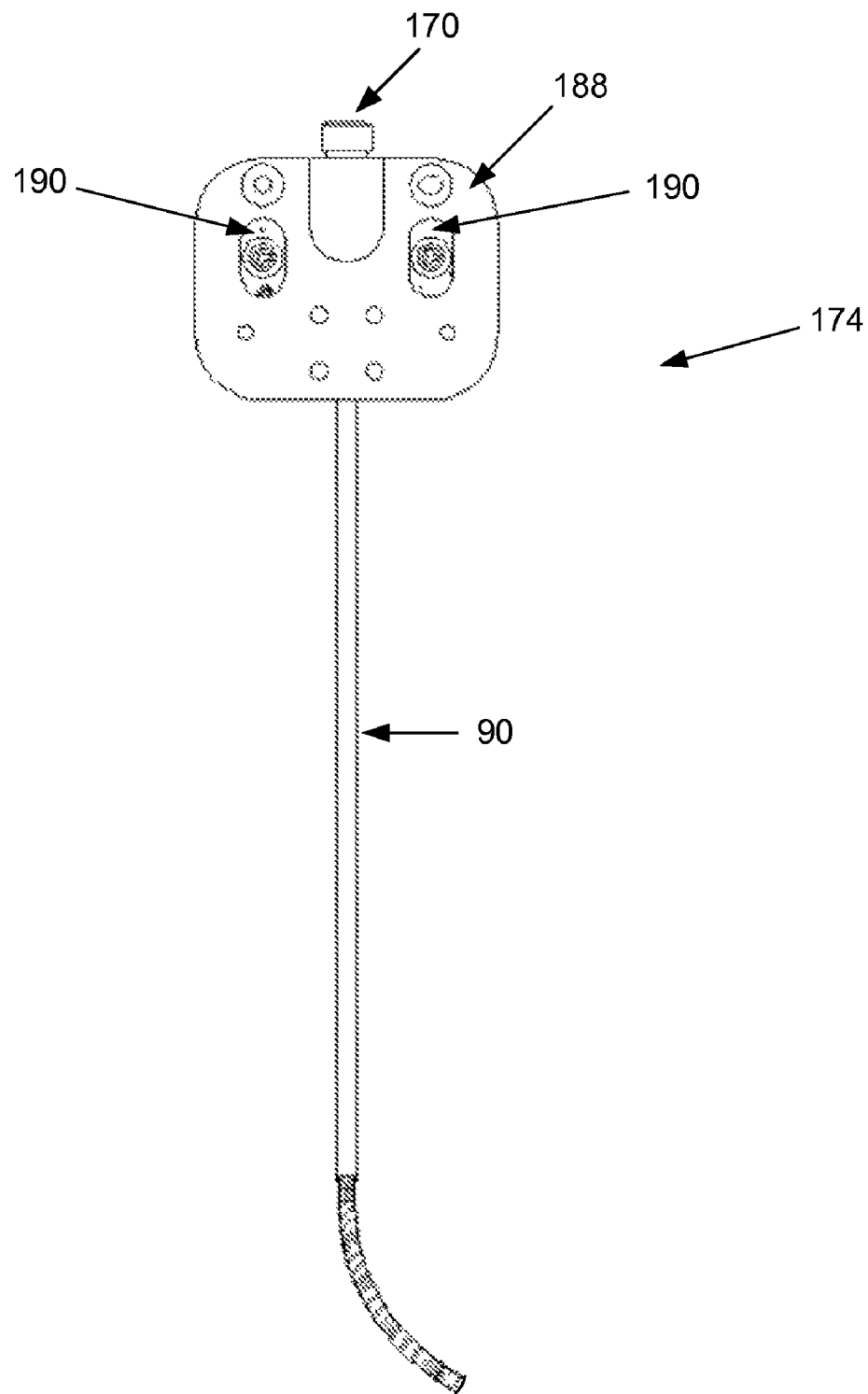
Figure 54:
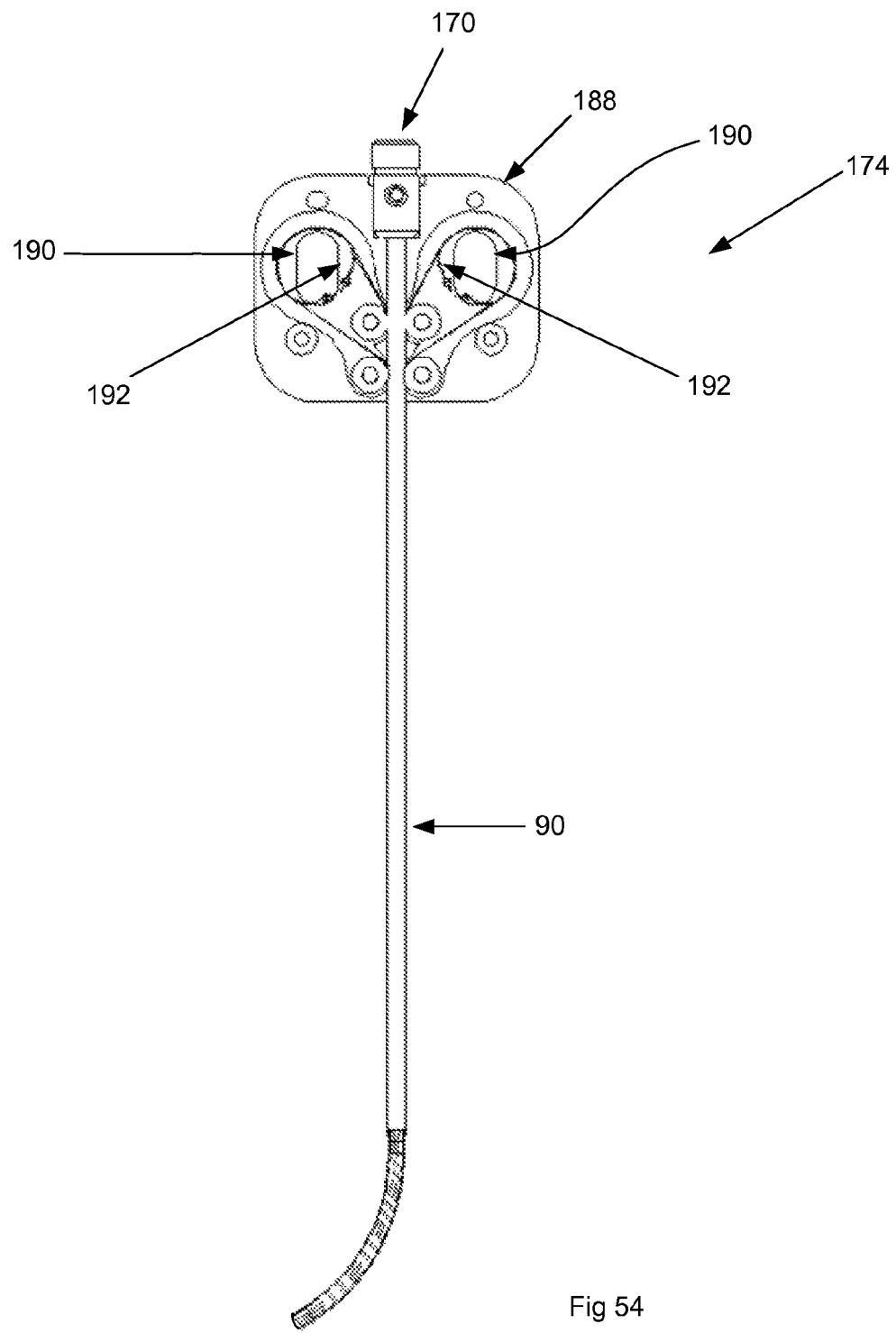

FIGS. 50, 51, and 52 illustrate an instrument (174) having two control element interface assemblies (132) is depicted in three orthogonal views. While this embodiment has only two control element interface assemblies, it is configured to drive four control elements and keep them in tension through either pre-tensioning, or active tensioning through a slotted guide instrument base (188) to a tensioning mechanism in the instrument driver (16). FIG. 53 illustrates an instrument (174) similar to that in FIG. 52, but shown from a back or bottom side orthogonal view. In particular, one side of the guide instrument base (188) includes slots (190) through which an instrument driver tensioning mechanism may keep control elements taut during operation of the instrument (174). FIG. 54 is a reverse orthogonal view of the structure in FIG. 53, with one side of the guide instrument base and both control element interface assemblies removed (132) to show the slots (190) and four control elements (192).

Figure 55:
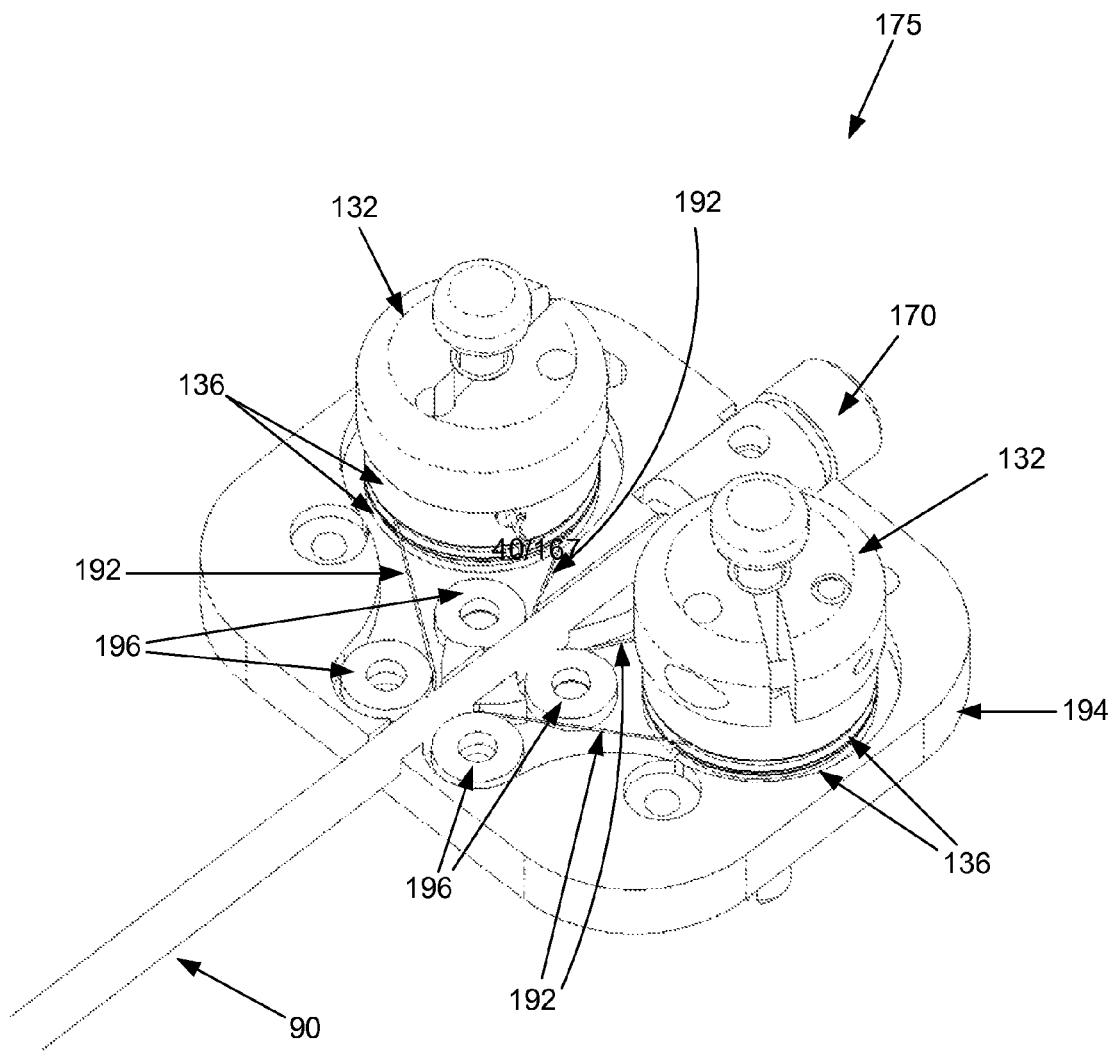
Figure 56:
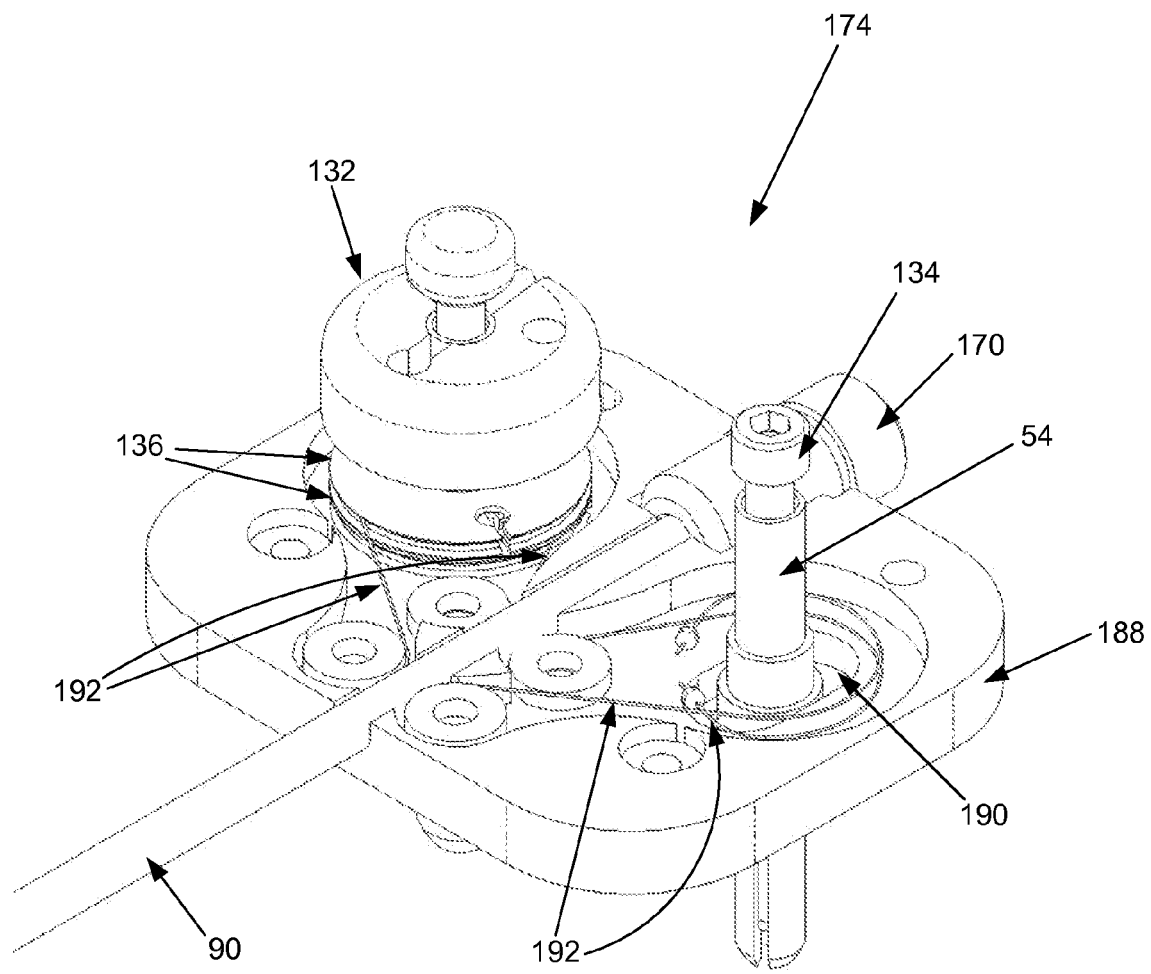

FIG. 55 illustrates an instrument (175) similar to that in FIGS. 53 and 54, with the exception that the guide instrument base (194) does not have slots—but rather has only fixed idler control element pathways (196) to align the cables with the sets of two pulleys (136) comprising each control element interface assembly (132). In this embodiment, tension may be maintained in the control elements (192), with pre-tensioning, or pre-stressing, to prevent control element slack. FIG. 56 also illustrates an instrument (174) similar to that of FIGS. 53 and 54, including slots to allow for active tensioning of the control elements (192) from the underlying instrument driver. One of the control element interface assemblies (132) is shown intact, and one is shown partially intact, with the axle (54) and drive engagement knob (134) depicted to show the control elements (192). A notable difference between the embodiment in FIG. 56 and that in FIG. 55 is the addition of the tensioning slots (190).

Figure 57:
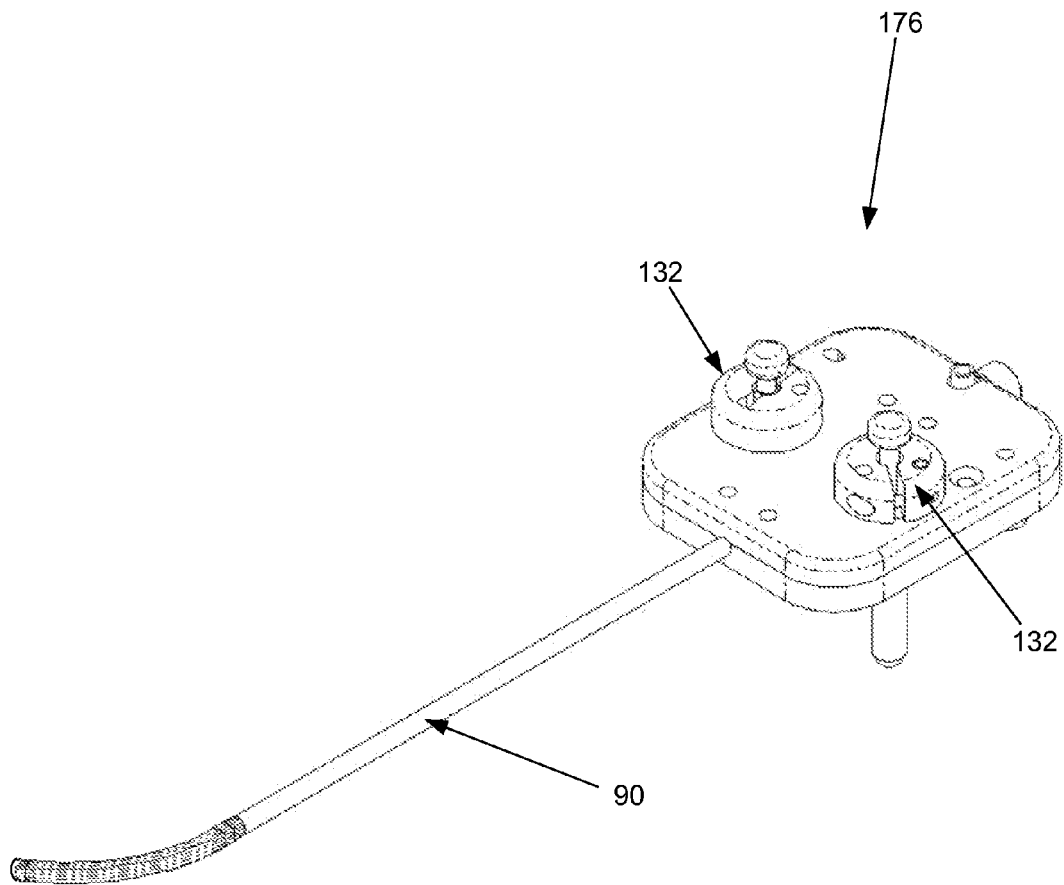
Figure 58:
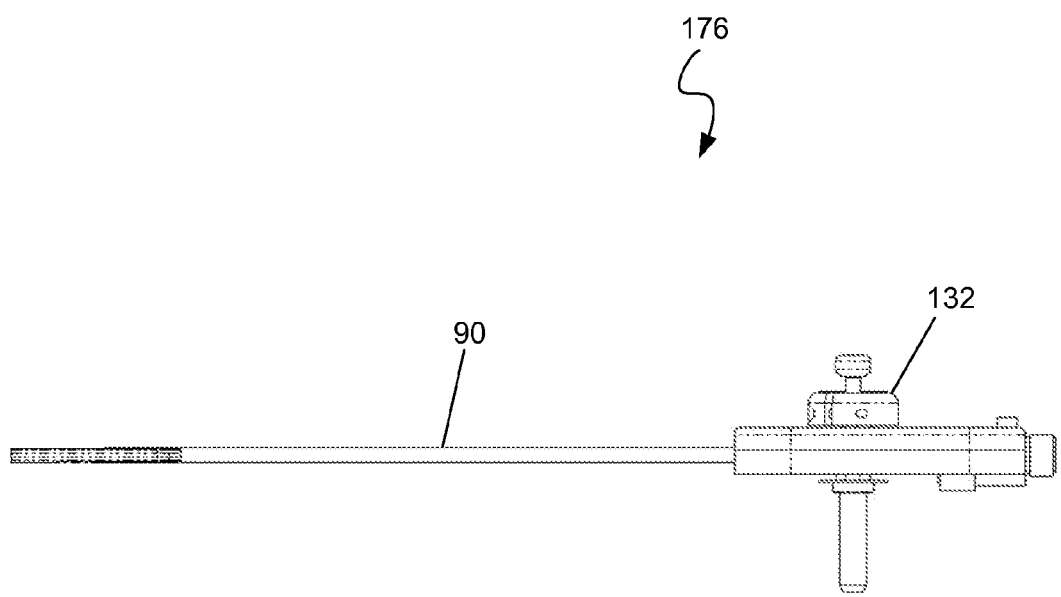
Figure 59:
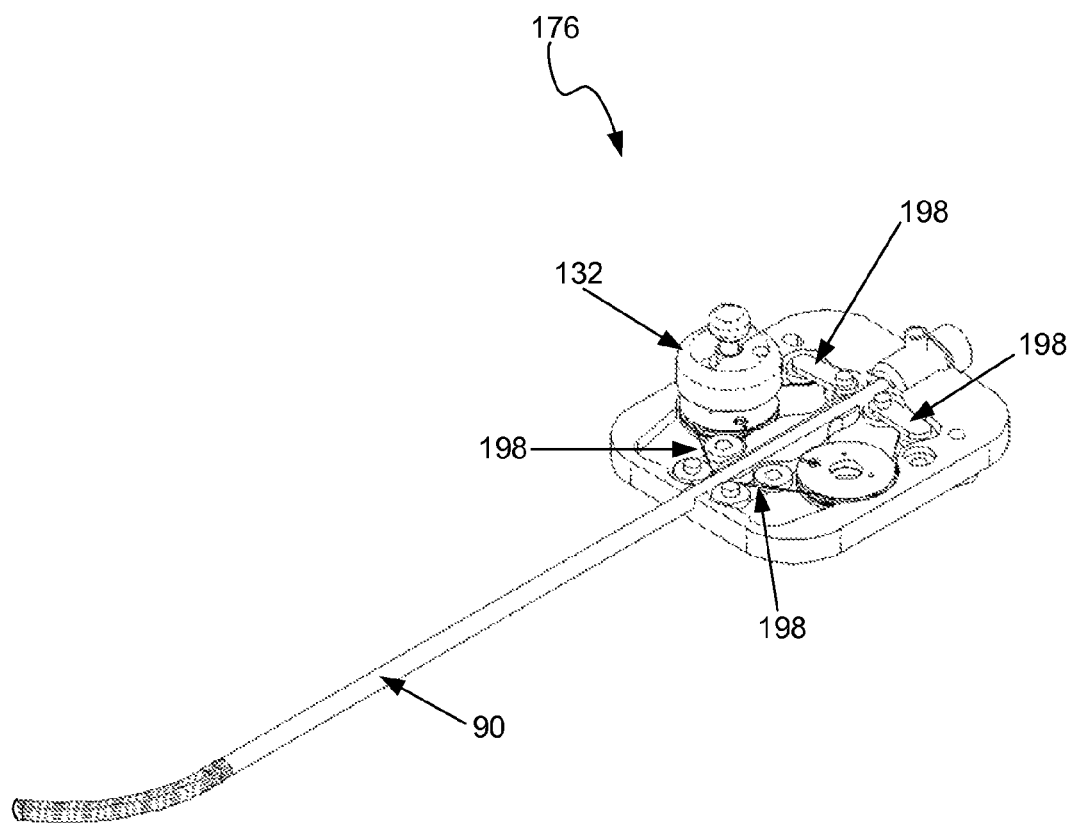
Figure 60:
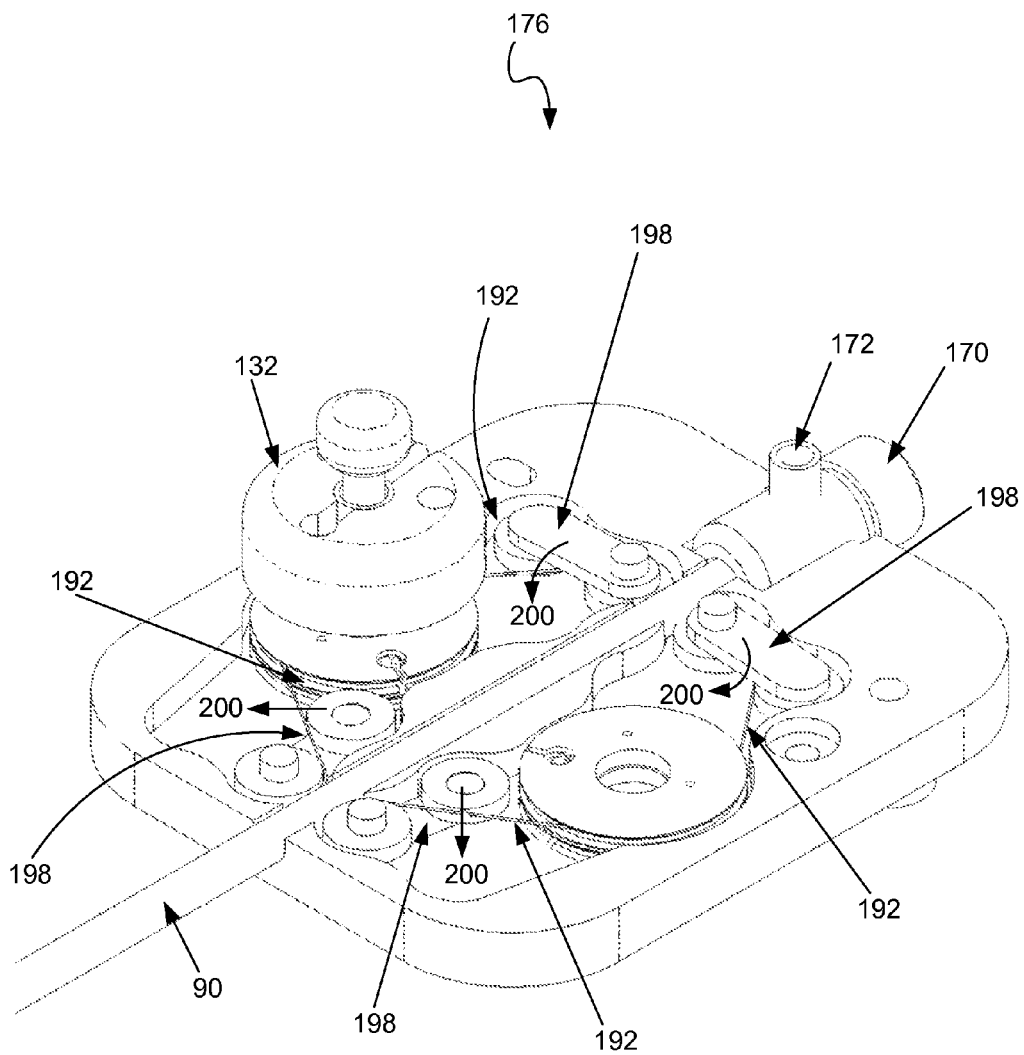
Figure 61:
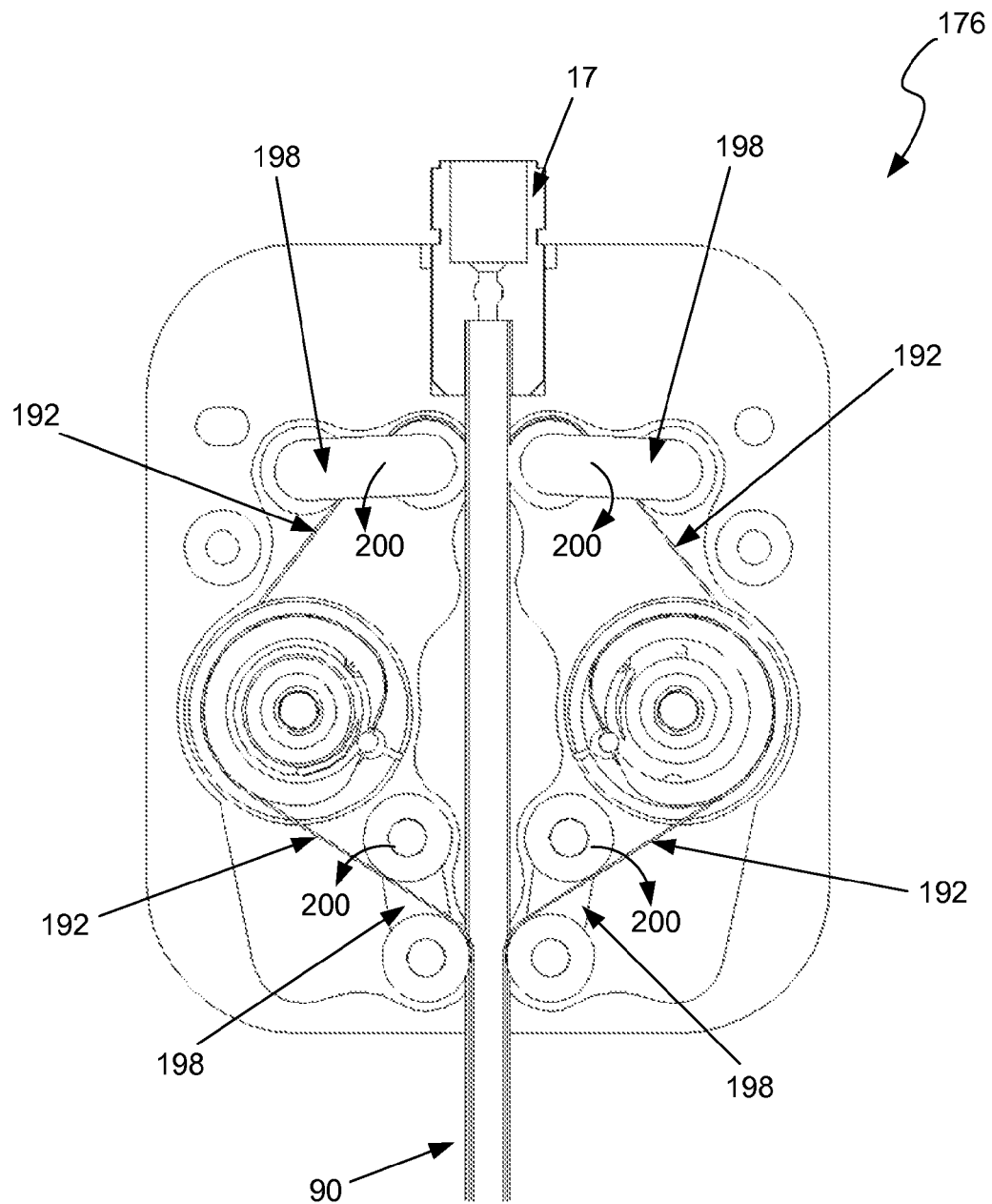
Figure 62:
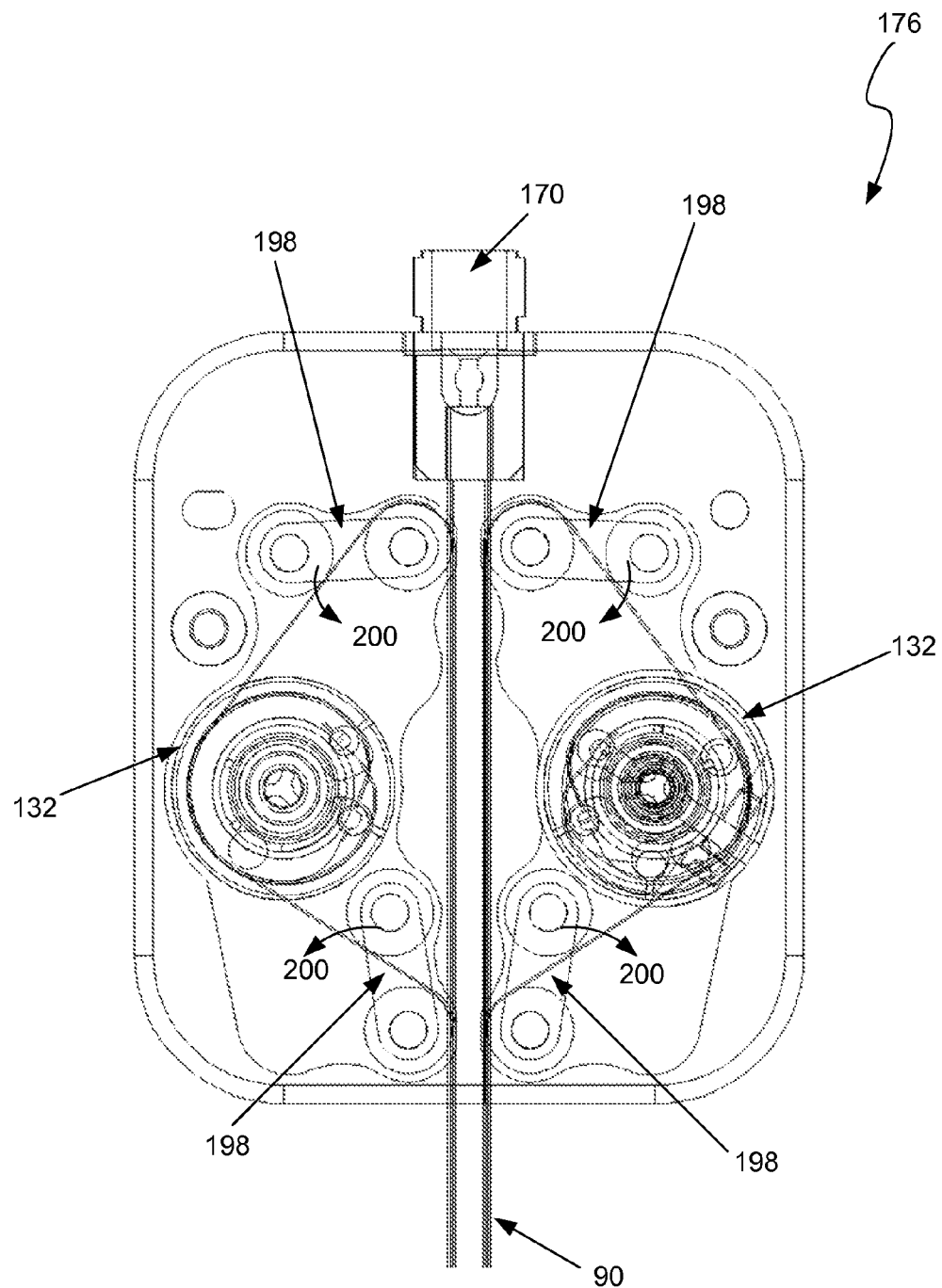

Referring to FIGS. 57 and 58, yet another instrument embodiment (176) is depicted in isometric and side views, respectively, with this embodiment having two control element interface assemblies (132) to drive four control elements (192). As shown in the partial cutaway isometric view of FIG. 59, and close up cutaway view of FIG. 60, this embodiment differs from the fixed idler embodiment of FIG. 55, or the slotted embodiment of FIG. 56, in that it has four spring-loaded idlers (198) to assist with tensioning each of the four control elements (192). Referring to FIG. 60, each of the control elements (192) passes through a spring loaded idler (198), which urges the control element (192) into tension by trying to rotate (200). This tensioning schema may be easiest to visualize in the orthogonal cutaway view of FIG. 61, wherein the spring loaded idlers (198) are depicted urging (200) the four control elements (192) into tension. The wireframe orthogonal view of FIG. 62 also shows the stacks of two pulleys (136) each on each control element interface assembly (132) to accommodate four control elements (192).

Figure 63:
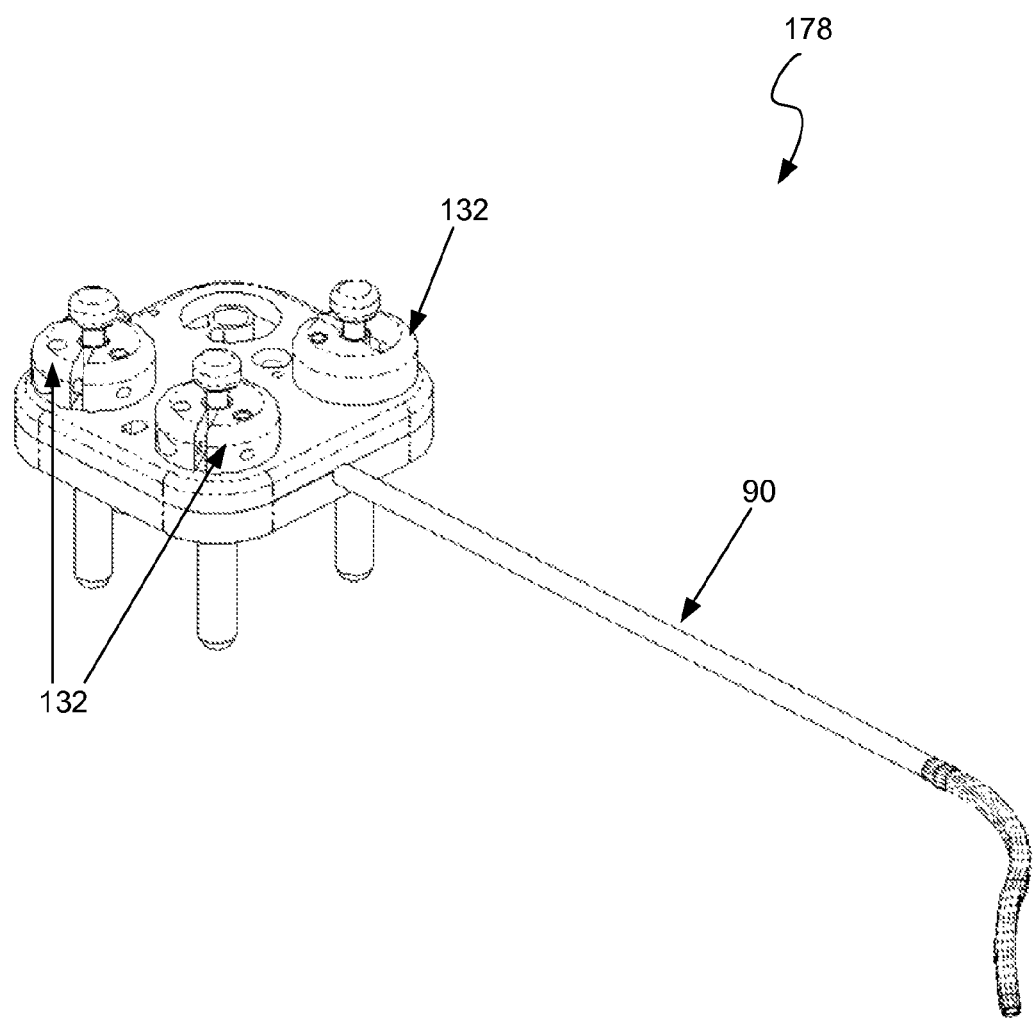
Figure 64:
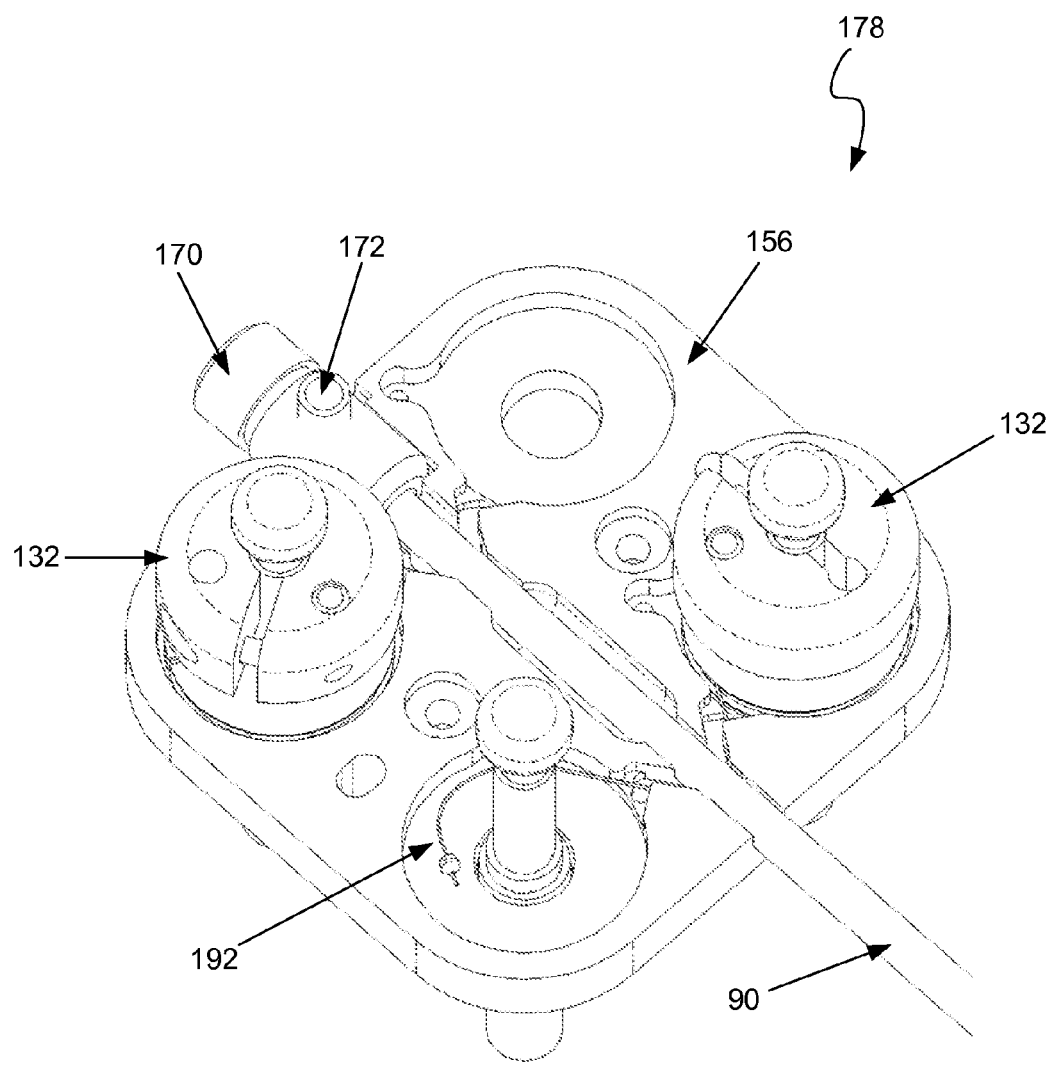
Figure 65:
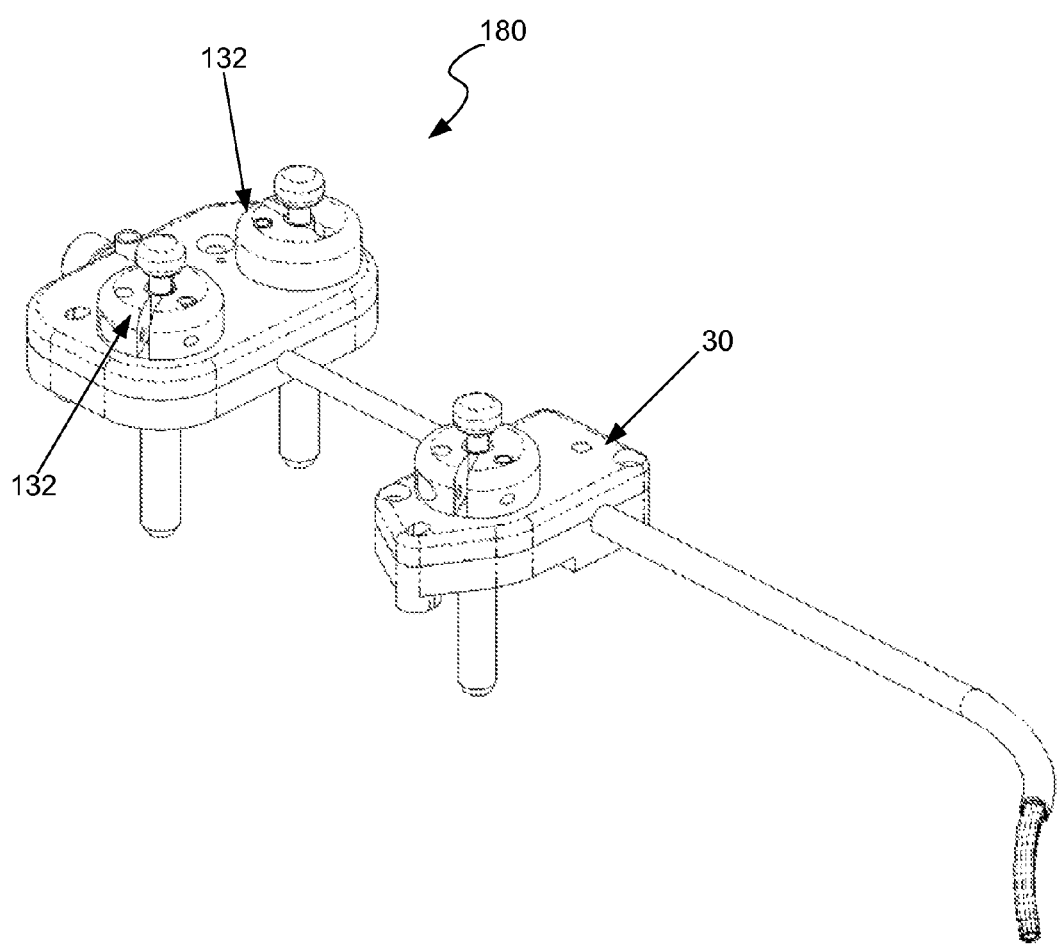
Figure 66:
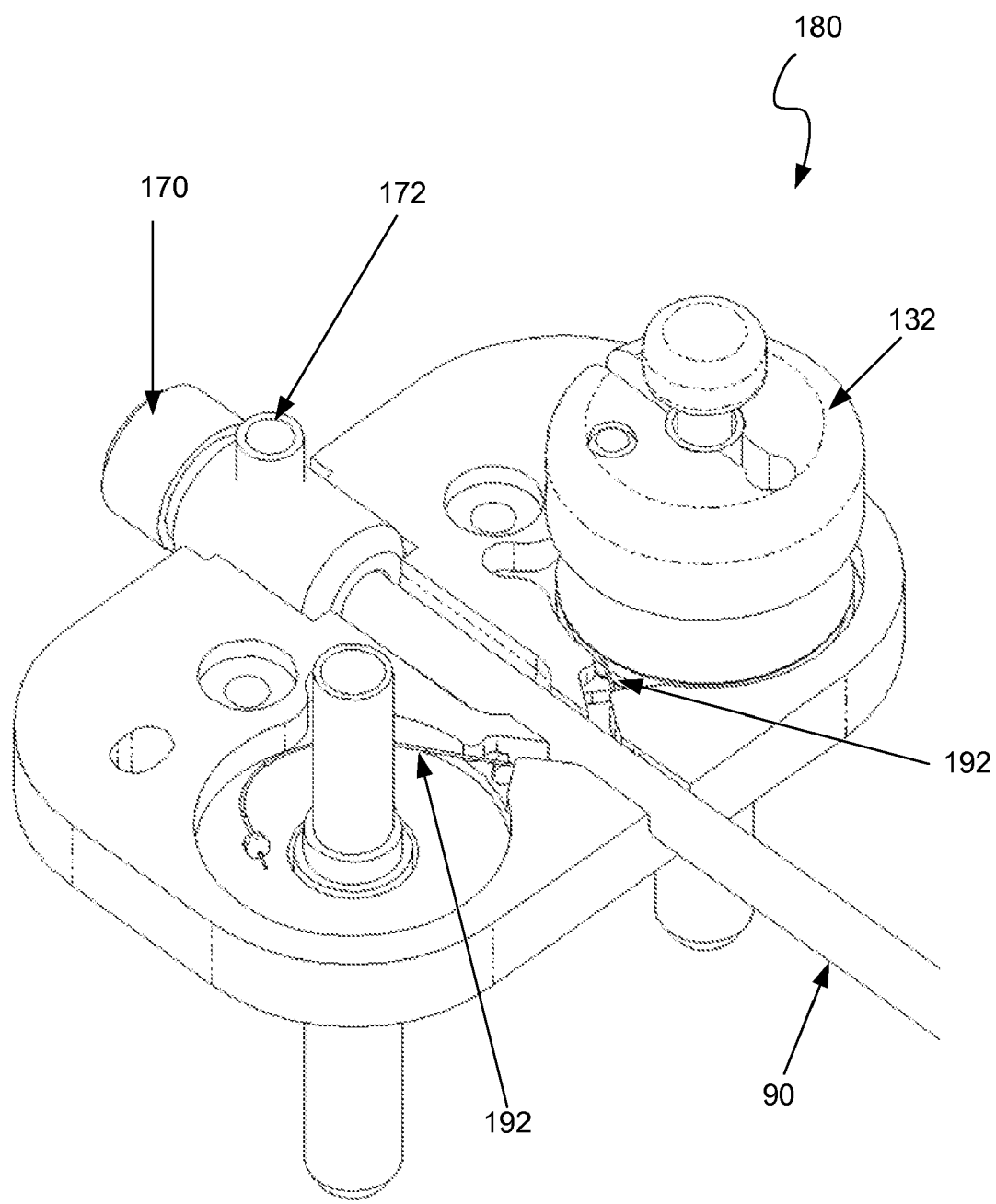

FIGS. 63 and 64 depict another instrument embodiment (178), this one having three control element interface assemblies (132) for three independent control elements (192). As best seen in FIG. 64, this embodiment is similar to that of FIG. 47, for example, except that it has one less control element and one less control element interface assembly (132). FIG. 65 depicts yet another guide instrument embodiment (180) coupled with a sheath instrument (30). In particular, instrument (180) has two control element interface assemblies (132) and two control elements. As seen in FIG. 66, the guide instrument (180) of this embodiment is not configured for slotted tensioning or spring-loaded tensioning. Instead, the control elements (192) of this embodiment may be actively tensioned independently, and/or pre-tensioned, to facilitate maintenance of tension for control purposes.

Figure 67:
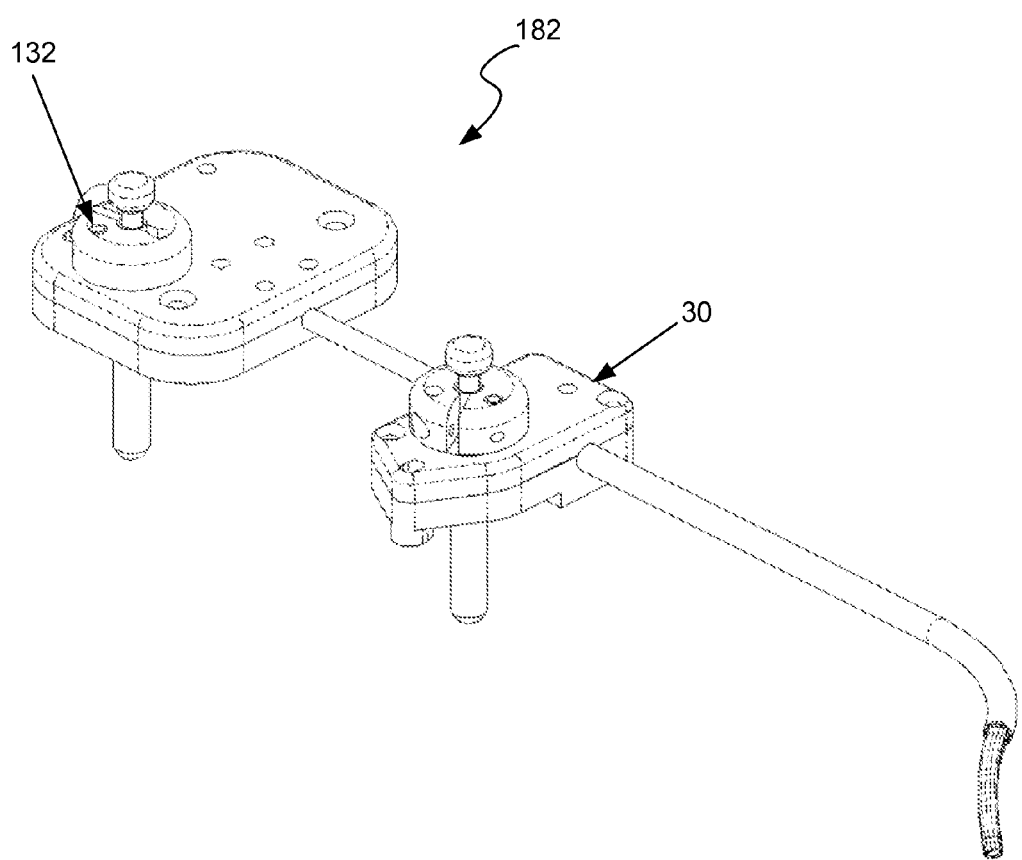
Figure 68:
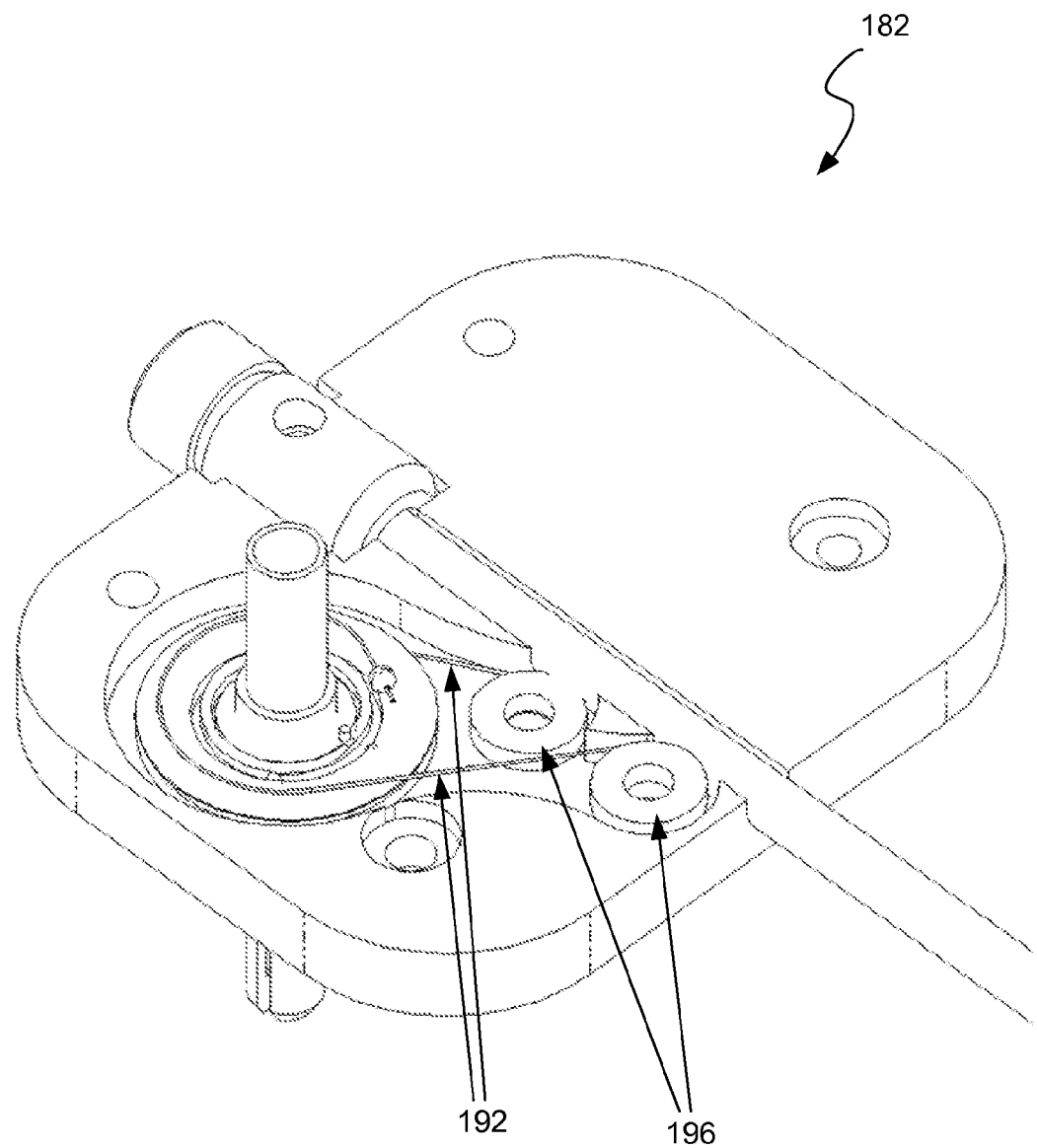
Figure 69:
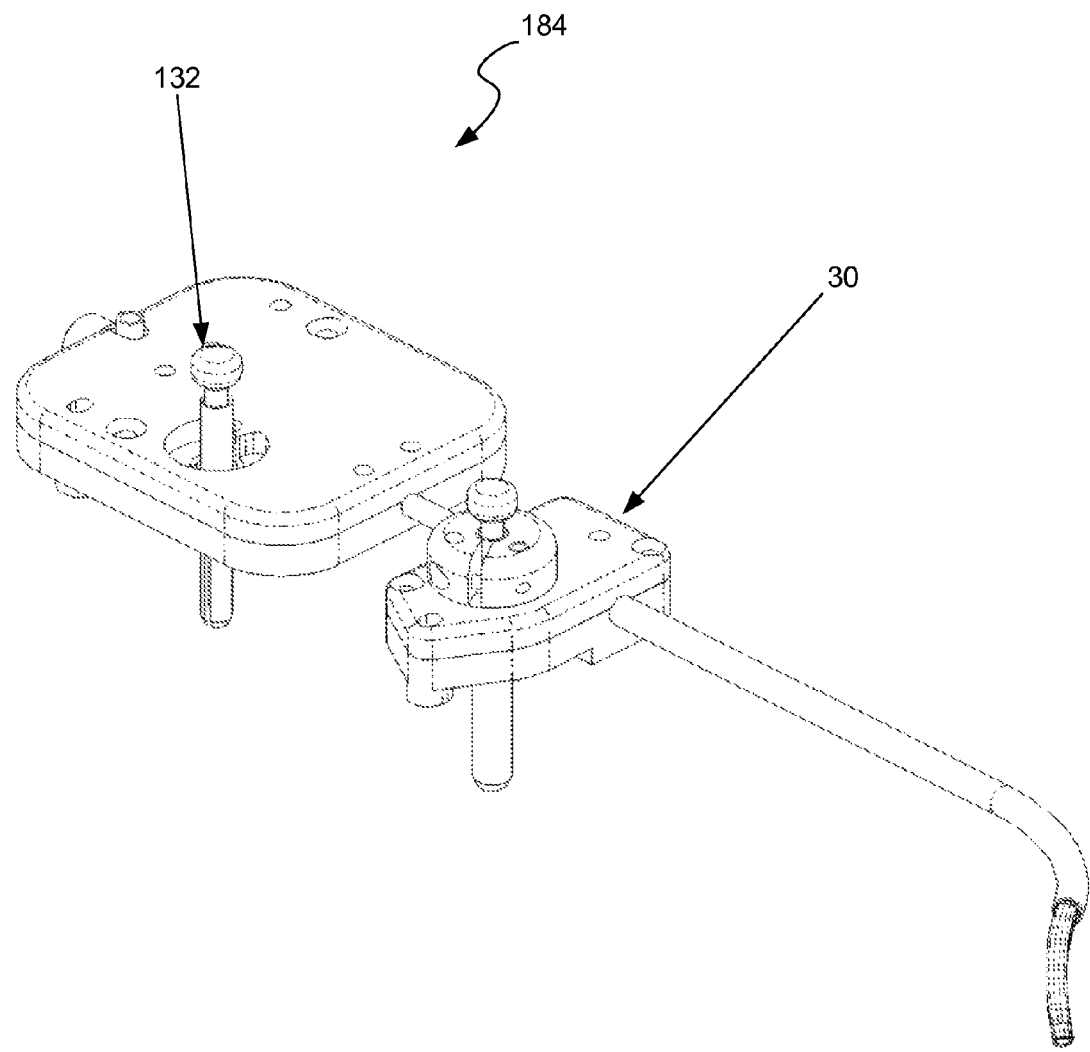
Figure 70:
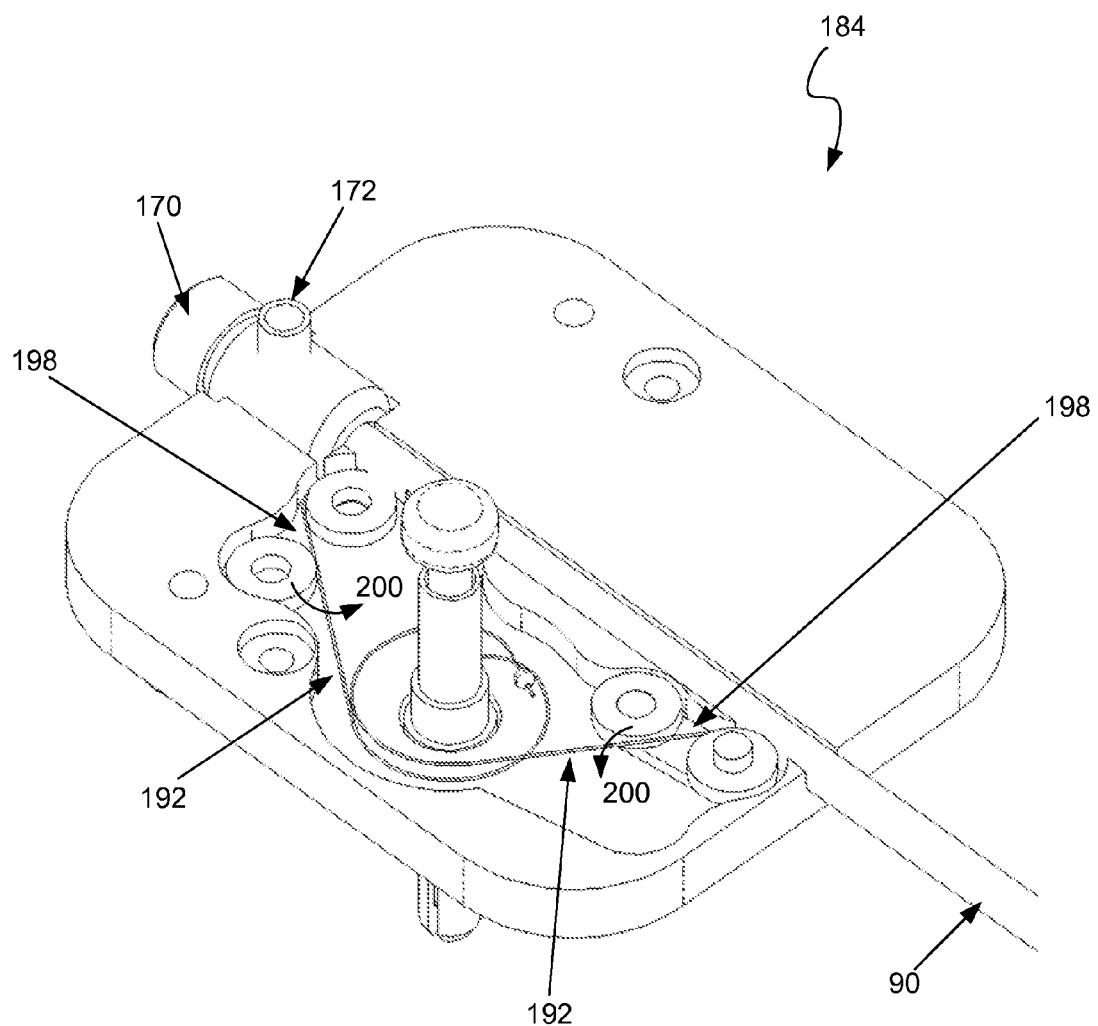

Referring to FIG. 67, yet another instrument embodiment (182) is shown coupled with a sheath instrument (30). Instrument (182) has a single control element interface assembly (132) and two control elements. As seen in FIG. 68, this embodiment of the instrument (182) is also not configured for slotted tensioning or spring-loaded tensioning. Instead, the control elements (192) of this embodiment may be pre-tensioned and kept in position with the help of a fixed idler control element pathway (196) to facilitate maintenance of tension for control purposes. FIG. 69 illustrates still another instrument embodiment (184), which is shown coupled with a sheath instrument (30). Instrument (184) has a single control element interface assembly (132) and two control elements (192), with a spring-loaded idler (198) tensioning of the control elements (192), as shown in FIG. 70. As with the aforementioned spring-loaded idler tensioning instrument embodiments, the spring-loaded idlers urge (200) the control elements (192) into tension to facilitate control.

Figure 71:
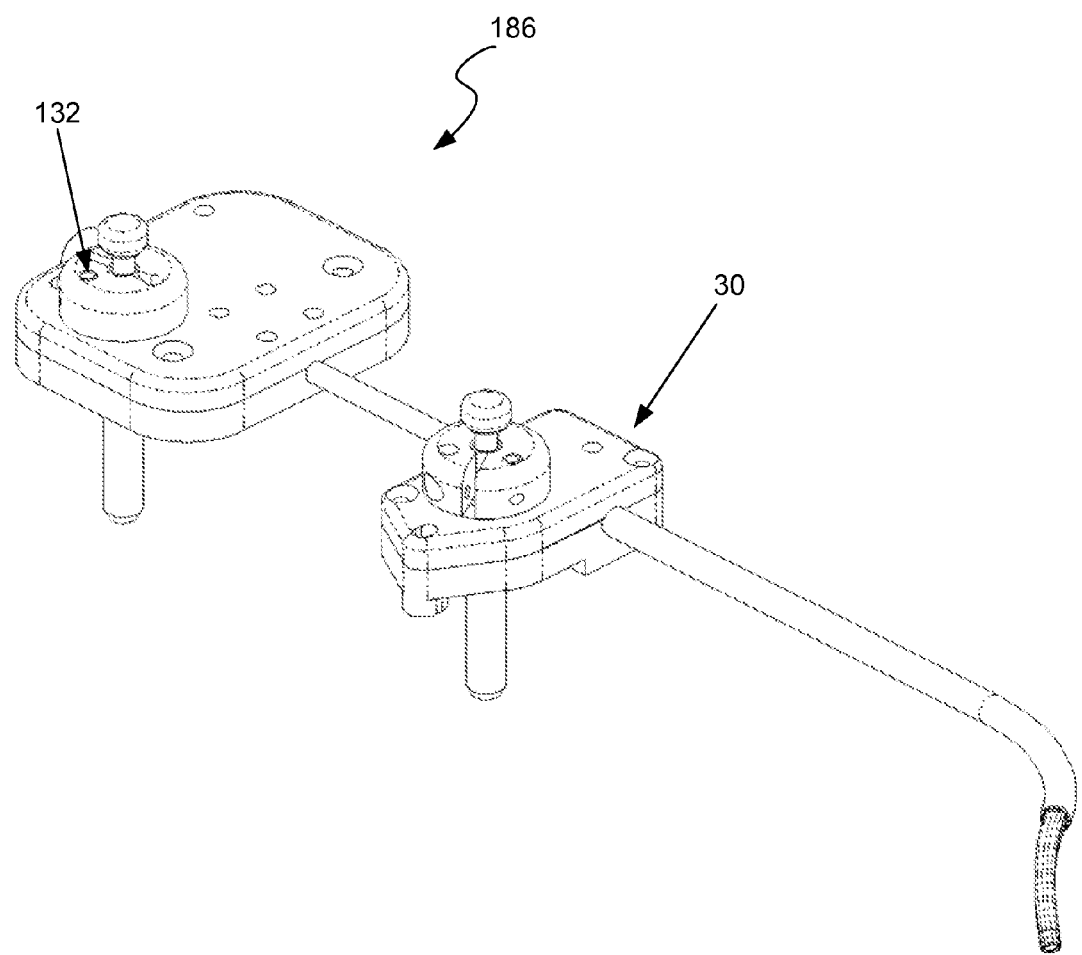
Figure 72:
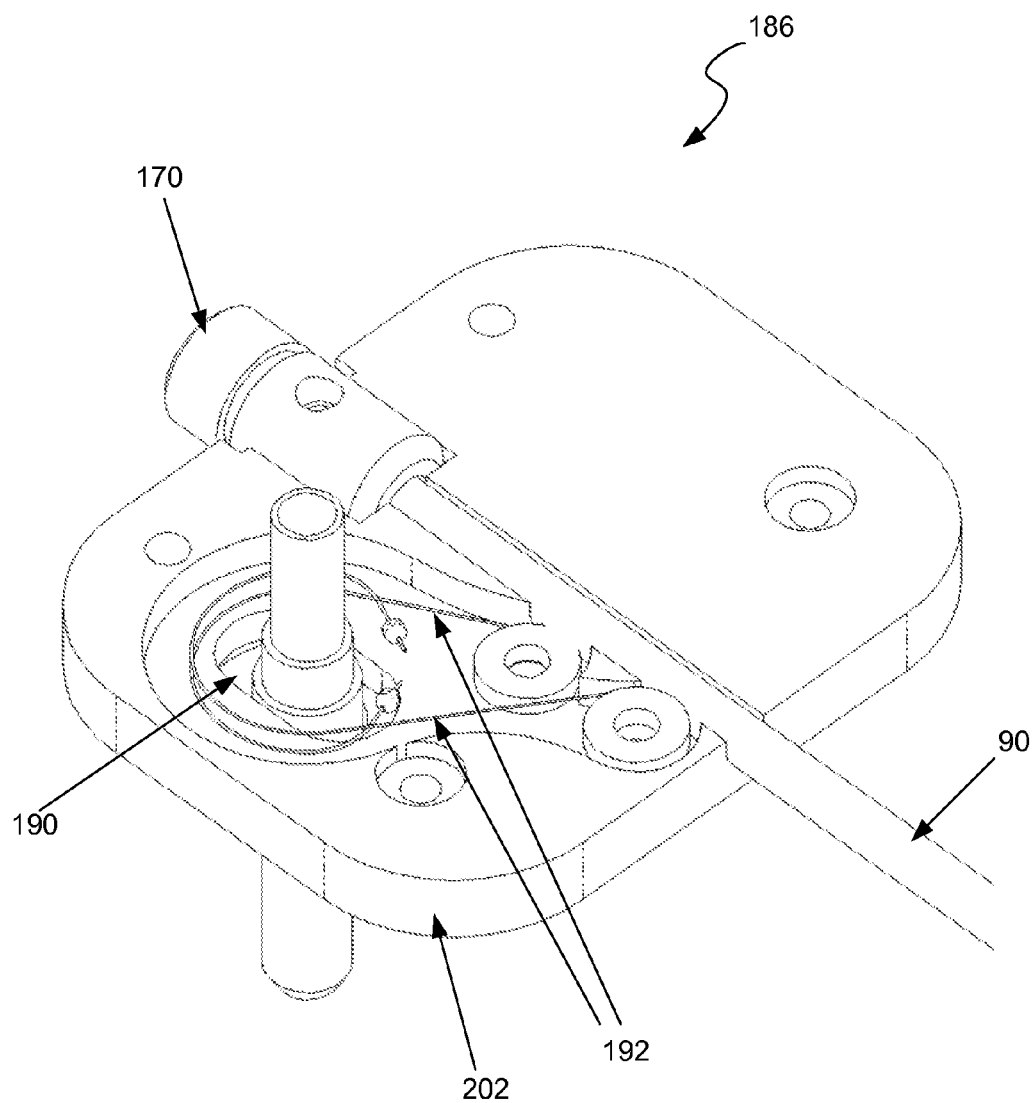
Figure 73:
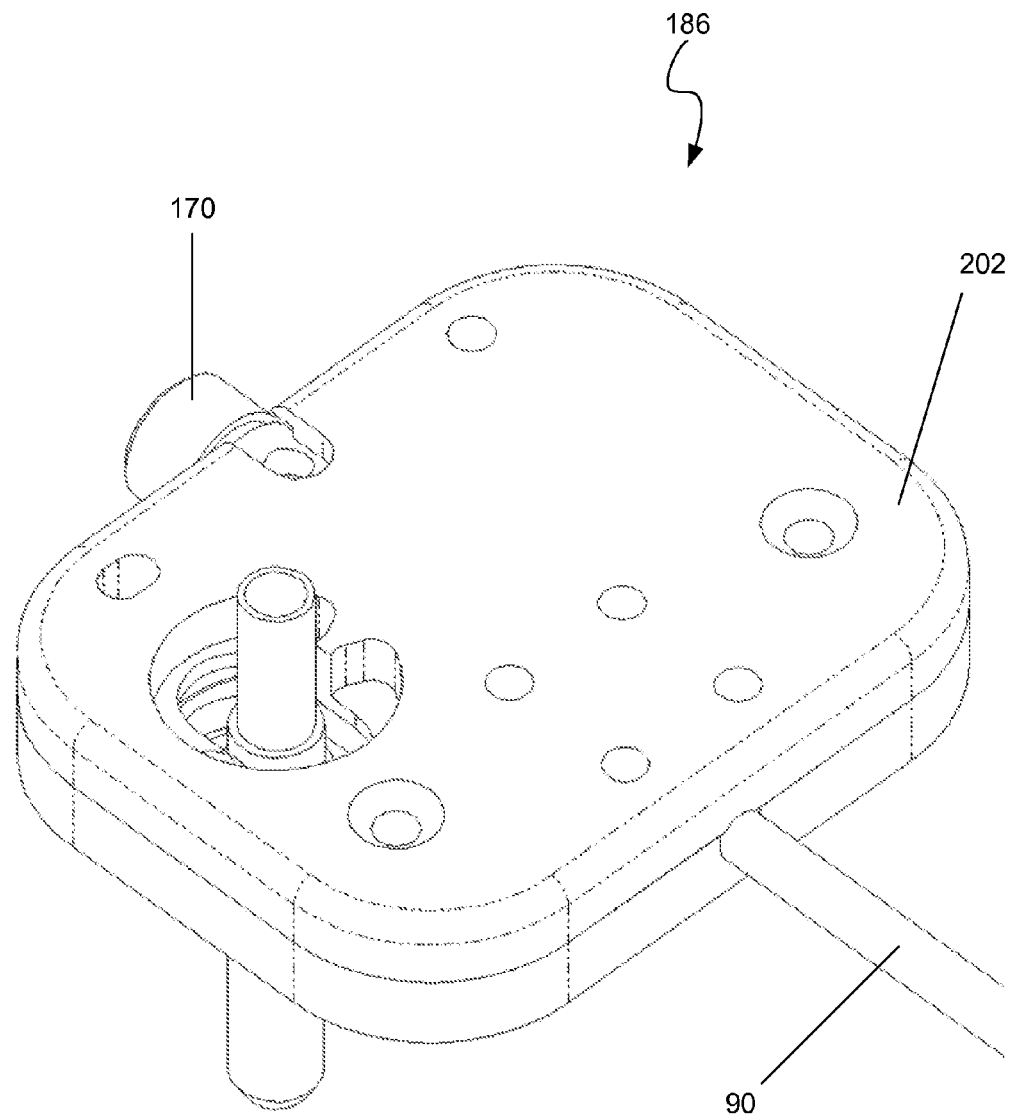

FIG. 71 illustrates a still further instrument embodiment (186), which is shown coupled with a sheath instrument (30). Instrument (186) has a single control element interface assembly (132) and two control elements (192), with a single-slotted guide instrument base, as shown in FIG. 72. As with the aforementioned slotted-tensioning instrument embodiments, the slot (190) facilitates tensioning of the control elements (192) from a mechanism in the instrument driver below (16). FIG. 73 depicts the embodiment of FIG. 72, with both portions of the slotted guide instrument base (202) intact. Depending upon the amount of tensioning deflection within the slot (190), it may be desirable to remove the rotational range of motion limitation pin (not shown) from the manual adjustment knob (not shown) to prevent impingement of the pin, knob, and instrument base (202), as the control element interface assembly (132) is moved in the slot (190) relative to the rest of the instrument base (202).

Referring to FIGS. 74-93, elements of a sheath instrument embodiment will now be described. Again, for ease in illustration, many of the same components from the previously described instrument embodiments is utilized in these further embodiments, although such component matching is by no means required to accomplish the described functions.

Figure 74:
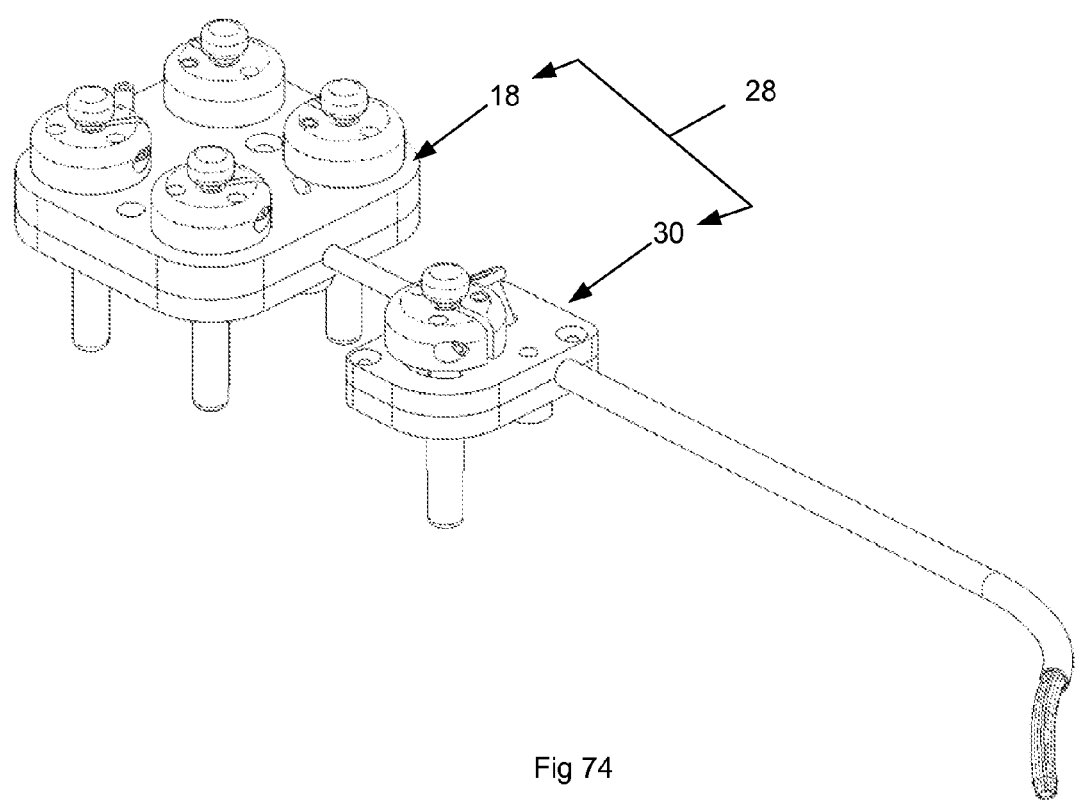
FIGS. 74-85 illustrate various aspects of a sheath instrument in accordance to one embodiment.
Figure 75:
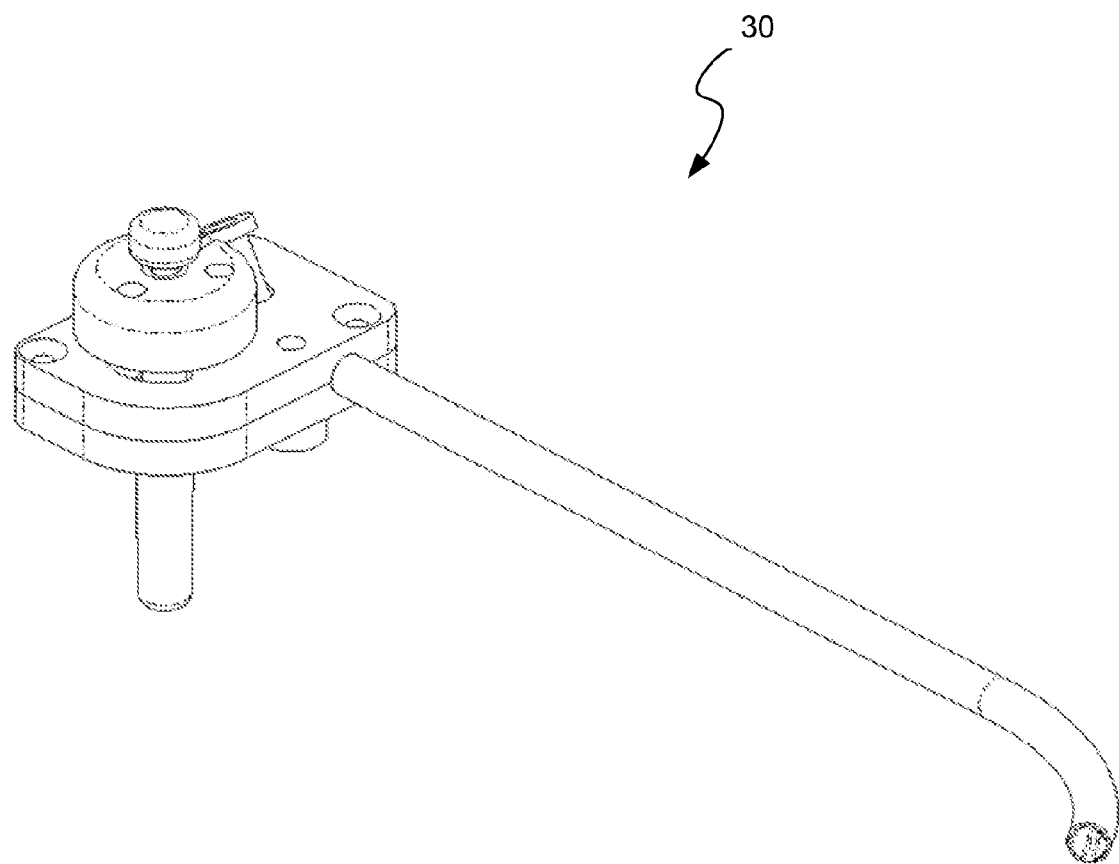
Figure 76:
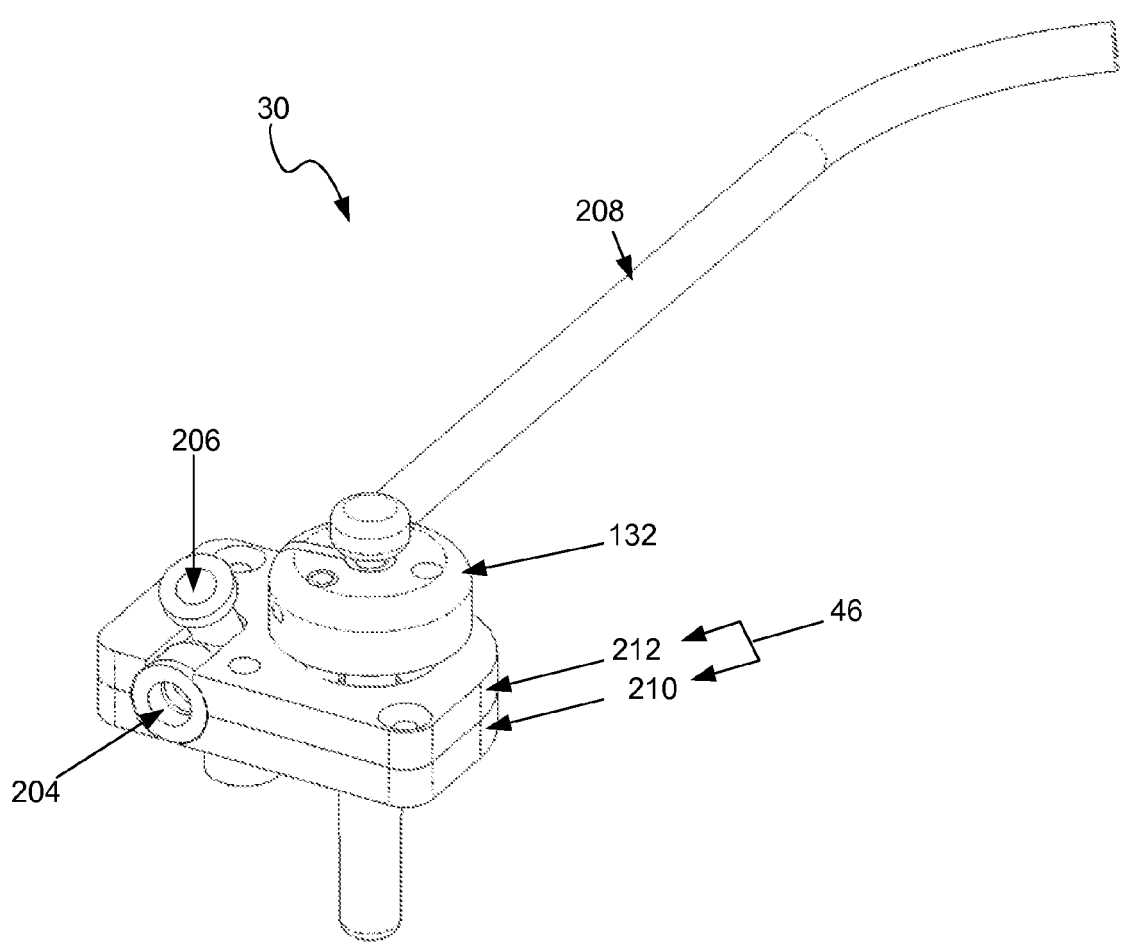

FIG. 74 depicts a guide instrument (18) shown coupled coaxially with a sheath instrument (30), together forming what has been described as a set of instruments (28). In FIGS. 75 and 76, the sheath instrument (30) is depicted without the guide instrument of FIG. 74. In FIG. 76, the sheath instrument (30) of one embodiment is depicted having one control element interface assembly (132), and preferably only one control element (not shown). From a functional perspective, in most embodiments the sheath instrument need not be as drivable or controllable as the associated guide instrument, because the sheath instrument is generally used to contribute to the remote tissue access schema by providing a conduit for the guide instrument, and to point the guide in generally the right direction. Such movement is controlled by rolling the sheath relative to the patient, bending the sheath in one or more directions with a control element, and inserting the sheath into the patient. The seal (204) is generally larger than the seal on the guide instrument due to the larger diameters of elongate members that may be inserted into the sheath instrument (30) as part of a medical procedure. Adjacent the seal (204) is an access port (206), which may be utilized to purge the instrument, or circulate fluids or instruments. The bottom (210) and top (212) portions of the sheath instrument base (46) are preferably sandwiched to house portions of the control element interface assembly (132), such as the single pulley (136) in this embodiment, and the proximal portion of the sheath catheter member (208).

Figure 77:
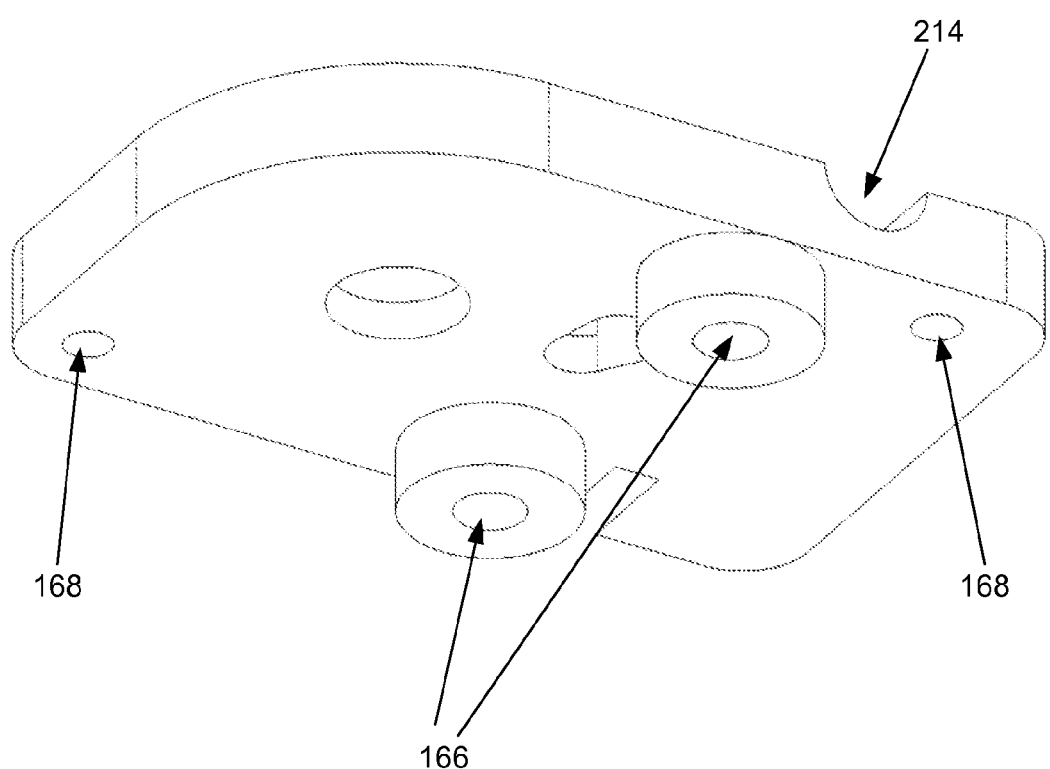
Figure 78:
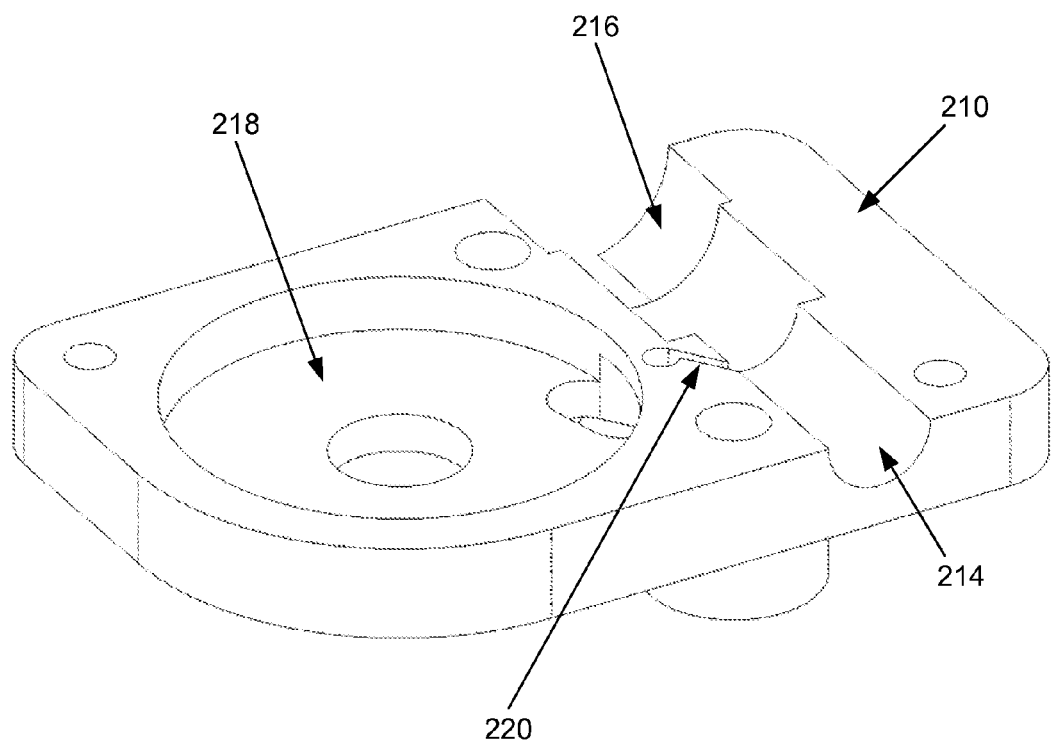
Figure 79:
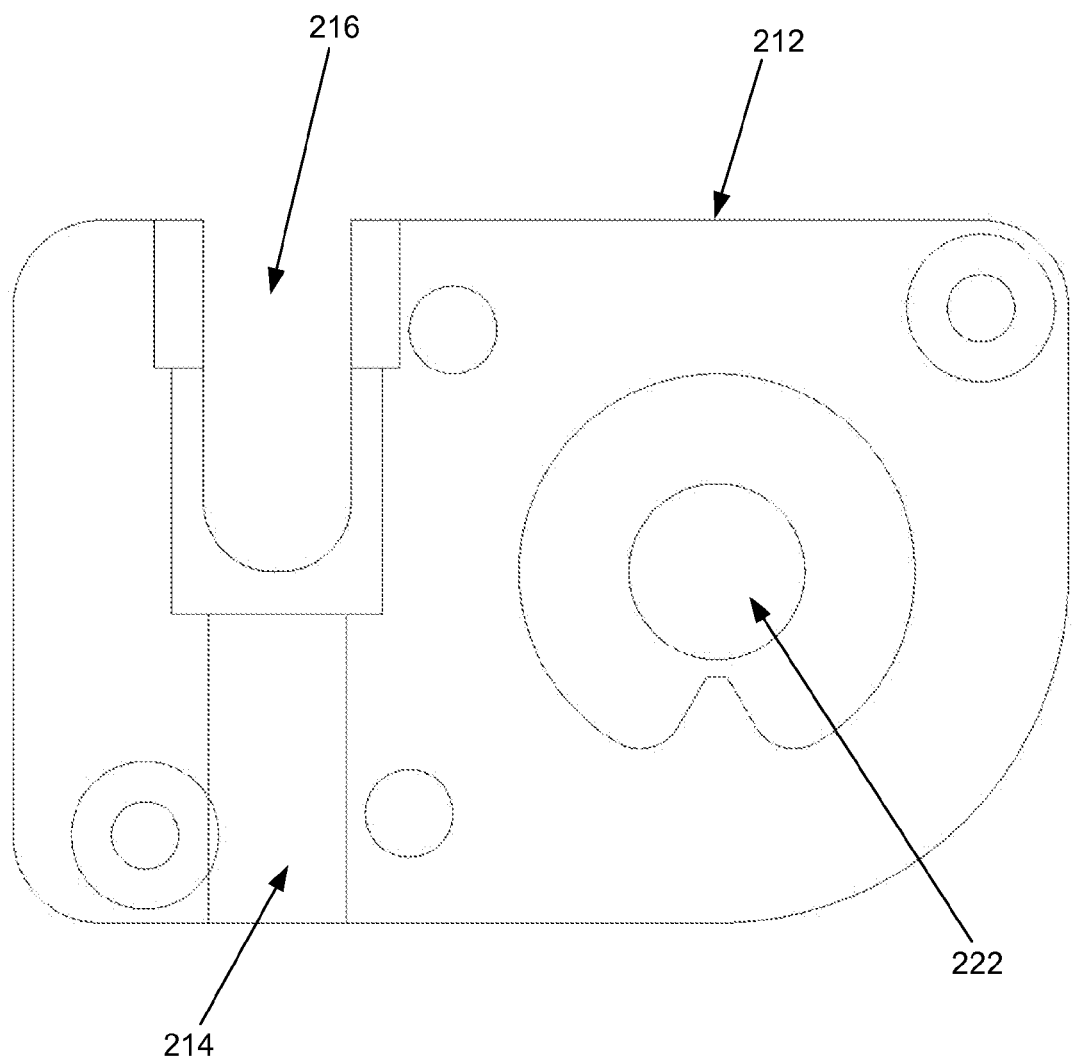

Referring to FIG. 77, the bottom portion (210) of one embodiment of a sheath instrument base (46) is depicted showing two magnets (166) utilized to facilitate mounting against an instrument driver (16). Mounting pin interface holes (168) also assist in accurate interfacing with an instrument driver (16). The opposite surface is formed with a sheath catheter member geometry accommodation (214) to interface with the sheath catheter (not shown). FIG. 78 shows this opposite surface of the bottom portion (210) in further detail, having a pulley geometry accommodation (218), a seal geometry accommodation (216), and a sheath catheter geometry accommodation (214). There is also a control element splay track (220) similar to those depicted in reference to the embodiments of the guide instrument. In FIG. 79, a bottom view of a top portion (212) of one embodiment of a sheath instrument base (46) is depicted showing the sheath catheter geometry (214) and seal geometry (216) accommodations formed therein, and an axle interface hole (222) formed there through.

Figure 80:
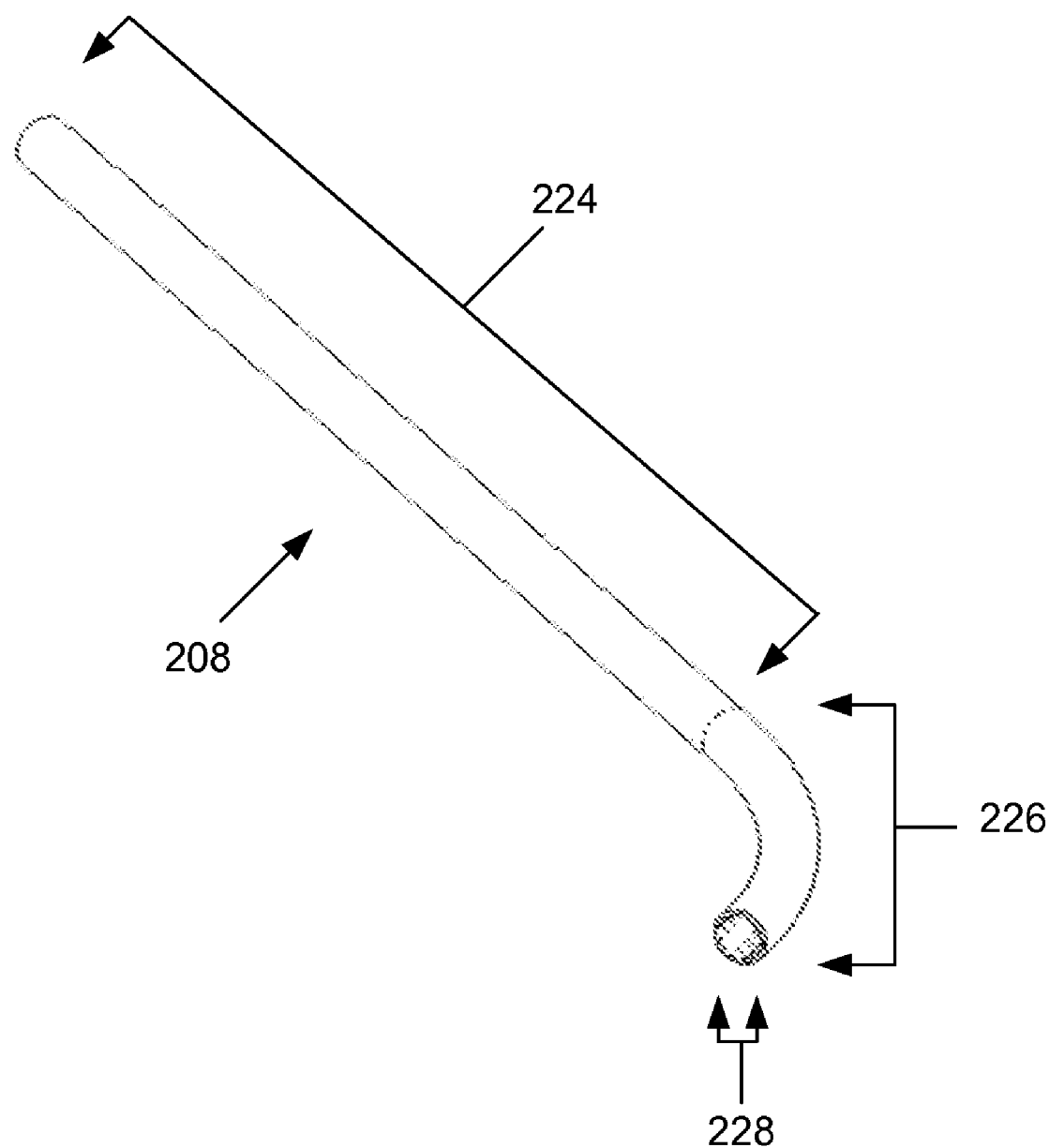

FIG. 80 illustrates yet another embodiment of the sheath catheter member (208) in a pre-bent formation, which may be desirable depending upon the anatomical issue pertinent to the medical procedure. The sheath catheter member (208) preferably has a construction somewhat similar to that of the aforementioned guide catheter member embodiments, with notable exceptions. For one embodiment, the sheath catheter member (208) preferably does not have a flexible structural element disposed within its distal end as it is not within the preferred functionality of the sheath instrument to have very tight radius bendability, particularly given the high bendability of the associated guide instrument. Preferably both the proximal (224) and distal (226) portions comprise a low-friction inner layer, a braiding layer, and an outer layer, as described below with reference to FIG. 81. It is preferable to have more bending flexibility in the distal portion than in the proximal portion. This may be accomplished in one embodiment by selecting a outer layer polymeric material for the distal portion (226) having approximately half the durometer of the polymeric material utilized for the outer layer of the proximal portion (224). In the depicted embodiment, an atraumatic distal tip (228) comprising an extension of the low-friction inner layer and outer layer extends slightly beyond the termination of the braiding layer by between about ¼ inch and ⅛ inch to prevent damage to tissues in various medical procedures.

Figure 81:
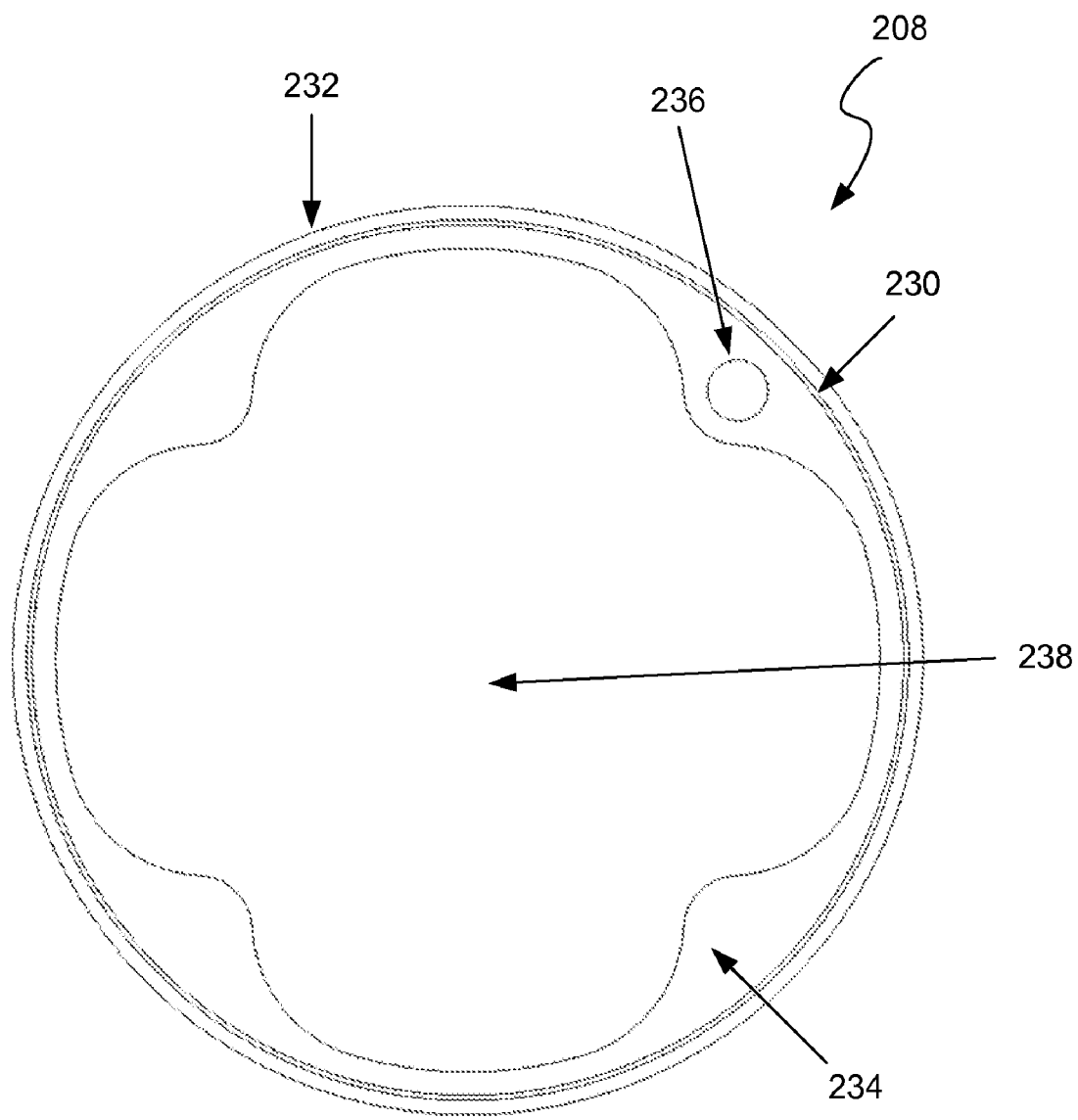
Figure 82:
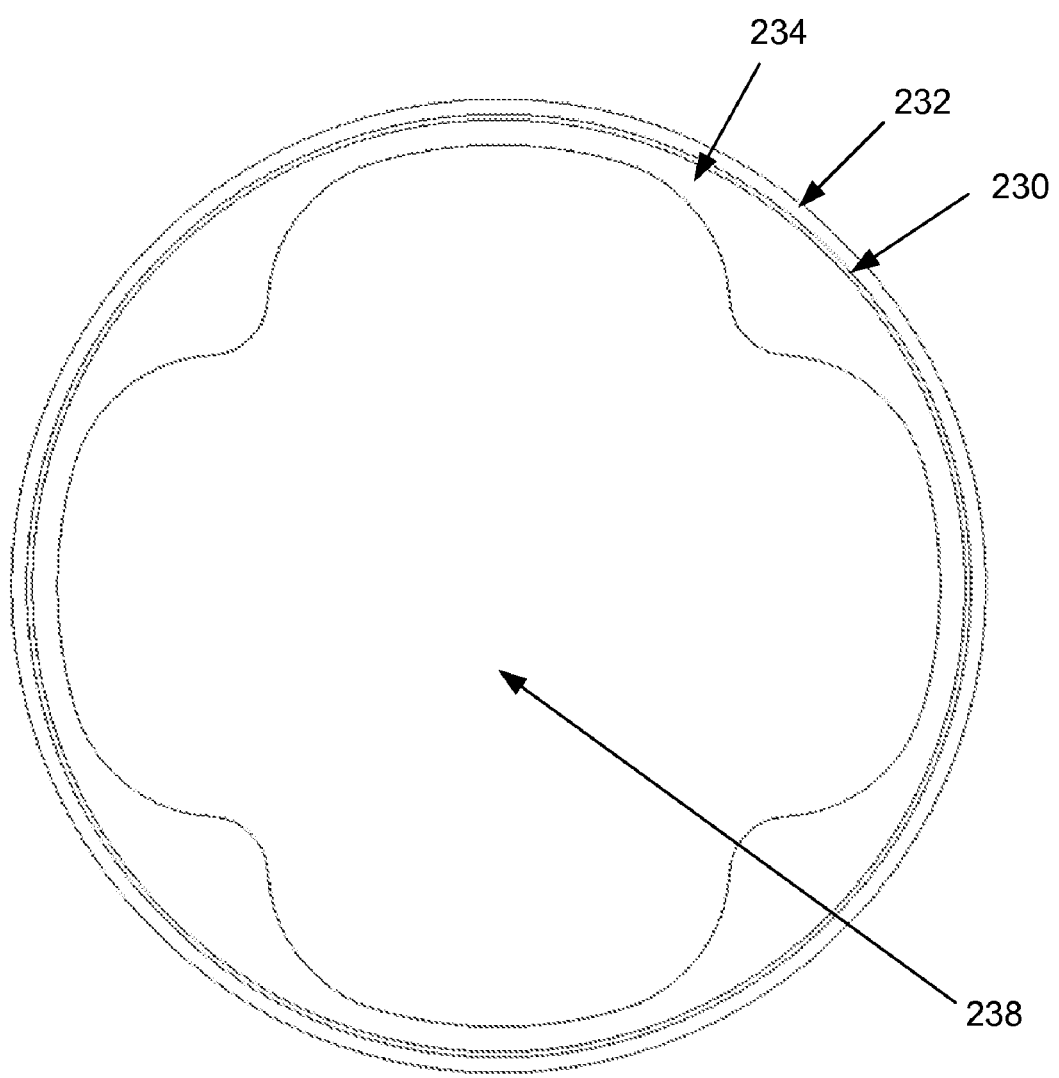

FIG. 81 is a cross sectional view of a proximal or distal portion of a sheath catheter member (208), similar to that shown in FIG. 80. A braiding layer (230) is surrounded by an outer layer (232) preferably comprising a polymer such as Pebax® with a durometer hardness value between 30 to 80 Shore D hardness and an inner layer (234) preferably comprising a low-friction polymeric material into which one or more lumens may be optionally extruded. The embodiment of FIG. 81 depicts one control element lumen (236). The geometry of the inner layer (234) may be configured to "key" or restrictively interface with a guide catheter member outer geometry to prevent rotation of the guide catheter member as discussed below with reference to FIGS. 85-91. The central lumen (238) of the sheath catheter preferably is sized to closely fit an associated guide catheter member. FIG. 82 depicts an embodiment similar to that shown in FIG. 81, with the exception that this embodiment does not have a control element lumen. In some embodiments, it is preferable not to have a steerable sheath catheter, but instead to have a straight or pre-bent sheath catheter, or no sheath catheter at all, surrounding a portion of the guide catheter.

Figure 83:
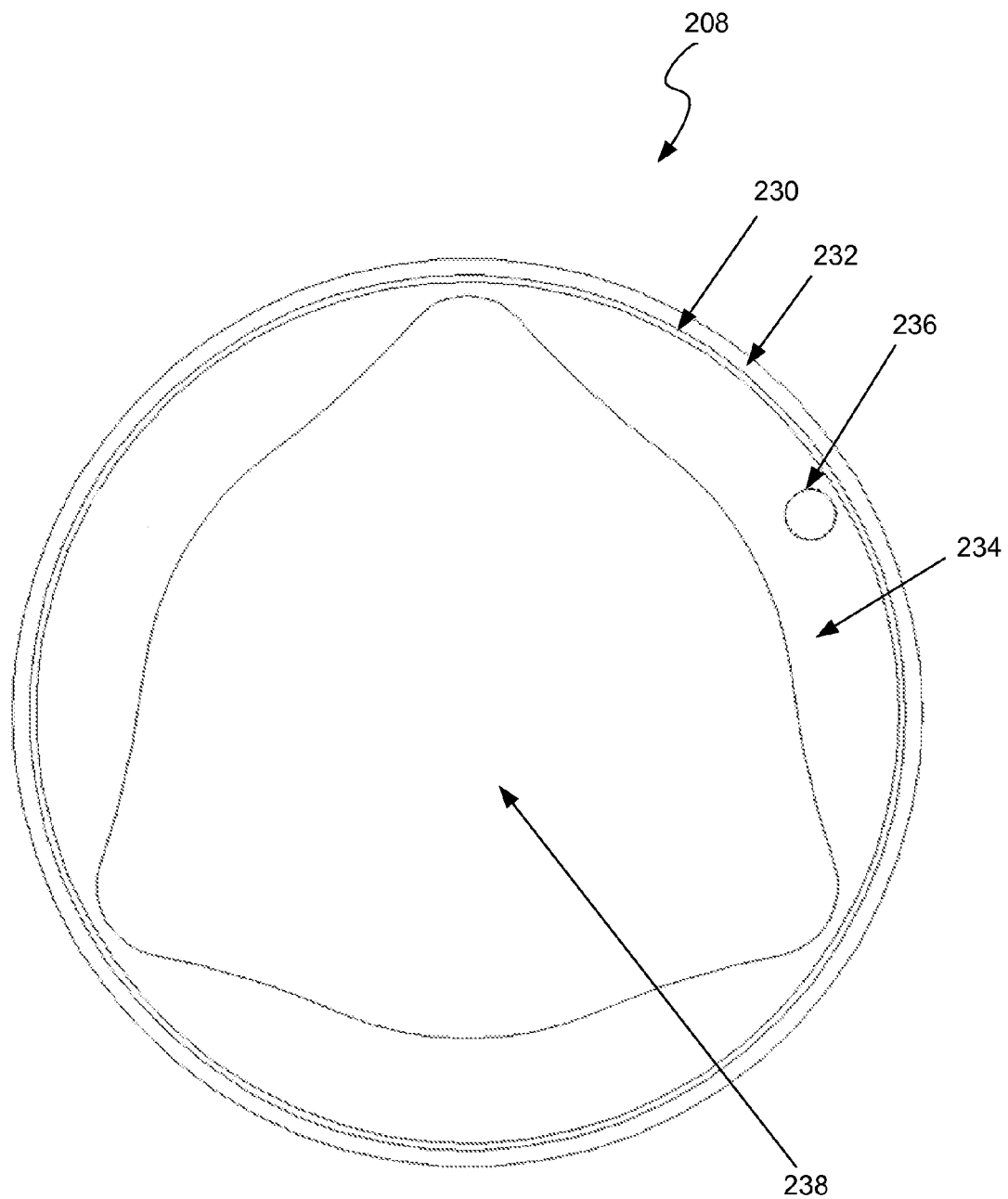
Figure 84:
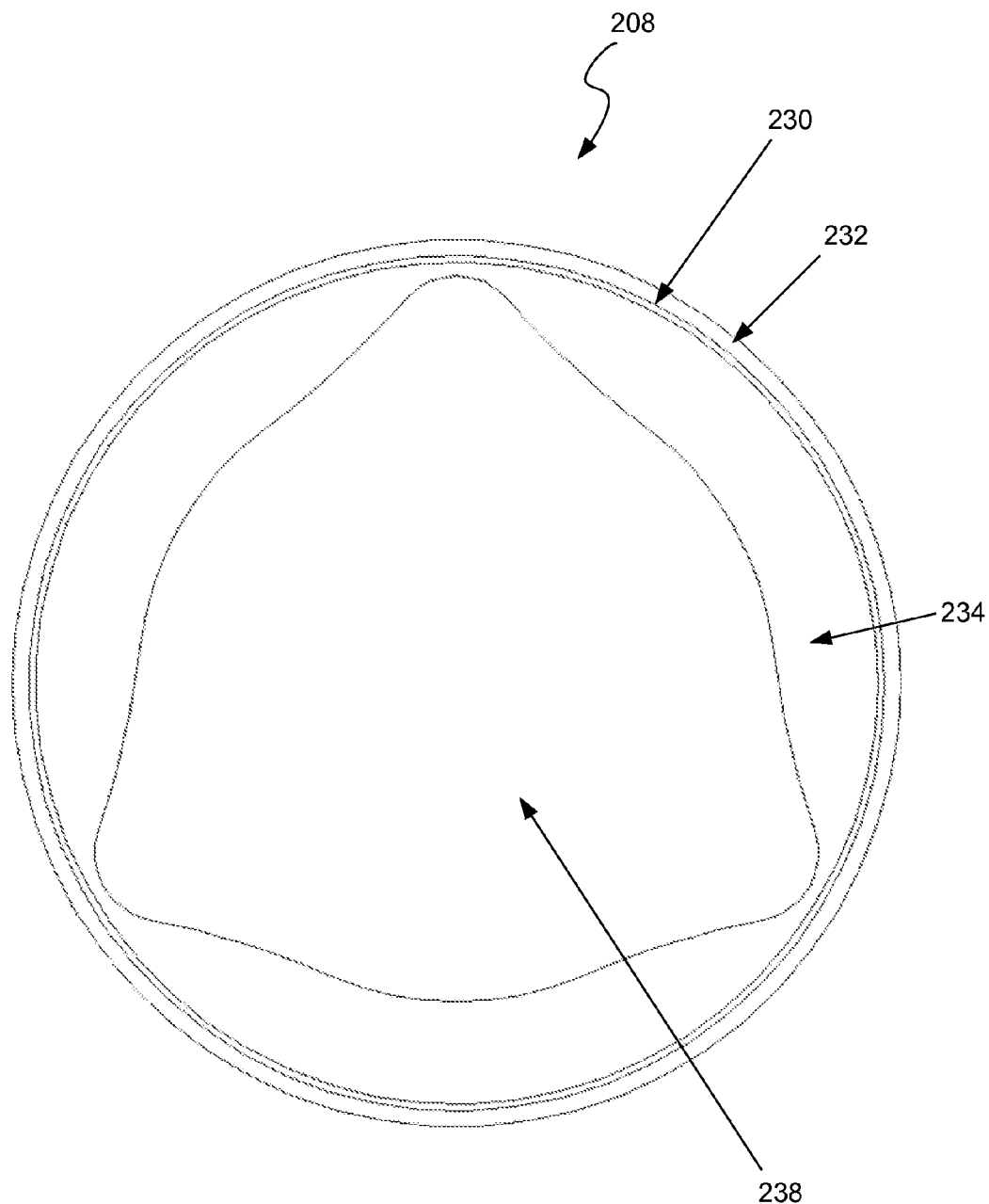
Figure 85:
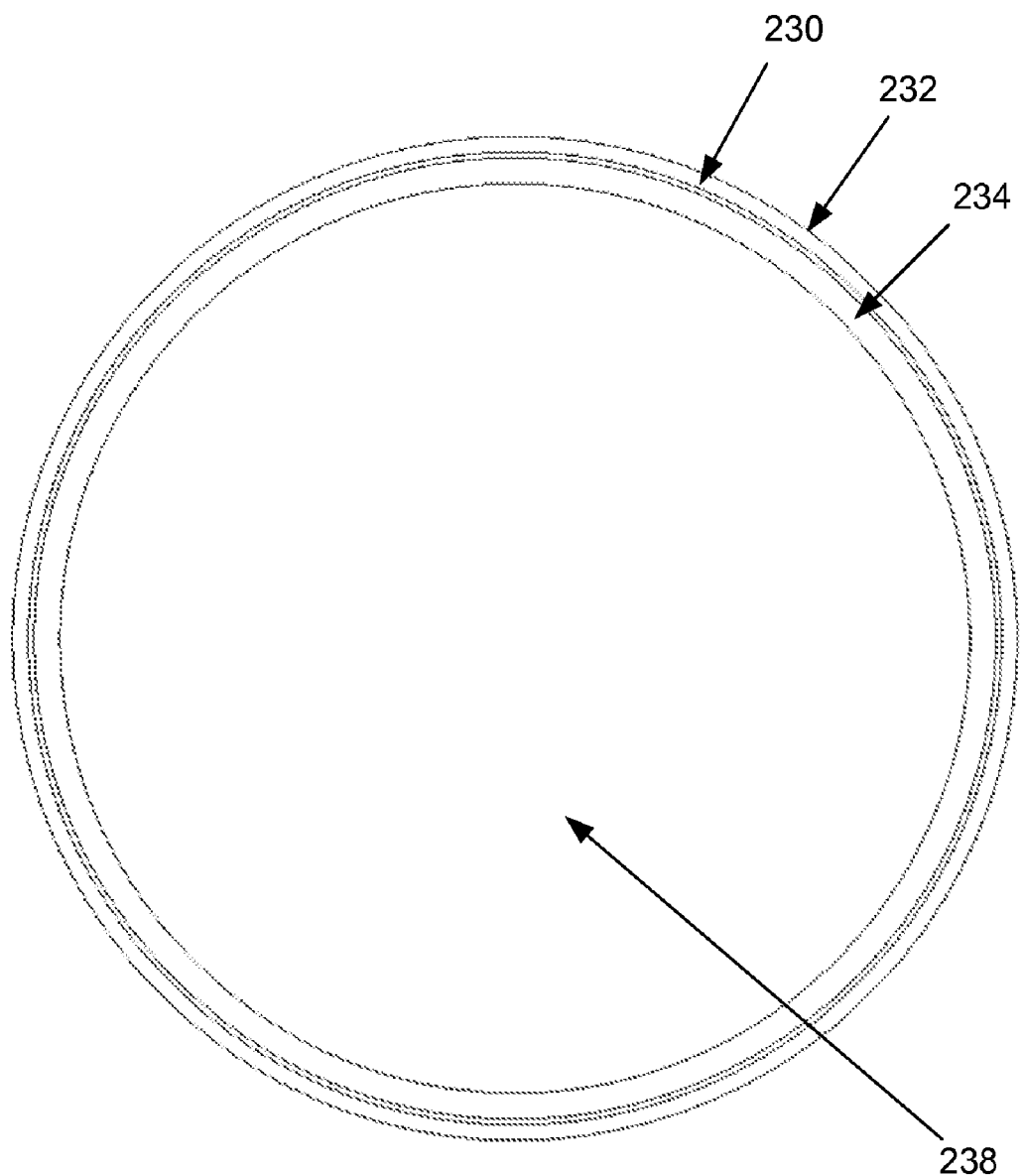

Referring to FIGS. 83 and 84, an embodiment of a sheath catheter member is depicted with an inner layer (234) configured to key with a 3-control-element guide geometry, such as that depicted in FIG. 21. FIG. 84 depicts a similar embodiment without a control element lumen (236). FIG. 85 depicts an non-keyed sheath without any control element lumens to illustrate that keying and steerable control is not necessary or desired in some embodiments or procedures—particularly when more bendability of the sheath is desired. The embodiment of FIG. 85 is relatively thin walled, and while it still comprises a braiding layer (230) surrounded by an outer layer (232) and an inner layer (234) of polymeric material, it is generally more easily bendable through tortuous paths than are other more thick-walled embodiments. Further, without the keying geometry of the inner layer (234), the central lumen (238) is effectively larger.

FIGS. 86-91 illustrate cross sectional representations of various embodiments of coaxially coupled guide catheter (90) and sheath catheter (208) combinations.

Figure 86:
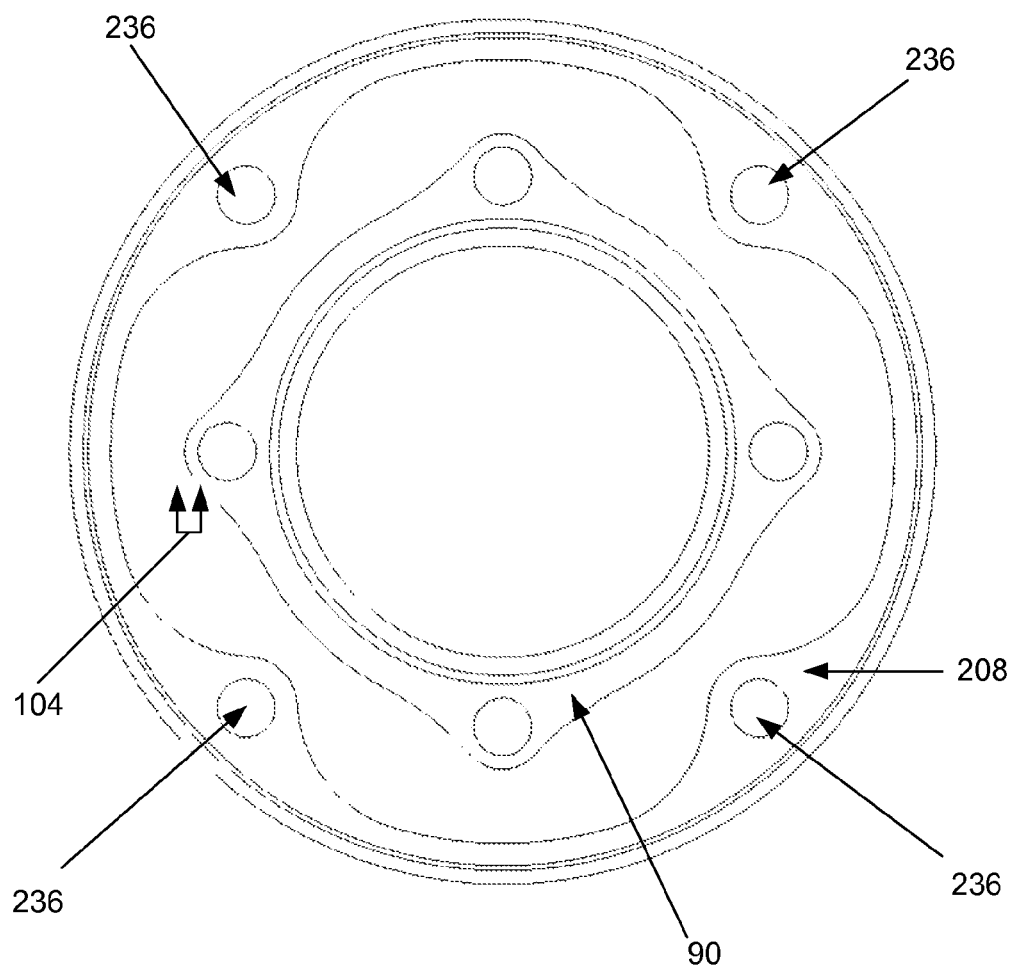
FIGS. 86-91 illustrate cross sectional views of various embodiments of coaxially coupled catheters.

Referring to FIG. 86, a relatively low surface profile (104) guide catheter (90) is disposed within sheath catheter (208) having four control element lumens (236). The fit between the two structures is fairly loose, and some relative rotational displacement is to be expected if the guide catheter (90) is torqued significantly more than the sheath catheter (208). To help prevent such relative rotational displacement, a higher profile guide catheter (90) geometry may be utilized, as shown in the embodiment of FIG. 87, in order to decrease the freedom of movement between the two structures (90, 208) as they are bent through the pathways required by a medical procedure.

Figure 87:
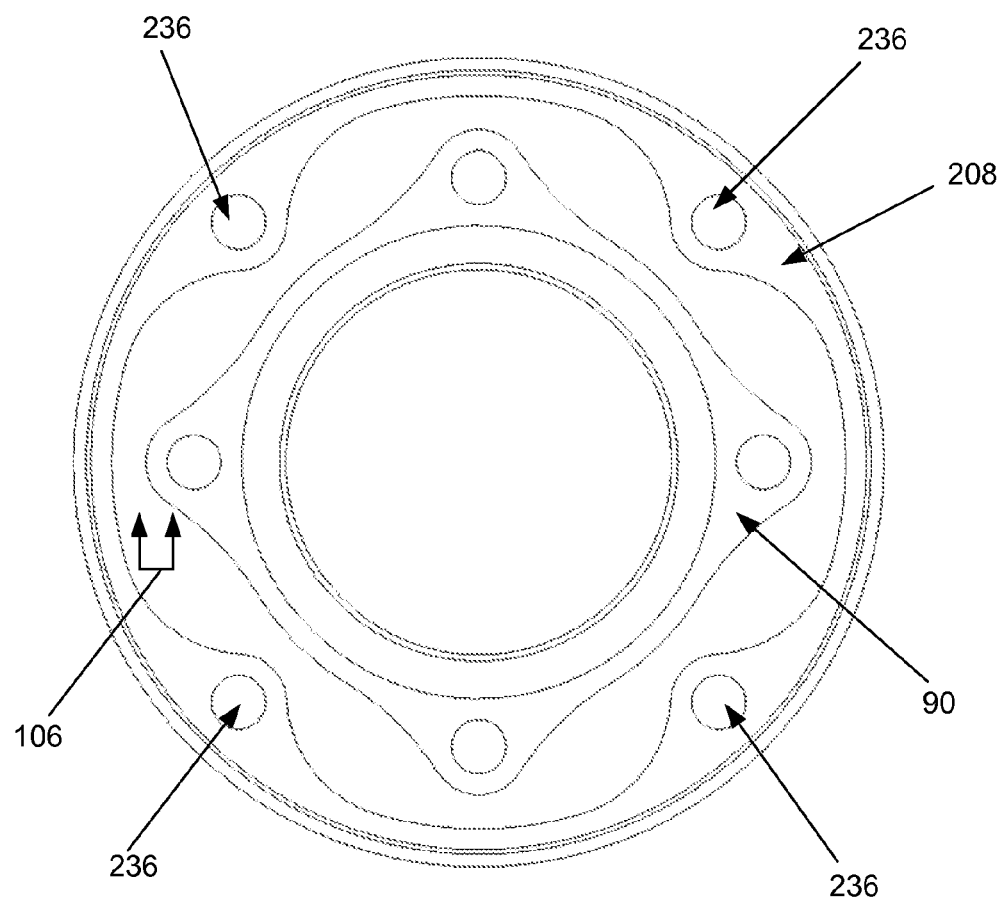
Figure 88:
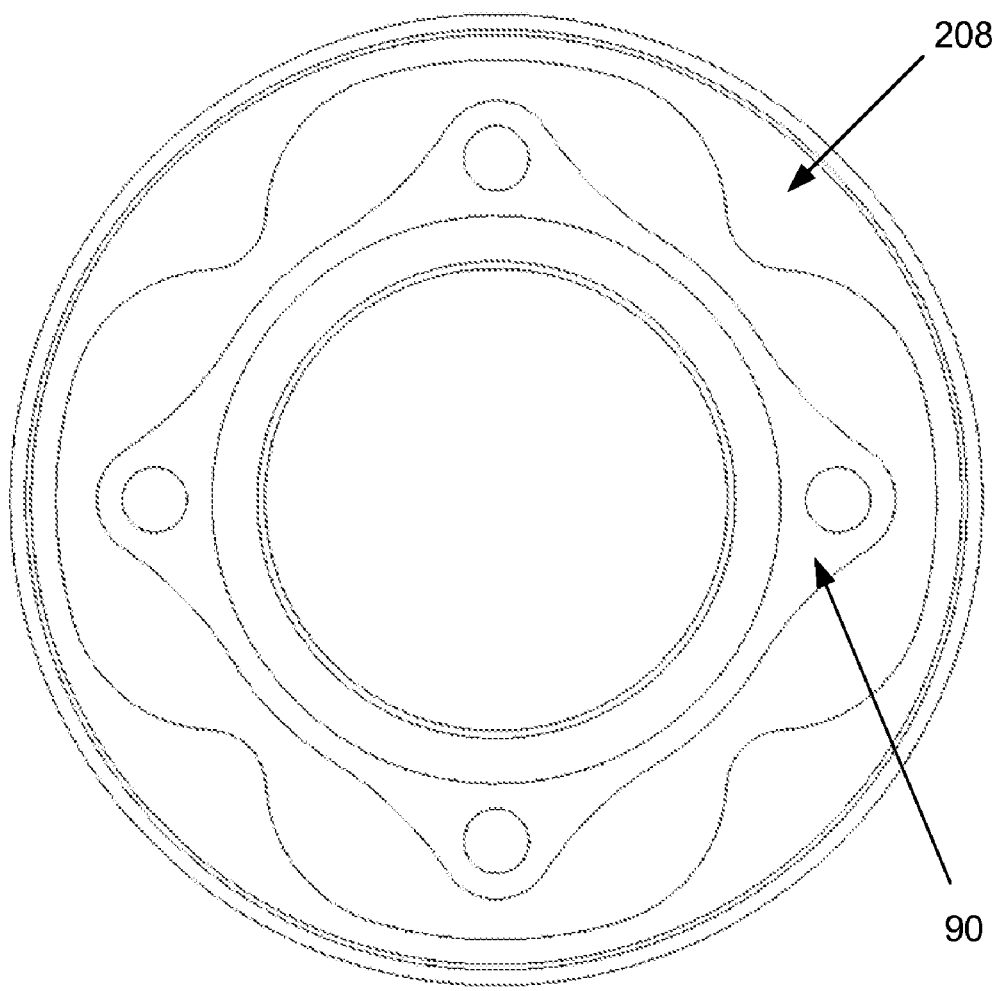

FIG. 88 depicts an embodiment similar to that in FIG. 87, but without the control element lumens (236) in the sheath catheter member (208). It may be desirable to have control element lumens formed into the walls of the guide catheter or sheath catheter for reasons other than passing control elements through such lumens. These lumens may also function as stress relief structures to increase bendability. The lumens may also be utilized to form preferred bending axes for the overall structure. Further, they may be utilized as working channels for flushing, drug delivery, markers, sensors, illumination fibers, vision fibers, and the like. It may be desirable to have a homogeneous patterning of control lumens across the cross section of a particular structure in order to promote homogeneous bending. For example, a sheath catheter with four control lumens, one of which is occupied by a control element in tension, may bend more homogeneously than a sheath catheter with only one or two control lumens, one of which occupied by a control element.

Figure 89:
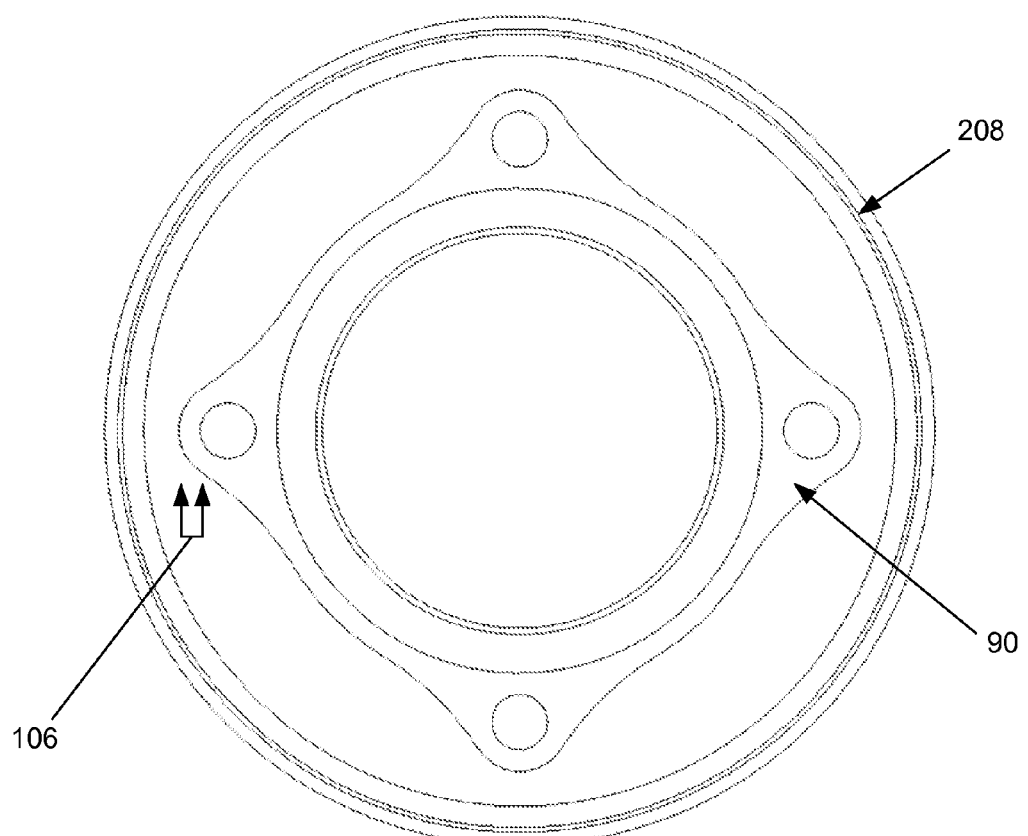
Figure 90:
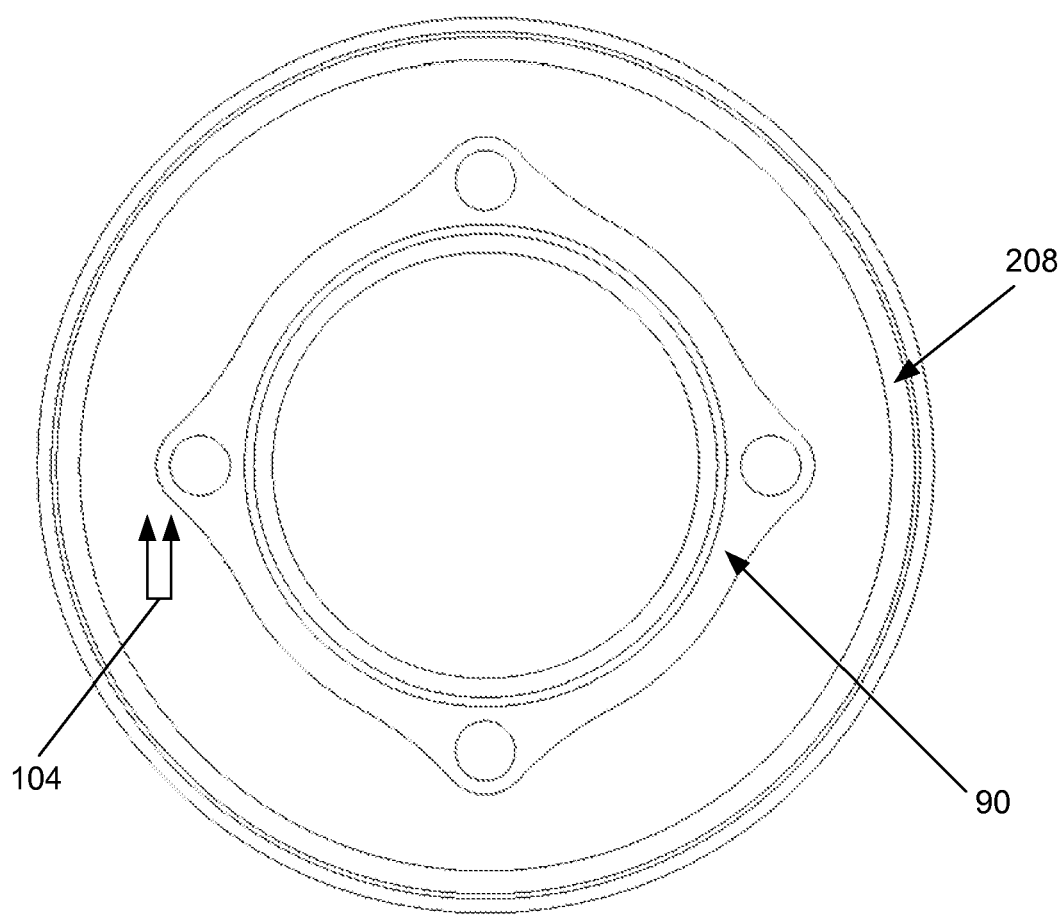
Figure 91:
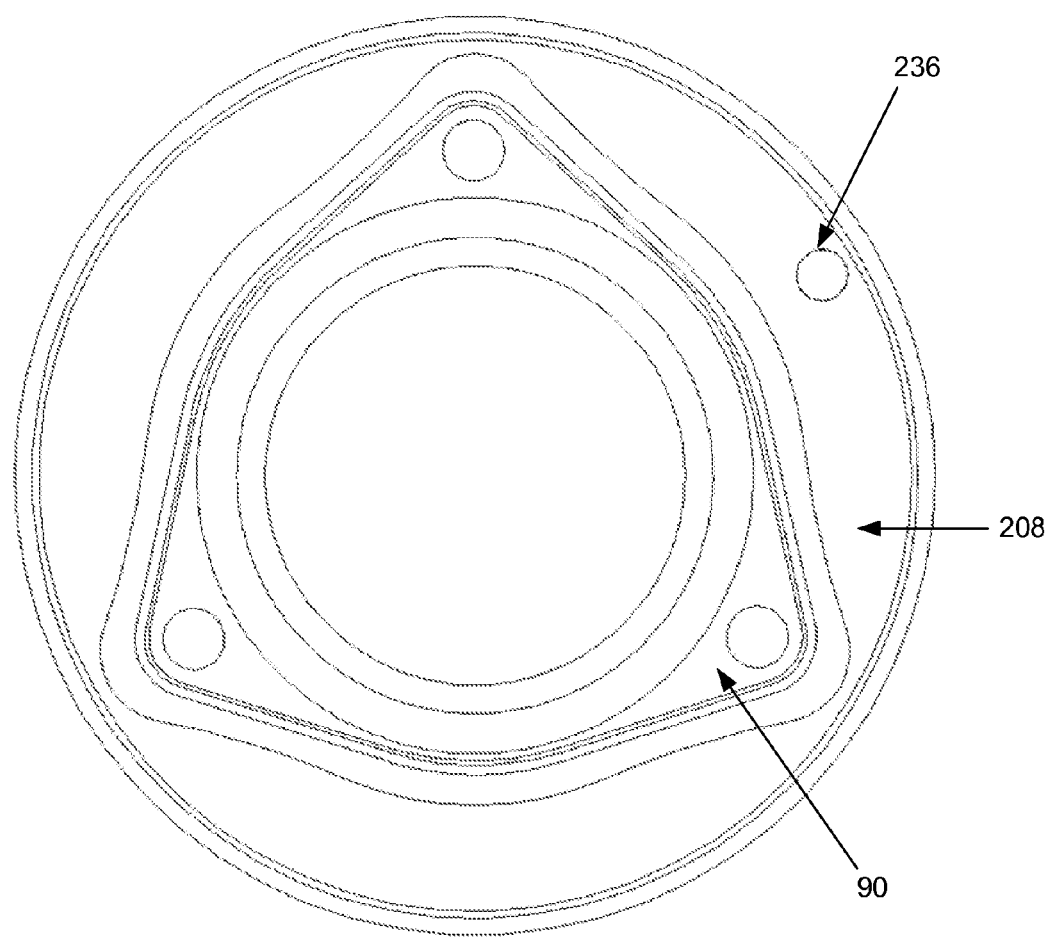
Figure 92:
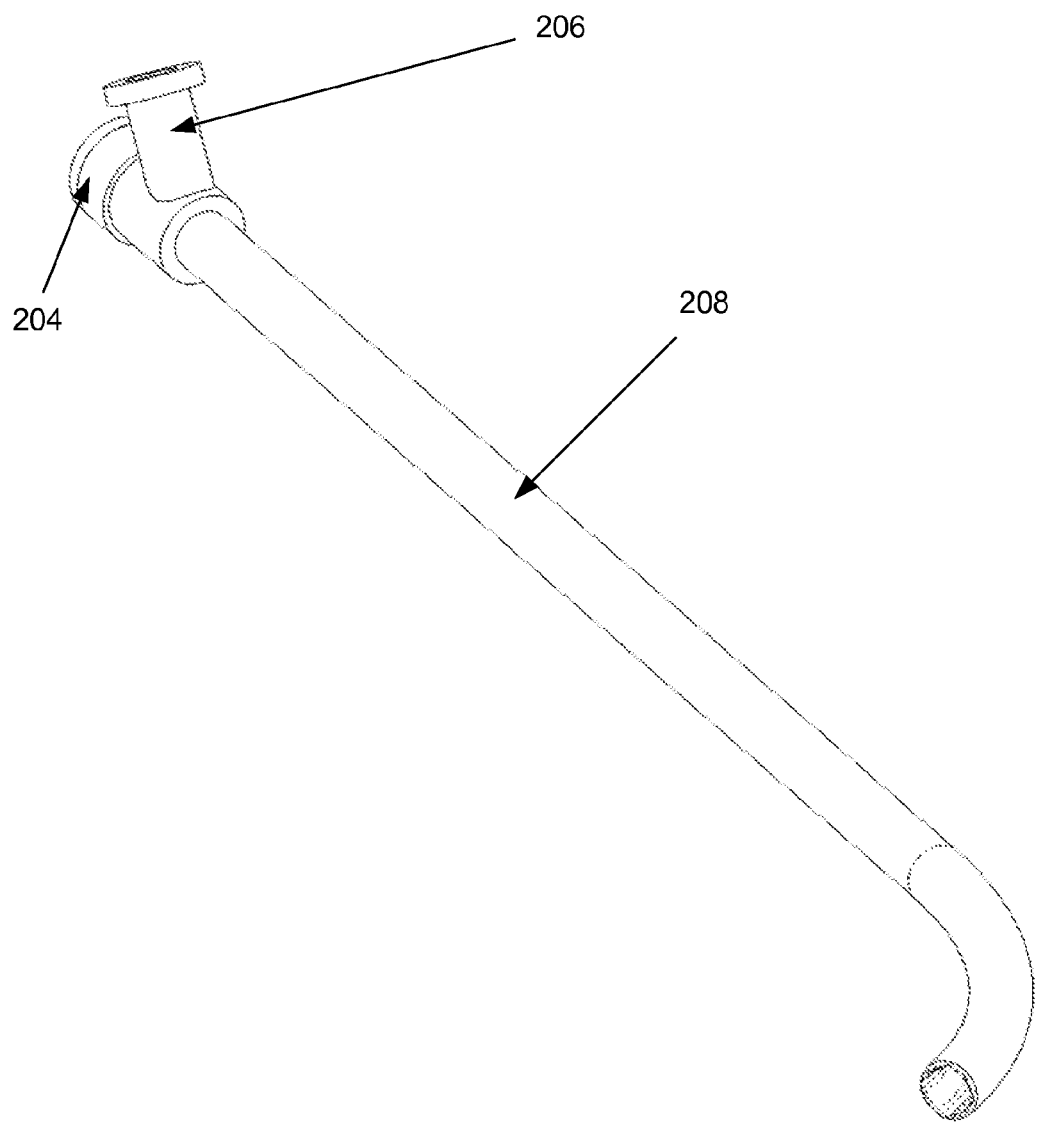
FIGS. 92-94 illustrate the coupling of a seal and access port with the sheath catheter member of one embodiment.
Figure 93:
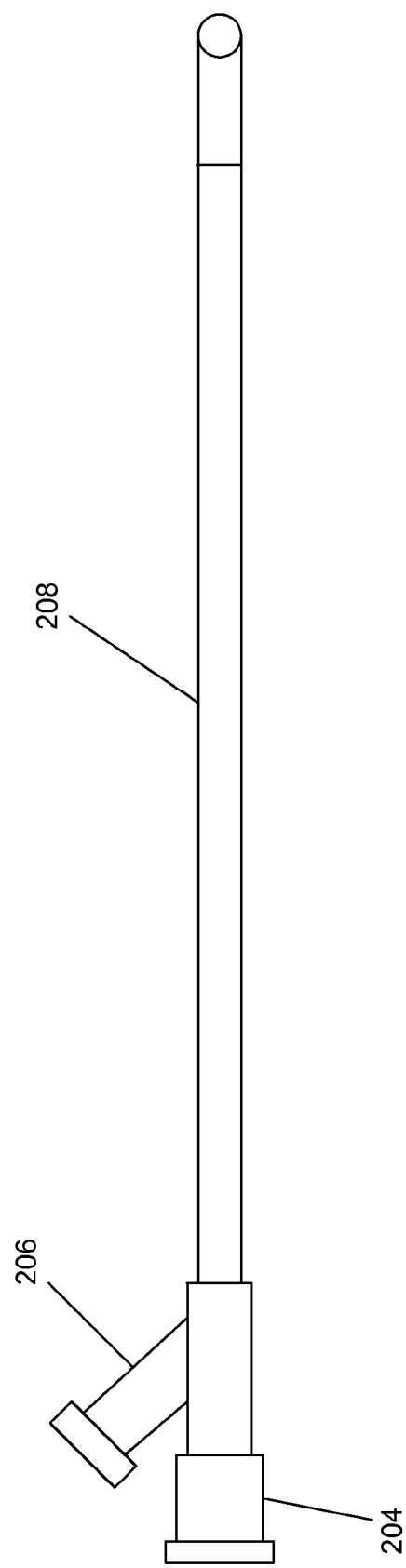
Figure 94:
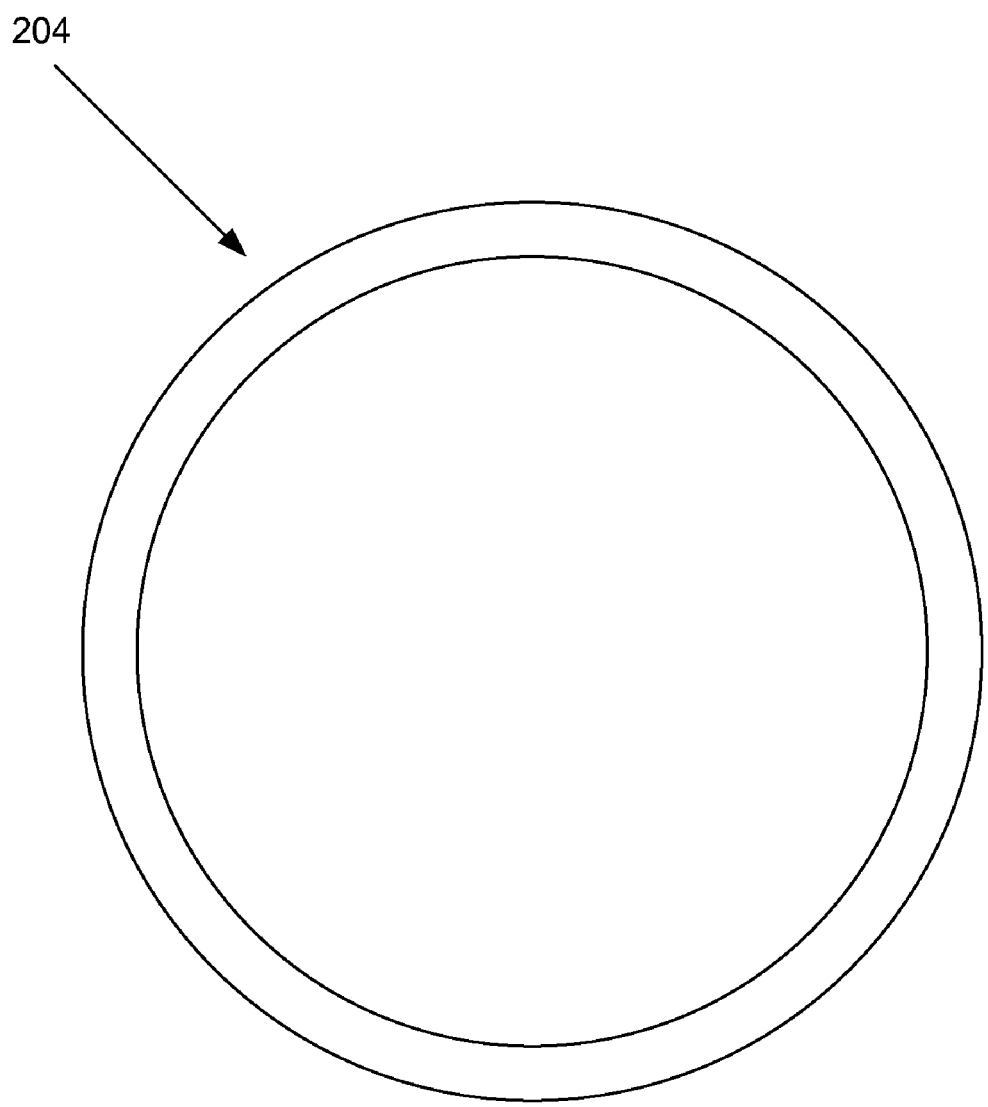

Referring to FIG. 89, a relatively high surface profile (106) guide catheter (90) is depicted within a non-keyed sheath catheter (208). In this embodiment, a 4-control-element guide catheter is disposed within a pre-bent sheath instrument that is not remotely steerable. FIG. 90 depicts a similar embodiment to that of FIG. 89 with the exception of a lower surface profile (104) guide catheter (90) disposed within the non-keyed sheath catheter (208). FIG. 91 depicts an example of keying to resist relative rotational displacement between a guide catheter (90) and a sheath catheter (208). Significant resistance to rotational displacement is traded for higher degrees of overall system bendability, as will be apparent to those skilled in the art. As shown in FIG. 92, a preferably elastomeric seal (204) and access port (206) construct may be fitted onto the sheath catheter member (208), prior to mounting within the confines of the sheath instrument base (46). FIG. 93 is a side view of the sheath catheter member (208) coupled to the seal (204) and access port (206). FIG. 94 is an end view of the seal (204).

FIGS. 95-103 depict various aspects of embodiments of an instrument driver configured for use with the above-described instrument embodiments.

Figure 95:
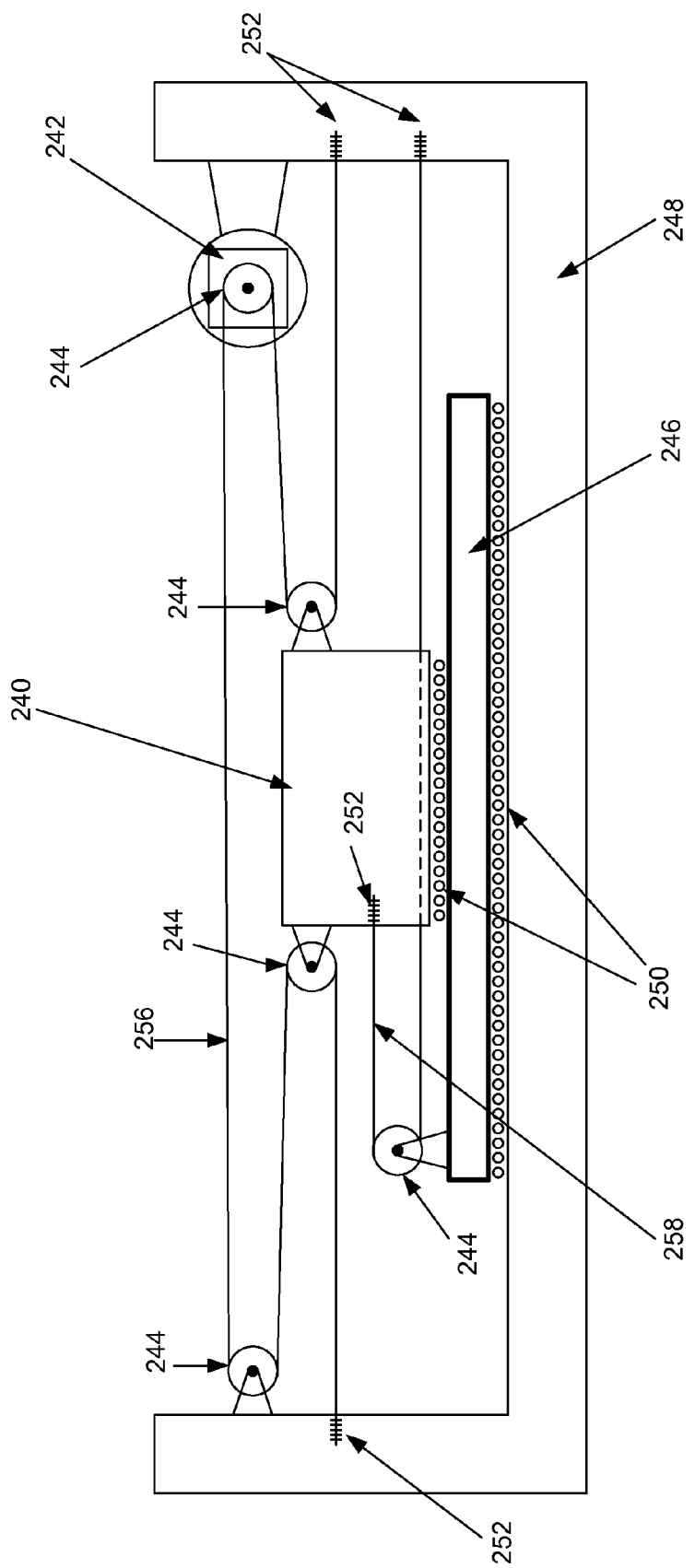
FIGS. 95-96 illustrate internal features of one embodiment of an instrument driver schematically.
Figure 96:
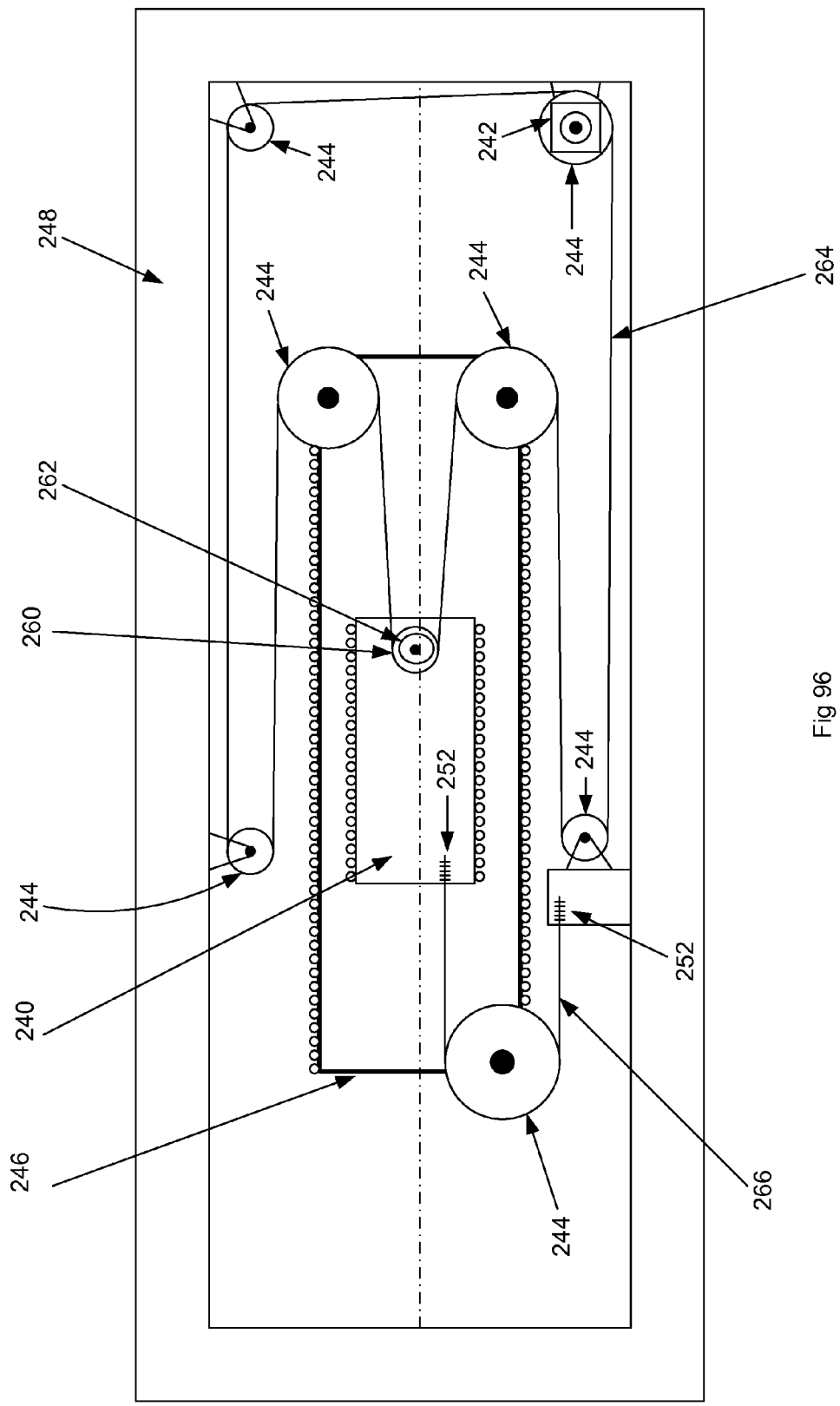

FIGS. 95 and 96 are simplified schematics that illustrate internal features and functionalities of one embodiment of an instrument driver (16). In FIG. 95, a carriage (240) is slidably mounted upon a platform (246), which is slidably mounted to a base structure (248). The slidable mounting (250) at these interfaces may be accomplished with high-precision linear bearings. The depicted system has two cables (256, 258) running through a plurality of pulleys (244) to accomplish motorized, synchronized relative motion of the carriage (240) and platform (246) along the slidable mounting interfaces (250). As will be apparent to those skilled in the art, as the motor (242) pulls on the carriage displacement cable (256) with a tension force T, the carriage (240) feels a force of 2*T. Further, as the motor pulls the carriage displacement cable (256) by a displacement X, the carriage moves by X/2, and the platform moves by half that amount, or X/4, due to its "pulleyed" synchronization cable (258).

FIG. 96 illustrates a top view of a separate (but similar) system configured to drive an instrument interface pulley (260) associated with an instrument interface socket (262) to produce both directions of rotation independently from the position of the carriage (240), to which it is coupled, along the linear pathway prescribed by the slidable mounting interfaces (250). With a mechanical schema similar to that in FIG. 95, as the motor (242) pulls a deflection X in the instrument interface cable (264), the same deflection is seen directly at the instrument interface pulley (260), regardless of the position of the carriage (240) relative to the motor (242), due to the synchronizing cable (266) positioning and termination (252).

Figure 97:
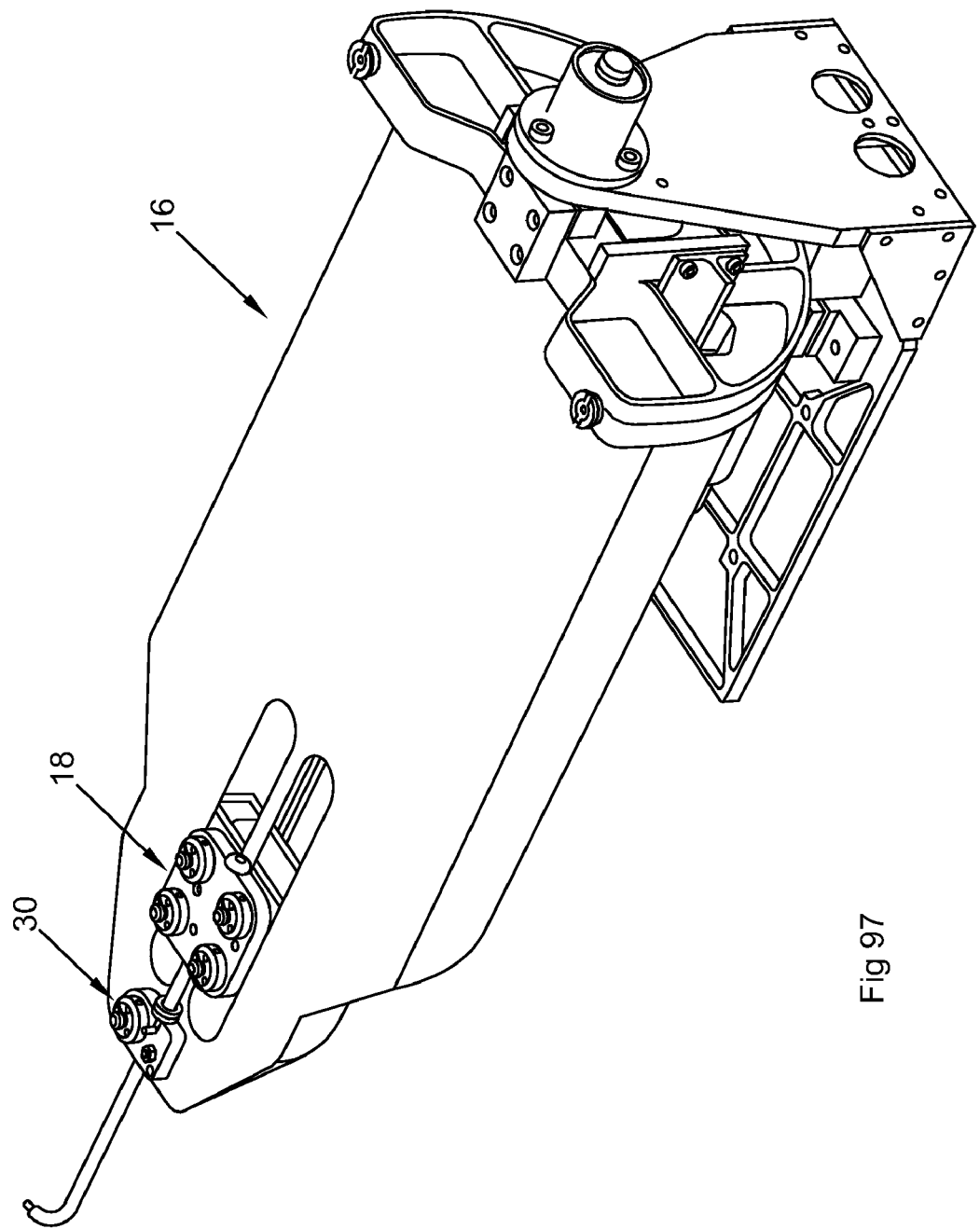
FIGS. 97-102 illustrate various aspects of the instrument driver of one embodiment.
Figure 98:
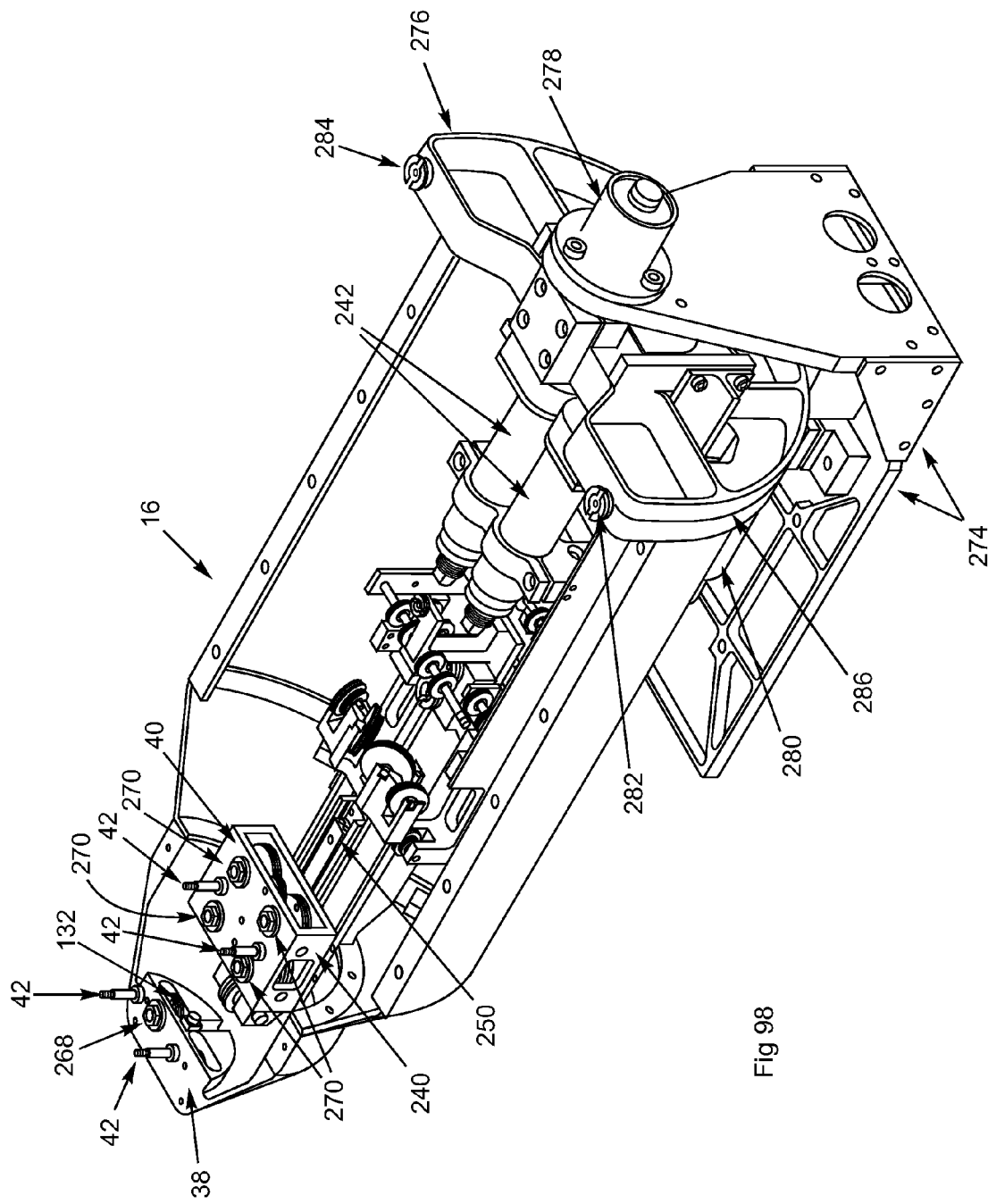
Figure 99:
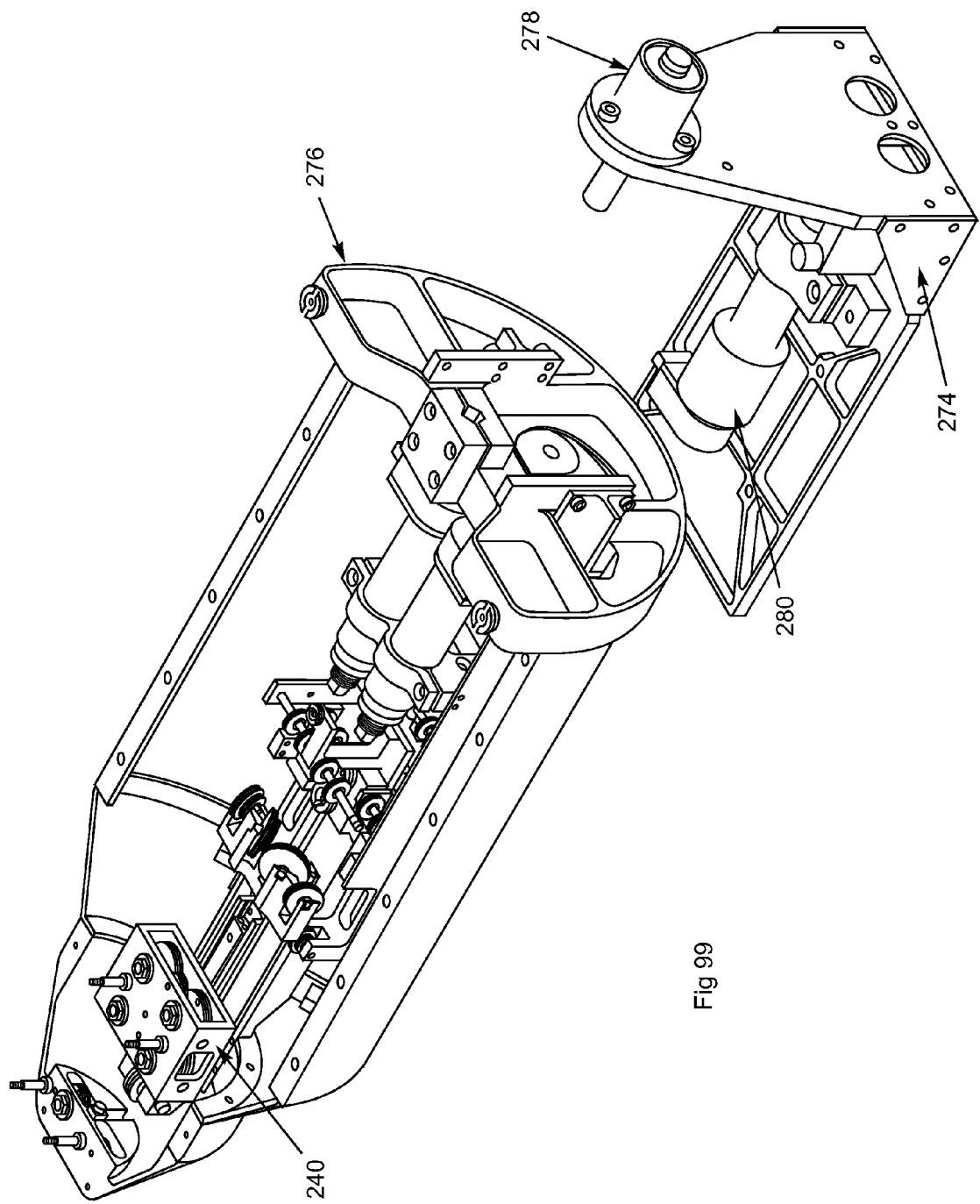

Referring to FIGS. 97-103, systems similar to those depicted in FIGS. 95 and 96 are incorporated into various embodiments of the instrument driver (16). In FIG. 97, an instrument driver (16) is depicted as interfaced with a steerable guide instrument (18) and a steerable sheath instrument (30). FIG. 98 depicts an embodiment of the instrument driver (16), in which the sheath instrument interface surface (38) remains stationary, and employs a simple motor actuation in order for a sheath to be steered using an interfaced control element via a control element interface assembly (132). This may be accomplished with a simple cable loop about a sheath socket drive pulley (272) and a capstan pulley (not shown), which is fastened to a motor, similar to the two upper motors (242) (visible in FIG. 98). The drive motor for the sheath socket drive schema is hidden under the linear bearing interface assembly.

The drive schema for the four guide instrument interface sockets (270) is more complicated, due in part to the fact that they are coupled to a carriage (240) configured to move linearly along a linear bearing interface (250) to provide for motor-driven insertion of a guide instrument toward the patient relative to the instrument driver, hospital table, and sheath instrument. The cabling and motor schema that moves the carriage (240) along the linear bearing interface (250) is an implementation of the diagrammatic view depicted in FIG. 95. The cabling and motor schema that drives each of the four depicted guide instrument interface sockets is an implementation of the diagrammatic view depicted in FIG. 96. Therefore, in the embodiments of FIGS. 98-103, wherein four separate cable drive loops serve four separate guide instrument interface sockets (270), and wherein the carriage (240) has motorized insertion, there is achieved a functional equivalent of a system such as that diagrammed in FIGS. 95 and 96, all fit into the same construct. Various conventional cable termination and routing techniques are utilized to accomplish a preferably high-density instrument driver structure with the carriage (240) mounted forward of the motors for a lower profile patient-side interface.

Still referring to FIG. 98, the instrument driver (16) is rotatably mounted to an instrument driver base (274), which is configured to interface with an instrument driver mounting brace (not shown), such as that depicted in FIG. 1, or a movable setup joint construct (not shown), such as that depicted in FIG. 2. Rotation between the instrument driver base (274) and an instrument driver base plate (276) to which it is coupled is facilitated by a heavy-duty flanged bearing structure (278). The flanged bearing structure (278) is configured to allow rotation of the body of the instrument driver (16) about an axis approximately coincident with the longitudinal axis of a guide instrument (not shown) when the guide instrument is mounted upon the instrument driver (16) in a neutral position. This rotation preferably is automated or powered by a roll motor (280) and a simple roll cable loop (286), which extends around portions of the instrument driver base plate and terminates as depicted (282, 284). Alternatively, roll rotation may be manually actuated and locked into place with a conventional clamping mechanism. The roll motor (280) position is more easily visible in FIG. 99.

Figure 100:
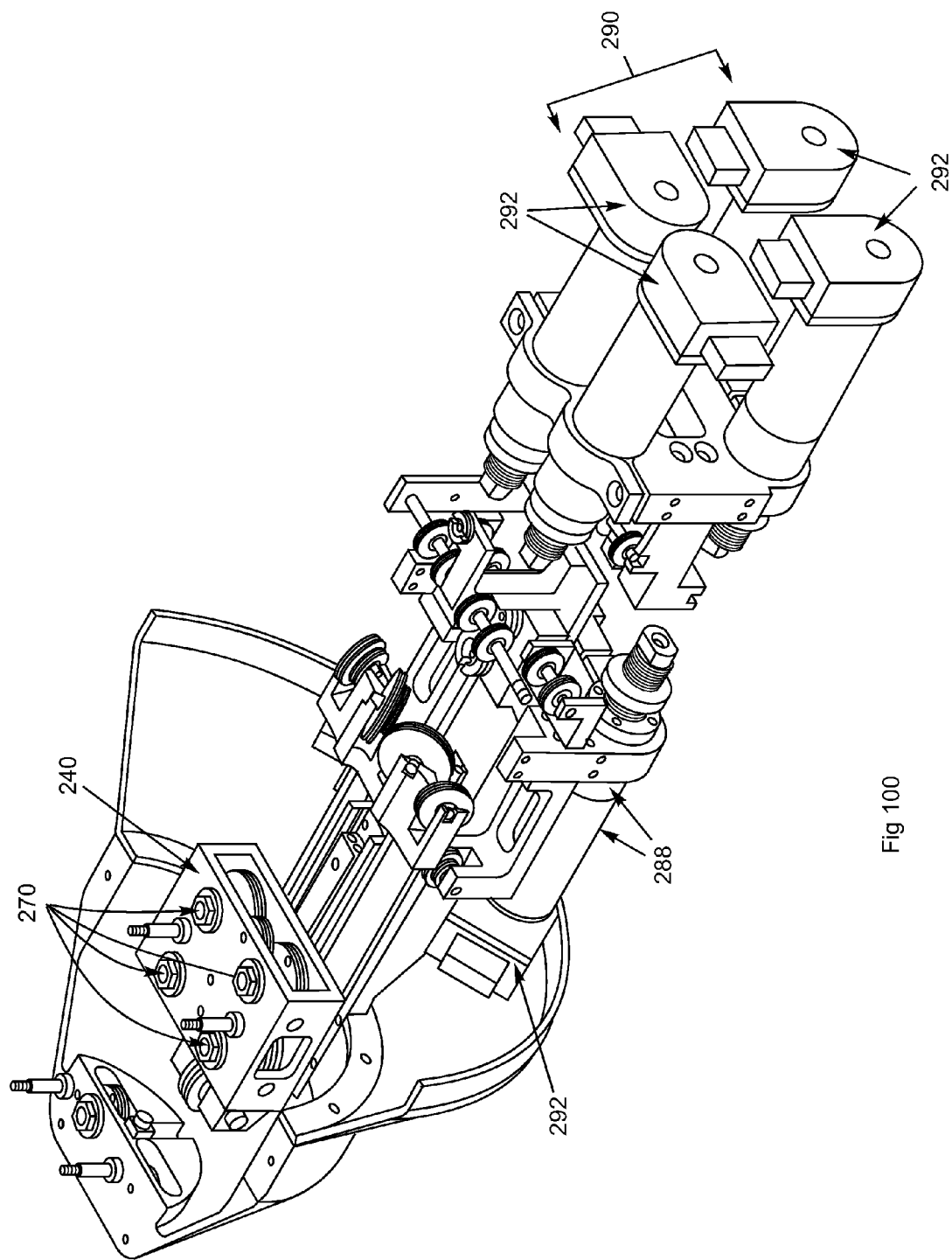

FIG. 100 illustrates another embodiment of an instrument driver, including a group of four motors (290). Each motor (290) has an associated high-precision encoder (292) for controls purposes and being configured to drive one of the four guide instrument interface sockets (270), at one end of the instrument driver (16). Another group of two motors (one hidden, one visible —288) with encoders (292) are configured to drive insertion of the carriage (240) and the sheath instrument interface socket (268).

Figure 101:
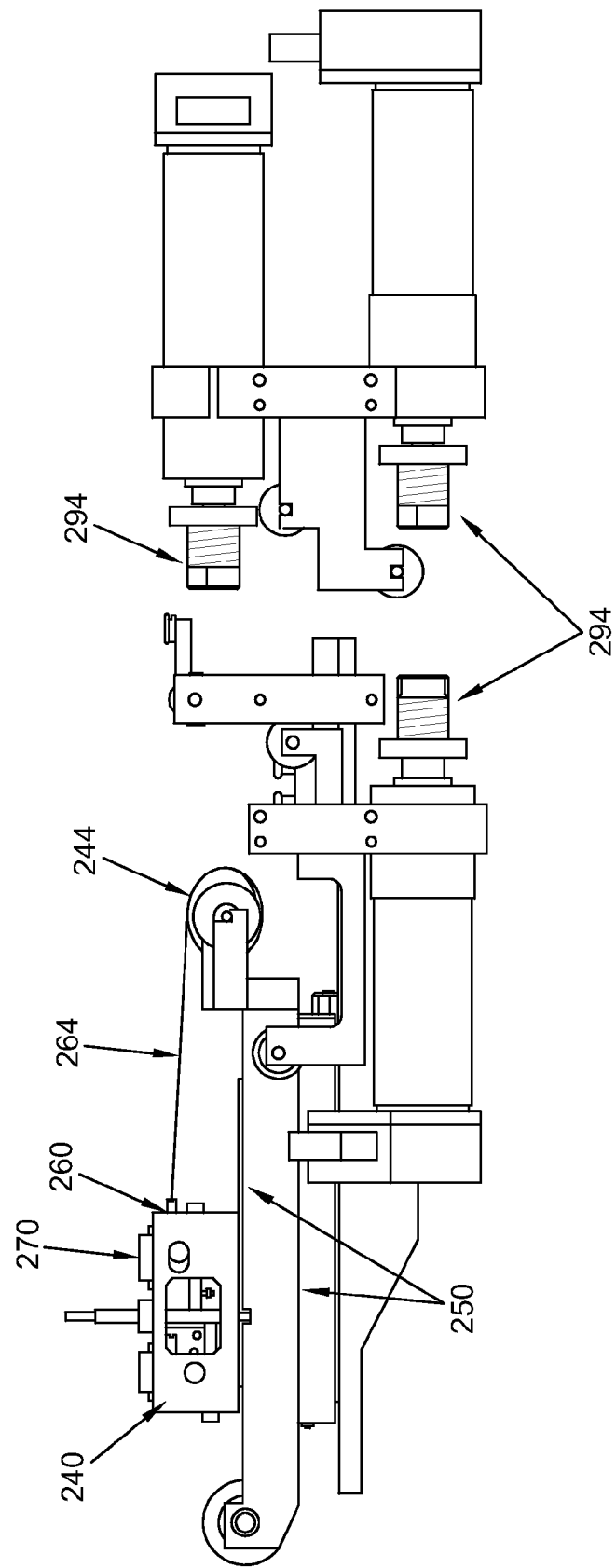

Referring to FIG. 101, a further embodiment of an instrument driver is depicted to show the position of the carriage (240) relative to the linear bearing interfaces (250). Also shown is the interfacing of a portion of a instrument interface cable (264) as it bends around a pulley (244) and completes part of its loop to an instrument interface pulley (260) rotatably coupled to the carriage (240) and coupled to a guide instrument interface socket (270), around the instrument interface pulley (260), and back to a motor capstan pulley (294). To facilitate adjustment and installation of such cable loops, and due to the fact that there is generally no requirement to have a loop operating for a long period of time in one direction, thereby perhaps requiring a true unterminated loop, two ends of a cut cable loop preferably are terminated at each capstan pulley (294).

The carriage (240) depicted in the embodiments of FIGS. 97-101 generally comprises a structural box configured to house the instrument interface sockets and associated instrument interface pulleys. Referring to FIGS. 102A-B, a split carriage (296) is depicted, comprising a main carriage body (304) similar to that of the non split carriage (240) depicted in previous embodiments (240), and either one or two linearly movable portions (302), which are configured to slide relative to the main carriage body (304) when driven along either forward or backward relative to the main carriage body by a gear (300) placed into one of the guide instrument interface sockets, the gear (300) configured to interface with a rack (298) mounted upon the main carriage body (304) adjacent the gear (300). In an alternate embodiment, the carriage need not be split on both sides, but may have one split side and one non-split side. Further, while a carriage with four guide instrument interface sockets is suitable for driving a guide instrument with anywhere from one to four control element interface assemblies, the additional hardware required for all four control element interface assemblies may be undesirable if a particular instrument simply needs one or two.

Figure 102:
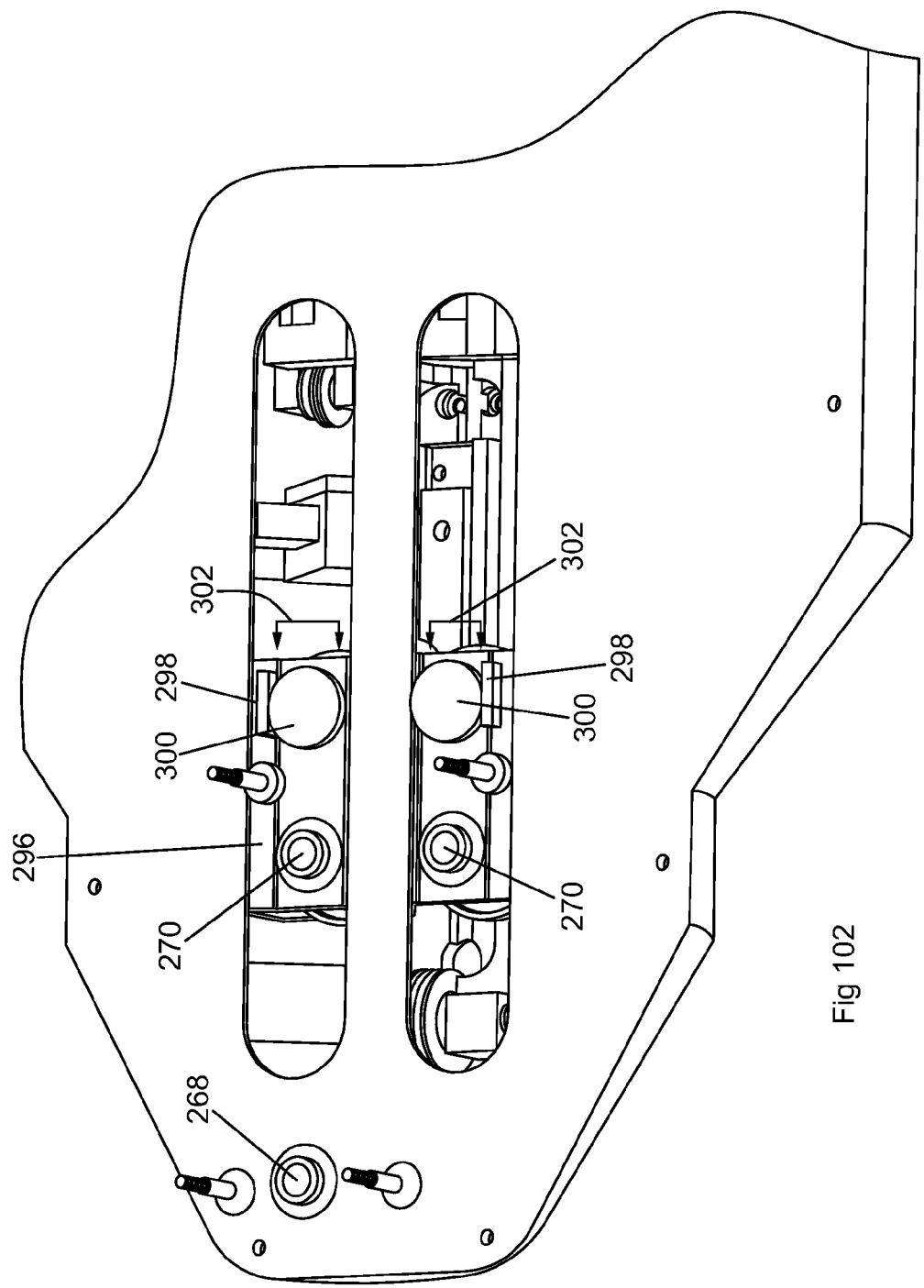

Referring to FIGS. 103.1-103.11, another variation of an instrument driver is depicted, comprising a variation of a split carriage design, such as that depicted in FIG. 102B. As opposed to the embodiment of FIG. 102, wherein each instrument base interface is moved straight along a slot, or rotated, or both (independently), the embodiment of FIGS. 103.1-103.11 provides rotation and/or arcuate slot motion by a "winged" split carriage design, wherein the tension member pulleys and axles may be rotated about the axle axis, or moved along an arcuate pathway, independently.

Referring to FIG. 103.1, a winged split carriage instrument driver (135) is depicted coupled to a guide instrument (215) configured for the winged split carriage with a specialized guide instrument base (141) having two arcuate slots (145) as opposed to the straight slots of other embodiments, such as those described in reference to FIGS. 53, 54, and 72, for example. One or more electronics boards (139) preferably are coupled to the main housing structure (137) of the winged split carriage instrument driver (135). The depicted assembly also comprises a sheath instrument (30) movably threaded over at least a portion of the guide instrument (215) and coupled to the sheath frame block (185) which is coupled to the main housing structure (137) when the depicted assembly is fully assembled.

Referring to FIG. 103.2, a guide instrument base (141) for one embodiment of a winged instrument driver is depicted showing the arcuate slots (145) in greater detail, as well as a winged instrument driver guide instrument base top plate (143), which is configured to be fitted down upon the proximal tubular portion of a guide instrument catheter member (not shown) to maintain the relative positioning of the catheter member (not shown) relative to the guide instrument base (141). An underside isometric view of the same structures depicted in FIG. 103.2 is depicted in FIG. 103.3. In the depicted embodiment, a low-profile control element interface assembly (147) is configured to rotate about the longitudinal axis (219) of the interface assembly while also slidably translating through its associated arcuate slot (145). FIG. 103.4 depicts an exploded view of the guide instrument base (141) of FIG. 103.2. In FIG. 103.4, the guide instrument base top plate (143) and the guide instrument base bottom plate (133) are shown separately. Furthermore, the arcuate slots (145) are shown defined in the bottom plate (133).

Referring to FIG. 103.5, a low-profile control element interface assembly (147) is shown in isometric view comprising a splined axle (157) coupled to a pulley flange (153), and also coupled to a set of control element pulleys (155) which are compressed between a low-profile manual adjustment knob (151) and the pulley flange (153) with a retaining fastener (149), such as a screw. An exploded view of the same structures is depicted in FIG. 103.6. Also shown in FIG. 103.6 is a pin (159) configured to prevent relative rotational displacement between the two control element pulleys (155) when the low-profile control element interface assembly (147) is assembled. The depicted embodiment of low-profile control element interface assembly (147) may be utilized with any of the aforementioned instrument base and instrument driver assemblies, provided that the instrument interface sockets (44) are also geometrically matched for a splined interface between socket and axle facilitating highly-efficient transfer of loads between the matched socket and axle. The low-profile control element interface assembly (147) preferably comprises polymers or metals which may be formed or machined into very high precision subassemblies or parts which are low in weight, high in hardness, and low in fracture toughness. In one embodiment, each of the components of the low-profile control element interface assembly (147) comprises polycarbonate or ultra-high-molecular-weight polyethylene.

Referring to FIG. 103.7, a winged split carriage assembly is depicted in semi-exploded view. The winged carriage base (173) is configured to rotatably support two independently rotatable wing structures (221), each comprising a bottom portion (165) and a top portion (163). A further exploded view of the wing structures (221) and associated members are depicted in FIG. 103.8. Rotatably coupled to the rotatable wing structures (221) is a set of control element pulleys (167) to which a splined instrument interface socket (161) is coupled. The winged carriage base (173) is configured to slidably couple to a carriage interface frame (not shown) with bearings (179). As shown in FIG. 103.9, slots (181) constrain the motion of the winged carriage base (173) relative to the carriage interface frame (191) to linear motion. Shafts and bearings are utilized to rotatably couple the wing structures (221) to the winged carriage base and facilitate rotational motion of the wing structures (221) about the axis of the pertinent coupling shaft (171). Similar shaft and bearing configurations are utilized to provide for rotation of the control element pulleys (167) relative to the wing structures (221). Thus, the winged split carriage design is configured to allow for independent motion of each of two wing structures (221), while also allowing for independent rotational motion of two sets of control element pulleys (167) and thereby instrument interface sockets (161). In other words, with a winged guide instrument (215) such as that depicted in FIG. 103.1 coupled to an instrument base mounting plate (187) having an arcuate slot (145), and two control element interface assemblies (147) coupled to two instrument interface sockets positioned below the mounting plate (187) in the configuration depicted in FIG. 103.1, each of the control element interface assemblies (147) may be rotated about their longitudinal axis (169), and also arcuately translated through the arcuate slot (145) formed in the instrument base (141), to provide for tensioning and control of two control elements, one around each of the control element pulleys (167) on each of the control element interface assemblies (147), with actuation of a single control element interface assembly (147). Thus four control elements may be driven with the actuation of only two control element interface assemblies (147).

Referring to FIG. 103.10, an exploded view of an assembly similar to that depicted in FIG. 103.1 is depicted. The sheath instrument (30), the two control element interface assemblies (147), and the guide catheter instrument member of FIG. 103.1 are illustrated in FIG. 103.10. As with aforementioned embodiments, the instrument driver roll assembly (195) and instrument driver motor/gear assembly (193) are coupled to the frame of the main housing structure (137) of the instrument driver. As shown in FIG. 103.11, redundant encoder readers (211) associated with each of four control element drive motors (209) of this embodiment facilitate high precision rotational position readings of the motor shafts and prevent position read errors. The motor output shafts are coupled to bevel gears (207) which are interfaced with another set of bevel gears (213) and thereby configured to drive the depicted vertical output shafts (205). The motor/gear interface block (203) is utilized to couple the motors, gears, and shafts into positions relative to each other and the main frame of the instrument driver (not shown), while constraining motions generally to rotational motions of shafts, motors, gears, and bearings. The rotation and arcuate translation of the winged structure instrument interface sockets (161) relative to the winged carriage base (173) and wing structures (221) is a key difference between the winged split carriage instrument driver and the non-winged embodiments described herein.

Figure 104:
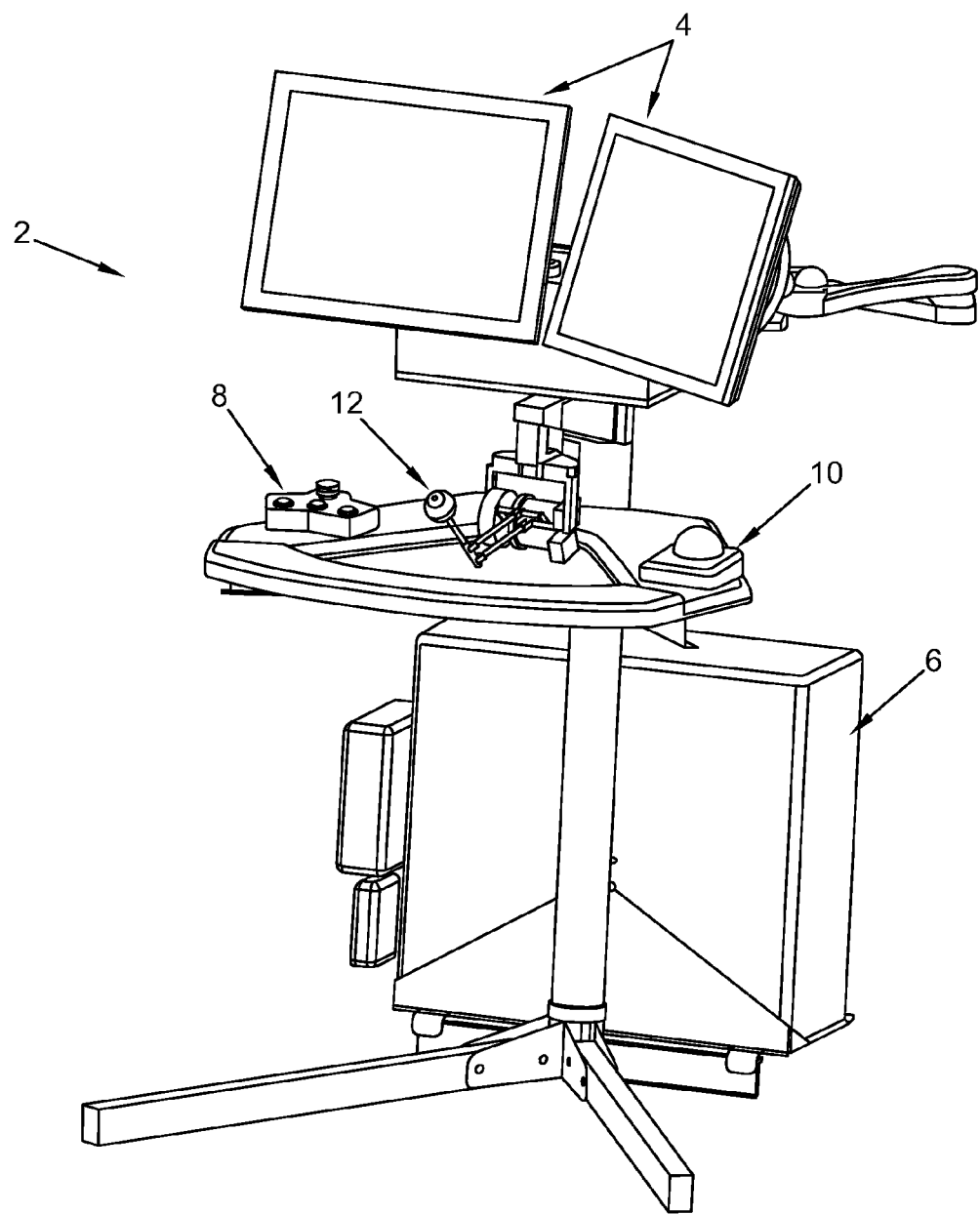
FIG. 104 illustrates one embodiment of an operator control station.
Figure 105:
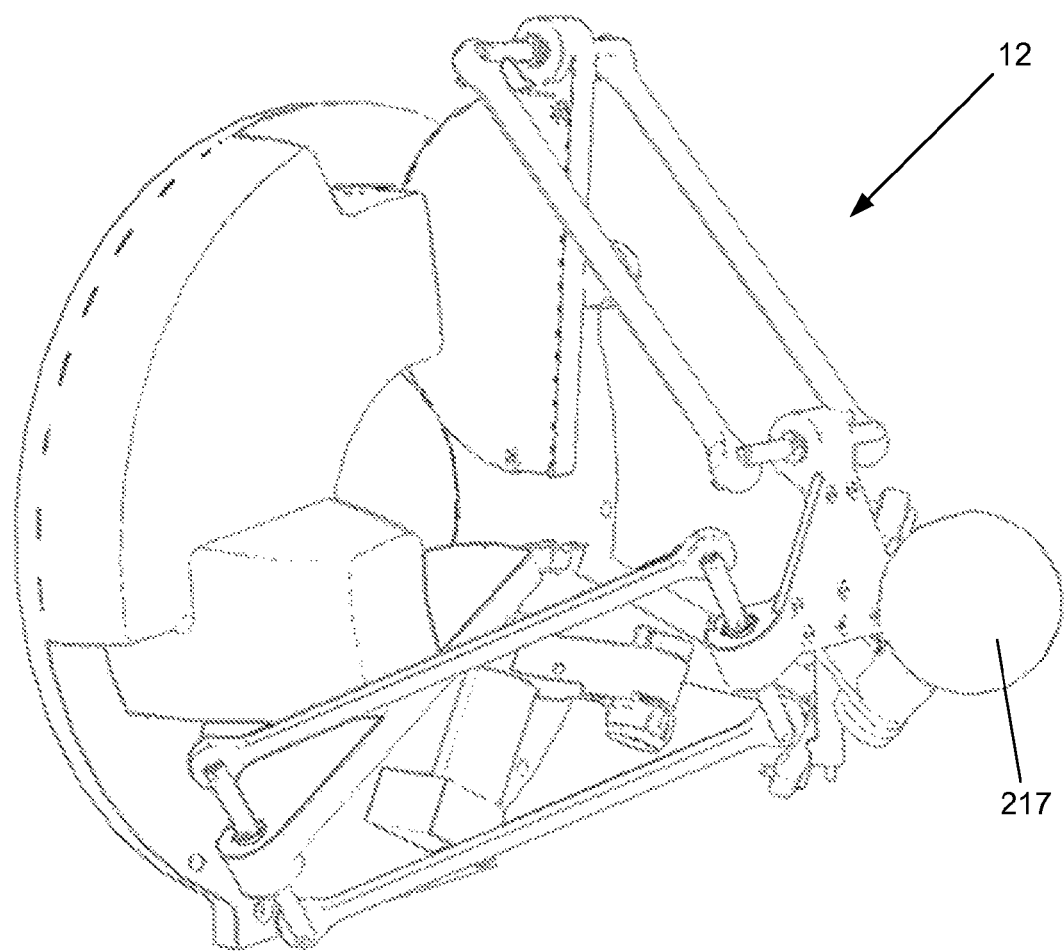
FIGS. 105A-B illustrate embodiments of master input devices.

Referring to FIG. 104, one embodiment of an operator control station is depicted showing a control button console (8), a computer (6), a computer control interface device (10), such as a mouse, a visual display system (4) and a master input device (12). In addition to buttons on the button console (8), footswitches and other known types user control interfaces may be utilized to provide an operator interface with the system controls. Referring to FIG. 105A, in one embodiment, the master input device (12) is a multi-degree-of-freedom device having multiple joints and associated encoders (306). An operator interface (217) is configured for comfortable interfacing with the human fingers. The depicted embodiment of the operator interface (217) is substantially spherical. Further, the master input device may have integrated haptics capability for providing tactile feedback to the user. Another embodiment of a master input device (12) is depicted in FIG. 105B having a similarly-shaped operator interface (217). Suitable master input devices are available from manufacturers such as SensAble Technologies, Inc. of Woburn, Mass. under the trade name Phantom® Haptic Devices or from Force Dimension of Lausanne, Switzerland under the trade name Omega Haptic Device. In one embodiment featuring an Omega-type master input device, the motors of the master input device are utilized for gravity compensation. In other words, when the operator releases the master input device from his hands, the master input device is configured to stay in position, or hover around the point at which is was left, or another predetermined point, without gravity taking the handle of the master input device to the portion of the master input device's range of motion closest to the center of the earth. In another embodiment, haptic feedback is utilized to provide feedback to the operator that he has reached the limits of the pertinent instrument workspace. In another embodiment, haptic feedback is utilized to provide feedback to the operator that he has reached the limits of the subject tissue workspace when such workspace has been registered to the workspace of the instrument (i.e., should the operator be navigating a tool such as an ablation tip with a guide instrument through a 3-D model of a heart imported, for example, from CT data of an actual heart, the master input device is configured to provide haptic feedback to the operator that he has reached a wall or other structure of the heart as per the data of the 3-D model, and therefore help prevent the operator from driving the tool through such wall or structure without at least feeling the wall or structure through the master input device). In another embodiment, contact sensing technologies configured to detect contact between an instrument and tissue may be utilized in conjunction with the haptic capability of the master input device to signal the operator that the instrument is indeed in contact with tissue.

Referring to FIGS. 106A-109, the basic kinematics of a catheter with four control elements is reviewed.

Referring to FIGS. 106A-B, as tension is placed only upon the bottom control element (312), the catheter (90) bends downward, as shown in FIG. 106A. Similarly, pulling the left control element (314) in FIGS. 107A-B bends the catheter (90) left, pulling the right control element (310) in FIGS. 108A-B bends the catheter (90) right, and pulling the top control element (308) in FIGS. 109A-B bends the catheter (90) up. As will be apparent to those skilled in the art, well-known combinations of applied tension about the various control elements results in a variety of bending configurations at the tip of the catheter member (90). One of the challenges in accurately controlling a catheter or similar elongate member with tension control elements is the retention of tension in control elements, which may not be the subject of the majority of the tension loading applied in a particular desired bending configuration. If a system or instrument is controlled with various levels of tension, then losing tension, or having a control element in a slack configuration, can result in an unfavorable control scenario.

Figure 110E:
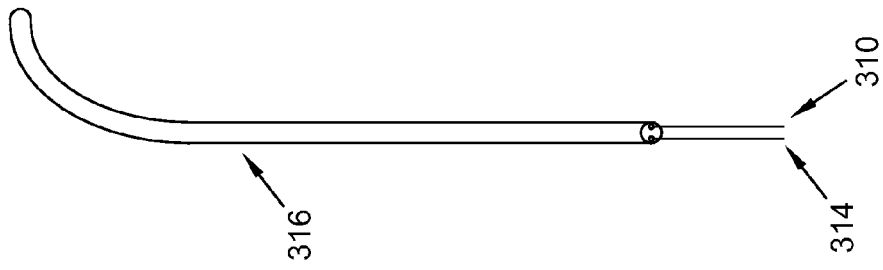
FIGS. 110A-E illustrate catheter control in accordance to one embodiment.
Figure 110D:
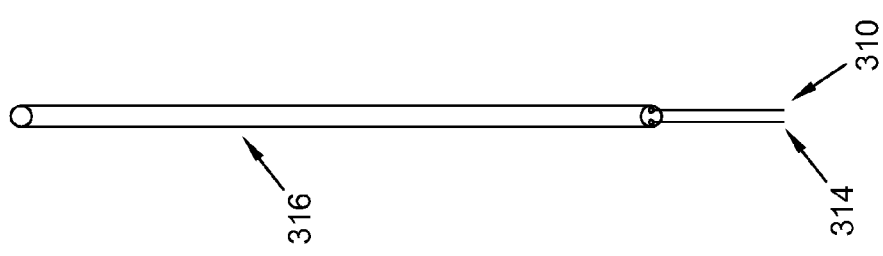
Figure 110C:
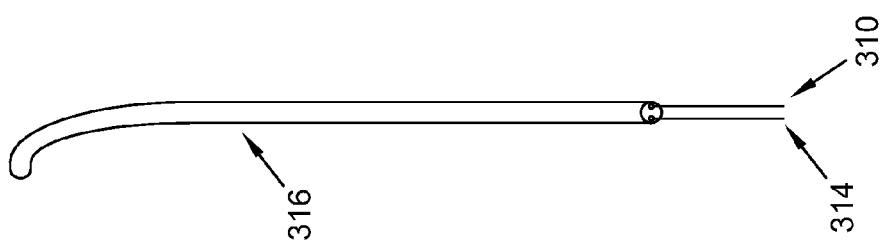
Figure 110B:
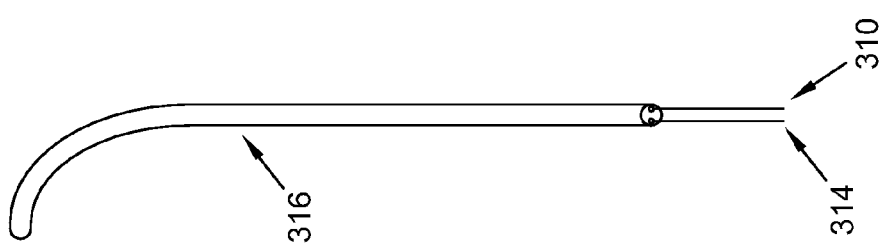
Figure 110A:
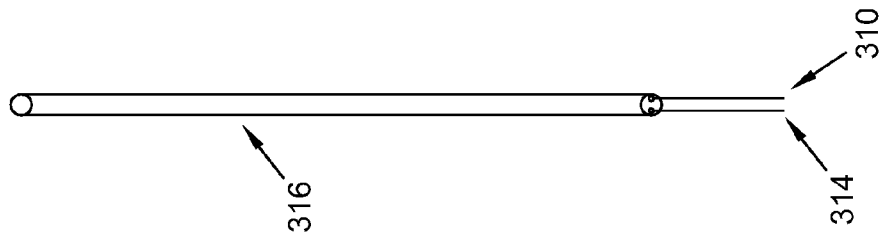

Referring to FIGS. 110A-E, a simple scenario is useful in demonstrating this notion. As shown in FIG. 110A, a simple catheter (316) steered with two control elements (314, 310) is depicted in a neutral position. If the left control element (314) is placed into tension greater than the tension, if any, which the right control element (310) experiences, the catheter (316) bends to the left, as shown in FIG. 110B. If a change of direction is desired, this paradigm needs to reverse, and the tension in the right control element (310) needs to overcome that in the left control element (314). At the point of a reversal of direction like this, where the tension balance changes from left to right, without slack or tension control, the right most control element (310) may gather slack which needs to be taken up before precise control can be reestablished. Subsequent to a "reeling in" of slack which may be present, the catheter (316) may be may be pulled in the opposite direction, as depicted in FIGS. 110C-E, without another slack issue from a controls perspective until a subsequent change in direction.

The above-described instrument embodiments present various techniques for managing tension control in various guide instrument systems having between two and four control elements. For example, in one set of embodiments, tension may be controlled with active independent tensioning of each control element in the pertinent guide catheter via independent control element interface assemblies (132) associated with independently-controlled guide instrument interface sockets (270) on the instrument driver (16). Thus, tension may be managed by independently actuating each of the control element interface assemblies (132) in a four-control-element embodiment, such as that depicted in FIGS. 17 and 47, a three-control-element embodiment, such as that depicted in FIGS. 63 and 64, or a two-control-element embodiment, such as that depicted in FIGS. 56 and 66.

In another set of embodiments, tension may be controlled with active independent tensioning with a split carriage design, as described in reference to FIG. 102. For example, with an instrument embodiment similar to that depicted in FIGS. 53, 54, and 56, a split carriage with two independent linearly movable portions, such as that depicted in FIG. 102, may be utilized to actively and independently tension each of the two control element interface assemblies, each of which is associated with two dimensions of a given degree of freedom. For example, there can be + and − pitch on one interface assembly, + and − yaw on the other interface assembly, with slack or tension control provided for pitch by one of the linearly movable portions (302) of the split carriage (296), and slack or tension control provided for yaw by the other linearly movable portion (302) of the split carriage (296).

Similarly, with an embodiment similar to that of FIGS. 71-73, slack or tension control for a single degree of freedom, such as yaw or pitch, may be provided by a single-sided split carriage design similar to that of FIG. 102, with the exception that only one linearly movable portion would be required to actively tension the single control element interface assembly of an instrument.

In another set of embodiments, tensioning may be controlled with spring-loaded idlers configured to keep the associated control elements out of slack, as in the embodiments depicted in FIGS. 57-62 and 69-70. The control elements preferably are pre-tensioned in each embodiment to prevent slack and provide predictable performance. Indeed, in yet another set of embodiments, pre-tensioning may form the main source of tension management, as in the embodiments depicted in FIGS. 55 and 67-68. In the case of embodiments only having pre-tensioning or spring-loaded idler tensioning, the control system may need to be configured to reel in bits of slack at certain transition points in catheter bending, such as described above in relation to FIGS. 110A-B.

To accurately coordinate and control actuations of various motors within an instrument driver from a remote operator control station such as that depicted in FIG. 1, an advanced computerized control and visualization system is preferred. While the control system embodiments that follow are described in reference to a particular control systems interface, namely the Simulink® and xPC Target control interfaces available from The MathWorks, Inc. of Natick, Mass., and PC-based computerized hardware configurations, many other configurations may be utilized, including various pieces of specialized hardware, in place of more flexible software controls running on PC-based systems.

Referring to FIG. 111, an overview of an embodiment of a controls system flow is depicted. A master computer (400) running master input device software, visualization software, instrument localization software, and software to interface with operator control station buttons and/or switches is depicted. In one embodiment, the master input device software is a proprietary module packaged with an off-the-shelf master input device system, such as the Phantom® from SensAble Technologies, Inc., which is configured to communicate with the Phantom® Haptic Device hardware at a relatively high frequency as prescribed by the manufacturer. Other suitable master input devices, such as that (12) depicted in FIG. 105B are available from suppliers such as Force Dimension of Lausanne, Switzerland. The master input device (12) may also have haptics capability to facilitate feedback to the operator, and the software modules pertinent to such functionality may also be operated on the master computer (400). Preferred embodiments of haptics feedback to the operator are discussed in further detail below.

Figure 112B:
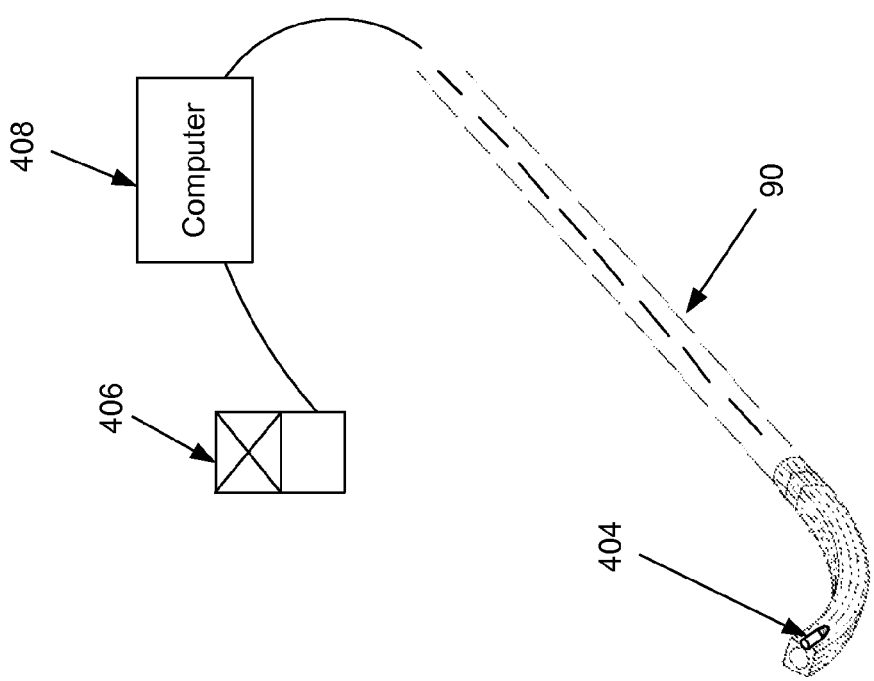
FIGS. 112A-B illustrate examples of localization systems.
Figure 112A:
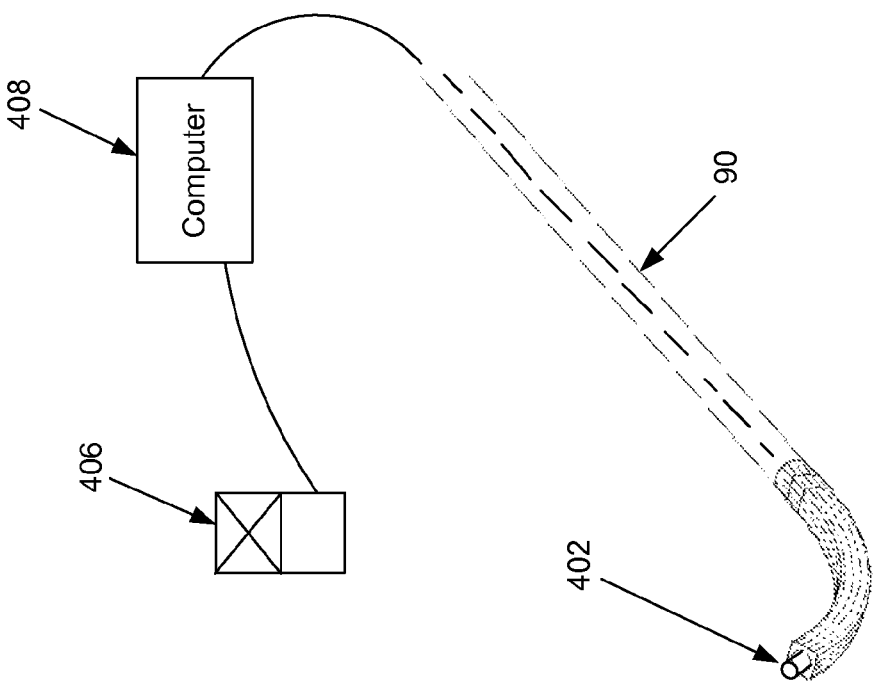

The term "localization" is used in the art in reference to systems for determining and/or monitoring the position of objects, such as medical instruments, in a reference coordinate system. In one embodiment, the instrument localization software is a proprietary module packaged with an off-the-shelf or custom instrument position tracking system, such as those available from Ascension Technology Corporation of Burlington, Vt.; Biosense Webster, Inc. of Diamond Bar, Calif.; Endocardial Solutions—St. Jude Medical, Inc. of St. Paul, Minn.; EP Technologies—Boston Scientific Corporation of Natick, Mass.; Medtronic, Inc. of Minneapolis, Minn.; and others. Such systems may be capable of providing not only real-time or near real-time positional information, such as X-Y-Z coordinates in a Cartesian coordinate system, but also orientation information relative to a given coordinate axis or system. Some of the commercially-available localization systems use electromagnetic relationships to determine position and/or orientation, while others, such as some of those available from Endocardial Solutions—St Jude Medical, Inc., utilize potential difference or voltage, as measured between a conductive sensor located on the pertinent instrument and conductive portions of sets of patches placed against the skin, to determine position and/or orientation. Referring to FIGS. 112A and 112B, various localization sensing systems may be utilized with the various embodiments of the robotic catheter system disclosed herein. In other embodiments not comprising a localization system to determine the position of various components, kinematic and/or geometric relationships between various components of the system may be utilized to predict the position of one component relative to the position of another. Some embodiments may utilize both localization data and kinematic and/or geometric relationships to determine the positions of various components.

As shown in FIG. 112A, one preferred localization system comprises an electromagnetic field transmitter (406) and an electromagnetic field receiver (402) positioned within the central lumen of a guide catheter (90). The transmitter (406) and receiver (402) are interfaced with a computer operating software configured to detect the position of the detector relative to the coordinate system of the transmitter (406) in real or near-real time with high degrees of accuracy. Referring to FIG. 112B, a similar embodiment is depicted with a receiver (404) embedded within the guide catheter (90) construction. Preferred receiver structures may comprise three or more sets of very small coils spatially configured to sense orthogonal aspects of magnetic fields emitted by a transmitter. Such coils may be embedded in a custom configuration within or around the walls of a preferred catheter construct. For example, in one embodiment, two orthogonal coils are embedded within a thin polymeric layer at two slightly flattened surfaces of a catheter (90) body approximately ninety degrees orthogonal to each other about the longitudinal axis of the catheter (90) body, and a third coil is embedded in a slight polymer-encapsulated protrusion from the outside of the catheter (90) body, perpendicular to the other two coils. Due to the very small size of the pertinent coils, the protrusion of the third coil may be minimized. Electronic leads for such coils may also be embedded in the catheter wall, down the length of the catheter body to a position, preferably adjacent an instrument driver, where they may be routed away from the instrument to a computer running localization software and interfaced with a pertinent transmitter.

In another similar embodiment (not shown), one or more conductive rings may be electronically connected to a potential-difference-based localization/orientation system, along with multiple sets, preferably three sets, of conductive skin patches, to provide localization and/or orientation data utilizing a system such as those available from Endocardial Solutions—St. Jude Medical, Inc. The one or more conductive rings may be integrated into the walls of the instrument at various longitudinal locations along the instrument, or set of instruments. For example, a guide instrument may have several conductive rings longitudinally displaced from each other toward the distal end of the guide instrument, while a coaxially-coupled sheath instrument may similarly have one or more conductive rings longitudinally displaced from each other toward the distal end of the sheath instrument—to provide precise data regarding the location and/or orientation of the distal ends of each of such instruments.

Figure 113:
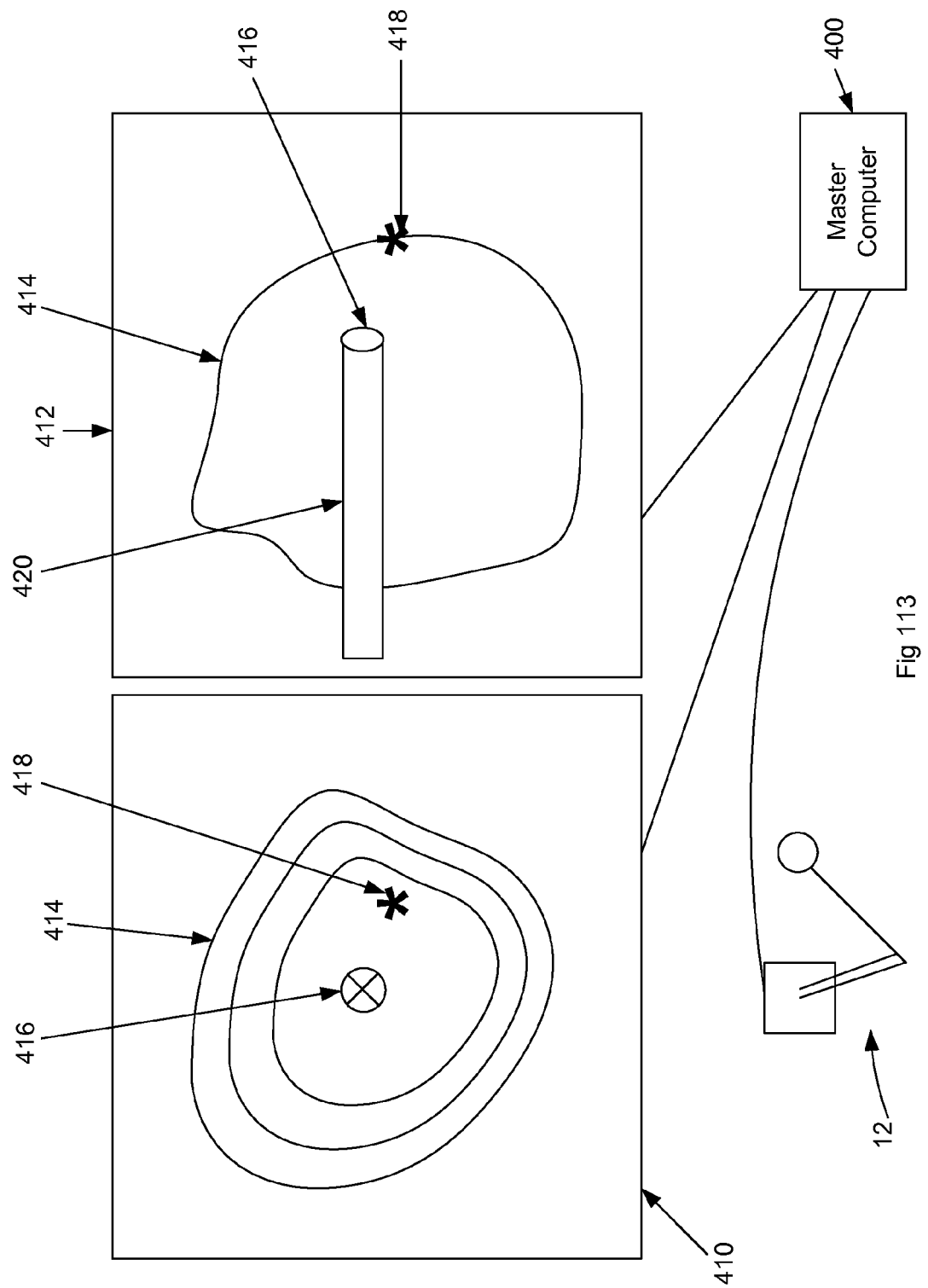
FIG. 113 illustrates the relationship between visualization and navigation for one embodiment.

Referring back to FIG. 111, in one embodiment, visualization software runs on the master computer (400) to facilitate real-time driving and navigation of one or more steerable instruments. In one embodiment, visualization software provides an operator at an operator control station (2), such as that depicted in FIG. 1, with a digitized dashboard or windshield display to enhance instinctive drivability of the pertinent instrumentation within the pertinent tissue structures. Referring to FIG. 113, a simple illustration is useful to explain one embodiment of a preferred relationship between visualization and navigation with a master input device (12). In the depicted embodiment, two display views (410, 412) are shown. One preferably represents a primary navigation view (410) and one may represent a secondary navigation view (412). To facilitate instinctive operation of the system, it is preferable to have the master input device coordinate system at least approximately synchronized with the coordinate system of at least one of the two views. Further, it is preferable to provide the operator with one or more secondary views which may be helpful in navigating through challenging tissue structure pathways and geometries.

Using the operation of an automobile as an example, if the master input device is a steering wheel and the operator desires to drive a car in a forward direction using one or more views, his first priority is likely to have a view straight out the windshield, as opposed to a view out the back window, out one of the side windows, or from a car in front of the car that he is operating. The operator might prefer to have the forward windshield view as his primary display view, such that a right turn on the steering wheel takes him right as he observes his primary display, a left turn on the steering wheel takes him left, and so forth. If the operator of the automobile is trying to park the car adjacent another car parked directly in front of him, it might be preferable to also have a view from a camera positioned, for example, upon the sidewalk aimed perpendicularly through the space between the two cars (one driven by the operator and one parked in front of the driven car), so the operator can see the gap closing between his car and the car in front of him as he parks. While the driver might not prefer to have to completely operate his vehicle with the sidewalk perpendicular camera view as his sole visualization for navigation purposes, this view is helpful as a secondary view.

Referring still to FIG. 113, if an operator is attempting to navigate a steerable catheter in order to, for example, contact a particular tissue location with the catheter's distal tip, a useful primary navigation view (410) may comprise a three dimensional digital model of the pertinent tissue structures (414) through which the operator is navigating the catheter with the master input device (12), along with a representation of the catheter distal tip location (416) as viewed along the longitudinal axis of the catheter near the distal tip. This embodiment illustrates a representation of a targeted tissue structure location (418), which may be desired in addition to the tissue digital model (414) information. A useful secondary view (412) displayed upon a different monitor or in a different window upon the same monitor or even within the same user interface window, for example, may comprise an orthogonal view representation depicting the catheter tip location (416) and also perhaps a catheter body representation (420) to facilitate the operator's driving of the catheter tip toward the desired targeted tissue location (418).

In one embodiment, subsequent to development and display of a digital model of pertinent tissue structures, an operator may select one primary and at least one secondary view to facilitate navigation of the instrumentation. By selecting which view is a primary view, the user can automatically toggle a master input device (12) coordinate system to synchronize with the selected primary view. In an embodiment with the leftmost depicted view (410) selected as the primary view, to navigate toward the targeted tissue site (418), the operator should manipulate the master input device (12) forward, to the right, and down. The right view will provide valued navigation information, but will not be as instinctive from a "driving" perspective.

To illustrate: if the operator wishes to insert the catheter tip toward the targeted tissue site (418) watching only the rightmost view (412) without the master input device (12) coordinate system synchronized with such view, the operator would have to remember that pushing straight ahead on the master input device will make the distal tip representation (416) move to the right on the rightmost display (412). Should the operator decide to toggle the system to use the rightmost view (412) as the primary navigation view, the coordinate system of the master input device (12) is then synchronized with that of the rightmost view (412), enabling the operator to move the catheter tip (416) closer to the desired targeted tissue location (418) by manipulating the master input device (12) down and to the right.

The synchronization of coordinate systems described herein may be conducted using fairly conventional mathematic relationships. For example, in one embodiment, the orientation of the distal tip of the catheter may be measured using a 6-axis position sensor system such as those available from Ascension Technology Corporation, Biosense Webster, Inc., Endocardial Solutions—St. Jude Medical, Inc., EP Technologies—Boston Scientific Corporation, and others. A 3-axis coordinate frame C for locating the distal tip of the catheter is constructed from this orientation information. The orientation information is used to construct the homogeneous transformation matrix, $T_{C0}^{G0}$, which transforms a vector in the Catheter coordinate frame C to the fixed Global coordinate frame G in which the sensor measurements are done (the subscript $C_0$ and superscript $G_0$ are used to represent the 0'th, or initial, step). As a registration step, the computer graphics view of the catheter is rotated until the master input and the computer graphics view of the catheter distal tip motion are coordinated and aligned with the camera view of the graphics scene. The 3-axis coordinate frame transformation matrix $T_{Gref}^{G0}$ for the camera position of this initial view is stored (subscripts $G_{ref}$ and superscript $C_{ref}$ stand for the global and camera "reference" views). The corresponding catheter "reference view" matrix for the catheter coordinates is obtained as:

$$T_{Cref}^{C0} = T_{G0}^{C0} T_{Gref}^{G0} T_{Cref}^{Gref} = (T_{C0}^{G0})^{-1} T_{Gref}^{G0} T_{C1}^{G1}$$

Also note that the catheter's coordinate frame is fixed in the global reference frame G, thus the transformation matrix between the global frame and the catheter frame is the same in all views, i.e., $T_{C0}^{G0} = T_{Cref}^{Gref} = T_{Ci}^{Gi}$ for any arbitrary view i.

The coordination between primary view and master input device coordinate systems is achieved by transforming the master input as follows: Given any arbitrary computer graphics view of the representation, e.g. the i'th view, the 3-axis coordinate frame transformation matrix $T_{Gi}^{G0}$ of the camera view of the computer graphics scene is obtained form the computer graphics software. The corresponding catheter transformation matrix is computed in a similar manner as above:

$$T_{Ci}^{C0} = T_{G0}^{C0} T_{Gi}^{G0} T_{Ci}^{Gi} = (T_{C0}^{G0})^{-1} T_{Gi}^{G0} T_{Ci}^{Gi}$$

The transformation that needs to be applied to the master input which achieves the view coordination is the one that transforms from the reference view that was registered above, to the current ith view, i.e., $T_{Cref}^{Ci}$. Using the previously computed quantities above, this transform is computed as:

$$T_{Cref}^{Ci} = T_{C0}^{Ci} T_{Cref}^{C0}$$

The master input is transformed into the commanded catheter input by application of the transformation $T_{Cref}^{Ci}$. Given a command input $$r_{master} = \begin{bmatrix} x_{master} \\ y_{master} \\ y_{master} \end{bmatrix},$$

one may calculate:

$$r_{catheter} = \begin{bmatrix} x_{catheter} \\ y_{catheter} \\ y_{catheter} \end{bmatrix} = T_{Cref}^{Ci} \begin{bmatrix} x_{master} \\ y_{master} \\ y_{master} \end{bmatrix}.$$

Under such relationships, coordinate systems of the primary view and master input device may be aligned for instinctive operation.

Referring back to embodiment of FIG. 111, the master computer (400) also comprises software and hardware interfaces to operator control station buttons, switches, and other input devices which may be utilized, for example, to "freeze" the system by functionally disengaging the master input device as a controls input, or provide toggling between various scaling ratios desired by the operator for manipulated inputs at the master input device (12). The master computer (400) has two separate functional connections with the control and instrument driver computer (422): a first connection (426) for passing controls and visualization related commands, such as commands for a desired XYZ in the catheter coordinate system and a second connection (428) for passing safety signal commands. Similarly, the control and instrument driver computer (422) has two separate functional connections with the instrument and instrument driver hardware (424): a first connection (430) for passing control and visualization related commands such as required-torque-related voltages to the amplifiers to drive the motors and encoders and a second connection (432) for passing safety signal commands.

In one embodiment, the safety signal commands represent a simple signal repeated at very short intervals, such as every 10 milliseconds, such signal chain being logically read as "system is ok, amplifiers stay active". If there is any interruption in the safety signal chain, the amplifiers are logically toggled to inactive status and the instrument cannot be moved by the control system until the safety signal chain is restored.

Also shown in the signal flow overview of FIG. 111 is a pathway (434) between the physical instrument and instrument driver hardware back to the master computer to depict a closed loop system embodiment wherein instrument localization technology, such as that described in reference to FIGS. 112A-B, is utilized to determine the actual position of the instrument to minimize navigation and control error, as described in further detail below.

FIGS. 114-124 depict various aspects of one embodiment of a SimuLink® software control schema for an embodiment of the physical system, with particular attention to an embodiment of a "master following mode." In this embodiment, an instrument is driven by following instructions from a master input device, and a motor servo loop embodiment, which comprises key operational functionality for executing upon commands delivered from the master following mode to actuate the instrument.

Figure 114:
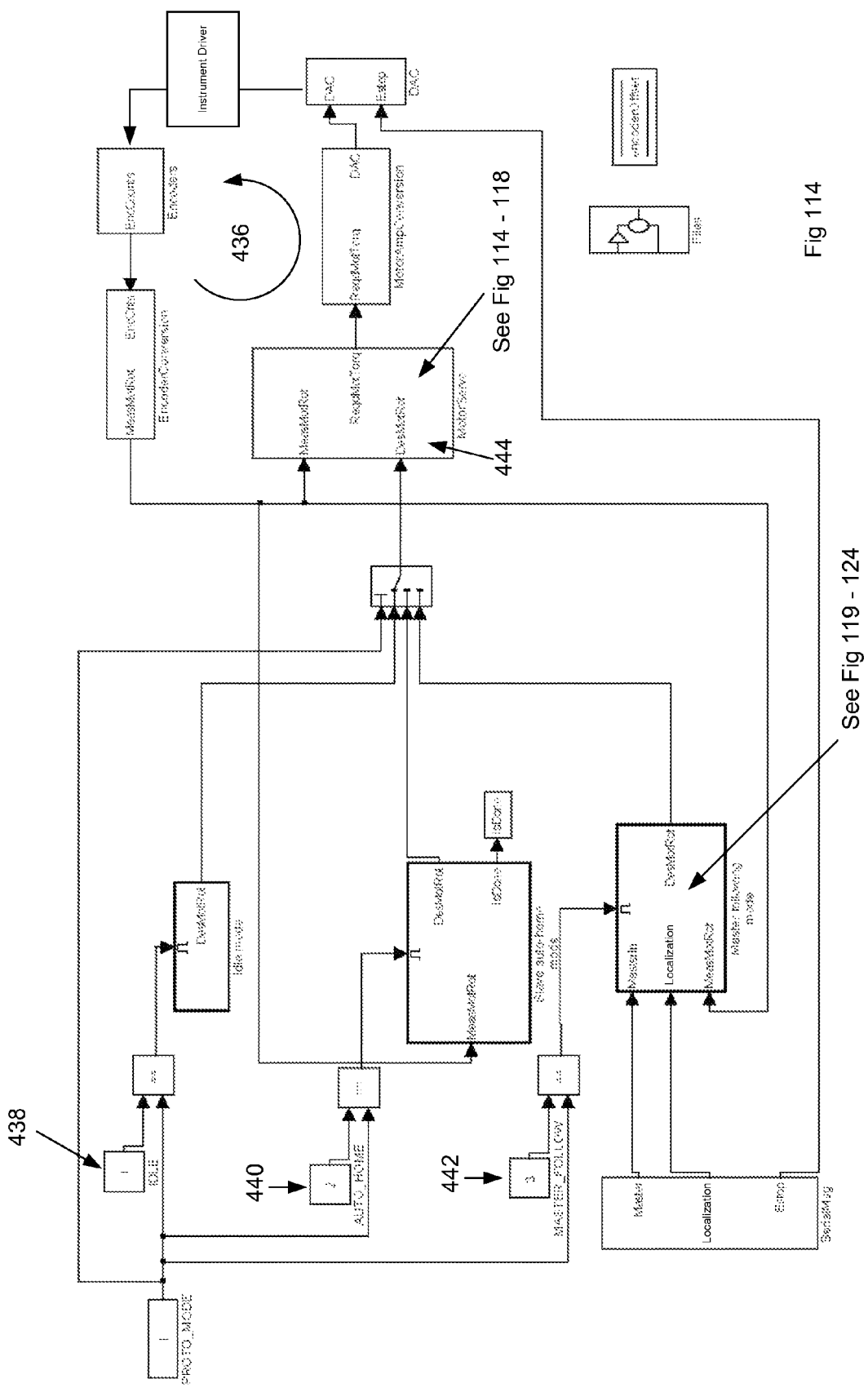
FIGS. 114-124 illustrate various aspects of a control schema for one embodiment.

FIG. 114 depicts a high-level view of an embodiment wherein any one of three modes may be toggled to operate the primary servo loop (436). In idle mode (438), the default mode when the system is started up, all of the motors are commanded via the motor servo block (444) to servo about their current positions, their positions being monitored with digital encoders associated with the motors. In other words, idle mode (438) deactivates the motors, while the remaining system stays active. Thus, when the operator leaves idle mode, the system knows the position of the relative components. In auto home mode (440), cable loops within an associated instrument driver, such as that depicted in FIG. 98, are centered within their cable loop range to ensure substantially equivalent range of motion of an associated instrument, such as that depicted in FIG. 17, in both directions for a various degree of freedom, such as + and − directions of pitch or yaw, when loaded upon the instrument driver. This is a setup mode for preparing an instrument driver before an instrument is engaged.

In master following mode (442), the control system receives signals from the master input device, and in a closed loop embodiment from both a master input device and a localization system, and forwards drive signals to the primary servo loop (436) to actuate the instrument in accordance with the forwarded commands. Aspects of this embodiment of the master following mode (442) are depicted in further detail in FIGS. 119-124. Aspects of the primary servo loop and motor servo block (444) are depicted in further detail in FIGS. 115-118.

Figure 119:
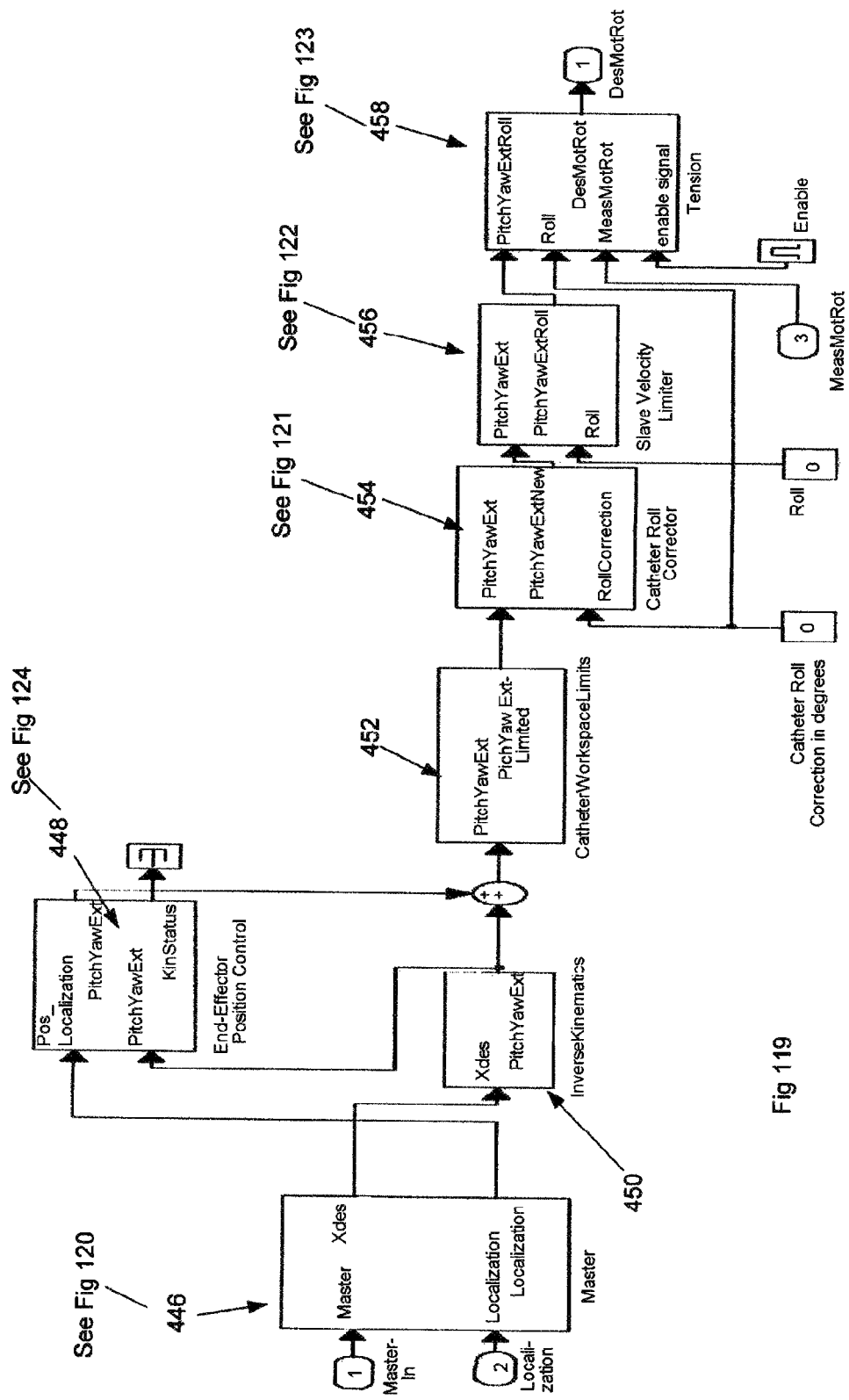
Figure 120:
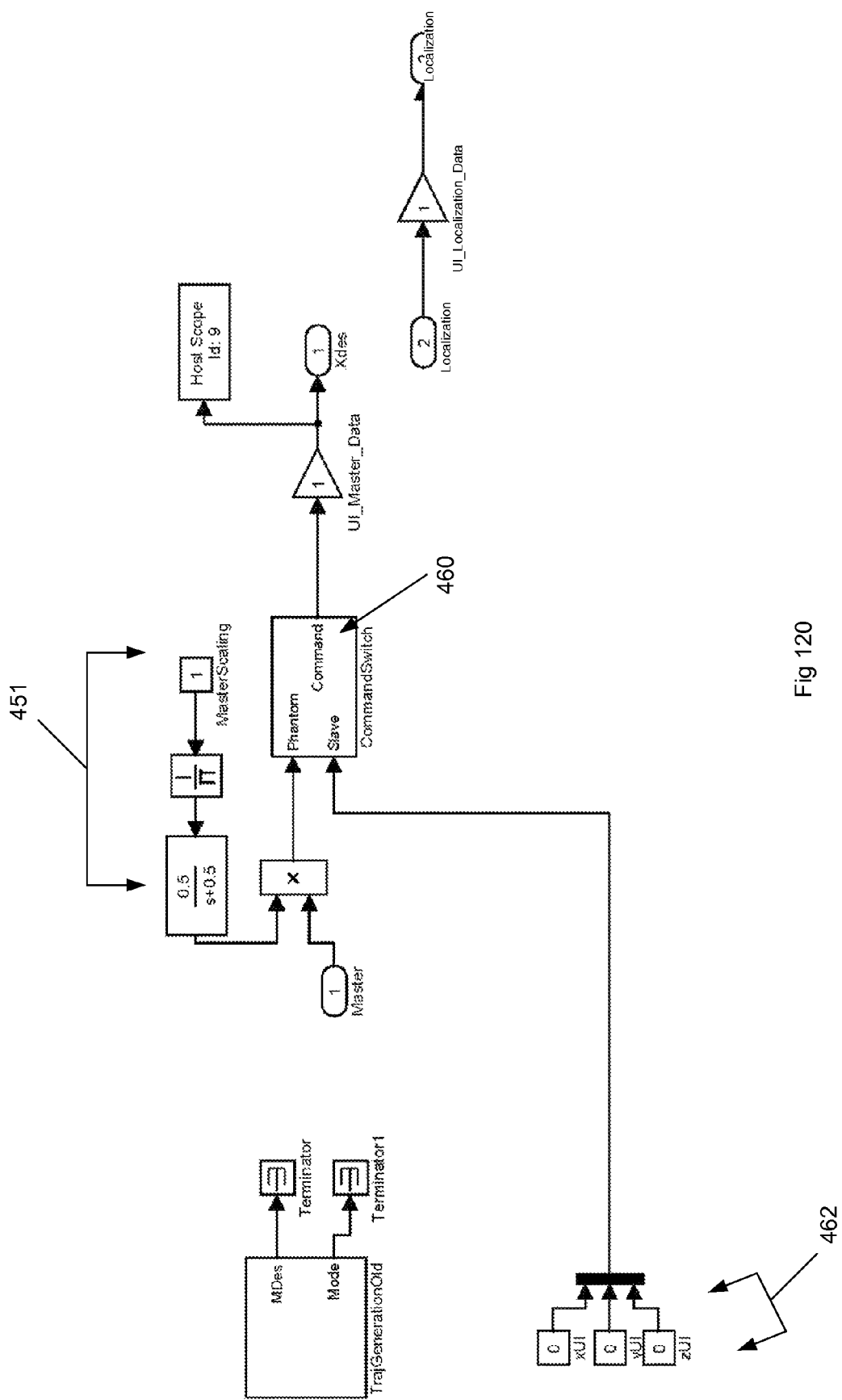

Referring to FIG. 119, a more detailed functional diagram of an embodiment of master following mode (442) is depicted. As shown in FIG. 119, the inputs to functional block (446) are XYZ position of the master input device in the coordinate system of the master input device which, per a setting in the software of the master input device may be aligned to have the same coordinate system as the catheter, and localization XYZ position of the distal tip of the instrument as measured by the localization system in the same coordinate system as the master input device and catheter. Referring to FIG. 120 for a more detailed view of functional block (446) of FIG. 119, a switch (460) is provided at block to allow switching between master inputs for desired catheter position, to an input interface (462) through which an operator may command that the instrument go to a particular XYZ location in space. Various controls features may also utilize this interface to provide an operator with, for example, a menu of destinations to which the system should automatically drive an instrument, etc. Also depicted in FIG. 120 is a master scaling functional block (451) which is utilized to scale the inputs coming from the master input device with a ratio selectable by the operator. The command switch (460) functionality includes a low pass filter to weight commands switching between the master input device and the input interface (462), to ensure a smooth transition between these modes.

Referring back to FIG. 119, desired position data in XYZ terms is passed to the inverse kinematics block (450) for conversion to pitch, yaw, and extension (or "insertion") terms in accordance with the predicted mechanics of materials relationships inherent in the mechanical design of the instrument.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and − directions. Other motorized tension relationships may drive other instruments, active tensioning, or insertion or roll of the catheter instrument. The relationship between actuated inputs and the catheter's end point position as a function of the actuated inputs is referred to as the "kinematics" of the catheter.

Figure 126:
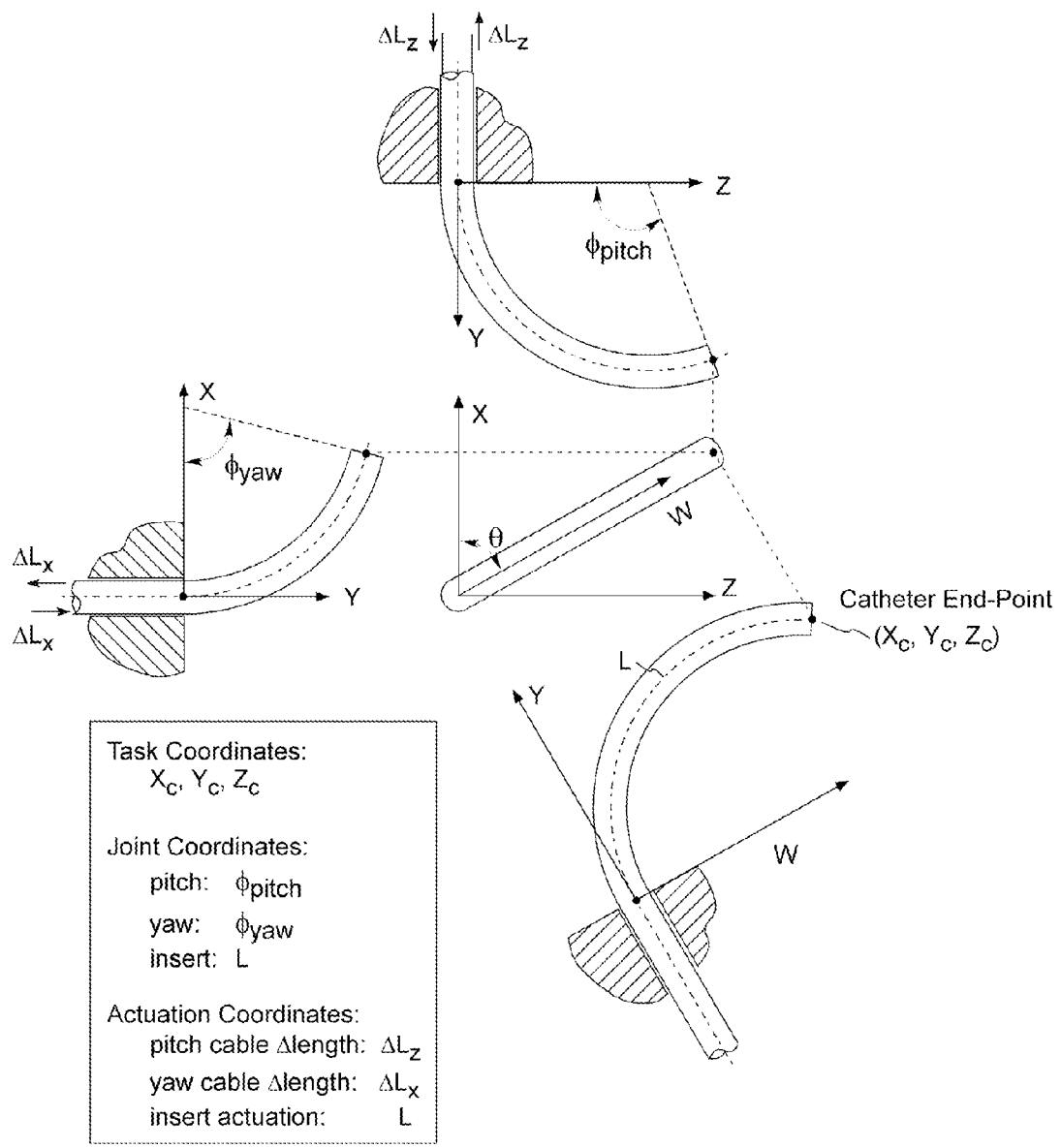
FIGS. 126-127 illustrate actuation coordinates for the kinematics of example.

Referring to FIG. 125, the "forward kinematics" expresses the catheter's end-point position as a function of the actuated inputs while the "inverse kinematics" expresses the actuated inputs as a function of the desired end-point position. Accurate mathematical models of the forward and inverse kinematics are essential for the control of a robotically controlled catheter system. For clarity, the kinematics equations are further refined to separate out common elements, as shown in FIG. 125. The basic kinematics describes the relationship between the task coordinates and the joint coordinates. In such case, the task coordinates refer to the position of the catheter end-point while the joint coordinates refer to the bending (pitch and yaw, for example) and length of the active catheter. The actuator kinematics describes the relationship between the actuation coordinates and the joint coordinates. The task, joint, and bending actuation coordinates for the robotic catheter are illustrated in FIG. 126. By describing the kinematics in this way we can separate out the kinematics associated with the catheter structure, namely the basic kinematics, from those associated with the actuation methodology.

The development of the catheter's kinematics model is derived using a few essential assumptions. Included are assumptions that the catheter structure is approximated as a simple beam in bending from a mechanics perspective, and that control elements, such as thin tension wires, remain at a fixed distance from the neutral axis and thus impart a uniform moment along the length of the catheter.

Figure 127:
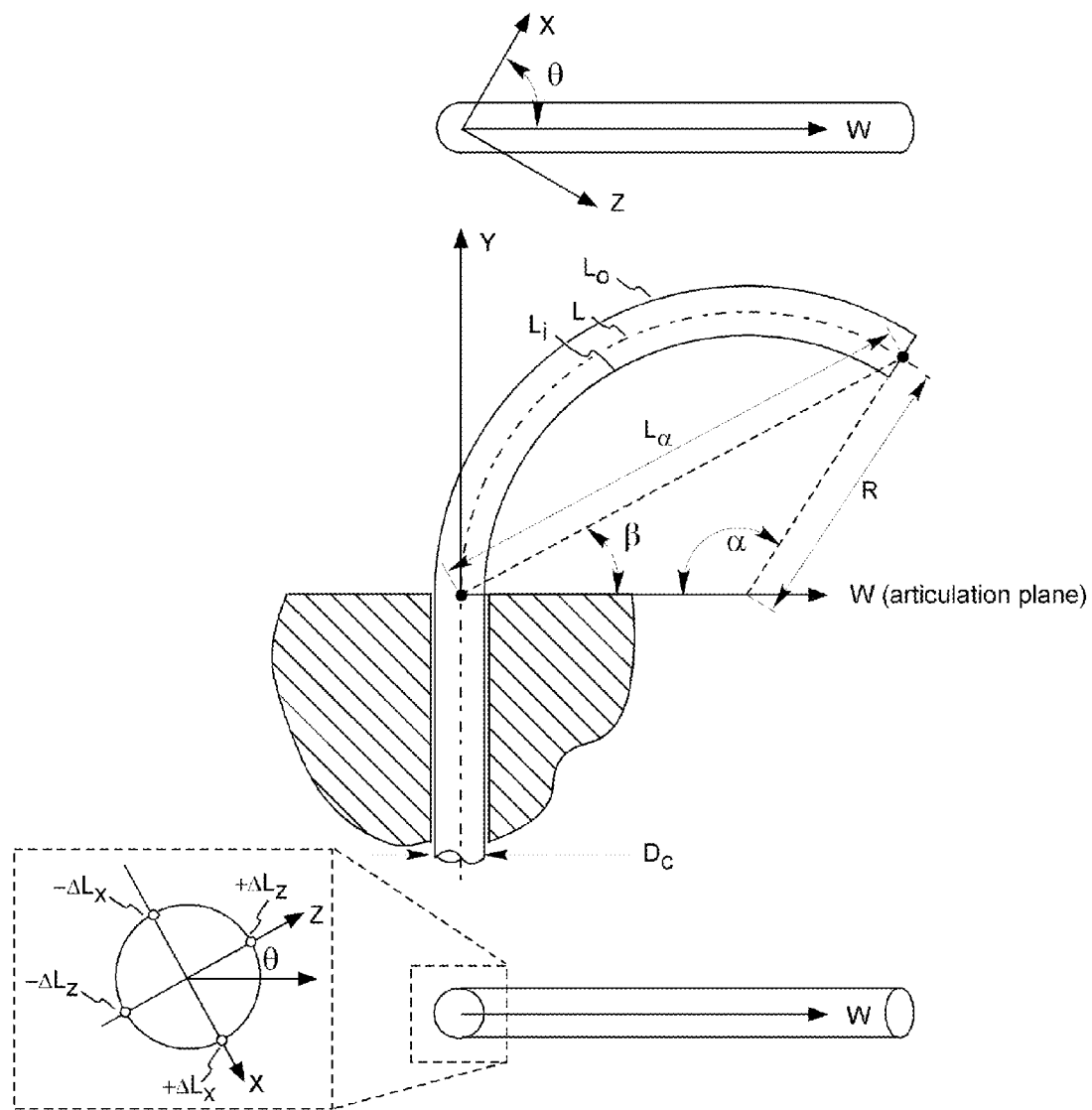

In addition to the above assumptions, the geometry and variables shown in FIG. 127 are used in the derivation of the forward and inverse kinematics. The basic forward kinematics, relating the catheter task coordinates ($X_c$, $Y_c$, $Z_c$) to the joint coordinates ($\phi_{pitch}$, $\phi_{pitch}$, L), is given as follows:

$$X_c = w \cos(\theta)$$

$$Y_c = R \sin(\alpha)$$

$$Z_c = w \sin(\theta)$$

where $$w = R(1 - \cos(\alpha))$$

-continued $$\alpha = [(\phi_{pitch})^2 + (\phi_{yaw})^2]^{1/2} \text{ (total bending)}$$

$$R = \frac{L}{\alpha} \text{ (bend radius)}$$

$$\theta = a\tan2(\phi_{pitch}, \phi_{yaw}) \text{ (roll angle)}$$

The actuator forward kinematics, relating the joint coordinates ($\phi_{pitch}$, $\phi_{pitch}$, L) to the actuator coordinates ($\Delta L_x$, $\Delta L_z$, L) is given as follows:

$$\phi_{pitch} = \frac{2\Delta L_z}{D_c}$$

$$\phi_{yaw} = \frac{2\Delta L_x}{D_c}$$

As illustrated in FIG. 125, the catheter's end-point position can be predicted given the joint or actuation coordinates by using the forward kinematics equations described above.

Calculation of the catheter's actuated inputs as a function of end-point position, referred to as the inverse kinematics, can be performed numerically, using a nonlinear equation solver such as Newton-Raphson. A more desirable approach, and the one used in this illustrative embodiment, is to develop a closed-form solution which can be used to calculate the required actuated inputs directly from the desired end-point positions.

As with the forward kinematics, we separate the inverse kinematics into the basic inverse kinematics, which relates joint coordinates to the task coordinates, and the actuation inverse kinematics, which relates the actuation coordinates to the joint coordinates. The basic inverse kinematics, relating the joint coordinates ($\phi_{pitch}$, $\phi_{pitch}$, L), to the catheter task coordinates (Xc, Yc, Zc) is given as follows:

$$\phi_{pitch} = \alpha \sin(\theta)$$

$$\phi_{yaw} = \alpha \cos(\theta)$$

$$L = R\alpha$$

$$\rightarrow \text{where} \rightarrow \rightarrow \quad \begin{aligned} \theta &= a\tan2(Z_c, X_c) & \beta &= a\tan2(Y_c, W_c) \\ R &= \frac{l \sin\beta}{\sin 2\beta} & \rightarrow \quad W_c &= (X_c^2 + Z_c^2)^{1/2} \\ \alpha &= \pi - 2\beta & l &= (W_c^2 + Y_c^2)^{1/2} \end{aligned}$$

The actuator inverse kinematics, relating the actuator coordinates ($\Delta L_x$, $\Delta L_z$, L) to the joint coordinates ($\phi_{pitch}$, $\phi_{pitch}$, L) is given as follows:

$$\Delta L_x = \frac{D_c \phi_{yaw}}{2}$$

$$\Delta L_z = \frac{D_c \phi_{pitch}}{2}$$

Figure 124:
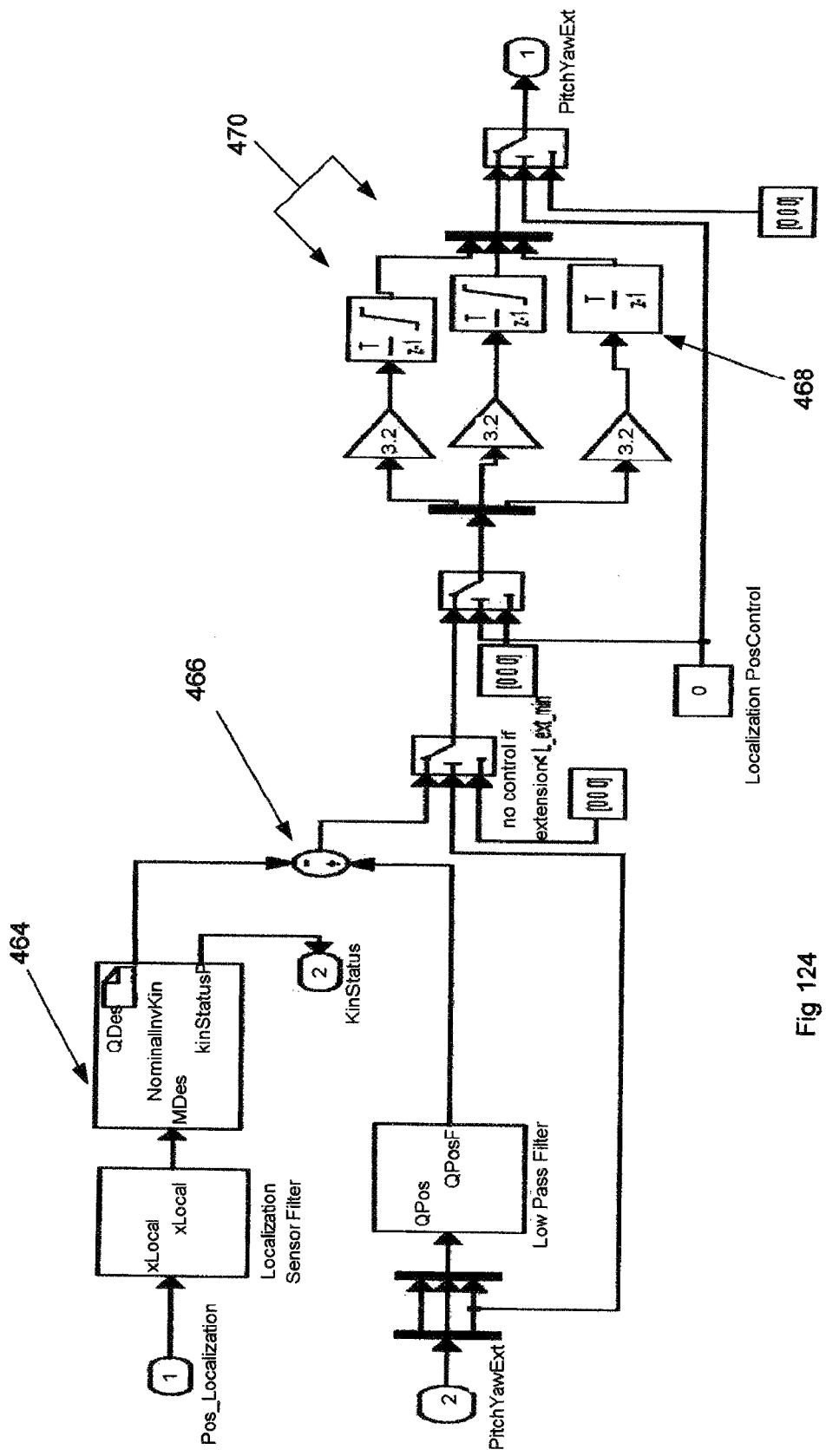

Referring back to FIG. 119, pitch, yaw, and extension commands are passed from the inverse kinematics block (450) to a position control block (448) along with measured localization data. FIG. 124 provides a more detailed view of the position control block (448). After measured XYZ position data comes in from the localization system, it goes through a inverse kinematics block (464) to calculate the pitch, yaw, and extension the instrument needs to have in order to travel to where it needs to be. Comparing (466) these values with filtered desired pitch, yaw, and extension data from the master input device, integral compensation is then conducted with limits on pitch and yaw to integrate away the error. In this embodiment, the extension variable does not have the same limits (468), as do pitch and yaw (470). As will be apparent to those skilled in the art, having an integrator in a negative feedback loop forces the error to zero. Desired pitch, yaw, and extension commands are next passed through a catheter workspace limitation block (452), which may be a function of the experimentally determined physical limits of the instrument beyond which componentry may fail, deform undesirably, or perform unpredictably or undesirably. This workspace limitation essentially defines a volume similar to a cardioid-shaped volume about the distal end of the instrument. Desired pitch, yaw, and extension commands, limited by the workspace limitation block, are then passed to a catheter roll correction block (454).

Figure 121:
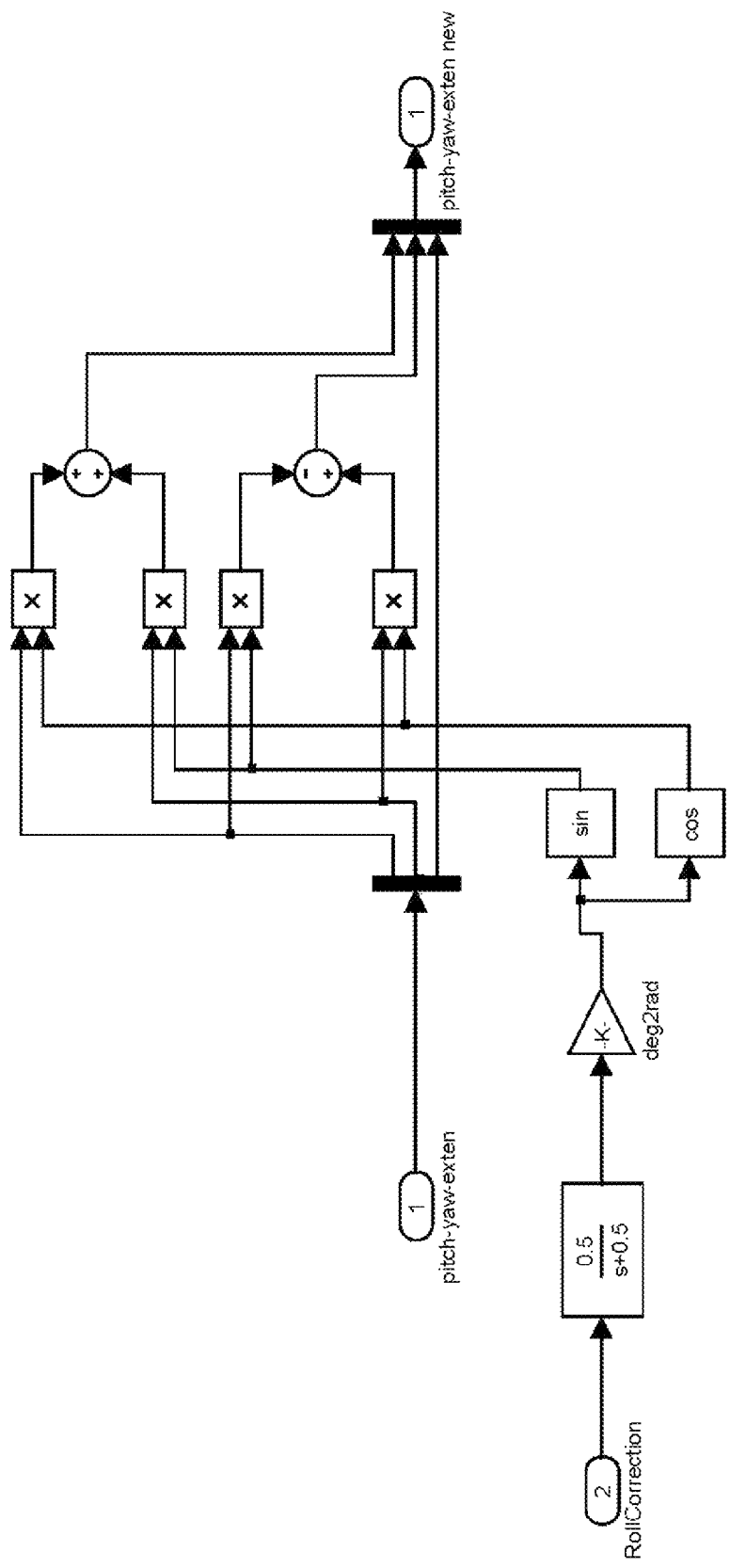

This functional block is depicted in further detail in FIG. 121, and essentially comprises a rotation matrix for transforming the pitch, yaw, and extension commands about the longitudinal, or "roll", axis of the instrument—to calibrate the control system for rotational deflection at the distal tip of the catheter that may change the control element steering dynamics. For example, if a catheter has no rotational deflection, pulling on a control element located directly up at twelve o'clock should urge the distal tip of the instrument upward. If, however, the distal tip of the catheter has been rotationally deflected by, say, ninety degrees clockwise, to get an upward response from the catheter, it may be necessary to tension the control element that was originally positioned at a nine o'clock position. The catheter roll correction schema depicted in FIG. 121 provides a means for using a rotation matrix to make such a transformation, subject to a roll correction angle, such as the ninety degrees in the above example, which is input, passed through a low pass filter, turned to radians, and put through rotation matrix calculations.

In one embodiment, the roll correction angle is determined through experimental experience with a particular instrument and path of navigation. In another embodiment, the roll correction angle may be determined experimentally in-situ using the accurate orientation data available from the preferred localization systems. In other words, with such an embodiment, a command to, for example, bend straight up can be executed, and a localization system can be utilized to determine at which angle the defection actually went—to simply determine the in-situ roll correction angle.

Figure 122:
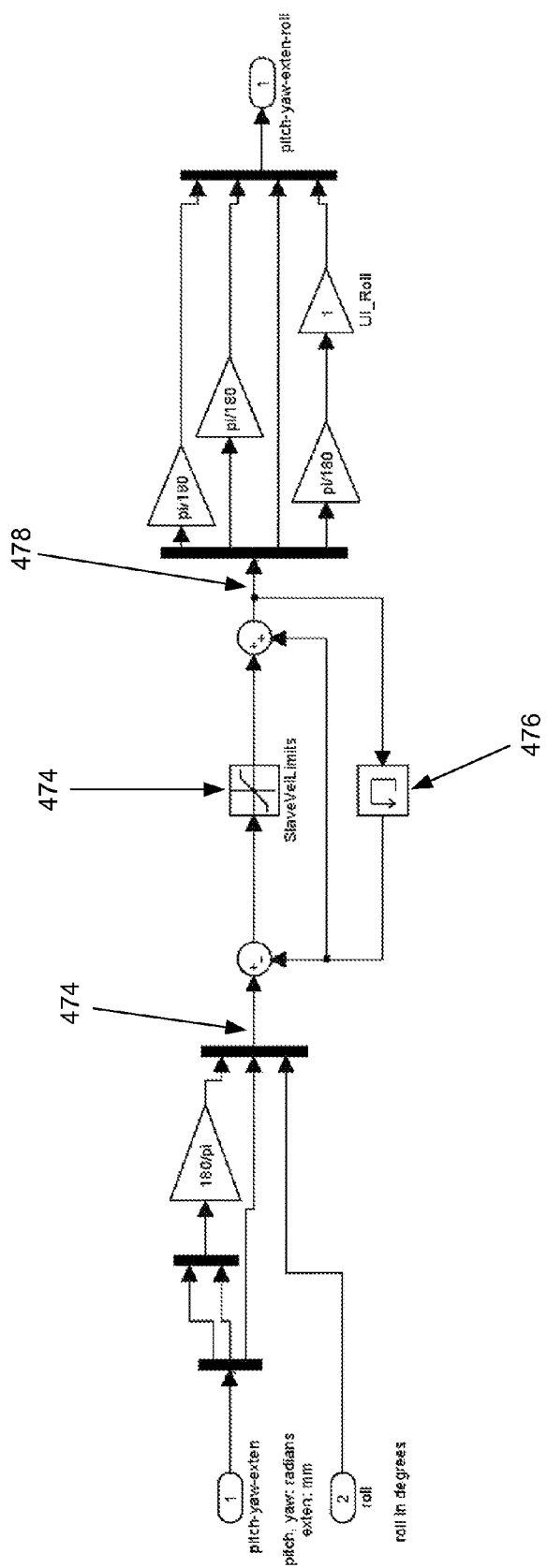

Referring briefly back to FIG. 119, roll corrected pitch and yaw commands, as well as unaffected extension commands, are output from the catheter roll correction block (454) and may optionally be passed to a conventional velocity limitation block (456). Referring to FIG. 122, pitch and yaw commands are converted from radians to degrees, and automatically controlled roll may enter the controls picture to complete the current desired position (472) from the last servo cycle. Velocity is calculated by comparing the desired position from the previous servo cycle, as calculated with a conventional memory block calculation (476), with that of the incoming commanded cycle. A conventional saturation block (474) keeps the calculated velocity within specified values, and the velocity-limited command (478) is converted back to radians and passed to a tension control block (458).

Figure 123:
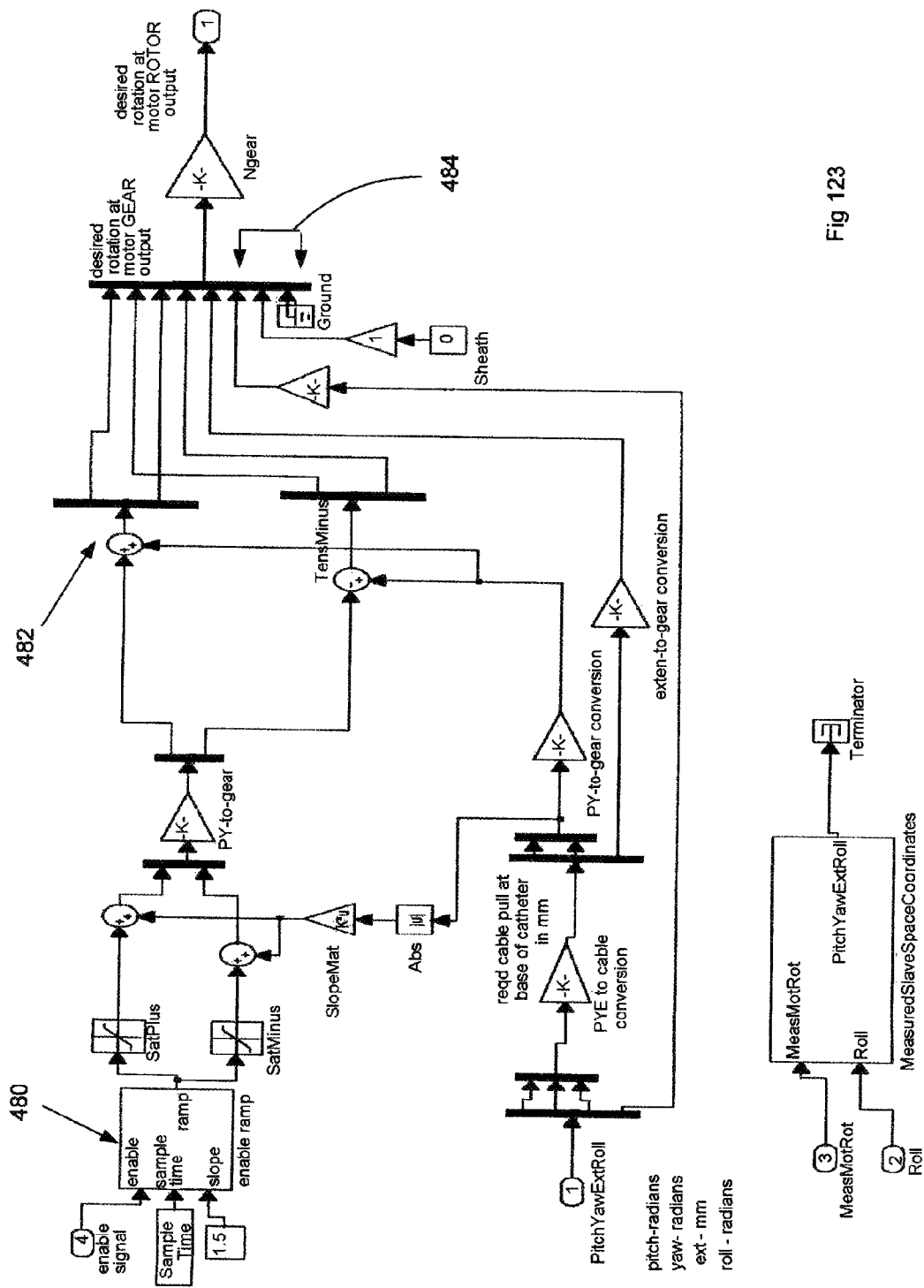

Tension within control elements may be managed depending upon the particular instrument embodiment, as described above in reference to the various instrument embodiments and tension control mechanisms. As an example, FIG. 123 depicts a pre-tensioning block (480) with which a given control element tension is ramped to a present value. An adjustment is then added to the original pre-tensioning based upon a preferably experimentally-tuned matrix pertinent to variables, such as the failure limits of the instrument construct and the incoming velocity-limited pitch, yaw, extension, and roll commands. This adjusted value is then added (482) to the original signal for output, via gear ratio adjustment, to calculate desired motor rotation commands for the various motors involved with the instrument movement. In this embodiment, extension, roll, and sheath instrument actuation (484) have no pre-tensioning algorithms associated with their control. The output is then complete from the master following mode functionality, and this output is passed to the primary servo loop (436).

Referring back to FIG. 114, incoming desired motor rotation commands from either the master following mode (442), auto home mode (440), or idle mode (438) in the depicted embodiment are fed into a motor servo block (444), which is depicted in greater detail in FIGS. 115-118.

Figure 115:
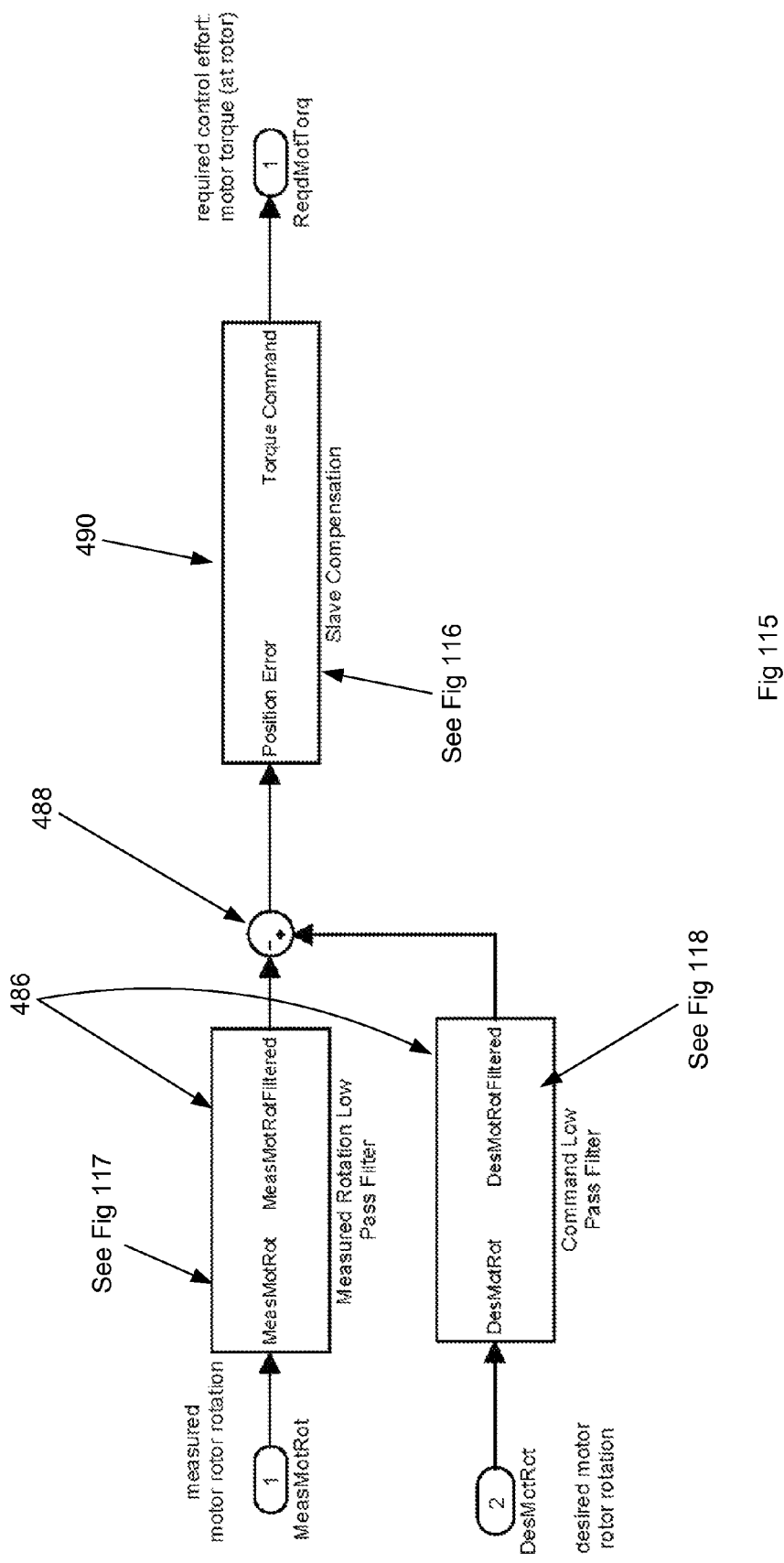
Figure 117:
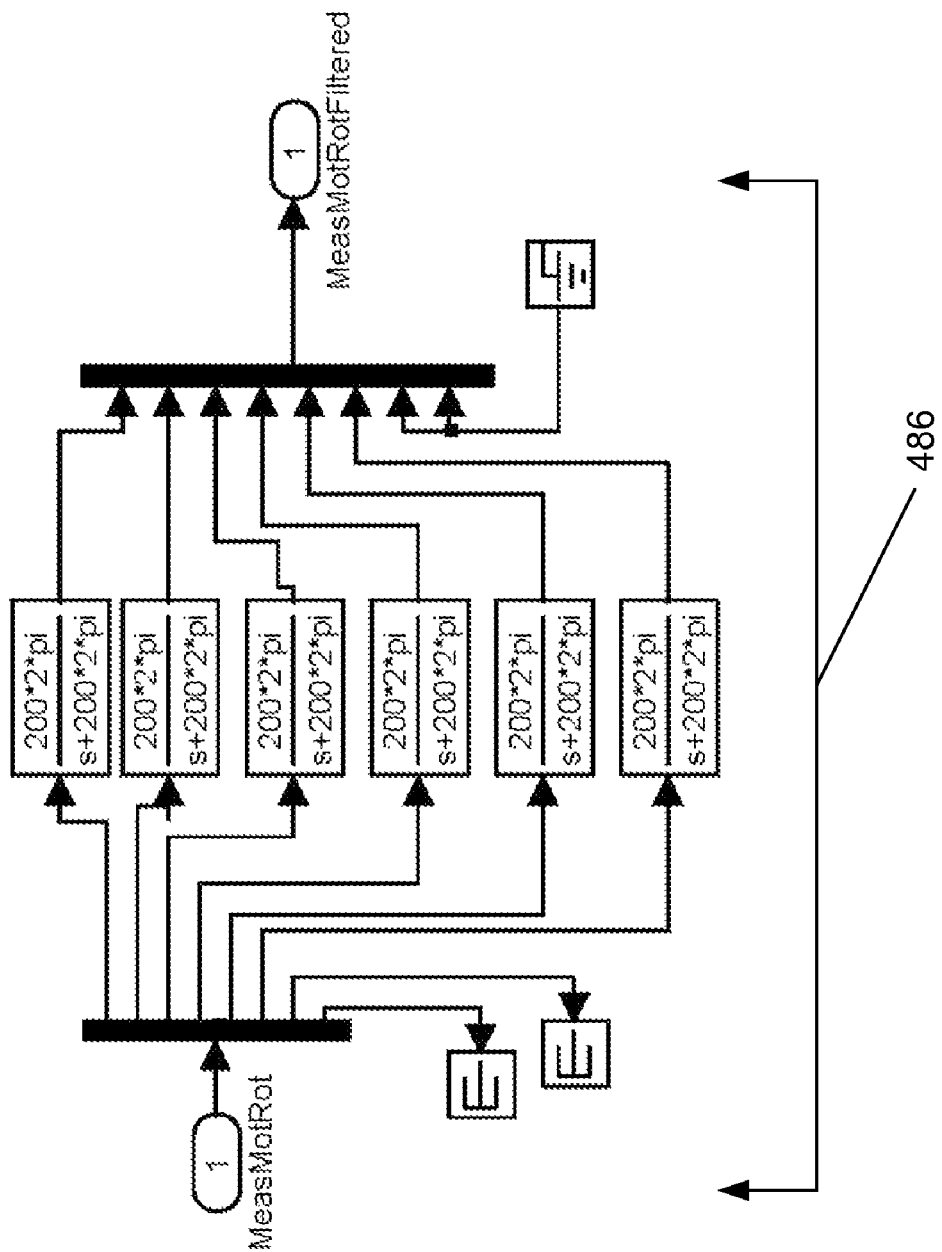
Figure 118:
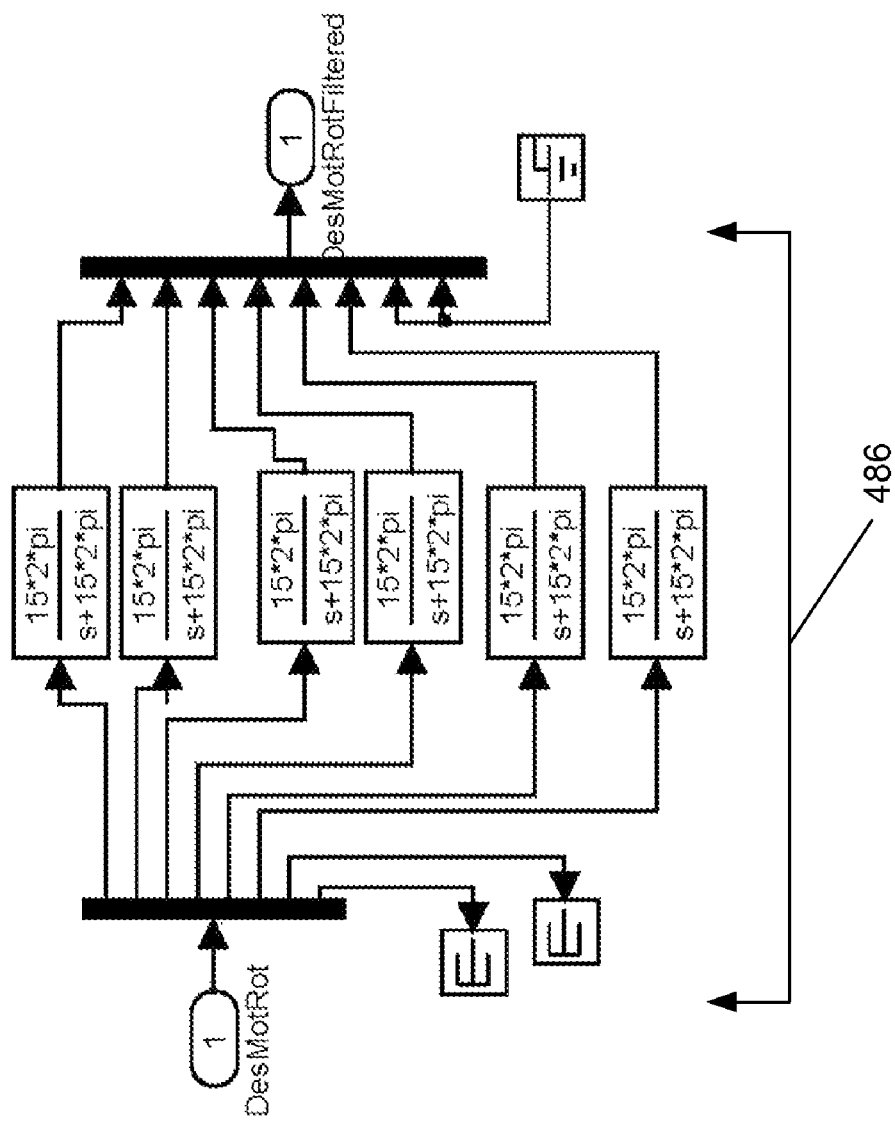

Referring to FIG. 115, incoming measured motor rotation data from digital encoders and incoming desired motor rotation commands are filtered using conventional quantization noise filtration at frequencies selected for each of the incoming data streams to reduce noise while not adding undue delays which may affect the stability of the control system. As shown in FIGS. 117 and 118, conventional quantization filtration is utilized on the measured motor rotation signals at about 200 hertz in this embodiment, and on the desired motor rotation command at about 15 hertz. The difference (488) between the quantization filtered values forms the position error which may be passed through a lead filter, the functional equivalent of a proportional derivative ("PD")+low pass filter. In another embodiment, conventional PID, lead/lag, or state space representation filter may be utilized. The lead filter of the depicted embodiment is shown in further detail in FIG. 116.

Figure 116:
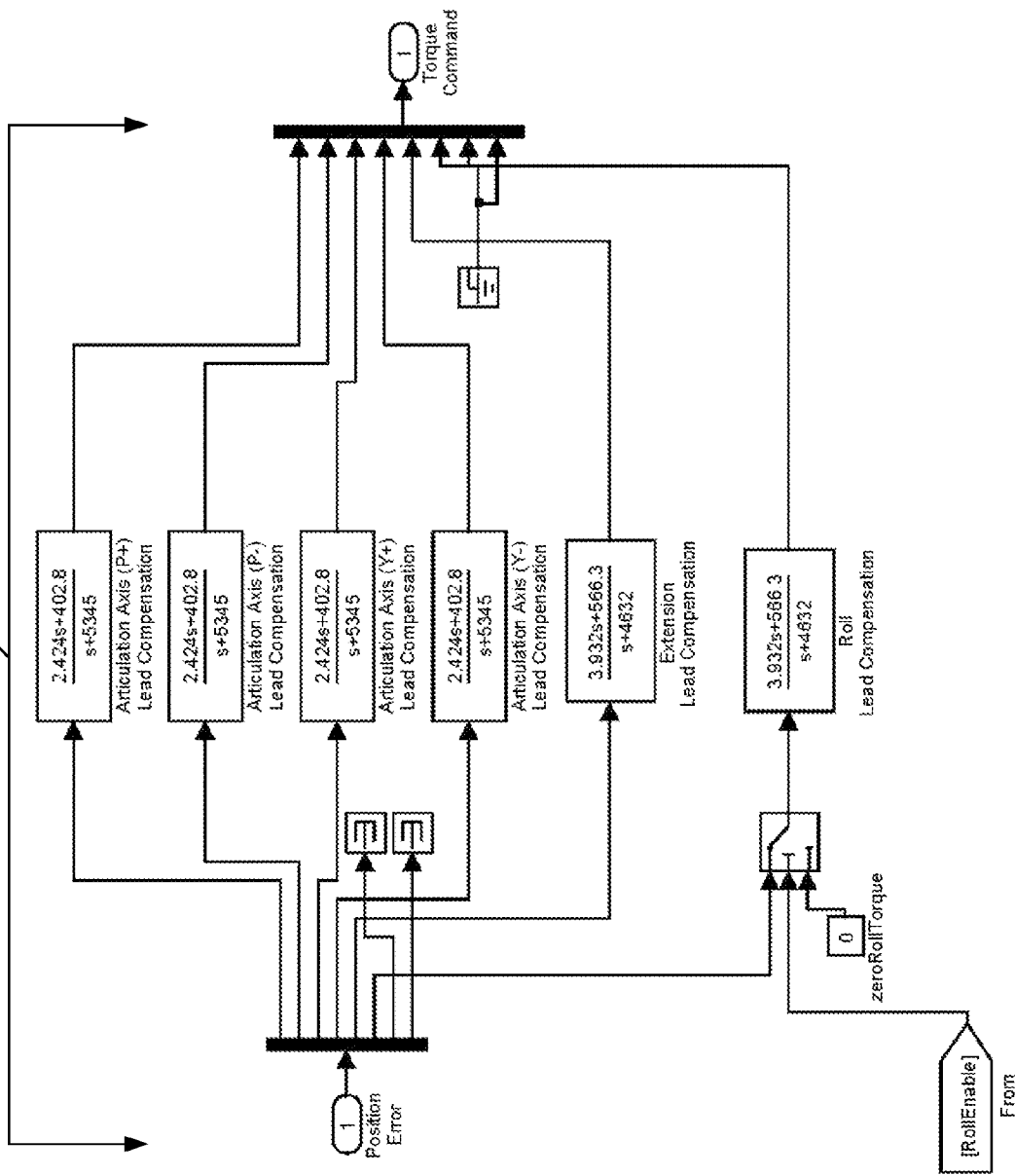

In particular, the lead filter embodiment in FIG. 116 comprises a variety of constants selected to tune the system to achieve desired performance. The depicted filter addresses the needs of one embodiment of a 4-control element guide catheter instrument with independent control of each of four control element interface assemblies for +/− pitch and +/− yaw, and separate roll and extension control. As demonstrated in the depicted embodiment, insertion and roll have different inertia and dynamics as opposed to pitch and yaw controls, and the constants selected to tune them is different. The filter constants may be theoretically calculated using conventional techniques and tuned by experimental techniques, or wholly determined by experimental techniques, such as setting the constants to give a sixty degree or more phase margin for stability and speed of response, a conventional phase margin value for medical control systems.

In an embodiment where a tuned master following mode is paired with a tuned primary servo loop, an instrument and instrument driver, such as those described above, may be "driven" accurately in three-dimensions with a remotely located master input device. Other preferred embodiments incorporate related functionalities, such as haptic feedback to the operator, active tensioning with a split carriage instrument driver, navigation utilizing direct visualization and/or tissue models acquired in-situ and tissue contact sensing, and enhanced navigation logic.

Referring to FIG. 128, in one embodiment, the master input device may be a haptic master input device, such as those available from SensAble Technologies, Inc., under the trade name Phantom® Haptic Devices, and the hardware and software required for operating such a device may at least partially reside on the master computer. The master XYZ positions measured from the master joint rotations and forward kinematics are generally passed to the master computer via a parallel port or similar link and may subsequently be passed to a control and instrument driver computer. With such an embodiment, an internal servo loop for a Phantom® Haptic Device generally runs at a much higher frequency in the range of 1,000 Hz, or greater, to accurately create forces and torques at the joints of the master.

Referring to FIG. 129, a sample flowchart of a series of operations leading from a position vector applied at the master input device to a haptic signal applied back at the operator is depicted. A vector (344) associated with a master input device move by an operator may be transformed into an instrument coordinate system, and in particular to a catheter instrument tip coordinate system, using a simple matrix transformation (345). The transformed vector (346) may then be scaled (347) per the preferences of the operator, to produce a scaled-transformed vector (348). The scaled-transformed vector (348) may be sent to both the control and instrument driver computer (422) preferably via a serial wired connection, and to the master computer for a catheter workspace check (349) and any associated vector modification (350). This is followed by a feedback constant multiplication (351) chosen to produce preferred levels of feedback, such as force, in order to produce a desired force vector (352), and an inverse transform (353) back to a force vector (354) in the master input device coordinate system for associated haptic signaling to the operator in that coordinate system.

A conventional Jacobian may be utilized to convert a desired force vector (352) to torques desirably applied at the various motors comprising the master input device, to give the operator a desired signal pattern at the master input device. Given this embodiment of a suitable signal and execution pathway, feedback to the operator in the form of haptics, or touch sensations, may be utilized in various ways to provide added safety and instinctiveness to the navigation features of the system, as discussed in further detail below.

FIG. 130 is a system block diagram including haptics capability. As shown in summary form in FIG. 130, encoder positions on the master input device, changing in response to motion at the master input device, are measured (355), sent through forward kinematics calculations (356) pertinent to the master input device to get XYZ spatial positions of the device in the master input device coordinate system (357), then transformed (358) to switch into the catheter coordinate system and (perhaps) transform for visualization orientation and preferred controls orientation, to facilitate "instinctive driving".

The transformed desired instrument position (359) may then be sent down one or more controls pathways to, for example, provide haptic feedback (360) regarding workspace boundaries or navigation issues, and provide a catheter instrument position control loop (361) with requisite catheter desired position values, as transformed utilizing catheter inverse (362) kinematics relationships for the particular instrument into yaw, pitch, and extension, or insertion, terms (363) pertinent to operating the particular catheter instrument with open or closed loop control.

Referring to FIGS. 131-136, relationships pertinent to tension control via a split carriage design such as that depicted in FIGS. 102A-B are depicted to illustrate that such a design may isolate tension control from actuation for each associated degree of freedom, such as pitch or yaw of a steerable catheter instrument.

Figures 131, 132:
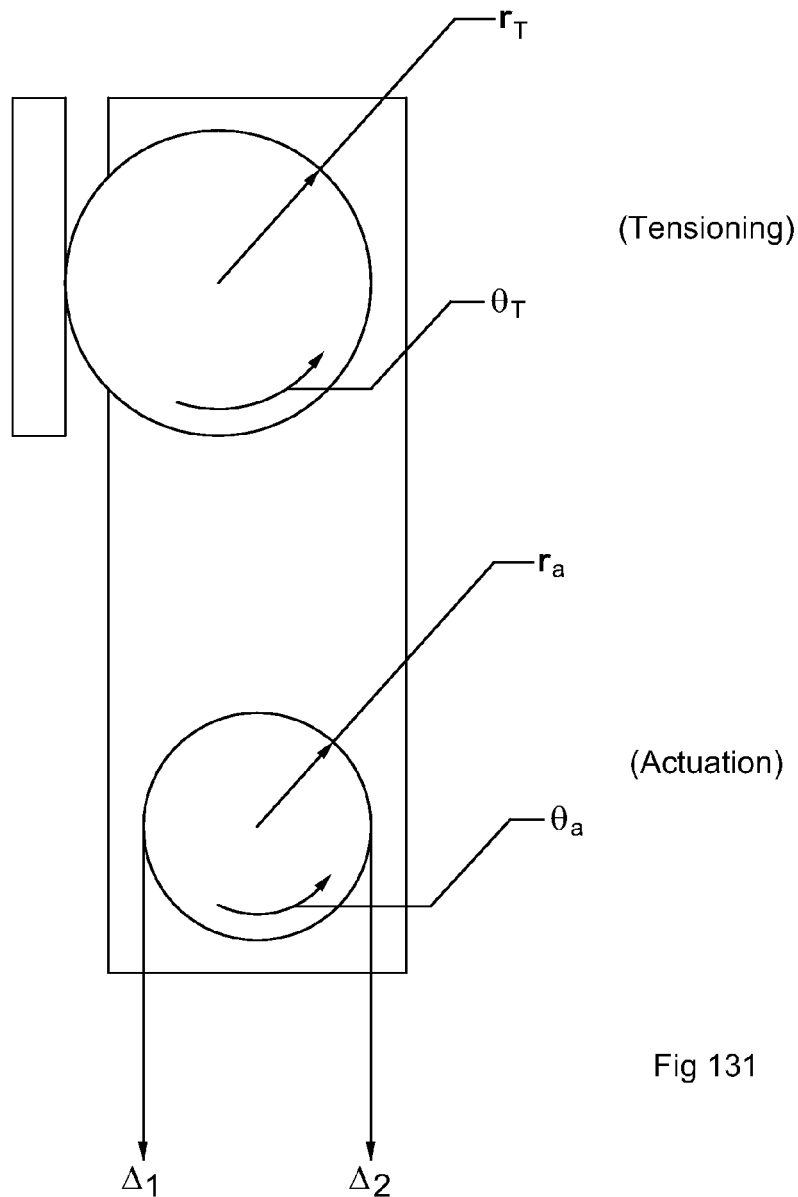
FIGS. 131-136 illustrate tension control relationships for a split carriage design of one embodiment.
Figure 133:
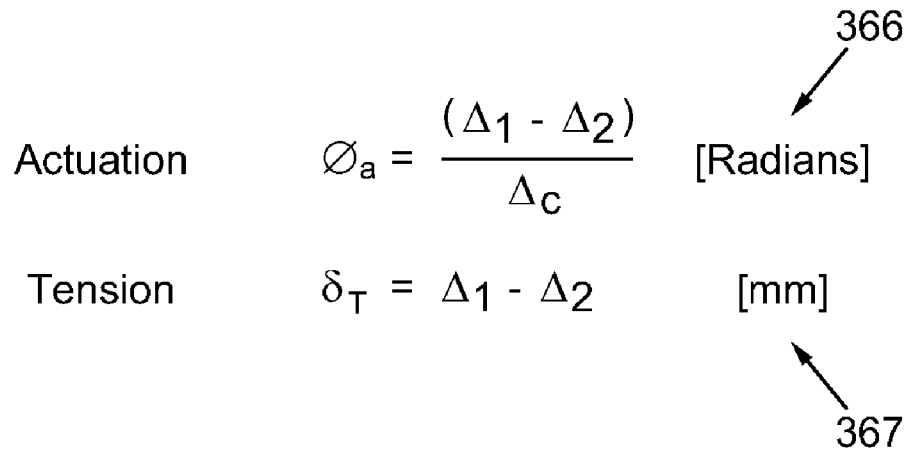
Figure 134:
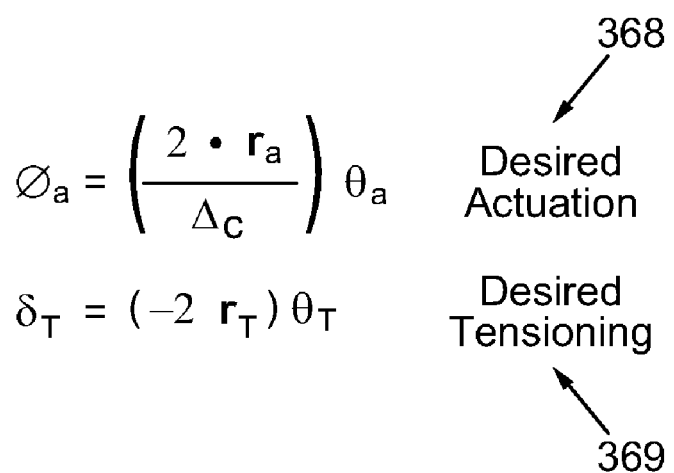

Referring to FIG. 131, some of the structures associated with a split carriage design, such as the embodiments depicted in FIGS. 102 and 103, include a linearly movable portion (302), a guide instrument interface socket (270), a gear (300), and a rack (298). Applying conventional geometric relationships to the physical state of the structures related in FIG. 131, the equations (364, 365) of FIG. 132 may be generated. Utilizing forward kinematics of the instrument, such as those described above in reference to a pure cantilever bending model for a catheter instrument, the relationships of FIG. 133 may be developed for the amount of bending as a function of cable pull and catheter diameter ("$D_c$") as an actuation equation (366), and as a tension equation (367), wherein tension is defined as the total amount of common pull in the control elements. Combining the equations of FIGS. 132 and 133, the relationships (368, 369) depicted in FIG. 134 can be obtained, wherein desired actuation (368) and desired tensioning (369) are decoupled by the mechanics of the involved structures. Desired actuation (368) of the guide instrument interface socket (270) depicted in FIG. 131 is a function of the socket's angular rotational position. Desired tensioning (369) of the associated control elements is a function of the position of the tensioning gear (300) versus the rack (298).

Figures 135, 136:
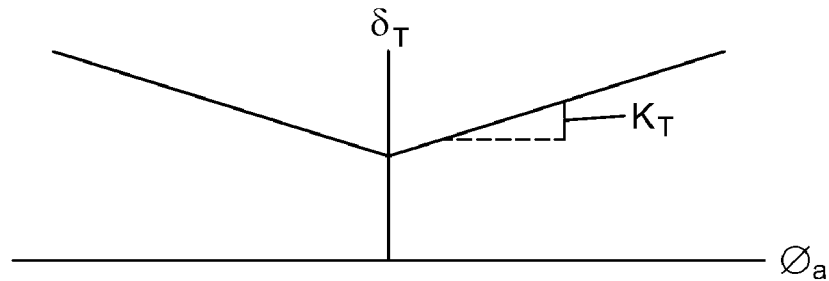

Referring to FIG. 135, with a single degree of freedom actuated, such as +/− pitch or +/− yaw, and active tensioning via a split carriage mechanism, desired tension is linearly related to the absolute value of the amount of bending, as one would predict per the discussion above in reference to FIGS. 110A-E. The prescribed system never goes into slack—desired tension is always positive, as shown in FIG. 135. Referring to FIG. 136, a similar relationship applies for a two degree of freedom system with active tensioning—such as a four-cable system with +/− pitch and +/− yaw as the active degrees of freedom and active tensioning via a split carriage design. Because there are two dimensions, tension coupling terms (370) are incorporated to handle heuristic adjustments to, for example, minimize control element slacking and total instrument compression.

As discussed in reference to FIG. 113, in one embodiment, a tissue structure model (414) may be utilized to enhance navigation. It is particularly desirable to utilize actual data, acquired in situ, from the patient onto which a procedure is to be conducted, due to anatomic variation among the patient population which may be significant, depending generally upon the subject tissue structures. For example, the geometry of the left atrium of the human heart varies significantly from patient to patient, according to published reports and experimental verification in animals.

In one embodiment, focused magnetic resonance imaging, gated for heart cycle motion, and preferably gated for respiratory cycle motion, may be utilized along with conventional image cropping and thresholding techniques to produce a three dimensional tissue structure model. One of the challenges with such an imaging modality as applied to modeling active tissue structures such as those of the heart is the gating. In one embodiment, the gating comprises waiting for cardiac resting periods during diastole which are also correlated to substantially limited respiratory-induced motion. Acquiring a three-dimensional image of a left atrium, for example, utilizing gated magnetic resonance, may require an unacceptable amount of acquisition time, not to mention the generally large and expensive instrumentation required to accomplish the acquisition and fusion into a usable tissue structure model. Such a modality, however, may be preferred where cardiac and/or respiratory cyclic motion is negligible, and wherein an image or series of images may be acquired and synthesized into a usable tissue structure model comparatively quickly.

Figure 137:
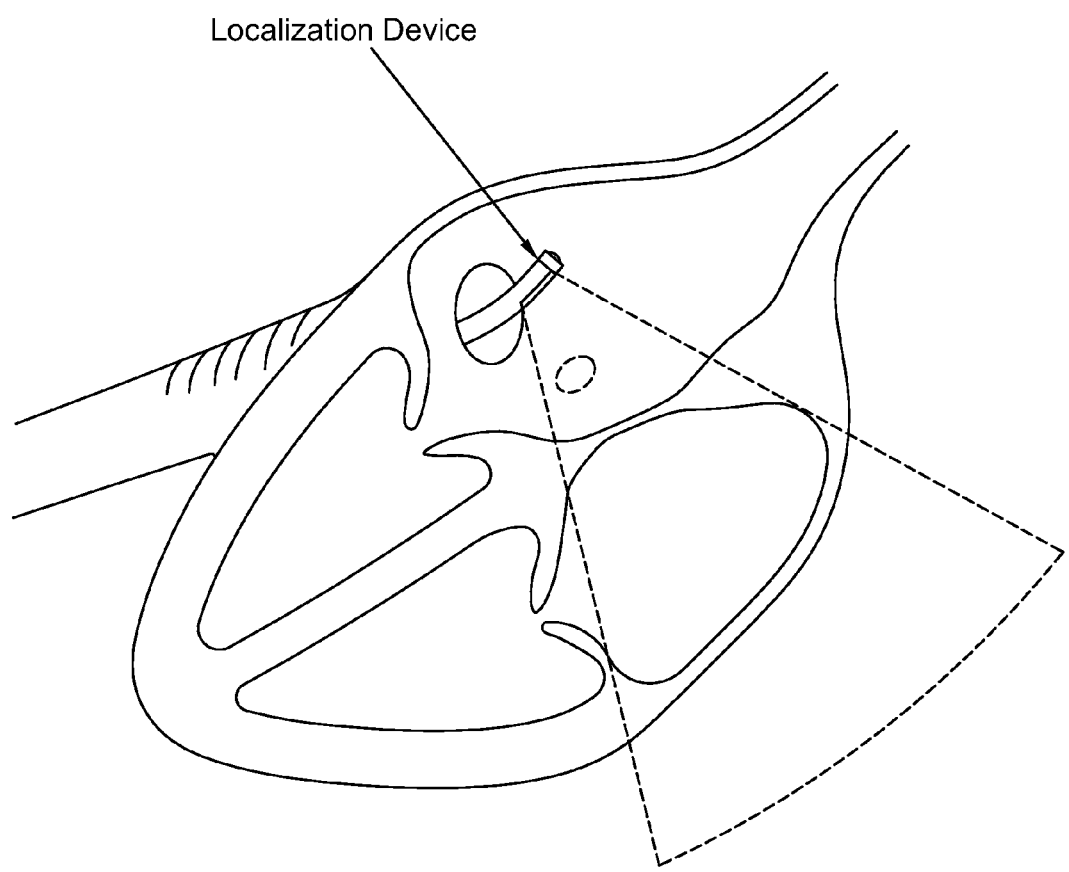
FIGS. 137-139 illustrate one method for synthesizing a tissue structure model.
Figure 138:
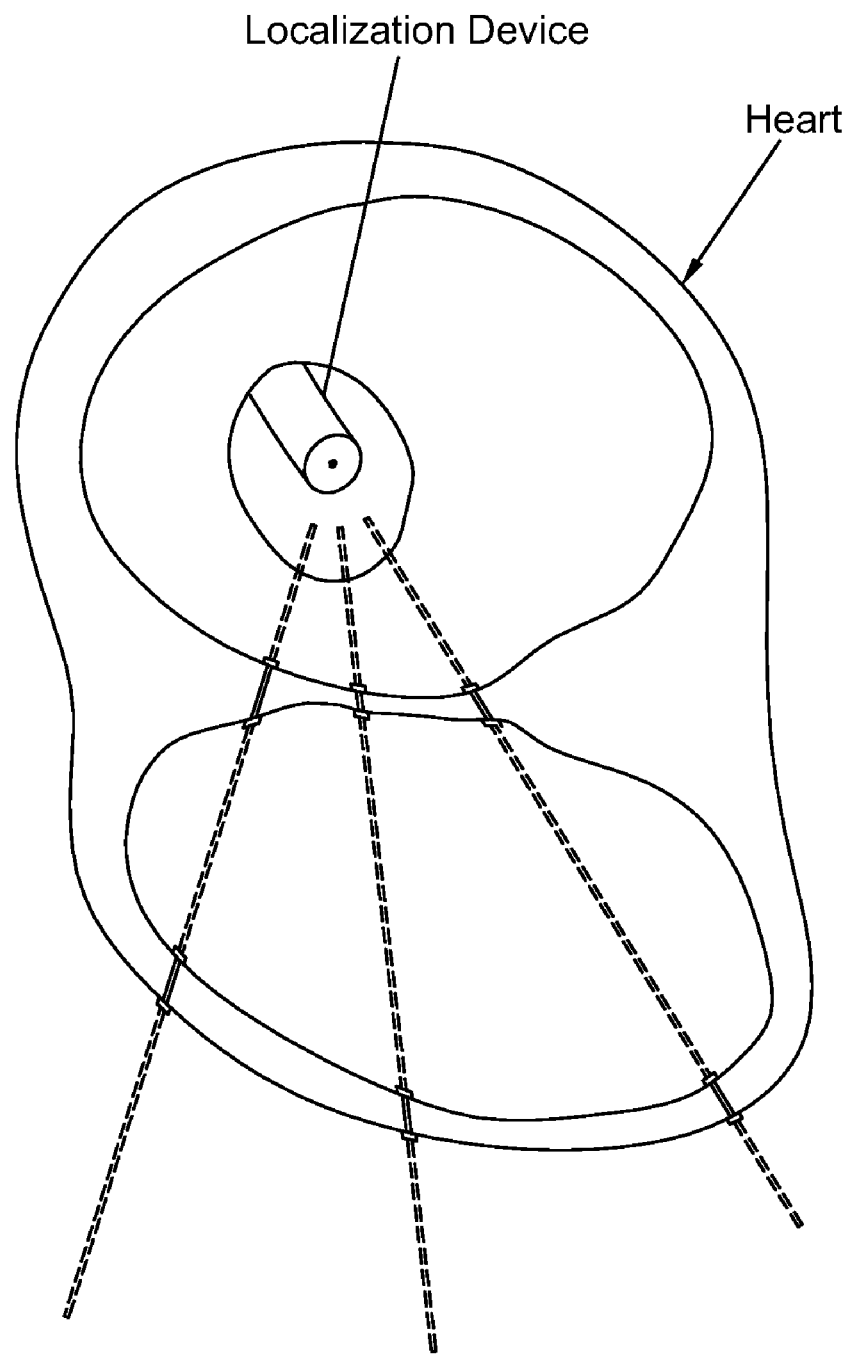
Figure 139:
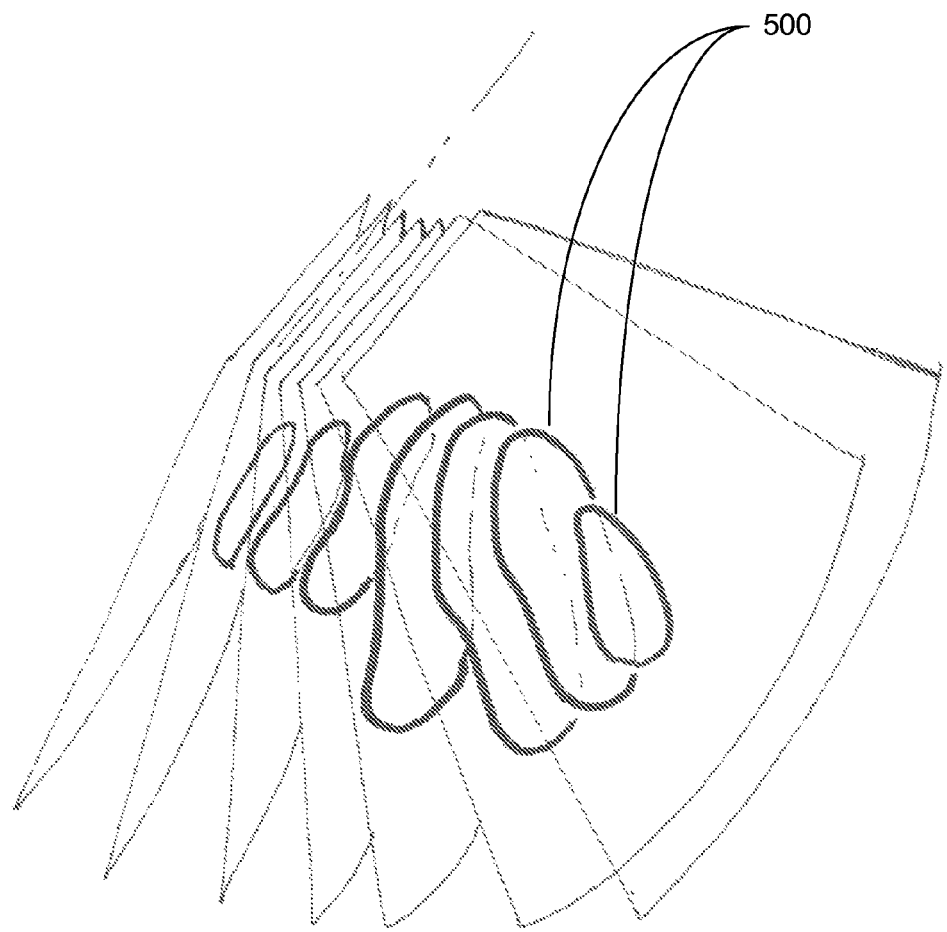

Referring to FIGS. 137-139 a technique is depicted through which a tissue structure model may be synthesized given appropriate hardware, such as an ultrasound transducer mounted upon a catheter or similar structure, and a localization system mounted upon the same structure to enable the capture of not only ultrasound slice data, but also the position and orientation of the transducer at the time of each slice acquisition. In other embodiments, a similar robotic system does not include a localization system, in which case kinematic and/or geometric relationships may be used to predict the location of the imaging device.

FIG. 137 depicts a human heart with a side-firing ultrasound catheter, such as those available under the trade name ACUSON AcuNav™ Diagnostic Ultrasound Catheter by Siemens AG of Erlangen, Germany, entering the left atrium via the inferior vena cava blood vessel. Coupled to the ultrasound catheter, at or near the location of the ultrasound transducer, is a localization device, such as a set of orthogonally oriented electromagnetic receiving coils, to determine the position and orientation of the ultrasound transducer at each acquired "slice" of acquired reflected data. FIG. 138 is a view along the longitudinal axis of the distal end of the ultrasound catheter illustrating that, by rotating the ultrasound catheter, multiple slices (500) of reflected ultrasound image data, comprising multiple structural tissue mass location points, may be acquired, along with the position and orientation of the ultrasound transducer for each slice of reflected ultrasound data. With such an embodiment and a targeted tissue structure that is cyclically mobile, such the heart, each of the slices preferably is acquired during the resting period of diastole to prevent motion-based image distortion.

In post-acquisition processing, the acquired image slice data and associated position and orientation data may be utilized to construct a three-dimensional tissue structure model, such as that represented by the series of slices in FIG. 139. As will be apparent to those skilled in the art, to achieve a finer mesh of points for image formation, more slices may be acquired and assembled as shown in FIG. 139. Utilizing conventional image thresholding techniques available, for example, on most ultrasound mainframe devices, such as that sold under the trade name ACUSON Sequoia™ ultrasound system by Siemens AG, points of transition between blood or other fluid-filled cavity and tissue mass may be clearly resolved to establish transition points such as those depicted in FIG. 138.

Figure 140:
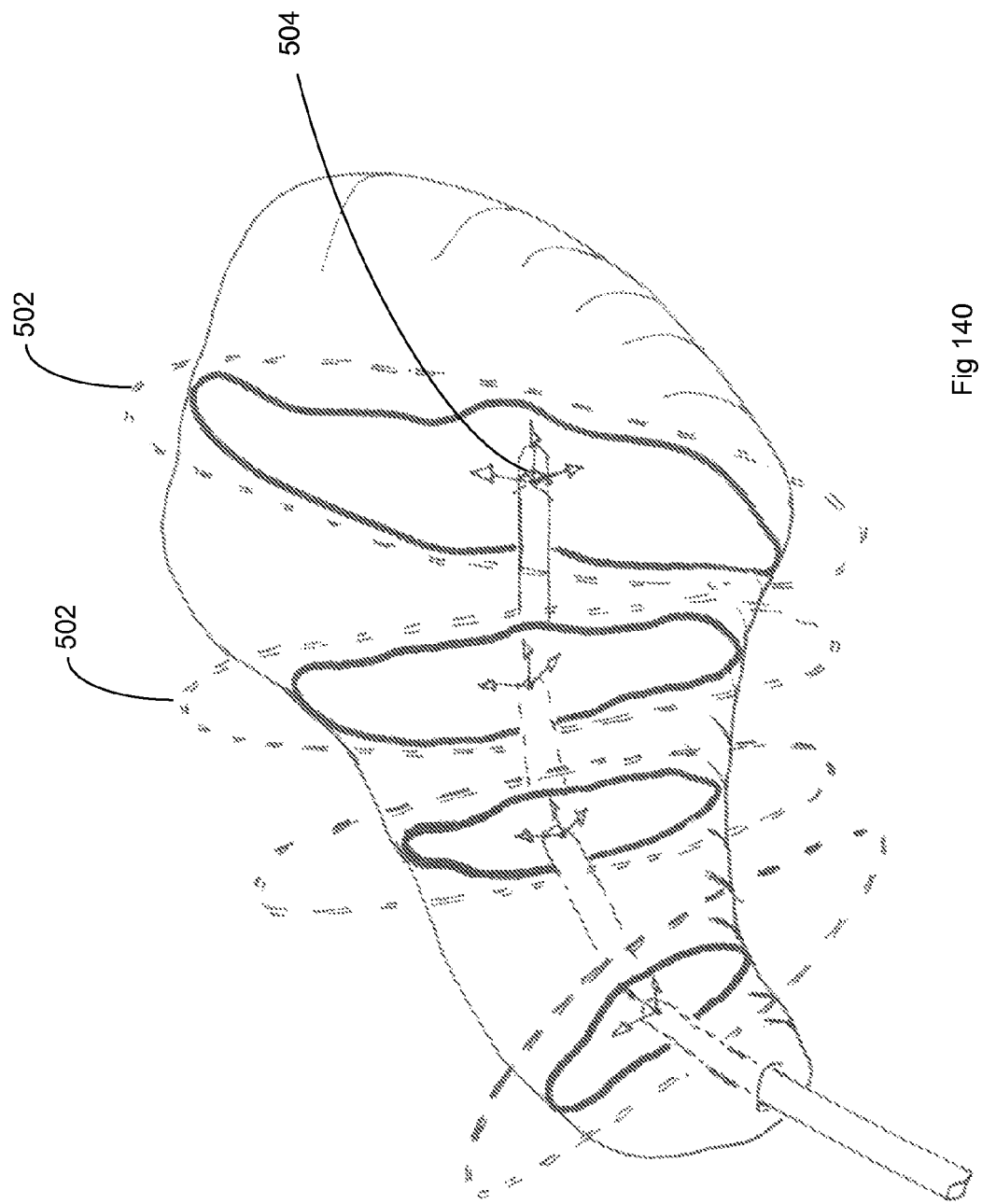

Referring to FIGS. 140-148, various aspects of another embodiment for acquiring and compiling a tissue structure image is depicted. Referring to FIG. 140, applying similar principles as applied in reference to the embodiment of FIGS. 137-139, a perimetrically-firing ultrasound image acquisition device, such as that sold under the trade name Ultra ICE™ catheter by Boston Scientific Corporation, may be utilized in concert with a localization system to acquire a series of perimetric slices (502) and associated position and orientation data for the transducer (504) to assemble a series of tissue-cavity threshold points (506) related in space, as depicted in FIG. 141. As illustrated in FIG. 140, a series of related slices (502) is gathered as the transducer (504) is inserted, retrieved, or both, through a cavity. As with the embodiment above, in the case of mobile heart tissue, each of the slices preferably is acquired during the resting period of diastole to prevent motion-based image distortion. Further, a finer resolution tissue structure image may be created with higher density image acquisition as the transducer is repositioned within the targeted cavity, as will be apparent to those skilled in the art.

Figure 144:
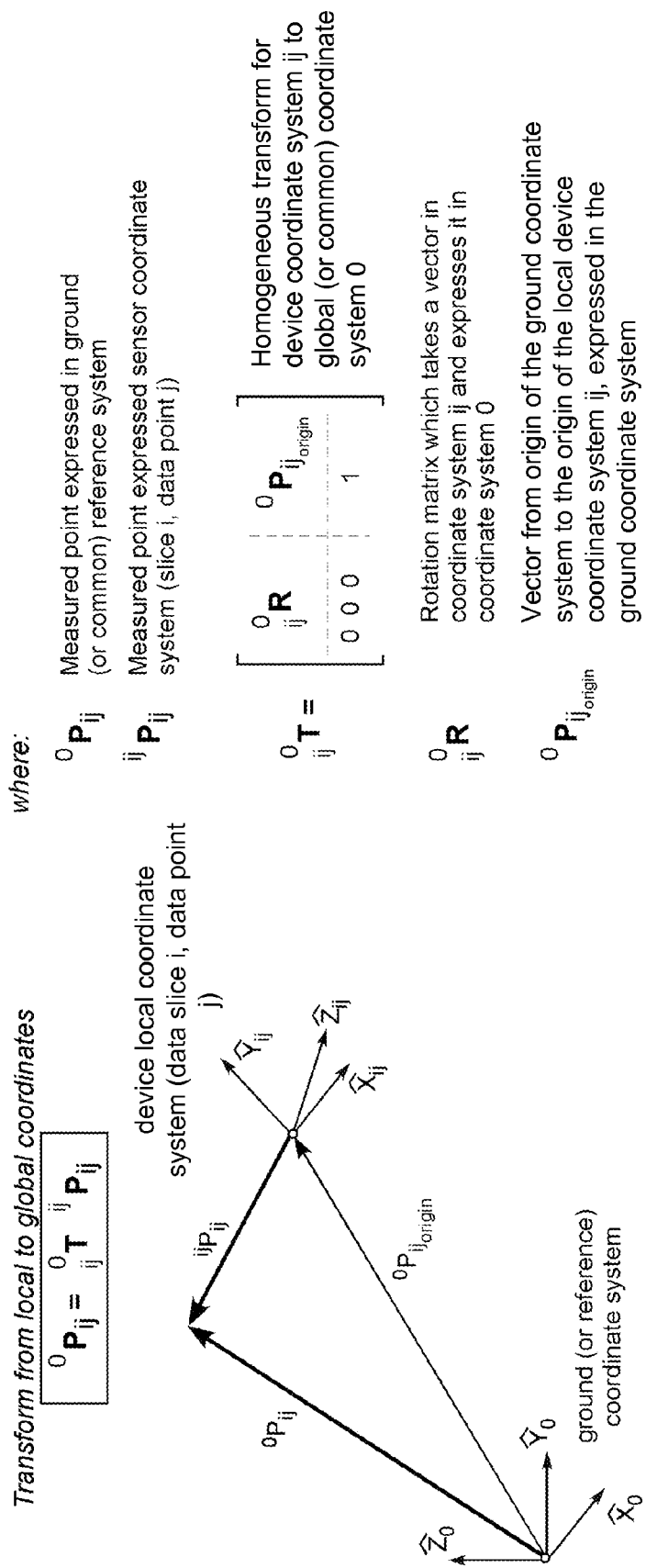
Figure 145B:
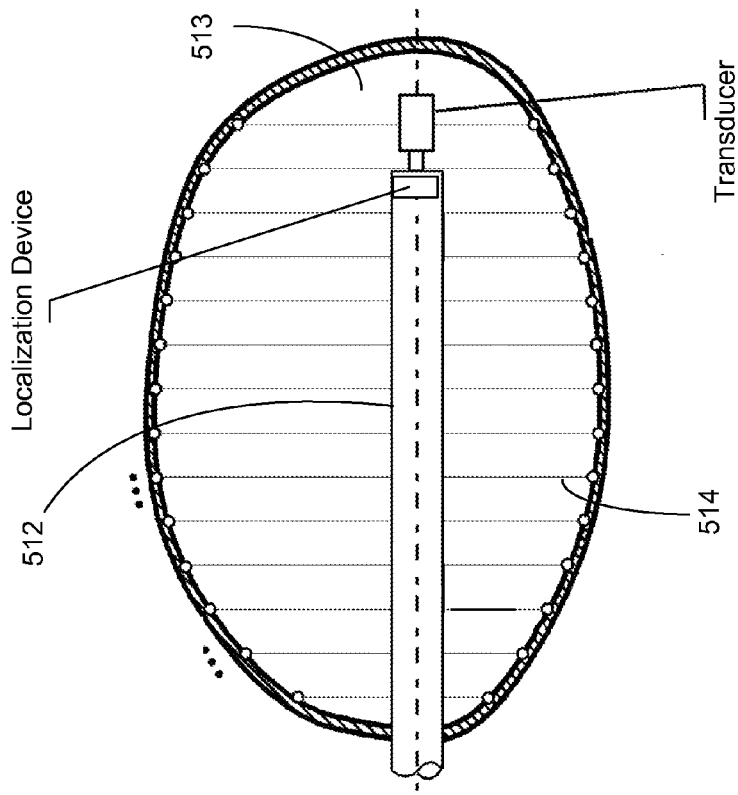
Figure 145A:
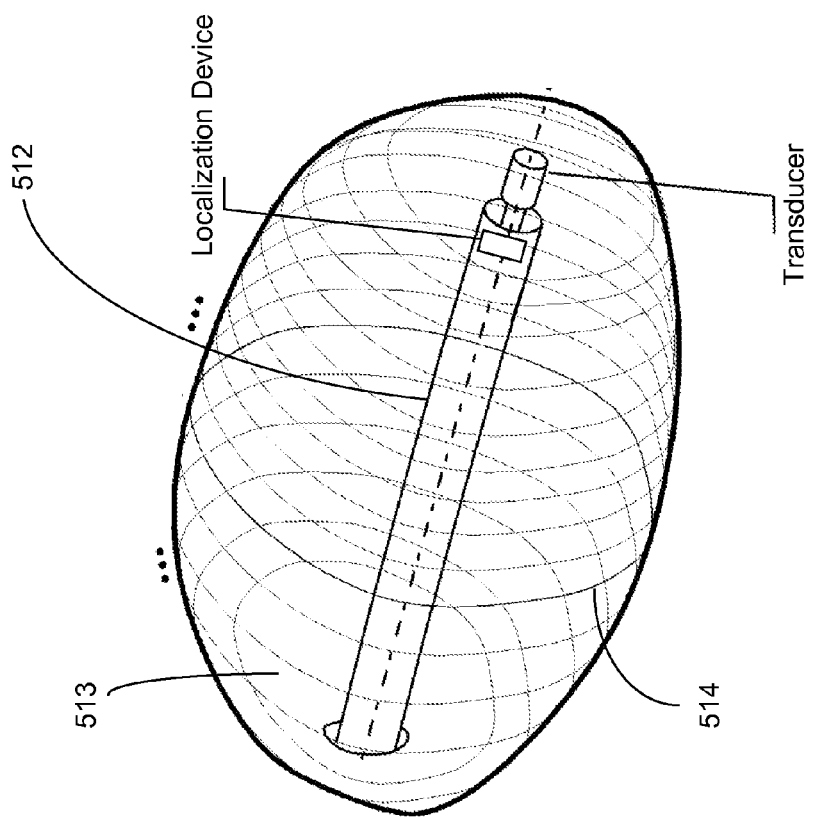

Referring to FIG. 142, a close-up isometric view of a circumferentially-firing ultrasound catheter device (508) comprising a localization device (509) and an ultrasound transducer (510) is depicted within a tissue cavity acquiring a slice of data (511) with an illustrative measured point at a detected density threshold at the transition between empty cavity and tissue wall. FIG. 143 depicts two views down the longitudinal axis of such a catheter system to depict acquisition of a series of density transition points about the catheter which form a slice which may be compiled into a larger three-dimensional image of the subject cavity. Referring to FIG. 144, the conventional transformation mathematics which may be utilized to transform position and orientation data within the acquiring catheter tip frame of reference to the ground frame of reference, or some other desired frame of reference. FIGS. 145A-B depict two different views of a catheter (512) inserting straight through a tissue cavity (513) and acquiring a series of data slices (514) along the way.

Figure 146B:
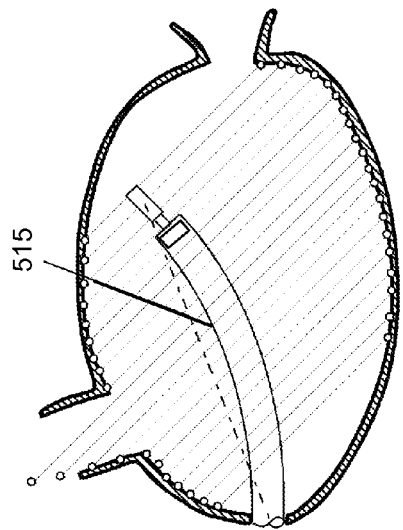
Figure 146D:
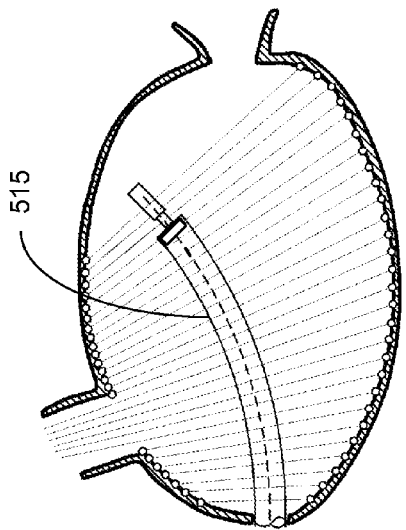
Figure 146A:
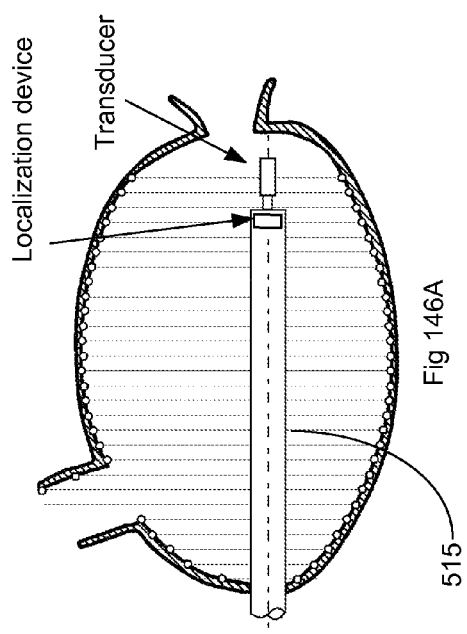
Figure 146C:
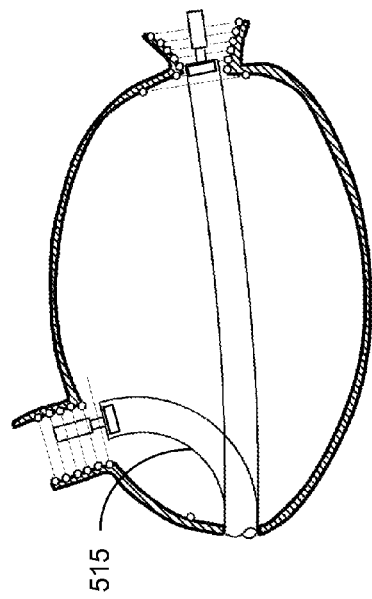

FIGS. 146A-D depict respective variations for imaging a given tissue structure geometry with the subject embodiment. In the embodiment depicted in FIG. 146A, a circumferentially-firing ultrasound catheter (515) is inserted straight through a cavity without regard to incoming slice data. In FIG. 146B, a variation is depicted wherein the catheter structure (515) carrying the ultrasound transducer and localization device is bent as it moves through the subject tissue cavity to provide a series of slices occupying substantially parallel planes. FIG. 146C depicts a variation wherein the catheter structure (515) carrying the ultrasound transducer and localization device is directed into specific sub-portions of the subject tissue mass. In one embodiment, such directing may be the result of real-time or near-real-time image analysis by the operator. For example, fluoroscopy or other conventional imaging techniques may be utilized to position the catheter into such a location in one embodiment. In another embodiment, the catheter may be automatically or semi-automatically guided to such as position, as discussed below. As shown in FIG. 146D, the catheter (515) may be inserted and steered through the subject tissue cavity such that the planes of the slices of data acquired are not parallel. Given the known position and orientation of the ultrasound transducer from an associated localization system, it is by no means a requirement that the planes within a given image stack be parallel. Indeed, in some embodiments, it may be desirable to controllably bend an imaging catheter (516) near a location of interest to acquire multiple images (517) of a particular portion of the subject tissue, as depicted in FIG. 147. Such controlled bending through a preset range of motion as additional image slices are acquired may be termed "bend detailing" a particular portion of the subject tissue structures.

Figure 148A:
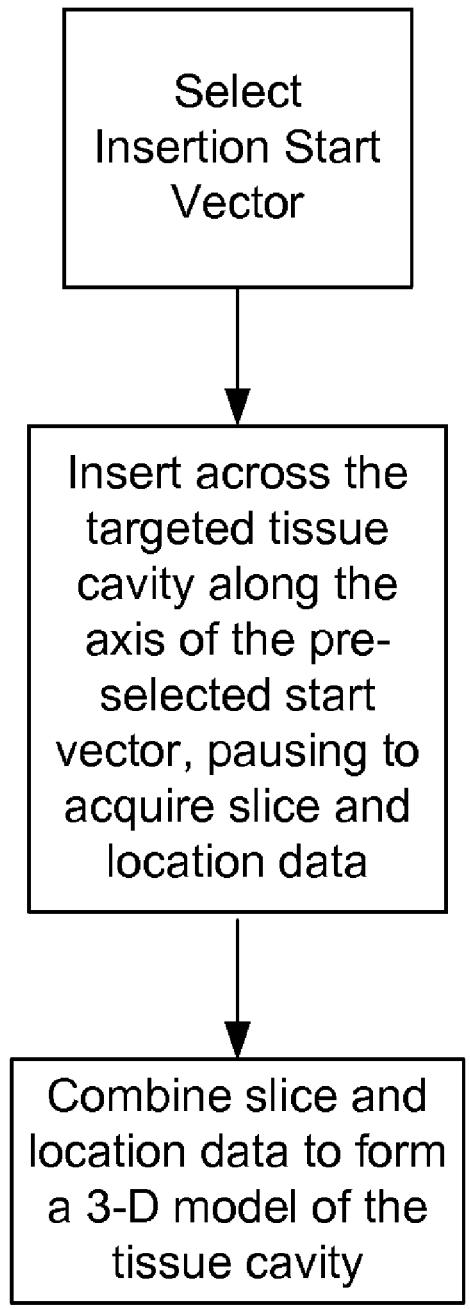
Figure 148B:
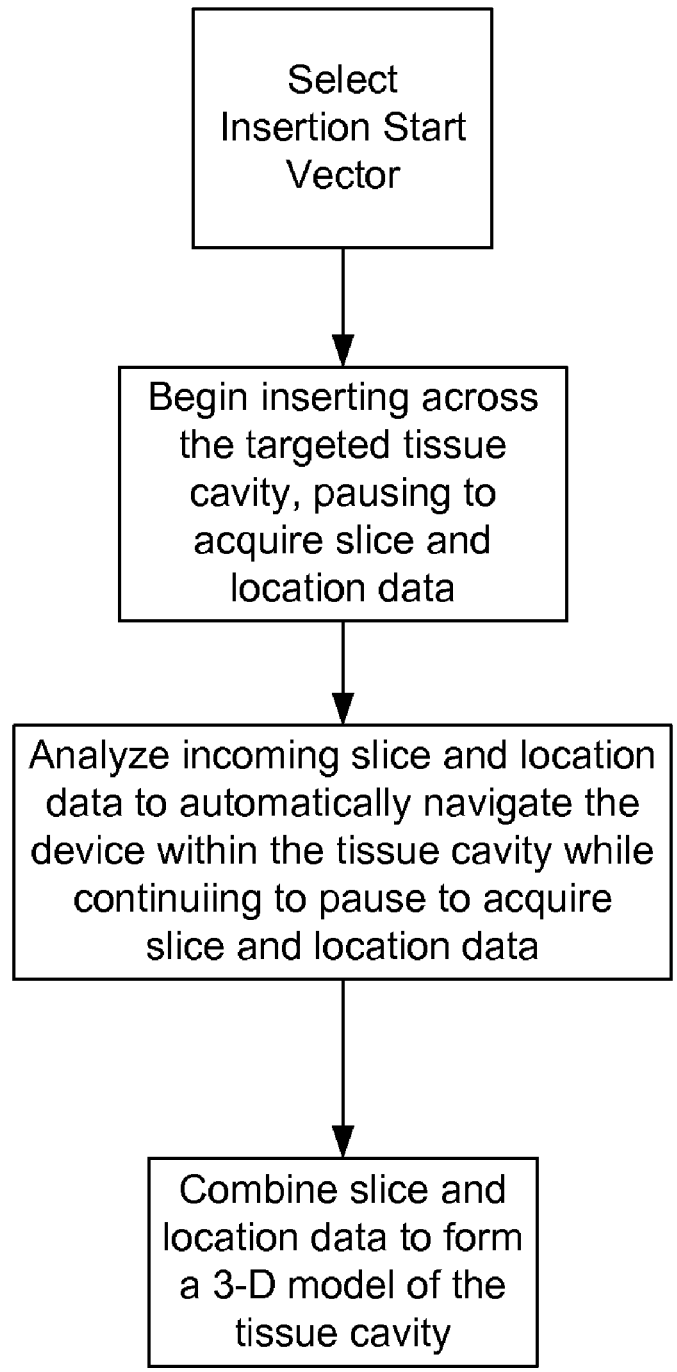
Figure 148C:
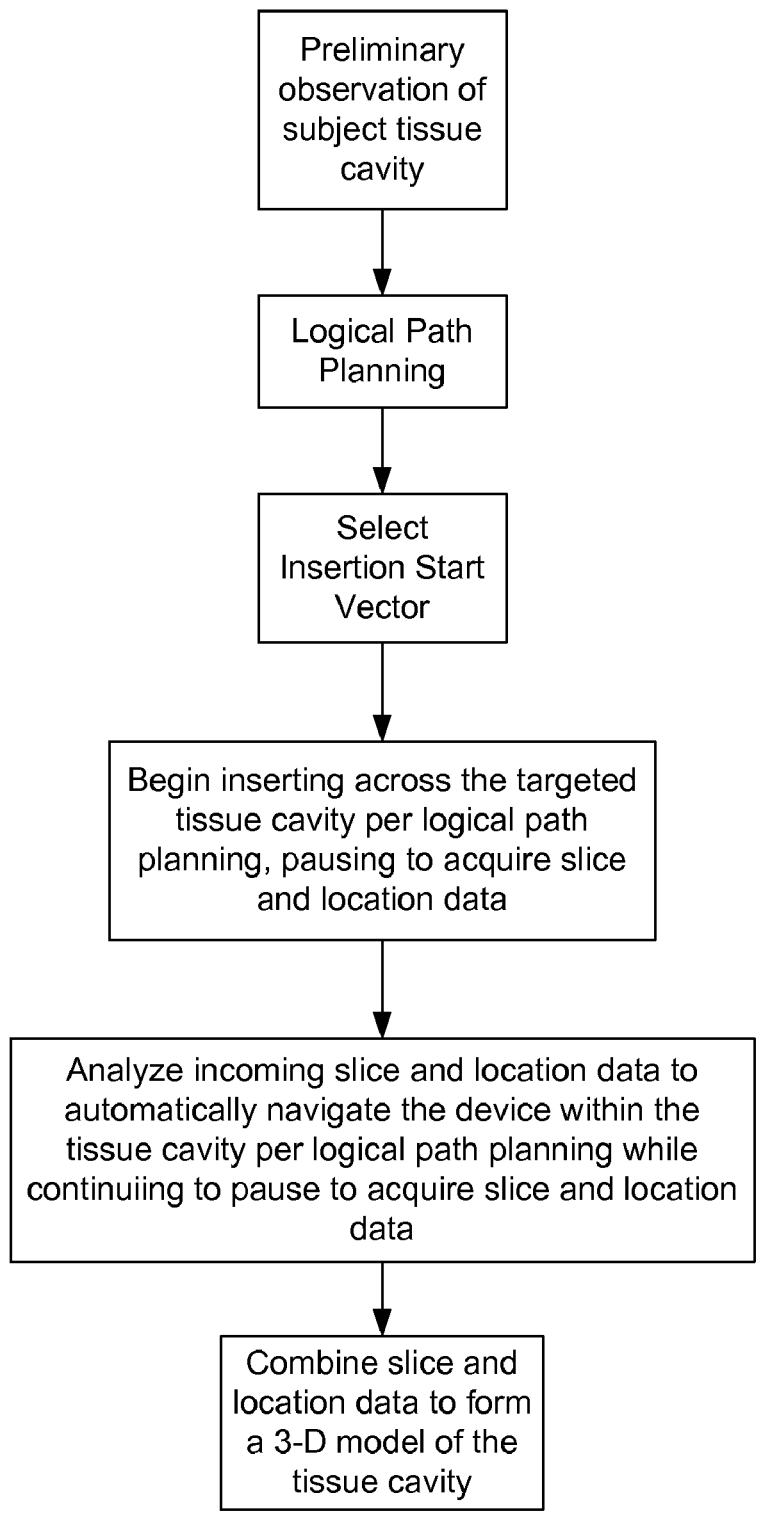

Referring to FIGS. 148A-C, several acquisition protocol embodiments are depicted for implementing the aforementioned acquisition system embodiment. In a simple embodiment as illustrated in FIG. 148A, an insertion vector is selected, subsequent to which an ultrasound transducer is inserted across a subject tissue cavity, pausing to acquire slice and position/orientation data along the way, leading to the combination of slice and location/orientation data into a three-dimensional model. In another embodiment as shown in FIG. 148B, rather than following a pre-determined program for inserting across the subject cavity and acquiring data slices, a closed-loop system analyzes incoming slice data and applies preprogrammed logic to automatically navigate as the image acquisition continues. FIG. 148C depicts an embodiment similar to that of FIG. 148B, with the exception that logical path planning is integrated into the controls logic operating the catheter instrument driver to provide automated or semi-automated image acquisition functionality. For example, the system may watch acquired images time-of-flight between emitted radiation and detected reflection of such radiation to steer the instrument directly down the middle of the cavity, as interpreted utilizing the time-of-flight data. This may be referred to as "time-of-flight center drive". In another embodiment, significant changes in time-of-flight data for a given sector of an image series over a given period of time or distance may be interpreted as a change in tissue surface geometry worth higher density localized imaging, or even an automatic bending to take the transducer closer to the site of interest—or to rotate the transducer for higher-resolution imaging of the particular area without insertion adjustment, as described above in reference to FIG. 147.

Figure 149:
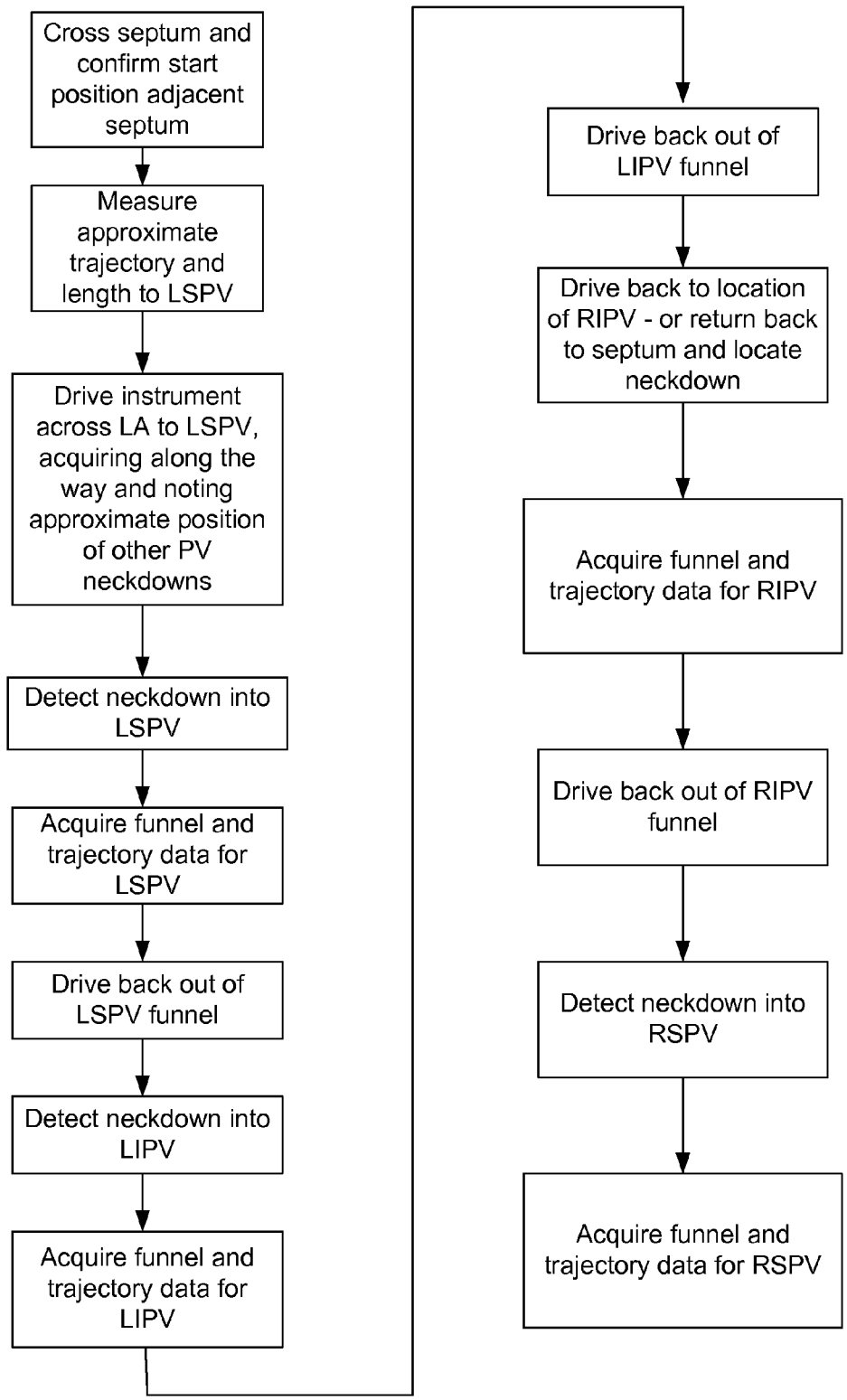
FIGS. 149-150 illustrate multiple embodiments for acquiring a three-dimensional tissue structure model of a human left atrium.
Figure 150:
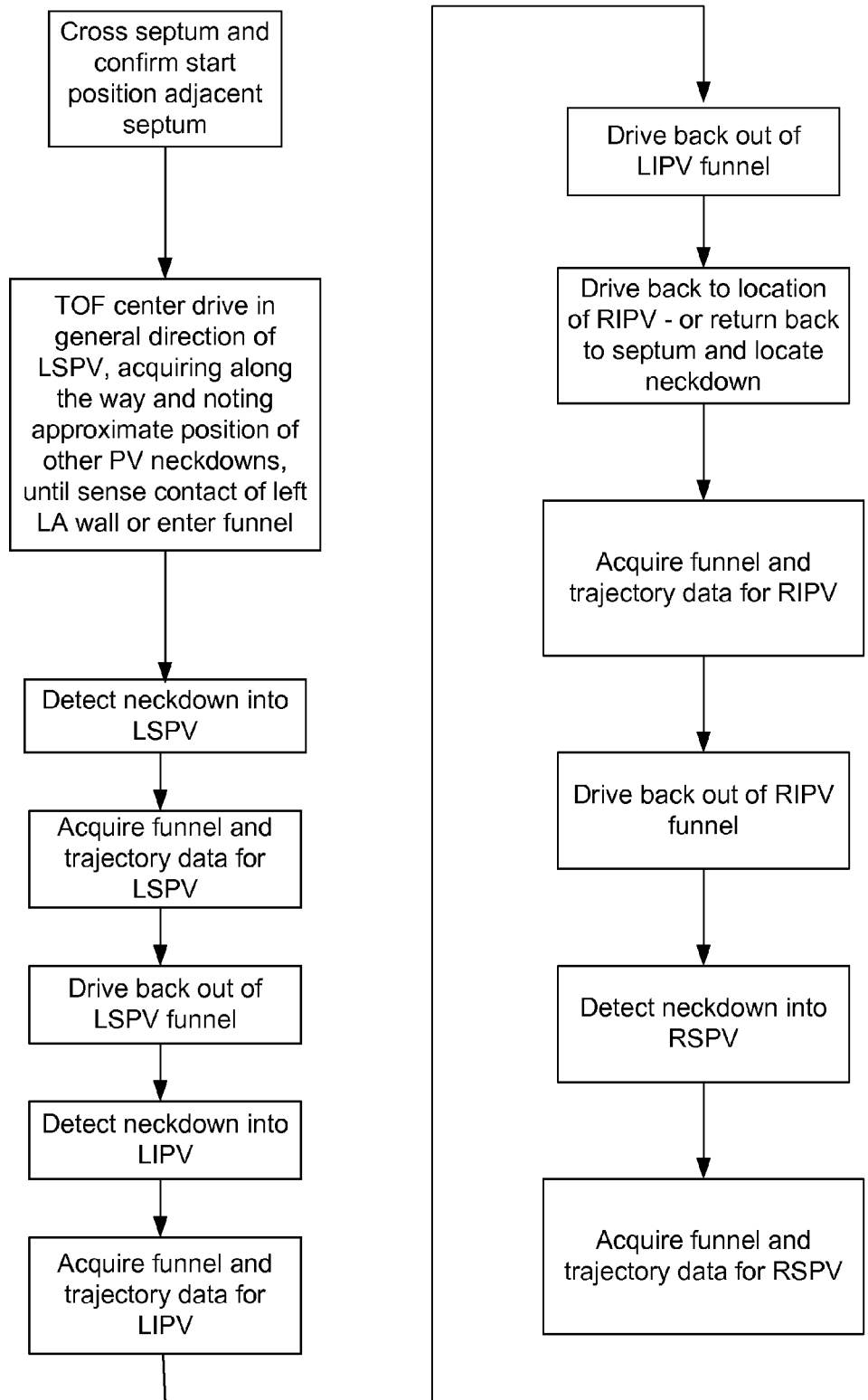

FIGS. 149 and 150 depict respective embodiments for acquiring a three-dimensional tissue structure model of a human left atrium.

Referring to FIG. 149, subsequent to crossing the septal wall, confirming an acquisition start position adjacent the septum, and measuring the approximate trajectory and insertion length to reach the left superior pulmonary vein funnel into the left atrium with the instrument utilizing a conventional technology such as fluoroscopy or ultrasound, the instrument may be driven across the left atrium cavity along the approximate trajectory, gathering slices along the way and noting, via time of flight calculations and anatomy logic, approximate positioning of any other pulmonary vein funnel neckdown positions. As the instrument reaches the end of the predicted trajectory to the left inferior pulmonary vein funnel, neckdown into the funnel may be detected using time of flight calculations and added data from bend-detailing, as described above in reference to FIG. 147. After the neckdown is detected, the instrument may be driven into the funnel and funnel shape and trajectory data acquired for the left superior pulmonary vein structure. In one embodiment, a preset insertion limit prevents insertion beyond a set value into a pulmonary vein funnel structure. In another embodiment (such as that described in reference to FIG. 150), a tissue contact sensing means may be utilized to provide feedback to an operator or automated drive system that a tissue structure has been physically encountered by the instrument, and that the instrument insertion should be limited, as directed by the pertinent controls logic.

Referring still to FIG. 149, subsequent to acquiring funnel shape and trajectory data for a first pulmonary vein funnel of the left atrium, a similar procedure may be utilized to do the same for second, third, and fourth pulmonary vein funnels. After driving back out of the left superior pulmonary vein funnel, preferably along the trajectory utilized to minimally invasively enter the funnel, the neckdown into the left inferior pulmonary vein funnel is detected utilizing similar techniques, such as bend-detailing, and funnel and trajectory data pertinent to the left inferior pulmonary vein is acquired. Subsequently, the instrument may be driven back to the location of the right pulmonary vein neckdowns, preferably starting with the more easily accessed, in most patients, right inferior pulmonary vein neckdown. To increase the amount and variation of data comprising the ultimate left atrium model, data slices may be continually gathered as the instrument is driven back, forth, and around the left atrium.

After locating the right inferior pulmonary vein funnel, the instrument may be driven into the funnel and data acquired for the trajectory and shape, as discussed above in reference to the left pulmonary vein funnels. Similar, shape and trajectory data may be acquired for the right superior pulmonary vein funnel, which in most patients, is the most difficult to access due to its location relative to the septum. Should bend-detailing or acquisition of slices and time of flight analysis as facilitated by driving the instrument around within the atrium be ineffective in location any of the pulmonary vein neck down locations, conventional systems, such as fluoroscopy or intracardiac ultrasound, may be utilized during the depicted acquisition procedure to assist in generally driving the instrument to the location of the pertinent tissue structures, after which the appropriate portion of the depicted procedure may be resumed in a more automated fashion.

Referring to FIG. 150, another embodiment of a procedure for acquiring a three-dimensional image of a left atrium is depicted, this embodiment differing from that of FIG. 149 in that the pertinent system also incorporates a contact sensing means at the distal tip of the instrument for sensing contact between the instrument tip and the subject tissue structures. With such added functionality and logic to incorporate the information from it, the subject system may be configured to stop or indicate to the operator that a tissue structure or wall has been engaged. Such a feature may be utilized to streamline the acquisition process. For example, rather than planning a trajectory based upon data from imaging modalities such as fluoroscopy or ultrasound, the instrument merely may be pointed in roughly the appropriate direction across the left atrium toward the left pulmonary veins, and insertion driving and data slice acquisition engaged. The contact sensing feedback may be logically utilized to stop insertion of the instrument at or near the left wall of the left atrium, or within the bends of the pulmonary veins as they narrow away from the funnels of the left atrium.

A number of references have reported methods for determining contact between medical device instrumentation and tissue. For example, U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342 disclose various aspects of determining electrode-tissue contact by measuring changes in impedance between an instrument electrode and a reference electrode. In an embodiment of the subject invention wherein the instrument comprises suitably positioned electrodes, techniques such as those disclosed in the art may be utilized. Other preferred embodiments of contact sensing means are described in reference to FIGS. 151-157.

Figure 151:
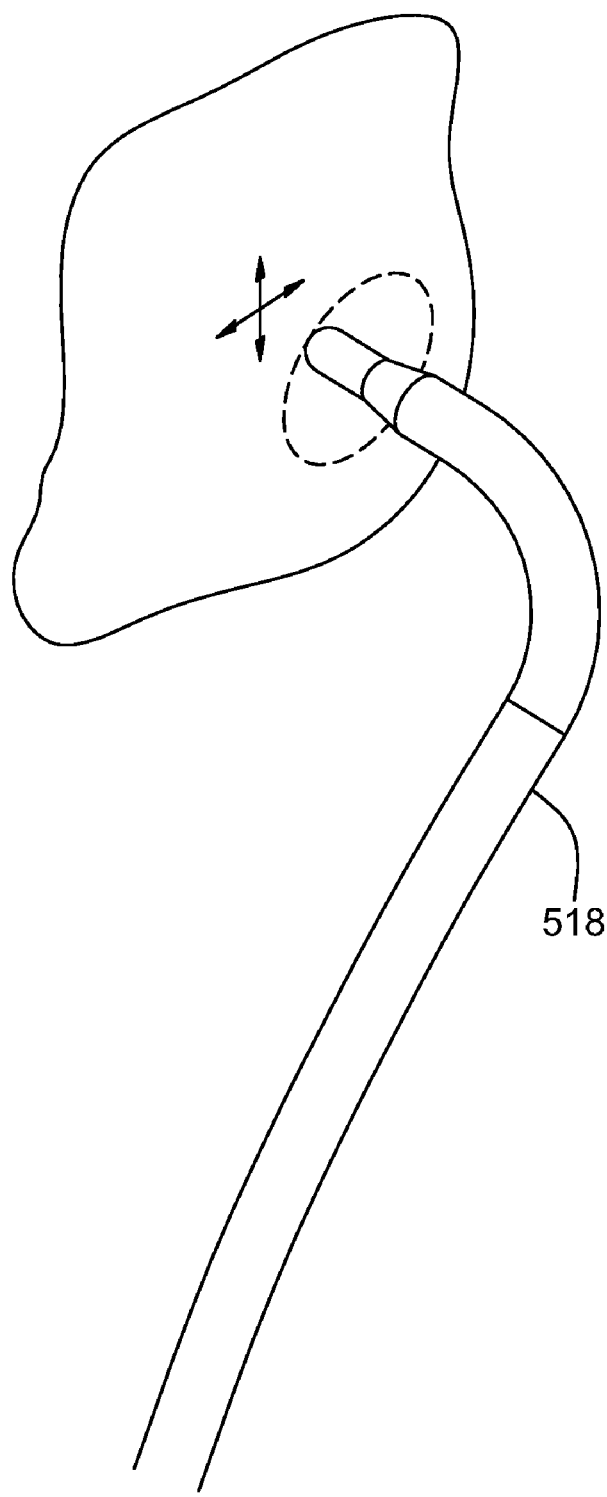
FIGS. 151-157 illustrate various embodiments of contact sensing means.

Referring to FIG. 151, an instrument (518) operated by an instrument driver and a closed-loop control system incorporating a localization technology to measure actual instrument position is depicted. When the instrument tip is driven through a range of motion, such as + pitch to − pitch, then back to neutral and + yaw to − yaw, at some cyclic interval, loads encountered by tissue structure contact, as opposed to free cavity space in blood, for example, will tend to increase the error detected between the measured tip position determined by the localization system, and the predicted tip location, determined via the inverse kinematics of the instrument structure. Other cyclic patterns of motion may also be utilized, such as repeated spiral motion, circular motion, etc. Depending upon the experimentally determined systematic error between the predicted and measured tip locations in free space given a particular instrument structure, a threshold may be utilized, beyond which error is considered an indicator of tissue contact. Depending upon the cyclic motion pattern selected, the direction of contact between the instrument and another object may also be detected by observing the directionality of error between predicted and measured instrument position.

Figure 152:
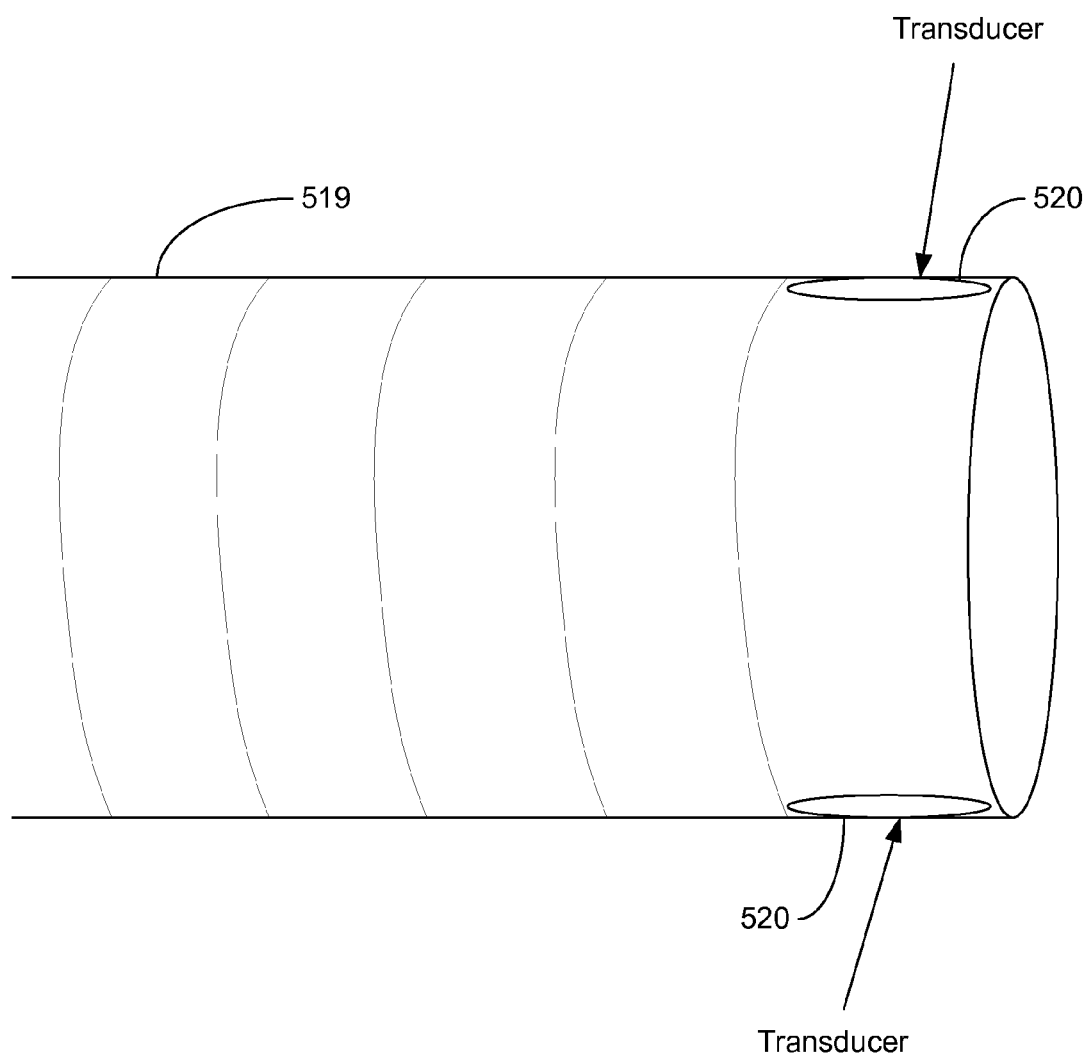

Referring to FIG. 152, a distal tip of an instrument (519) is depicted having two vibratory devices (520). In one embodiment, one device is a vibratory transmitter, such as a piezoelectric crystal adjacent a membrane, and the other device is a vibratory receiver comprising, for example, a membrane adjacent another piezoelectric crystal. In another embodiment, both devices, a single device, or more than two devices may comprise both transmitters and receivers. In free cavity space, the instrument will vibrate more freely than it will when in mechanical contact with a tissue structure, and in this embodiment, the difference is detected and logically interpreted as a tissue structure contact indicator.

Figure 153:
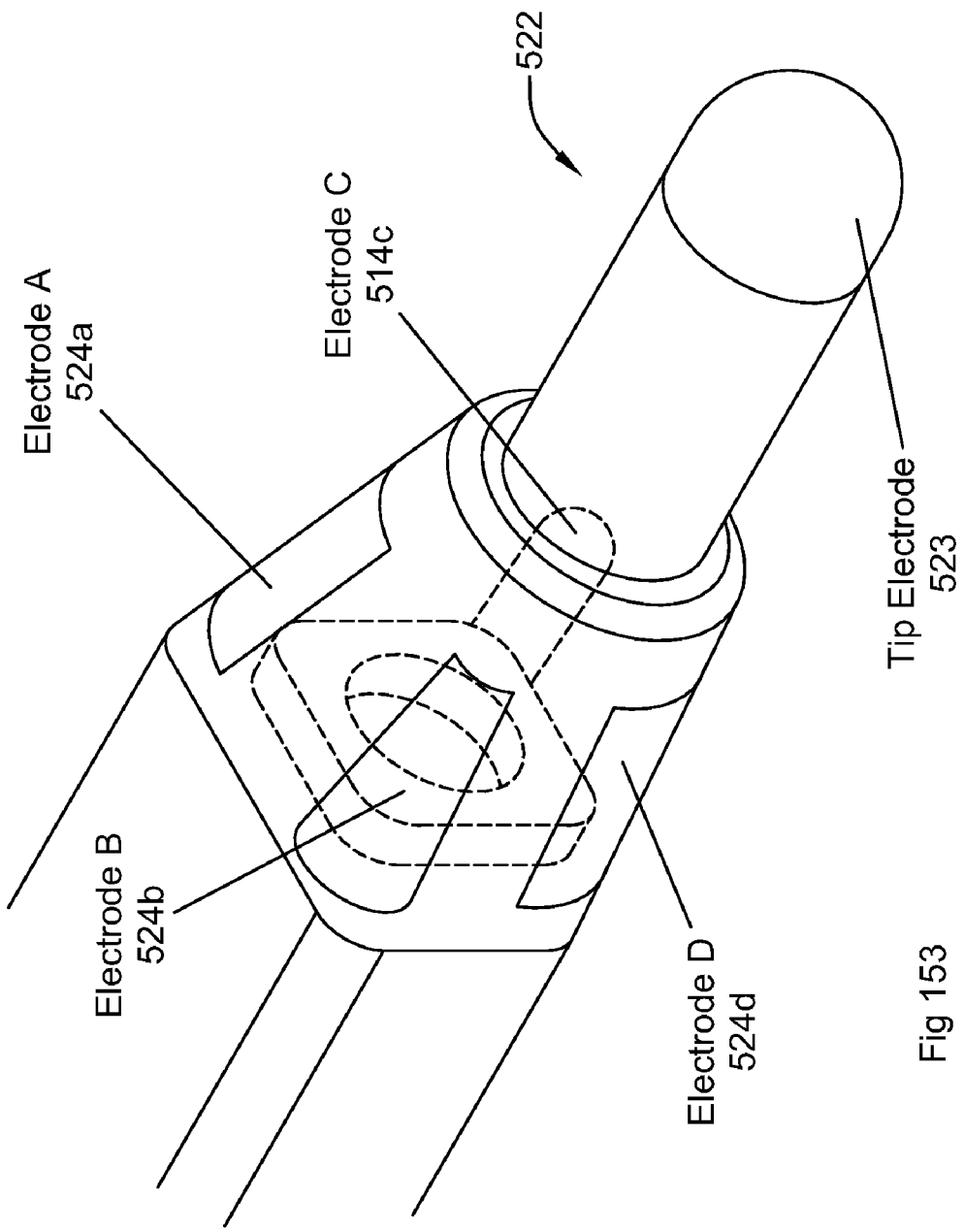
Figure 154:
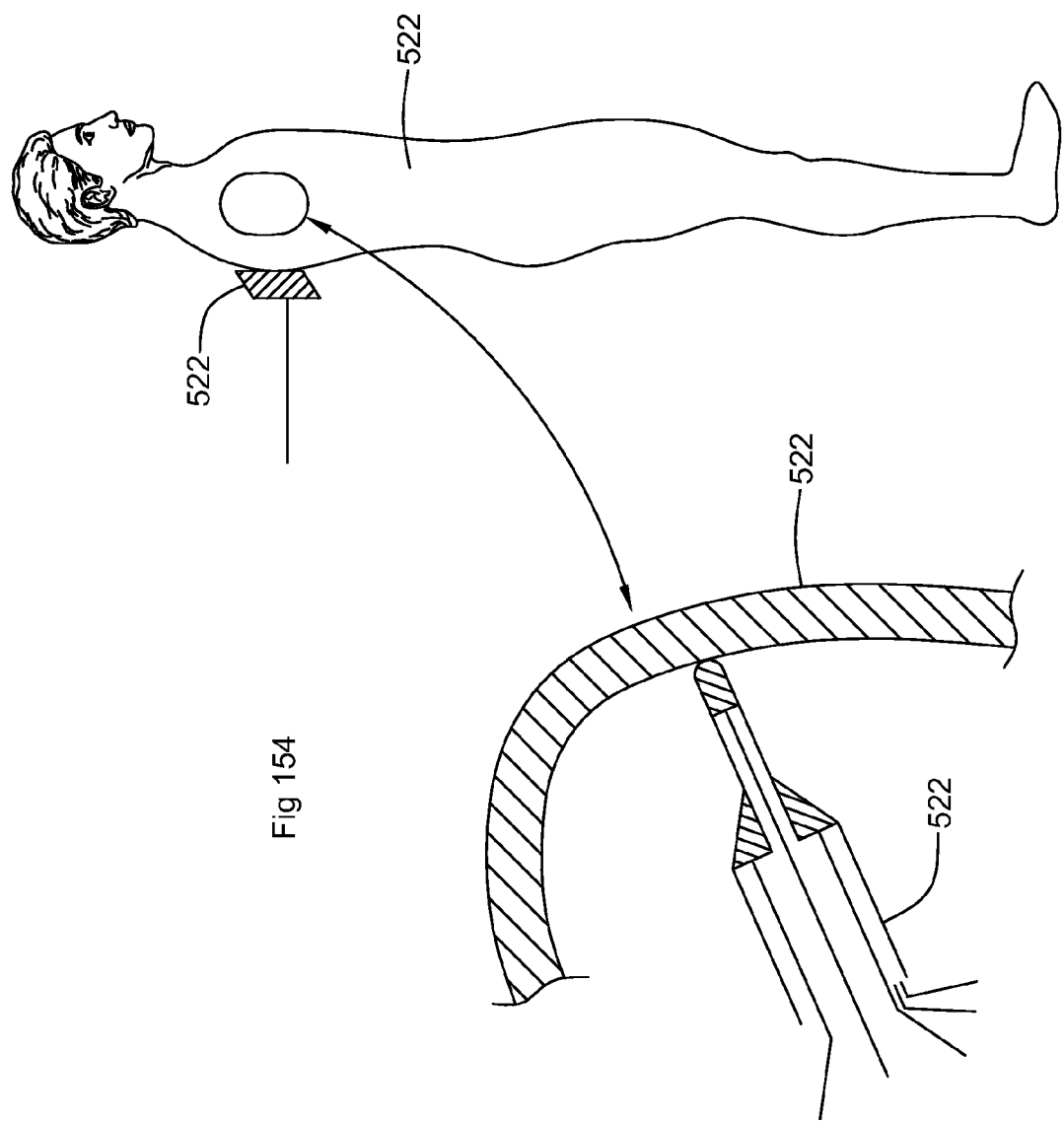
Figure 155:
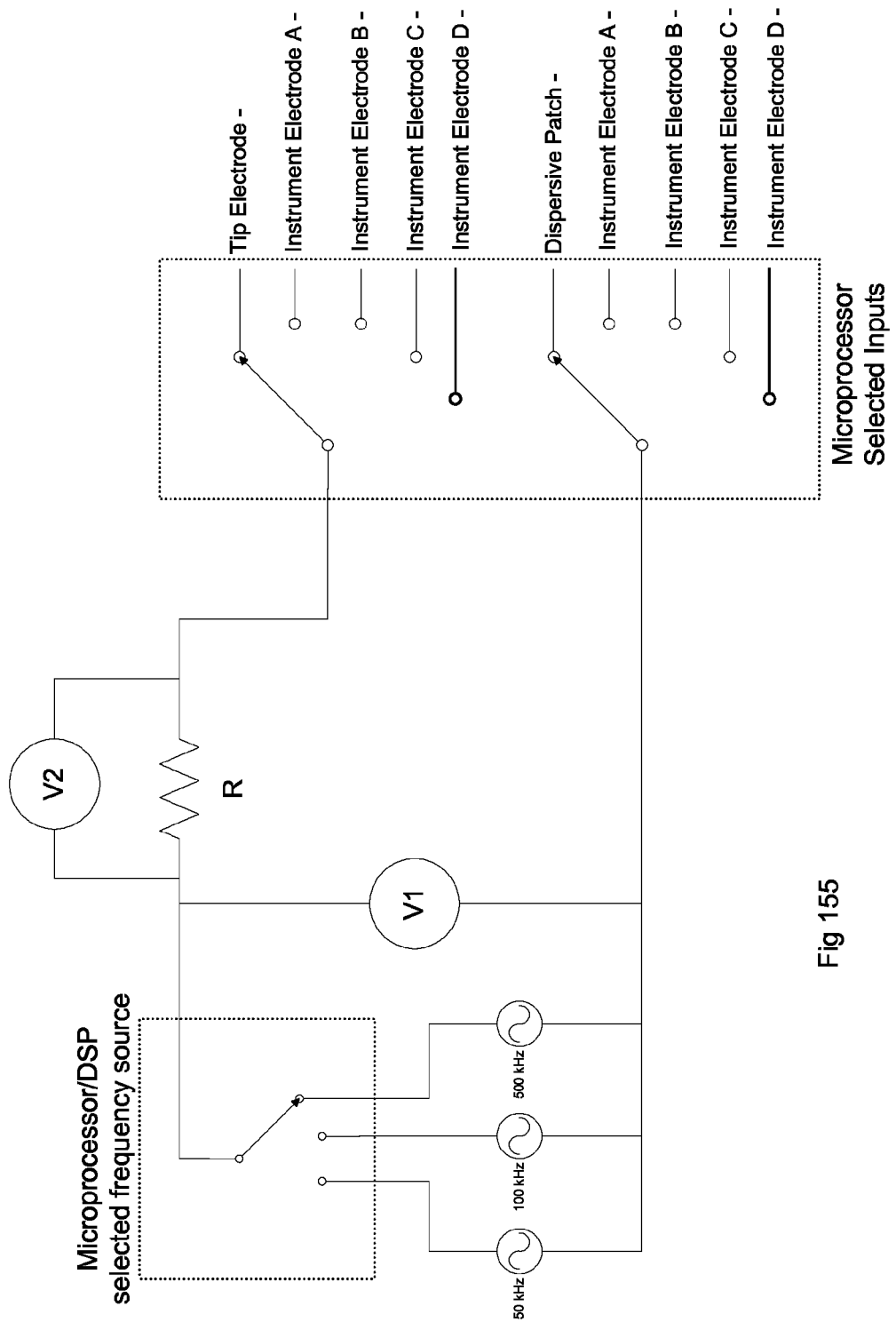

Referring to FIGS. 153-155, another embodiment of a tissue contact sensing means is depicted wherein impedance monitoring through multiple paths at multiple frequencies may be utilized as an indicator of tissue contact. Conductivity measured through blood varies relatively little with frequency modulation, whereas conductivity does vary more significantly with frequency modulation when measured through a tissue structure. By quickly switching frequencies and taking measurements at various frequencies, using, for example, a microprocessor, one can make a determination regarding contact with tissue or not based upon the associated modulation in conductivity or impedance.

Such a technique may be combined with conductivity path modulation. Conventionally, impedance is measured between an instrument tip electrode and a dispersive ground mounted, for example, upon the skin of a patient's back. With such a configuration, conductivity increases, and impedance decreases, when the instrument is in contact with, for example, the heart wall. Another measurement path of interest is conductivity between an instrument tip electrode and another electrode inside of the same chamber, but at a more proximal instrument location. As blood is relatively highly conductive, conductivity will be at a maximum when the tip electrode is not in contact with tissue, and will decrease when the tip electrode touches a tissue wall, resulting in obscuring at least a portion of the tip electrode. Indeed, previous studies have shown conductivity or impedance measurements take with such a configuration can be utilized to predict contact before it actually occurs, and that depth of tip electrode penetration may also be predicted given the relationship between conductivity and obstruction of the tip electrode by tissue.

FIG. 153 depicts a further embodiment of an instrument (522) having a distal tip configured to facilitate such functionality. The instrument (522) has a tip electrode (523) disposed distally, and four electrodes (524a-d) disposed more proximally at corner positions to facilitate contact with tissue structures as the instrument (522) is positioned adjacent a tissue structure in a near parallel or tangential manner. FIG. 154 depicts the instrument (522) adjacent a tissue structure (523) with reference to a dispersive patch electrode (524) located upon the skin of a patient's back. With such a configuration, impedance may be monitored between any pair of electrodes, with various frequencies, to provide a configuration combining not only frequency modulation to detect tissue-electrode contact, but also conductivity comparison path modulation to detect tissue-electrode contact.

Referring to FIG. 155, a schematic is depicted for utilizing fast switching hardware, such as microprocessors, to collect data with each of the pertinent combinations. Each cycle of acquisition through the various combinations yields impedance difference monitoring based upon path switching and frequency switching, which may be compiled and logically associated with determinations of tissue contact or not, and even the location of the instrument which is predicted to be in contact with tissue. Many other variations of electrode arrays may be utilized in addition to the configuration depicted in FIG. 153, and frequency may be modulated between more than three frequencies, as depicted in FIG. 155, to produce additional data for each combination acquisition cycle.

Figure 156:
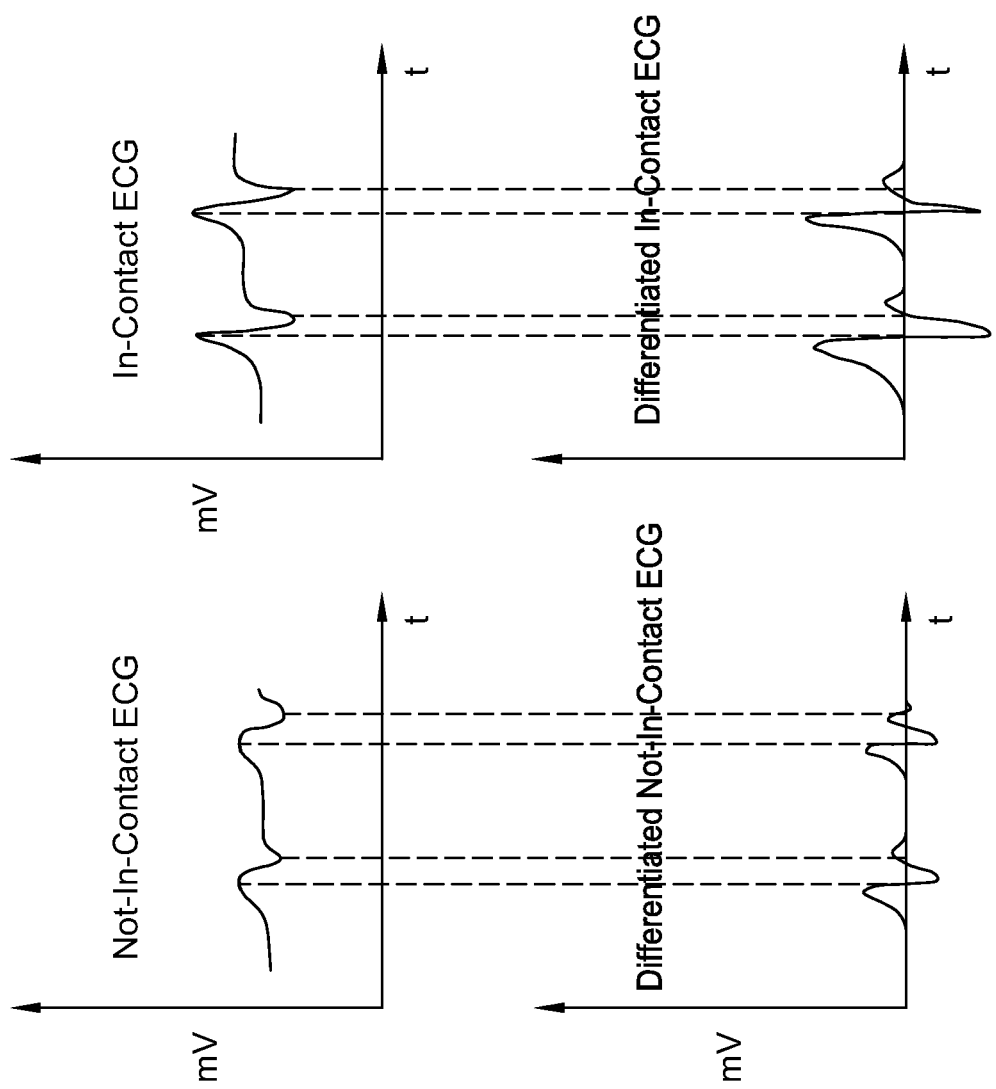
Figure 157:
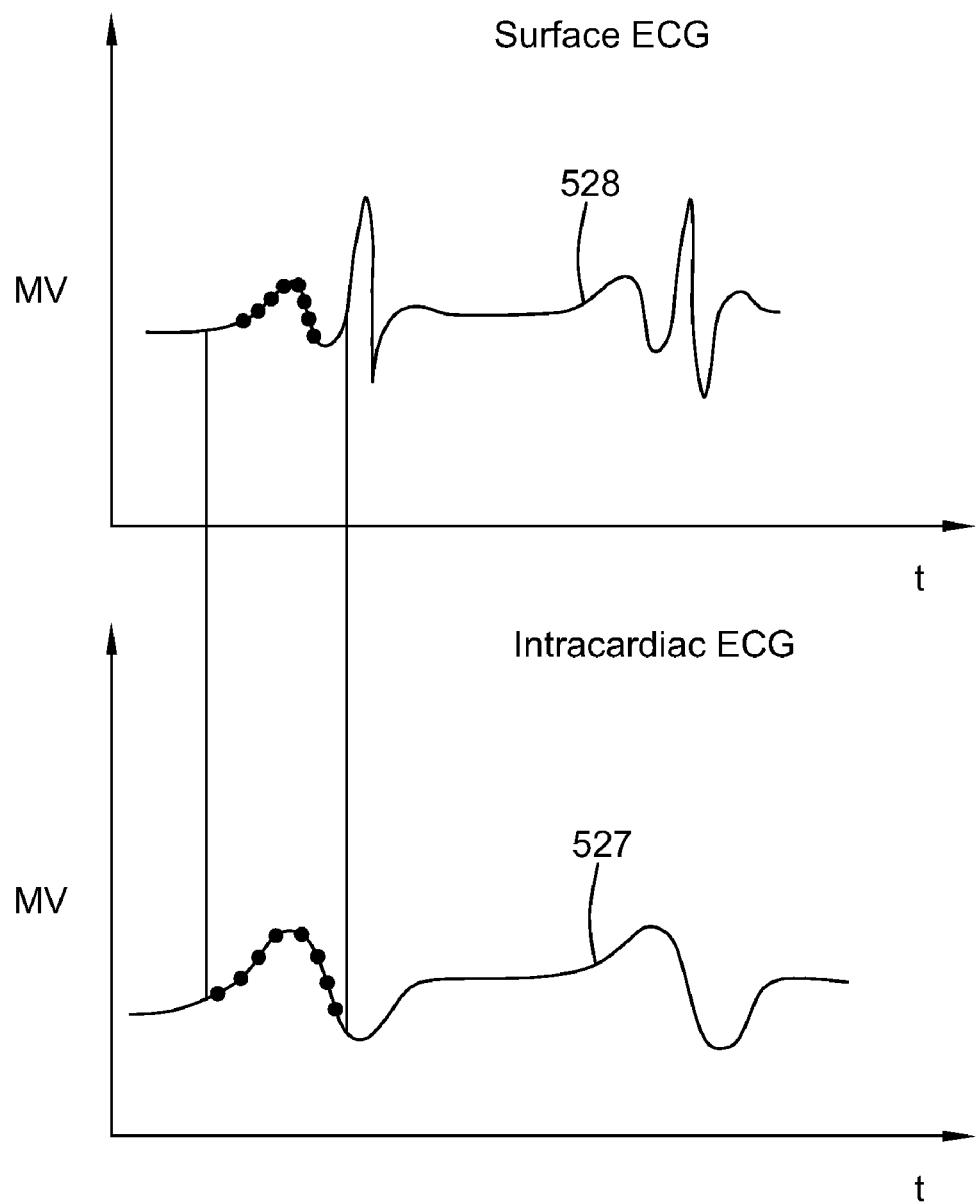
Figure 158A:
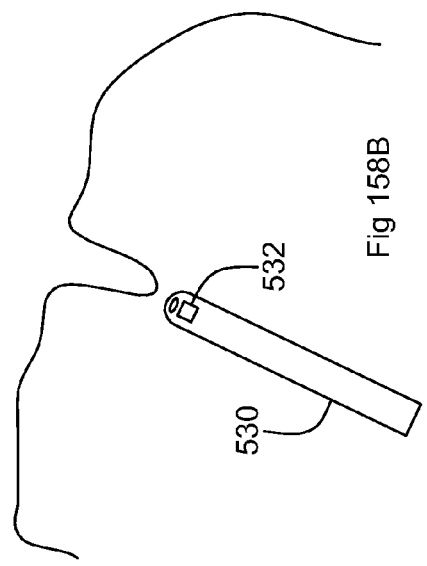
FIGS. 158A-160D illustrate examples of interpreted master following.
Figure 158B:
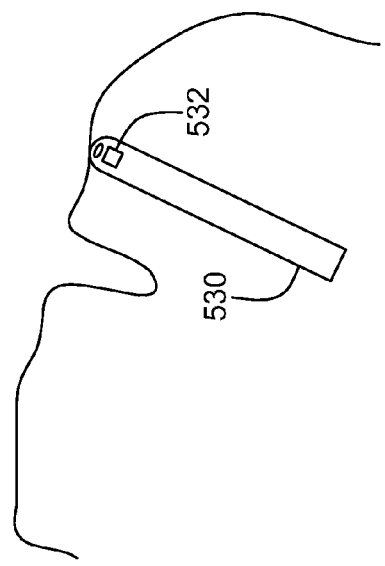
Figure 158C:
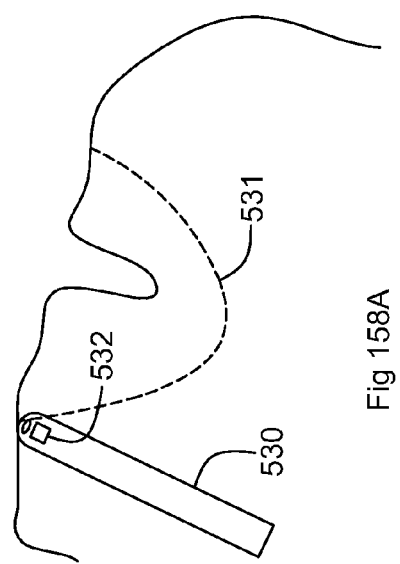
Figure 158D:
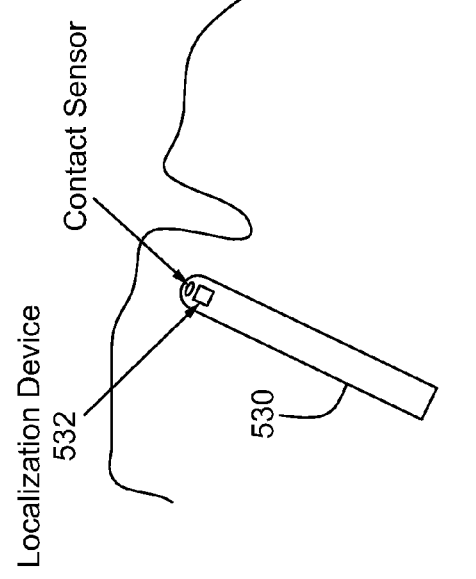
Figure 159A:
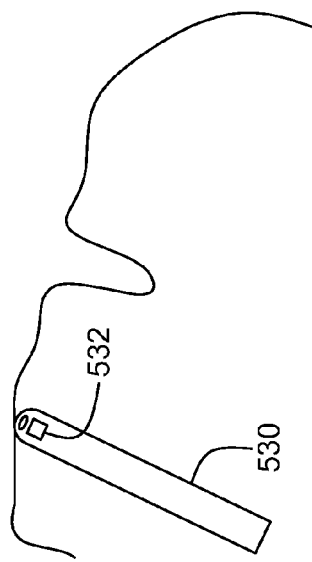
Figure 159B:

Figure 159C:
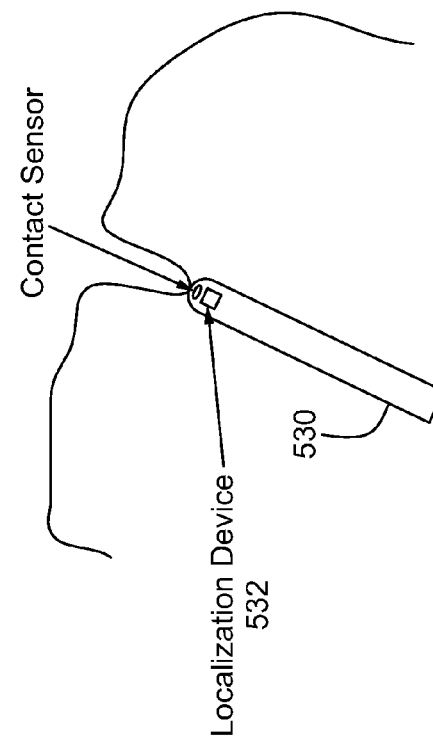
Figure 159D:
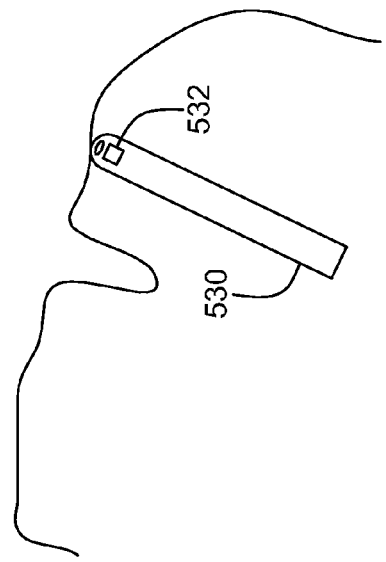
Figure 160A:
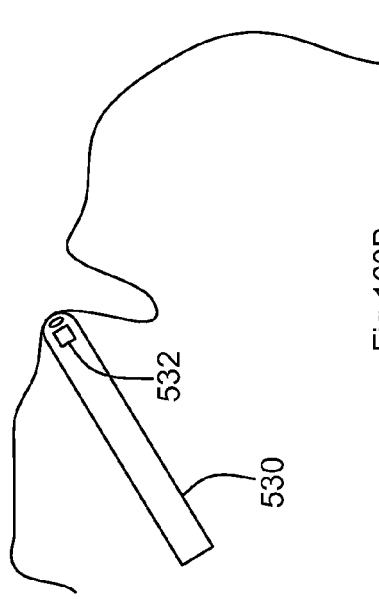
Figure 160B:
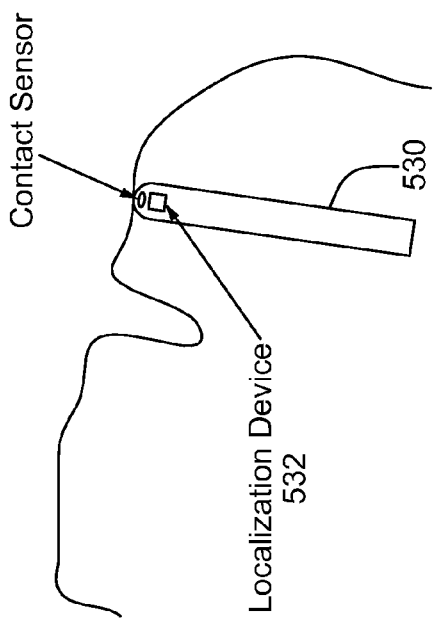
Figure 160C:
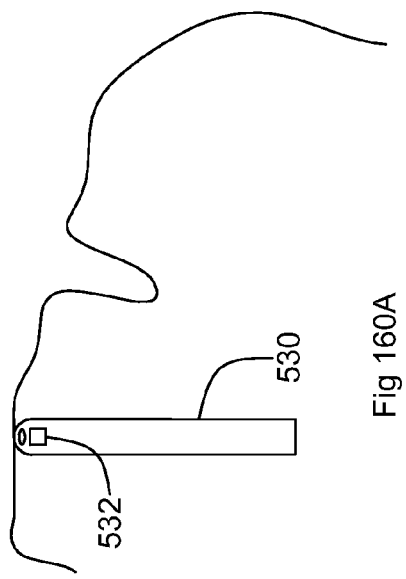
Figure 160D:
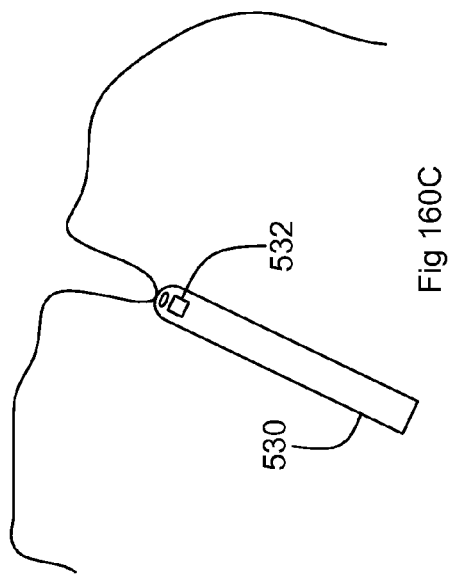

FIGS. 156 and 157 depict another embodiment of a means for detecting contact between an instrument electrode and a tissue structure, such as a cardiac wall. The electrocardiogram ("ECG") signal acquired by an instrument electrode positioned in free blood in the heart shows a discernable signal, but from a signal processing perspective, is less sharp and lower in amplitude due to the attenuation of high frequency signal content, as compared with similar signals detected when the electrode is in contact with a cardiac wall. When the ECG signal is differentiated with respect to time, the resulting differentiated signal has higher amplitude when the electrode is in contact, as compared with a slower-rising curve for a not-in-contact scenario. In one embodiment, a microcontroller or digital signal processor ("DSP") is utilized to perform sampling, differentiation, and analysis of acquired ECG waveforms. In another embodiment, the shape of incoming ECG waveforms is monitored to detect not only contact, but proximity to contact as the waveform shape changes with proximity to the pertinent tissue structure.

Referring to FIG. 157, similar signal processing means are utilized to compare an intracardiac ECG signal (527) with a body surface ECG signal (528), which essentially represents a superposition of the various ECG waveforms from subportions of the heart. The fit between the intracardiac ECG signal is compared with the body surface ECG signal to determine whether the intracardiac ECG signal does indeed appear to be a portion of the combined signal represented by the body surface ECG signal. If the superposition match does not meet an experimentally determined threshold, the result is logically related to a state of non-contact between the intracardiac electrode and the heart wall tissue structures.

When the intracardiac electrode is in contact with a particular wall of the heart, the intracardiac ECG signal is crisp, detailed, and fits well into a portion of the superimposed combined body surface ECG signal, as depicted in FIG. 157. In another embodiment, the body surface ECG signal may be split into, for example, four subportions, each of which may be compared in a similar manner to the intracardiac ECG signal for a determination of not only contact, but also a confirmation of position within the heart as associated with the four subportions. For example, the body surface ECG signal may be subdivided into four portions representative of the four chambers of the heart, or even four portions of the same chamber.

In a generic form, the aforementioned "master following mode" may be logically configured to follow directly each command as it comes through the control system from the master input device. In one closed loop control embodiment, however, a logic layer is configured to interpret data incoming from a master input device and a localization system in light of the integrated tissue structure model and certain system settings information pertinent to the particular procedure at hand, to make modifications to commands forwarded to the master following and subsequent main servo loop controls logic, resulting in movements of the physical instrument.

Referring to FIGS. 158A-160, some relatively simplistic examples illustrate challenges addressed by interpreted master following. The exemplary instrument embodiment depicted in each of these figures comprises a localization device and a contact sensing device. Many combinations or instrument componentry may be utilized with an interpreted master following logic layer to provide an operator with enhanced navigation functionality, depending upon the functional objectives.

As shown in FIGS. 158A-D, an instrument (530) has a distal end carrying a localization device (532) is positioned adjacent an irregular tissue wall which is represented in the system's visualization and control systems by a preferably three-dimensional tissue structure model acquired utilizing one of the aforementioned modalities. Supposing that the operator's objective is to move the instrument distal tip as indicated in FIGS. 158A-D, an operator's preferred movement path depends upon his preferred action in between the two locations. For example, if the operator merely wishes to touch the instrument (530) to the tissue wall in each location without contacting any tissue in between, the operator may prefer a path of efficiency (531) around the irregularity in the tissue structure, such as that depicted by a dashed line. Following this path, the operator may drive the instrument between the respective positions/locations.

Additionally or alternately, the operator may wish to lightly touch the instrument (530) against the tissue structure and keep the instrument in contact as the instrument is driven between the locations depicted in FIG. 159A-D via a series of hops between the two locations, rather than a constant dragging type of contact as described in the aforementioned embodiment. Further, in another embodiment, as depicted in FIG. 160A-D, the operator may wish to move the instrument between positions, while maintaining the instrument substantially normal to the tissue structure wall, perhaps due to the preferred orientation of a distal instrument feature, e.g., an electrode.

In addition, the operator may wish to have safety functionality built into the controls logic to, for example, prevent the instrument from damaging the subject tissue structures by excessively dragging along the tissue with an excessive load, overloading or overstressing a particular portion of a tissue structure with a concentrated load, or occupying a region that may cause tissue damage, such as an active valve entrance.

Such operator objectives are addressed in various embodiments of an interpreted master following logic layer interposed into the controls logic. In one embodiment, interpreted master following interprets commands that would normally lead to dragging along the tissue structure surface as commands to execute a succession of smaller "hops" to and from the tissue structure surface, while logging each contact as a new point to add to the tissue structure surface model. Hops are preferably executed by backing the instrument out the same trajectory it came into contact with the tissue structure, then moving normally along the wall per the tissue structure model, and re-approaching with a similar trajectory. In addition to saving to memory each new XYZ surface point, in one embodiment, the system saves the trajectory of the instrument with which the contact was made by saving the localization orientation data and control element tension commands to allow the operator to re-execute the same trajectory at a later time if so desired. By saving the trajectories and new points of contact confirmation, a more detailed contour map is formed from the tissue structure model, which may be utilized in the procedure and continually enhanced. The length of each hop may be configured, as well as the length of non-contact distance in between each hop contact.

In one embodiment, interpreted master following performs a variety of safety checking steps to ensure that the operator does not accidentally damage the subject tissue structure by driving into it or through it with the instrument. For example, the controls logic may be configured to disallow driving of the instrument beyond or into the subject tissue structure, as determined utilizing a tissue structure model with localization data and/or contact sensing. Such a mode may be manually overridden with an operator command in certain scenarios, for example, in order to purposefully puncture a tissue wall such as the septum at the location of the fossa ovalis. In one embodiment, the controls logic may be configured to prevent instrument electrode activation while the operator is attempting to move the instrument, or may attempt to prevent electrode activation in the same location for more than a predetermined time or amount of energy delivered.

In another embodiment, interpreted master following assists the operator in automating various clinical procedures. For example, where the instrument comprises a distal ablation electrode, the controls may be configured to automatically fit a circular ablation pattern through three contact points selected by the operator. Further, an operator may select a hopping, intermittent electrode burning pattern to automatically apply has he merely moves the master input device linearly. Haptics functionality may be utilized to provide the operator with various feedback to assist in clinical procedures. For example, a haptic "groove" may be created along the insertion axis of the instrument to assist the operator in driving the instrument with the master input device. Further, previously selected points of desired contact may be haptically turned in to "gravity wells" to assist the operator in directing the instrument to such locations.

A control system embodiment, such as described above, facilitates precision steerability of a catheter-based instrument in order to conduct a medical procedure. As an exemplary application, a myocardial ablation procedure to address atrial fibrillation will now be described with reference to FIGS. 161-174.

Figure 161:
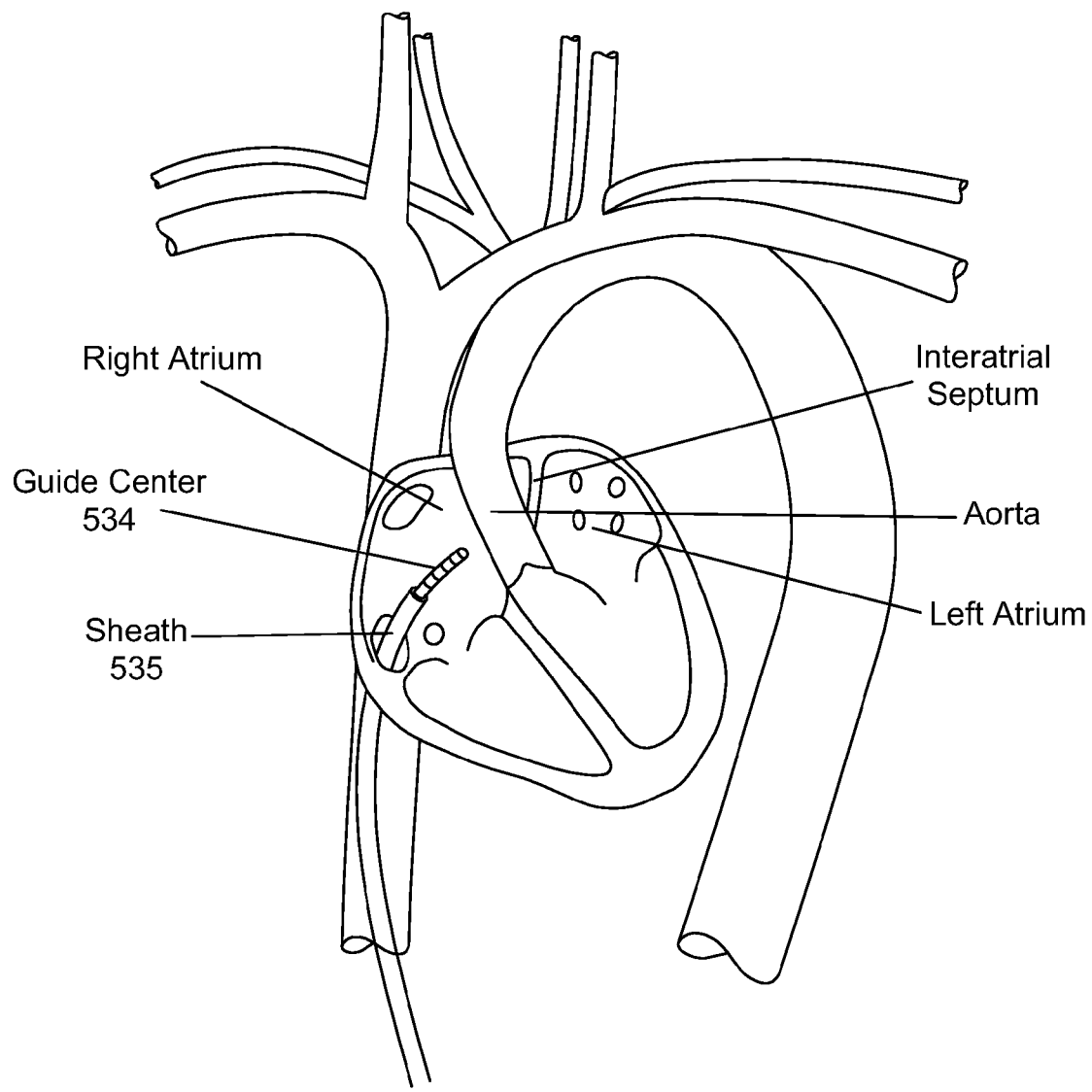
Figure 162:
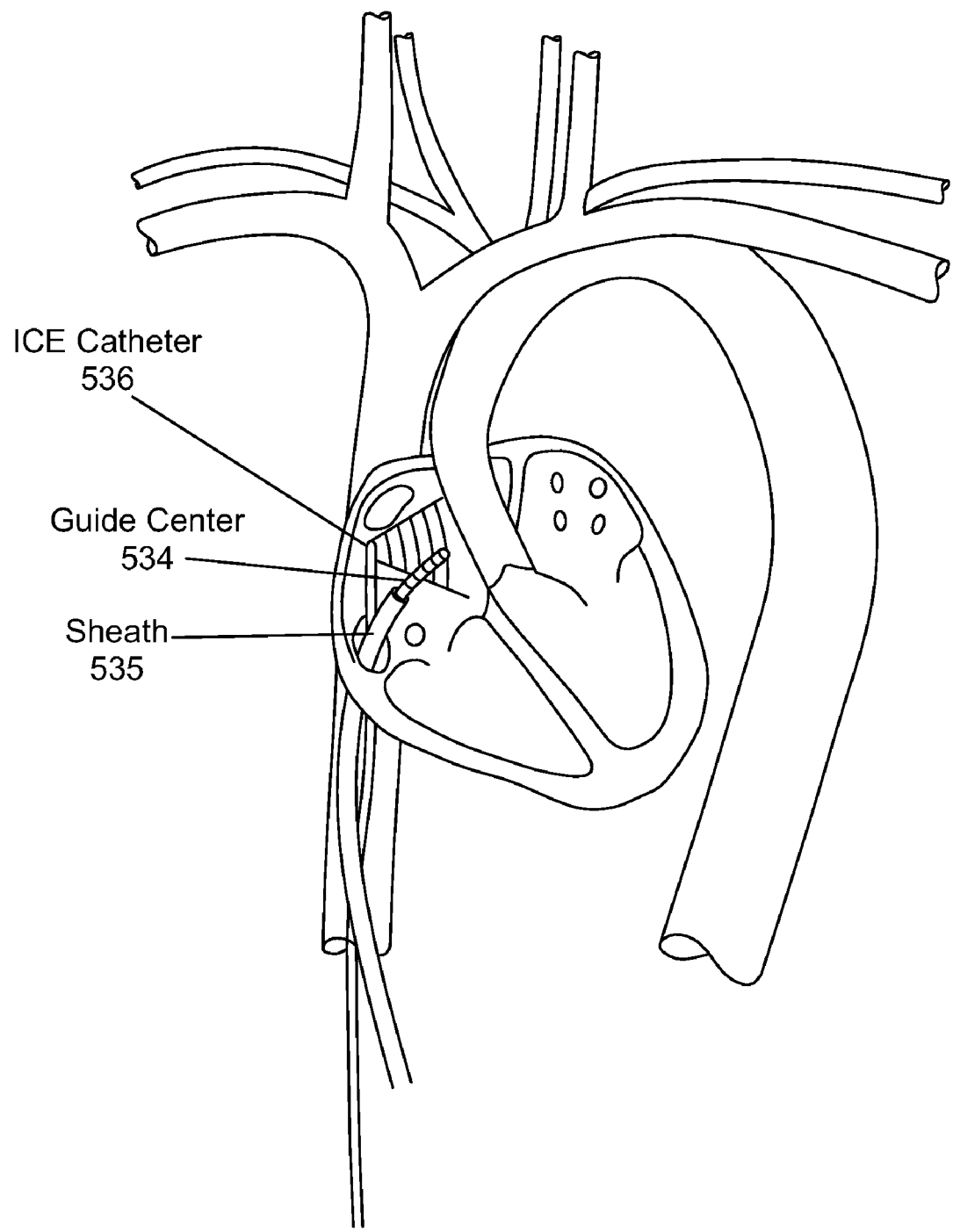
Figure 163:
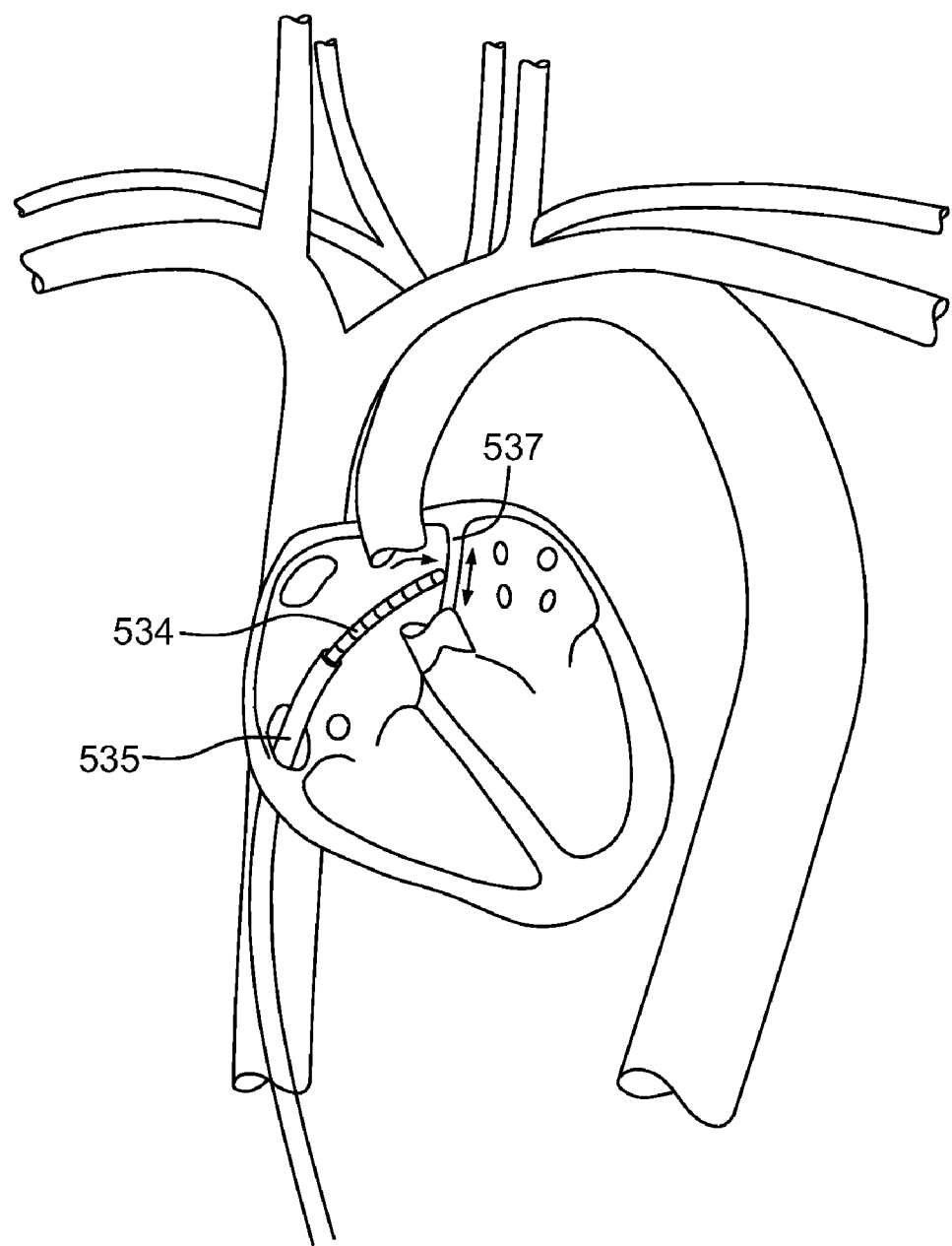
Figure 164:
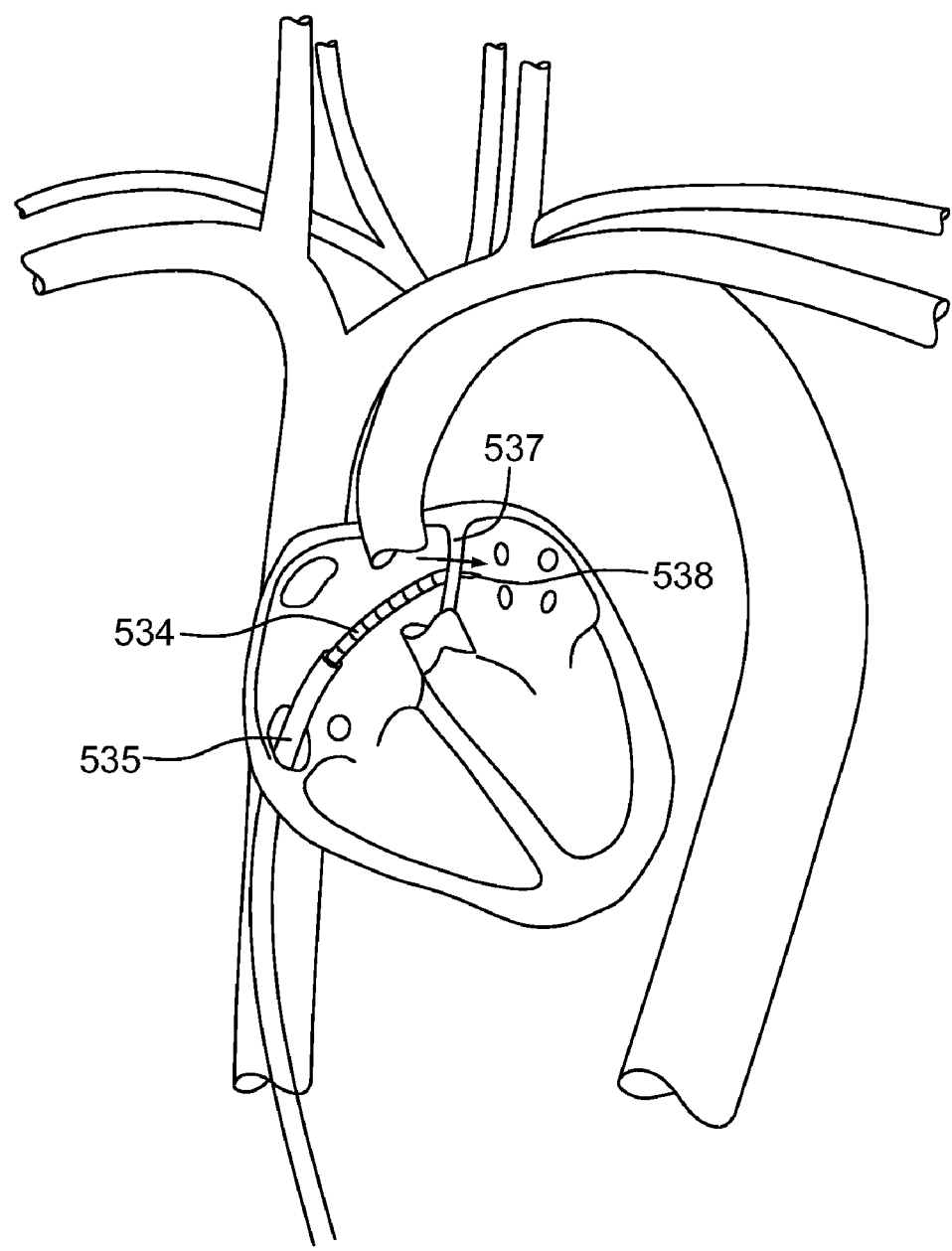
Figure 165:
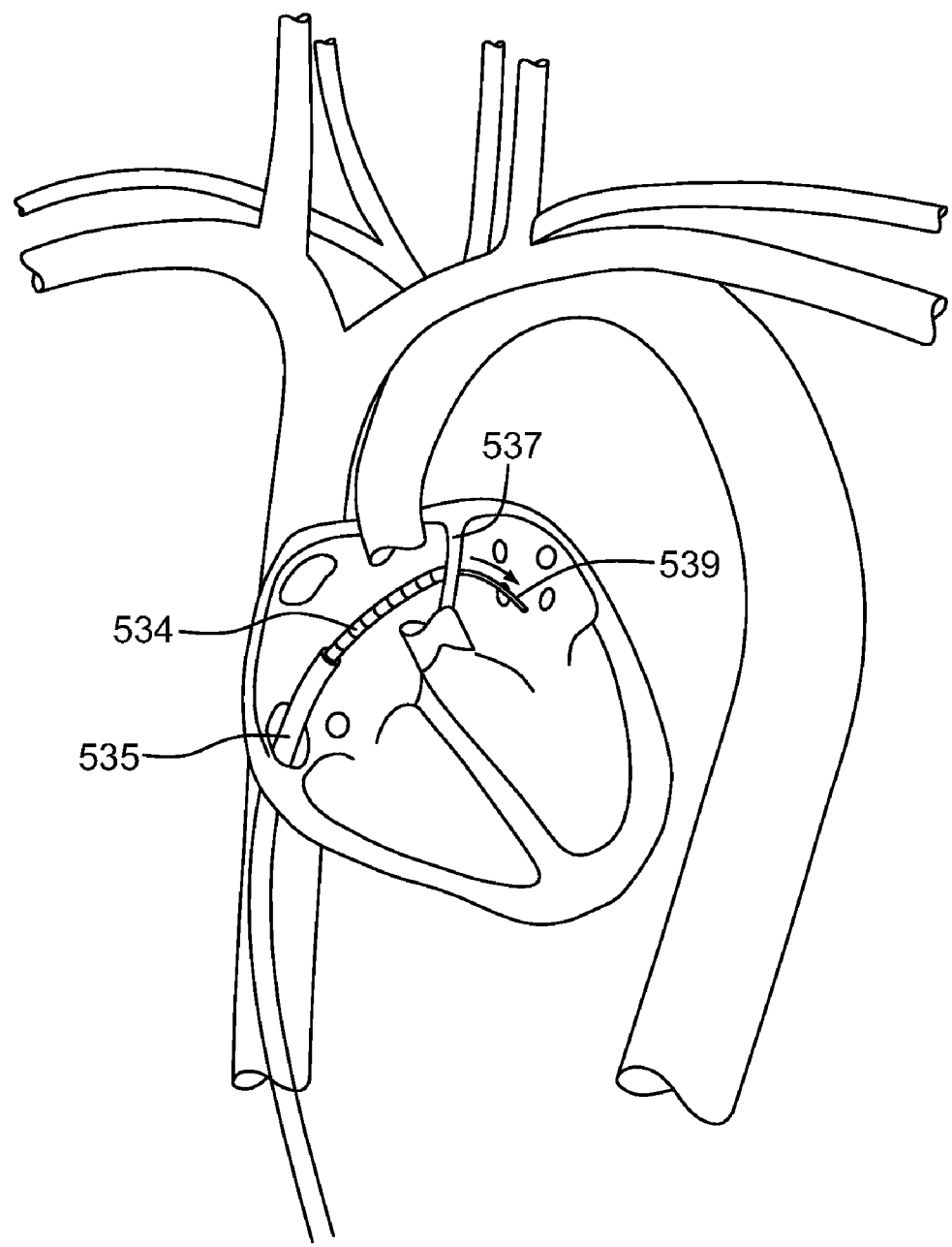
Figure 166:
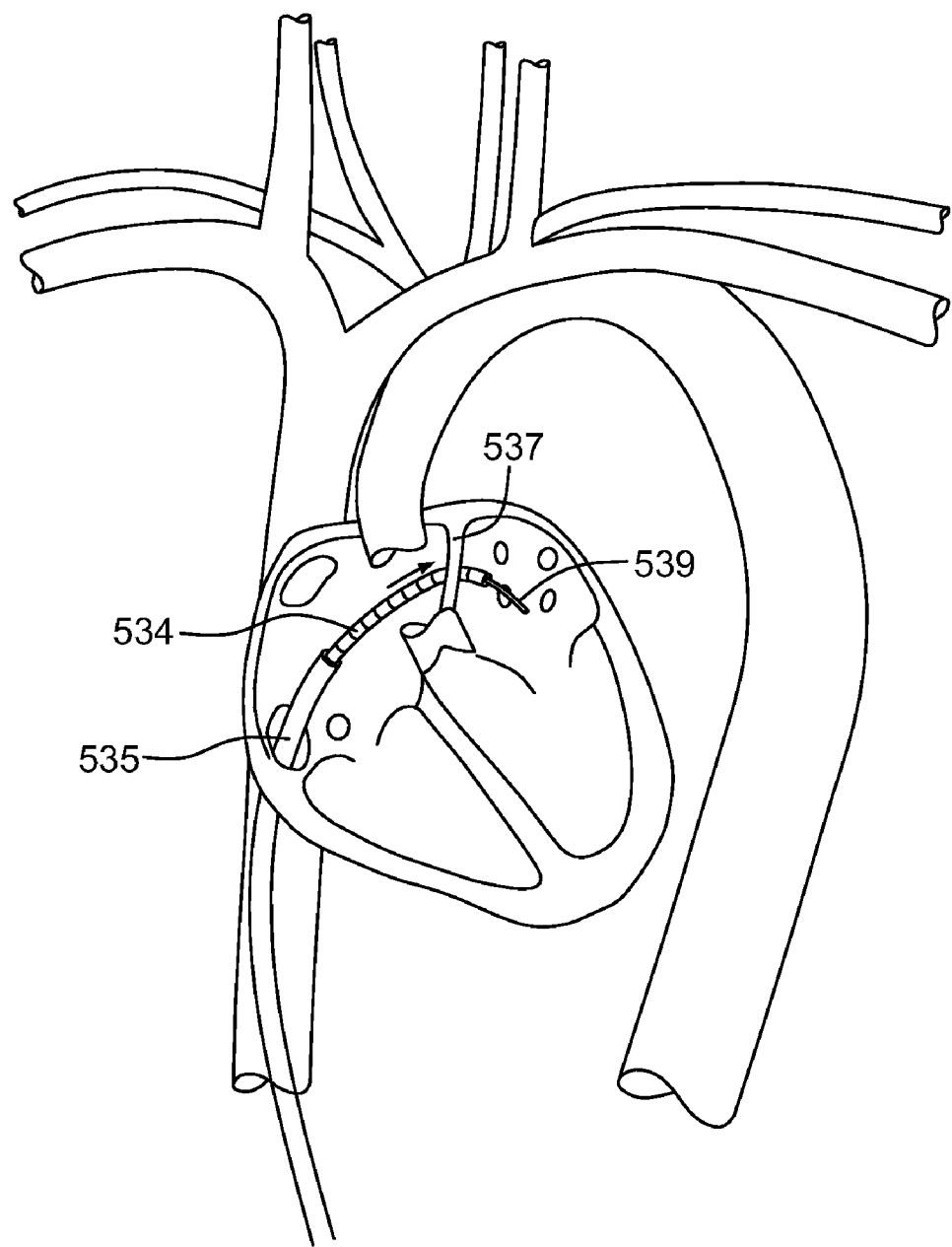

Referring to FIG. 161, a standard atrial approach is depicted with a robotically controlled guide catheter instrument (534) and sheath instrument (535) passing through the inferior vena cava and into the right atrium. Referring to FIG. 162, an imaging device, such as an intracardiac echo ("ICE") sonography catheter (536), is forwarded into the right atrium to provide a field of view upon the interatrial septum. The guide instrument is driven to the septum wall, as shown in FIG. 163. Referring to FIGS. 164 and 165, the septum (537) may be crossed using a conventional technique of first puncturing the fossa ovalis location with a sharpened device (538), such as a needle or wire, passed through the working lumen of the guide instrument (534), then passing a dilator (539) over the sharpened device and withdrawing the sharpened device to leave the dilator (539), over which the guide instrument (534) may be advanced, as shown in FIG. 166. It may be desirable in some embodiments to pass an instrument arrangement through the working lumen of the guide instrument comprising a needle positioned coaxially within a dilator, as is well known in conventional (i.e., non-robotic) septum crossing techniques.

Figure 167:
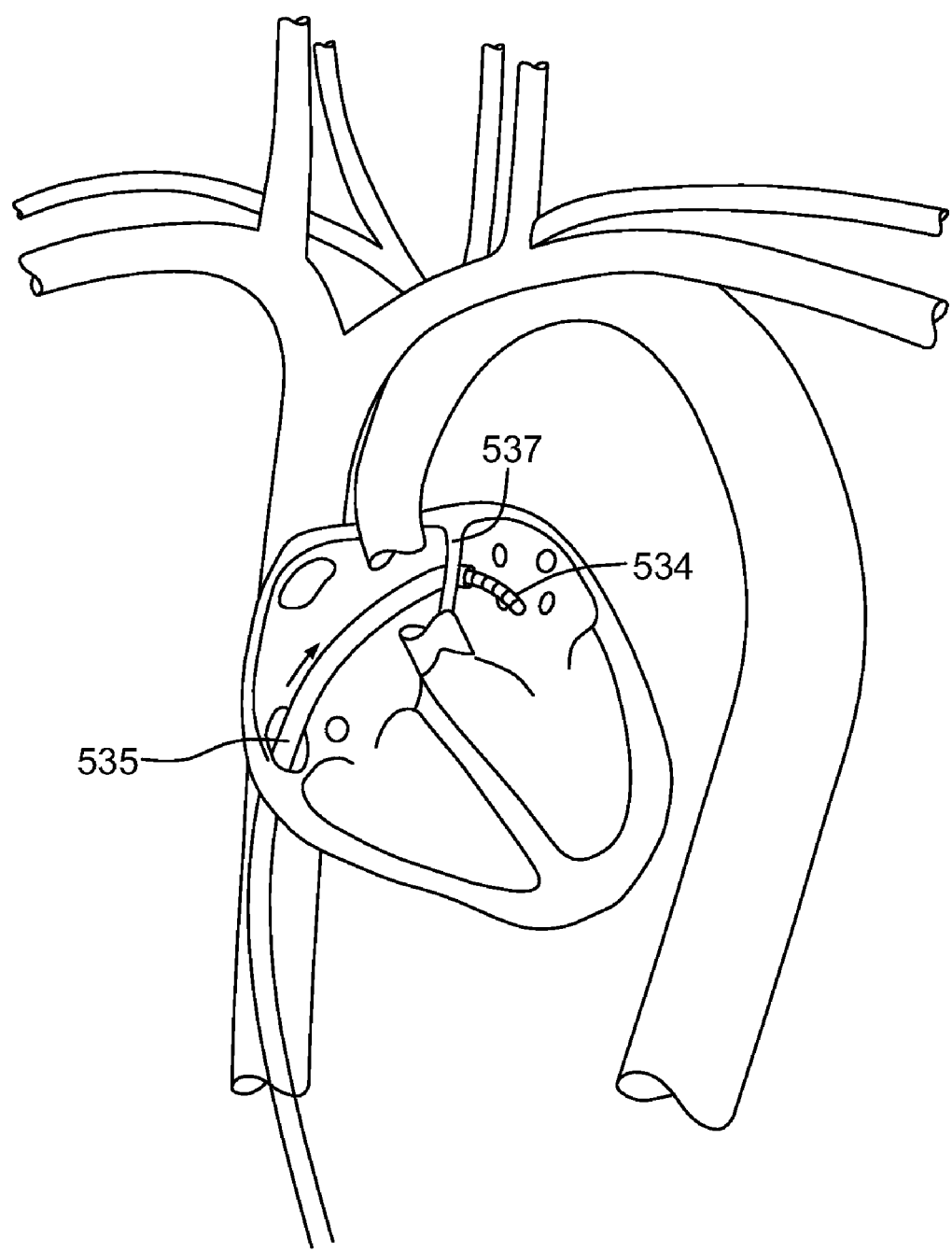
Figure 168:
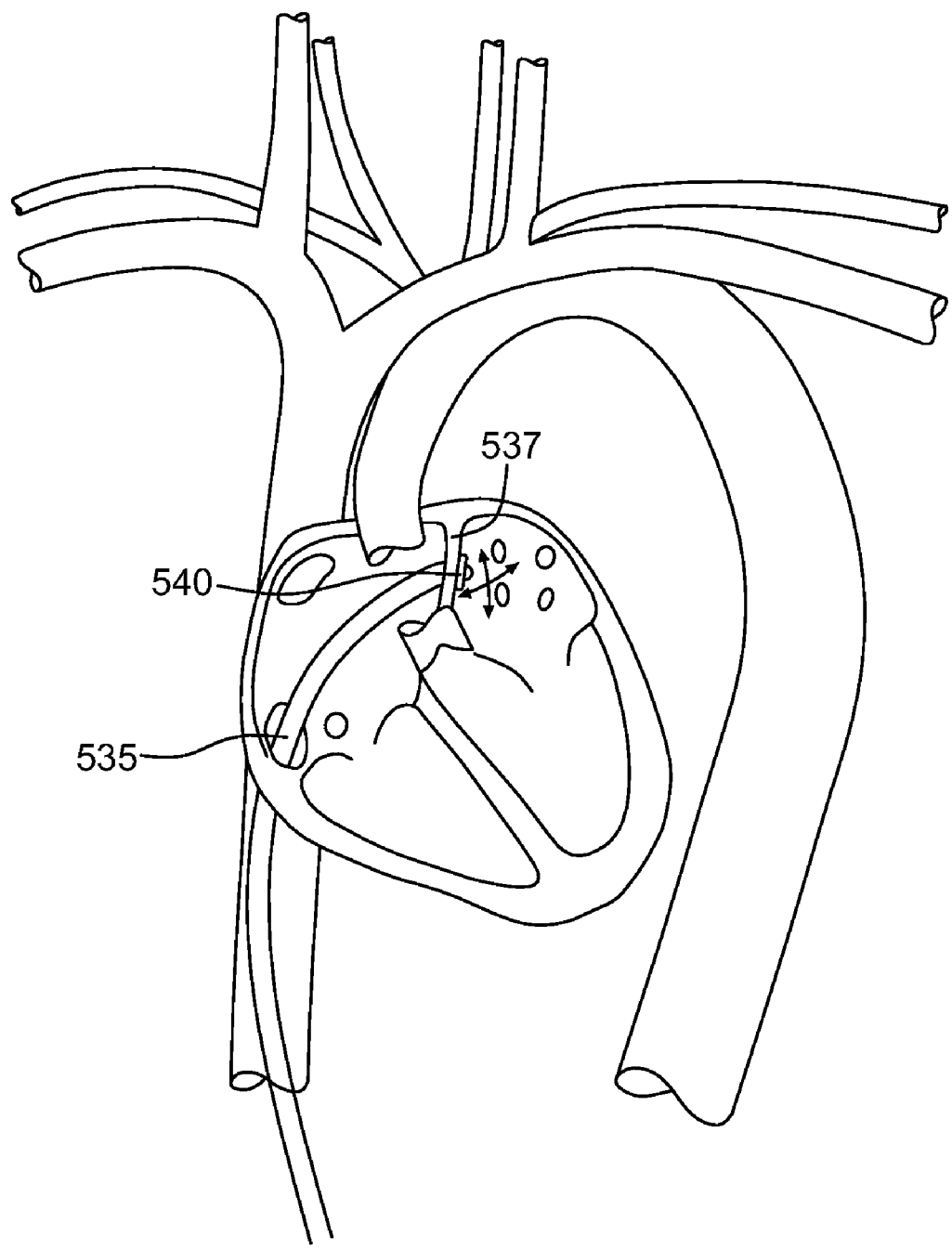
Figure 169:
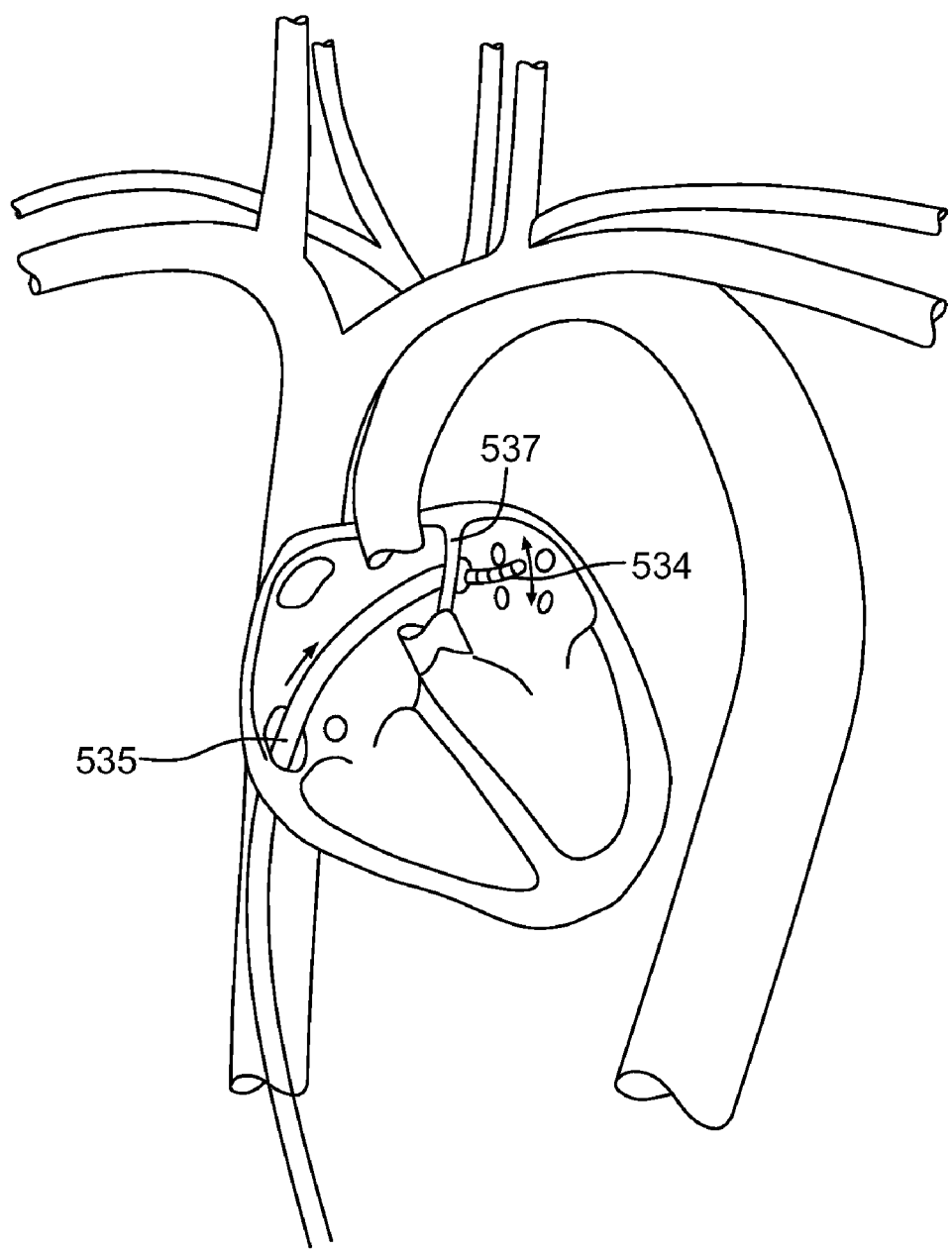

As shown in FIG. 167, subsequent to passing the guide instrument (534) across the septum (537), the guide instrument (534) may be utilized as a dilator to insert the sheath instrument (535) across the septum (537), thereby providing both instruments (534, 535) access and/or a view into the left atrium. It may be desirable to anchor the sheath instrument (535) in place just across the septum (537). For example, as shown in FIG. 168, an expanding structure such as a conventional balloon anchor (540) may be employed. As shown in FIG. 169, the guide instrument (534) may then be used to navigate inside the left atrium.

Figure 170:
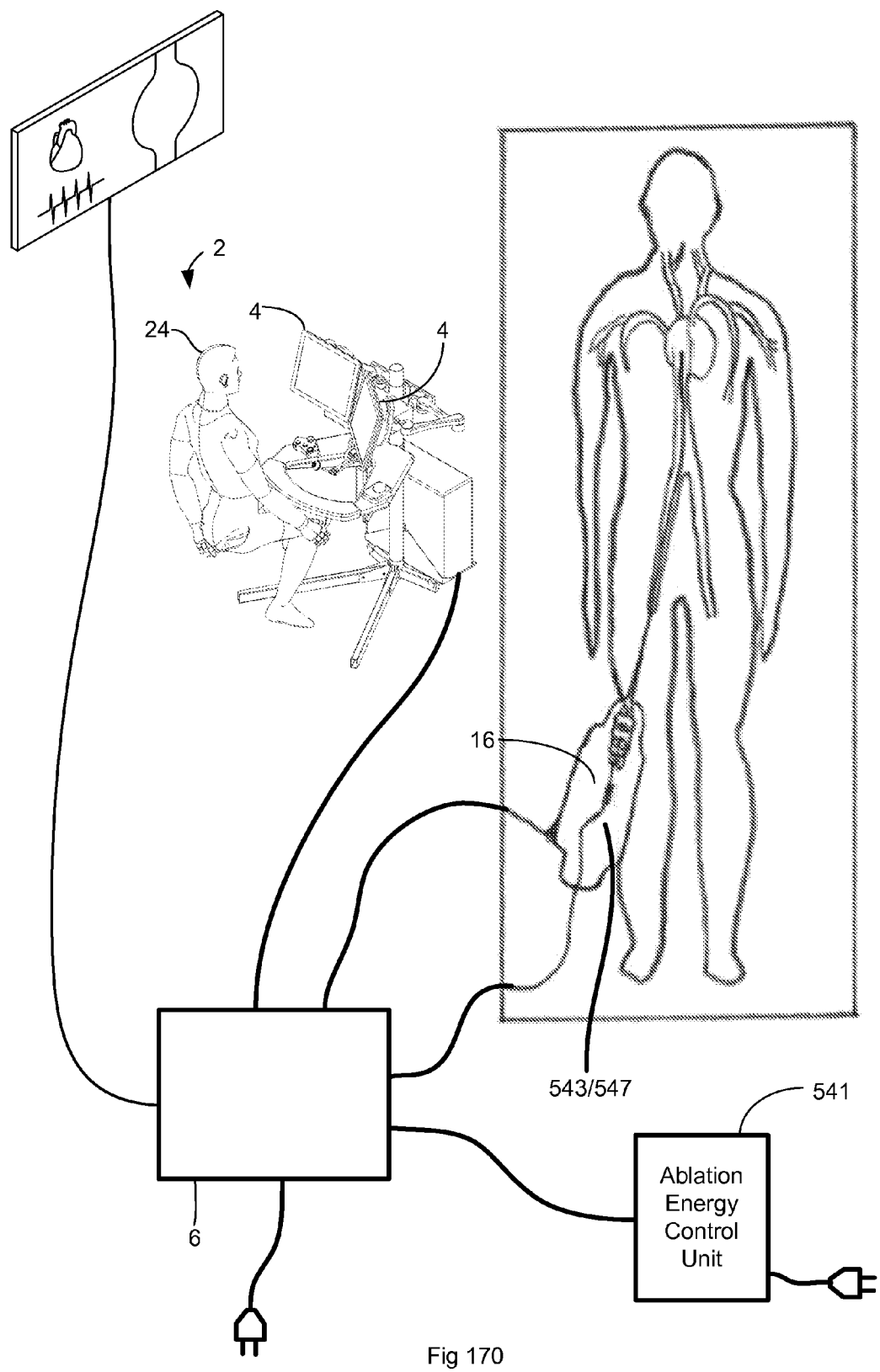

In one embodiment, a radio frequency (RF) ablation system is used with the robotic catheter system to supply energy to perform myocardial tissue ablation procedures in order block undesirable conduction pathways within the wall of the left atrium and adjoining vessels (e.g., pulmonary vein). By way of illustration, FIG. 170 depicts a system level view of such arrangement, including an operator control station (2), a computer (6), an instrument driver (16), a RF ablation energy control unit (541), a guide instrument (543) and a working instrument (547).

Figure 171:
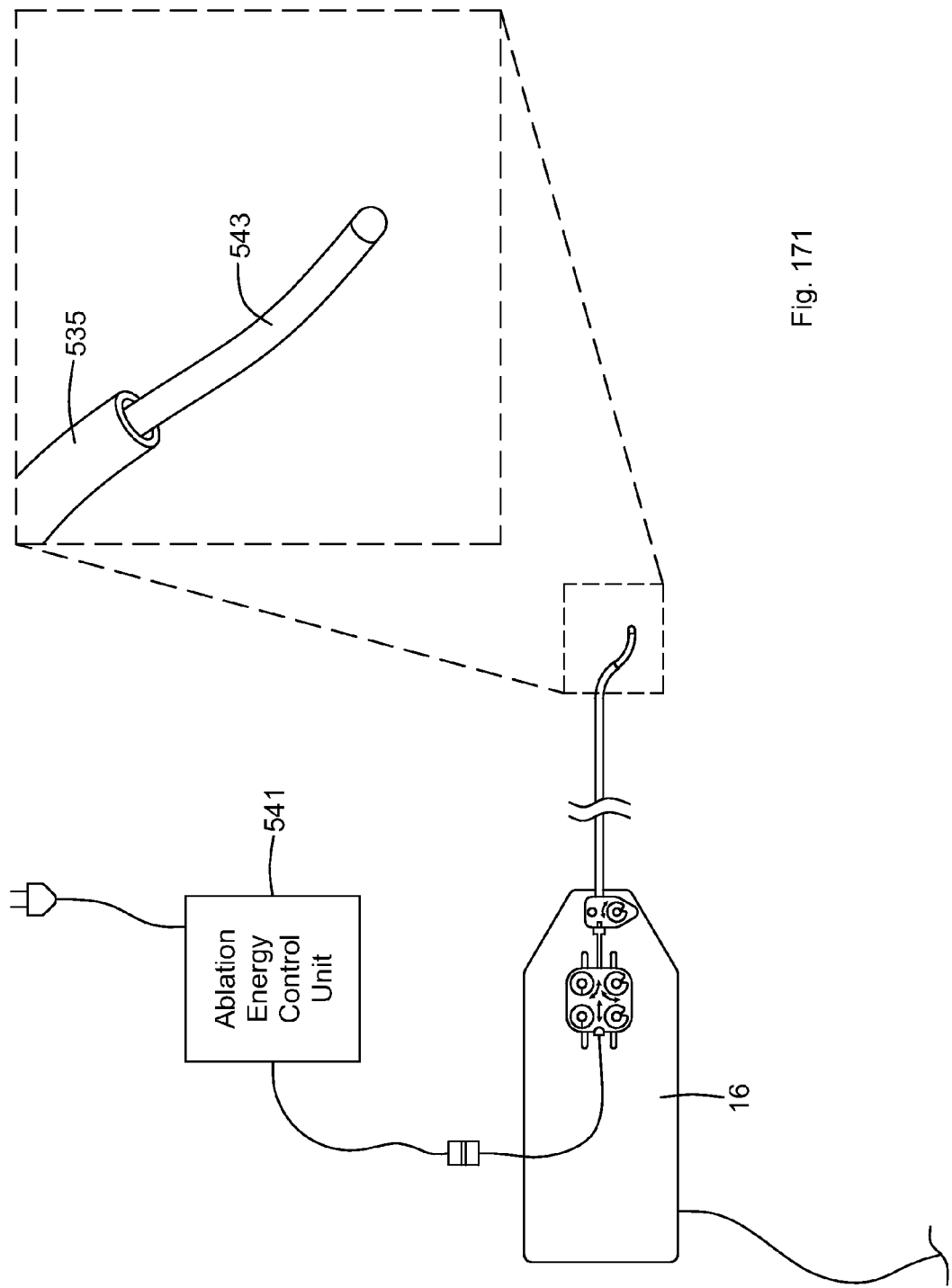

In one embodiment, shown in FIG. 171, a robotically controlled guide instrument (543), which may have an outer diameter of about 7 French, comprises an integrated ablation distal tip, and is passed through a sheath instrument (535). In another embodiment, shown in FIG. 172, a working instrument (547), in this instance an "off the shelf" ablation catheter such as that sold under the trade name Blazer II™ Cardiac Ablation Catheter by Boston Scientific Corporation, which may have an outer diameter of about 7 French, is passed through the working lumen of the guide instrument (534), which itself is passed through a sheath instrument (535). In such embodiments, the RF power may be supplied directly from the RF generator to the ablation catheter handle. Alternatively, the power supply may be coupled to the ablation catheter via a controller integrated with the robotic guide instrument in order to provide addition safety features, e.g., automatic power shut-off under defined circumstances. In such embodiments, only a small portion of the ablation catheter need be protruded beyond the distal tip of the guide instrument to expose the ablation electrodes, and the steering features which may be integrated into the "off the shelf" ablation catheter may not be needed as a result of the precision steerability provided by the robotically-controlled instrumentation through which the ablation catheter is coaxially positioned. Alternatively, a greater portion of the ablation catheter may be protruded beyond the distal tip of the guide instrument, preferably with the guide instrument held in a constant position by the system, and the manual steering functionality of the "off the shelf" ablation catheter may be utilized to place the distal portion of such device in a desired location, utilizing feedback to the operator from fluoroscopy, ultrasound, localization, or other real-time or near real-time systems. It will be appreciated by those skilled in the art that many of types of other ablation catheters or other working instruments may be passed through the working lumen of the guide instrument (534).

The precision provided by a system comprising a robotic guide instrument with an ablation catheter positioned coaxially within the robotic guide instrument facilitates precision mapping and creation of transmural lesions. In the right heart, without transseptal crossing, atrial flutter may be addressed by actively driving the distal tip of the ablation catheter to the lower right atrium. The right atrial isthmus may be contacted and ablated, along with the tricuspid annulus down to the junction of the right atrium and the inferior vena cava. Long linear lesions may be created through inputs to the master input device in various locations, such as the "intercavalline" between the superior vena cava and the inferior vena cava, or the "septal line" from the superior vena cava to the fossa ovalis, and then from the fossa ovalis down to the inferior vena cava. "Lasso" type ablation catheters may be driven using the subject robotic instrument system, to isolate pulmonary veins in the left heart, or conduct a segmental pulmonary vein isolation, wherein a subset of the electrodes positioned about the "Lasso" device are utilized to create ablation lesions. The procedure known as "Left Atrial Catheter Ablation" or "LACA", developed by clinicians such as Pappone and Morady, may be facilitated using the subject system. LACA, which may involve large ablations to isolate the right superior pulmonary vein and right inferior pulmonary vein, along with ablative isolation of the left superior pulmonary vein and left inferior pulmonary vein, a connecting ablation between the aforementioned lesions ("roofline" ablation), and a left atrial isthmus linear ablation from the left inferior pulmonary vein to the mitral valve annulus, may be addressed utilizing the robotic precision of the subject system. Ablation targets such as the right inferior pulmonary vein and the ridge between the left superior pulmonary vein and the left inferior pulmonary vein may be particularly difficult without the precision of the subject system.

There are many well-known diagnostic or therapeutic distal end electrode configurations of working instruments that may used in conjunction with the guide instrument (534), such as those shown by way of non-limiting examples in FIGS. 173A-D. In these examples, electrodes are located at the distal ends of a working instrument (547) that is coaxially passed through a robotically controlled guide instrument (543) and sheath instrument (535). For example, FIG. 173A illustrates one embodiment of a guide instrument with a Y-split end wherein a distal end electrode (600, 602) is located on the face each of the split ends. FIG. 173B illustrates one embodiment of a guide instrument wherein two electrodes (610) are radially located at two locations at the distal tip of the instrument. FIG. 173C illustrates another embodiment of an instrument wherein a single electrode (608) is located over the distal tip itself. The example in FIG. 173D illustrates a working instrument where an electrode (610) is located on a side surface at the distal tip.

Other tip options include non-contact means such as microwave or ultrasound energy as illustrated with an arrow emitted from distal tip element (612) in FIG. 174A, optical laser energy as indicated with multiple arrows emitted from distal tip element (614) in FIG. 174B, a penetrating electrode or chemical/drug injection needle (616) in FIG. 174C, or mechanical grasper (618) in FIG. 174D.

In another embodiment, the instrument may be navigated by "direct visualization" utilizing conventional fiberscope or CCD camera devices, preferably disposed within a distally-positioned viewing balloon containing a substantially clear fluid such as saline when in a blood environment. In yet another embodiment, an infrared visualization technology, such as those available from CardioOptics, Inc. of Wilmington, Mass., may be coupled to the instrument to provide direct visualization through a blood or similar medium without a viewing balloon or similar structure. In another embodiment wherein the instrument is navigated in a non-blood space, a viewing balloon need not be positioned to protect the camera device, and the camera lens or image intake may be positioned at the distal tip of the instrument. Whether the direct visualization device is assisted by a balloon-like visualization structure or not, the device preferably is coupled to the instrument either by insertion through the working lumen of an embodiment of the instrument, or integrated into one of the walls comprising the elongate instrument.

Conventional sensors may be disposed at and/or around the distal tip of the instrument, such as those which comprise strain gages and/or piezoelectric crystals. Also, more than one localization device may be coupled to the instrument along different positions of the instrument to allow for more complex monitoring of the position of the instrument. Such additional information may be utilized to help compensate for body movement or respiratory cycle related movement of tissues relative to a base coordinate system.

In still another embodiment of the tissue structure model acquisition modalities described above, including a contact sensor, the instrument may merely be driven around, in a planned fashion, or even at random, within a cavity to collect and store all points of contact to develop a three-dimensional model of the tissue structures. In a related embodiment, a rough model acquired utilizing a conventional imaging modality such as ultrasound or fluoroscopy may be utilized as a starting point, and then additional points added, particularly at points of interest, such as pulmonary vein and valve locations within the left atrium, utilizing a "tapping around" pattern with contact sensing to gather more points and refine the model.

As described above in reference to FIG. 113, in one embodiment, visualization software provides an operator at an operator control station (2), such as that depicted in FIG. 1, with a digitized "dashboard" or "windshield" display to enhance instinctive drivability of the pertinent instrumentation within the pertinent tissue structures.

It may be useful to present the operator with one or more views of various graphical objects in an overlaid format, to facilitate the user's comprehension of relative positioning of the various structures. For example, it may be useful to overlay a real-time fluoroscopy image with digitally-generated "cartoon" representations of the predicted locations of various structures or images. Indeed, in one embodiment, a real-time or updated-as-acquired fluoroscopy image including a fluoroscopic representation of the location of an instrument may be overlaid with a real-time representation of where the computerized system expects the instrument to be relative to the surrounding anatomy. In a related variation, updated images from other associated modalities, such as intracardiac echocardiography ultrasound (ICE), may also be overlaid onto the display with the fluoro and instrument "cartoon" image, to provide the operator with an information-rich rendering on one display.

Figure 175:
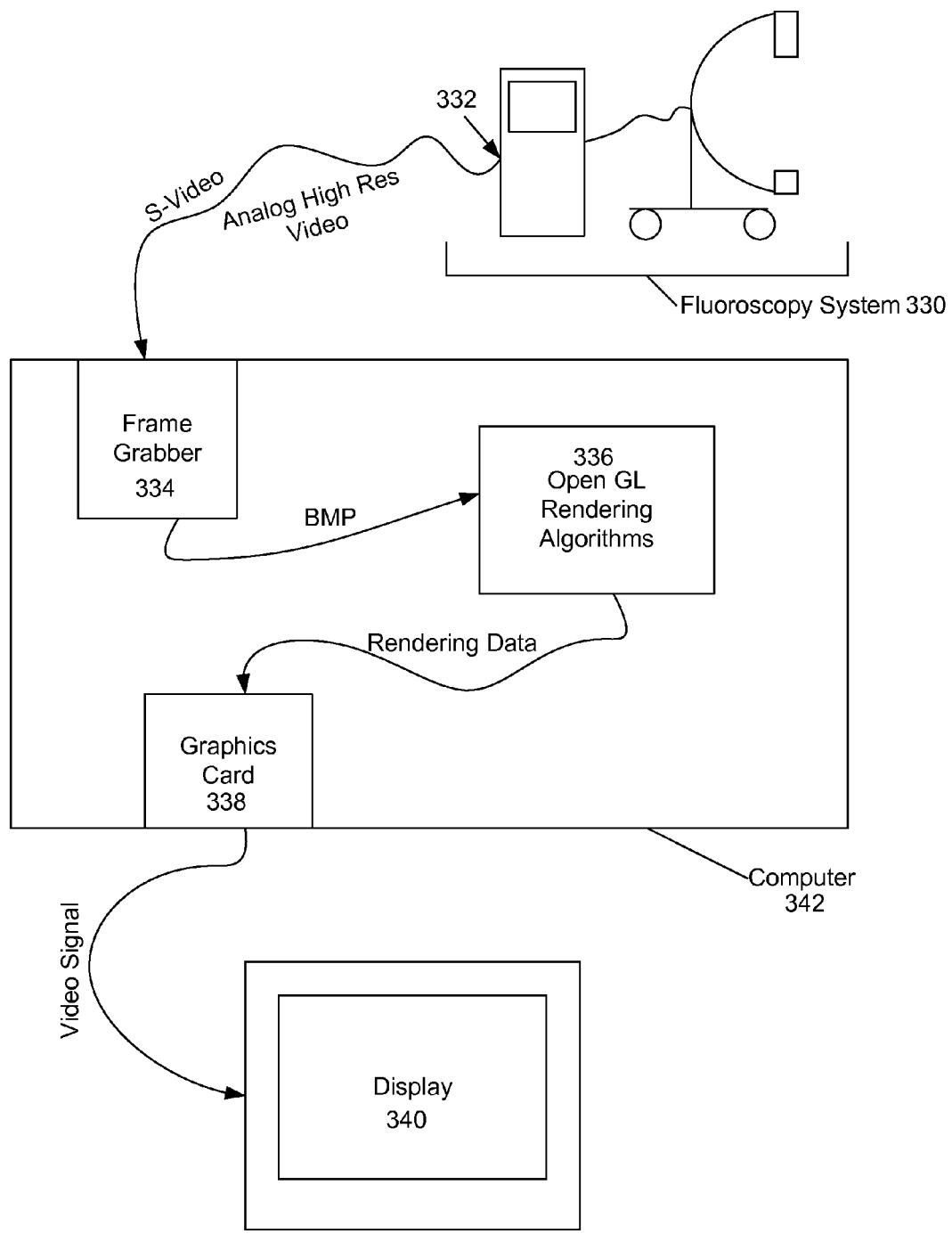
FIG. 175 illustrates a system block diagram.

Referring to FIG. 175, a systemic view configured to produce such an overlaid image is depicted. As shown in FIG. 175, a conventional fluoroscopy system (330) outputs an electronic image in formats such as those known as "S-video" or "analog high-resolution video". In image output interface (332) of a fluoroscopy system (330) may be connected to an input interface of a computer (342) based image acquisition device, such as those known as "frame grabber" (334) image acquisition cards, to facilitate intake of the video signal from the fluoroscopy system (330) into the frame grabber (334), which may be configured to produce bitmap ("BMP") digital image data, generally comprising a series of Cartesian pixel coordinates and associated grayscale or color values which together may be depicted as an image. The bitmap data may then be processed utilizing computer graphics rendering algorithms, such as those available in conventional OpenGL graphics libraries (336). In summary, conventional OpenGL functionality enables a programmer or operator to define object positions, textures, sizes, lights, and cameras to produce three-dimensional renderings on a two-dimensional display. The process of building a scene, describing objects, lights, and camera position, and using OpenGL functionality to turn such a configuration into a two-dimensional image for display is known in computer graphics as rendering. The description of objects may be handled by forming a mesh of triangles, which conventional graphics cards are configured to interpret and output displayable two-dimensional images for a conventional display or computer monitor, as would be apparent to one skilled in the art. Thus the OpenGL software (336) may be configured to send rendering data to the graphics card (338) in the system depicted in FIG. 175, which may then be output to a conventional display (340).

In one embodiment, a triangular mesh generated with OpenGL software to form a cartoon-like rendering of an elongate instrument moving in space according to movements from, for example, a master following mode operational state, may be directed to a computer graphics card, along with frame grabber and OpenGL processed fluoroscopic video data. Thus a moving cartoon-like image of an elongate instrument would be displayable. To project updated fluoroscopic image data onto a flat-appearing surface in the same display, a plane object, conventionally rendered by defining two triangles, may be created, and the updated fluoroscopic image data may be texture mapped onto the plane. Thus the cartoon-like image of the elongate instrument may be overlaid with the plane object upon which the updated fluoroscopic image data is texture mapped. Camera and light source positioning may be pre-selected, or selectable by the operator through the mouse or other input device, for example, to enable the operator to select desired image perspectives for his two-dimensional computer display. The perspectives, which may be defined as origin position and vector position of the camera, may be selected to match with standard views coming from a fluoroscopy system, such as anterior/posterior and lateral views of a patient lying on an operating table. When the elongate instrument is visible in the fluoroscopy images, the fluoroscopy plane object and cartoon instrument object may be registered with each other by ensuring that the instrument depicted in the fluoroscopy plane lines up with the cartoon version of the instrument. In one embodiment, several perspectives are viewed while the cartoon object is moved using an input device such as a mouse, until the cartoon instrument object is registered with the fluoroscopic plane image of the instrument. Because both the position of the cartoon object and fluoroscopic image object may be updated in real time, an operator, or the system automatically through image processing of the overlaid image, may interpret significant depicted mismatch between the position of the instrument cartoon and the instrument fluoroscopic image as contact with a structure that is inhibiting the normal predicted motion of the instrument, error or malfunction in the instrument, or error or malfunction in the predictive controls software underlying the depicted position of the instrument cartoon.

Referring back to FIG. 175, other video signals (not shown) may be directed to the image grabber (334), besides that of a fluoroscopy system (330), simultaneously. For example, images from an intracardiac echo ultrasound ("ICE") system, intravascular ultrasound ("IVUS"), or other system may be overlaid onto the same displayed image simultaneously. Further, additional objects besides a plane for texture mapping fluoroscopy or a elongate instrument cartoon object may be processed using OpenGL or other rendering software to add additional objects to the final display.

Figure 176A:
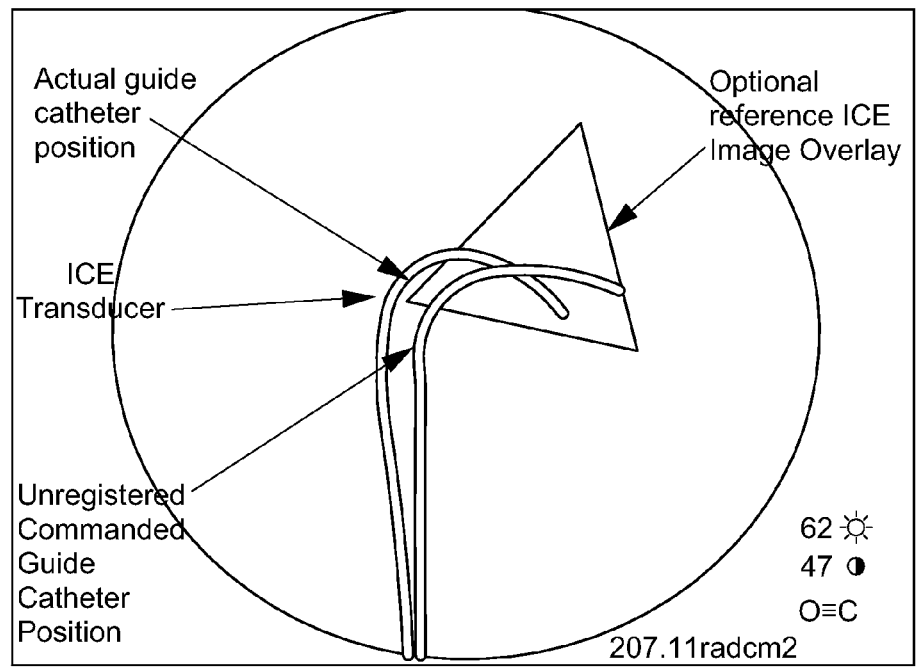
FIGS. 176A-B illustrate one embodiment for visualization of tissue by overlaying images.
Figure 176B:
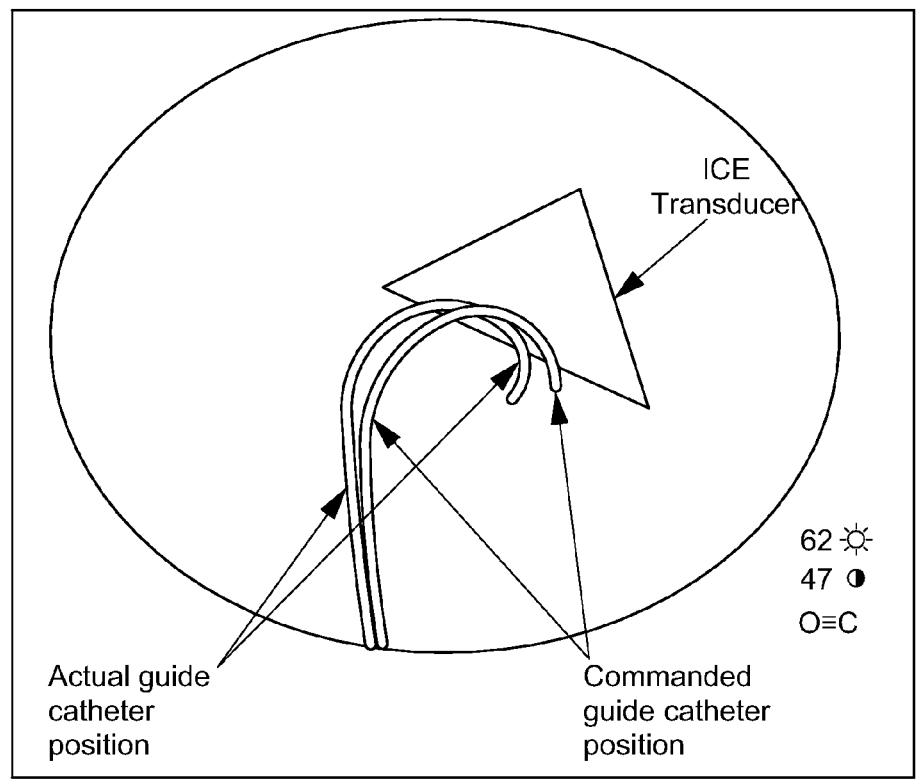
Figure 177:
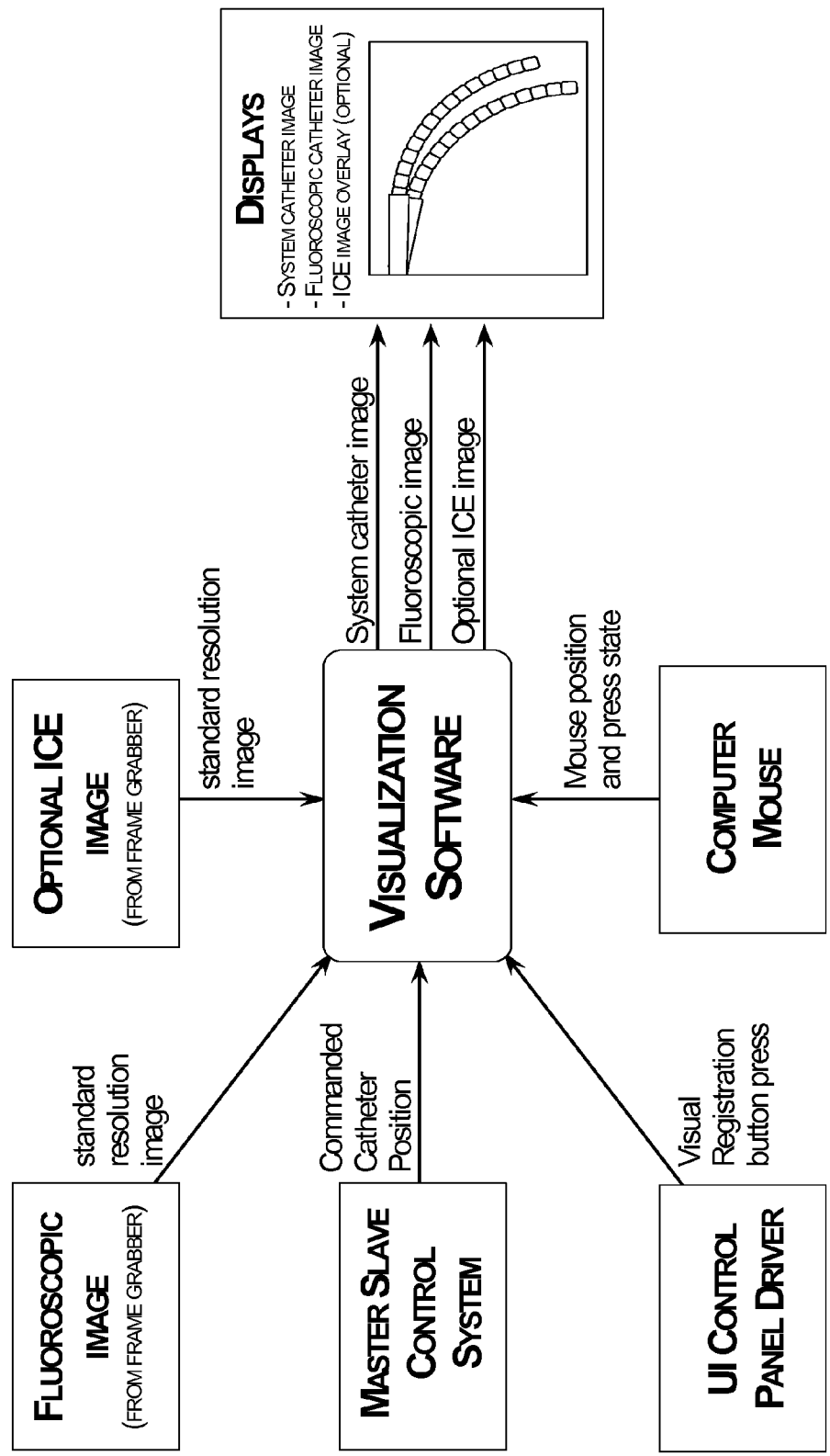
FIG. 177 illustrates a schematic for overlaying objects to the display of one embodiment.

Referring to FIGS. 176 A-B and FIG. 177, one embodiment is illustrated wherein the elongate instrument is a robotic guide catheter, and fluoroscopy and ICE are utilized to visualize the cardiac and other surrounding tissues, and instrument objects. Referring to FIG. 176A, a fluoroscopy image has been texture mapped upon a plane configured to occupy nearly the entire display area in the background. Visible in the fluoroscopy image as a dark elongate shadow is the actual position, from fluoroscopy, of the guide catheter instrument relative to the surrounding tissues. Overlaid in front of the fluoroscopy plane is a cartoon rendering (white in color in FIGS. 176A-B) of the predicted, or "commanded", guide catheter instrument position. Further overlaid in front of the fluoroscopy plane is a small cartoon object representing the position of the ICE transducer, as well as another plane object adjacent the ICE transducer cartoon object onto which the ICE image data is texture mapped by a technique similar to that with which the fluoroscopic images are texture mapped upon the background plane object. Further, mouse objects, software menu objects, and many other objects may be overlaid. FIG. 176B shows a similar view with the instrument in a different position. For illustrative purposes, FIGS. 176A-B depict misalignment of the instrument position from the fluoroscopy object, as compared with the instrument position from the cartoon object. As described above, the various objects may be registered to each other by manually aligning cartoon objects with captured image objects in multiple views until the various objects are aligned as desired. Image processing of markers and shapes of various objects may be utilized to automate portions of such a registration process.

Referring to FIG. 177, a schematic is depicted to illustrate how various objects, originating from actual medical images processed by frame grabber, originating from commanded instrument position control outputs, or originating from computer operating system visual objects, such as mouse, menu, or control panel objects, may be overlaid into the same display.

In another embodiment, a preacquired image of pertinent tissue, such as a three-dimensional image of a heart, may be overlaid and registered to updated images from real-time medical imaging modalities as well. For example, in one embodiment, a beating heart may be preoperatively imaged using gated computed tomography (CT). The result of CT imaging may be a stack of CT data slices. Utilizing either manual or automated thresholding techniques, along with interpolation, smoothing, and/or other conventional image processing techniques available in software packages such as that sold under the tradename Amira™ product available from Mercury Computer Systems of Chelmsford, Mass., a triangular mesh may be constructed to represent a three-dimensional cartoon-like object of the heart, saved, for example, as an object (".obj") file, and added to the rendering as a heart object. The heart object may then be registered as discussed above to other depicted images, such as fluoroscopy images, utilizing known tissue landmarks in multiple views, and contrast agent techniques to particularly see show certain tissue landmarks, such as the outline of an aorta, ventricle, or left atrium. The cartoon heart object may be moved around, by mouse, for example, until it is appropriately registered in various views, such as anterior/posterior and lateral, with the other overlaid objects.

Figure 178:
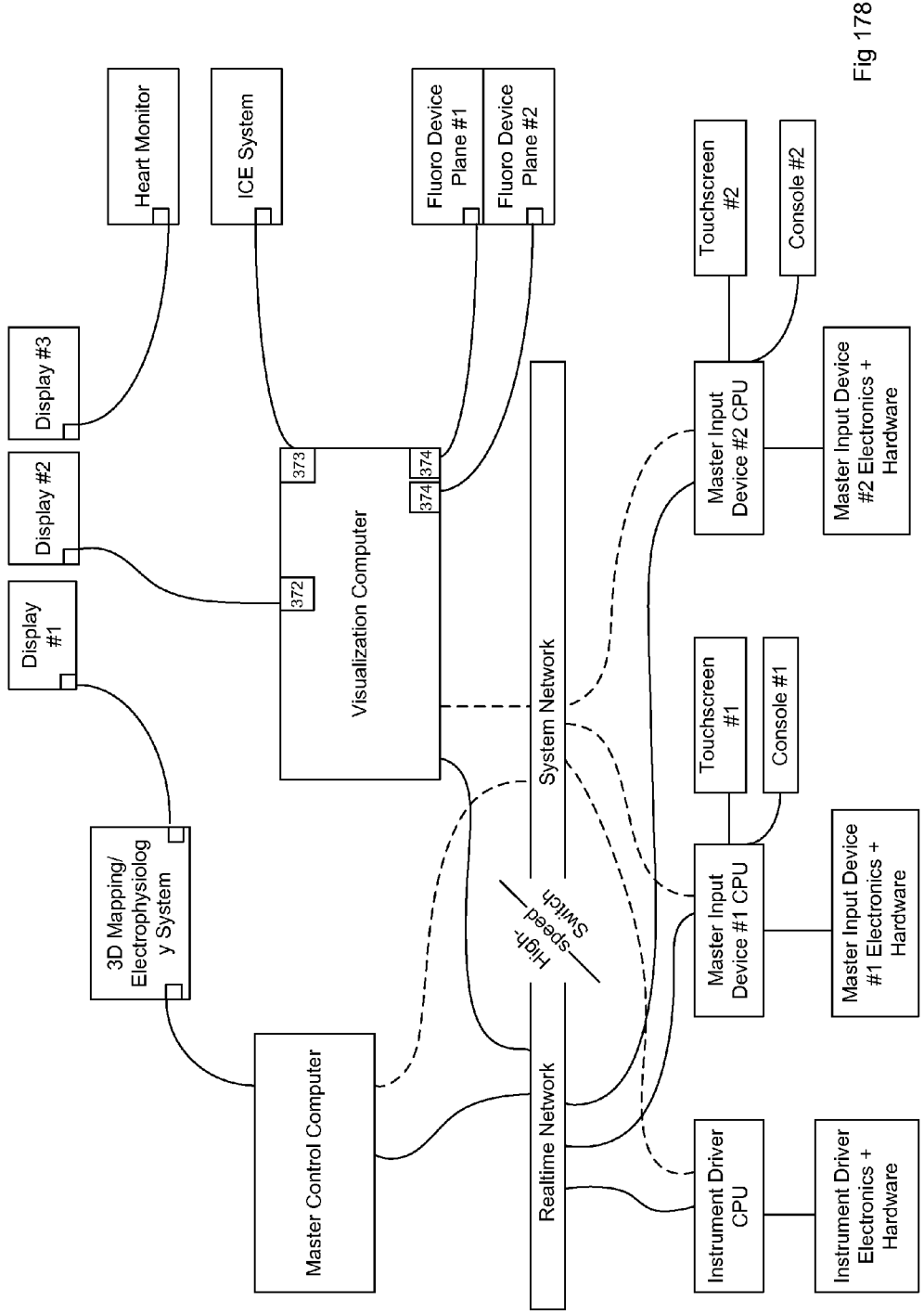
FIG. 178 illustrates one embodiment of a distributed system architecture.
Figure 179:
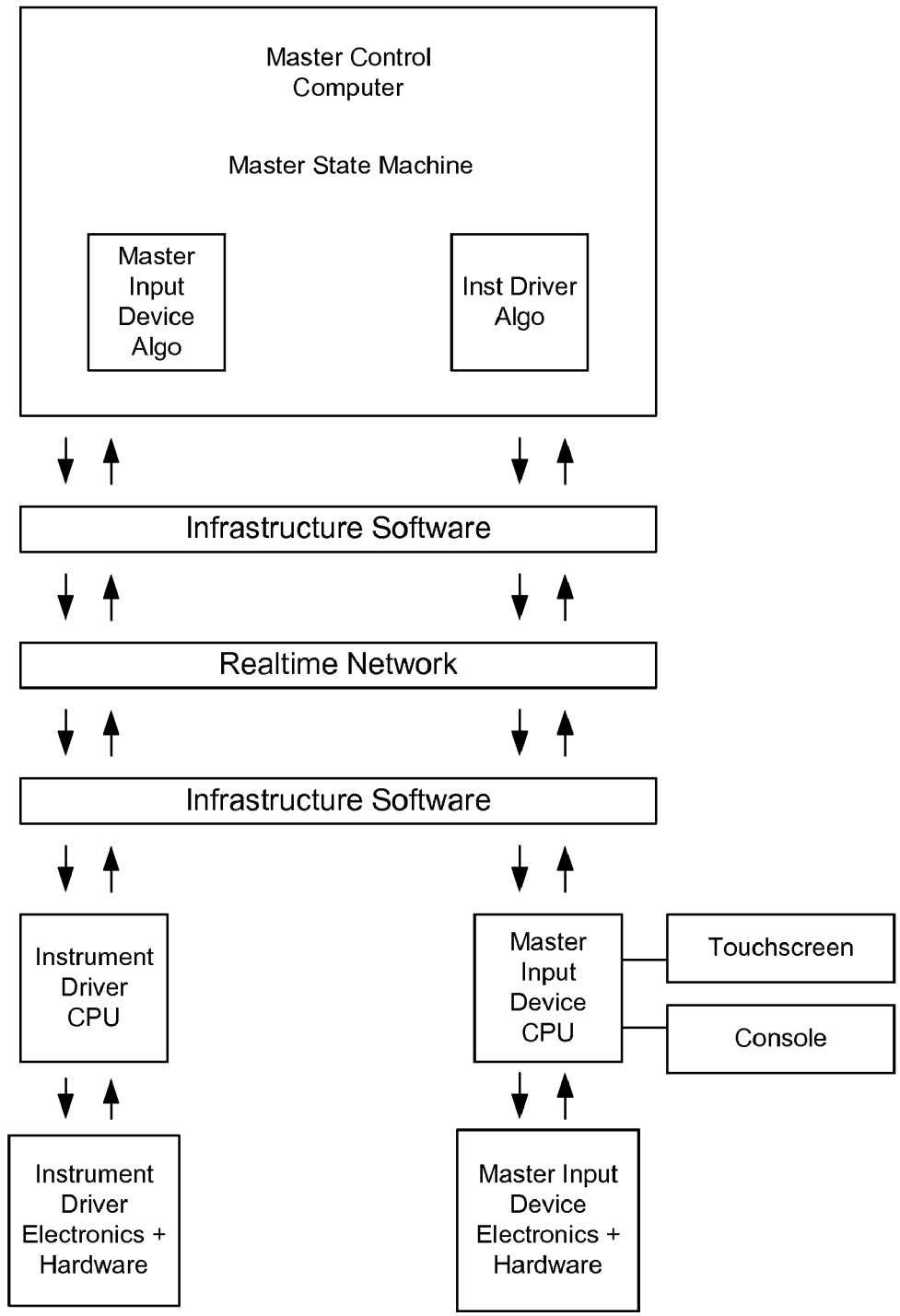
FIG. 179 illustrates the hardware and software interface of one embodiment.
Figure 180:
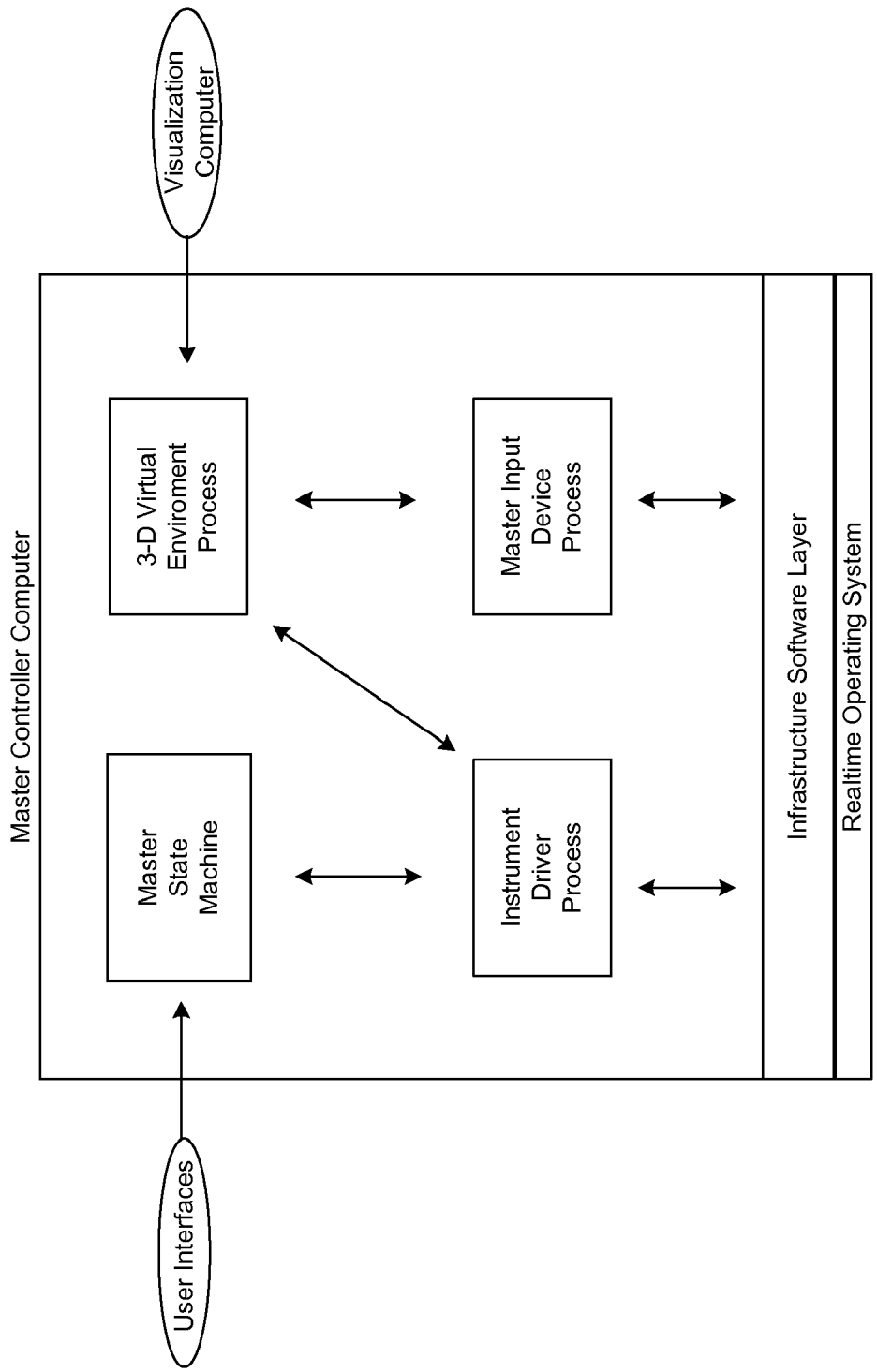
FIG. 180 illustrates the software interaction of one embodiment.

Referring to FIG. 178, a distributed system architecture embodiment is depicted. A master control computer running a real-time operating system, such as QNX, is connected to each of the other computers in the system by a 1 gigabit Ethernet "Real-time Network", and also by a 100 megabit Ethernet "System Network", using a conventional high-speed switch. This enables localized custom computing for various devices to be pushed locally near the device, without the need for large cabling or a central computing machine. In one embodiment, the master control computer may be powered by an Intel® Xeon® processor available from Intel Corporation of Santa Clara, Calif., the visualization computer powered by a personal computer (PC) with a high-end microprocessor based on the Intel architecture running Windows XP and having multiple video cards and frame grabbers, the instrument driver and master input device CPUs being PC 104 or "EPIC" standard boards with two Ethernet connections for the two networks. An additional master input device, touchscreen, and console may be configured into an addition operator workstation in a different location relative to the patient. The system is very expandable—new devices may be plugged into the switch and placed onto either of the two networks. Referring to FIG. 178, two high resolution frame grabber boards (374) acquire images from two fluoro devices (or one in the case of single plane fluoro), which a nominal resolution frame grabber board (373) acquires images from an intracardiac echo system. Such image data may be utilized for overlaying, etc, as described in reference to FIGS. 175-177, and displayed on a display, such as the #2 display, using a video card (372) of the visualization computer, as depicted. Heart monitor data, from a system such as the Prucka CardioLab EP System distributed by GE Healthcare of Waukesha, Wis., may be directly channeled from video out ports on the heart monitor device to one of the displays. Such data may also be acquired by a frame grabber. Similarly, electrophysiological mapping and treatment data and images from systems available from distributors such as Endocardial Solutions, Biosense Webster, Inc., etc., may be directed as video to a monitor, or data to a data acquisition board, data bus, or frame grabber. Preferably the master control computer has some interface connectivity with the electrophysiology system as well to enable single master input device driving of such device, etc. Referring to FIG. 179, a depiction of the software and hardware interaction is depicted. Essentially, the master state machine functionality of the master control system realtime operating system allows for very low latency control of processes used to operate master input device algorithms and instrument driver algorithms, such as those described in reference to the control systems description above. Indeed, XPC may be utilized to develop algorithm code, but preferably a universal modeling language such as IBM Rational Rose from IBM Corporation of Armonk, N.Y., or Rhapsody of 1-Logix of Andover, Mass., is utilized to build code and documentation using a graphical interface. With the gigabit real-time network, in a matter of 200-300 microseconds, the master input device or instrument driver algorithms are able to communicate with FPGA driver code in the electronics and hardware near the pertinent device to exchange new values, etc, and confirm that all is well from a safety perspective. This leaves approximately 700 microseconds for processing if a 1 millisecond motor shutoff time is required if all is not well—and this is easily achievable with the described architecture. The visualization PC may be configured to cycle data from the master control computer at a lower frequency, about 20 milliseconds. FIG. 180 illustrates the software interaction of one embodiment.

Figure 181:
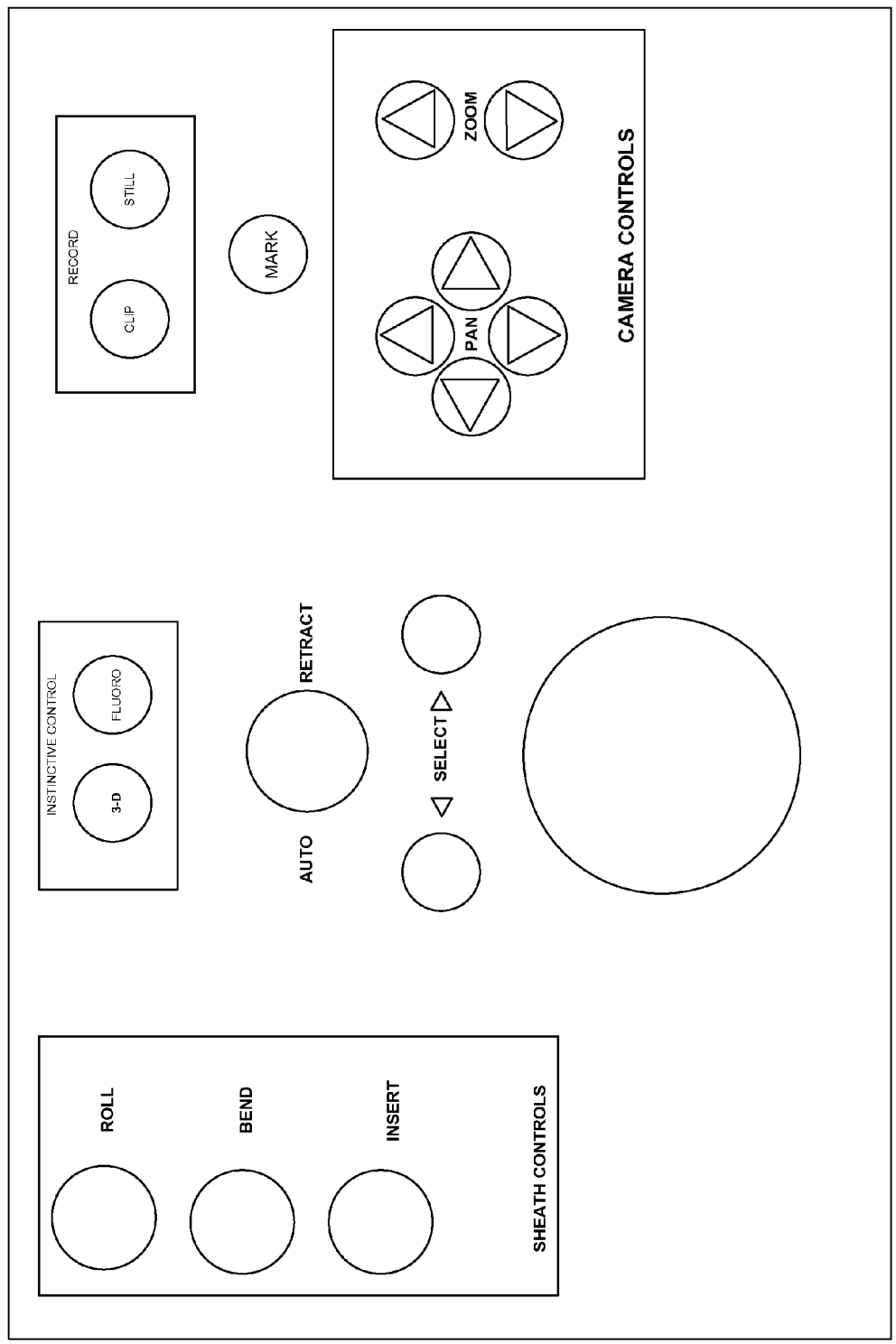
FIG. 181 illustrates one embodiment of a control console.
Figure 182:
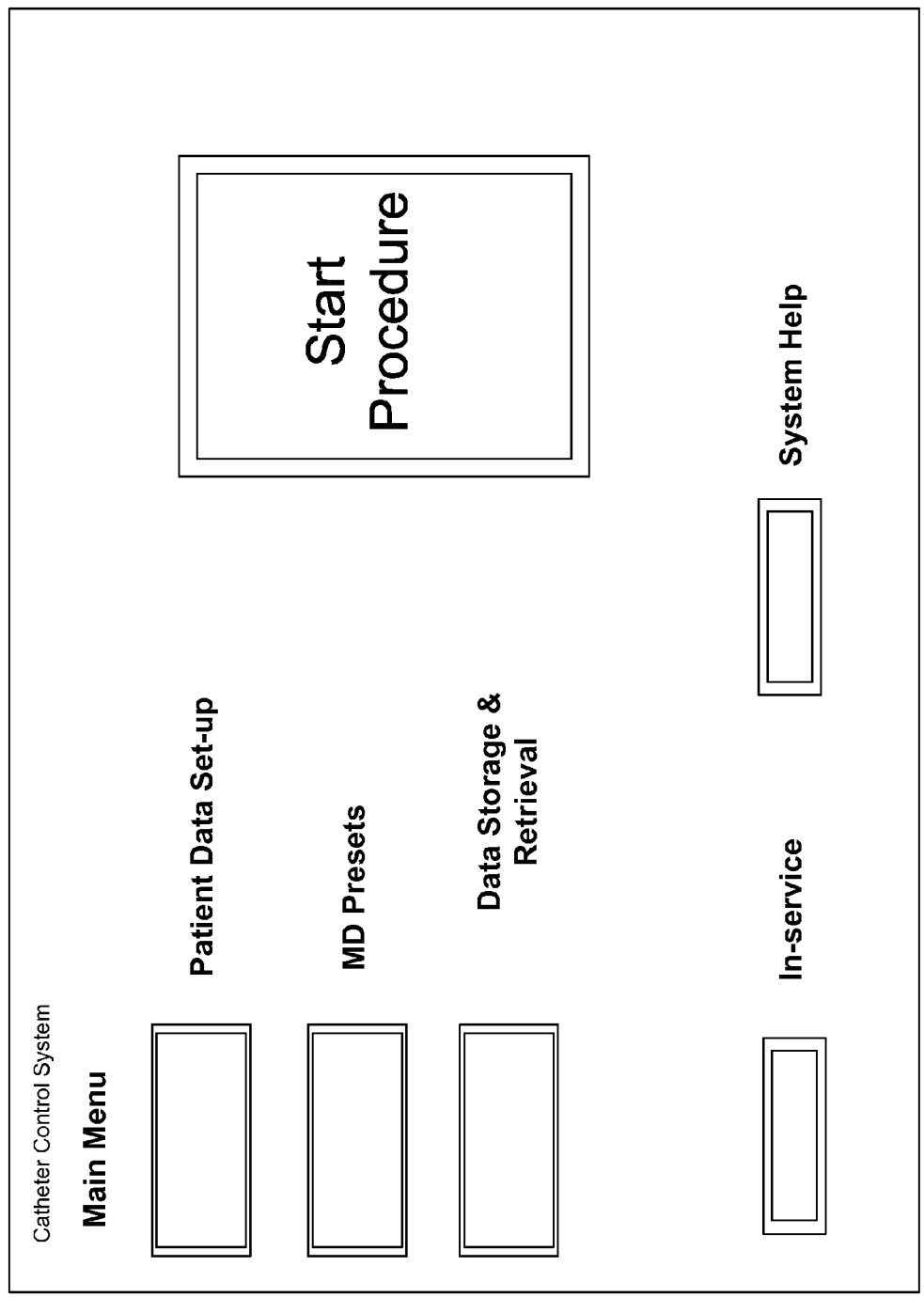
FIGS. 182-186D illustrate various touchscreens for the user interface of one embodiment.

Referring to FIG. 181, common features may be accessed by a console. Sheath control buttons for roll, bend, and insert, when depressed one at a time, cause the master input device to control roll of the sheath (in one embodiment, this meaning roll of the entire instrument driver) in one direction or another as directed by the master input device, +/− bending in one direction, and insertion of the sheath relative to the guide instrument. Instinctive control buttons determine whether the main display is to synchronize master input device movement with 3-D images, such as CT images, or fluoro images. An auto retract button pulls in the guide instrument to a zero insertion point along the trajectory that it was bent. A trackball and mouse select buttons may be used for some features not accessed by a touch screen interface. Record features record a digital clip of video on a selected monitor for a preset period of time, or acquire an image of the video on a selected monitor. Camera controls enable the operator to pan or zoom an image featured on a display.

Referring to FIGS. 182-186, a touchscreen interface provides a palate for virtually unlimited control configuration in one embodiment of the present invention. Various embodiments of patient data setup, operator preset, data storage and retrieval, and operational procedure aspects may be coded into the touch screen interface for easy access during an operation.

Figure 183B:
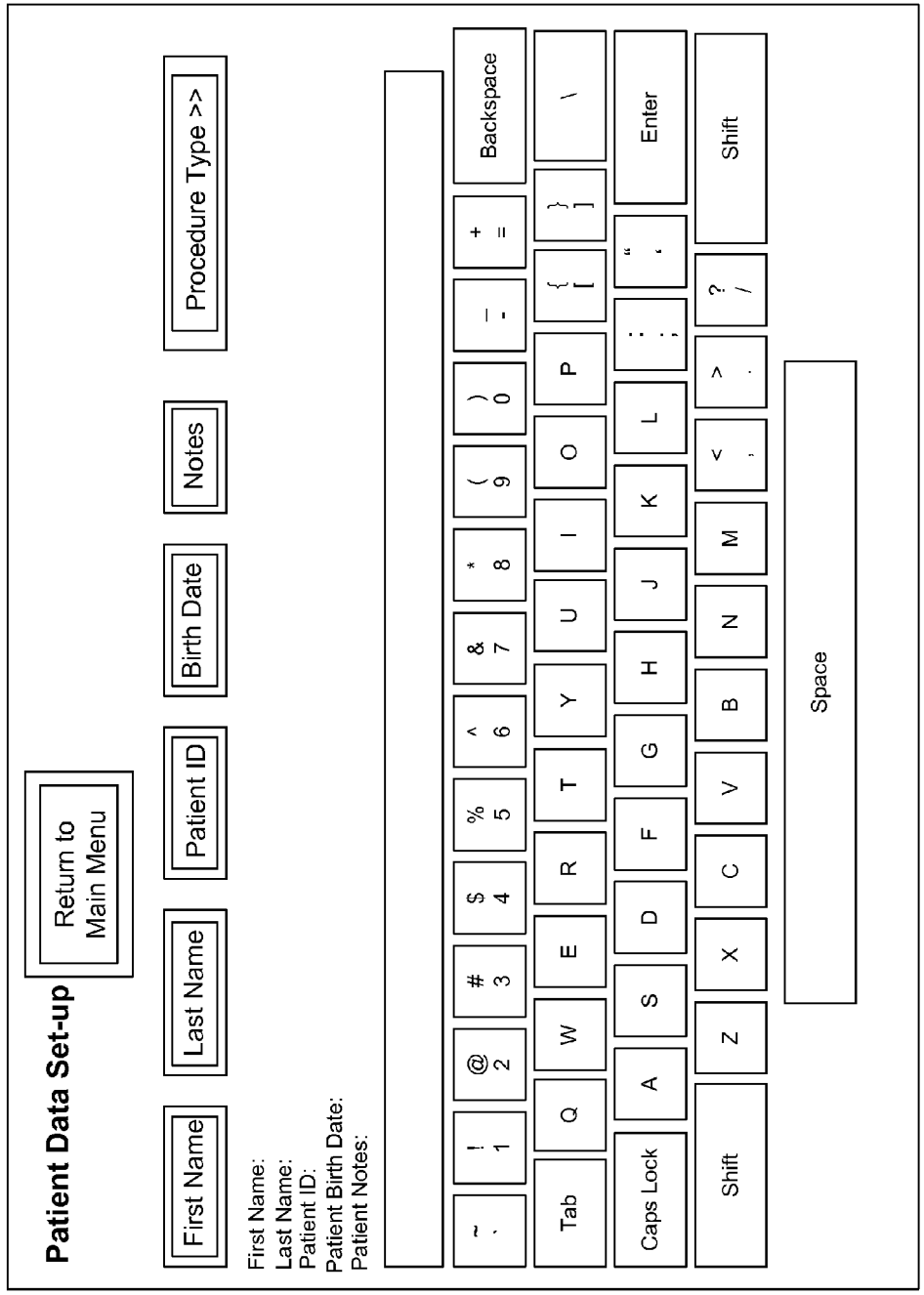
Figure 184A:
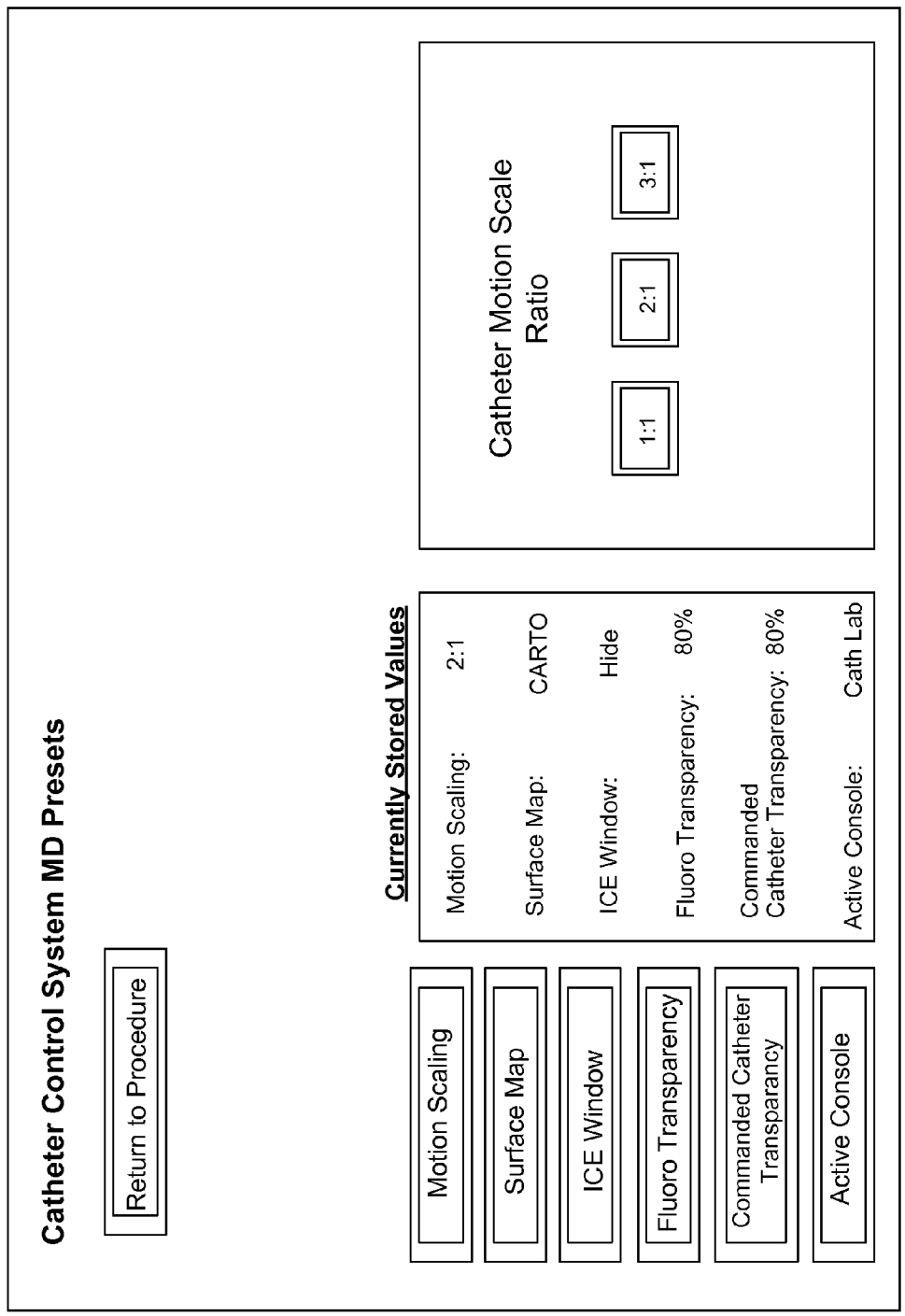
Figure 184B:
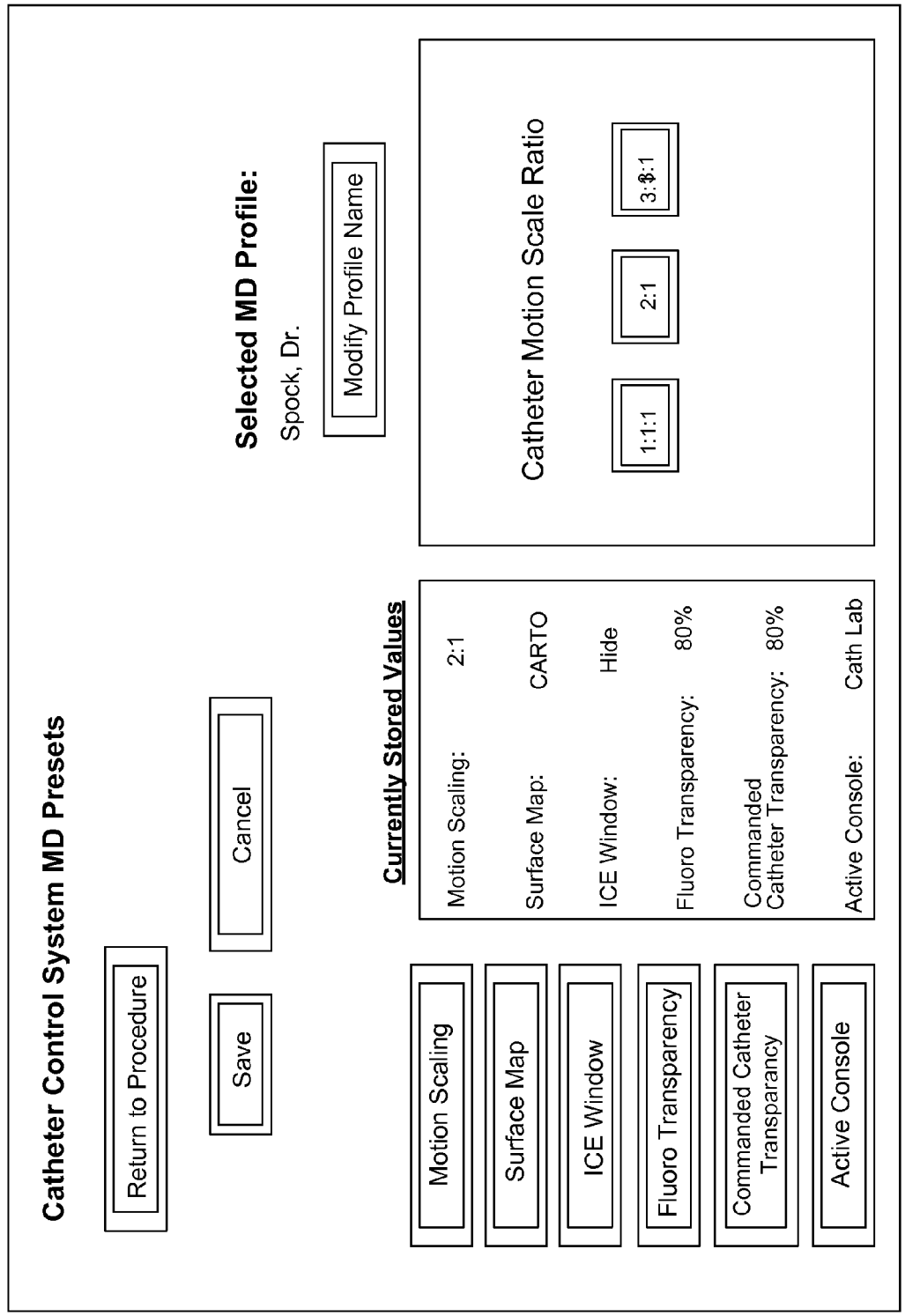
Figure 184C:
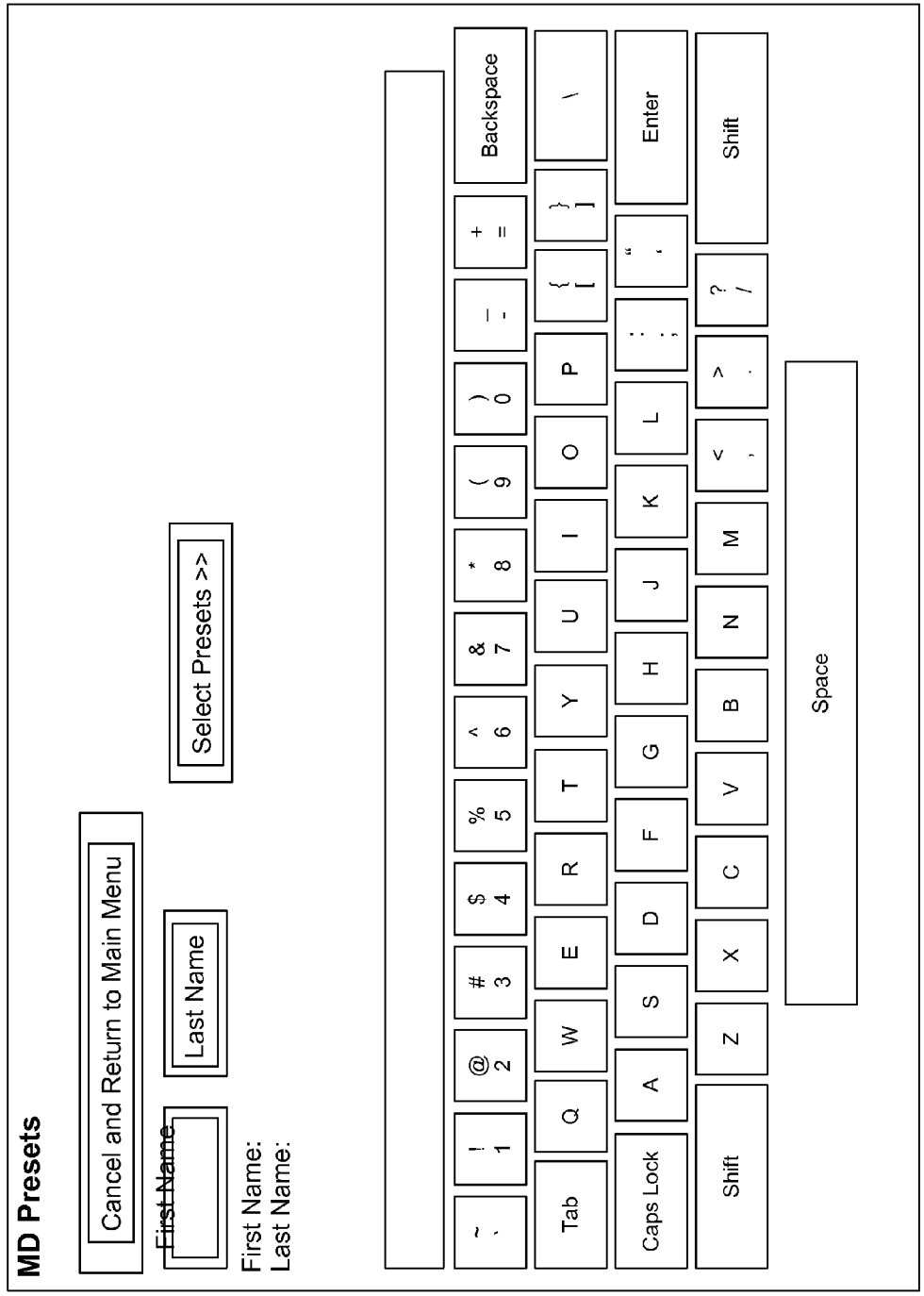
Figure 184D:
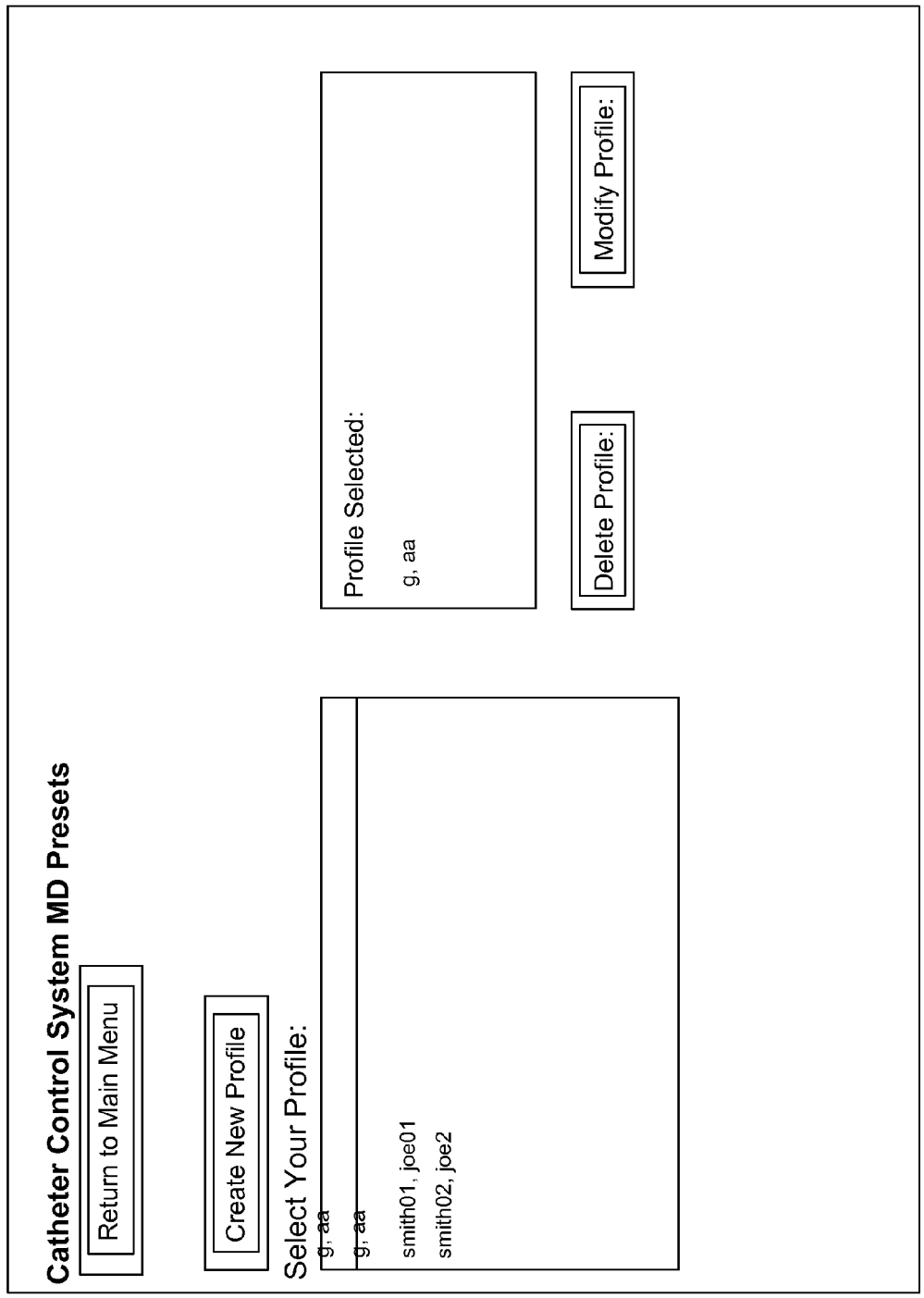
Figure 184E:
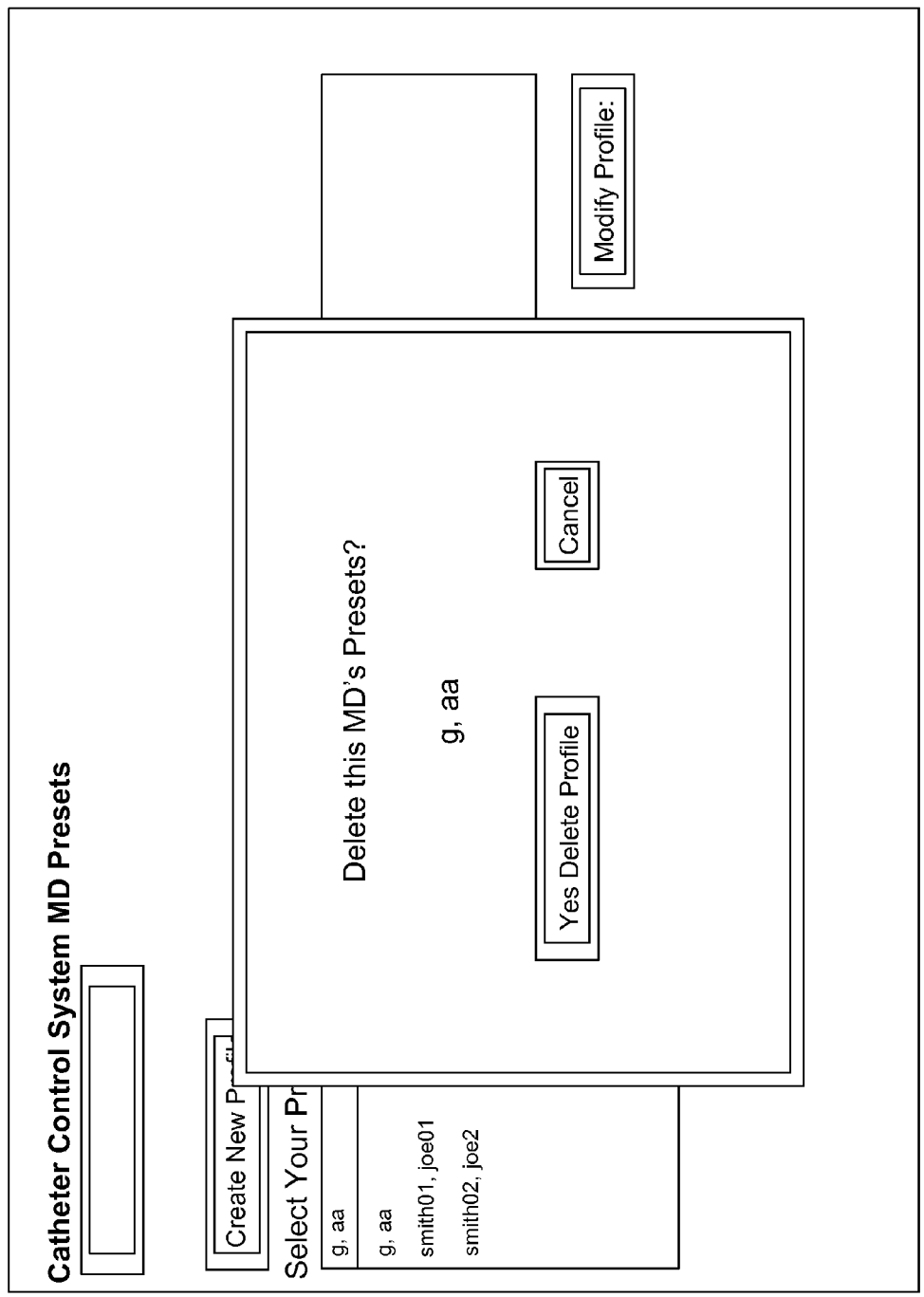
Figure 185A:
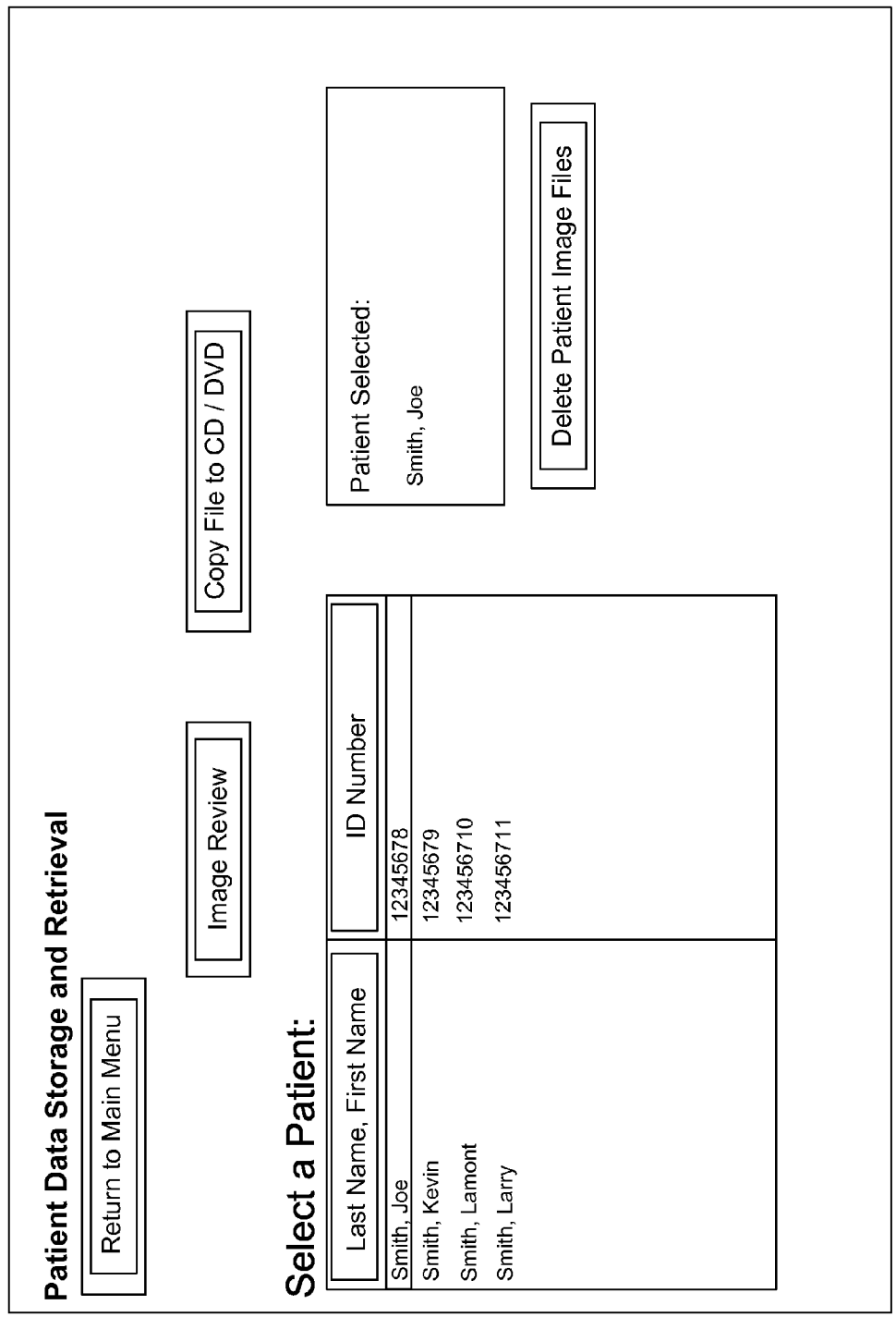
Figure 185B:
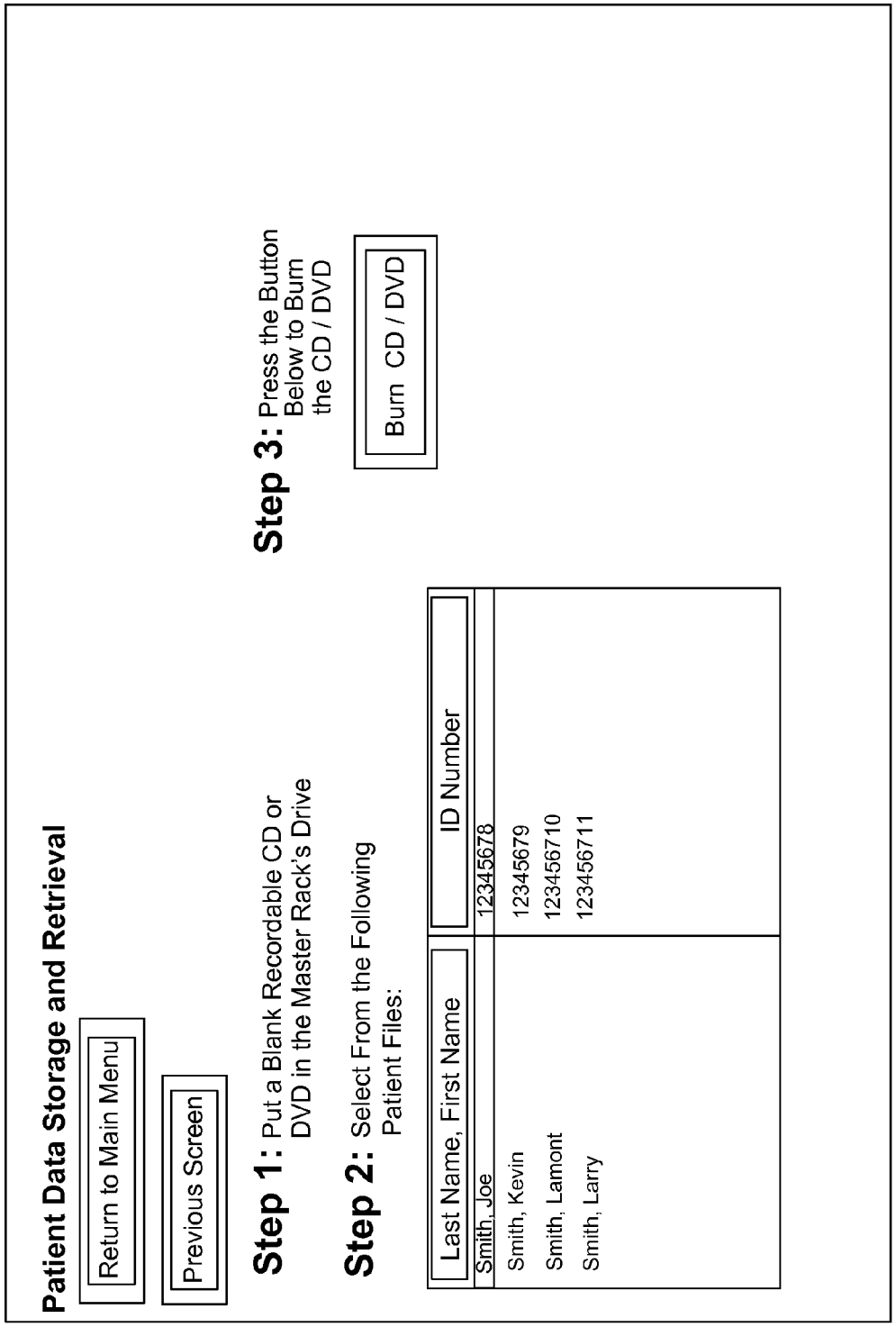
Figure 185C:
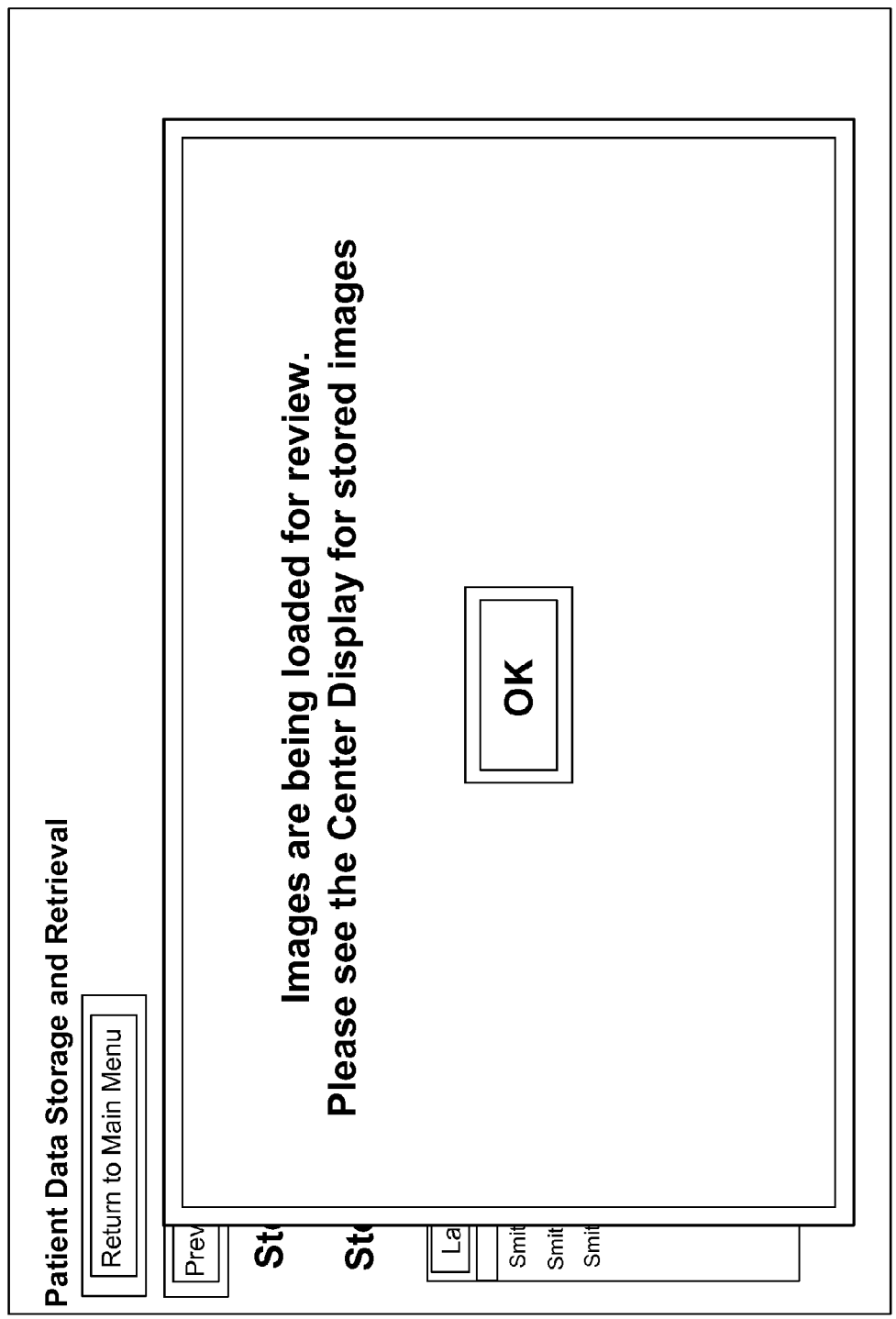
Figure 185D:
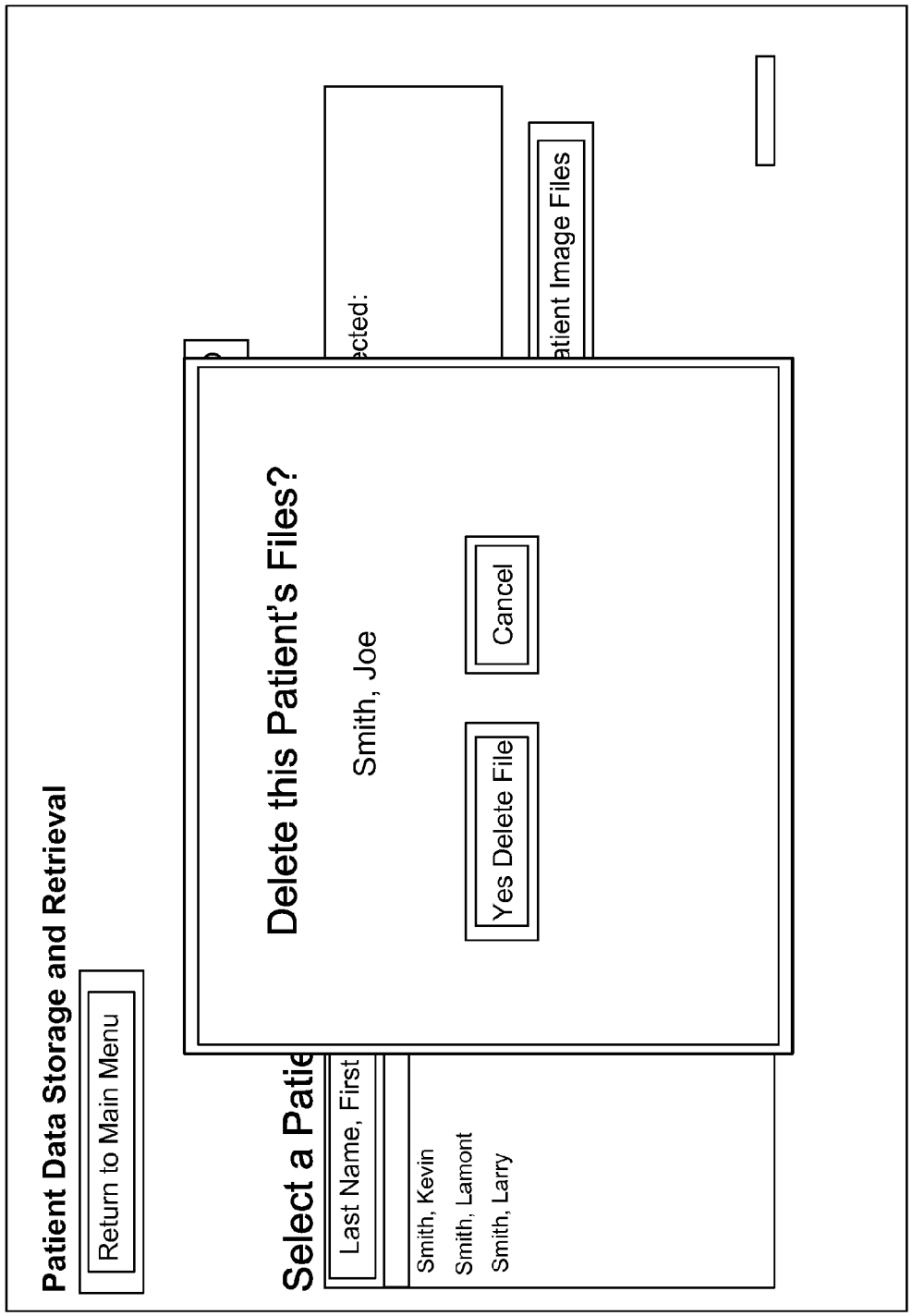
Figure 186A:
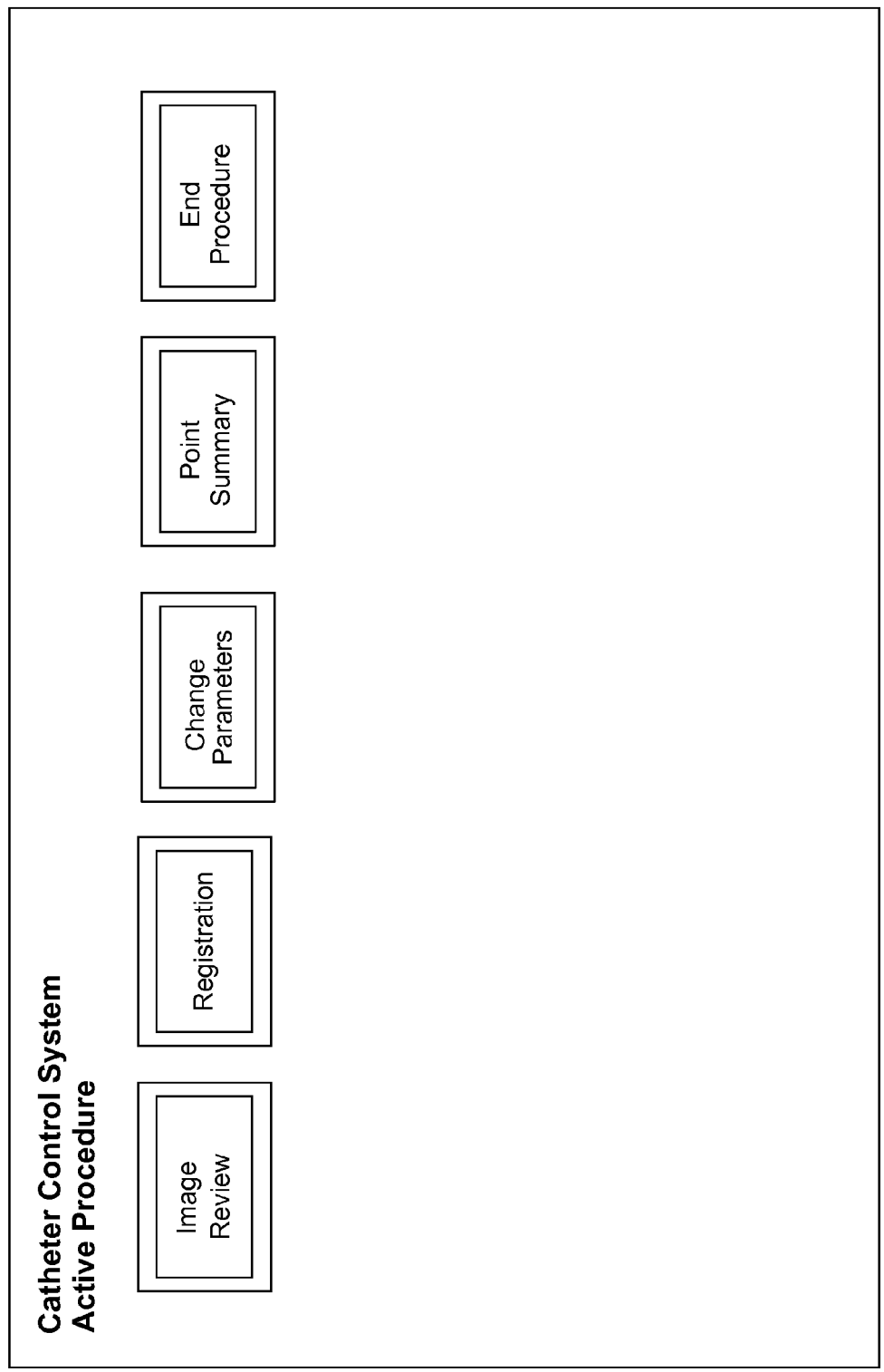
Figure 186B:
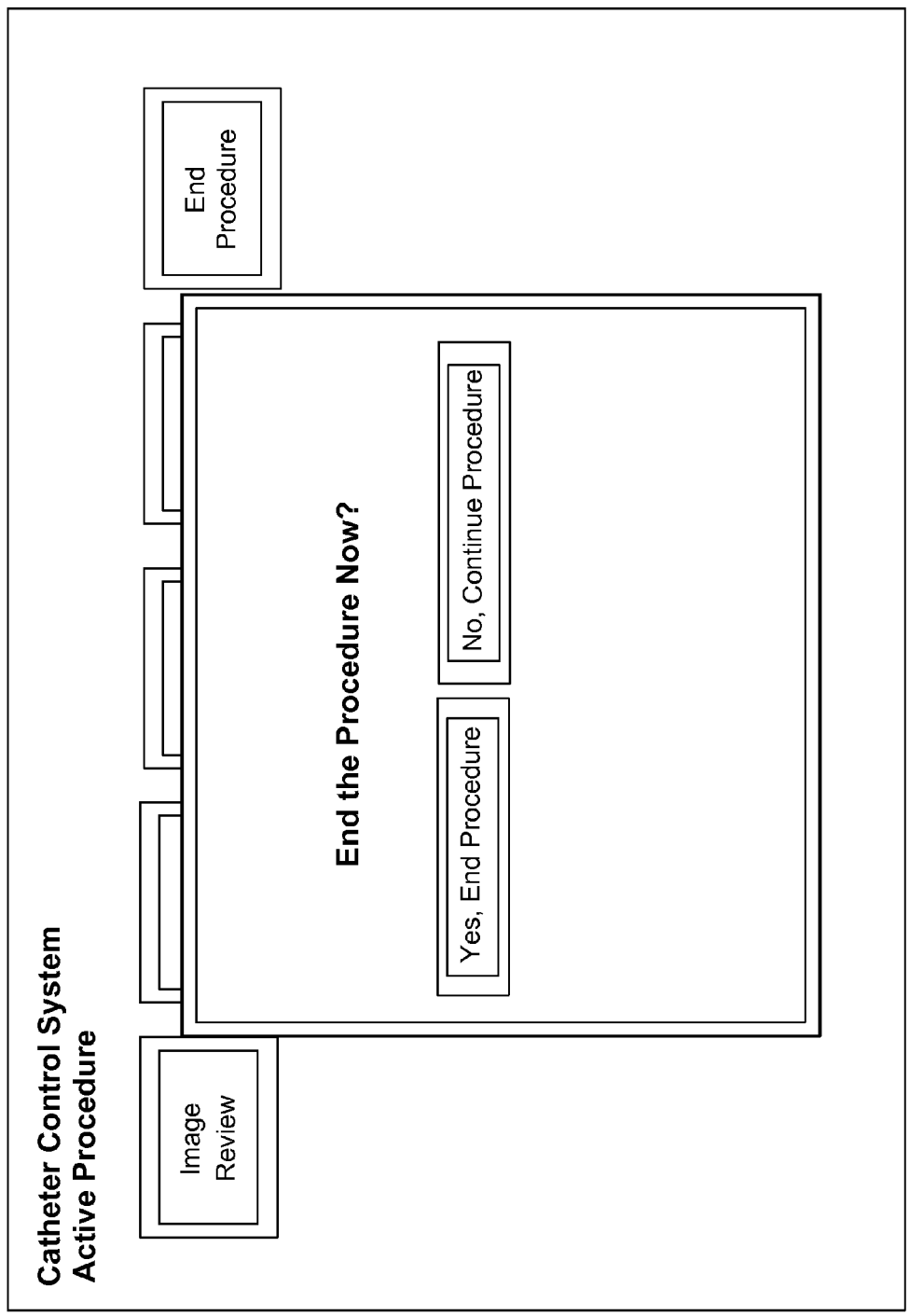
Figure 186C:
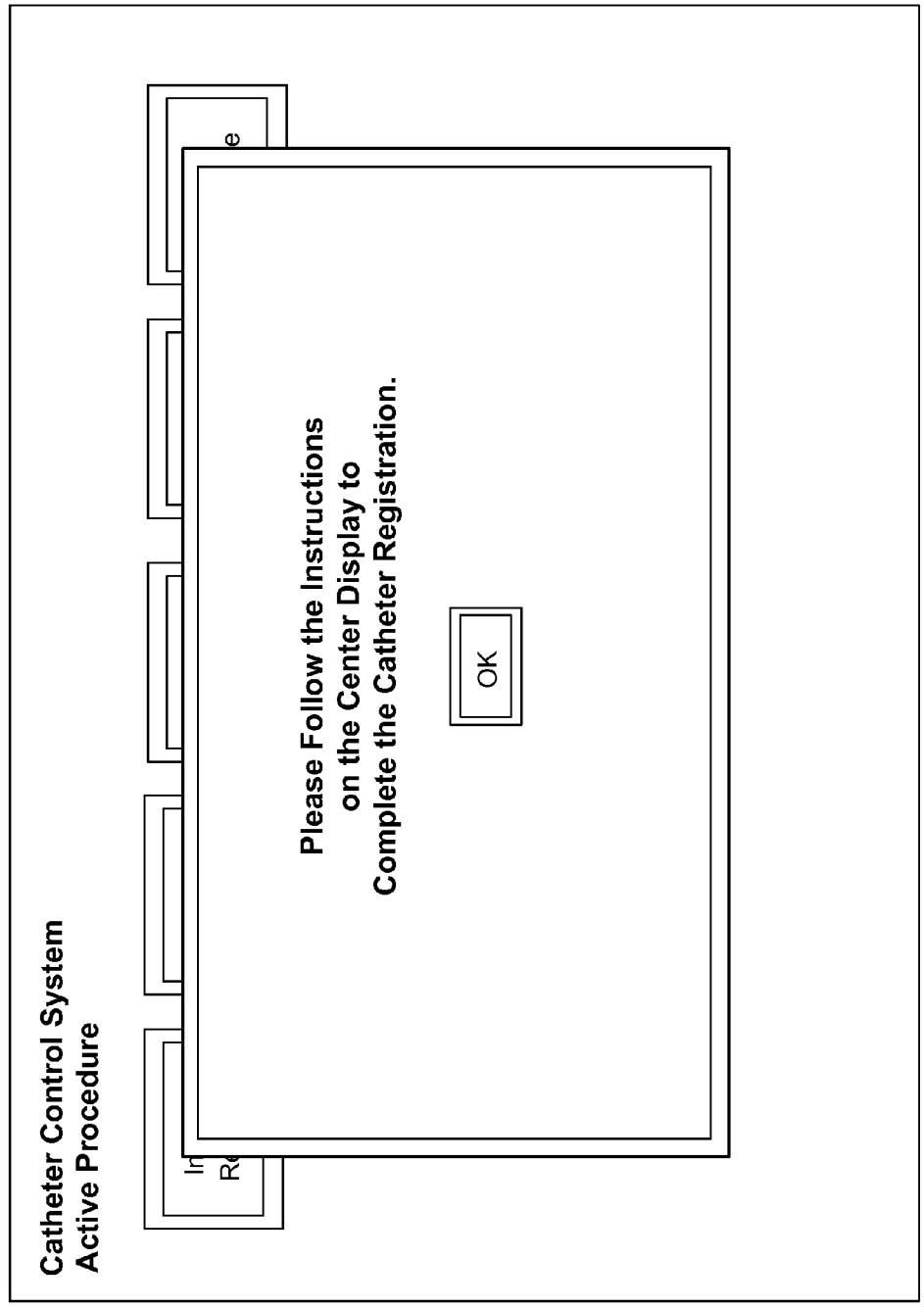
Figure 186D:
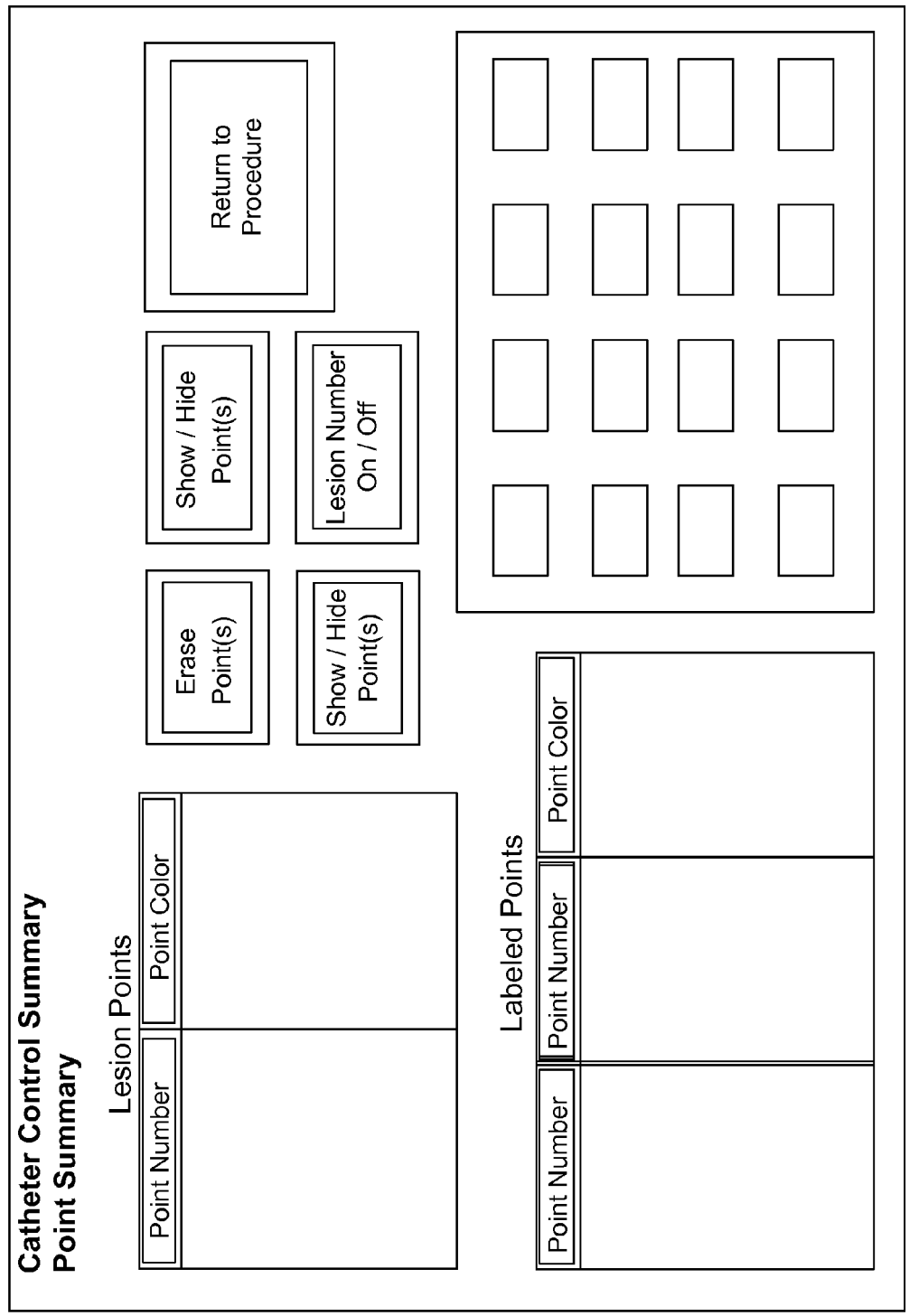

FIG. 183A illustrates an example touchscreen display for selecting a procedure type. FIG. 183B illustrates a touchscreen wherein patient data can be entered into the system with an onscreen QWERTY keyboard. FIG. 184A illustrates a touchscreen wherein various system presets can be viewed and modified for the current procedure. FIG. 184B illustrates a shot of screen wherein the user presets may be saved. FIG. 184C illustrates a screen fore entering a preset name. A screen for maintaining various system presets is displayed in FIG. 184D. FIG. 184E illustrates a screenshot of the display when a preset is deleted. FIG. 185A illustrates a screen for retrieving and maintaining patient data. FIG. 185B illustrates a screen wherein user data can be exported to or imported from a removable media such as a CD or DVD. A confirmation message relating to the loading of stored images is illustrated in FIG. 185C. FIG. 185D shows a confirmation message relating to the deletion of patient data. FIG. 186A illustrates one example of the menu available to an operator during a procedure. A confirmation message relating to the termination of a procedure is show in FIG. 186B. FIG. 186C illustrates the message displayed during the registration process for a catheter. FIG. 186D illustrates a screen for catheter control and marking of anatomical points of interests.

Referring to FIGS. 187A-191C, several embodiments of minimally invasive instruments and kits thereof which may be preferred for a cardiac ablation procedure in accordance with the present invention are depicted.

Referring to FIGS. 187A-188B, various aspects of one embodiment of a sheath instrument (227) are depicted. The finished assembly of the depicted embodiment preferably has an inner lumen of about 145 mils and 158 mils (noncircular x-section, the former being the smaller inner lumen diameter (ID), the latter being the larger ID) which is configured to fit the outer finish diameter, or (OD), of a guide instrument such as that described in reference to FIGS. 189A-189C, which has an inner diameter of approximately 8 French—a size configured to fit several approved off-the-shelf ablation catheters, as well as needle/dilator sets such as those described below.

Figure 187A:
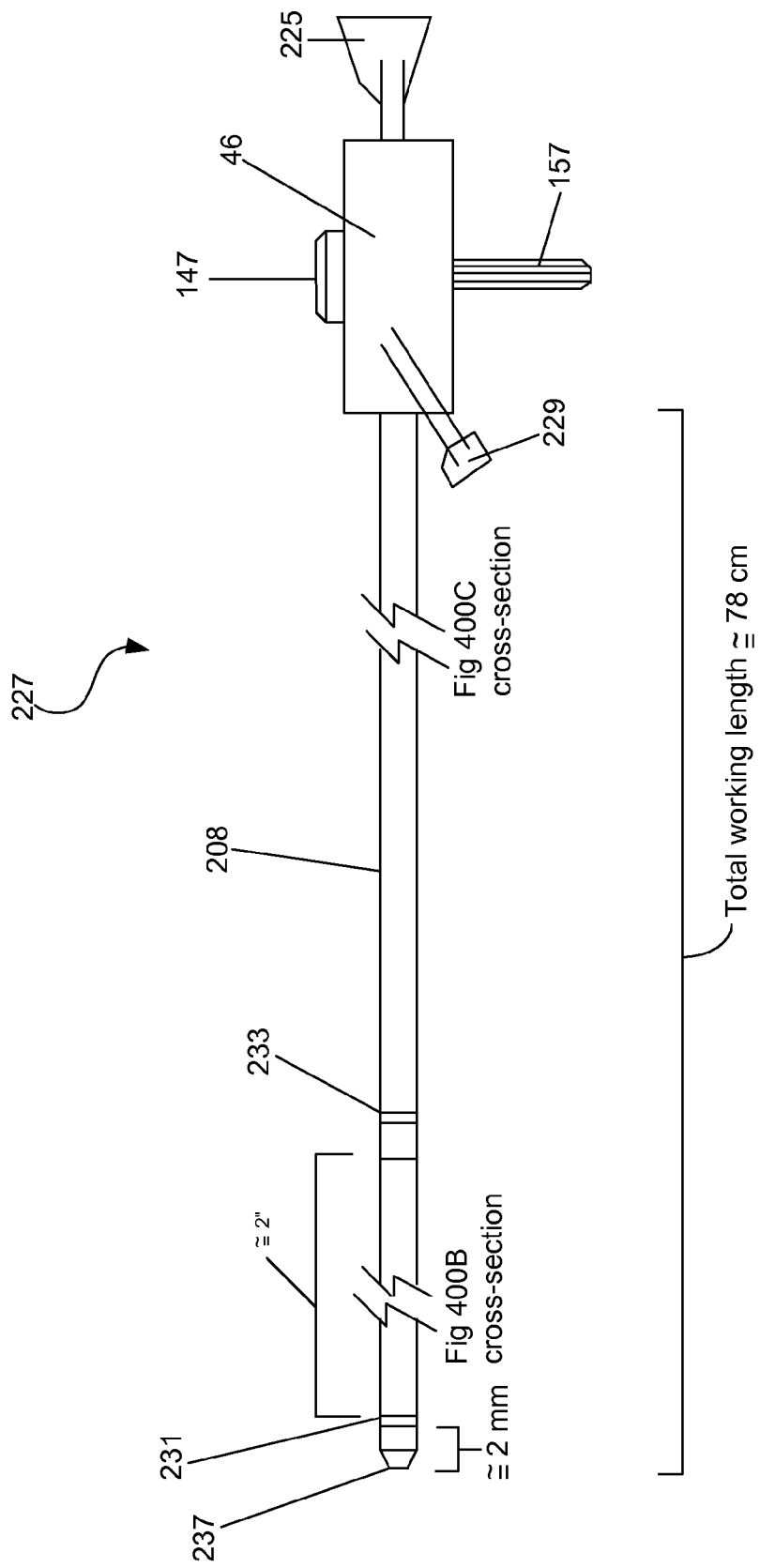

Referring to FIG. 187A, the depicted sheath instrument (227) embodiment comprises a sheath catheter member (208) which is proximally coupled to a sheath instrument base (46) which is coupled to a control element interface assembly (147) and Luer assembly (225). The control element interface assembly (147), similar to those described in reference to FIGS. 103.5 and 103.6, for example, has a splined axle (157) configured to interface with an instrument driver interface socket (not shown, see item (44) of FIG. 6, for example). The total working length of the portion of the catheter member (208) distal of the sheath instrument base (46) is approximately 78 centimeters in the depicted embodiment. Approximately 2.5 inches from the distal tip (237), a proximal ring (233) is integrated into the assembly to provide not only radio-opacity for fluoroscopy, and also conductivity for a potential difference type localization integration as discussed above, but also for termination and return of a proximal control element (not shown in FIG. 187A) which, in the depicted embodiment, is configured to extend from the one or more pulleys (not shown in FIG. 187A) associated with the manual adjustment knob (229) to the proximal ring (233) and back to the one or more pulleys (not shown in FIG. 187A) associated with the manual adjustment knob (229). Approximately 2 millimeters from the distal tip (237), a distal ring (231) is positioned to function similarly to the proximal ring (233), but for a distal control element which, in the depicted embodiment, preferably is looped from the one or more pulleys (not shown in FIG. 187A) comprising the control element interface assembly (147), which is configured to be servo-robotically actuated from an instrument driver to which it may be coupled. The looping configuration of the control elements preferably provides greater break strength, in the range of twice the break strength of a single strand of the same control element wire material under tension, because with the both-side-soldered (325) and looping configuration around the proximal (233) or distal (231) ring, as depicted in FIG. 187D, each of the two strands of the continuous control element is configured to share loads as separate tension elements. The portion approximately two inches proximal of the distal ring (231) is configured to have relatively high, yet controllable flexibility, as controlled by catheter member reinforcing structures or ribs discussed in reference to FIG. 187B.

Referring to FIG. 187B, a cross sectional view of a distal portion of this embodiment of a sheath instrument (227) depicted in FIG. 187A is depicted. As shown in FIG. 187B, the assembly is created around a mandrel (243) which is removed after assembly, which has a rounded-cornered-square cross section having a maximum diameter (257) of approximately 158 mils. Several layers are formed over the mandrel (243), as described in reference to FIG. 187E, including an inner layer (249), a distal control element (239) liner set (247), a braided layer (251), structural rib elements (245), and an outer jacket layer (255). The structural rib elements (245) function like small beams integrated into the walls of the construct and are configured to resist homogeneous omnidirectional cantilevered bending of the distal end of the sheath.

Referring to FIG. 187C, a cross sectional view of a more proximal portion of this embodiment of a sheath instrument (227) depicted in FIG. 400A is depicted. The same mandrel (243) is utilized to construct the proximal portion, over which an inner layer (249) is placed, followed by a liner sets (247) for each of the subsequently introduced proximal and distal control elements (241, 239), a braided layer (251), a second braided layer (254), and an outer jacket layer (253) different from the outer jacket layer (255) of the distal portion of the sheath instrument (227).

Figure 187E:
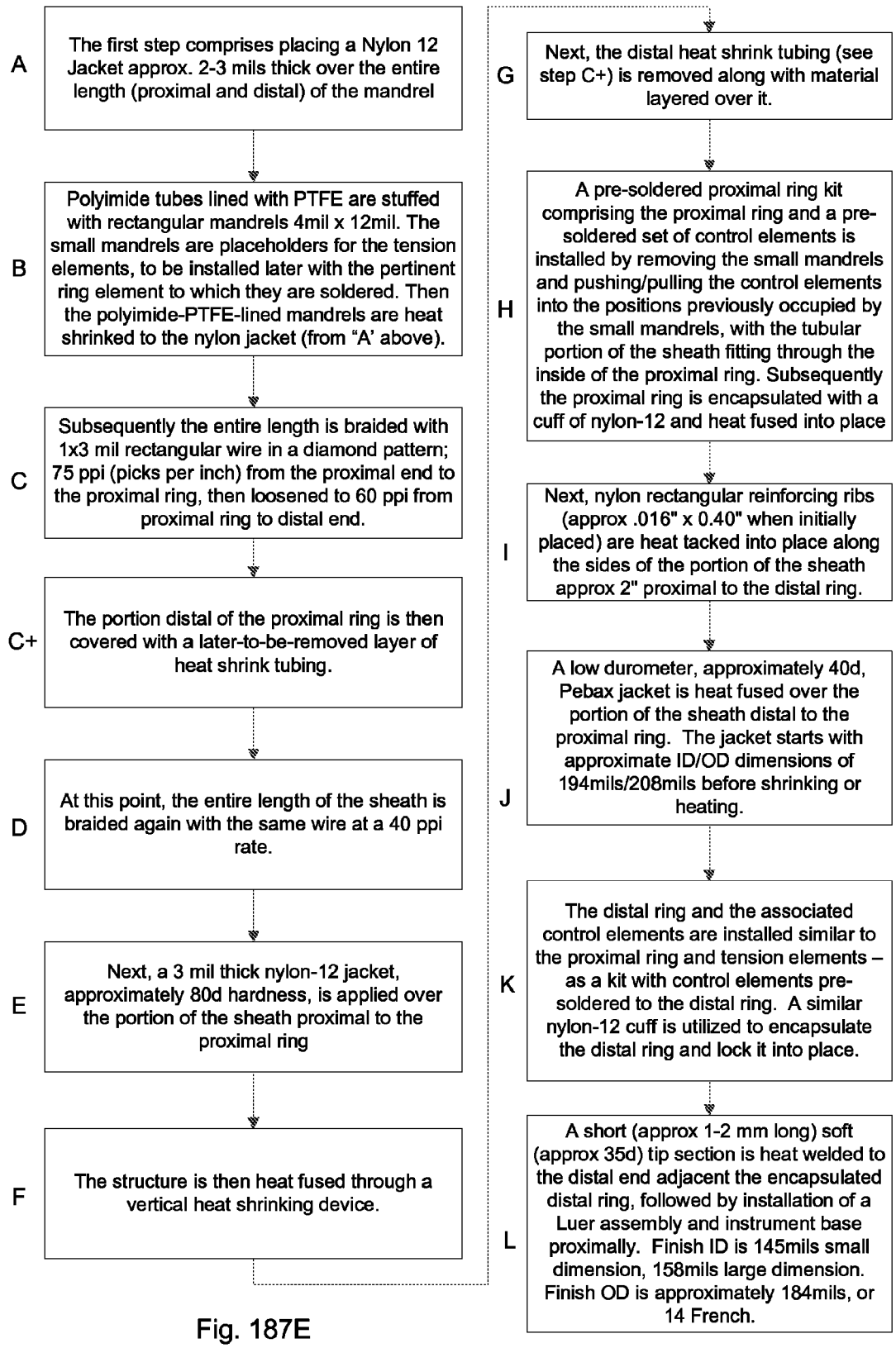

Referring to FIG. 187E, one embodiment of a method of constructing the embodiment depicted in FIGS. 187A-187D is illustrated as exemplary steps described in block A through L. The first step at block A comprises placing a nylon 12 jacket approximately 2-3 mils thick over the entire length (proximal and distal) of the mandrel. Next at block B, polyimide tubes lined with polytetrafluoroethylene (PTFE) are stuffed with rectangular mandrels 4 mil by 12 mil. These small mandrels are placeholders for the tension elements, to be installed later with the pertinent ring element to which they are pre-soldered. The polyimide, PTFE-lined, mandrels are heat shrink bonded to the nylon jacket, subsequent to which at block C, the proximal portion (proximal to the approximately two-inch more flexible distal section in this embodiment) is braided with 1×3 mil rectangular wire at 75 ppi (picks per inch) diamond pattern; the braiding is loosened in pattern over the distal section to 60 ppi. Next at block C+, the distal section is covered with a later-to-be-removed heat shrink tubing layer, subsequent to which at block D, the entire length of the construct is braided again with the same wire at a 40 ppi rate. Next at block E, a 3 mil thick nylon 12 jacket is applied over the proximal portion (proximal of the subsequent position of the proximal ring), and the structure is heat fused at block F through a vertical heat shrinking device. Next at block G, the distal heat shrink (from block C+ is removed along with any materials over it, and the pre-soldered proximal ring with looped proximal control element is installed at block H by pulling the small mandrels out and pushing/pulling the looped control element into the same positions, and subsequently encapsulating the proximal ring into place with a small cuff of nylon 12 material. Next at block I, rectangular reinforcing ribs (approximately 0.016×0.40 inches) are heat tacked into place along the sides of the portion of the sheath approximately two inches proximal to the position of the distal ring, and subsequently at block J, a low-durometer jacket, preferably a Pebax resin with a 40 Shore D durometer hardness value, is heat fused over the portion of the sheath distal to the proximal ring. Subsequently at block K, the distal ring and associated tension elements are installed similar to the installation of the proximal ring and tension elements, and at block L, a short (approximately 1-2 mm long in this embodiment) soft tip section, preferably 35 Shore D durometer hardness value, is heat welded to the distal end, followed by installation of a Luer assembly proximally, and final assembly instrument base, including exposure of the two looped control elements through the wall of the proximal portion of the catheter member, installation of termination balls, preferably by mechanical crimp, upon the proximal ends of the control elements, and winding about the pertinent pulleys of the control element interface assembly and manual-knob-driven proximal element pulley.

Figure 188A:
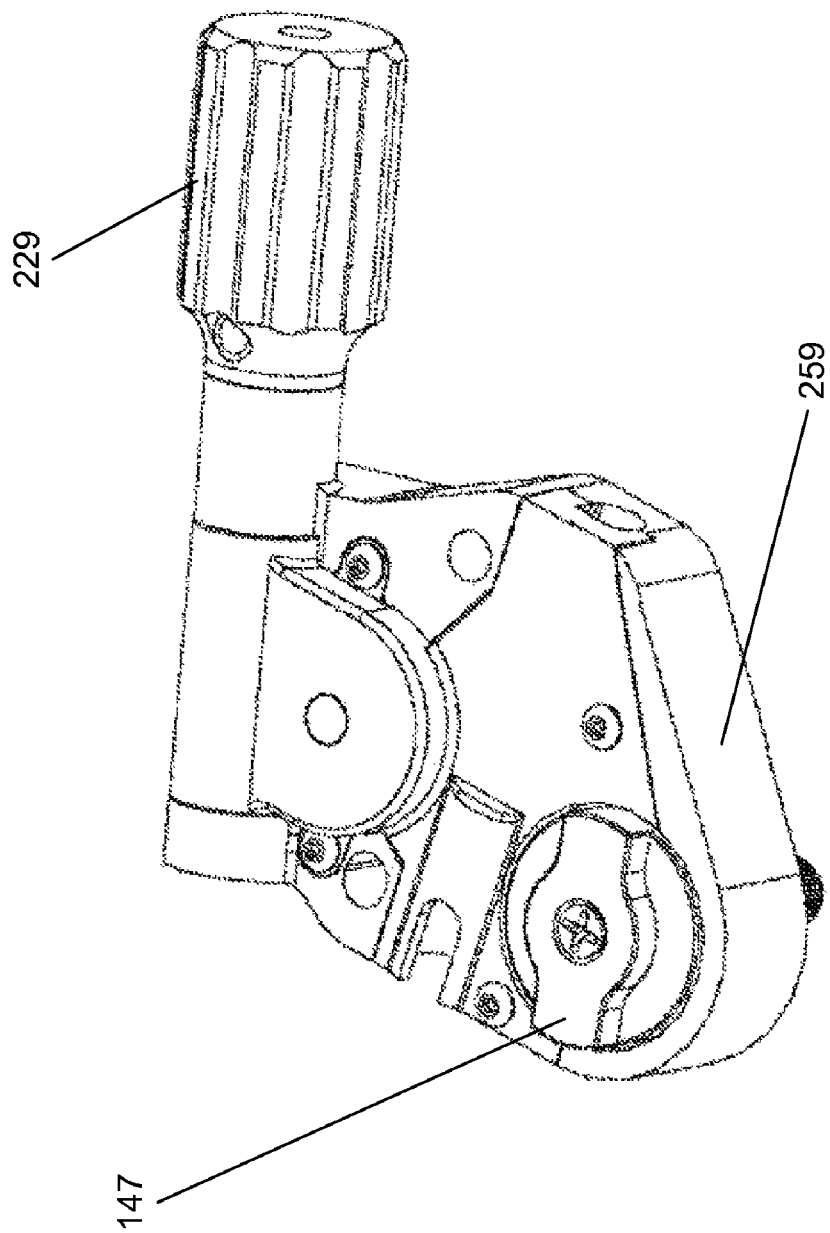
FIGS. 188A-B illustrate one embodiment of a sheath instrument base assembly.
Figure 188B:
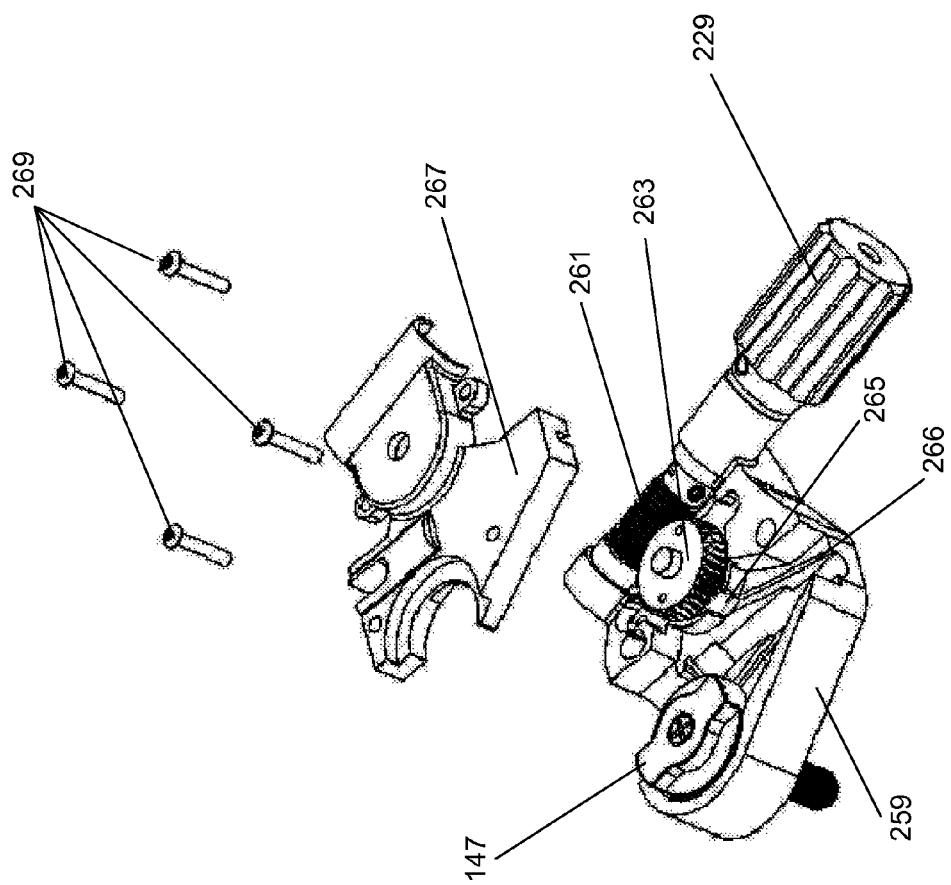

Referring to FIGS. 188A-B, isometric views of the sheath instrument base (259) assembly are depicted to illustrate that the distal control element loop (239) in the embodiment depicted in FIGS. 187A-E may be servo robotically driven through a control element interface assembly (147) configured to interface with an instrument driver interface socket (not shown), while the proximal control element loop (241) may be actuated with a worm screw mechanism associated with a manual tensioning knob (229). FIG. 188B depicts an exploded view of the assembly of FIG. 188A. With the top plate (267) removed from the sheath instrument base (259), where it is fastened with fasteners (269) such as screws when fully assembled, the work gear (261) coupled to the manual tensioning knob (229) and the associated control element drive gear (263) and associated control element pulley (265) is depicted. A track (235) is depicted, formed in the sheath instrument base (259), to provide a pathway for the proximal control element loop to exit the wall of the proximal catheter member and spool into the control element pulley (265).

Figure 189A:
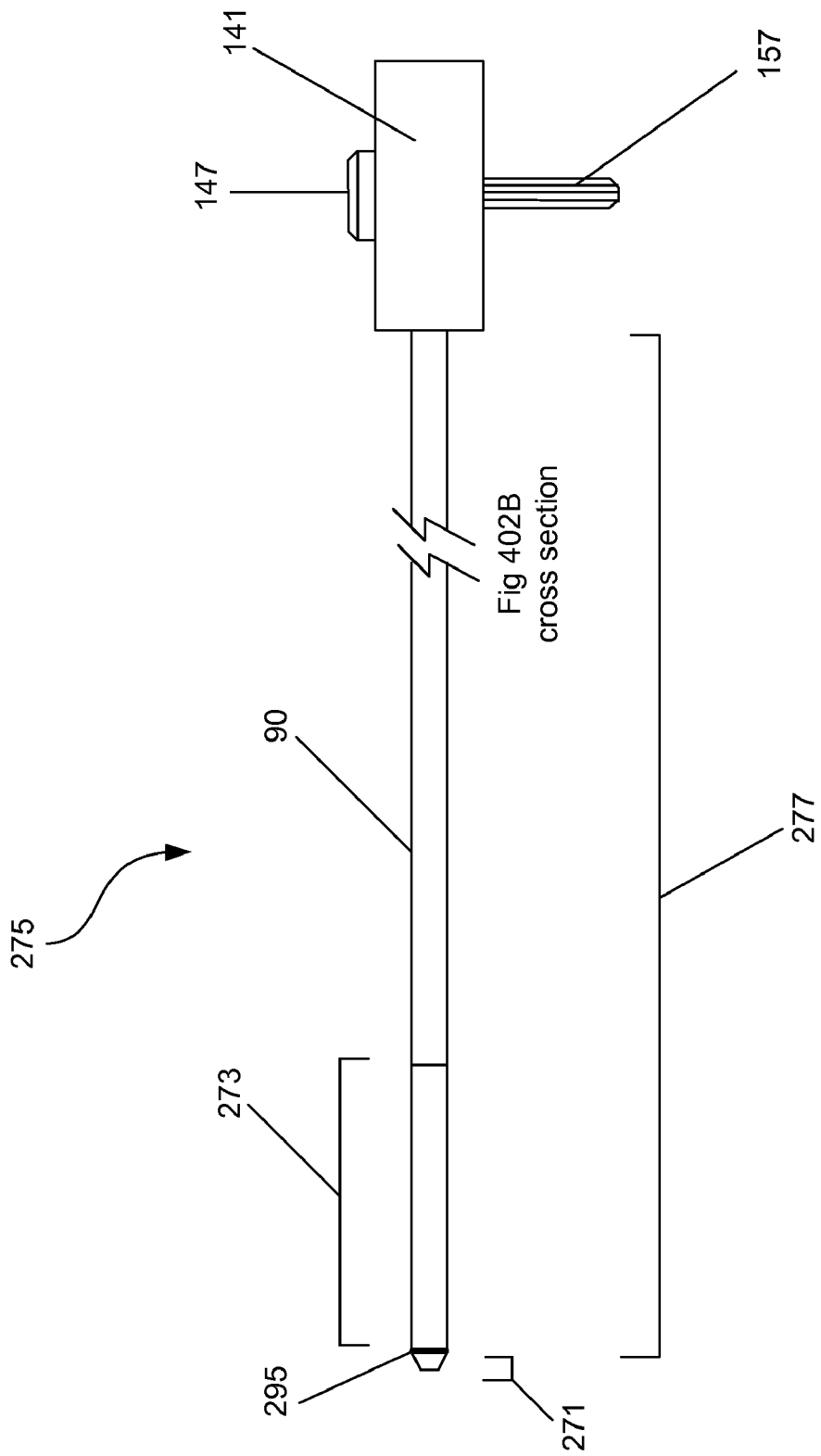
FIGS. 189A-C illustrate a guide instrument of one embodiment.
Figure 189B:
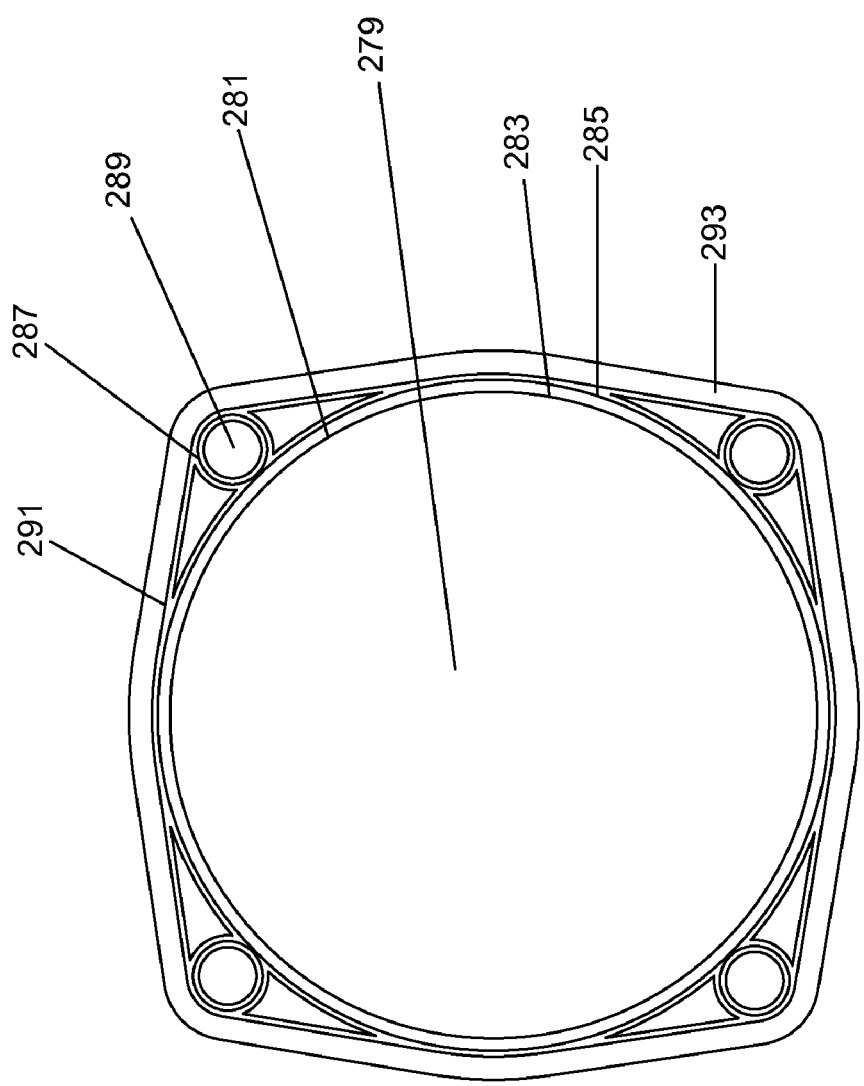
Figure 189C:
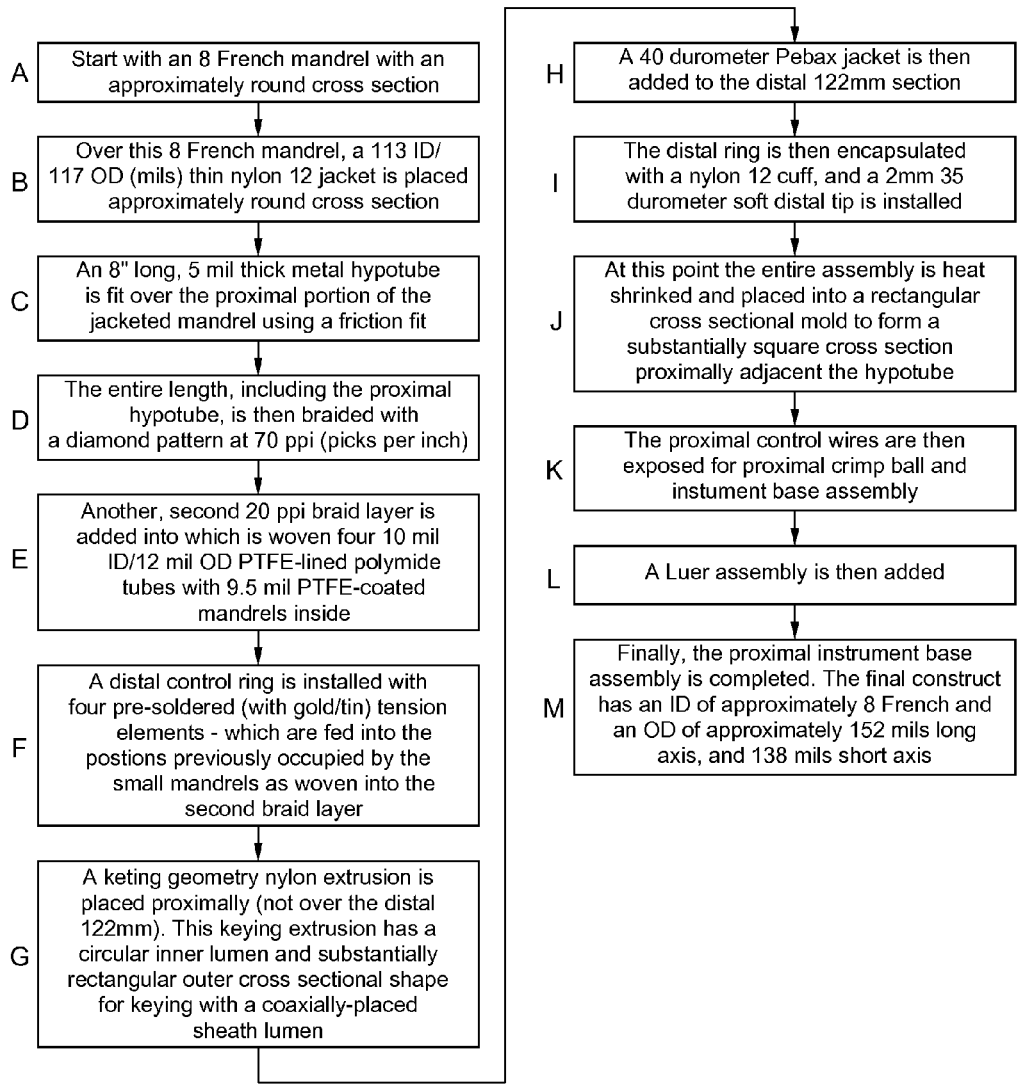

FIGS. 189A-C illustrate one embodiment of a guide instrument (275) configured to coaxially interface with an embodiment of the sheath instrument (227) depicted in FIGS. 187A-188B. The working length (277) of the depicted guide instrument catheter member (90) is about 92 centimeters, the most distal 122 millimeters of which (273, 271) are significantly more flexible or bendable than the proximal portions. The very distal 2 mm (271) comprises a soft tapered distal tip of an even more pliable polymeric material. This embodiment of the guide instrument has four control elements fastened to a single distal ring (295) and configured to facilitate omnidirectional distal tip navigation from a proximal interface to a servo robotic instrument driver, such as those described above. A guide instrument base (141) and two associated control element interface assemblies (147) and axles (157) are depicted in a configuration similar to that described in reference to FIGS. 103.1-103.6. In another embodiment, the guide instrument base (48) may comprise a configuration such as that depicted in FIG. 6 and be configured for a four interface socket (44) instrument driver (16) configuration such as that depicted in FIG. 6.

Referring to FIG. 189B, a proximal cross section of the guide instrument catheter member (90) depicted in FIG. 189A is depicted. Starting with an approximately circular mandrel (279) with a diameter of approximately 8 French, an inner layer (281) of nylon may be formed, followed by a metal hypotube layer (283) friction fit onto the most proximal eight inches of the construct, the metal hypotube layer (283) being about 5 mils in thickness. A braid layer (285) is subsequently added, followed by a second braiding layer (291) into which small mandrels (289) and liners (287) are woven, followed by installation of an outer jacket (293). Other details regarding this construction are described in reference to FIG. 189C.

Referring to FIG. 189C, steps for one method of constructing a guide instrument (275) embodiment such as that depicted in FIG. 189A are illustrated. At block B, a 113 ID, 117 OD (mils) thin nylon 12 jacket is placed over an 8 French mandrel from block A. Then an approximately 8" long 5 mil thick metal hypotube is fit over that proximally with a friction fit at block C. The entire length is then braided with diamond pattern (same wire as with above sheath) at 70 ppi at block D. Then at block E, another braid layer is installed at 20 ppi, into which is woven four 10 mil ID, 12 mil OD, PTFE-lined, polyimide tubes with 9.5 mil PTFE-coated mandrels inside. A distal control ring is installed at block F with four pre-soldered (with gold/tin) control elements or loops of control elements—which are fed into the positions of the small mandrels as woven into the second layer of braid. At block G, a keying extrusion is placed proximally (but not over the distal 122 mm portion in this embodiment). The guide instrument of this embodiment has a circular inner lumen and a substantially rectangular outer cross sectional shape for keying with a coaxially-positioned sheath lumen such as those depicted in FIGS. 187B and 187C, to prevent relative rotation between such sheath instrument and guide instrument when coaxially interfaced. The distal 12 mm section of the instrument gets a Pebax resin jacket with a 40 Shore D durometer hardness value at block H. At block I, the distal ring is encapsulated with a nylon 12 cuff and a 35 Shore D durometer hardness value soft distal tip is installed. The entire construct is heat shrunken at block J and pressed into a rectangular cross sectional mold to keep the keyed cross section in place (primarily proximally, about the region of the metal hypotube layer). AT block K, the proximal pullwires are exposed for instrument base installation. A Luer assembly is added at block L and the proximal instrument base is installed at block M. The final construct of the depicted embodiment has an inner diameter of approximately 8 French and an outer diameter of approximately 152 mils long axis, and 138 mils short axis.

Although both the guide and sheath instruments described in reference to FIGS. 187A-189C utilize braiding for added torquability and kink resistance, spiral winds or spine constructs, such as those described above in reference to FIGS. 25-32 may also be utilized or server a similar purpose.

Referring to FIGS. 190A-C, various views of one embodiment of a dilator compatible with the guide and sheath instruments described in reference to FIGS. 187A-189C are depicted. The depicted dilator embodiment (297) may be created by placing a thin polyimide liner (301) in FIG. 190C, which may be coated on the interior, mandrel-facing, lumen with a lubricious surface such as PTFE, over a PTFE-coated mandrel (not shown), then butt-welding a relatively long section of relatively rigid polymeric material, such as a Pebax resin having a 72 Shore D durometer hardness value, to a relatively short distal section (311) in FIG. 190A of relatively flexible polymeric material, such as 45 durometer Pebax, to form a main tubular body (299) which is more flexible distally than proximally. Proximally a Luer assembly (305) and hemostasis valve (307) are installed. A small platinum/iridium radio-opaque marker band (303) is installed distally, adjacent to which a 9-degree tapered end is created with a glass mold for tissue dilation at the distal tip of the dilator instrument embodiment (297). The inner lumen (309) diameter at the distal tip is configured to be very close to the outer diameter of the needle for which the dilator is configured to be used, while the outer diameter of the dilator is configured to fit within the inner diameter of the guide instrument with which is it configured to be utilized. In other words, each of the needle, dilator, guide, and sheath instruments preferably are configured for coaxial interfacing during a procedure.

Figure 191A:
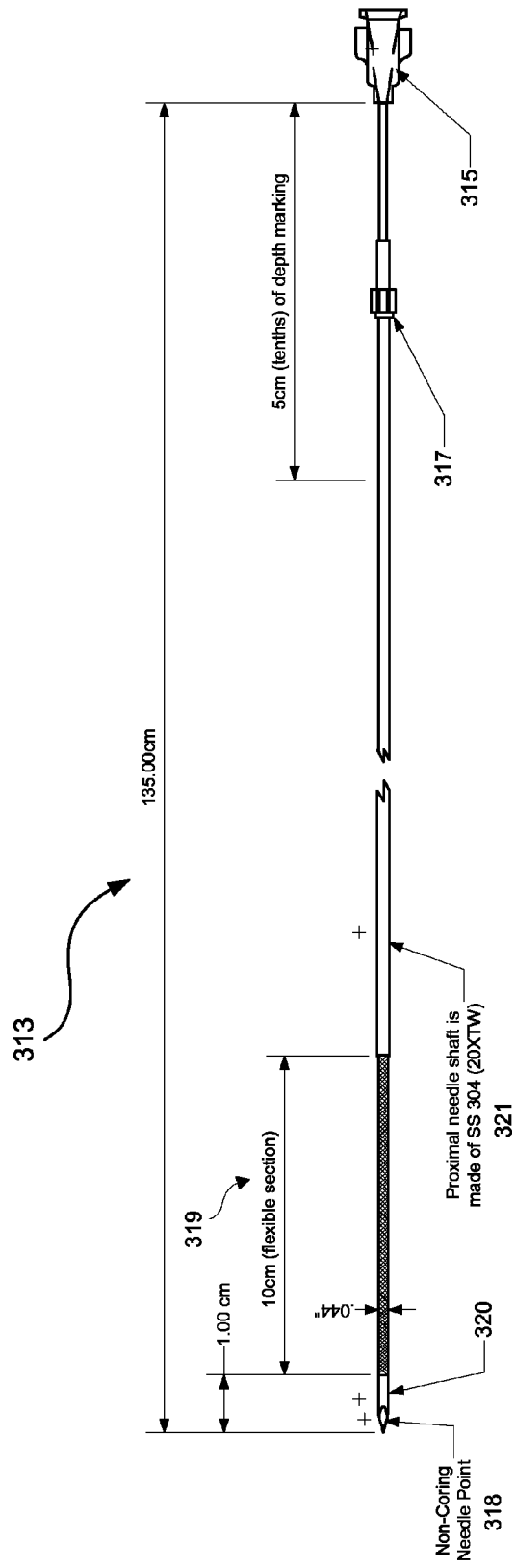
Figure 191B:
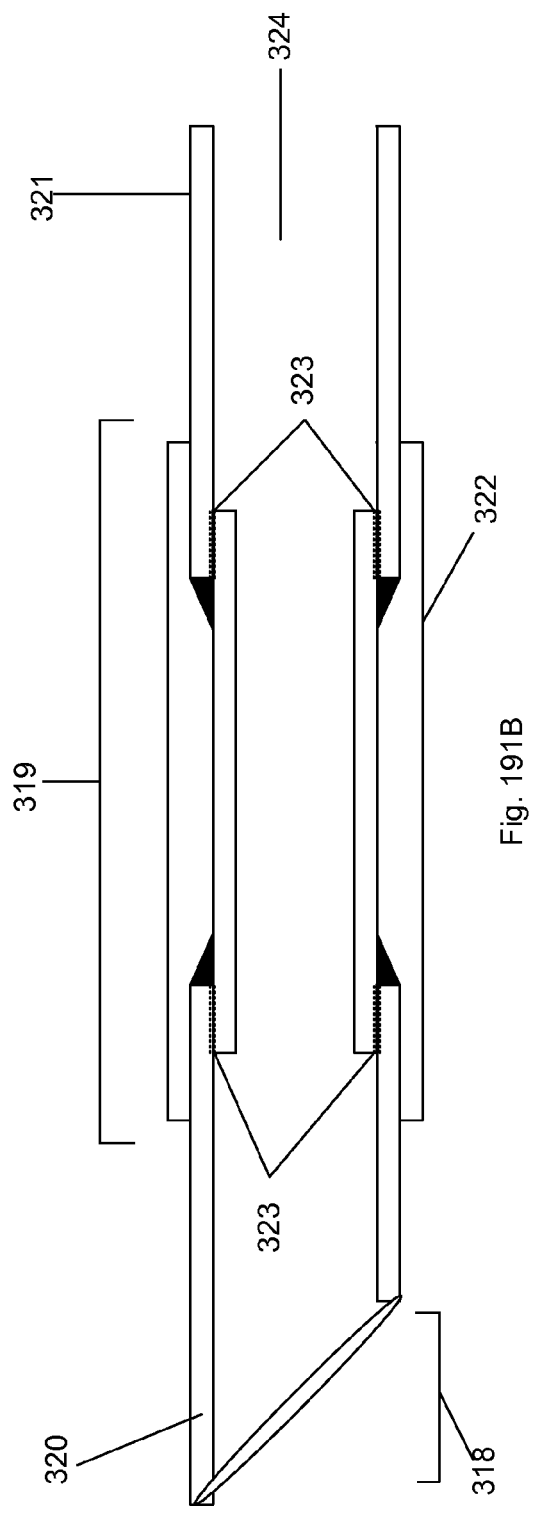
Figure 191C:
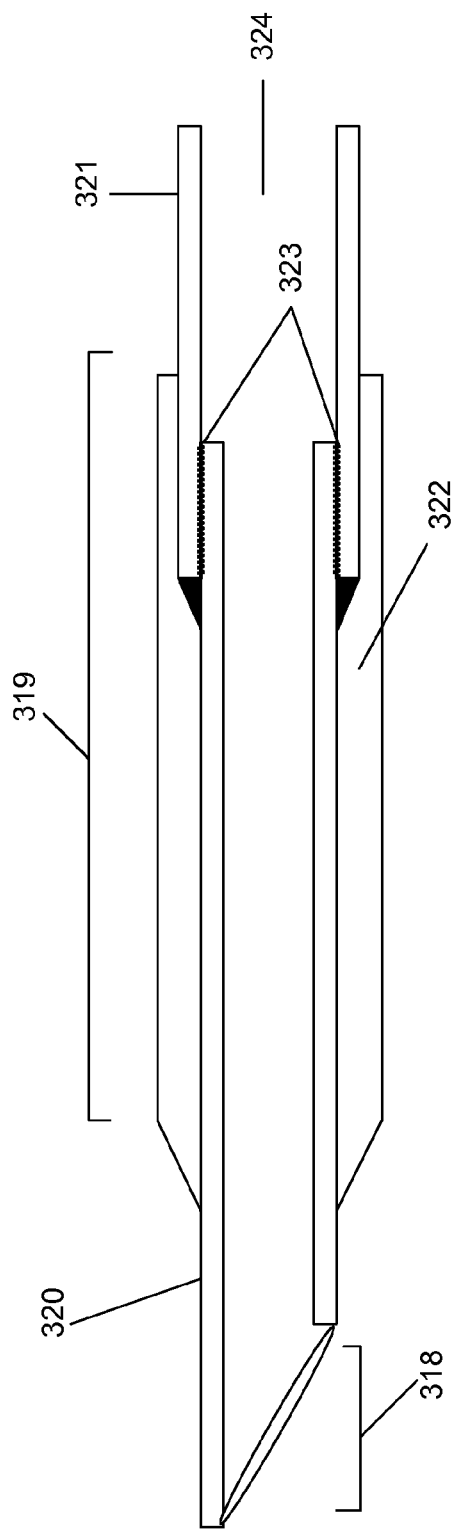

Referring to FIGS. 191A-191C, various views of one embodiment of a needle compatible with the guide, sheath, and dilator instruments described in reference to FIGS. 187A-190C are depicted, wherein a flexible section near the distal tip facilitates passage of the needle around tight turns within a constraining lumen. An instrument set comprising a coaxial coupling of a sheath instrument, a guide instrument, a dilator instrument, and a needle instrument such as those described herein may be utilized to conduct a trans-septal puncture, as described above in reference to FIGS. 163-167. Subsequently, the needle and dilator may be withdrawn, and an ablation or mapping catheter inserted down the working lumen of the guide catheter to conduct a robotically-controlled ablation or mapping procedure, as described above in reference to FIGS. 167-172, within the chambers of the heart.

At the heart of the needle embodiment (313) depicted in FIGS. 191A-C is an intermediate section (319) of greater flexibility positioned proximally adjacent the distal non-coring needle point (318) of the needle to enable the distal end (318, 320) of the needle to navigate around small radius of curvature turns more easily than a conventional needle without the highly flexible section (319). The distal end (318, 320) preferably is soldered with gold or platinum material to provide radio-opacity, thereby facilitating placement and positioning of the distal end (318, 320) during a procedure. Proximal of the highly flexible section (319), the proximal needle shaft (321) preferably comprises stainless steel, and may be coupled to a pin vise (317). Proximally a Luer assembly (315) is installed upon the proximal needle shaft (321).

Referring to FIGS. 191B and 191C, two embodiments of the distal end (318, 320) and highly flexible section (319) are depicted in close up cross sectional view. In both embodiments, to prevent kinking, a prefabricated construct of polyimide and wire (322), the wire embedded into the polyimide in a braided or spiral wound pattern, is placed over the highly flexible section (319). Proximal of the highly flexible section (319), both proximal needle shaft sections (321) preferably comprise stainless steel. In the embodiment of FIG. 191C, the distal section (320) comprises stainless steel, while the section in between the distal section (320) and proximal section (321) which lies at the center of the highly flexible section (319), also termed the flexible shaft portion (326), comprises nitinol. In the embodiment of FIG. 191D, the flexible shaft portion (326) and distal end section (320) comprise the same nitinol tube member. The depicted junctions between nitinol tubing and stainless steel tubing preferably are held together with an adhesive (323) such as epoxy, as depicted in FIGS. 191B-C. The distal section of the embodiment depicted in FIG. 404C may be created by merely necking down the anti-kink metal-reinforced polyimide layer and creating a needle tip (318). With nitinol extending distally from the proximal needle shaft section (321), the entire distal portion of the embodiment of FIG. 191C is highly flexible—facilitating tight turn radii through tortuous paths of constraining lumens such as catheters or vessels. The embodiment of FIG. 191C, also having a highly flexible section (319) due in part to a nitinol flexible shaft portion (326), has a less flexible distal end (318, 320), complements of the stainless steel material comprising it, which may be desirable when the more dramatic flexibility of the embodiment of FIG. 191C is not desired.

Many tools and sets of tools and instruments may be controllably delivered and actuated with the help of a guide, or guide+sheath instrument combination similar to those described in reference to the needle/dilator/guide/sheath instrument arrangement disclosed above. For example, in some embodiments of the present invention, a remotely-actuated grasper, such as those available from Intuitive Surgical, Inc. of Sunnyvale, Calif., or as described in U.S. patent application Ser. No. 10/011,371 to endoVia Medical, Inc., may be used in concert with a remotely steerable guide instrument system sized appropriately for the particular application. In other embodiments, a remotely steerable guide instrument system such as those described herein may be utilized to place a guidewire, inject with a needle gene or cell therapy into the heart wall, the parenchyma of an organ, etc. In yet other embodiments, a remotely steerable guide instrument system such as those described herein may be utilized to carry a camera and/or a radiation source (such as a light, or infrared source for cameras such as those available from CardioOptics, Inc.). In still other embodiments, a remotely steerable guide instrument system such as those described herein may be utilized to carry a cryo-ablation system or laser ablation system to a precise location adjacent an organ, inside the heart, etc. In still further embodiments, a remotely steerable guide instrument system such as those described herein may be utilized to place a pacing lead into the coronary sinus, or place a sensor within the heart or vessels for monitoring, for example, pressure within the left ventricle. Such pressure monitoring may be used, for example, to closely watch heart failure patients and adjust medicine, diuretics, fluid intake, etc. In yet further embodiments, a remotely steerable guide instrument system such as those described herein may be utilized to deploy an expandable or expanded medical device, such as a stent or stent graft, into a vessel or other lumen with a high degree of precision and visualization. In other embodiments, multiple remotely steerable guide instrument systems such as those described herein may be utilized in a procedure. For example, one guide instrument could be used for precisely positioning a camera and light source while another guide instrument could be used for precisely positioning an interventional instrument such as a grasper, ablation tool, injection needle, etc. Still further embodiments may include tools including but not limited to: graspers, 2 degree of freedom (DOF) articulating guidewires (roll+bend), biopsy forceps, high energy directed ultrasound probes, biopsy needles, lasers, aspiration needles, ultraviolet (UV) light sources, guides for pacing or other lead delivery, needles for drug delivery and biopsy, scissors, radio frequency (RF) ablation probes/tools/needles, clamp and stitch tools, cryo ablation devices, pledget placement devices, ultrasound ablation tools, clip delivery tools, ultrasound tissue welding probes, flow transducers, RF tissue welding tools, and pressure transducers. It should be appreciated that a complete embodiment of the invention may incorporate any more such tool or instrument.

Figure 192A:
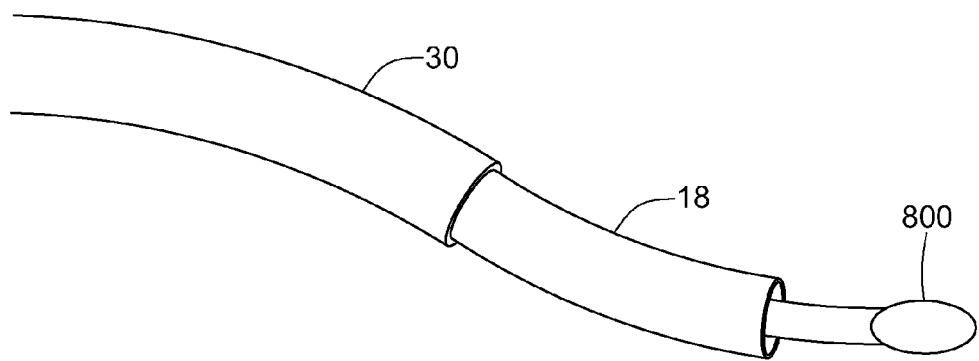
FIGS. 192A-192Q illustrate exemplary embodiments of various tools threaded through the working lumen of a guide instrument.
Figure 192B:
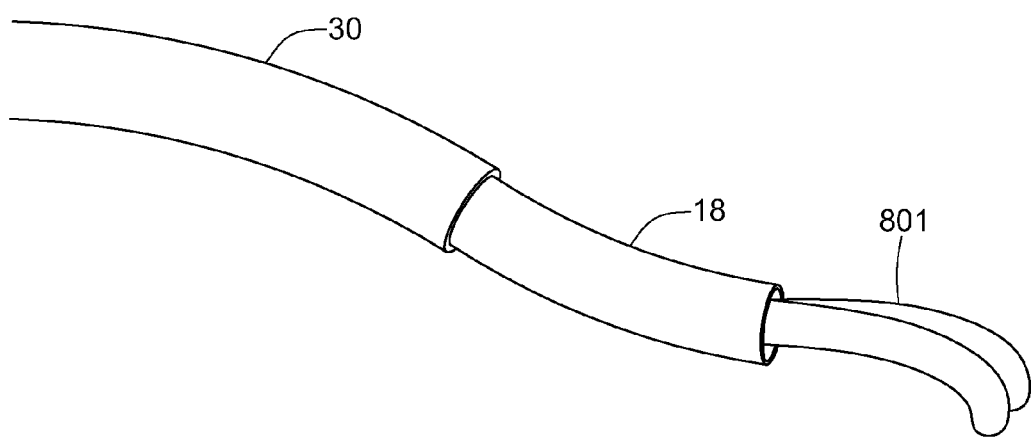
Figure 192C:
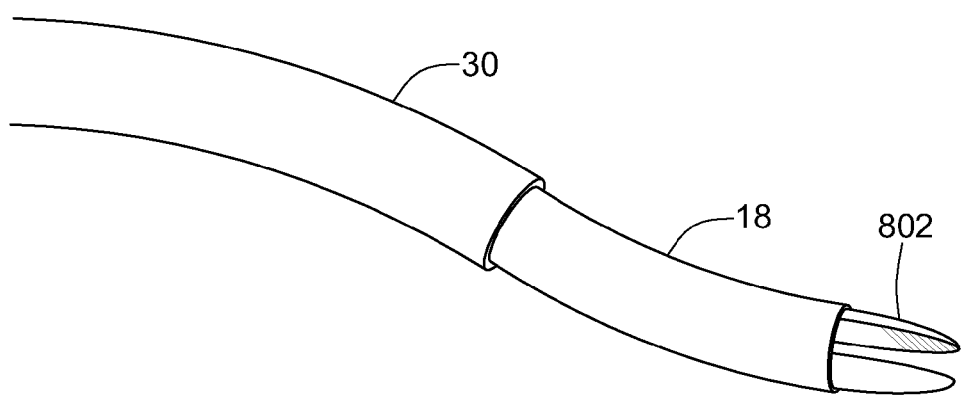
Figure 192D:
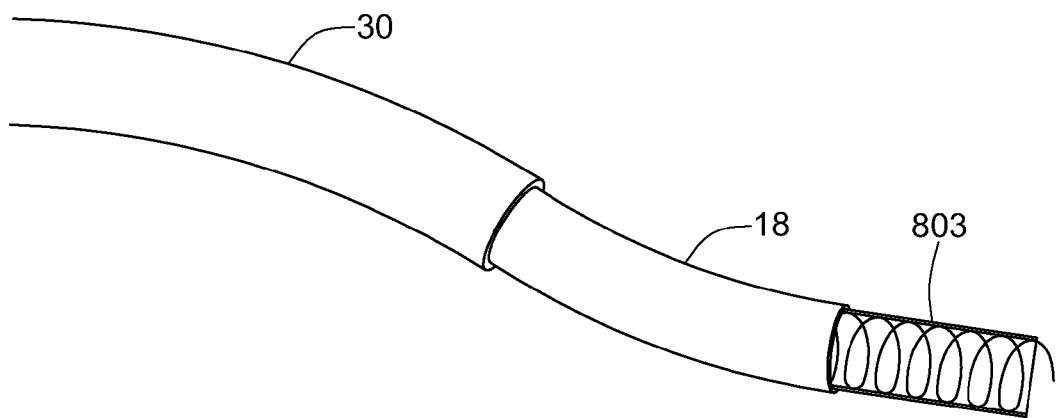
Figure 192E:
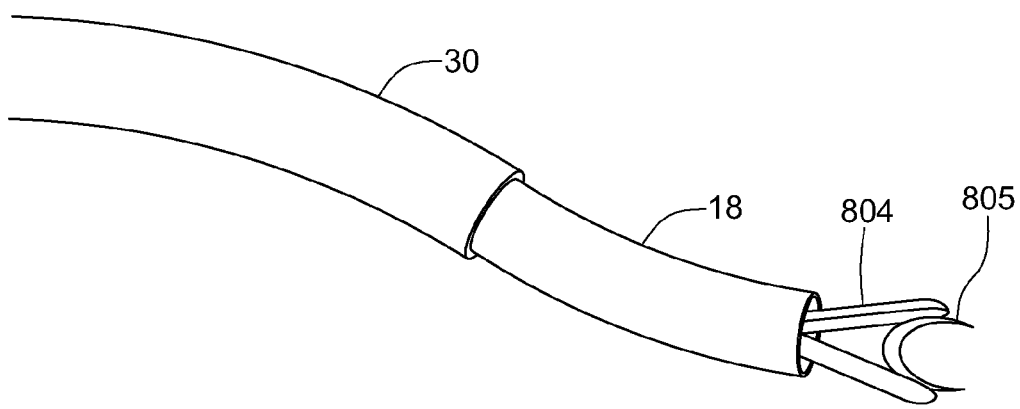
Figure 192F:
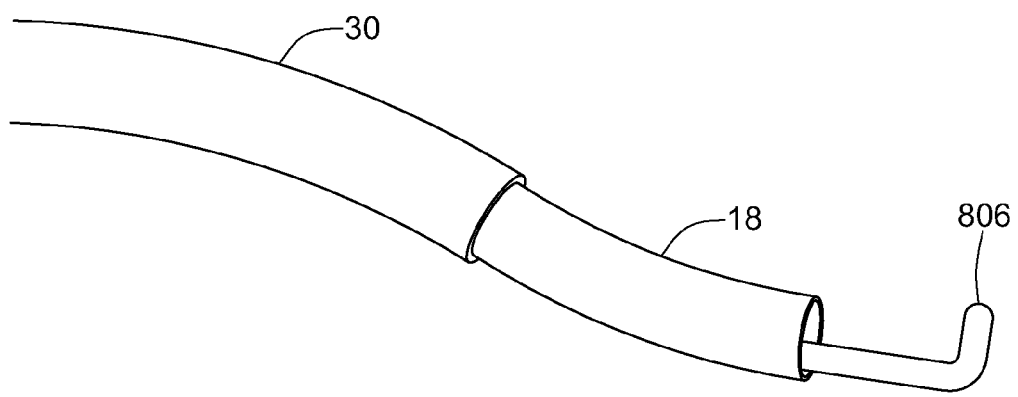
Figure 192G:
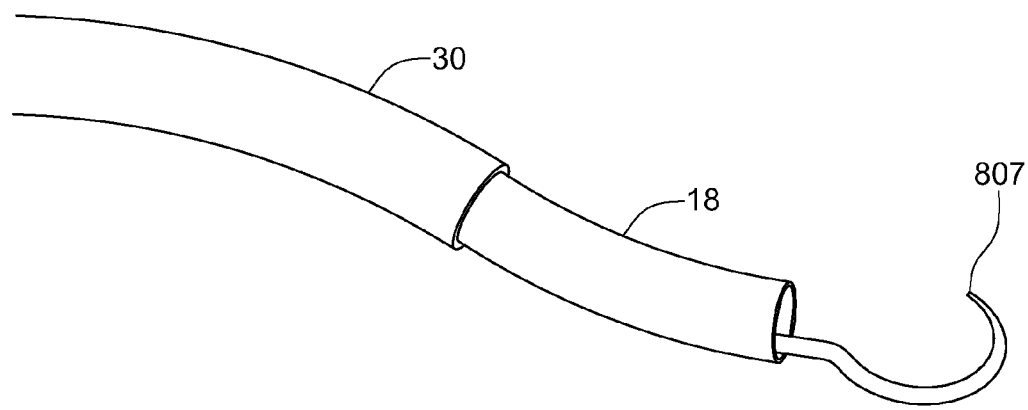
Figure 192H:
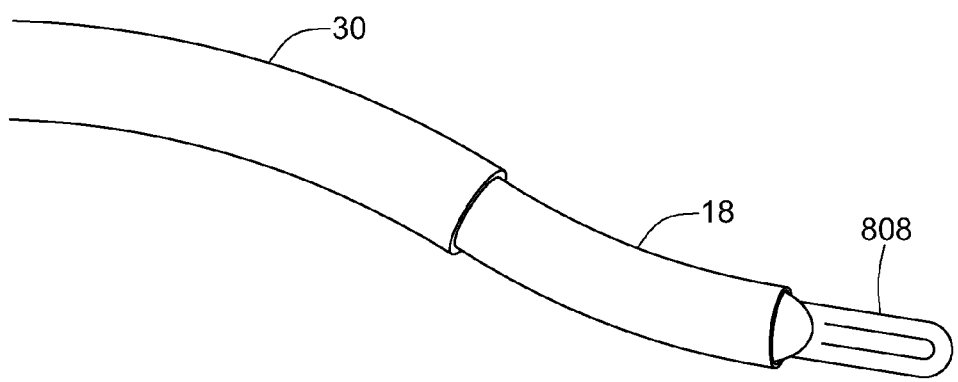
Figure 192I:
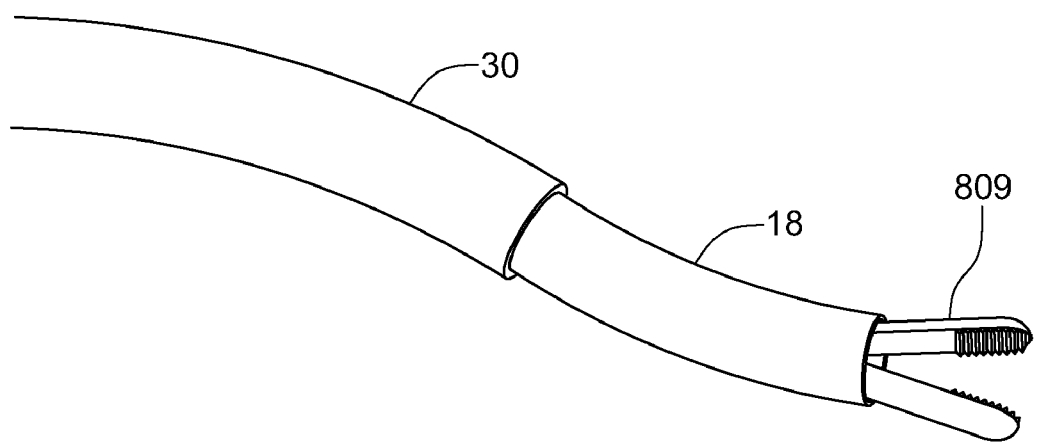
Figure 192J:
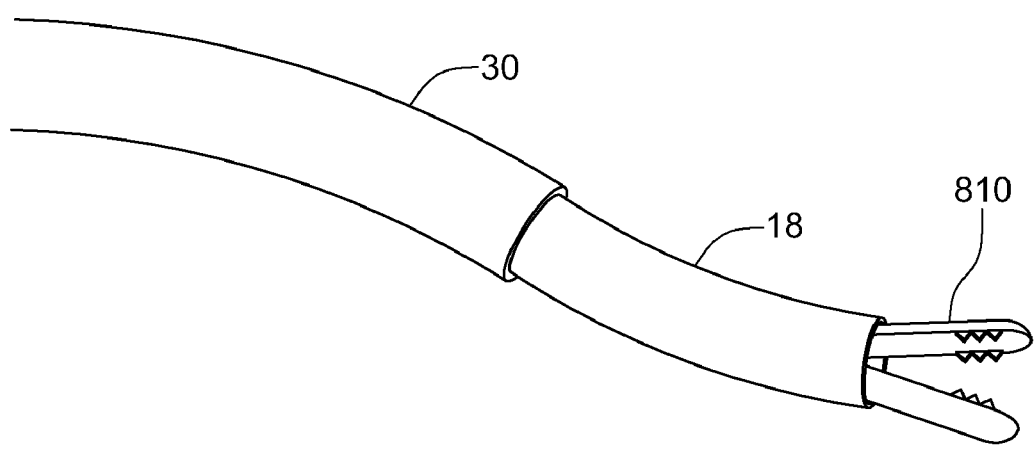
Figure 192K:
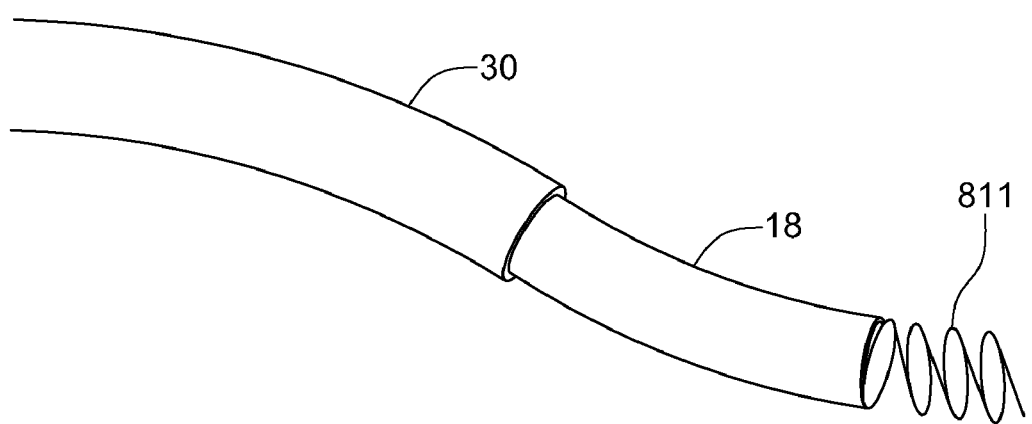
Figure 192L:
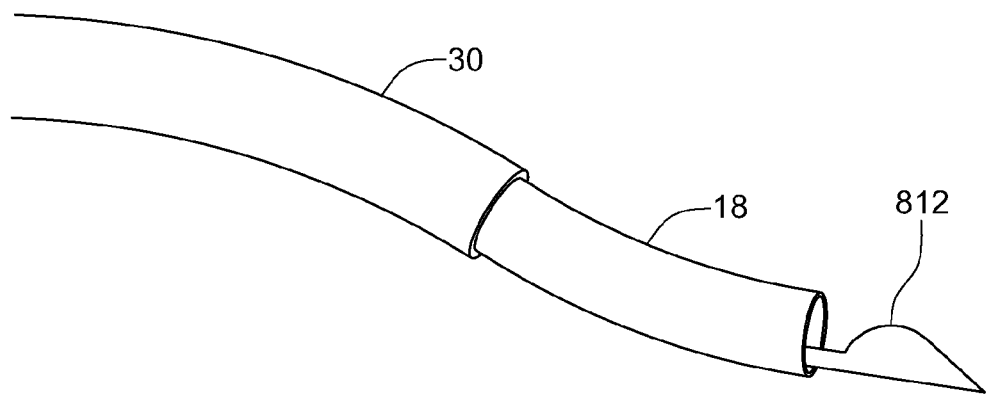
Figure 192M:
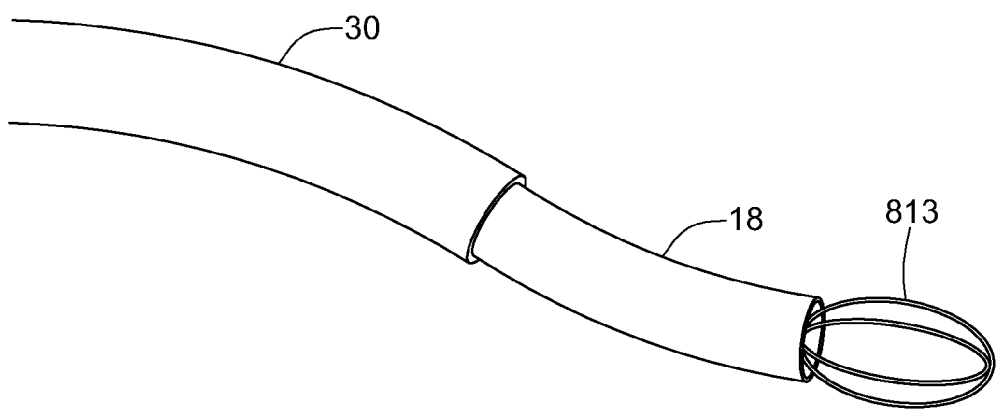
Figure 192N:
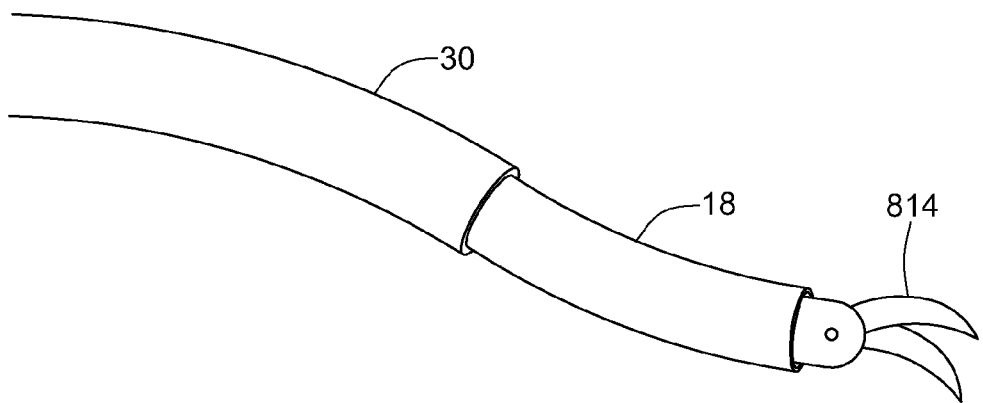
Figure 192O:
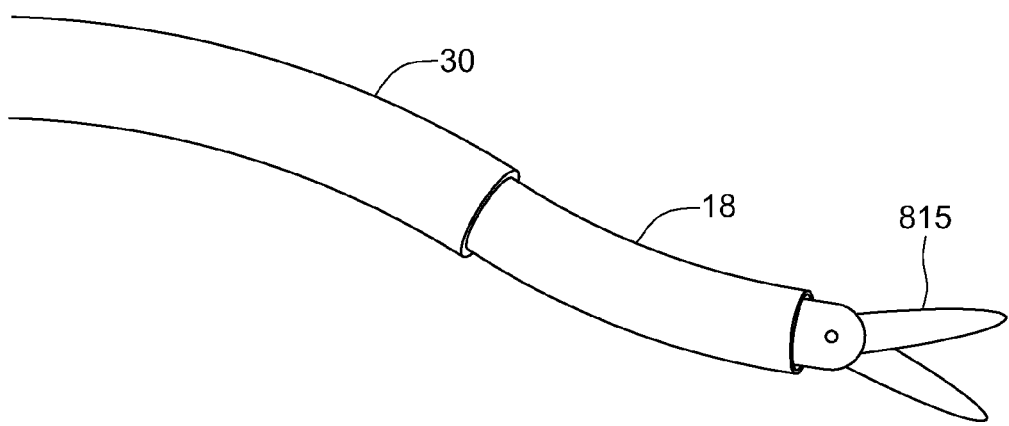
Figure 192P:
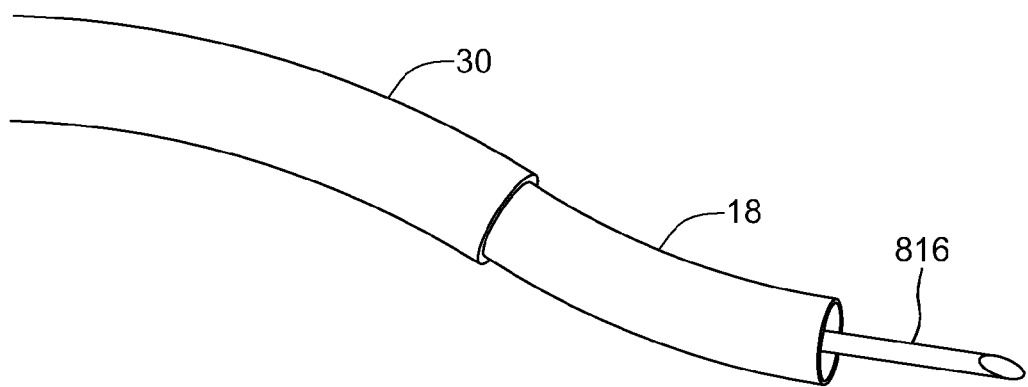
Figure 192Q:
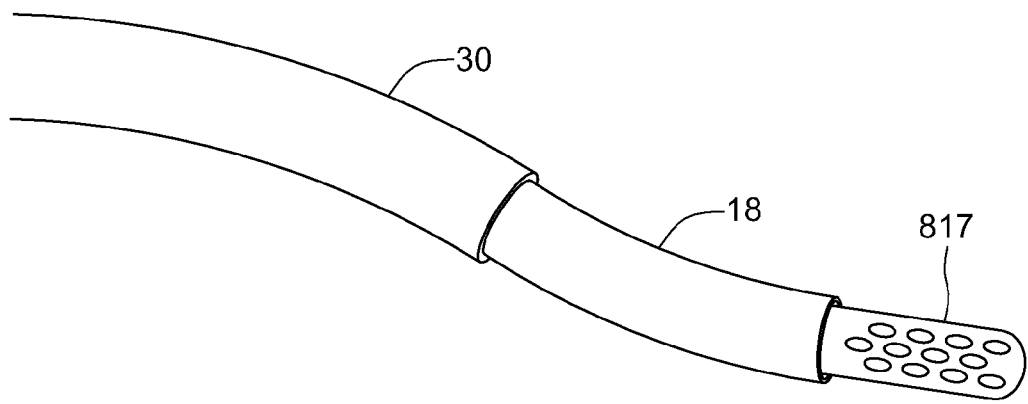

Referring to FIGS. 192A-192Q, various embodiments of the invention may employ many different tools that are positioned in the working lumen of a guide instrument (18), which is depicted as coaxially coupled to a sheath instrument (30), of a robotic catheter system. Tools such as the Kittner absorbent probe (800) of FIG. 192A, the Maryland dissector (801) of FIG. 192B, the needle holder/grasper (802) of FIG. 192C, the multi-fire coil tacker (803) of FIG. 192D, the stapler or clip applier (804) of FIG. 192E, configured to apply clips or staples (805), the cautery probe (806) of FIG. 192F, the cautery hook (807) of FIG. 192G, the shovel/spatula cautery probe (808) of FIG. 192H, the serrated graspers (809) of FIG.

192I, the tethered graspers (810) of FIG. 192J, the helical retraction probe (811) of FIG. 192K, the scalpel (812) of FIG. 192L, the basket capture tool (813) of FIG. 192M, the curved scissor (814) of FIG. 192N, the straight scissor (815) of FIG. 192O, the needle (816) of FIG. 192P, and the irrigation tool (817) of FIG. 192Q may be operated or positioned with an independent tool actuation through, for example, a separate tension member coaxially positioned along with or through the tool. For example, graspers may be spring-biased to stay open or stay closed—and may be forcibly opened or closed with a tension member specifically adapted to cause such actuation proximally.

Figure 193:
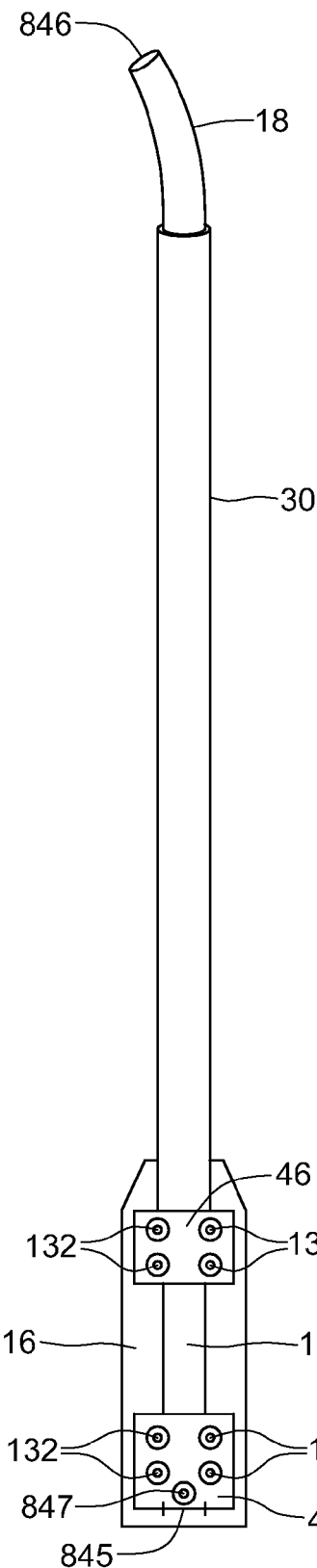
FIG. 193 illustrates an embodiment of instrument and tool control configuration for coaxially interfaced guide and sheath instruments.

With each use of a guide instrument (18), a sheath instrument (30) may also be used to provide greater functionality and load capability. FIG. 193 depicts an embodiment of a control/actuation configuration of an instrument assembly comprising a guide instrument (18) and sheath instrument (30), each of which are operated instrument by an instrument driver (16). FIG. 193 depicts an embodiment wherein a sheath instrument (30) having a sheath instrument base (46) configured with four control element interface assemblies (132) independently actuatable from the instrument driver (16) is paired with a guide instrument (30) having a guide instrument base (48) configured with four control element interface assemblies (132) independently actuatable from the instrument driver (16). The working lumen access port (845) and working lumen distal aperture or port (846) are also illustrated. Such an embodiment may be configured such that the sheath instrument (30) has steerability by four independent tension elements, while the guide instrument has steerability by four independent tension elements—i.e., all eight tension elements may be independently and simultaneously controlled by the same instrument driver (16).

FIG. 193 also depicts an embodiment wherein a tool may be positioned into the working lumen access port (845) and electromechanically actuated through the use of an electromechanical actuator fitting (847) which may be coupled to the guide instrument base (48), for example, and also operably coupled to a tool which may be positioned into the working lumen of the guide instrument (18). As described above, FIG. 193 illustrates an embodiment capable of four tension element sheath instrument (30) control and four tension element guide instrument (18) control, as well as actuation or positioning of a tool by virtue of its mechanical association with the depicted electromechanical actuator fitting (847). Thus the depicted embodiment is capable of eight independent and simultaneous tensioning or steering actuations, as well as one tool actuation simultaneously and independently, all from the same instrument driver, as depicted. For example, a tool, such as a tethered grasper, may be actuated with a tension element operably coupled to the actuator fitting (847) in a similar manner that the tension elements described above are operably coupled to the control element interface assemblies (132). In other embodiments, lead screws, racks and pinions, and other mechanical couplings are desirable for operating or controlling a tool. In other embodiments without electromechanical tool actuation, or in embodiments where additional actuation is desired besides electromechanical, tools may be actuated manually by the operator at a position proximal to the working lumen access port (845).

Figure 194A:
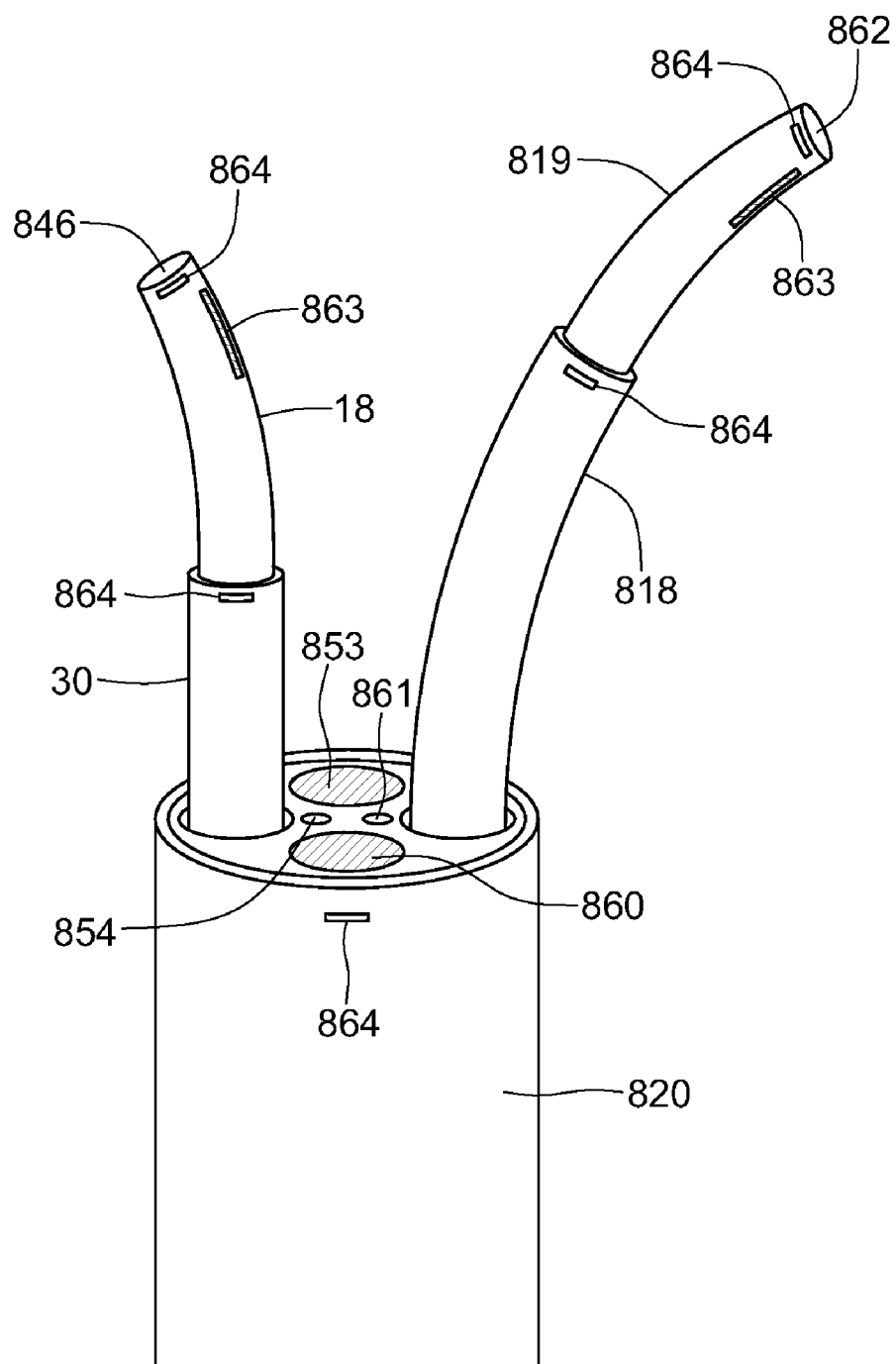
Figure 194B:
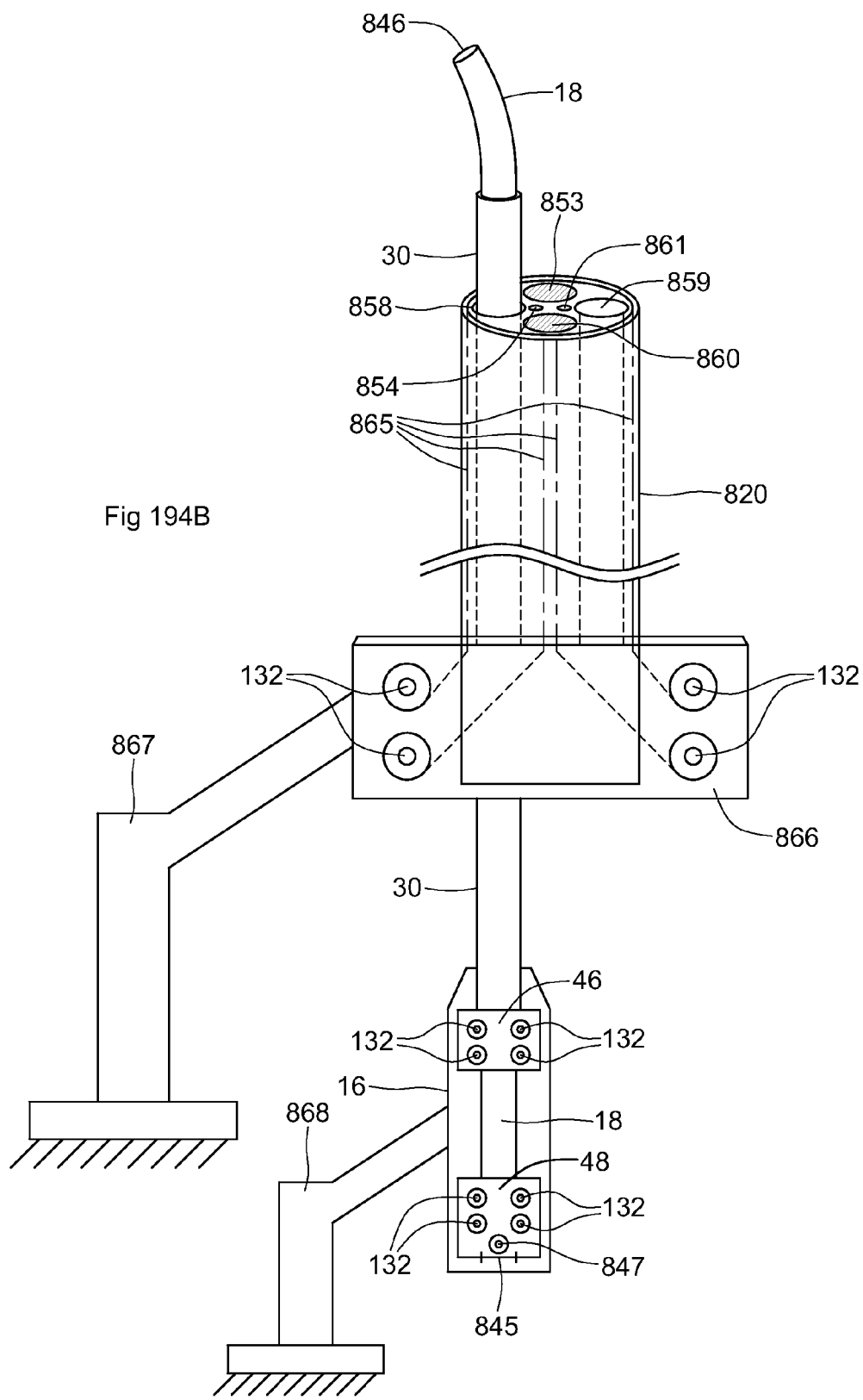
Figure 194C:
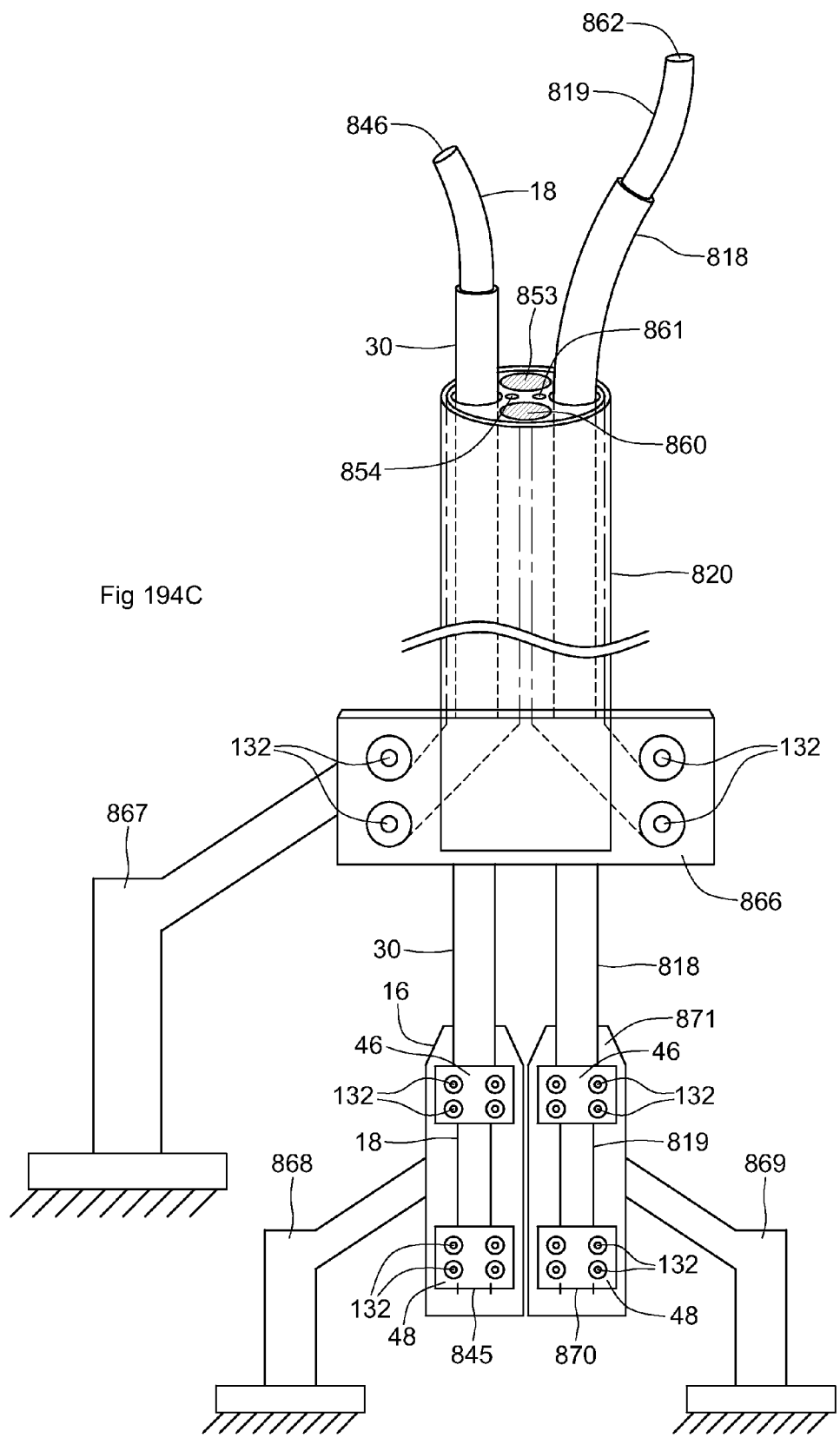

Referring to FIGS. 194C, D, F, and G, embodiments wherein one or more pairings of sheath instrument (30) and guide instrument (18) may be positioned through a larger diameter instrument which may have one or more working lumens and be configured to carry one or more image capture devices, an imaging radiation source, and an irrigation port, for example. Referring to FIG. 194C, a sheath (30) and guide (18) instrument pairing are positioned within a first working lumen (858) defined by a larger or "parent" endoscopic instrument (820), which carries first (853) and second (860) image capture devices, which may be utilized for stereoscopic imaging, an imaging radiation source (854), such a light radiation or infrared radiation source, and an irrigation port (861). Each of the image capture devices may, for example, comprise a lens, a CCD chip, optical fiber, or an infrared or other radiation detector. The working lumens (858, 859) preferably are sized to slidably interface with the outside of a sheath or guide instrument, such as the sheath/guide combination depicted in FIG. 193. The embodiment depicted in FIG. 194C also comprises another sheath instrument (818) and guide instrument (819), the guide (819) defining a working lumen distal aperture (862) through which various tools may be positioned.

Referring to FIG. 194C, each of the sheath instruments (30, 818), guide instruments (18, 819), and/or the larger endoscopic instrument (820) may carry a localization sensor (864) or an ultrasound device (863), among other things. Such instrumentation may be utilized to navigate, visualize, and coordinate the various instruments relative to each other and surrounding structures.

FIGS. 194D, F, and G illustrate embodiments similar to that depicted in FIG. 194C, with the exception that more proximal aspects of the embodiments of FIGS. 194D, F, and G are depicted as well as the more distal portions of such arrangements. Referring to FIG. 194D, an instrument base (866) is depicted for the parent instrument (820) having four control element interface assemblies (132) configured for independent interactions with four independent motors coupled thereto by a parent instrument driver (not shown) which is preferably similar to that illustrated in reference to instrument driver (16) variations above. The four control element interface assemblies (132) preferably are coupled to four independent tension elements (865) configured to omnidirectionally steer the preferably flexible parent instrument (820). In other variations, the parent instrument may have less than or more than four tension elements—or none, in which case the parent instrument is more similar to a conventional unsteerable endoscopic instrument. As depicted in the embodiment of FIG. 194D, a guide instrument (18) and sheath instrument (30) are positioned through a working lumen (858) of the parent instrument (820), and proximally, an instrument driver (16) for the guide (18) and sheath (30) instruments is depicted in a configuration similar to that described in reference to FIG. 502D. FIG. 194G depicts an embodiment having two instrument set and driver configurations similar to that described in reference to FIG. 194D, while FIG. 194F depicts an embodiment having two instrument set and driver configurations similar to that described in reference to FIG. 194D, absent the electromechanical tool actuator (847). The instrument drivers for sheath/guide instruments, and larger parent instrument may be coupled to an object such as an operating table, operating room floor, operating room ceiling, or other structure utilizing a support structure such as the fixed embodiments depicted (867, 868, 869) in FIGS. 194D, F, G, or support structure embodiments described above in reference to FIGS. 1, 2, and 3-3.10b.

Combinations and permutations of the instrumentation described in reference to the embodiments in FIGS. 192-194 may be utilized for medical diagnosis and/or intervention throughout the body. In some scenarios, it is useful to have a separate real-time imaging modality such as ultrasound, fluoroscopy, and/or optical or infrared camera casting a field of view from a separate position relative to operational instruments such as those depicted in reference to the embodiments in FIGS. 192A-192Q.

For example, in an insufflated laparoscopy procedure, it may be preferable to have an endoscope positioned near the umbilicus, and have an interventional tool, such as those embodiments depicted in FIGS. 192A-192Q, positioned into the insufflated interventional theater, in the field of view of the endoscope, from a different port. In other embodiments, it is preferable to have real-time imaging components coupled to the instrument or instruments, in configurations similar to those described in reference to FIGS. 194. For example, in a gastrointestinal procedure with limited interventional cavity space, it may be preferable to have one or more imaging devices coupled to the operational instruments, as in a configuration wherein a tool is within the field of view of the imaging device, and the tissue structure targeted for intervention is in the background. In other scenarios, it may be preferable to have both on-board imaging as well as remotely positioned imaging.

Figure 195A:
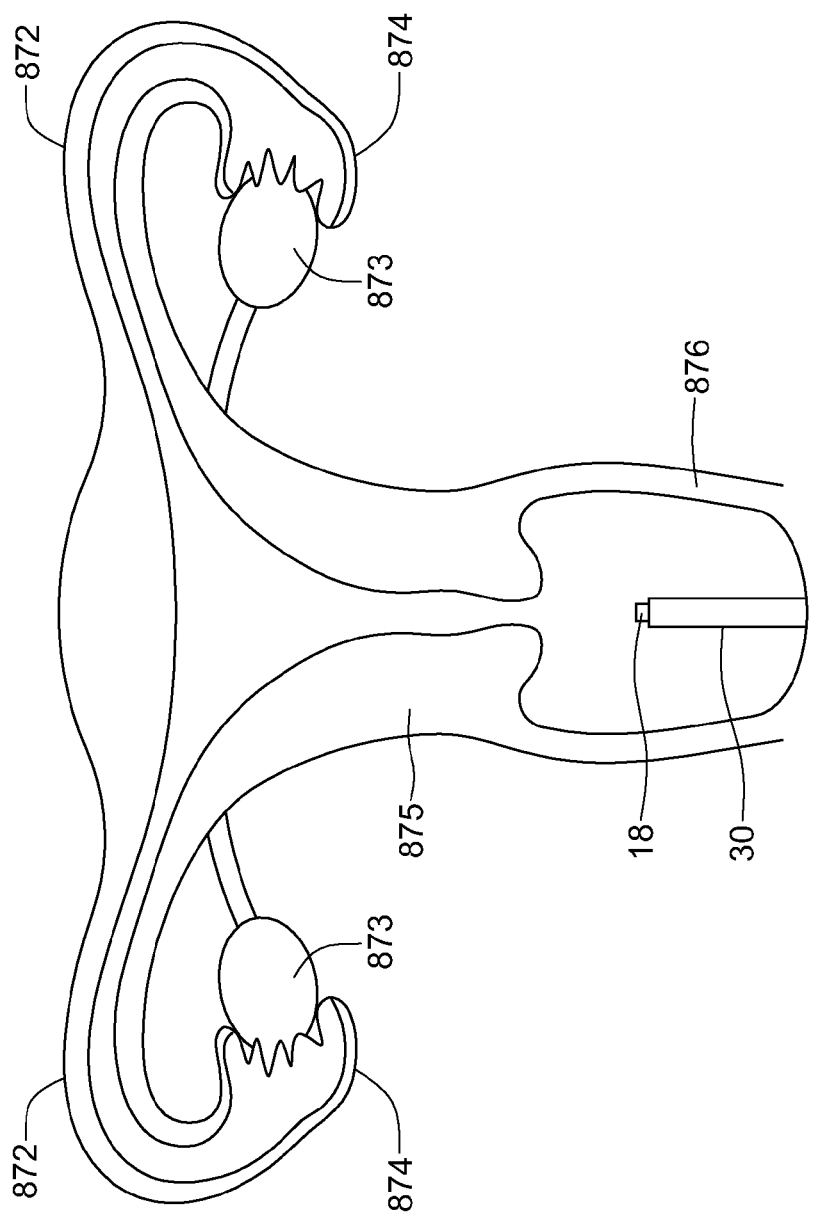
Figure 195C:
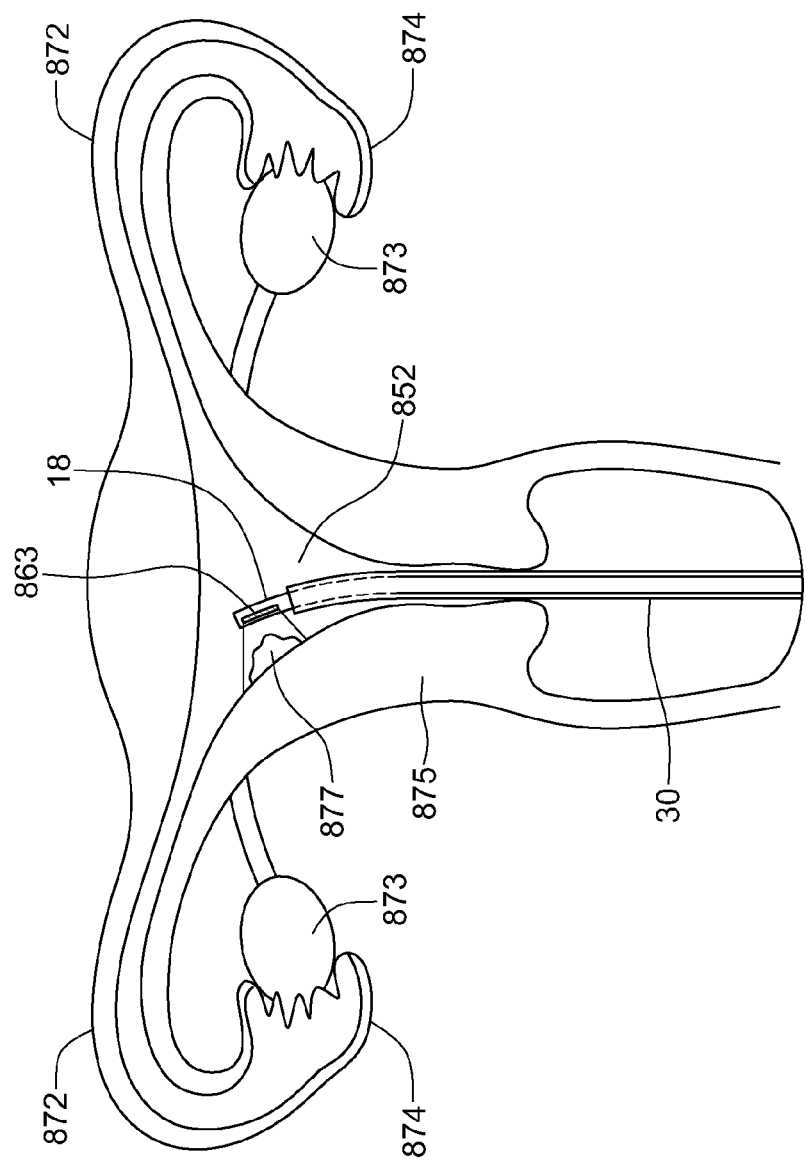
Figure 195D:
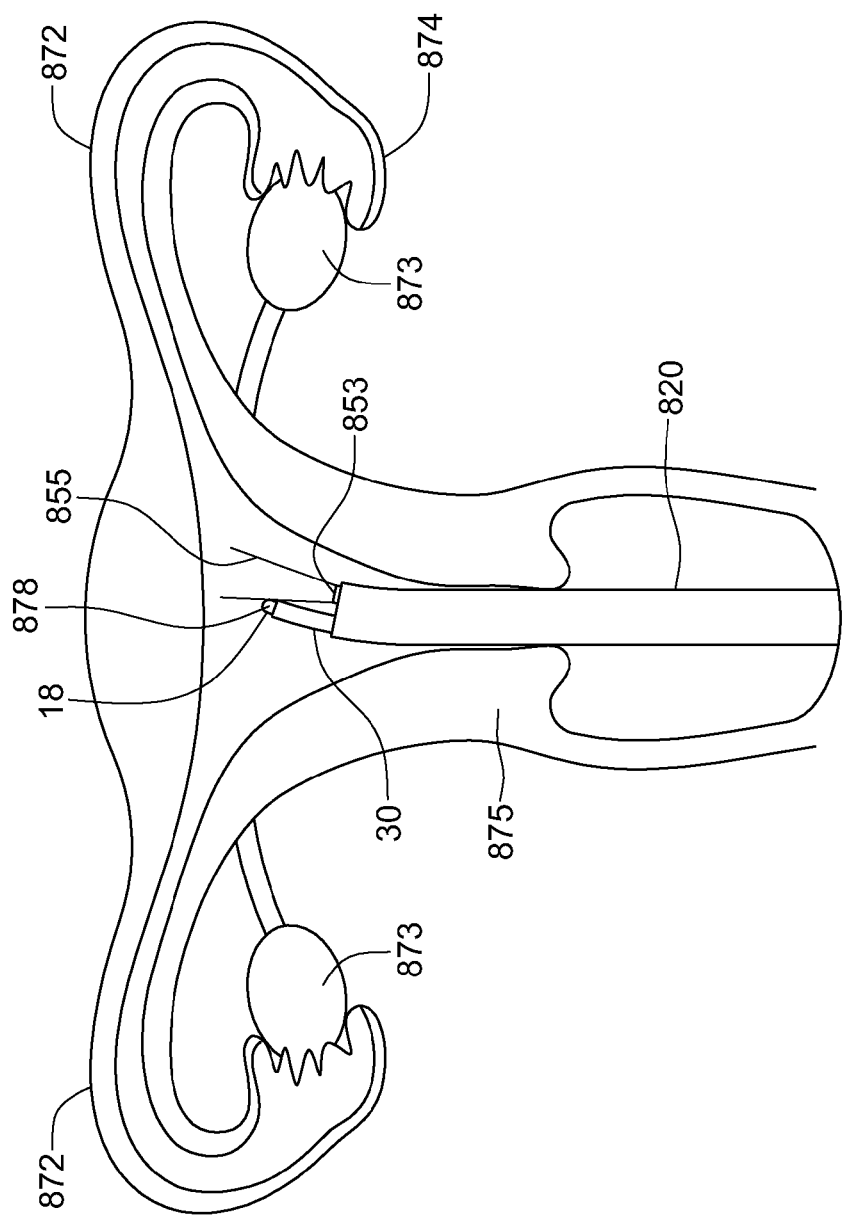
Figure 195E:
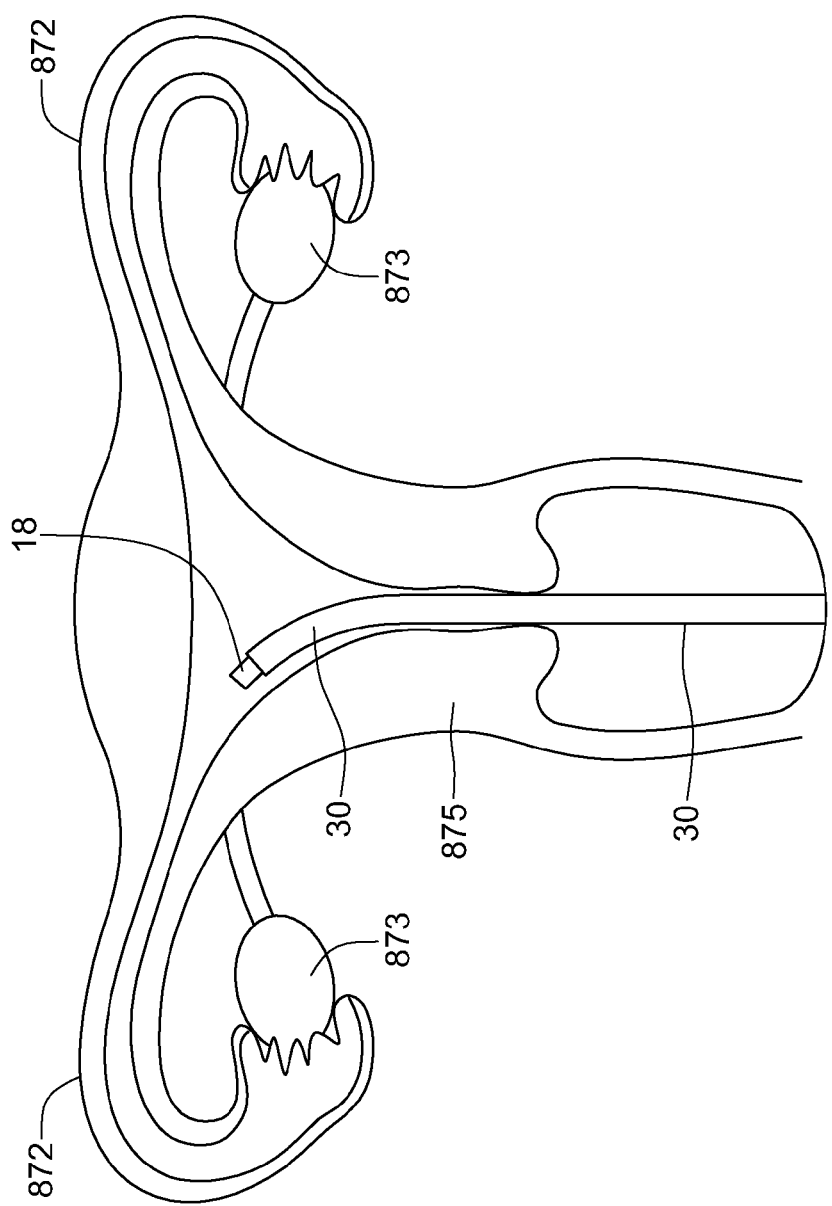

Transvaginal Intervention:

Referring to FIG. 195A, a steerable guide (18) instrument and steerable sheath instrument (30) according to one embodiment maybe be coaxially advanced transvaginally into the uterus (875). A tool (not shown), such as one of those disclosed in FIGS. 192A-Q may be coaxially coupled within the guide (18). Referring to FIG. 195B, the guide and sheath may be advanced as the assembly is also steered. Imaging modalities such as fluoroscopy, transcutaneous ultrasound, and instrument-mounted ultrasound may be utilized to navigate the uterus (875). The vagina (876), uterus (875), fallopian tubes (872), and salpinx (874), may be navigated to access the ovaries (873) and peritoneum (887). The uterus (875) may be injected with saline or other fluid to facilitate imaging. Referring to FIG. 195C, for example, a saline-filled uterus (875) may be imaged with an ultrasound device (863) coupled to the guide instrument (30), such as a side firing ultrasound array, to observe tissue lesions (877) of interest. Referring to FIG. 195D, in another scenario the uterus (875) may be insufflated, and a steerable endoscopic instrument assembly (820), such as that depicted in FIGS. 194, may be advanced with a forward-looking image capture device (853), such as an optical imaging device. This may assist in locating the opening of a fallopian tube (872). Injection of saline, and atraumatic tissue manipulation using the distal tip of the pertinent instrument may also assist in locating a fallopian tube (872) opening, in addition to advanced imaging modalities as discussed herein. Referring to FIG. 195E, a sheath (30) and guide (18) are depicted steerably advancing toward a fallopian tube (872) opening.

Figure 195F:
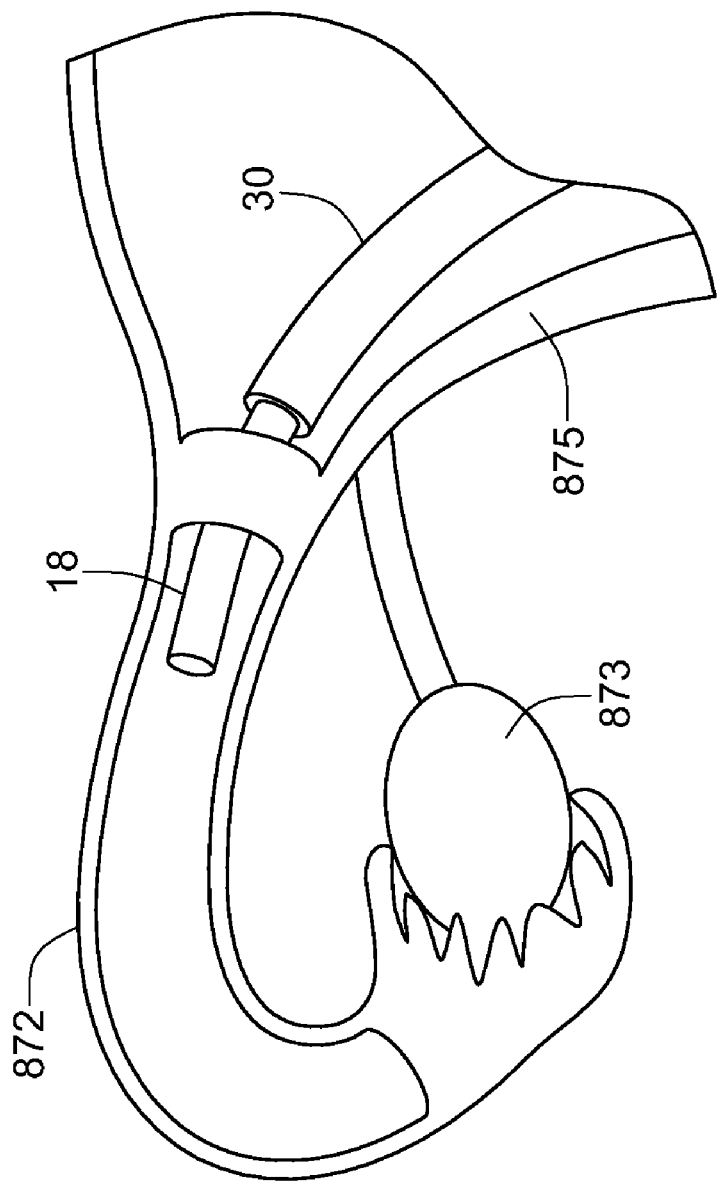
Figure 196A:
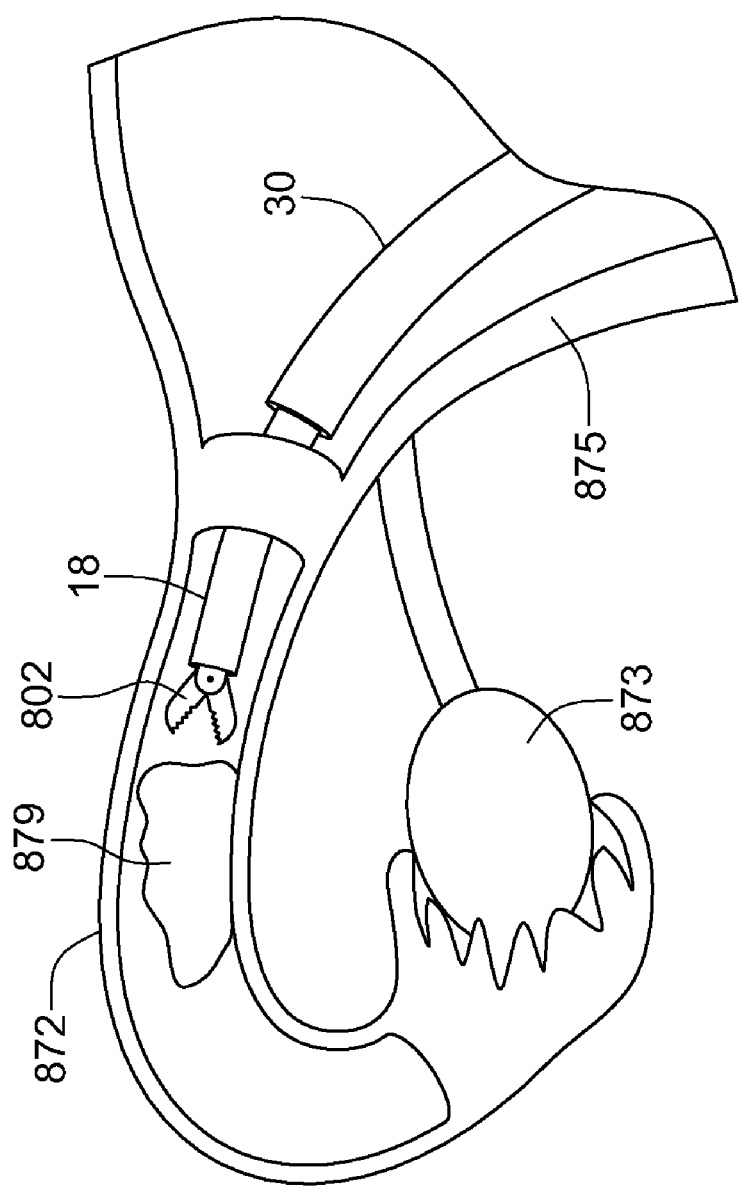
FIGS. 196A-196C illustrate an exemplary system and procedure to remove an occlusion from a fallopian tube with a remotely actuated grasper tool positioned in a guide instrument.
Figure 196B:
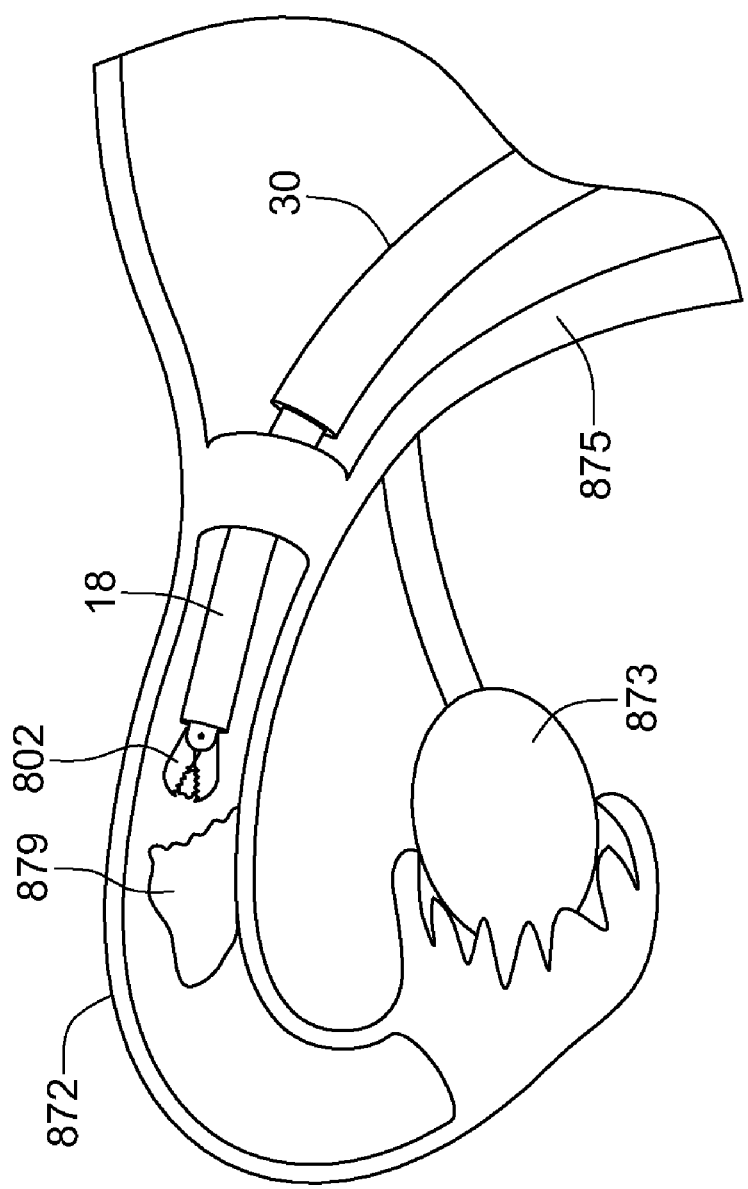
Figure 196C:
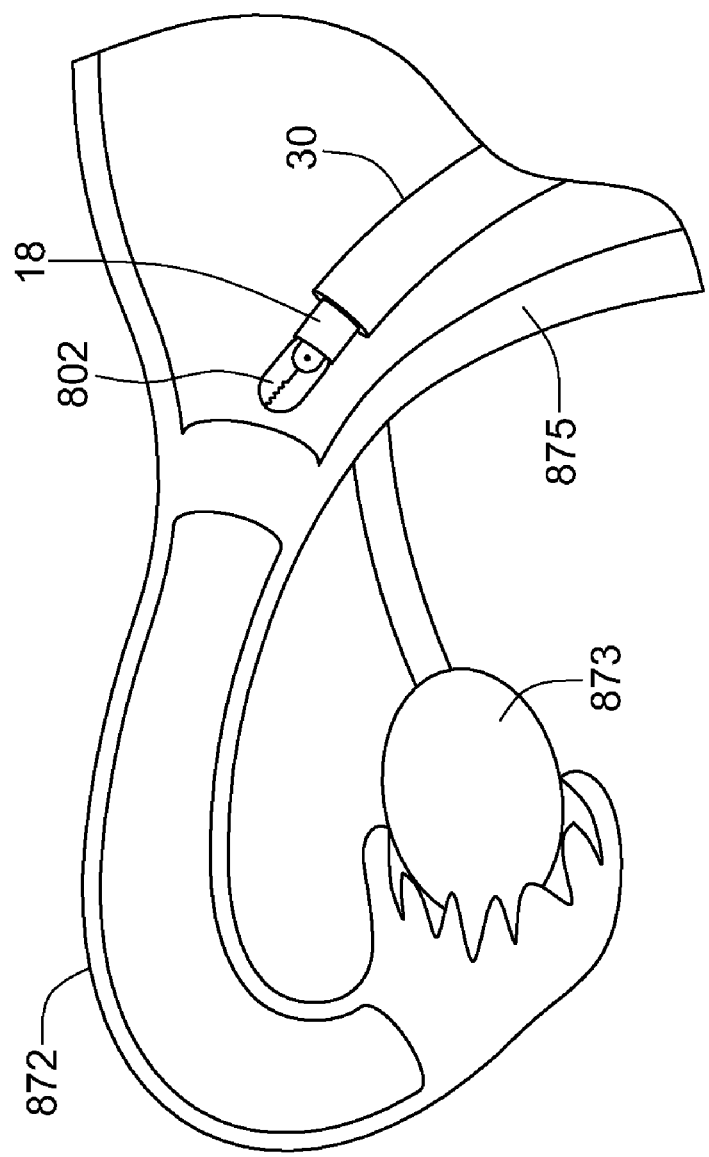

Referring to FIG. 195F, the sheath (30) has been advanced just proximal of the opening of the fallopian tube (872), while the guide (18) has been advanced into the fallopian tube (872). Such a configuration may be utilized to facilitate a falloposcopy procedure, a hystero-salpingogram with contrast agent and fluoroscopy (in one embodiment, utilizing the sheath or an associated balloon to proximally occlude the fallopian while injecting contrast through the guide or another lumen (thus avoiding pressurizing the entire uterus with contrast as in a conventional procedure), or to remove an occlusion (879), such as a tubal pregnancy, from a fallopian tube, as shown in FIGS. 196A-196C, where a grasper tool (802) is depicted positioned down the working lumen of a guide instrument, and is remotely actuated at a proximally-positioned instrument driver which may be manually or electromechanically actuated, as described above. In one embodiment, a configuration such as that depicted in FIG. 194D with a grasper tool (802) such as that depicted in FIG. 192J may be utilized. In another embodiment, a configuration such as that depicted in FIG. 194D, but absent the larger parent endoscopic instrument, may be utilized with a grasper tool (810) such as that depicted in FIG. 192J. Suction and/or injection of saline or other fluid may also be utilized to facilitate clearance of an occlusion (879) with an apparatus such as that depicted in FIG. 195F.

Figure 197A:
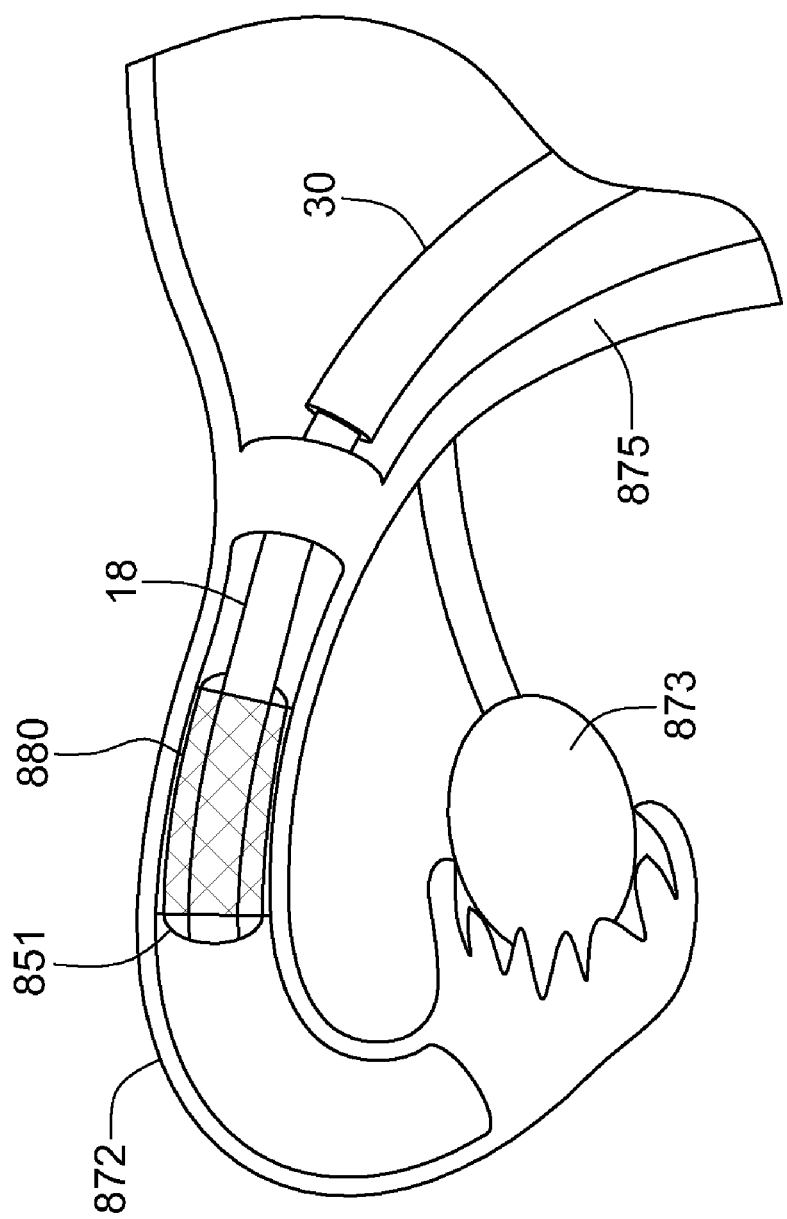
FIGS. 197A-197B illustrate an exemplary system and procedure to deploy an expandable prosthesis in a fallopian tube with a balloon and a guide instrument.
Figure 197B:
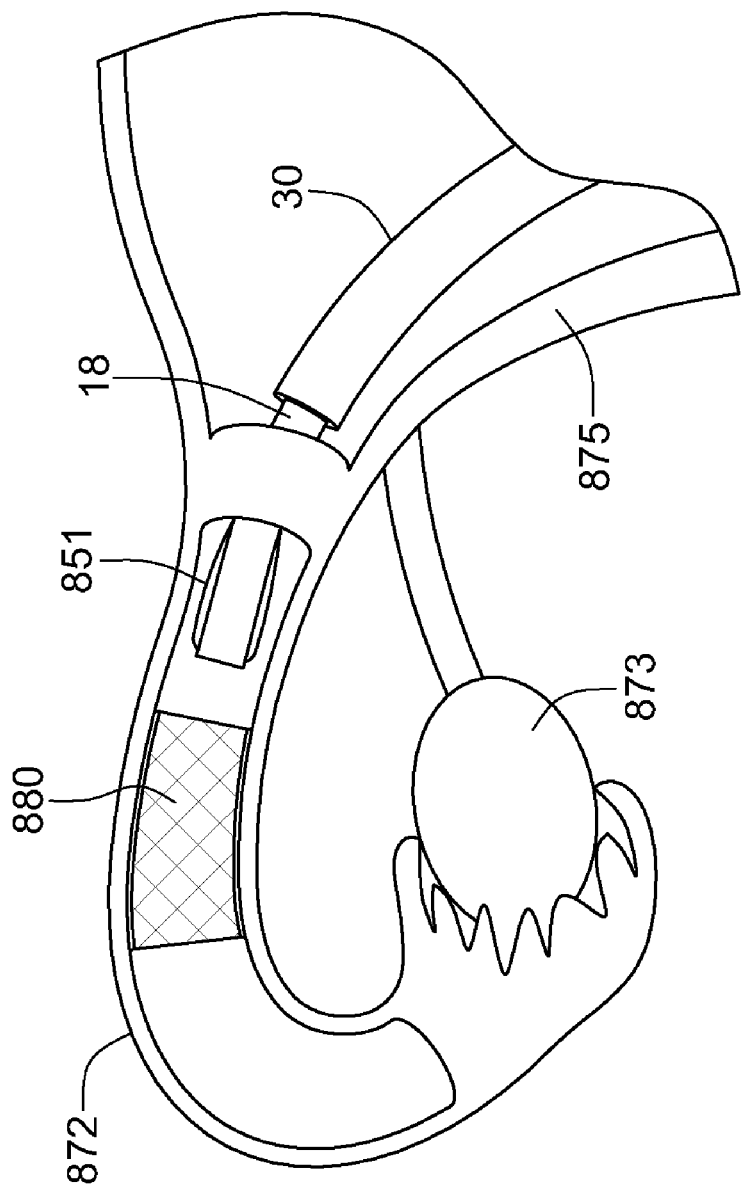

Referring to FIG. 197A, the guide may comprise an expandable balloon (851) at its distal end, and the expandable balloon (851) may be utilized to place an expandable prosthesis (880), such as a stent or stent graft configured to either prevent occlusion or occlude (in the case of a desired sterilization procedure) a fallopian tube (872). As shown in FIG. 197B, subsequent to deployment of the expandable prosthesis (880), the expandable balloon (851) may be contracted, and the guide (18) and sheath (30) retracted.

Figure 198A:
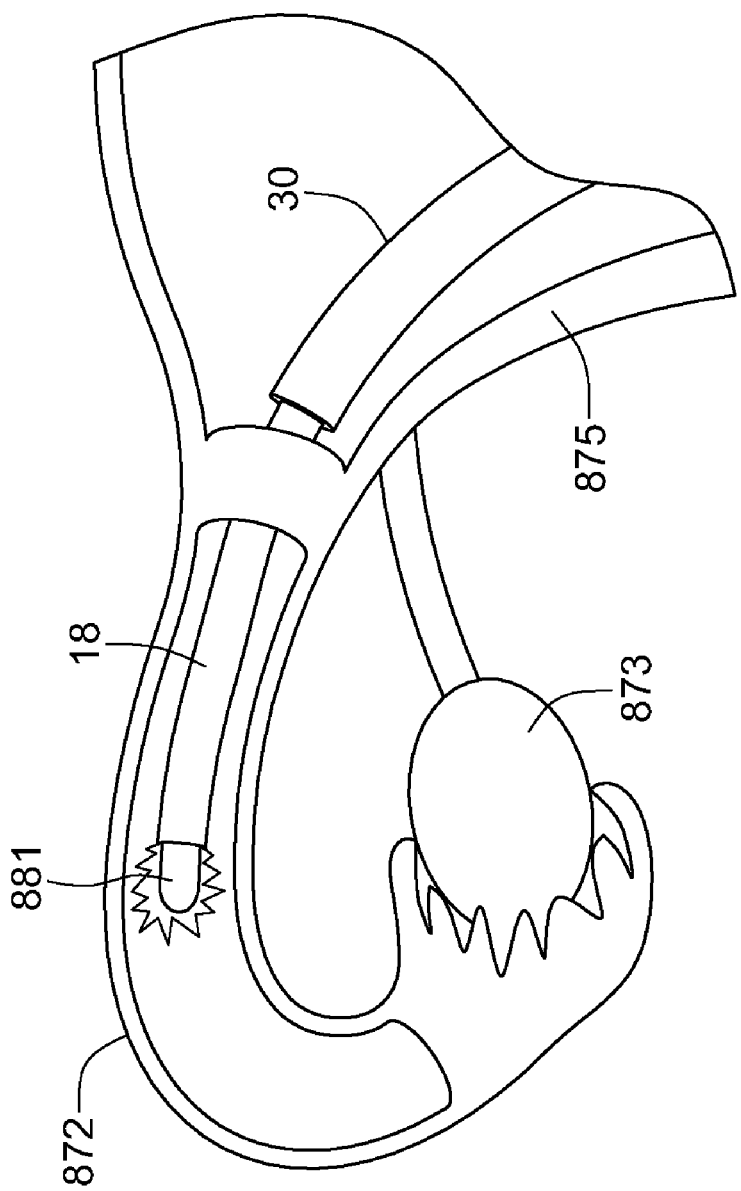
FIGS. 198A-198B illustrate an exemplary system and procedure to produce localized scarring and occlusion of a fallopian tube with an ablation probe and a guide instrument.
Figure 198B:
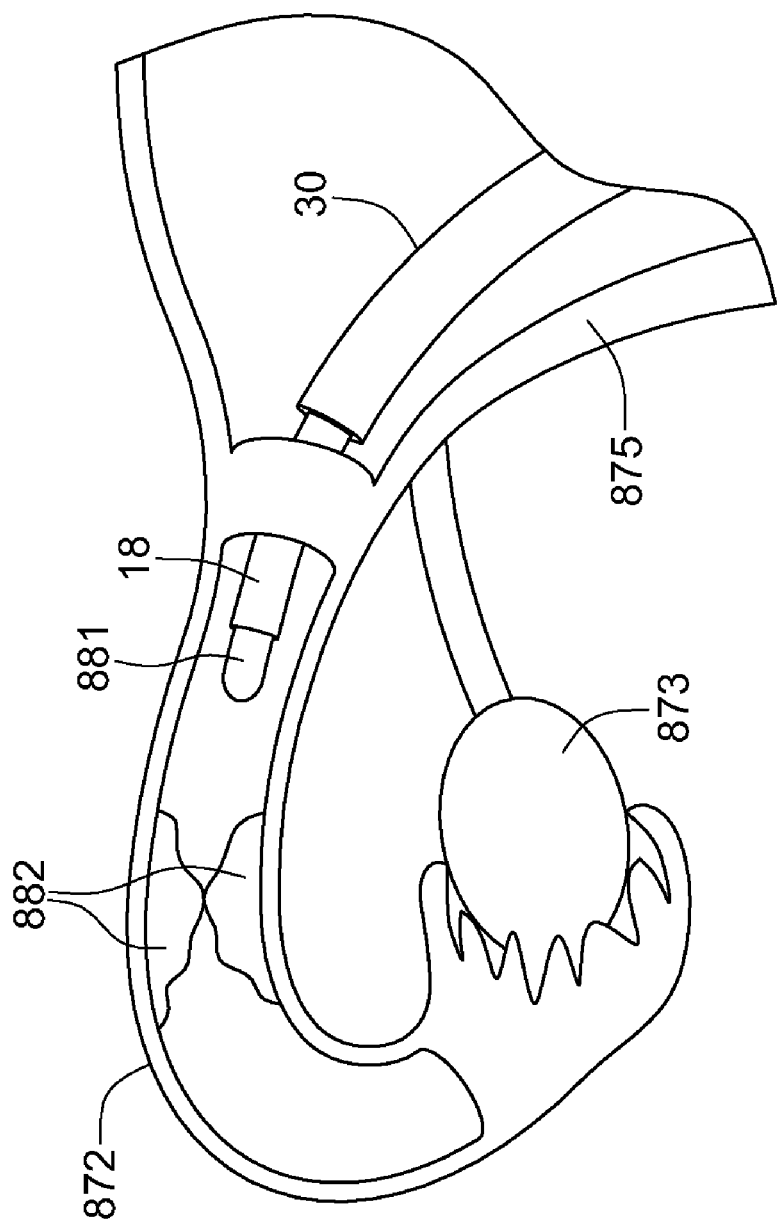
Figure 199A:
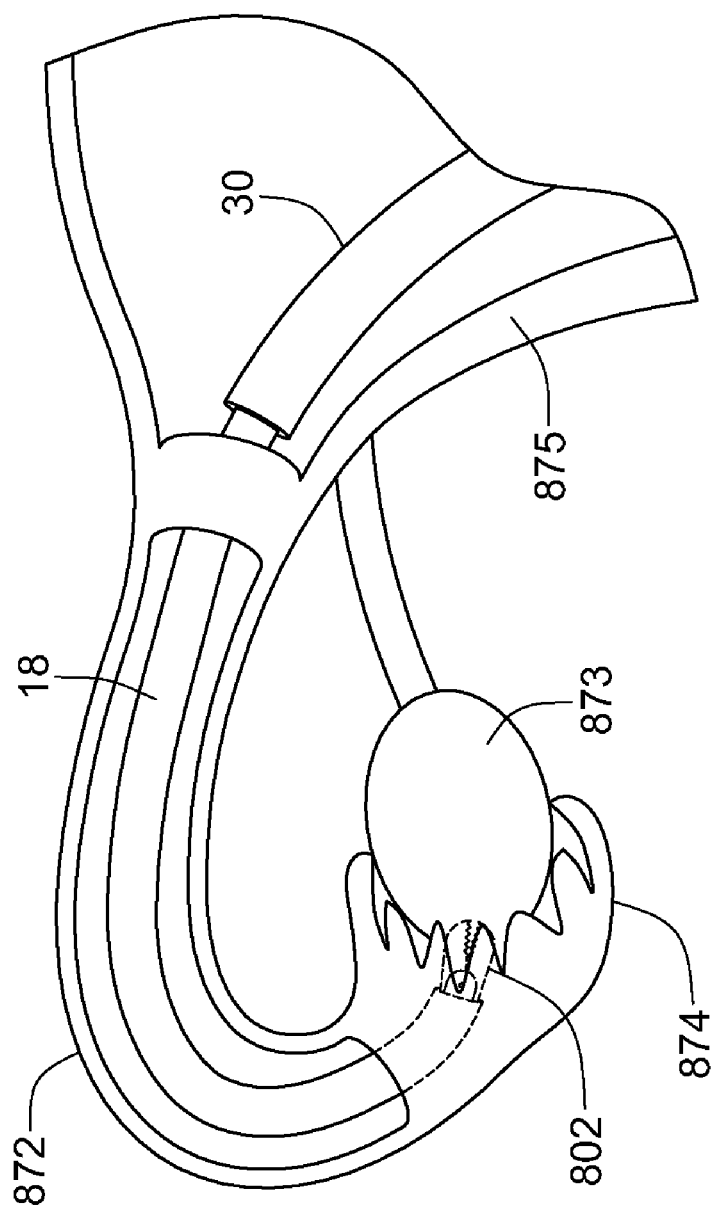
FIGS. 199A-199B illustrate an exemplary system and procedure to remove tissue from the salpinx with a grasping and/or cautery tool positioned in a guide instrument.
Figure 199B:
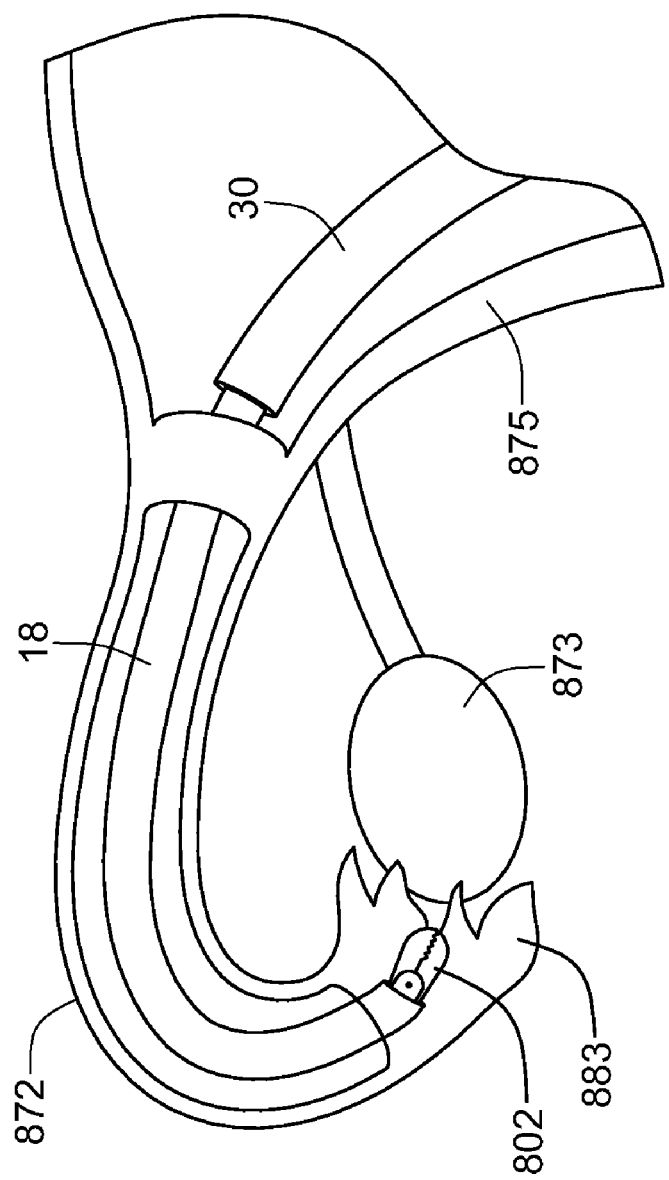

Referring to FIG. 198A, an ablation probe (881—RF, cryo, ultrasound, laser, etc) may be coupled to a guide (18) or positioned through the working lumen of a guide (18), precisely positioned, and activated to produce localized scarring (882) and intended occlusion of the fallopian for sterilization, as depicted in FIG. 198B. Referring to FIG. 509A, a grasping (802) and/or cautery tool, such as a bipolar scissors or graspers (not shown), may be utilized to remove extra tissue from the salpinx (874) which may be preventing movement of eggs from an ovary (873) into an adjacent fallopian tube (872). FIG. 509B depicts the tool resecting away a piece of tissue (883). Extra tissue, characterized as "wispy", is known to form at the salpinx (874) as a result of localized infection which may result from, for example, pelvic inflammatory disease.

Figure 200A:
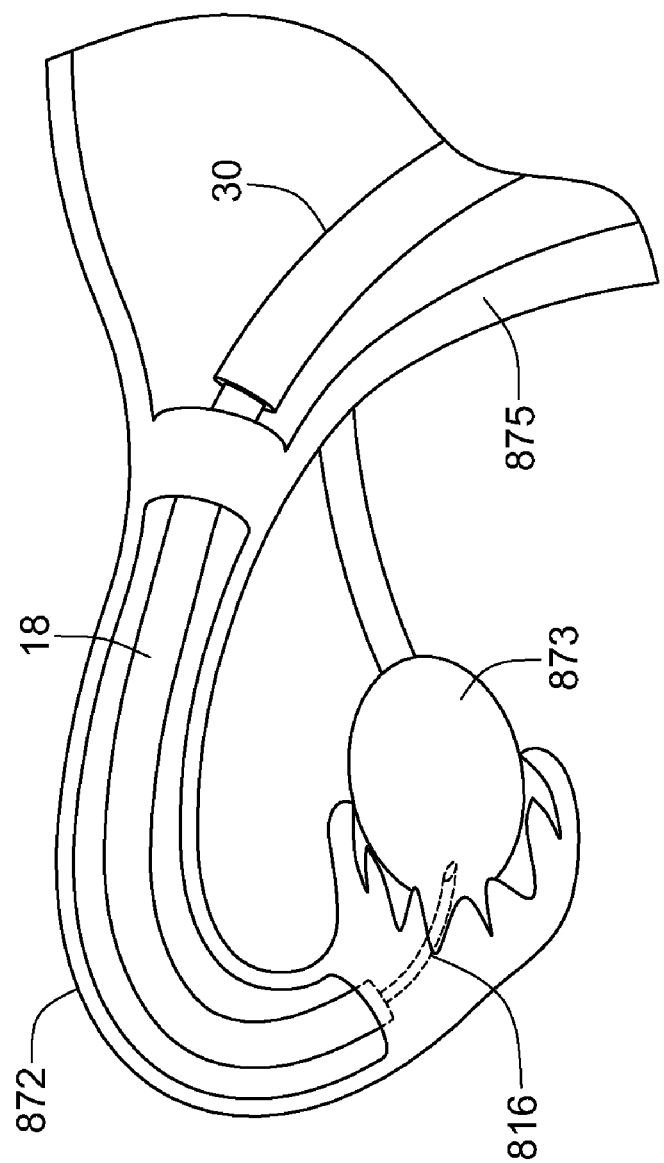
FIGS. 200A-200B illustrate an exemplary system and procedure for a punch biopsy of the ovary with a needle tool positioned in a steerable guide and sheath.
Figure 200B:
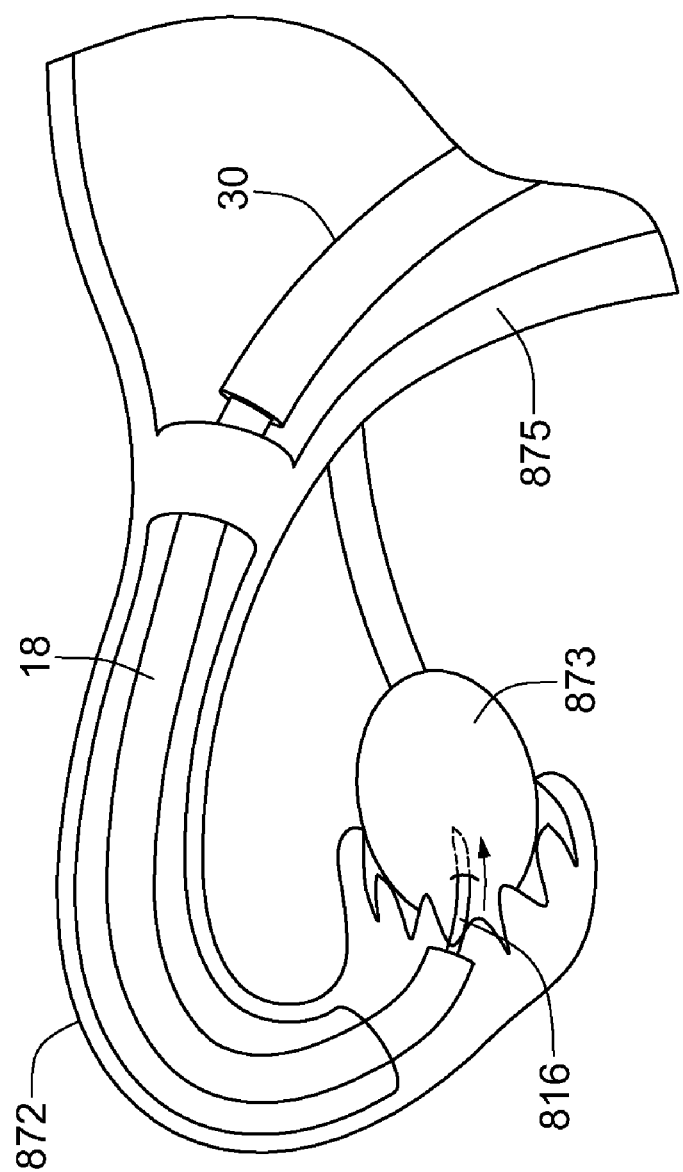

Referring to FIGS. 200A and 200B, a needle tool (816) according to one embodiment may be directed to the ovary (873) with a steerable guide (18) and sheath (30) for a precise punch biopsy of the ovary. Similarly, a needle tool (816) may be utilized to drain cysts or ablate/lyse undesirable tissue.

Figure 201B:
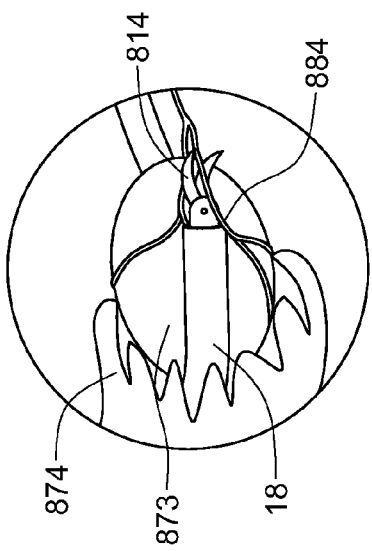
FIGS. 201A-201G illustrate an exemplary system and use of a robotic guide/sheath combination to perform a minimally invasive oophorectomy procedure.
Figure 201C:
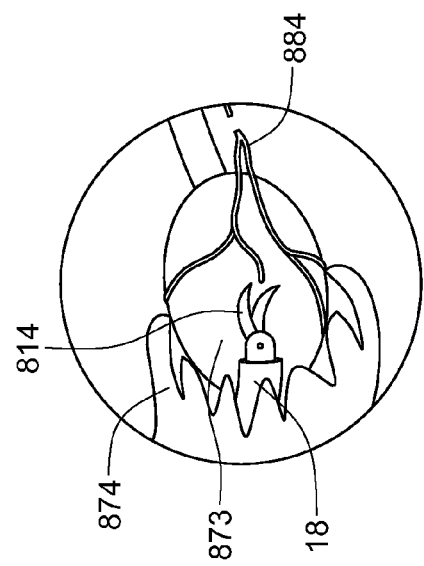
Figure 201A:
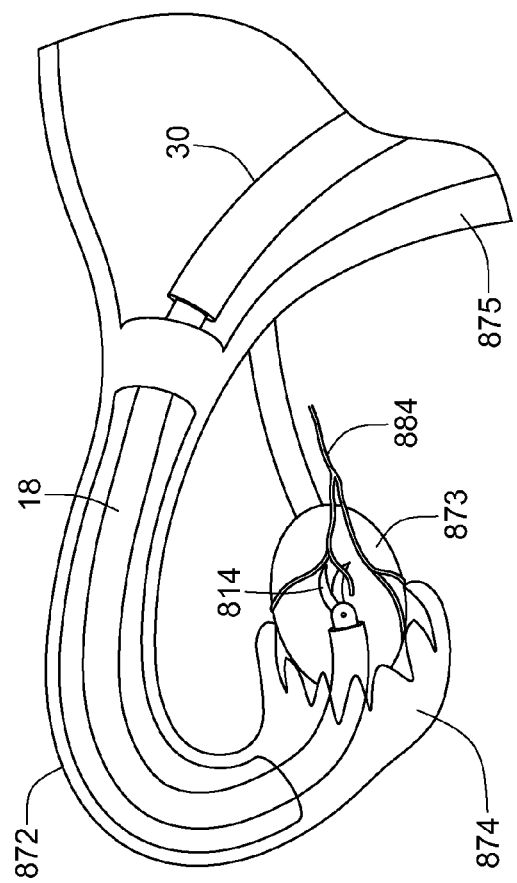
Figure 201E:
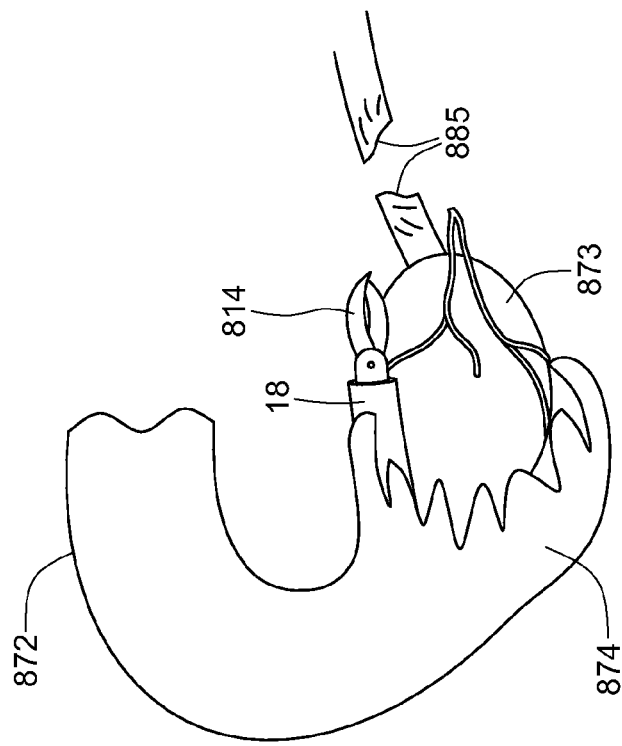
Figure 201D:
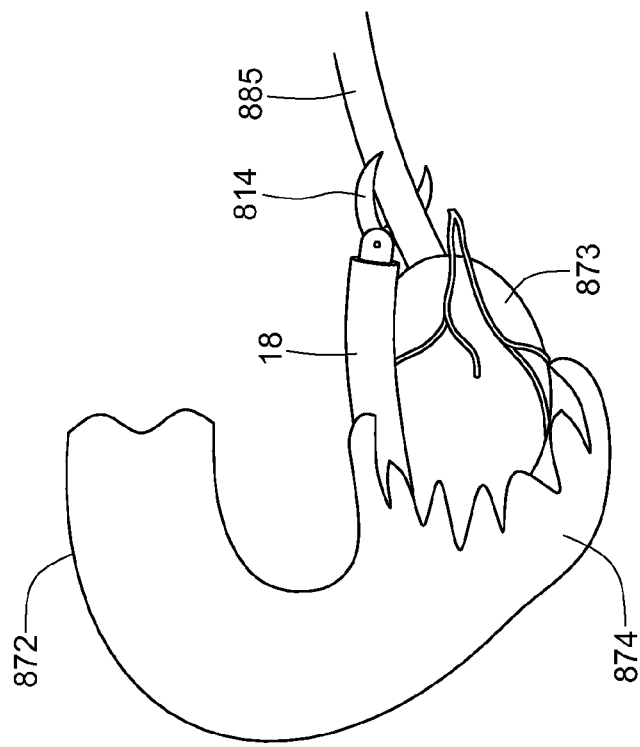
Figure 201G:
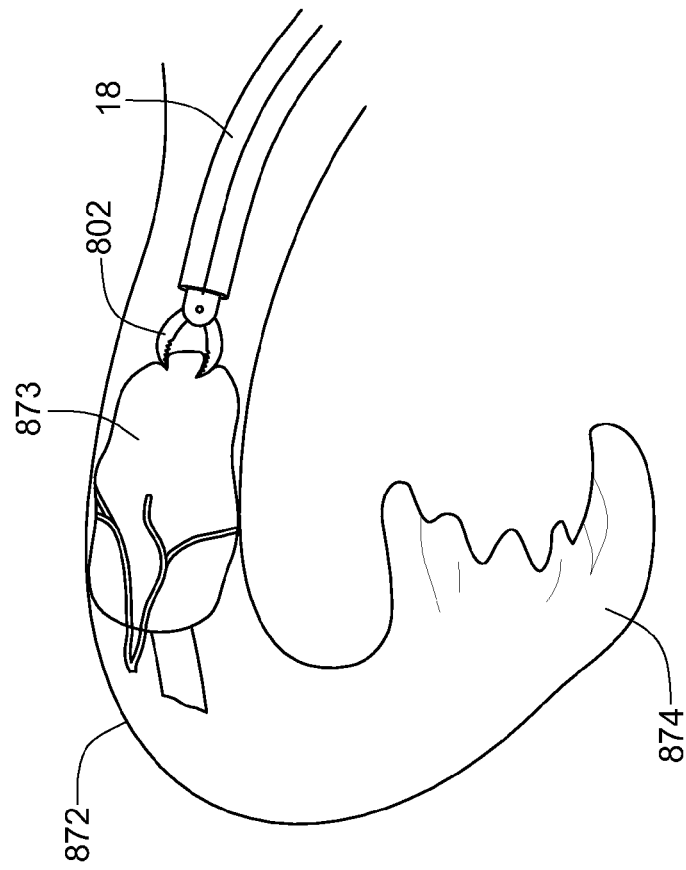
Figure 201F:
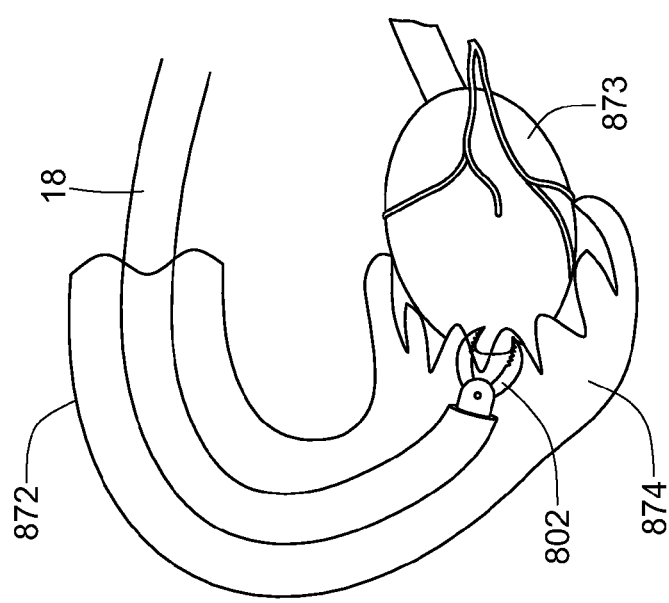

Referring to FIGS. 201A-G, a robotic guide/sheath combination (18, 30) according to one embodiment may be utilized to minimally invasively conduct an oophorectomy. As shown in FIGS. 201A-C, a cutting and/or cautery tool, such as a scissors (814) or bipolar scissors, may be advanced past the salpinx (874) to the location of the ovarian artery (884) where the ovarian artery may be cut and cauterized. Similarly, as depicted in FIGS. 201D-E, the ovarian ligament (885) may be severed which a tool such as a scissors (814), after which a grasping tool (802) may be utilized to pull out the ovary (873), as depicted in FIG. 201F-G.

Figure 202:
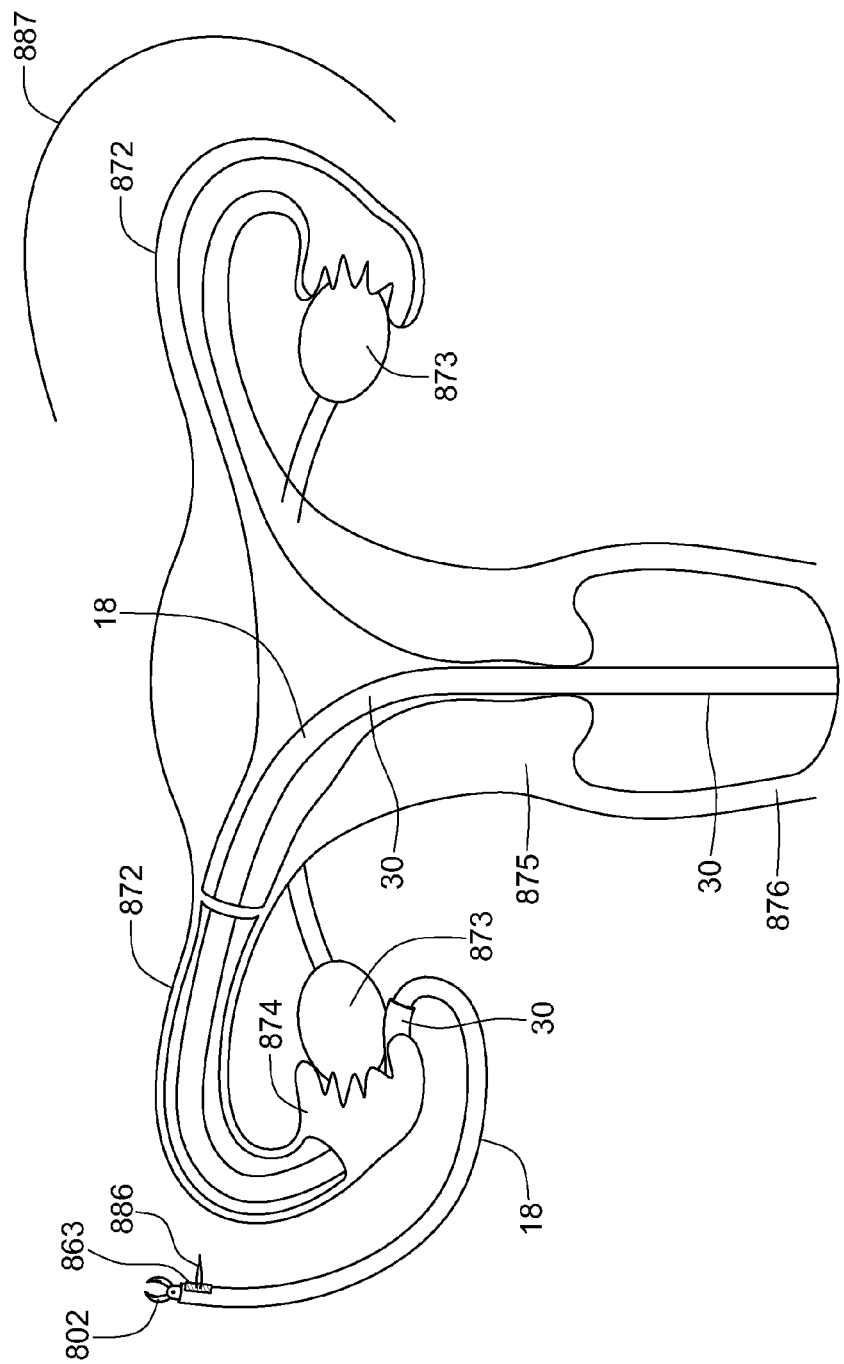
FIG. 202 illustrates one embodiment of a system and procedure wherein a sheath instrument is advanced past the salpinx to facilitate further steerable advancement of a guide instrument and an associated tool into the peritoneum.

Referring to FIG. 202, a sheath (30) may be advanced past the salpinx (874) to facilitate further steerable advancement of the guide (18) and an associated tool into the peritoneum (887). This is significant in that a steerable interventional assembly is depicted accessing the peritoneum (887) from a natural body orifice. The depicted guide configuration is coupled to an ultrasound device (863), such as a side-firing ultrasound array, and a retractable needle (886) aligned along or within the field of view of the ultrasound device (863) to be able to image a targeted tissue portion along with the retractable needle (886) in one image, a configuration which may be utilized for precision image-guided biopsy, ablation (RF, cryo, laser, etc), injection (chemotherapy, gene/cell therapy, etc) and other activity as accomplished with a distally-positioned tool, such as the depicted grasper (802).

Figure 203A:
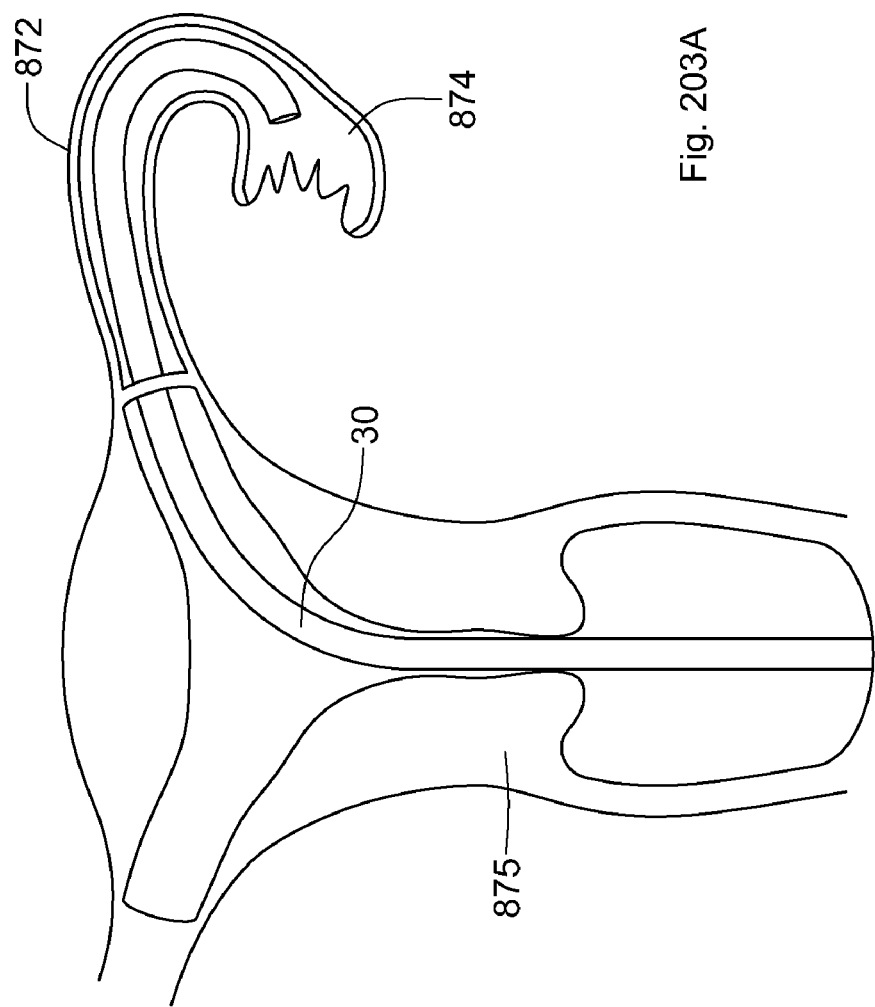
FIGS. 203A-203C illustrates one embodiment of a system and procedure wherein a sheath instrument repositions a fallopian tube to allow a coaxial device to advance through the sheath into the peritoneum.
Figure 203B:
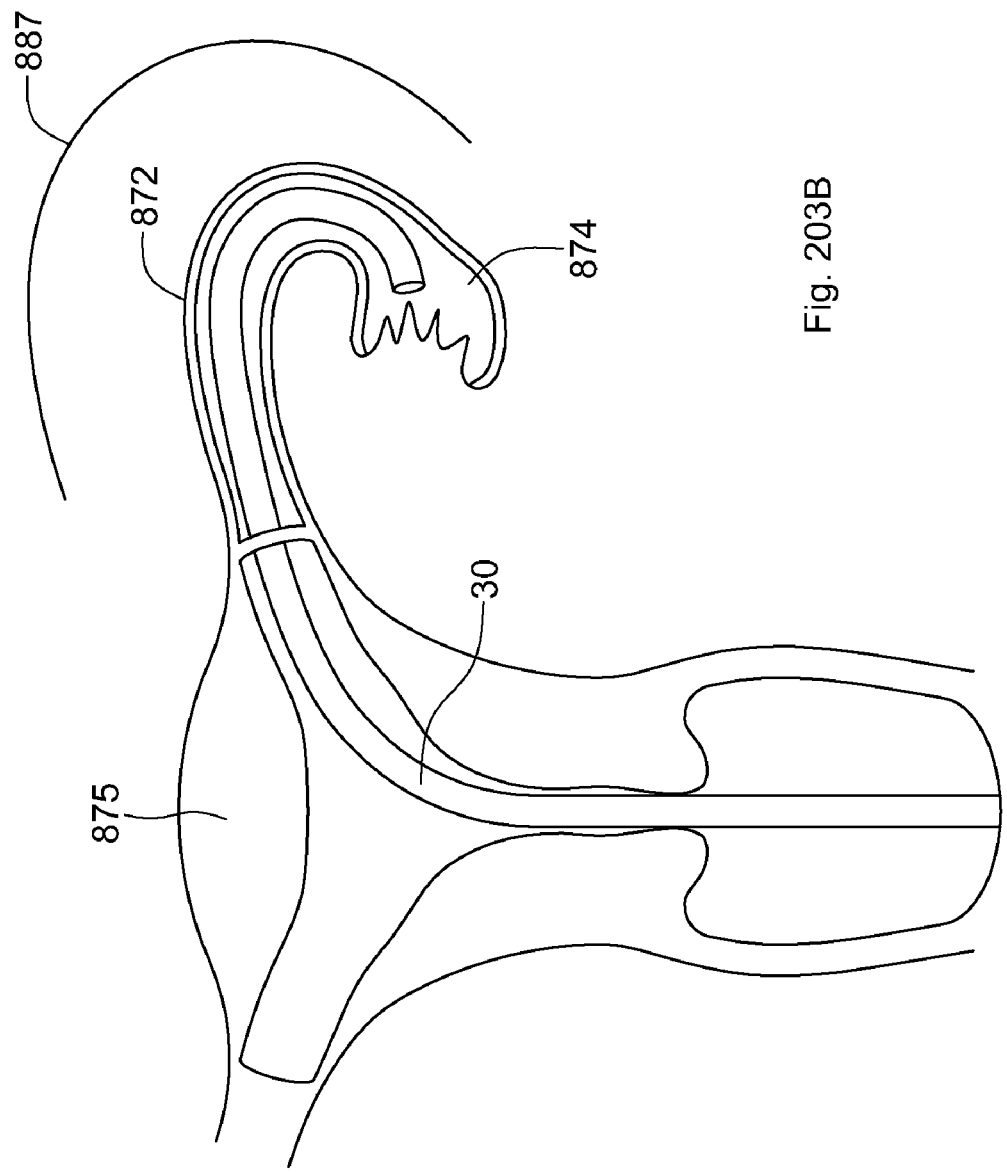
Figure 203C:
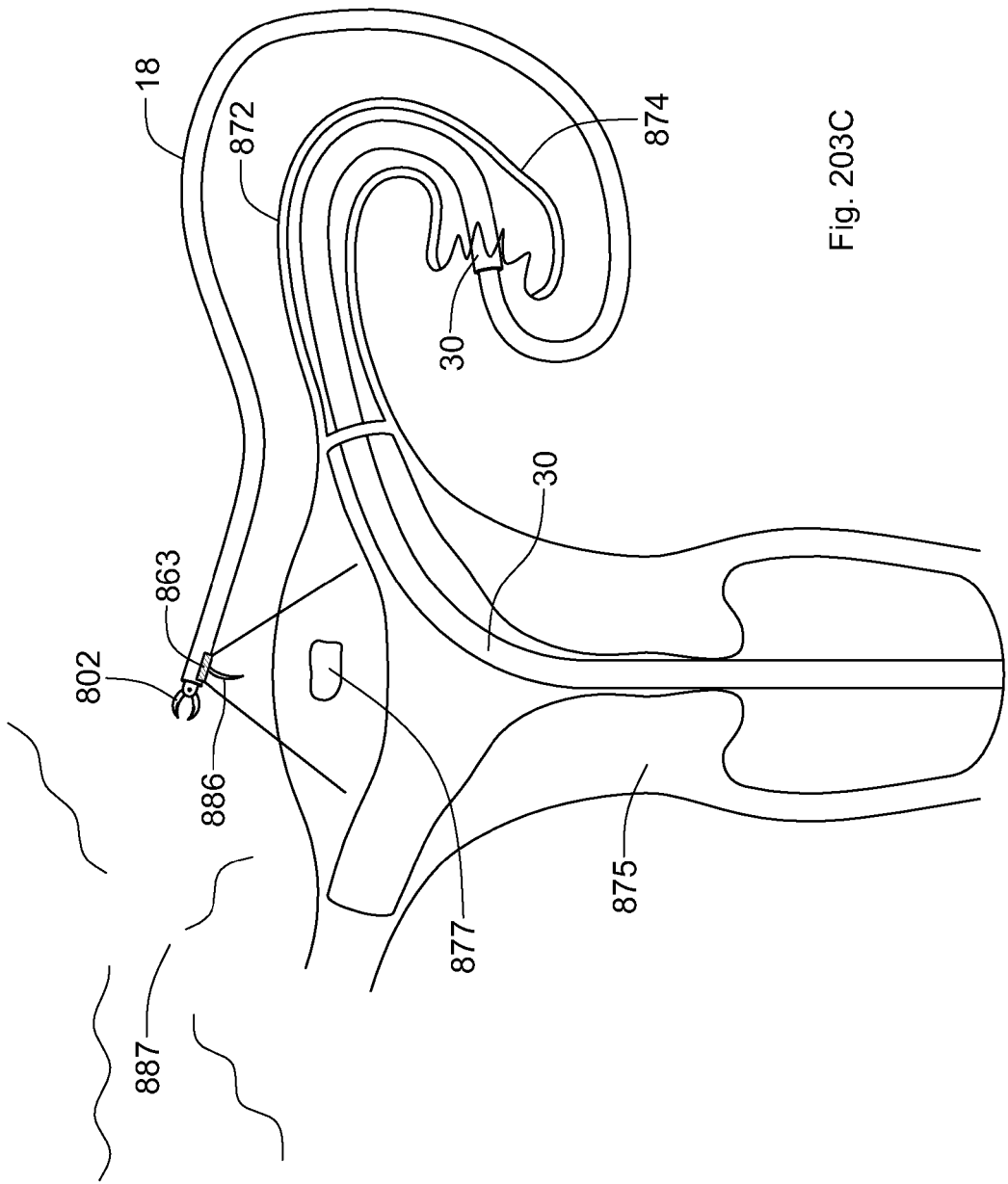

Referring to FIG. 203A-B, a steerable sheath alone maybe utilized to reposition and/or reorient a fallopian tube (872) to provide a preferred setup angle/orientation/position for another coaxial device which may be advanced through the sheath, past the salpinx, and into the peritoneum (887), to access targeted tissue lesions (877), as depicted in FIG. 203C. From an intra-peritoneal position, many different interventions may be accomplished (stomach, bowel, pancreas, gall bladder, liver, etc), in addition to access to and intervention in the retro-peritoneal space (spleen, kidneys, large arteries) and pre-peritoneal space (hernia repair). For example, an ablation tool (RF, cryo, laser) or lysing needle injection and/or ablation tool may be robotically driven into position and utilized to locate endometrial cells/lesions in the peritoneal space to lyse them and clinically minimize female endometriosis.

Figure 204A:
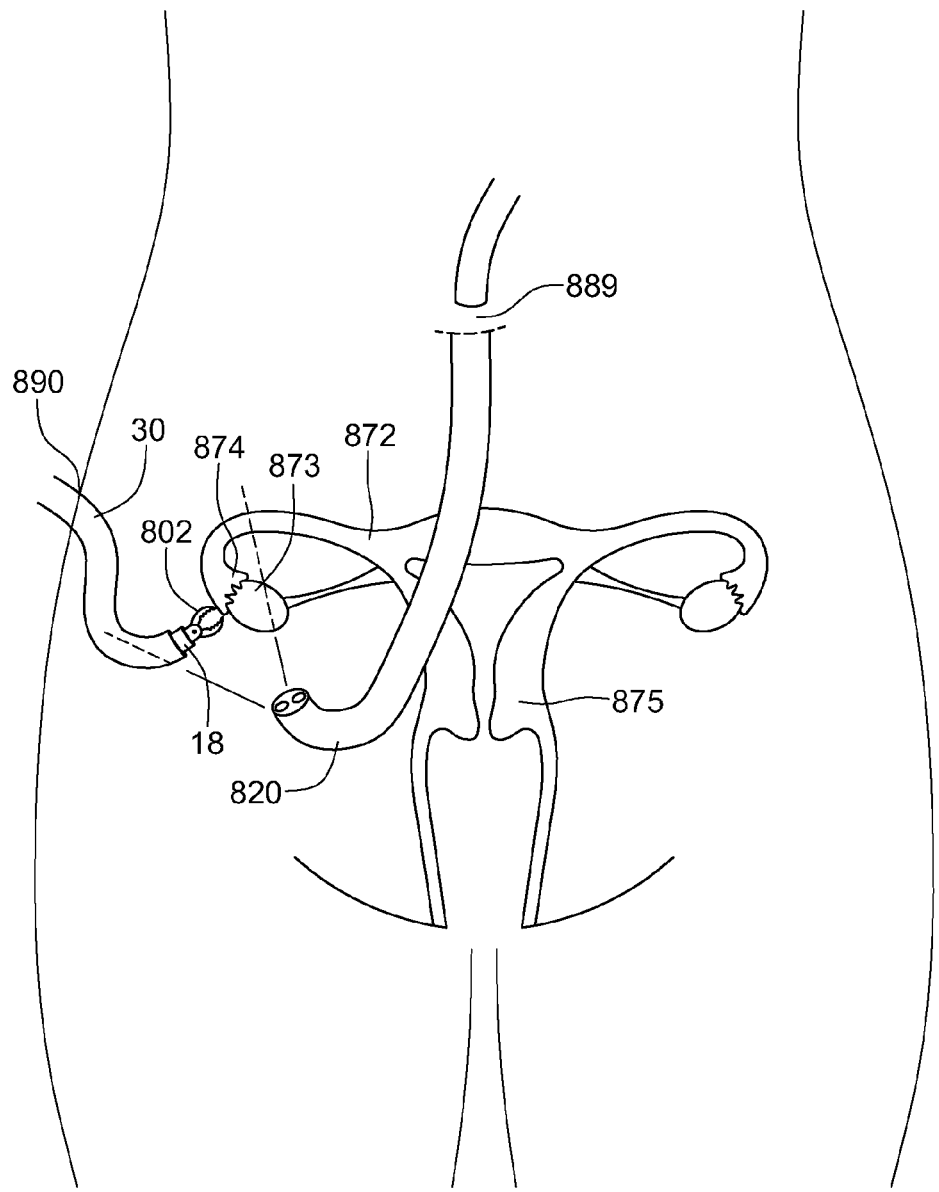
FIGS. 204A-204B illustrate an exemplary laparoscopic salpingectomy system and procedure wherein a steerable endoscope is deployed through an umbilicus port to facilitate viewing of a steerable instrument assembly.
Figure 204B:
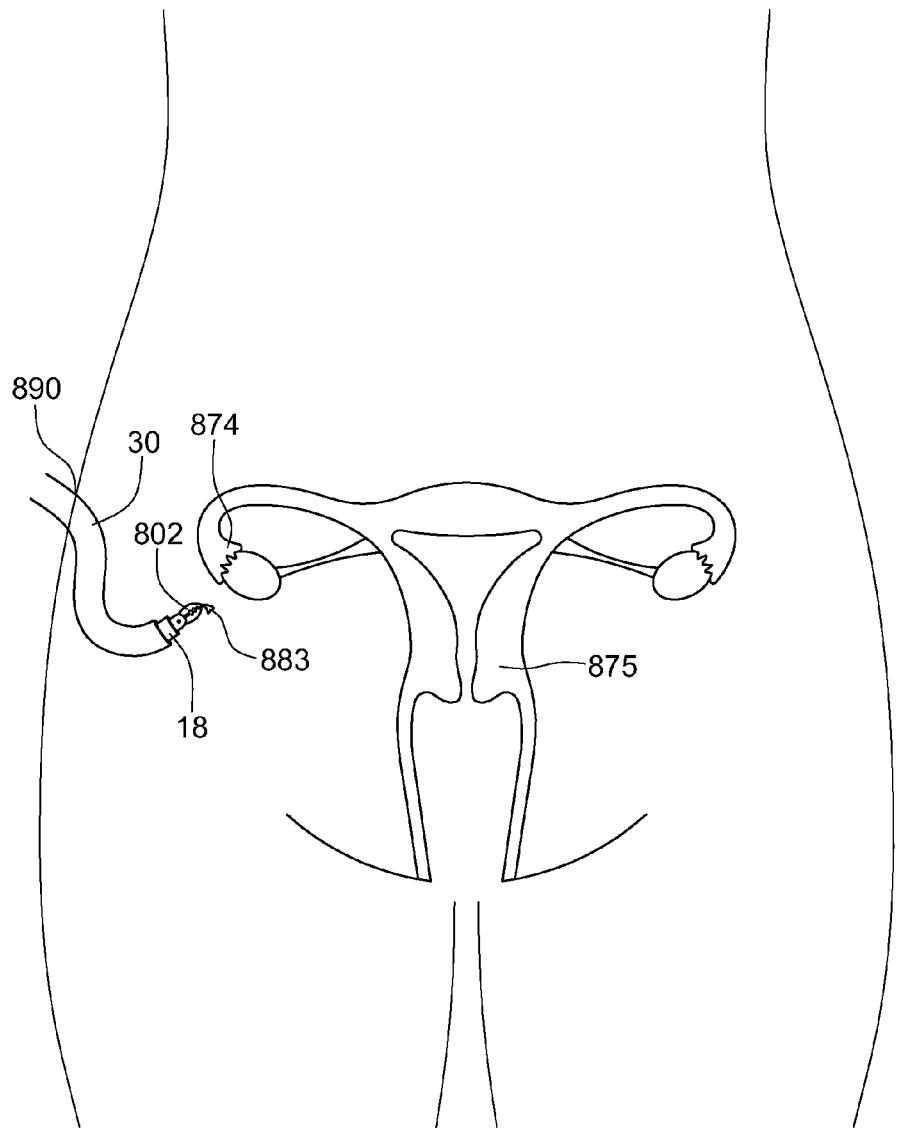

Laparoscopic Intervention:

Referring to FIGS. 514A-B, a laparoscopic salpingectomy employing one embodiment is depicted for purposes of better understanding. A steerable endoscope comprising a guide (18) and sheath (30) instrument, and image capture device, is brought into an insufflated surgical theater (888) through an umbilicus port (889) and steered to produce a field of view facilitating operation of a steerable instrument assembly which may comprise a cauterizing scissor or grasper, for example. Referring to FIGS. 203.5A-B, one or more instruments, such as additional sheath/guide pairings (818, 819), may be introduced through the umbilicus (889) or other ports (890) to access tissues located within the peritoneum, retro-peritoneally, infraperitoneally, etc. Insufflation at approximately 15 mm Hg and a Trendelenburg body position facilitates access and maneuvering of laparoscopic tools. As shown in FIGS. 204A-B, a piece of resected tissue (883) may be detached from the salpinx (874) and removed through the surgically created side port (890).

Many variations of port access may be utilized for laparoscopic procedures with high-precision steerable tool assemblies such as those described herein. Preferred port access locations include but are not limited to the umbilicus, and sub-bikini-line area. Insufflation at 15 mmHg is typical, and may be administered through a lumen of one of the instrument assemblies to produce a fairly large laparoscopic operational procedure. With a Trendelenburg patient orientation, the organs within the peritoneum are very accessible. As discussed above, visualization may comprise fluoroscopy, transcutaneous ultrasound, MR, and CT, but also may include visualization from within the operational theater using ultrasound arrays and optical imaging devices carried upon the operational instrument assemblies, as well as instrument assemblies specifically included to carry imaging devices. In other words, imaging may be carried along on an assembly with a tool assembly, or may be facilitated with one or more separate assemblies for carrying/steering/driving the imaging devices within the operational theater.

Referring to FIGS. 204.5A-E, a laparoscopic oophorectomy procedure using a robotic catheter system according to one embodiment is depicted. In comparison to the procedure described in reference to FIGS. 201A-G, the procedure depicted in FIGS. 204.5A-E is at least partially conducted through laparoscopic ports, such as through the umbilicus (889) and a side port (907), preferably located in the bikini line or sub-bikini-line area. As shown in FIG. 204.5A, a steerable endoscope, such as a parent instrument (820) described above, may be positioned through the umbilicus and steered remotely to provide the operator with a laparoscopic view of an ovary (873) and fallopian tube (872). A steerable instrument, such as the sheath/guide combination (30, 18) depicted in FIG. 204.5A, may be maneuvered into a position from which a tool, such as a scalpel (812), may be utilized along with other tools, such as cauterizing tools (806), to dissect the portion of the fallopian tube adjacent the salpinx (874), and also isolate the blood supply (884) and ligamentary support (885) of the subject ovary (873), to facilitate easier removal from an endolumenal, trans-cervical pathway, as depicted in FIGS. 204.5D and 204.5E, with a grasper (802) or similar tool.

Figure 205A:
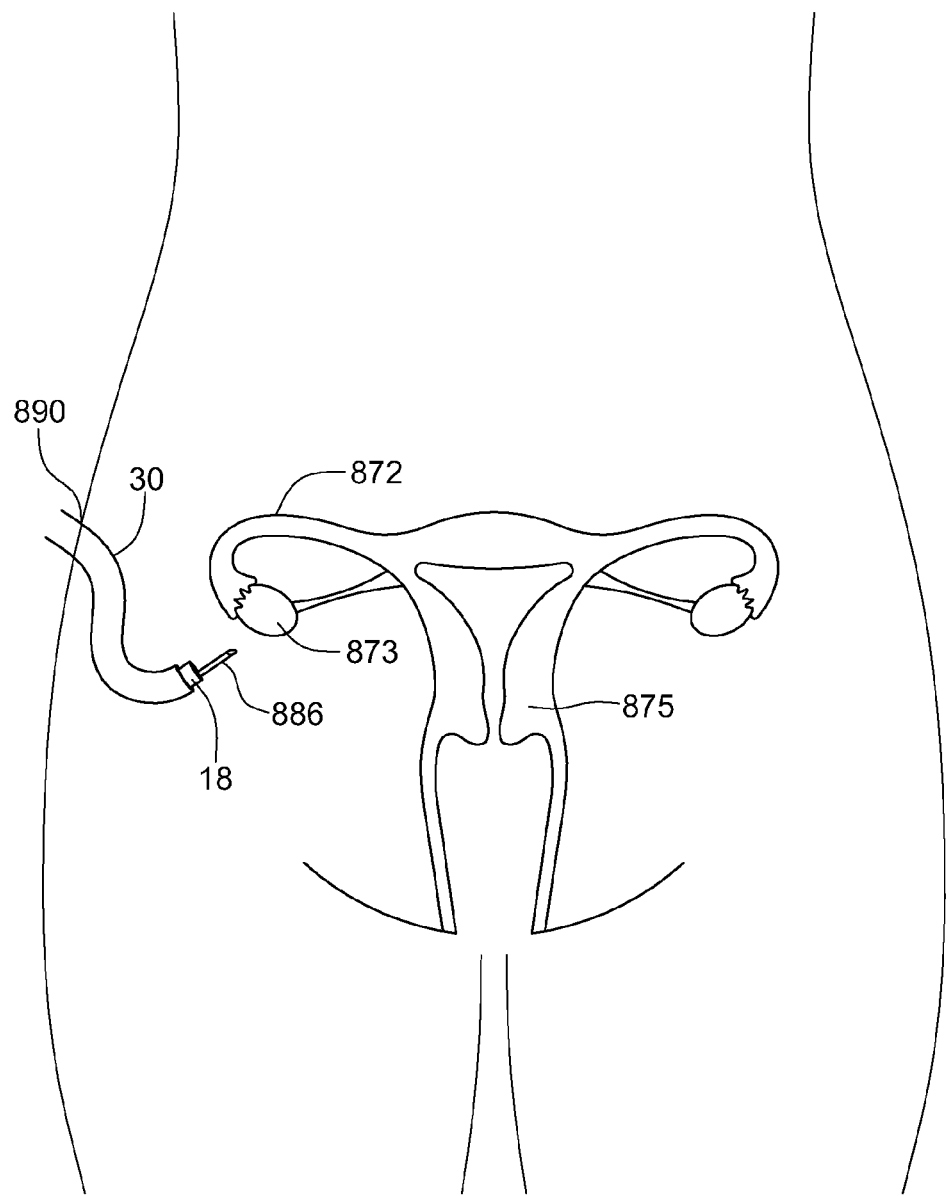
FIGS. 205A-205B illustrate an exemplary laparoscopic ovarian punch biopsy system and procedure with a needle tool inserted through a surgically created side port.
Figure 205B:
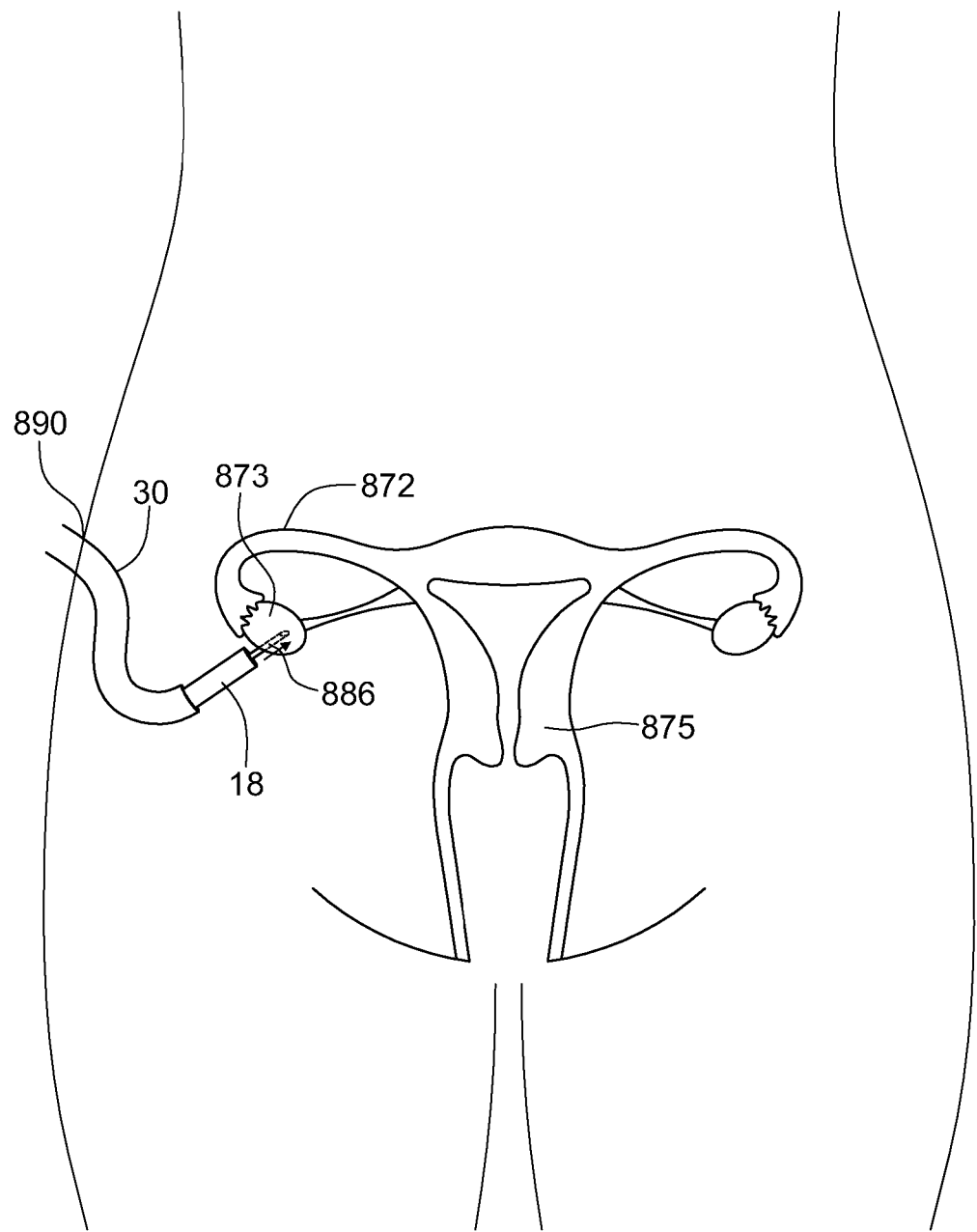

Referring to FIGS. 205A-B, a laparoscopic ovarian punch biopsy with a retractable needle tool (886) is depicted with access from a surgically created side port (890). Optical imaging (not shown) may be facilitated with an umbilicus port and endoscope, an imaging device carried on the sheath/guide/tool assembly (30, 18), external imaging devices (fluoro, MR, CT, etc).

Figure 206:
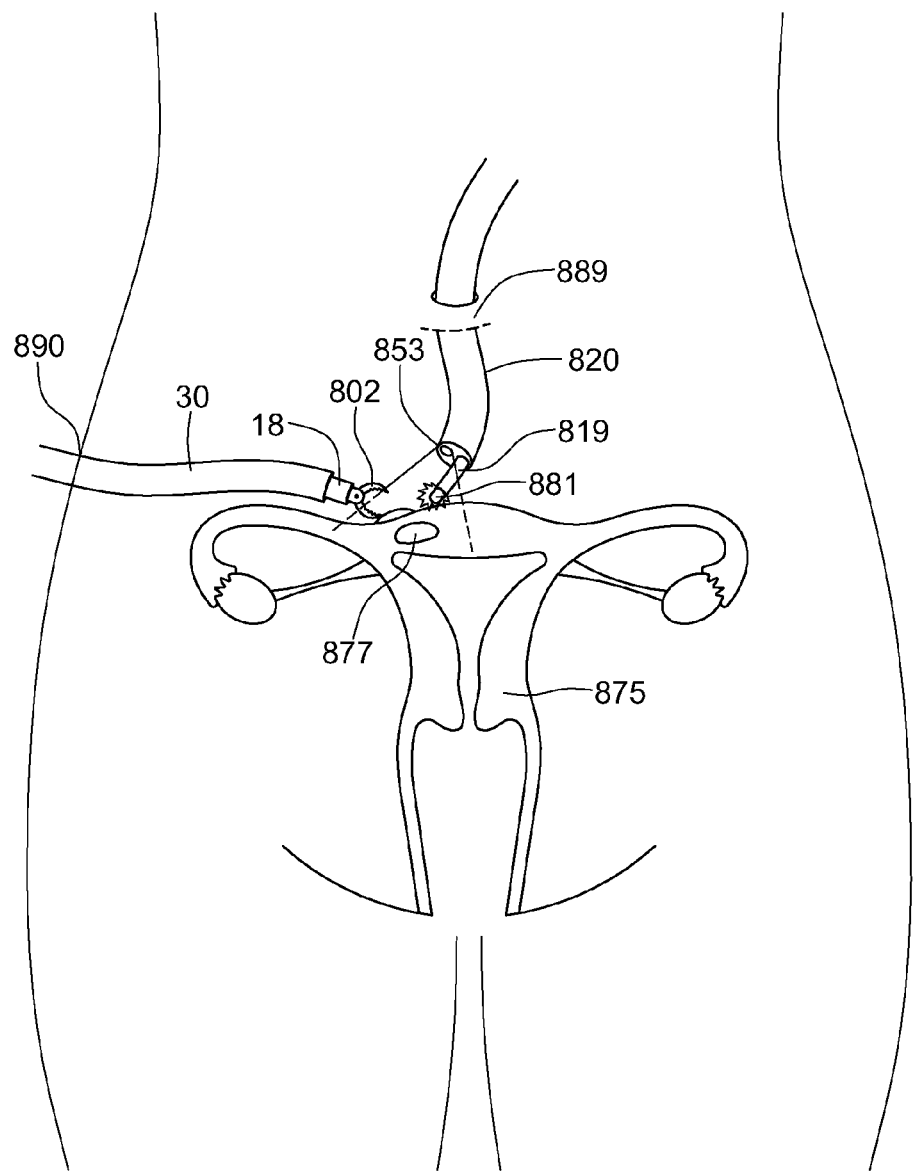
FIG. 206 illustrates one embodiment of a laparoscopic interventional system and procedure that employs a sheath/guide/tool assembly and a steerable endoscopic instrument.

Referring to FIG. 206, a first sheath/guide/tool assembly (30, 18) is depicted in the same insufflated laparoscopic interventional theater as a second instrument assembly, here comprising a steerable endoscopic instrument (820) similar to that depicted in FIG. 194 with only a guide instrument (819) coaxially associated therethrough (here without a sheath instrument to demonstrate that a sheath instrument is not a requirement; indeed, suitable interventional assemblies may comprise only a tool, a guide and tool, a tool/guide/sheath combination, a guide/endoscopic instrument combination, etc). The first instrument assembly is depicted comprising a grasping tool (802) while the second is depicted comprising an ablation (RF, cryo, laser, etc) tool (881).

Figure 207A:
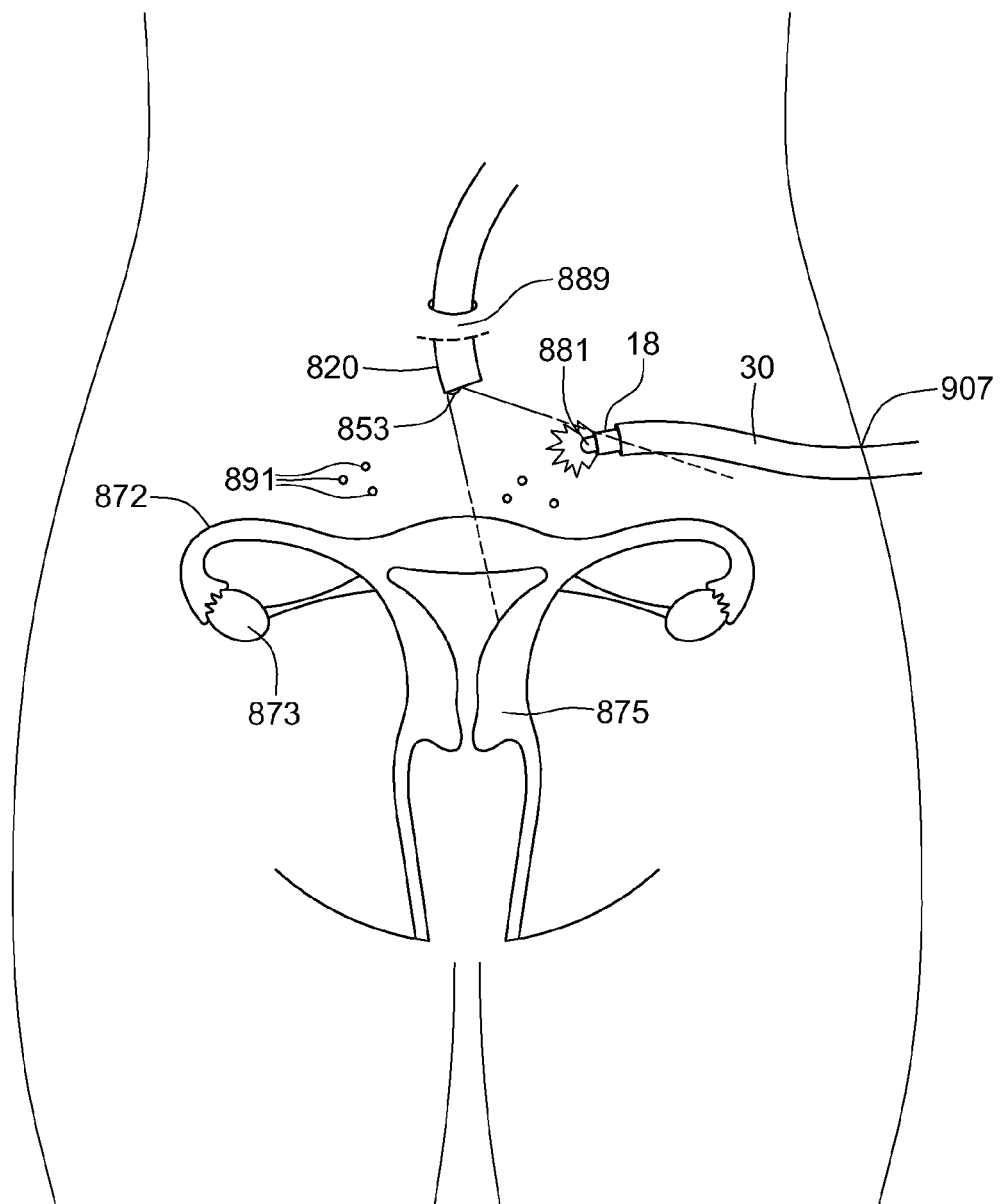
FIGS. 207A-207B illustrate one embodiment of a system and procedure wherein a steerable endoscopic instrument is used to keep the distal tip of an ablation tool in view during the locating and ablation of endometrial lesions.
Figure 207B:
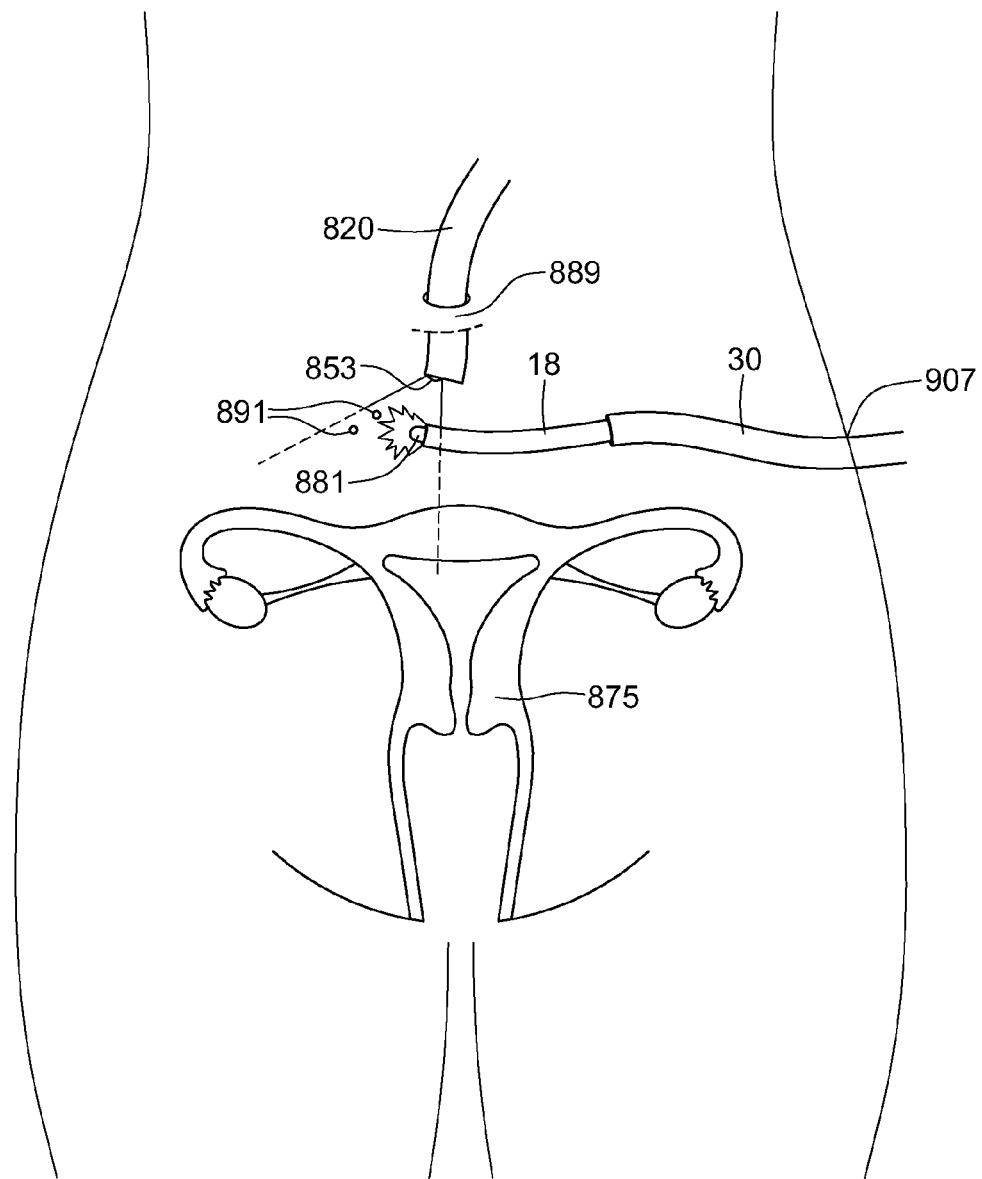

Referring to FIG. 207A-B, a steerable endoscopic instrument (820) is operated to keep the distal tip of an instrument assembly (18, 30) in the field of view of the imaging device at the tip of the steerable endoscopic instrument (820). The instrument assembly comprises an ablation tool (881) and is shown being driven around within the peritoneum to locate and ablate endometrial lesions (891).

Figure 208A:
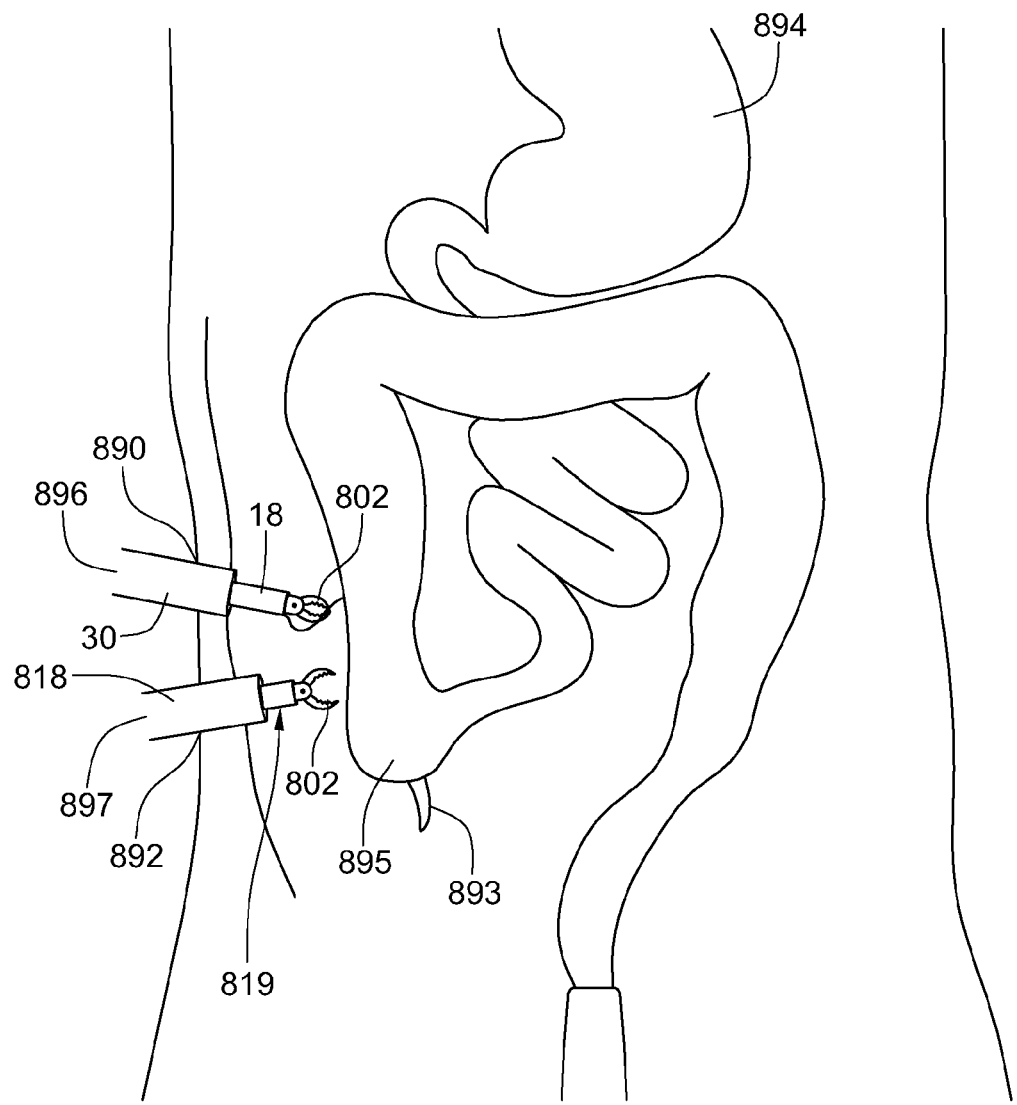
FIGS. 208A-208D illustrate one embodiment of a cecopexy system and procedure wherein two instruments assemblies with needle grasping tools are utilized laparoscopically through two access ports.
Figure 208B:
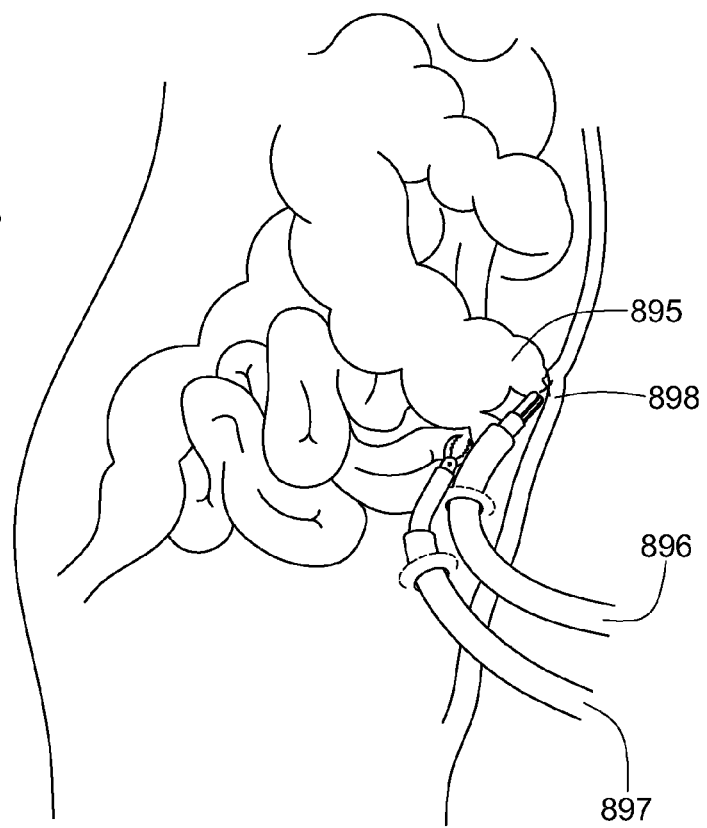
Figure 208C:
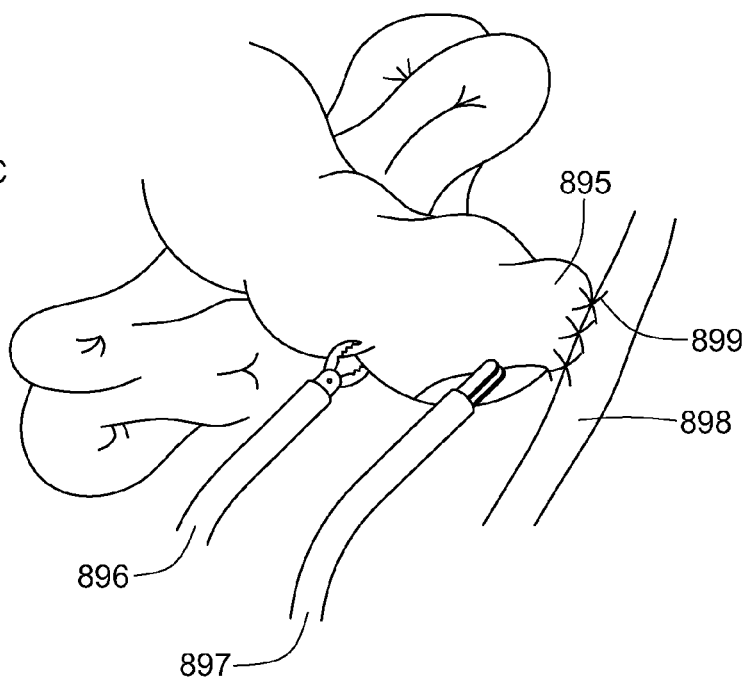
Figure 208D:
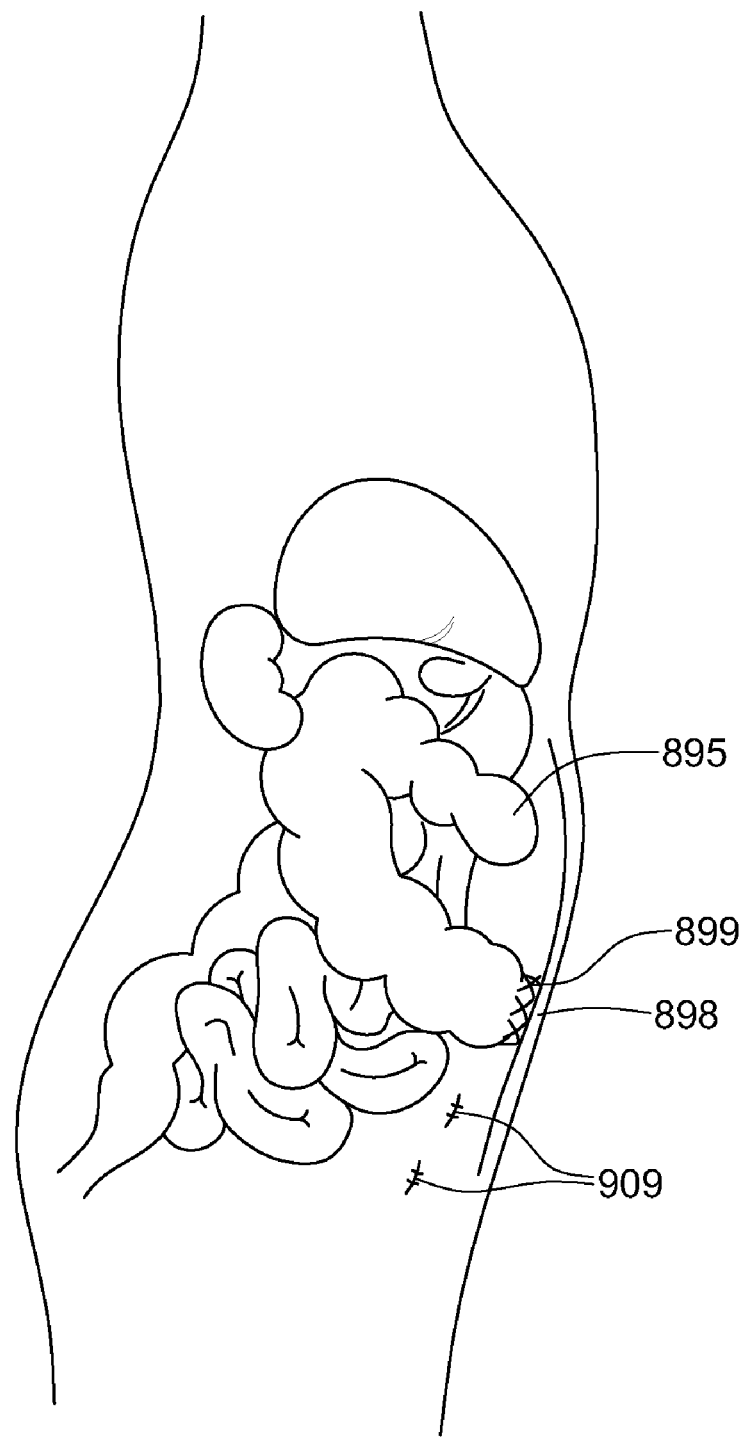
Figure 208E:
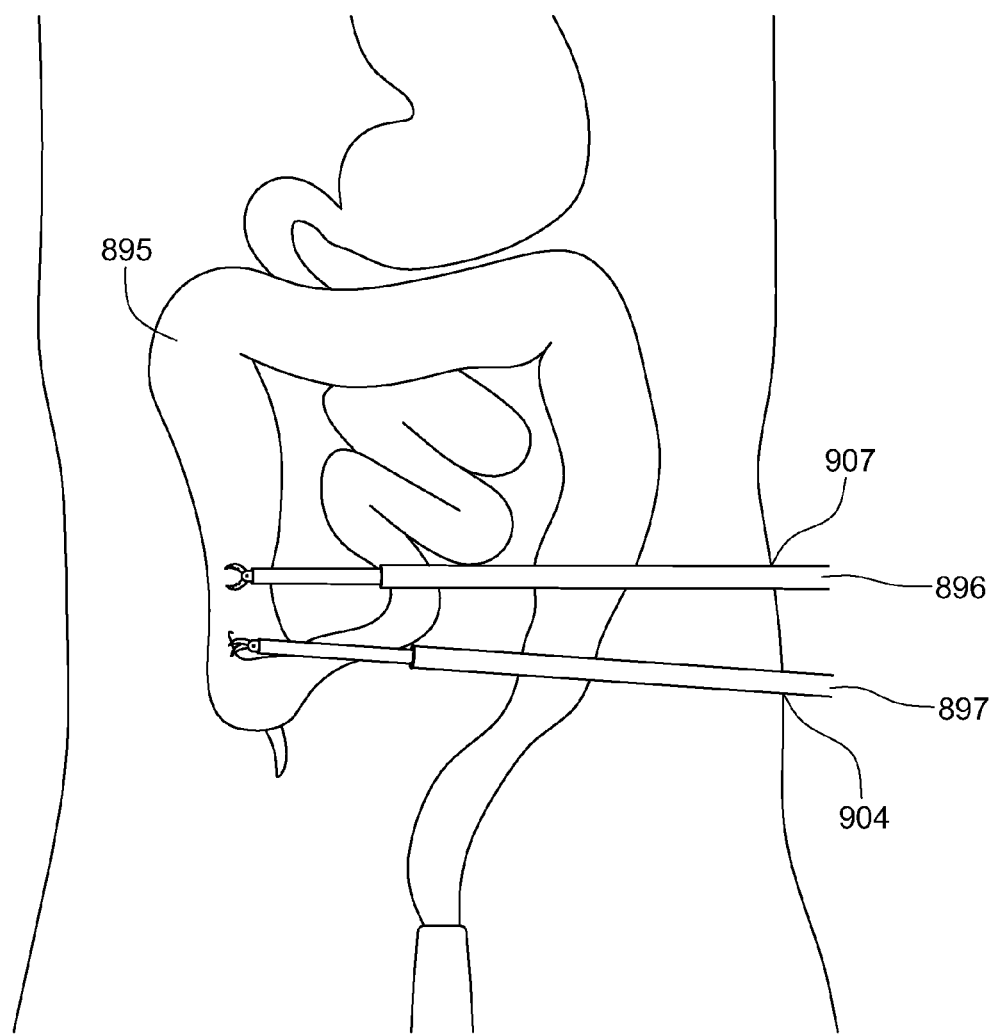
FIGS. 208E illustrates another embodiment of a cecopexy system and procedure wherein instrument assemblies are laparoscopically introduced from the side of the body opposite the cecum.

Referring to FIG. 208A-D, according to one embodiment, two instrument assemblies (896, 897) with needle grasping tools (802) may be utilized laparoscopically through two access ports (890, 892) to conduct a cecopexy by suturing a portion of the cecum (895) against a portion of the abdominal wall (898), after which closed ports (909) are left to heal. In another embodiment (not shown), the two instrument assemblies may be passed through lumens of the same steerable endoscopic instrument, and passed into a laparoscopic operational theater through a single larger port, as in configurations like those depicted in FIGS. 504. In another embodiment, as depicted in FIG. 208E, each of two instrument assemblies may be introduced into the laparoscopic operating theater from the side of the body (907, 904) opposite the cecum (895) to provide the operator with more room within the body to maneuver and approach the subject tissue. Two needle grasper instruments (802) are depicted in FIG. 208E suturing a portion of the cecum (895) to a portion of adjacent abdominal wall tissue to conduct a cecopexy.

In any of the cecopexy embodiments discussed herein, depending upon the imaging modalities utilized, it may be preferable to also have an endoscope (not shown), such as an endoscope with a robotically steerable electromechanical architecture as discussed herein, positioned through the umbilicus or other port to directly visualize the laparoscopic operating theater. One or more cameras or scopes may also be positioned upon or adjacent to either instrument assembly, in a configuration, for example, such as that depicted in FIGS. 194.

Figure 209A:
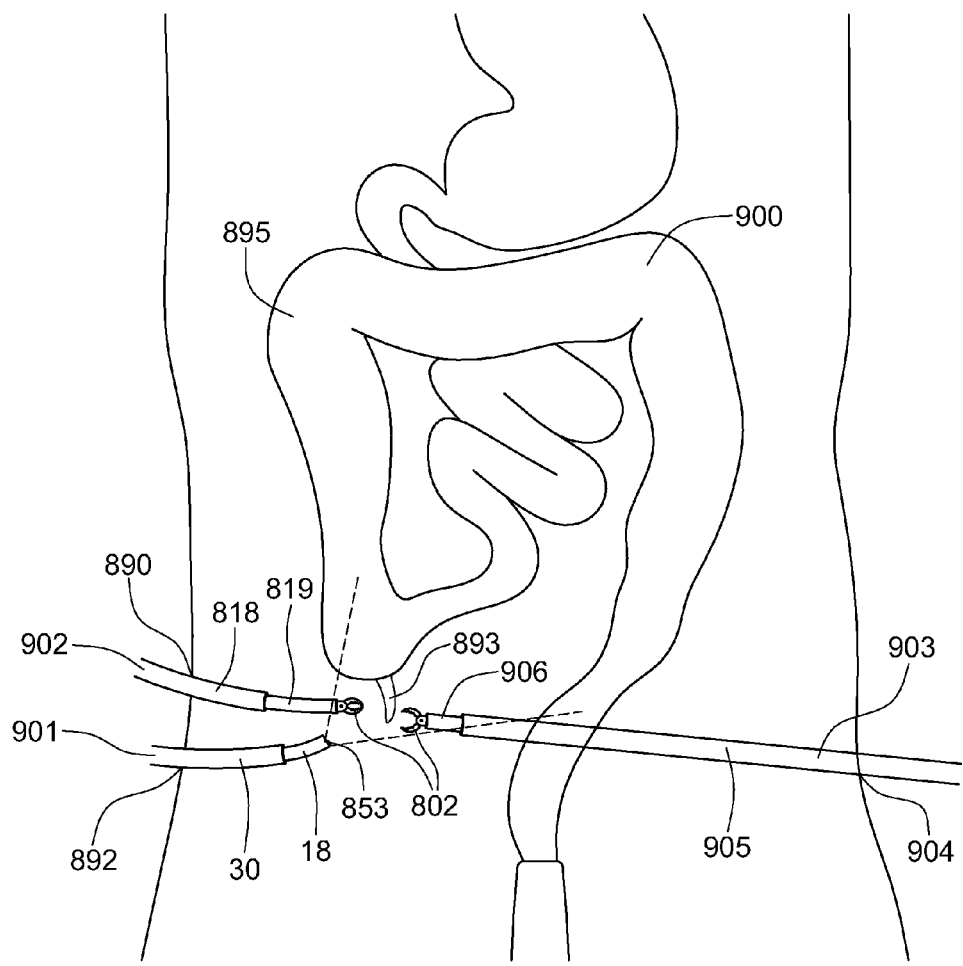
FIGS. 209A-209B illustrate an exemplary laparoscopic appendectomy system and procedure that utilizes three robotic steerable instrument assemblies.
Figure 209B:
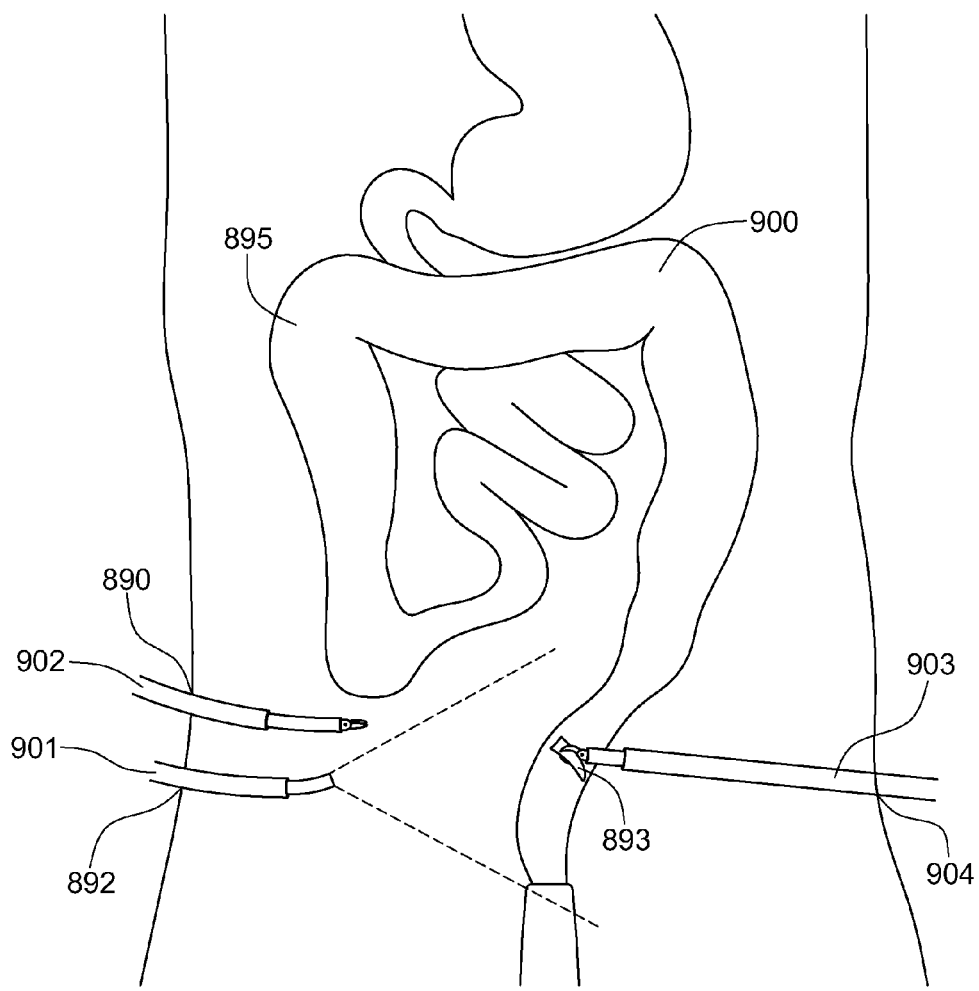
Figure 209C:
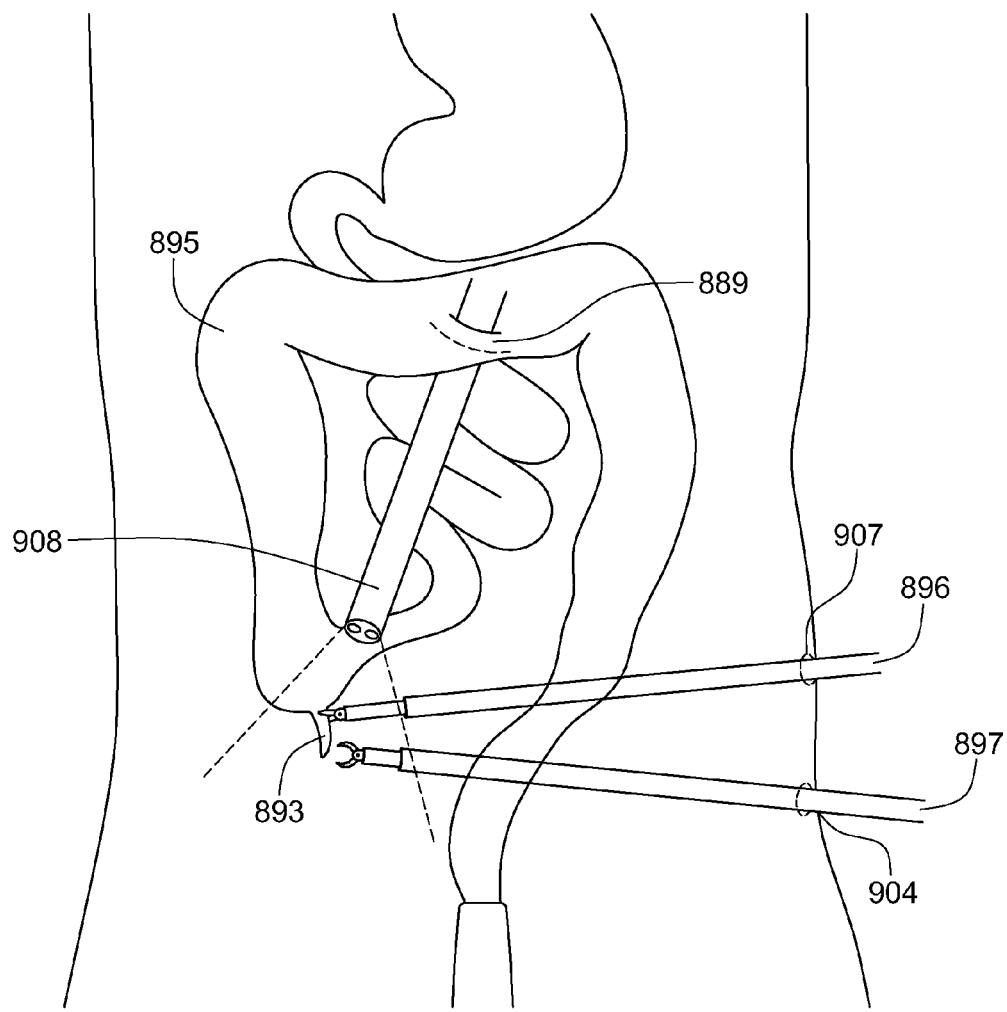
FIGS. 209C-209D illustrate another embodiment of a laparoscopic appendectomy system and procedure wherein an endoscopic instrument is positioned through the umbilicus and two other assemblies are introduced through side ports.
Figure 209D:
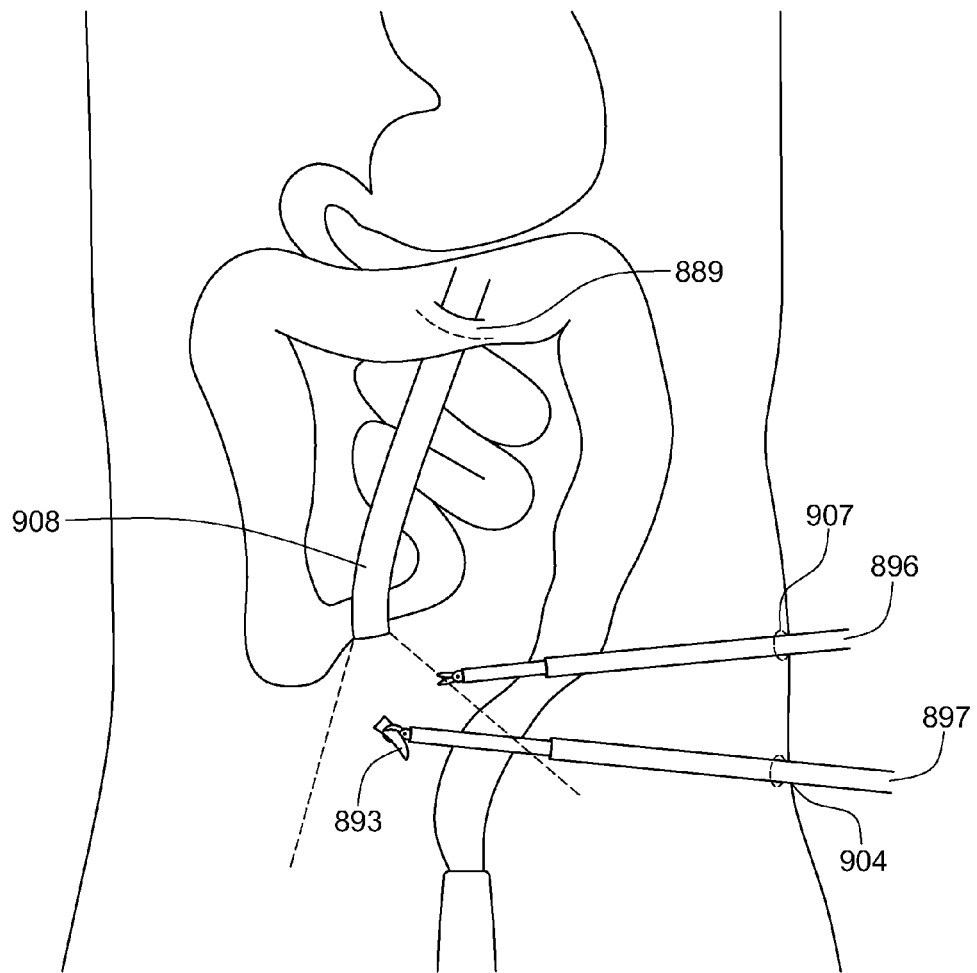

Referring to FIGS. 209A-B, a laparoscopic appendectomy (893) is depicted utilizing three robotic steerable instrument assemblies (901, 902, 903) through three side ports (904, 890, 892) according to certain embodiments of the invention, one carrying an image capture device (853), and the other two carrying grasping, cutting, and/or cauterizing tools (802). Referring to FIGS. 209C-D, another embodiment is depicted wherein an endoscopic instrument (908) is positioned through the umbilicus (889) while two other tool assemblies (896, 897) are introduced through side ports (904, 907) to grasp and remove the appendix (893) laparoscopically utilizing tools such as bipolar cauterizing scissors or graspers.

Figure 210A:
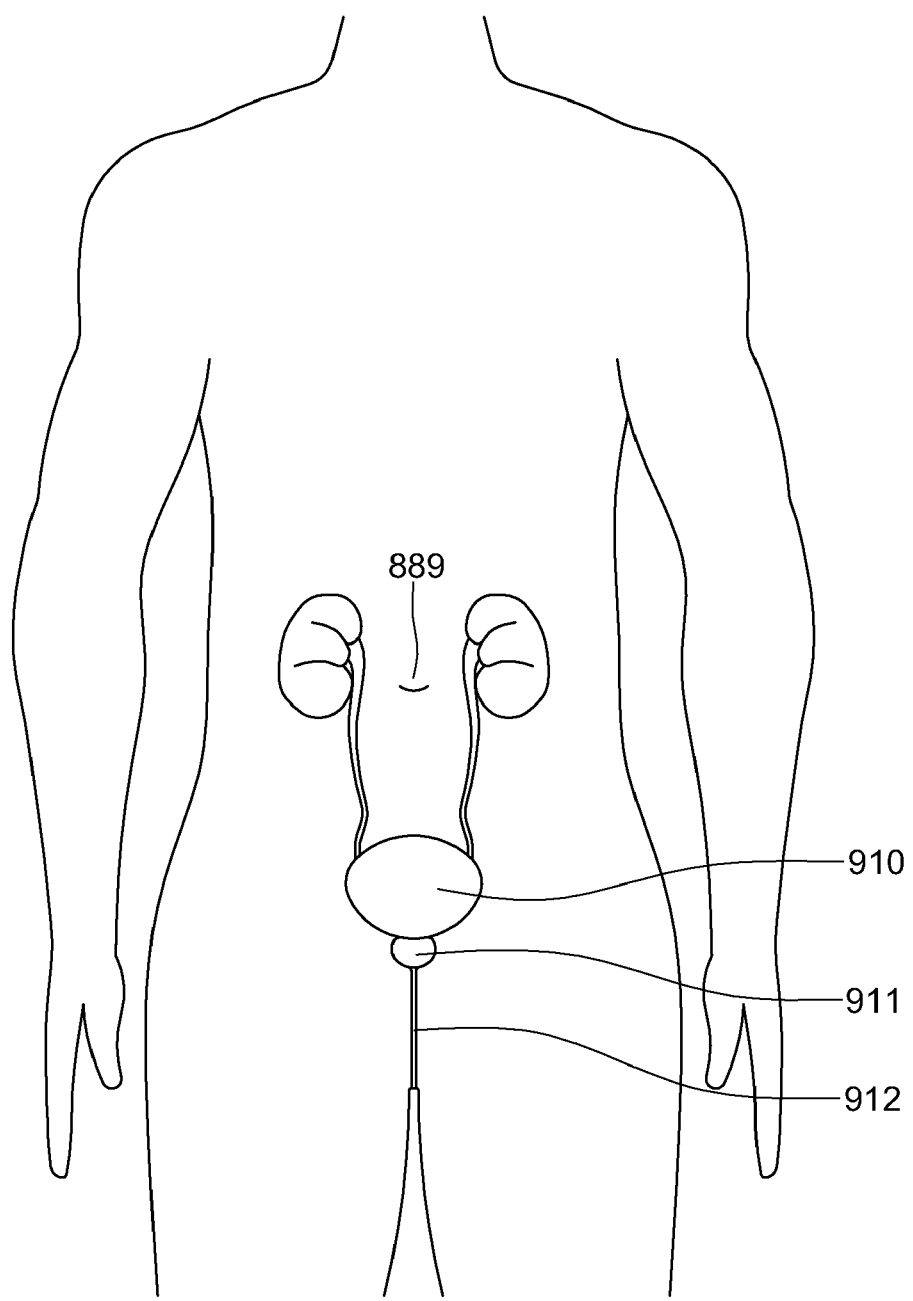
FIGS. 210A-210H illustrate one embodiment of a laparoscopic prostatectomy system and procedure utilizing robotic instrument assemblies.
Figure 210B:
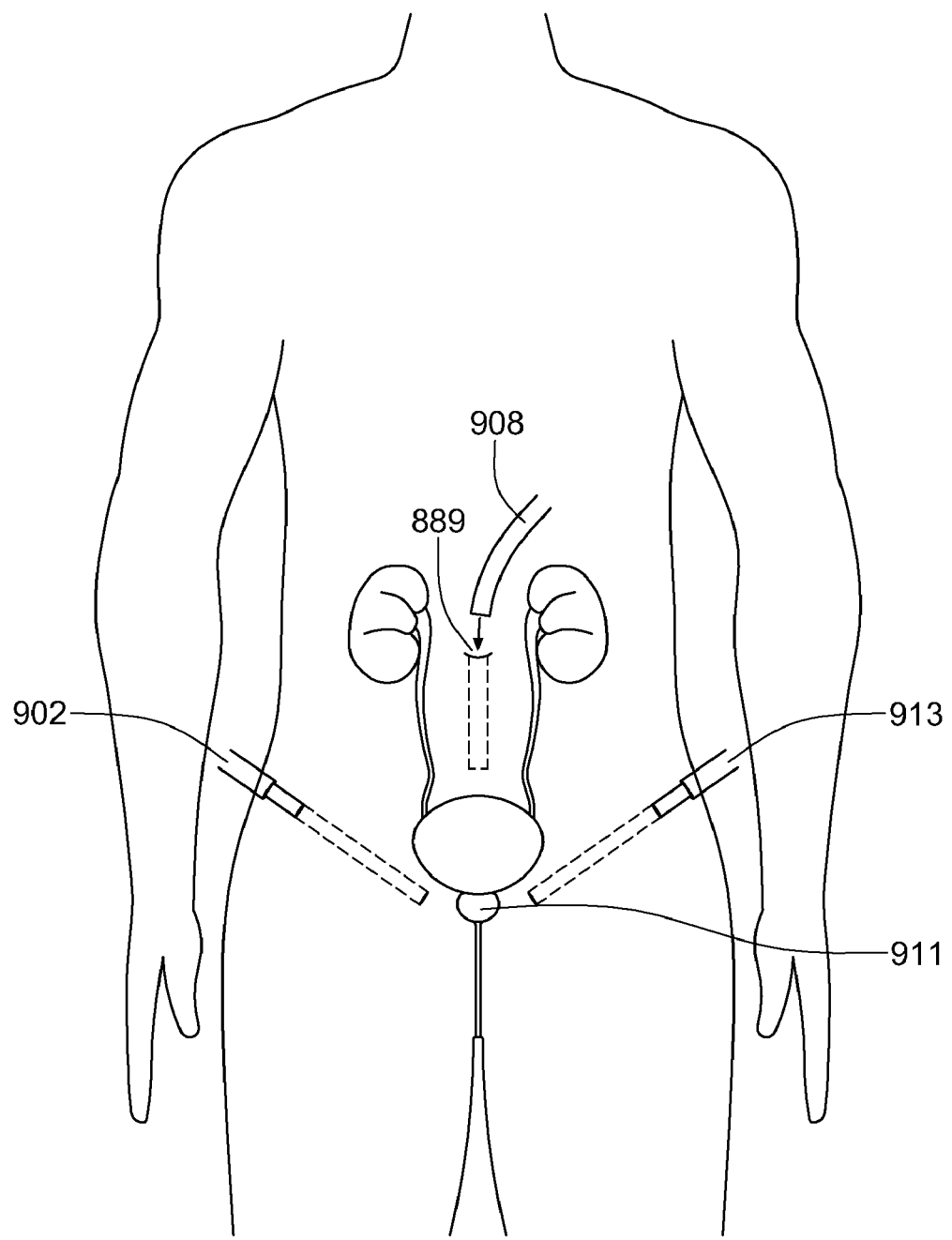
Figure 210C:
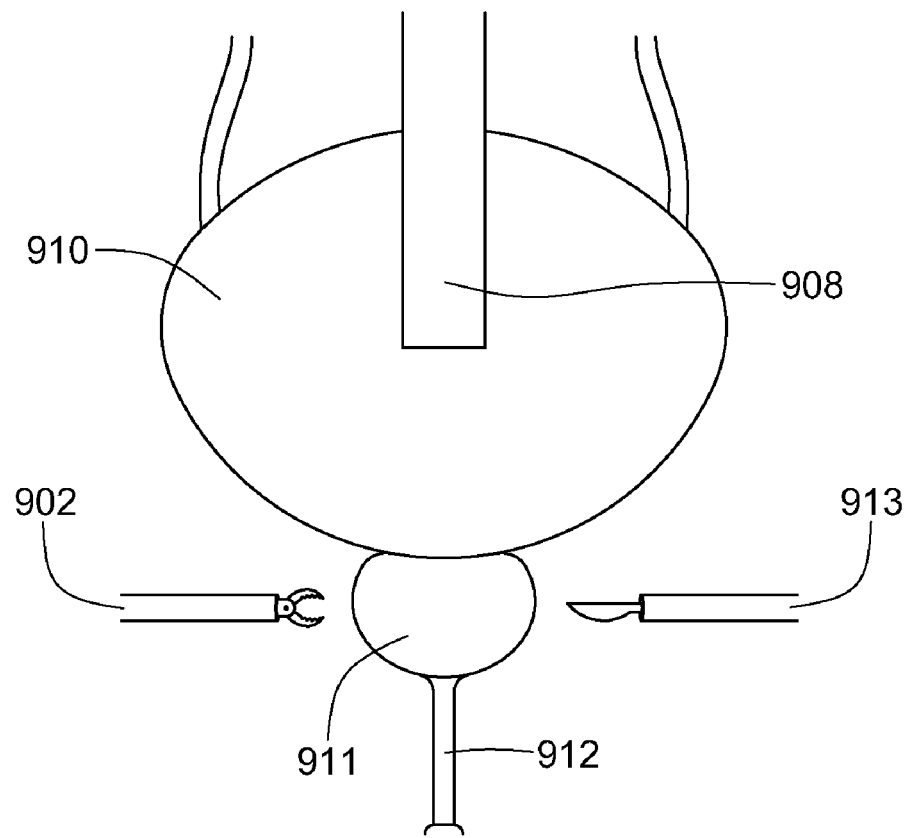
Figure 210D:
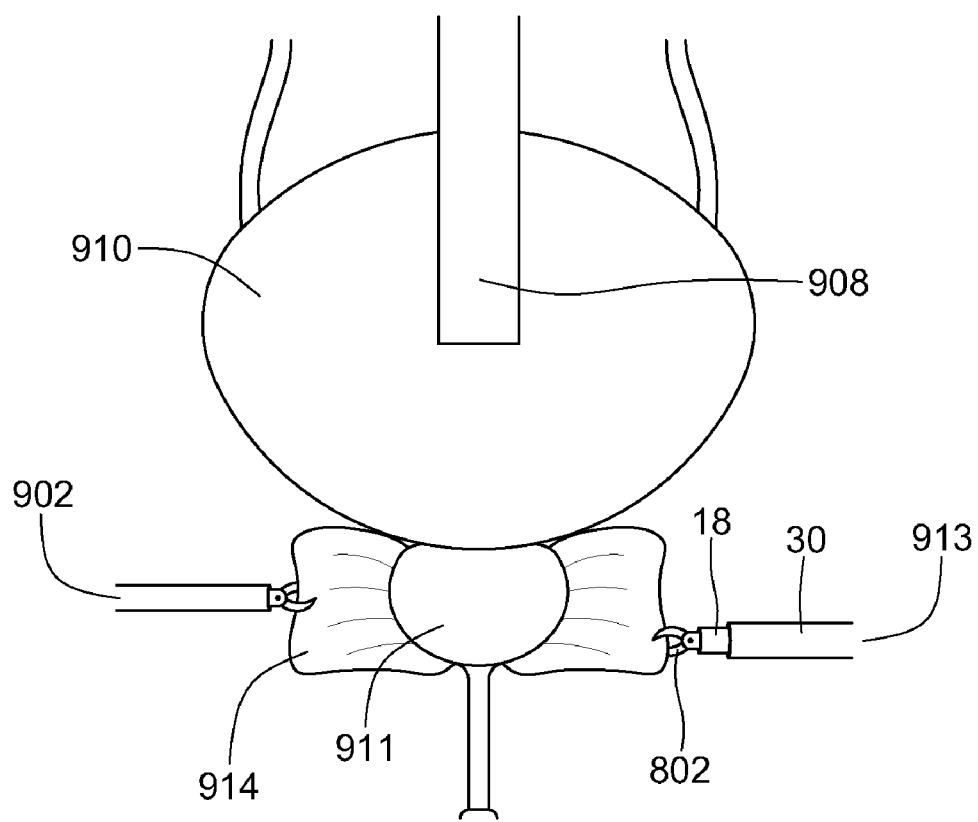
Figure 210E:
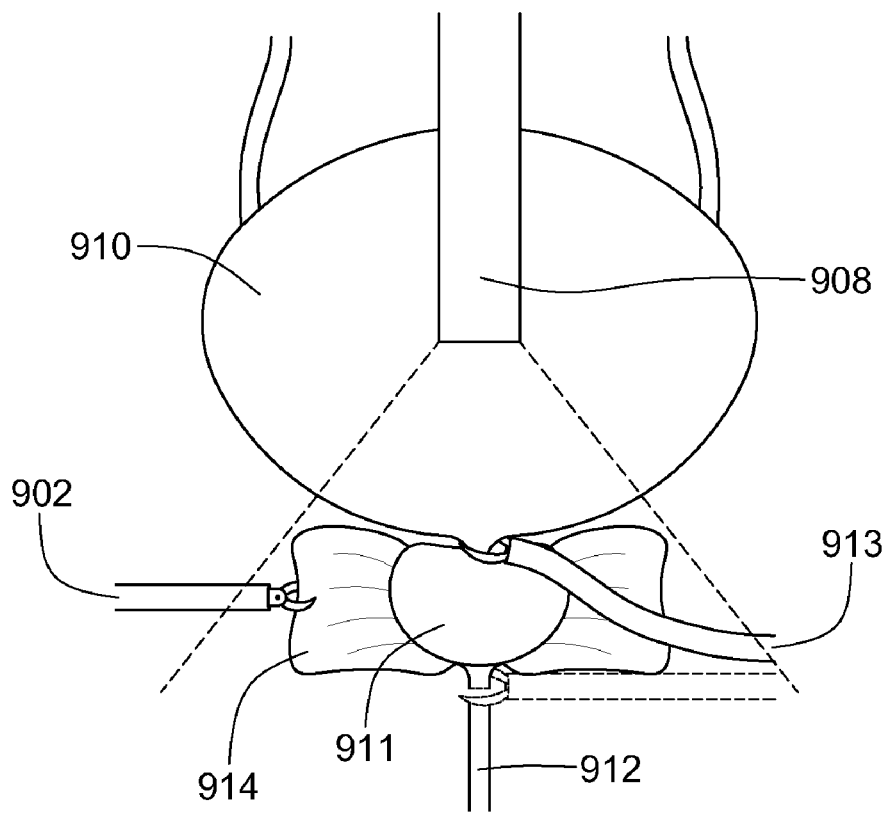
Figure 210F:
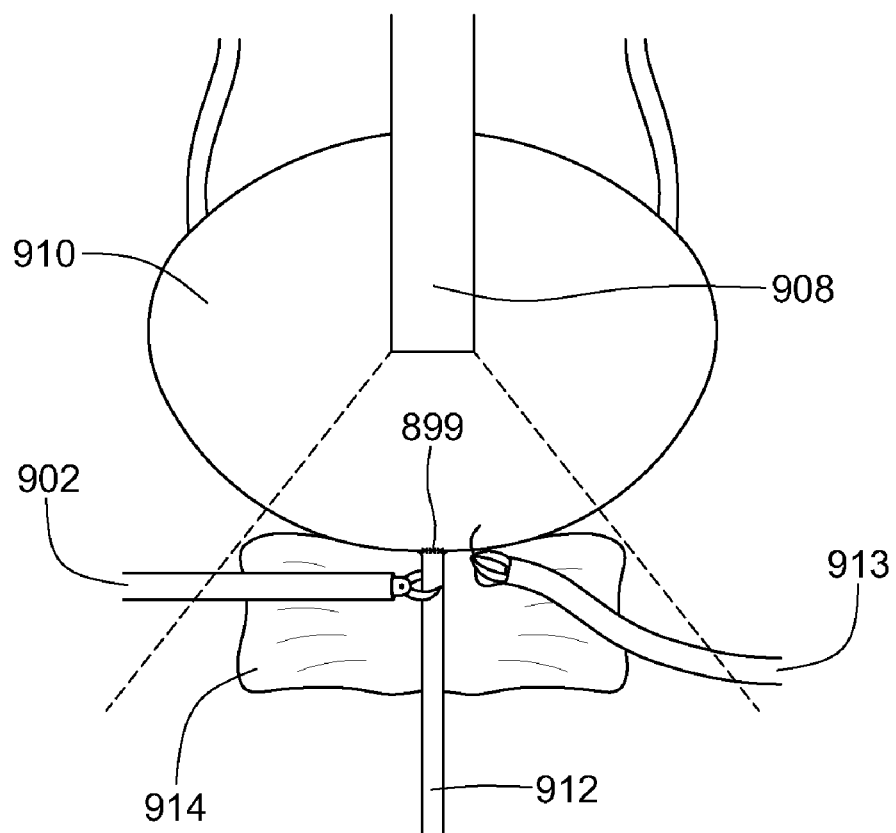
Figure 210G:
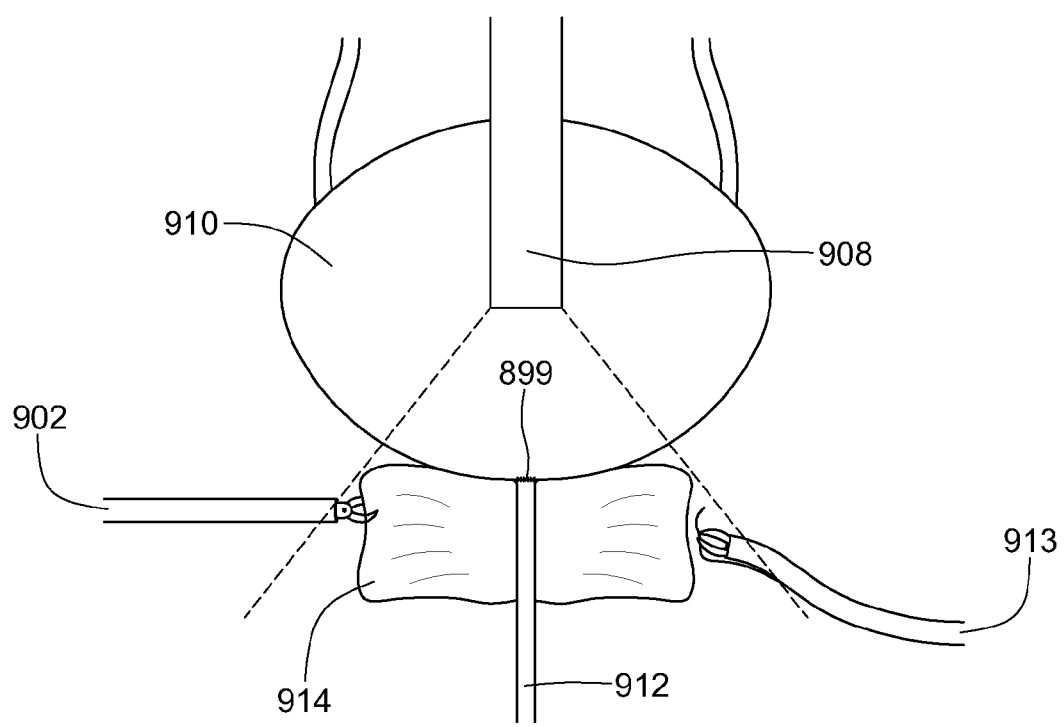
Figure 210H:
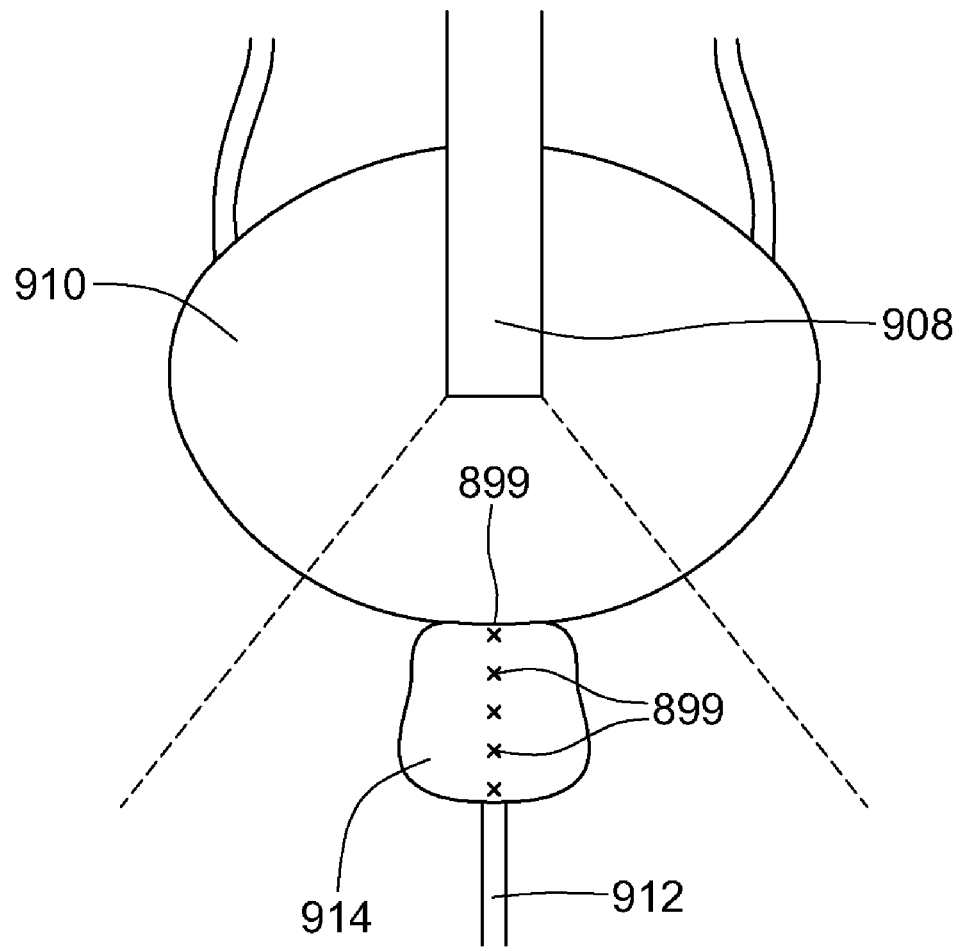

Referring to FIGS. 210A-H, one embodiment of a laparoscopic prostatectomy is depicted utilizing robotic instrument assemblies according to various embodiments of the invention. The umbilicus (889) and a variety of preferred laparoscopic surgical ports provide access to various facets of the male urinary system. Referring to FIG. 210A, the umbilicus (889) is a preferred port for a steerable endoscope (908) in a laparoscopic prostatectomy procedure given the pelvic anatomy and position of other tissues. Referring to FIG. 210B, two other instrument assemblies (902, 913) may be passed through bikini-line side ports to provide direct access to the prostate gland (911). As shown in FIG. 210C, a first instrument assembly (902) may comprise a grasping tool, while a second instrument assembly (913) may comprise a cutting tool, such as a bipolar scissors or scalpel. Referring to FIG. 210D, while one instrument assembly is utilized to dissect and manipulate the fascial tissue (914) around the prostate gland, the other instrument assembly may be utilized to cut, grasp, cauterize, etc., until the prostate gland (911) is exposed. Referring to FIG. 210E, a grasping tool on one instrument assembly and a cutting tool on the other may be utilized to detach and dissect out the prostate (911) and prostatic urethra (912). Referring to FIG. 210F, the remaining urethra (912) ends may be repaired with sutures (899). Referring to FIGS. 210G-H, the facial tissue (914) previously surrounding the prostate gland may be sutured (899) to itself to form a collar about the urethra (912).

Figure 211A:
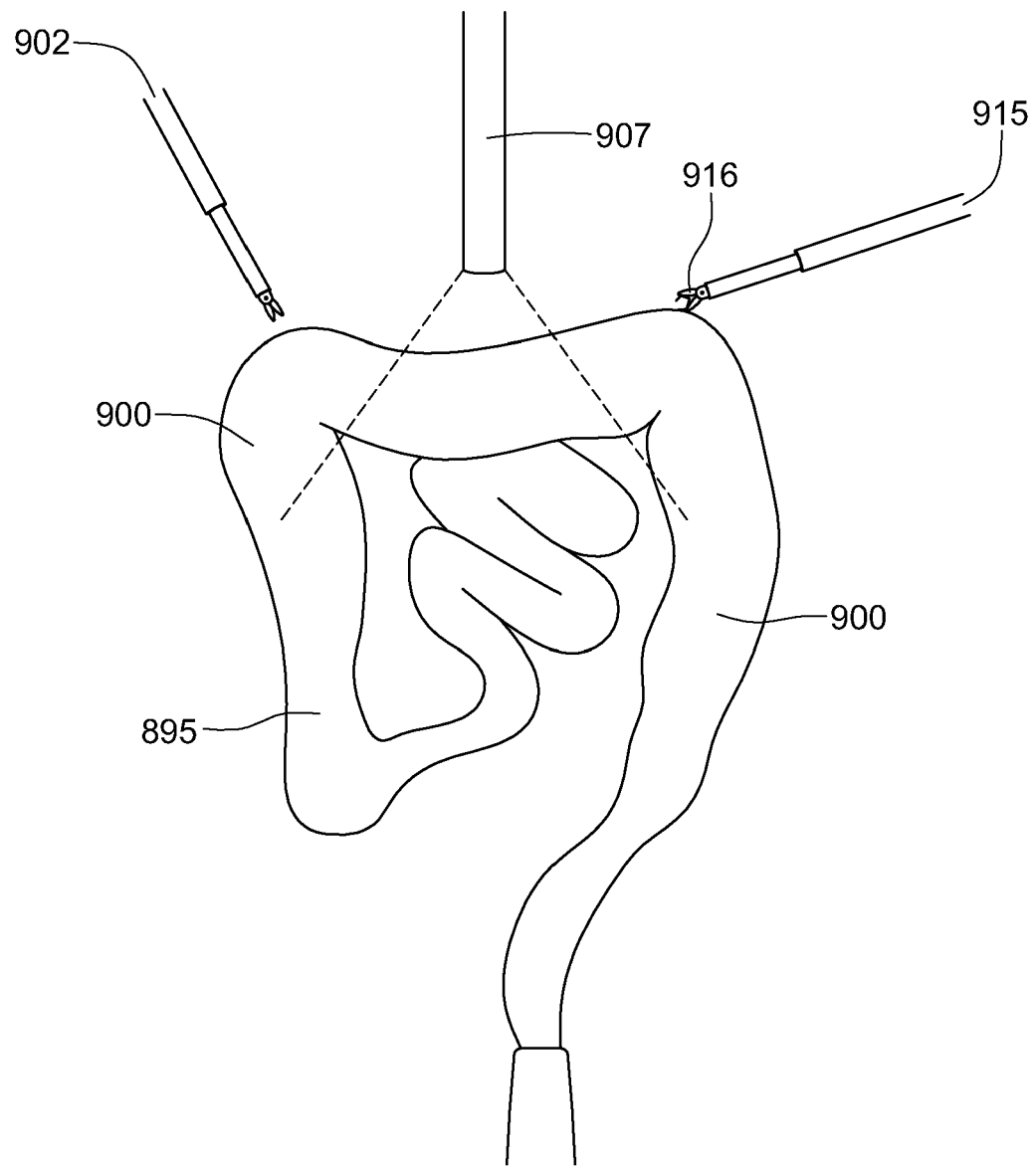
FIGS. 211A-211C illustrates one embodiment of a laparoscopic hemicolectomy system and procedure utilizing steerable instrument assemblies.
Figure 211B:
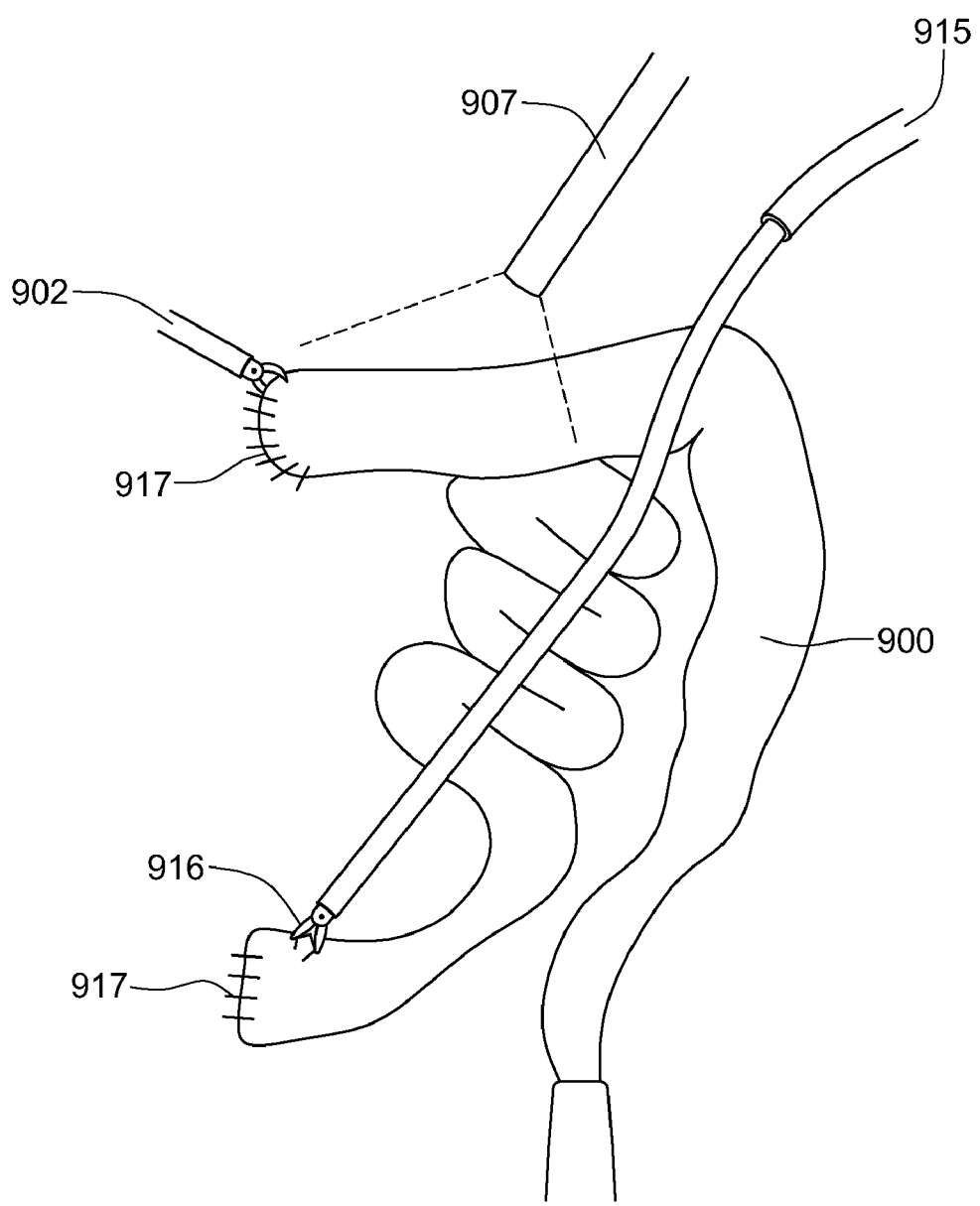
Figure 211C:
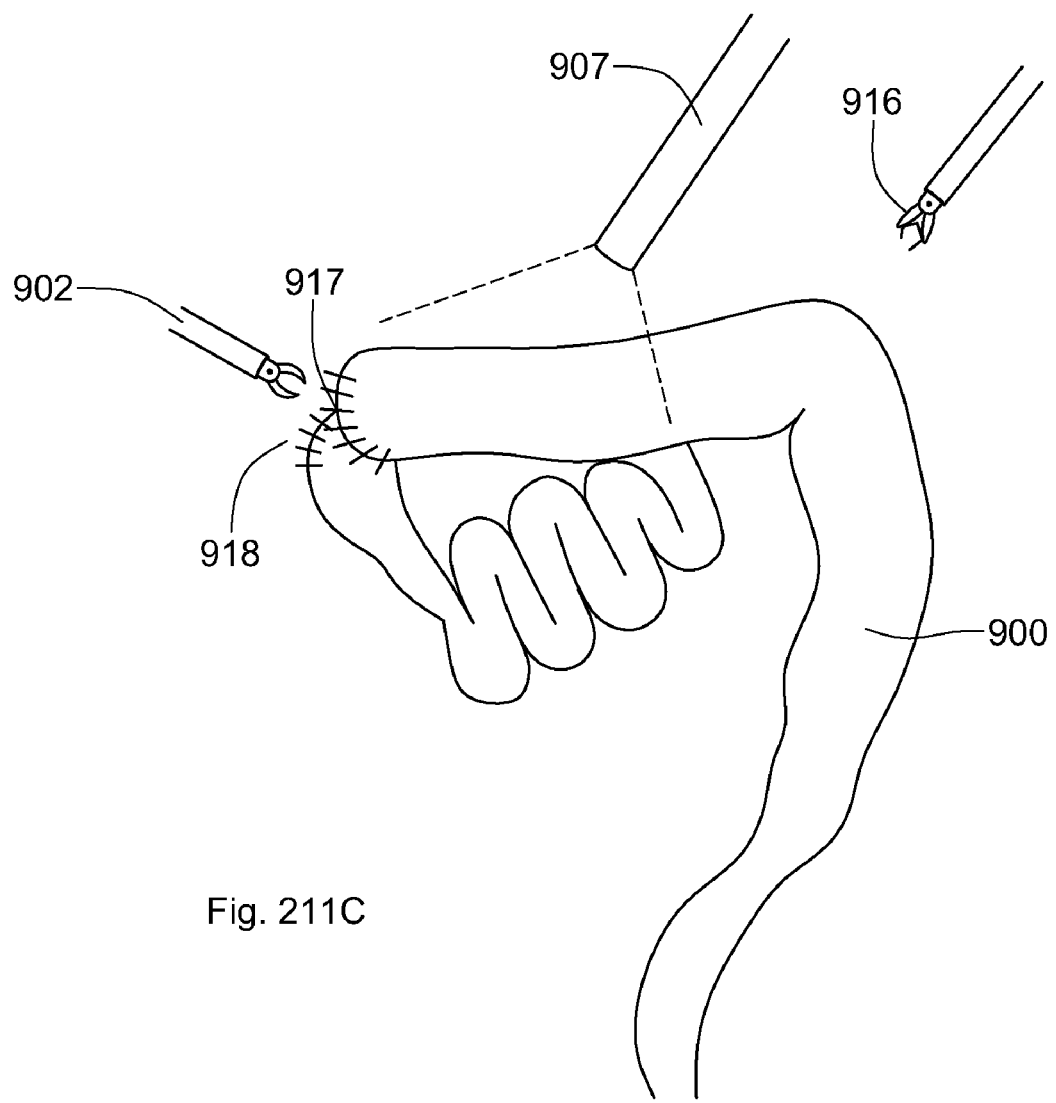

Referring to FIGS. 211A-C, two steerable instrument assemblies (902, 915) according to certain embodiments of the invention may be utilized to conduct a laparoscopic hemicolectomy, as facilitated by an image capture device positioned on a third instrument (907), as shown through an umbilicus access port, or upon a instrument which is coupled to the two steerable instrument assemblies, as shown in FIG. 194. Referring to FIG. 211A, one instrument assembly may introduce a stapling or clip-applying tool (916) while another instrument assembly may introduce a grasping, cutting, and/or cauterizing tool. Referring to FIG. 211B, a right hemicolectomy is conducted by stapling (917) off and isolating a portion of the right colon (900), then resecting and removing the isolated section, leaving two disconnected, stapled (917) ends. Referring to FIG. 211C, some or all of the staples may be removed while the discontinuity of the colon is addressed with additional staples or sutures to form an end-to-end anastomosis.

Figure 212A:
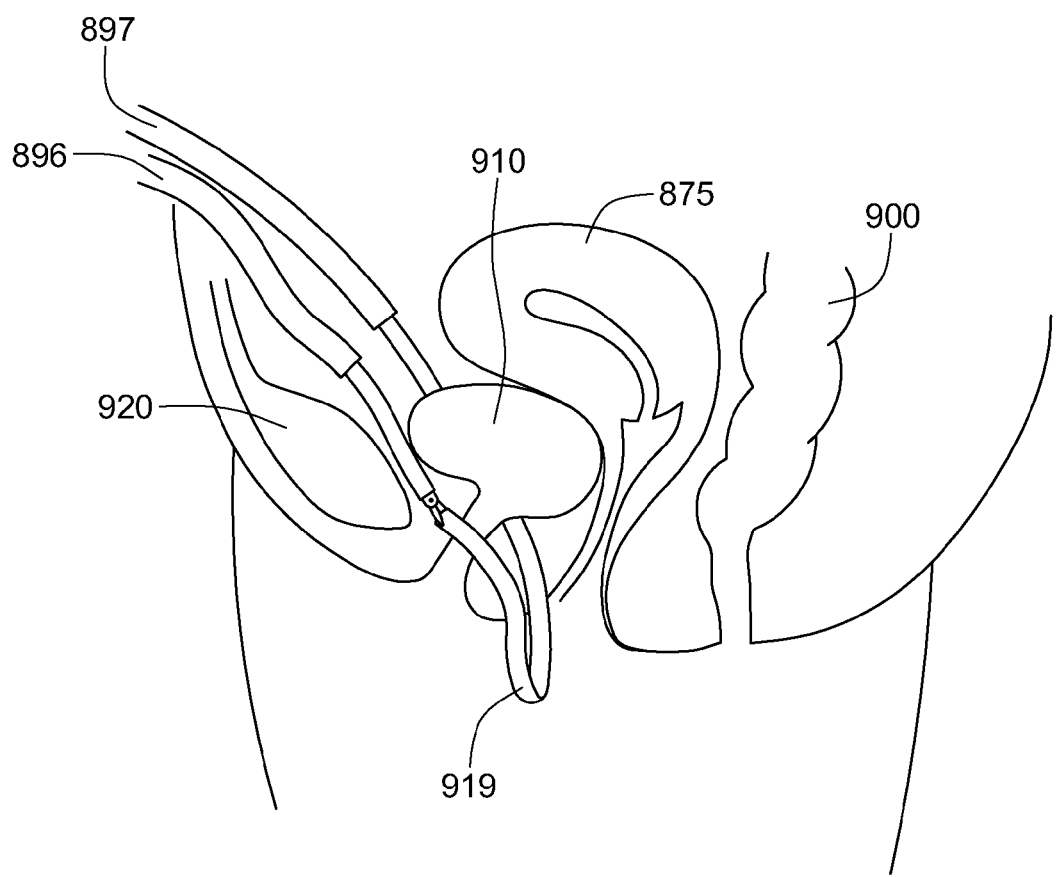
FIGS. 212A-212C illustrates one embodiment of a system and procedure using steerable instrument assemblies to place a sling prosthesis around the urethra.
Figure 212B:
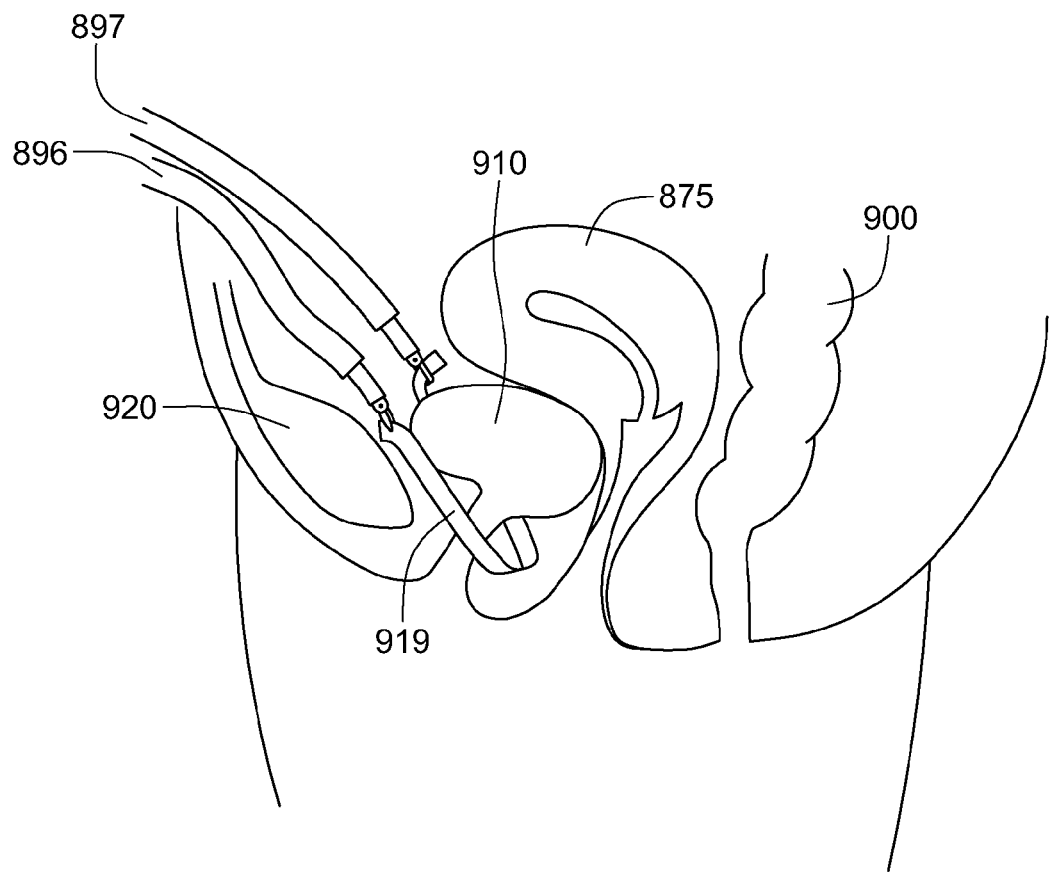
Figure 212C:
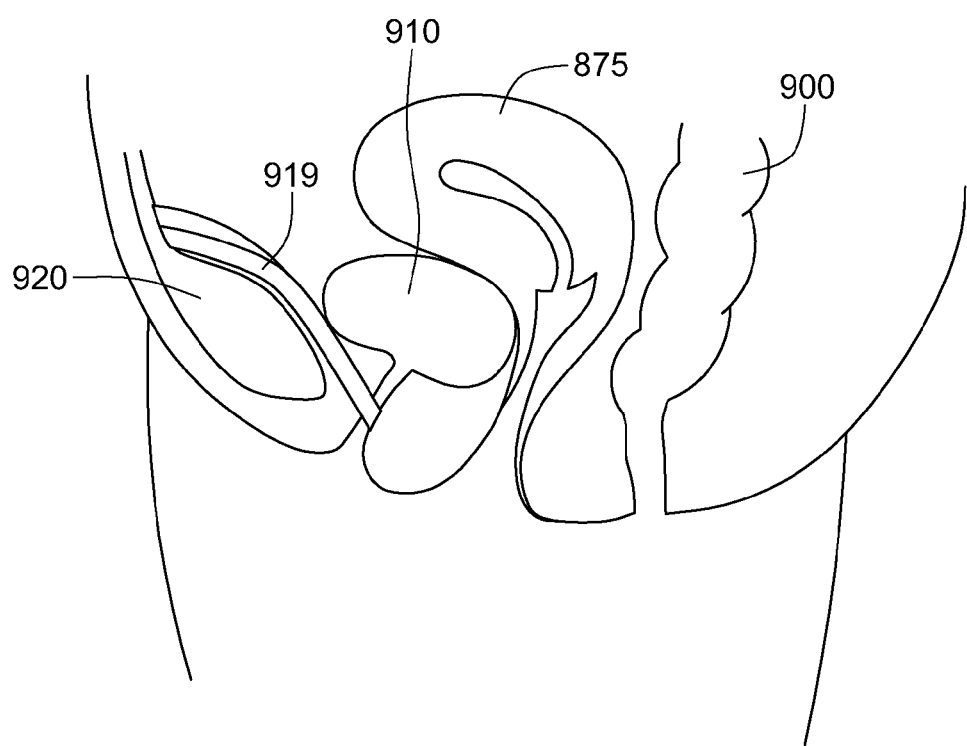
Figure 213A:
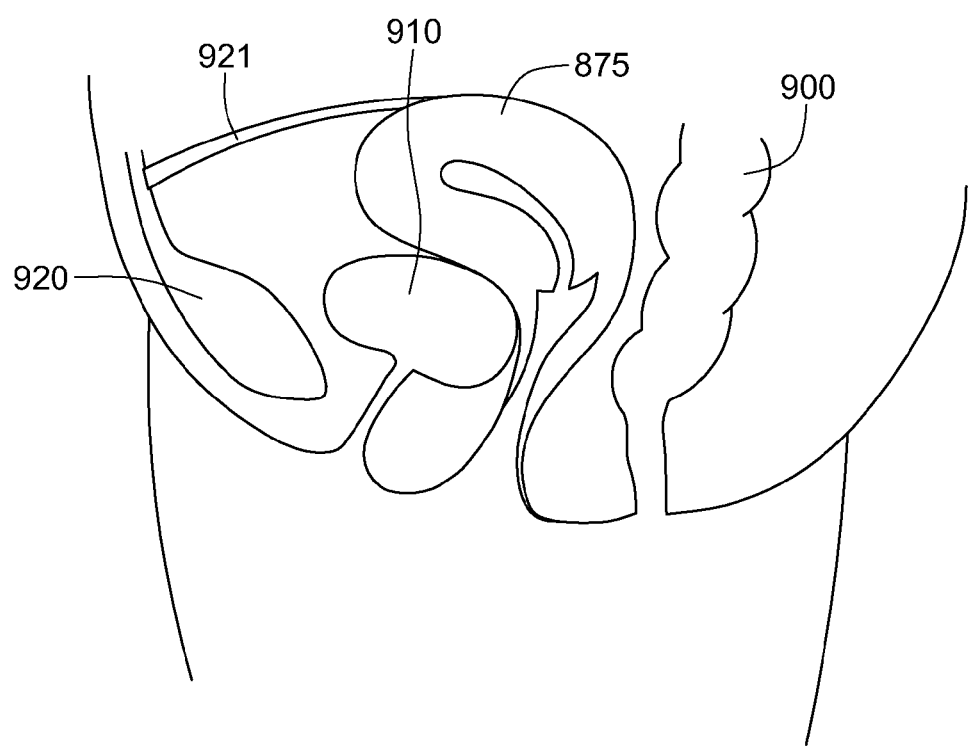
FIGS. 213A-213B illustrates one embodiment of a system and procedure using steerable instrument assemblies to install tensile suspension elements to support the uterus.
Figure 213B:
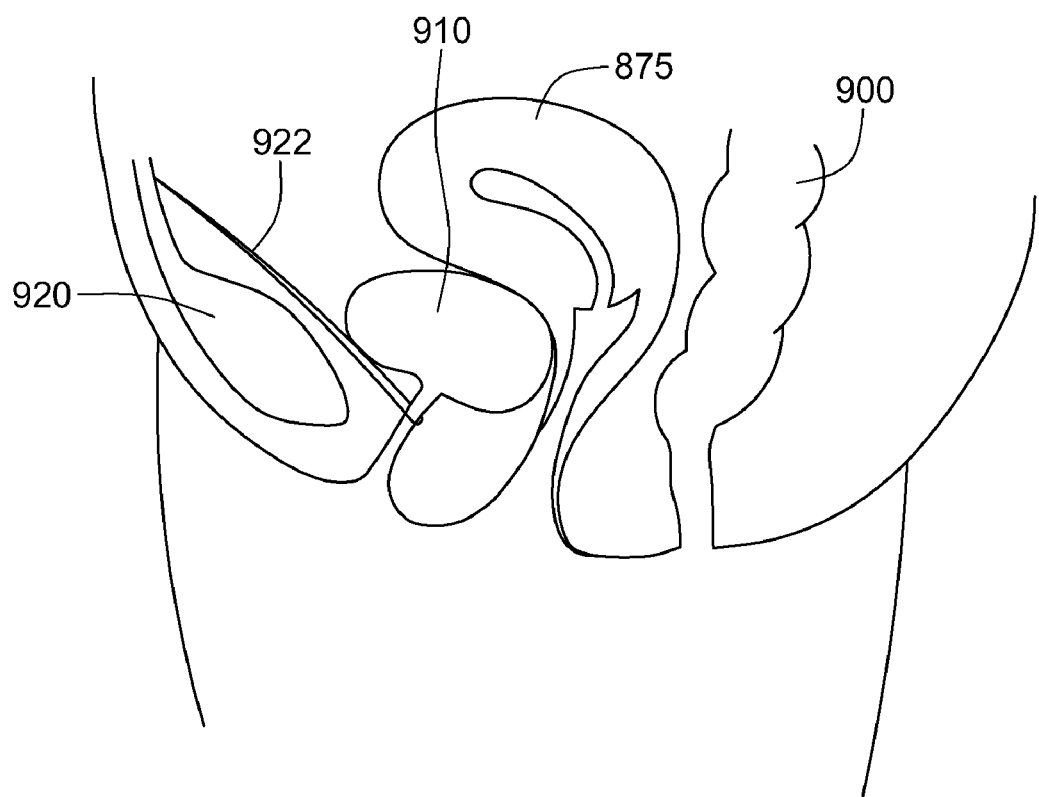

Referring to FIGS. 212A-C, one or more steerable instrument assemblies according to certain embodiments of the invention may be utilized to precisely navigate the tissues of the pelvic region to place a sling prosthesis (919) around the neck of the urethra as it exits the female bladder (910), to prevent prolapse of the bladder (910), urethra, or vagina (875). Appropriate suspension of the urethra may decrease symptoms of female incontinence. Referring to FIG. 212C, the sling prosthesis (919) may be fastened anterior/superiorly to bones comprising the pelvis (920) or soft tissue structures, such as Cooper's ligament, as recommended by the manufacturers distributing such prosthesis products. Similarly, referring to FIGS. 523A-B, tensile suspension elements (921), as simple as a single or multiple sutures, may be installed with steerable instrument assemblies and utilized to support the uterus (875) or urethral neck.

Figure 214A:
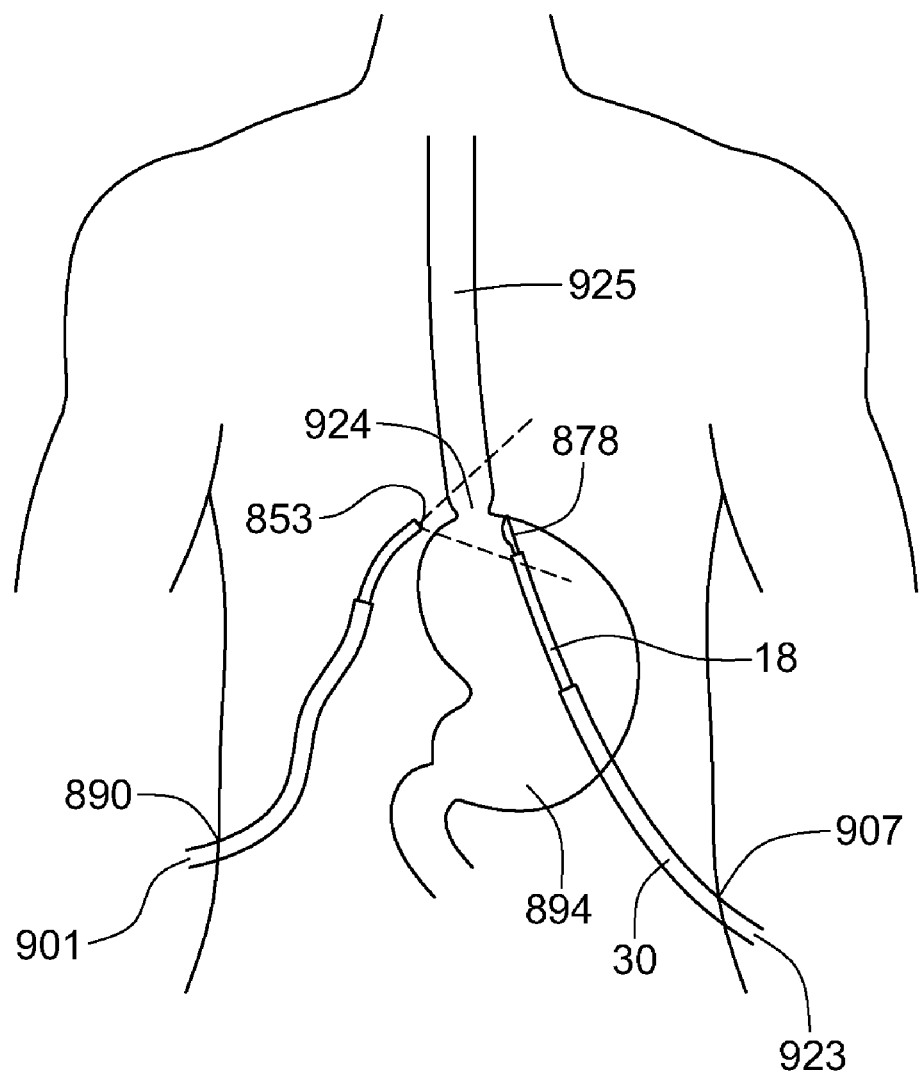
FIGS. 214A-214C illustrates one embodiment of a laparoscopic Heller myotomy system and procedure using a high precision instrument assembly.
Figure 214B:
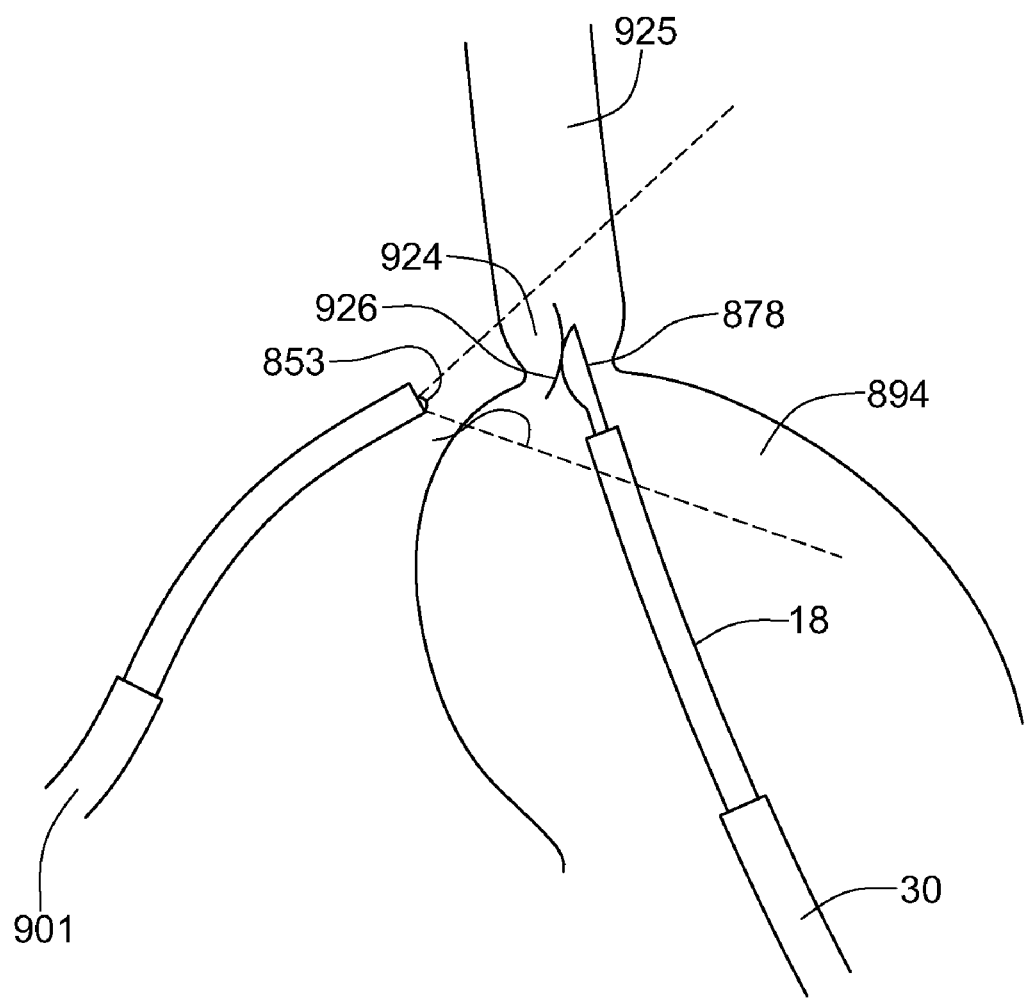
Figure 214C:
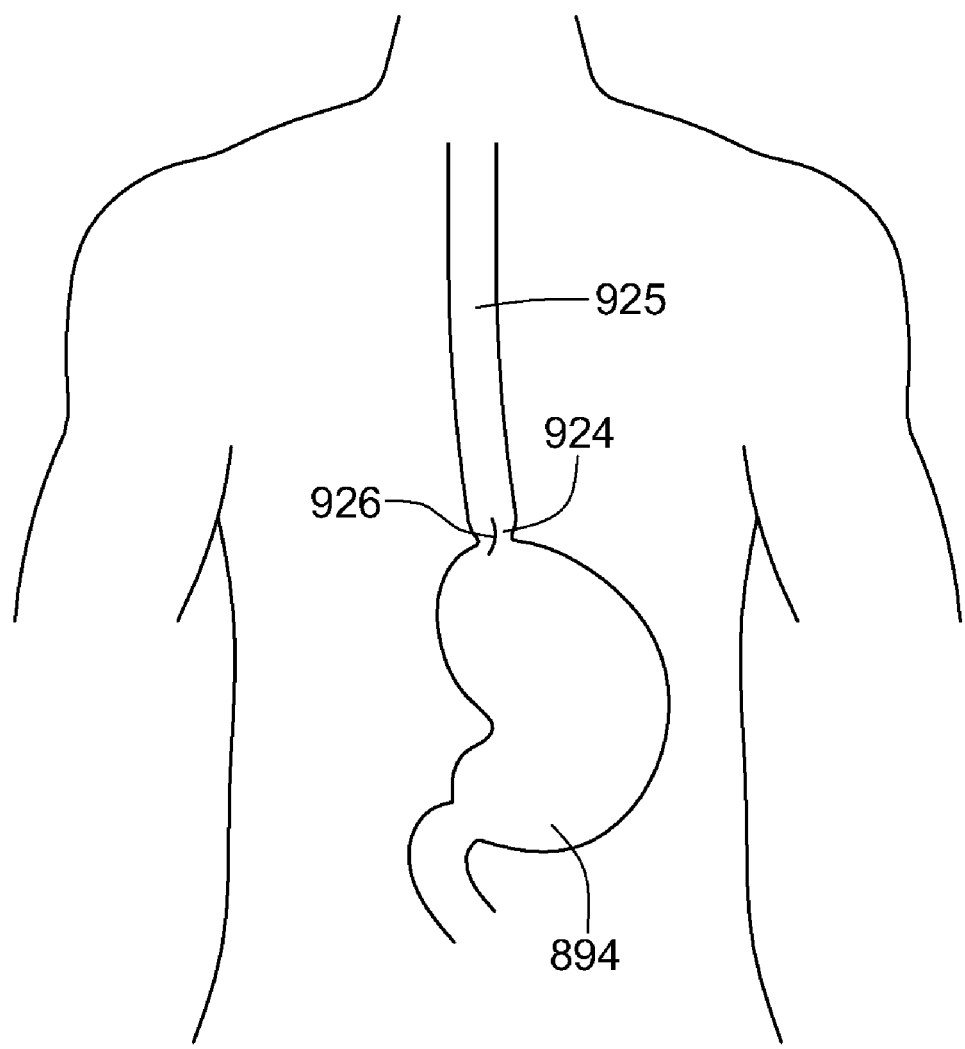
Figure 214D:
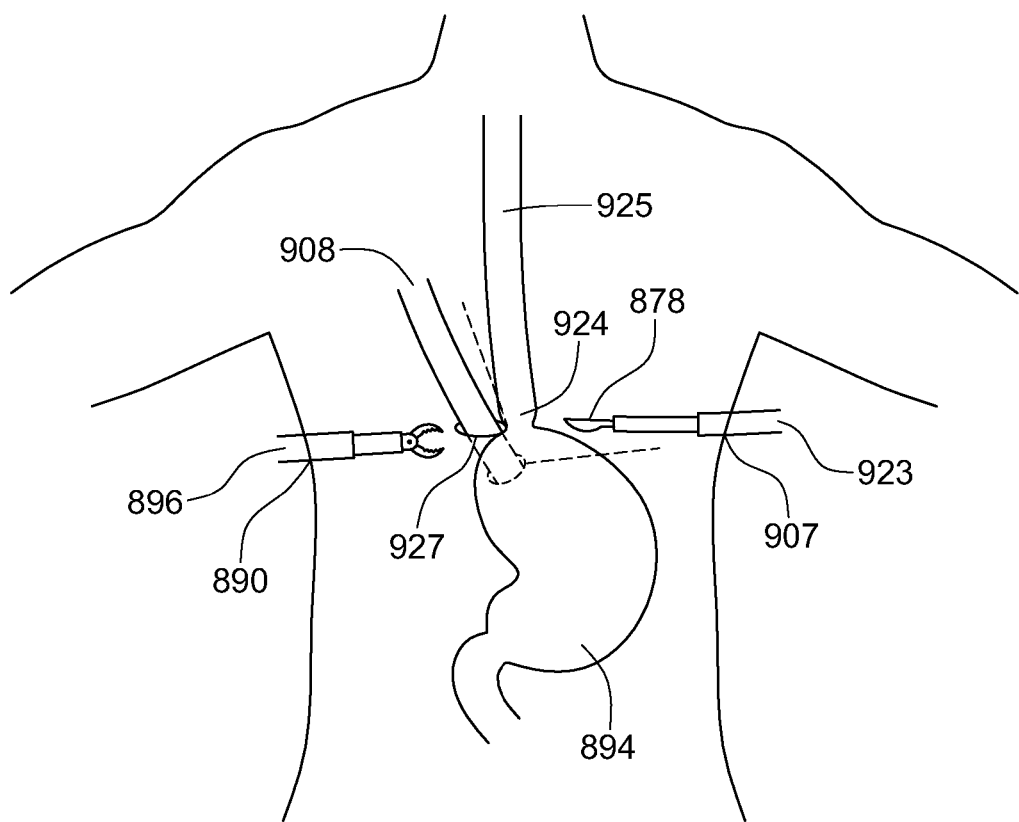
FIGS. 214D-214E illustrates another embodiment of a laparoscopic Heller myotomy system and procedure via a transthoracic approach.
Figure 214E:
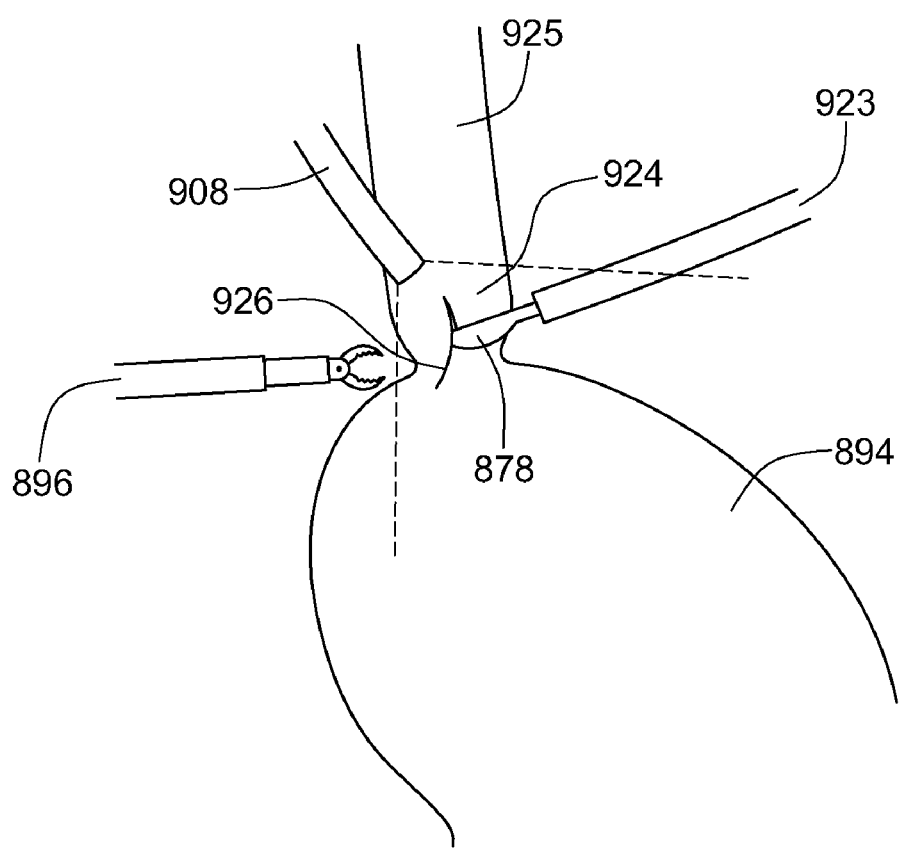

Referring to FIGS. 214A-C, a Heller myotomy may be conducted laparoscopically by approaching a clinically overtight lower esophageal sphincter (924—"LES") with a very high precision instrument assembly (923) according to one embodiment having a cutting or cauterizing tool (878), and surgically releasing (926) some of the muscle tissue that causes circumferential hoop stresses about the esophagus (925) at the LES (924). An image capture device (853) may be carried along on the same or a separate instrument assembly (901, 908). The access route may be from one or more surgically-created ports (901, 923), one of which may be the umbilicus (889). Referring to FIGS. 214D-E, a trans-thoracic approach with higher port locations may also be utilized due to the location of the LES (924) between the thorax and abdomen.

Figure 215A:
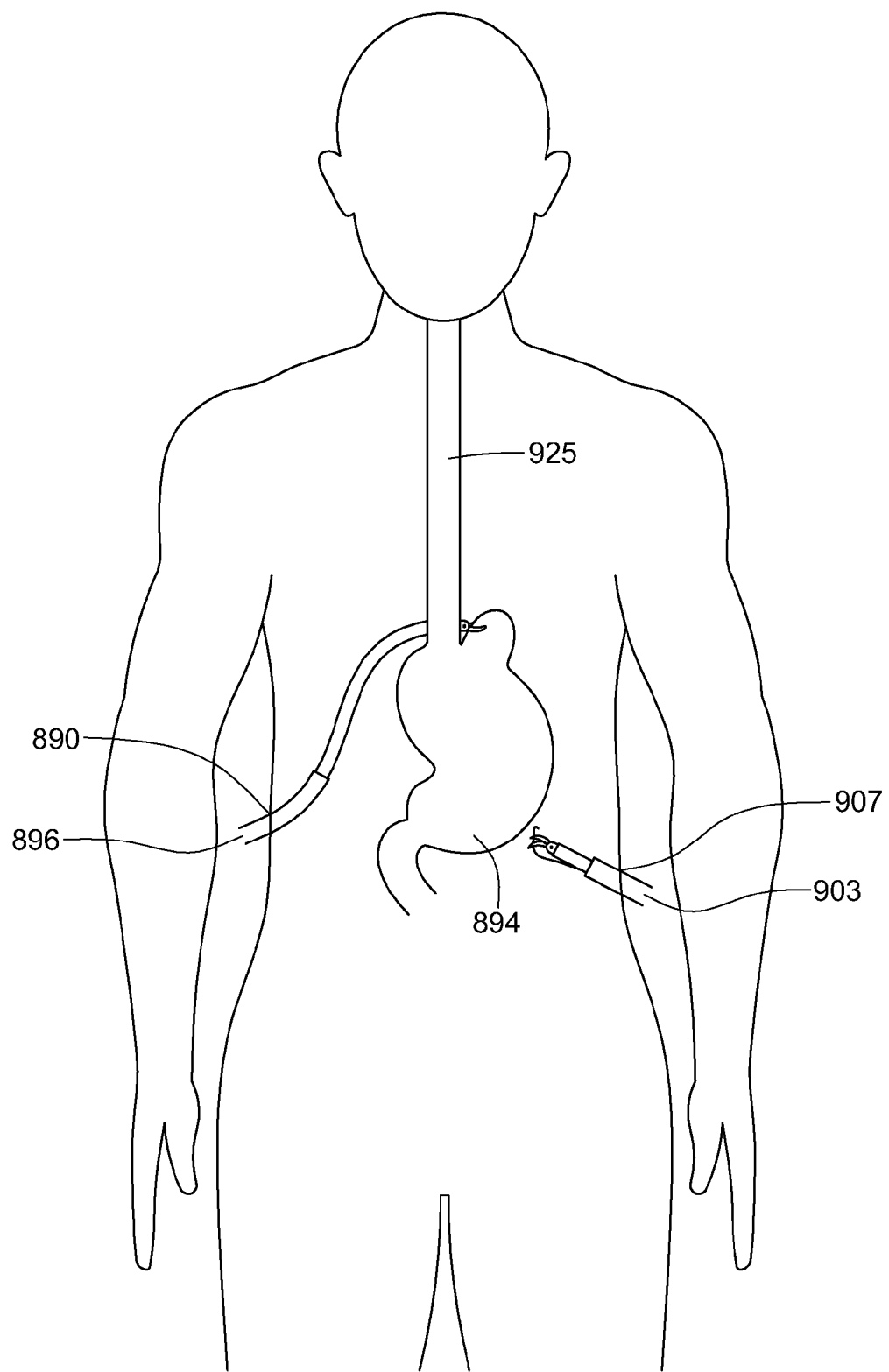
FIGS. 215A-215C illustrate one embodiment of a laparoscopic Nissen fundoplication system and procedure using instrument assemblies.
Figure 215B:
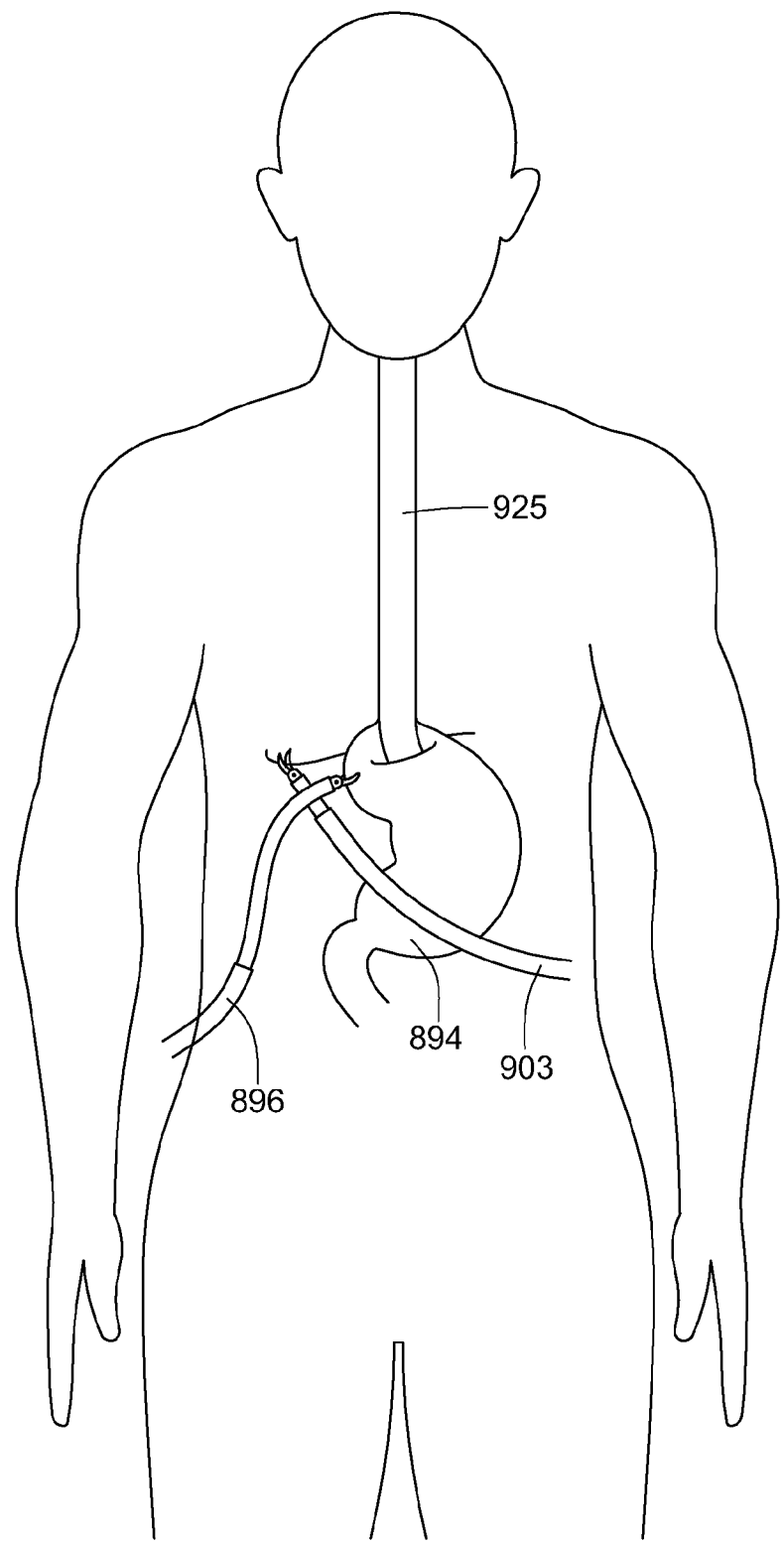
Figure 215C:
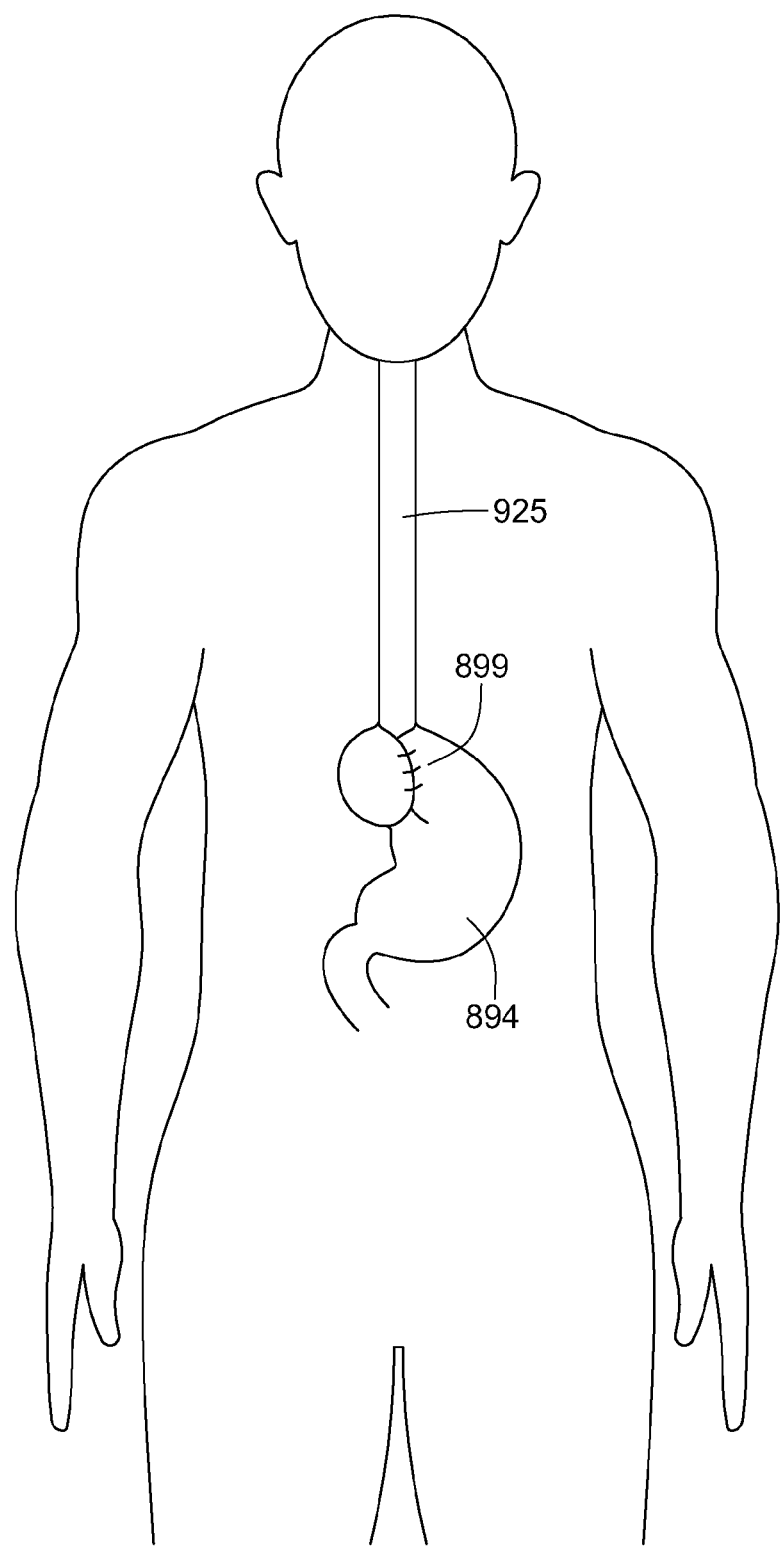
Figure 216A:
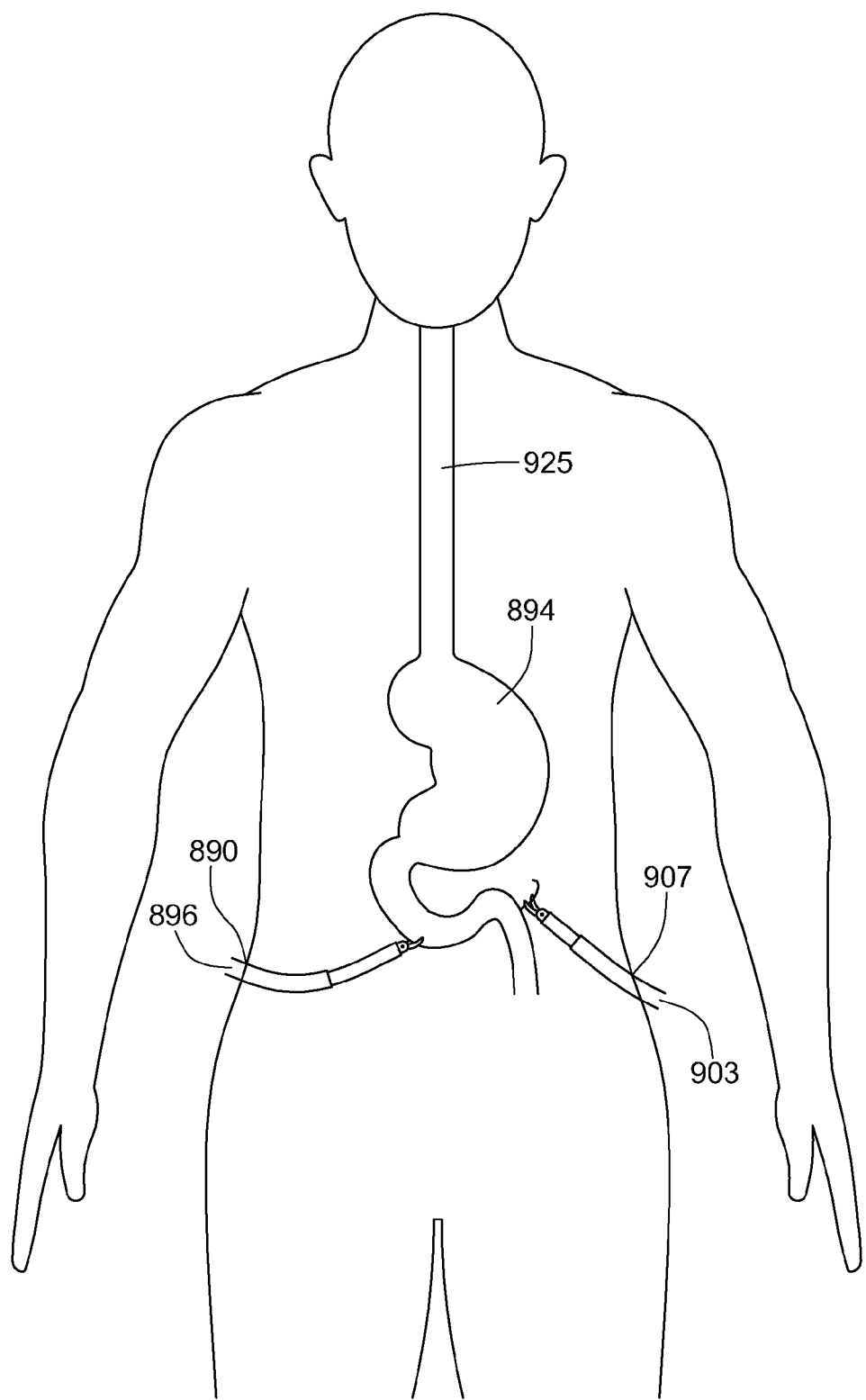
FIGS. 216A-216C illustrate one embodiment of a laparoscopic system and procedure to create a Roux-en Y anastomosis with instrument assemblies.
Figure 216B:
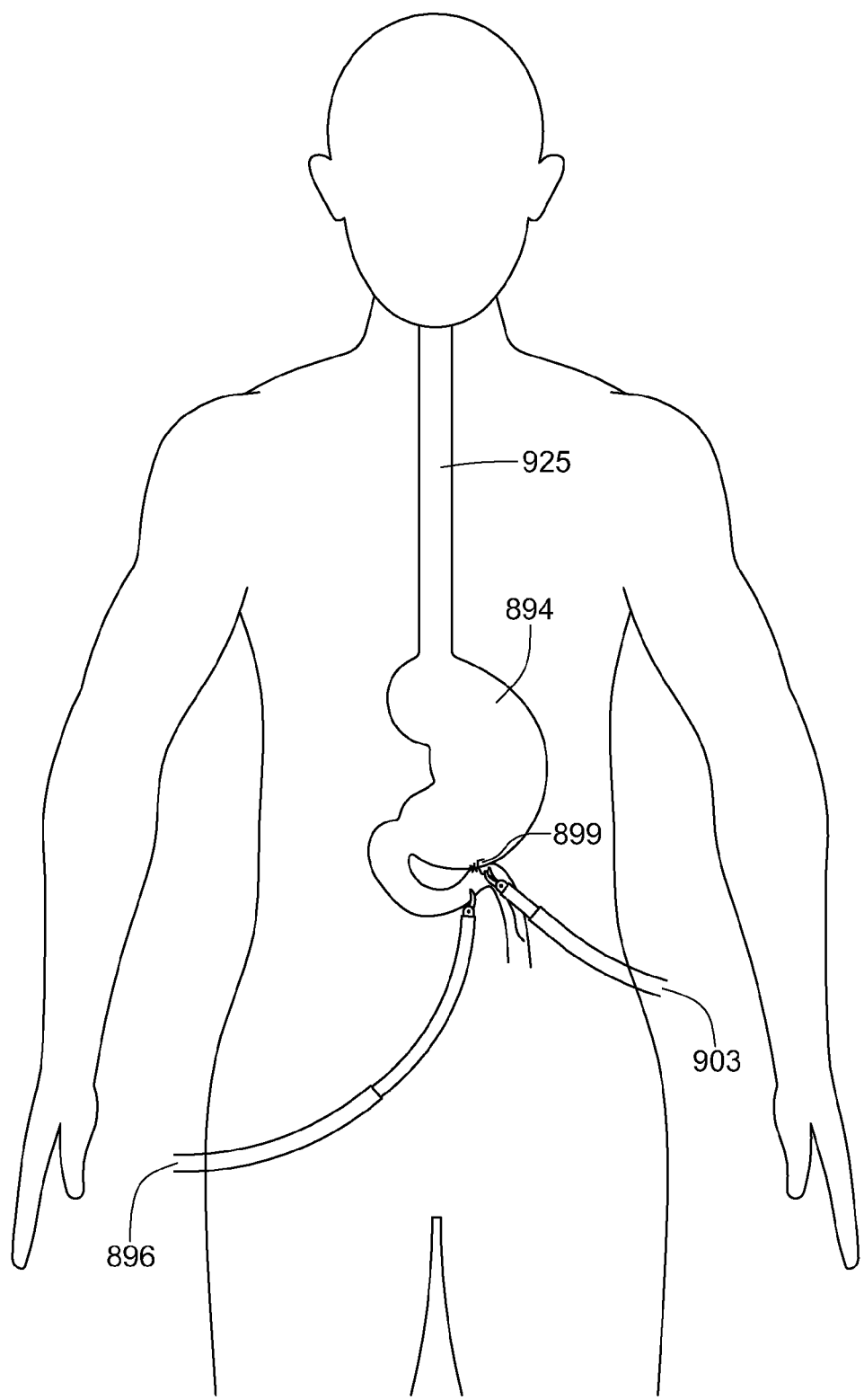
Figure 216C:
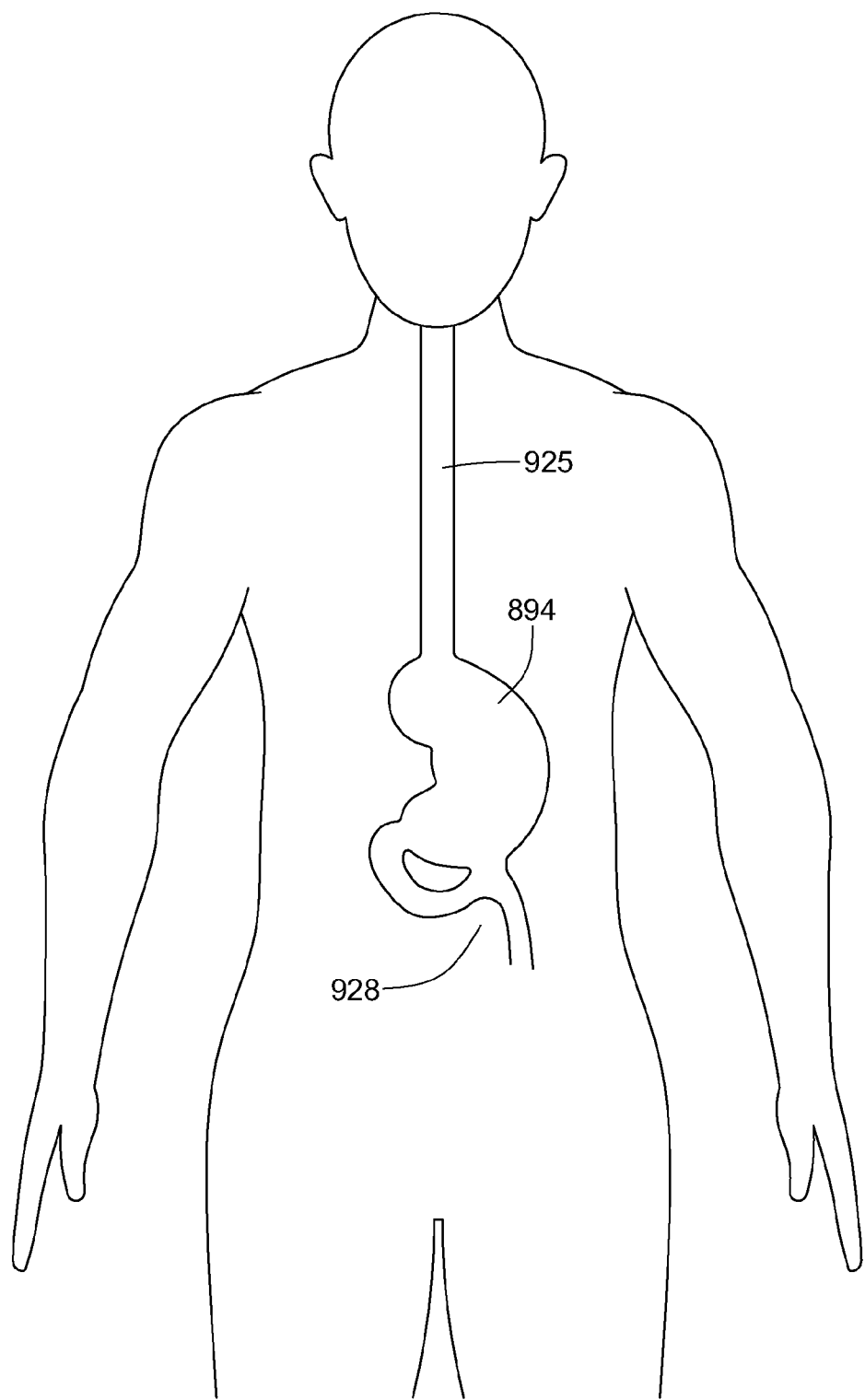
Figure 216D:
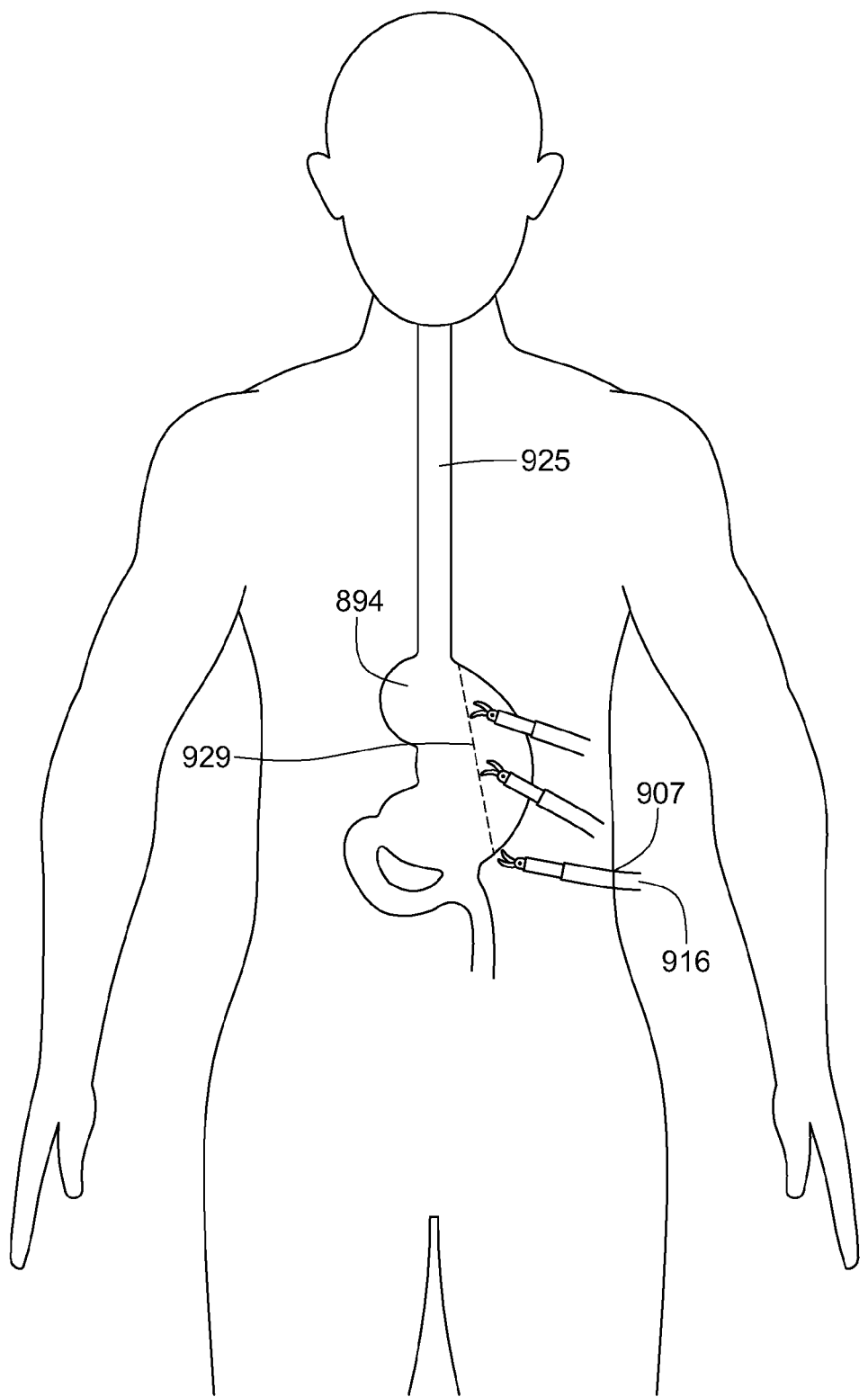
FIG. 216D illustrates one embodiment of a system and procedure for performing a stomach reduction with a robotic catheter platform.
Figure 216E:
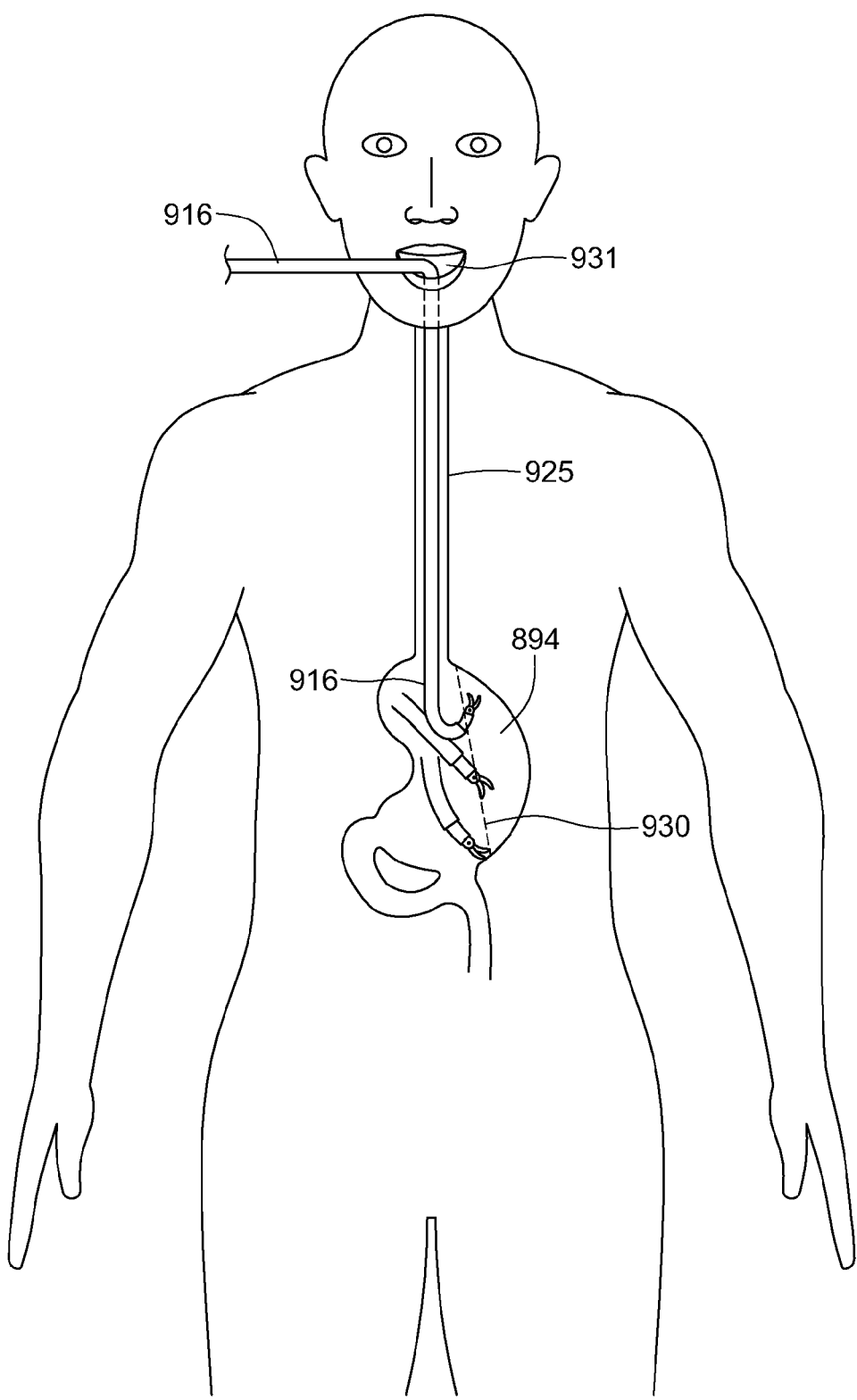
FIG. 216E illustrates another embodiment of a system and procedure for performing a stomach reduction with a steerable robotic catheter platform and an endolumenal fastening tool employed from inside the stomach.

Referring to FIGS. 215A-C, a Nissen fundoplication may be conducted laparoscopically with two or more instrument assemblies (896, 903) configured to grasp the upper stomach (894) according to certain embodiments of the invention, create a folded around collar for the LES region, and suture the collar into place, as depicted in FIG. 215C. Should the fundoplication produce an overly tight LES, one of the sutures (899) may be laparoscopically released to incrementally loosen the hoop stress upon the LES created by the fundoplication. A similar group of instruments (896, 903) may be utilized to create a Roux-en Y anastomosis (928), as shown in FIGS. 216A-C. Referring to FIG. 216D, along with a laparoscopic Roux-en Y anastomosis (928), a stomach reduction may be created with a series (929) of staples, sutures, and/or clips, installed from a robotic catheter platform such as those described herein. Alternatively, as depicted in FIG. 216E, a similar series (930) of staples, sutures, and/or clips may be installed from inside of the stomach (894), utilizing an endolumenal fastening tool (916) and a steerable robotic catheter assembly such as those described herein.

Figure 217A:
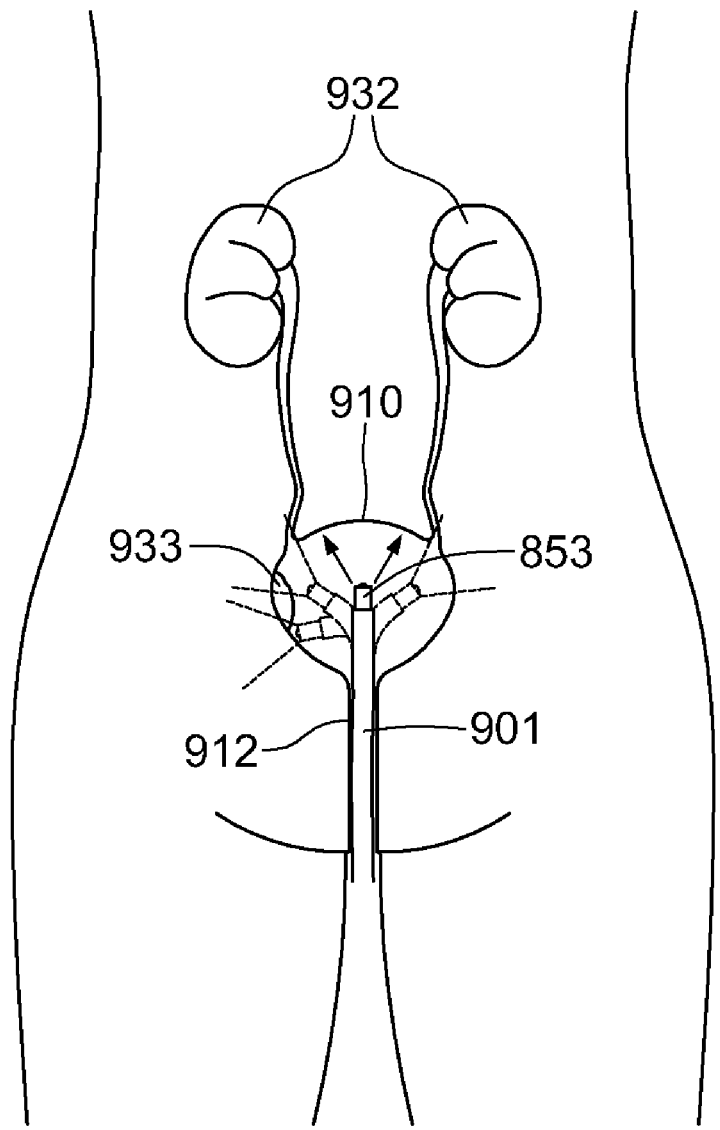
FIG. 217A illustrates one embodiment of a system and procedure using a steerable instrument with a camera device to conduct a cystoscopy.
Figure 217B:
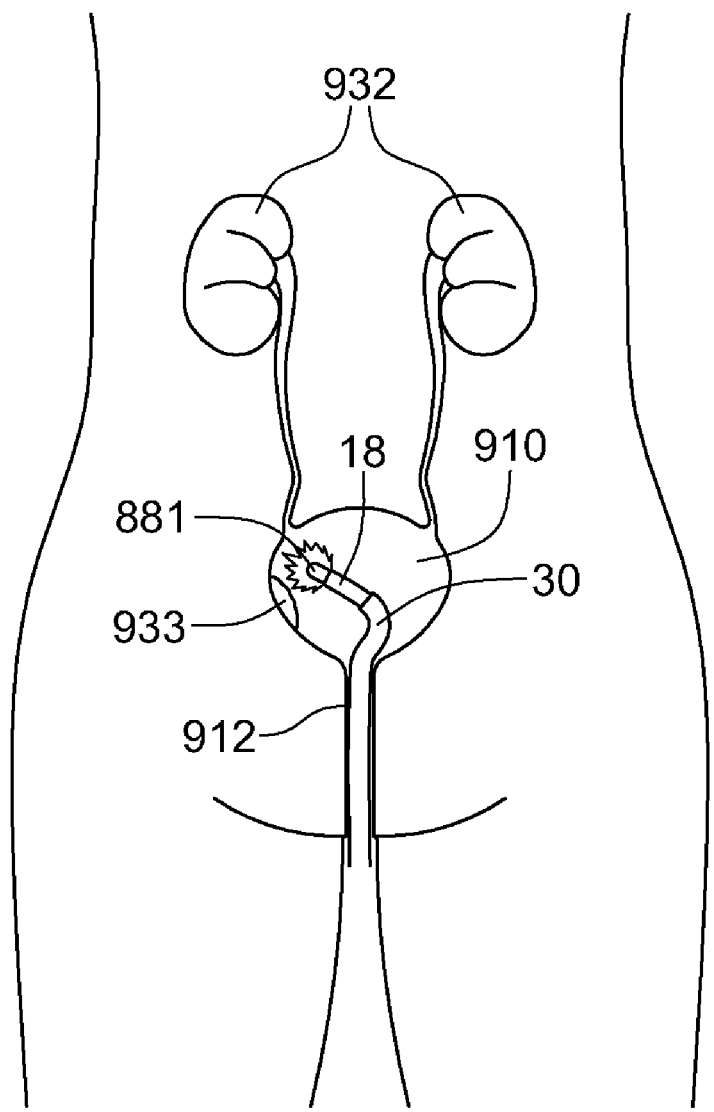
FIG. 217B illustrates one embodiment of a system and procedure using a steerable instrument with an ablation tool to perform ablation from within the bladder.
Figure 217C:
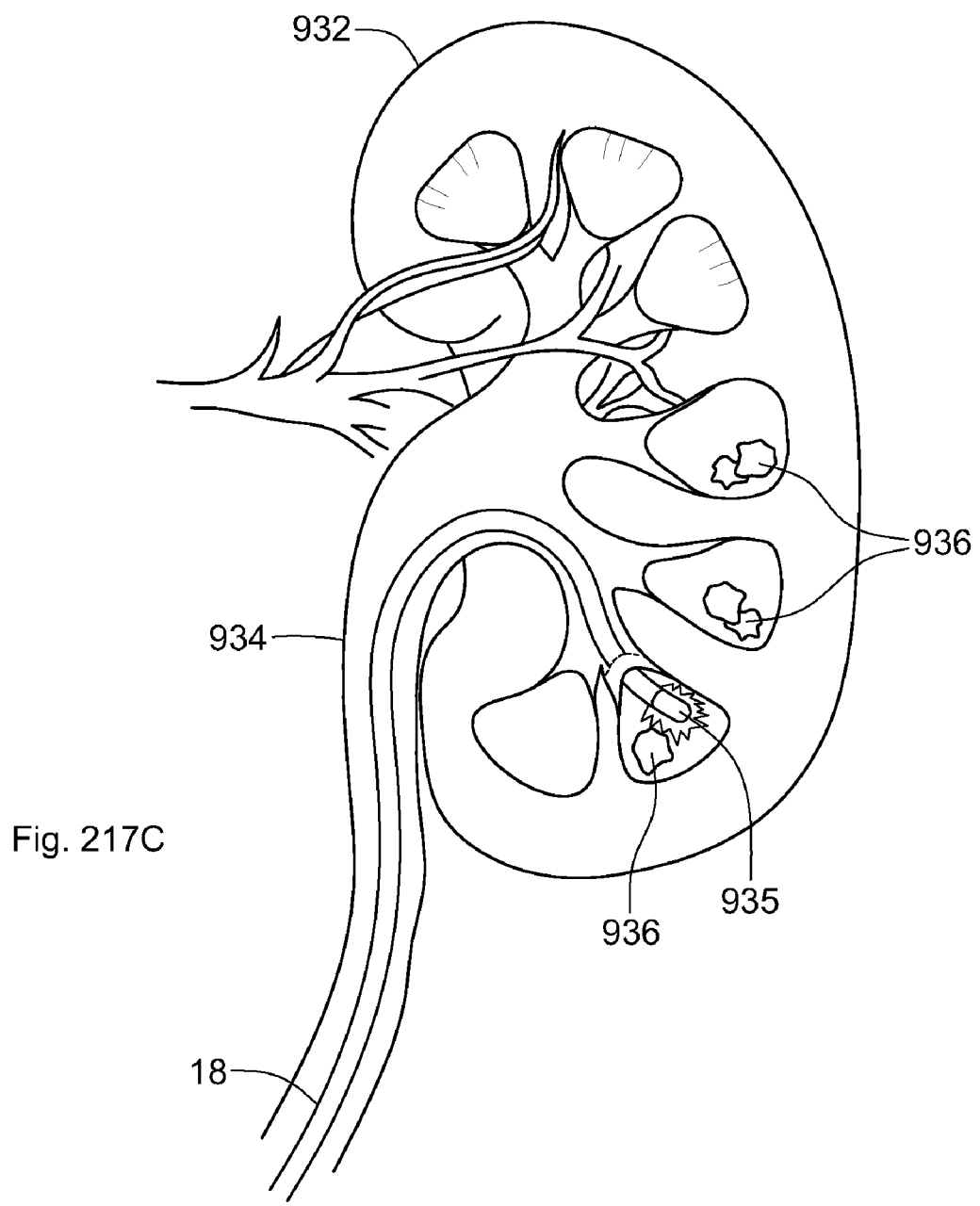
FIGS. 217C-217D illustrates one embodiment of a system and procedure steerably driving sheath and guide instruments to the kidney to handle kidney stones.
Figure 217D:
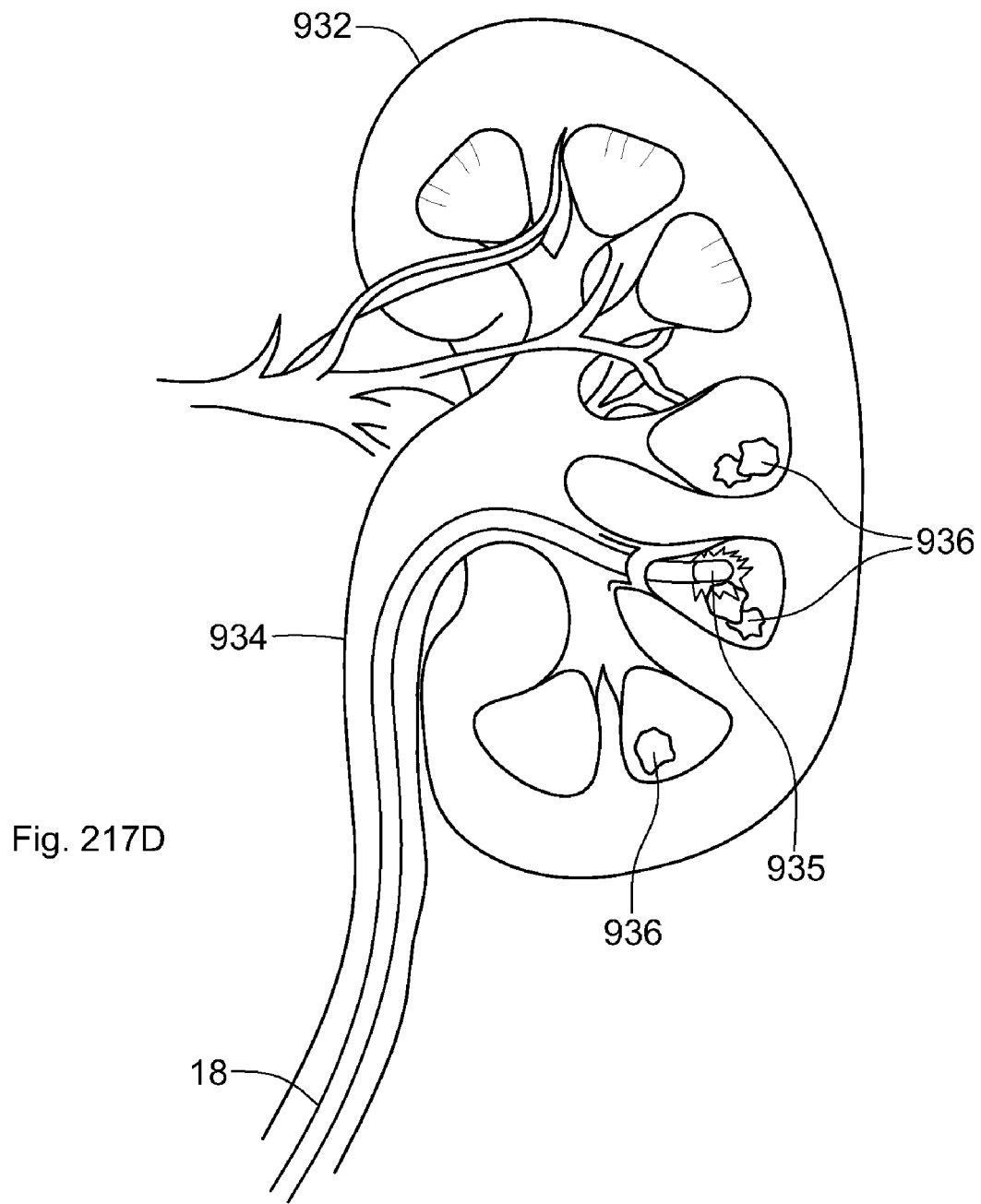

Urinary Intervention:

Referring to FIG. 217A, a steerable instrument assembly according to one embodiment may be steered through the urethra (912) and into the bladder (910), where an image capture device (853) may be utilized, as facilitated by injected saline, to conduct a cystoscopy and potentially observe lesions (933) of interest. The omni-directional steerability and precision of the robotic guide and/or sheath to which the image capture device is coupled facilitates collection of images of inside of the bladder (910) which may be patched together to form a 3-dimensional image. The instrument assembly (901) may also be utilized to advance toward and zoom the image capture device upon any defects, such as obvious bleeds or tissue irregularities. Referring to FIG. 217B, the instrument assembly (30, 18, 881) may alternatively or additional comprise an interventional tool such as an ablation tool (881) for ablating tumors or other lesions (933) within the bladder (910). Referring to FIGS. 217C-D, a portion of the instrument assembly (for example, a sheath distal tip may be positioned in the bladder at the entrance to the urethra while the more slender guide, 18, is driven toward and into the kidney, 932) may be advanced toward and steerably driven into the kidney (932), where stones (936) may be captured with graspers or other tools, or where stones may be destroyed using chemistry, cryo, RF, or laser ablation tools (935), or other radiative techniques, such as ultrasound, as depicted in FIGS. 217C-D.

Figure 218A:
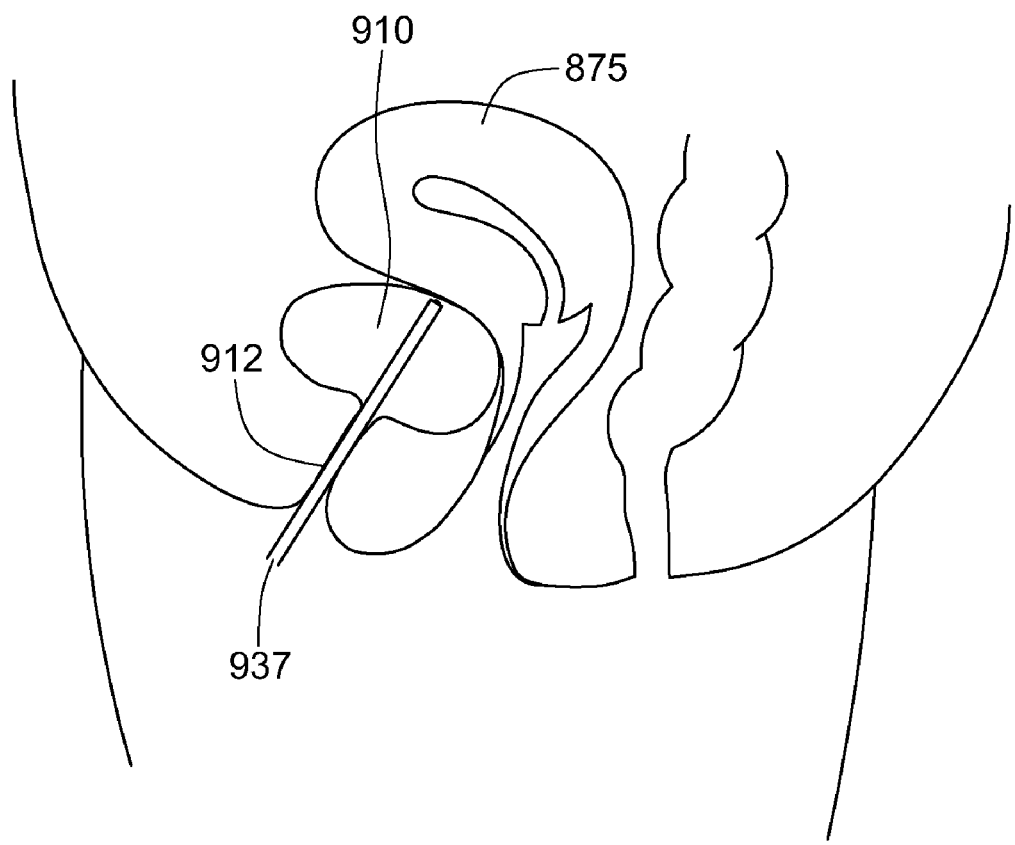
FIGS. 218A-218C illustrate one embodiment of a system and procedure using a steerable catheter platform to access intraperitoneal structures via the bladder.
Figure 218B:
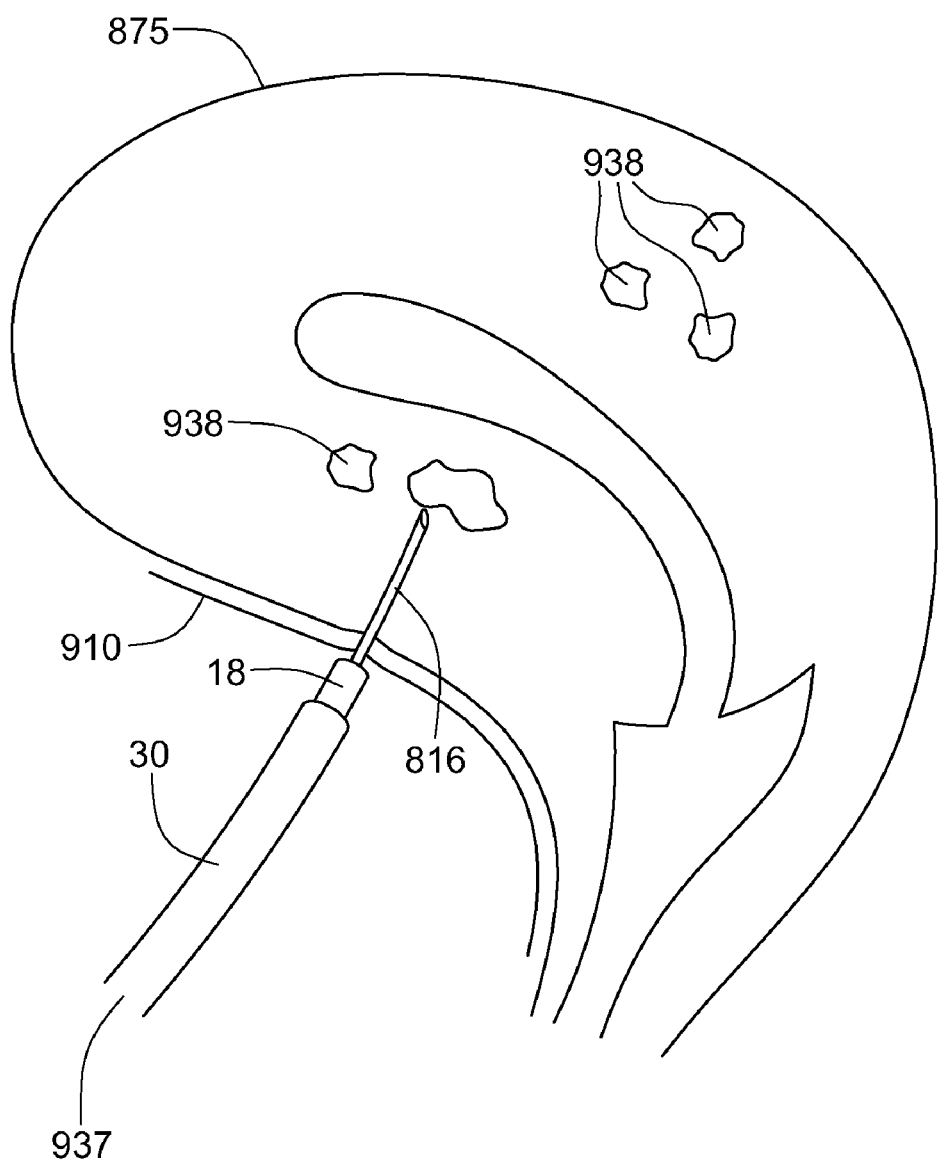
Figure 218C:
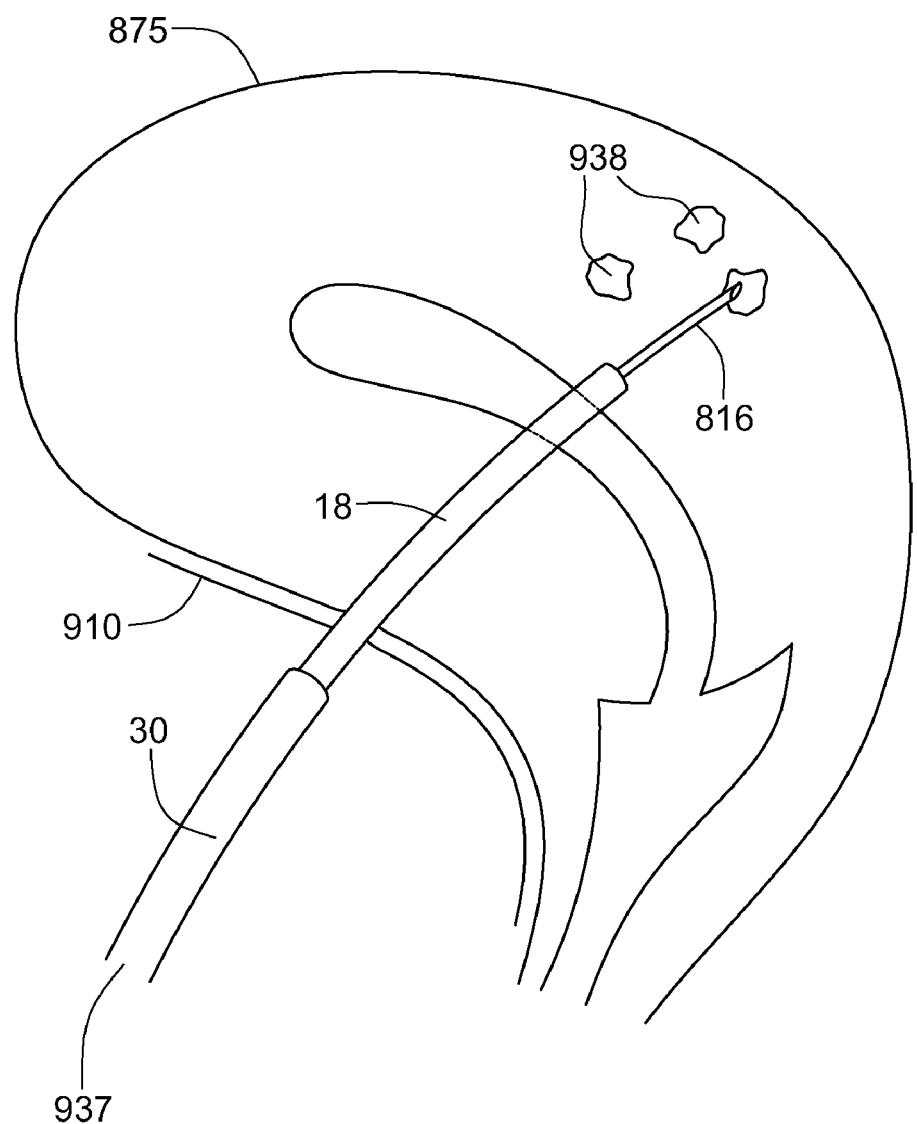

Referring to FIG. 218A, the relatively elastic bladder (910) may be utilized as a flexible access point or setup/approach space for intraperitoneal structures such as the uterus (875), subsequent to advancement past the urethra (912) and through the wall of the bladder (910) as shown in FIGS. 218A-C. As depicted in FIGS. 218B-C, this access route may be utilized for imaging/biopsy/lysing of tissue, ablation of tissue, injection of medication or cell/gene therapy, etc. within all areas of the uterus utilizing a slender tool, such as a retractable needle (816) coupled to a steerable catheter platform (937). This access route may be utilized to navigate to, biopsy, mark, and/or lyse tissue lesions (938) such as fibroid tumors.

Figure 219A:
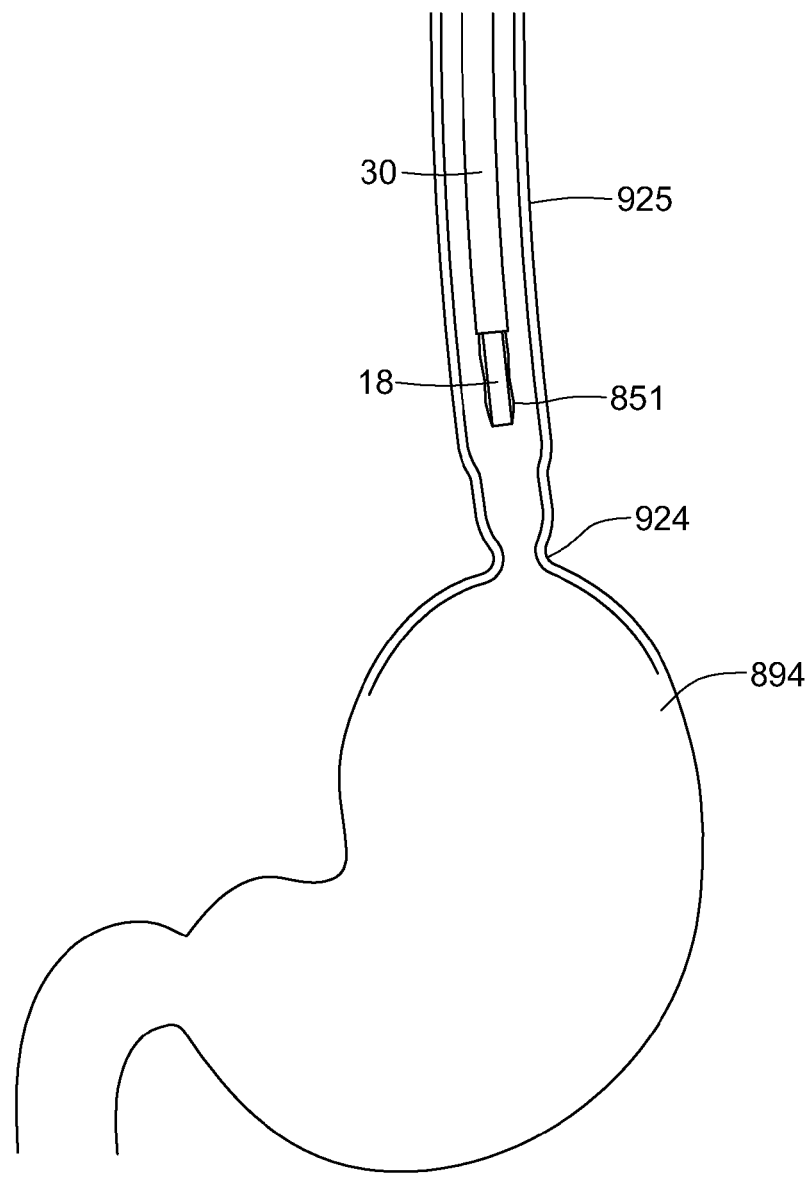
FIGS. 219A-219C illustrate one embodiment of a system and procedure to expand the lower esophageal sphincter by positing an expandable balloon with a steerable instrument assembly.
Figure 219B:
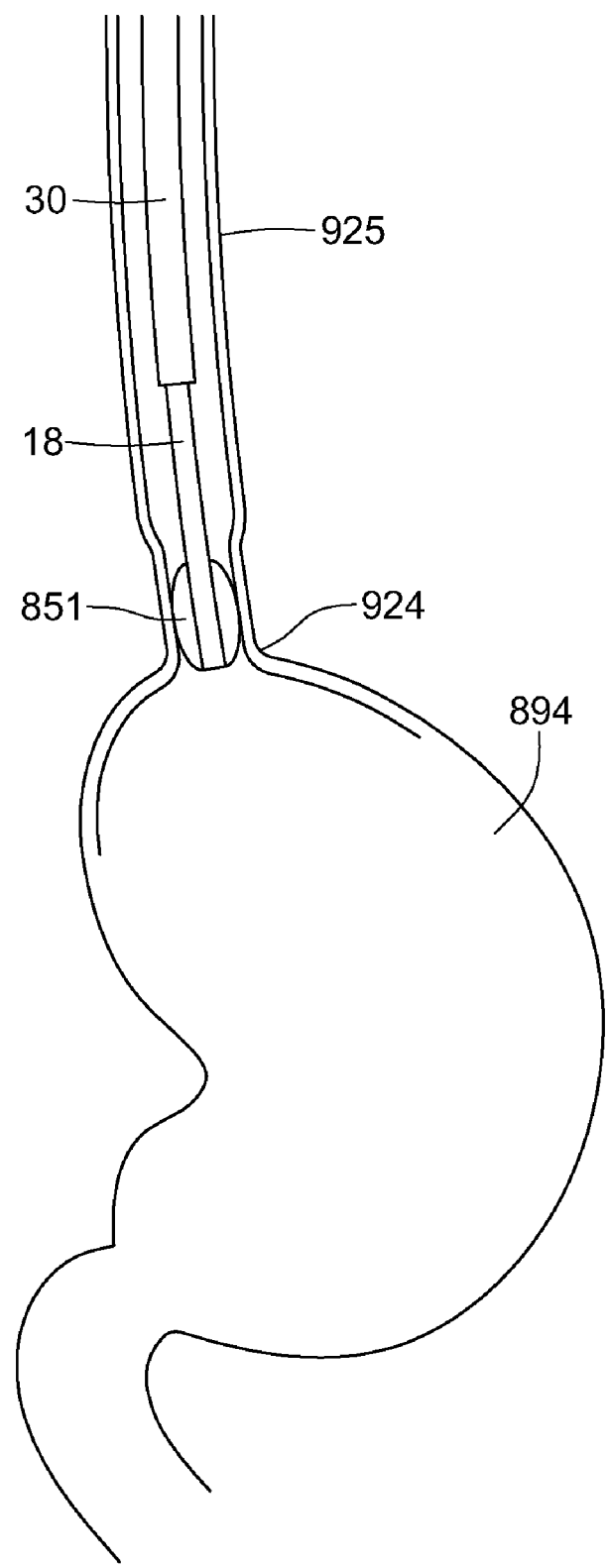
Figure 219C:
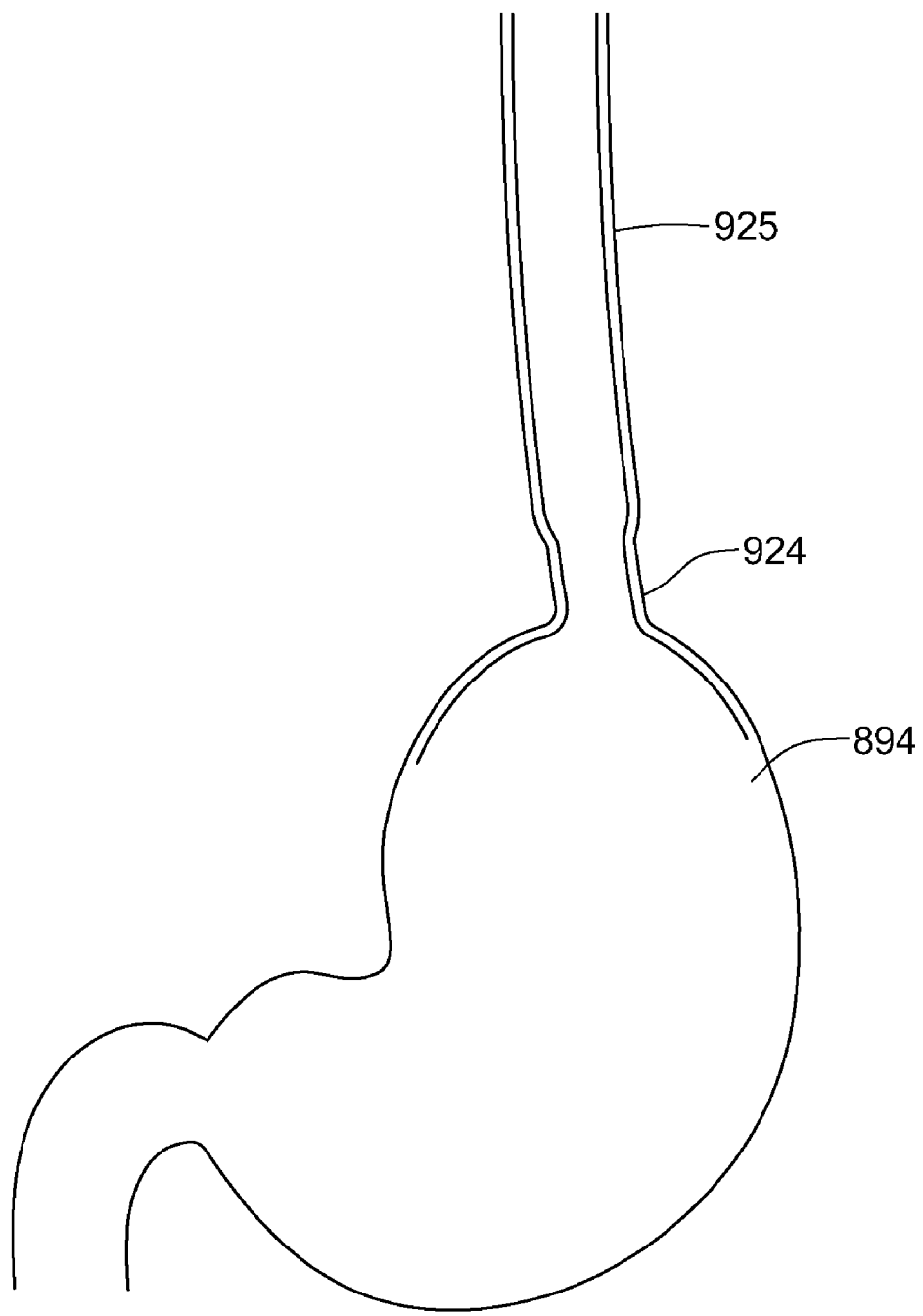
Figure 220A:
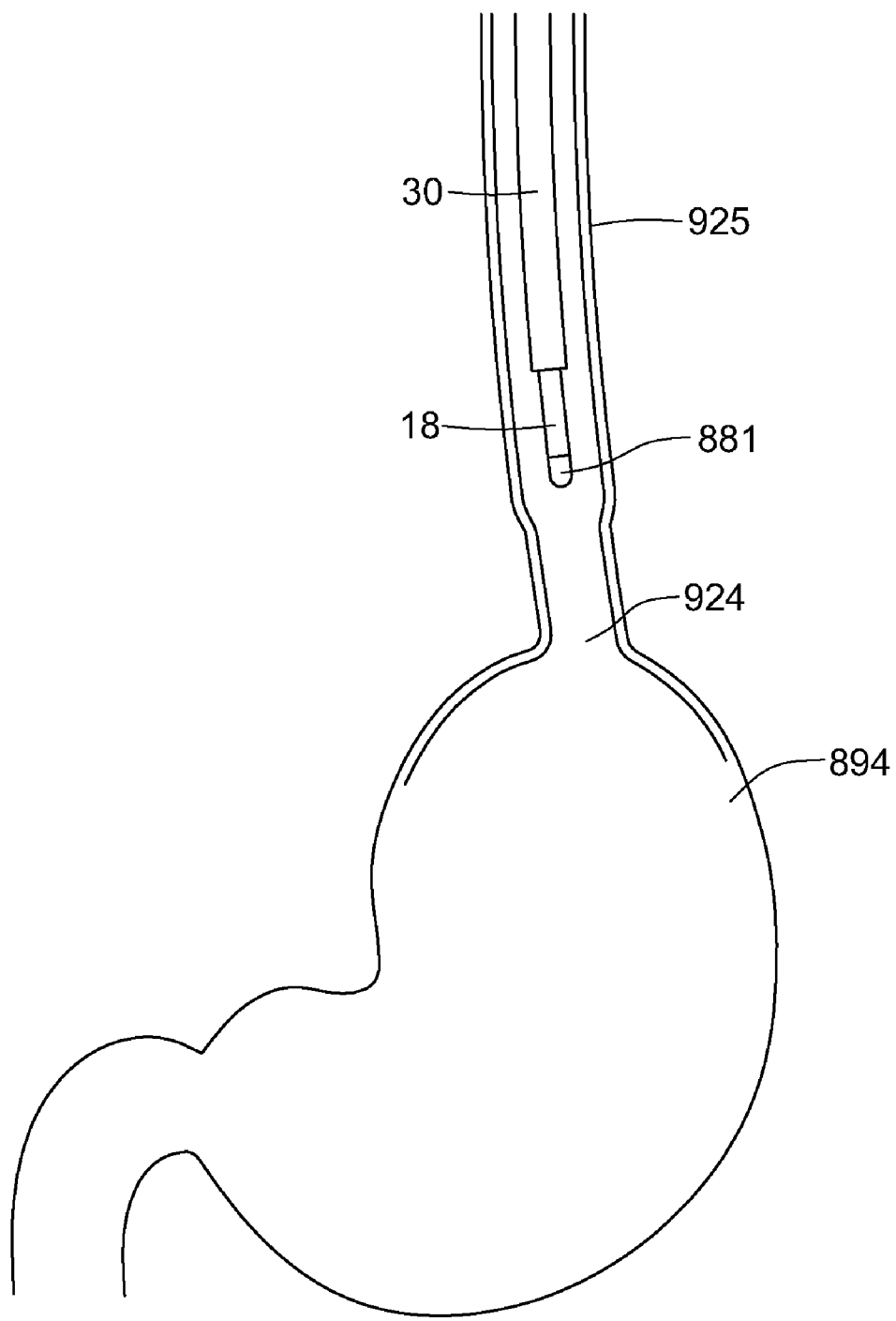
FIGS. 220A-220C illustrate one embodiment of a system and procedure to ablate a lower esophageal sphincter by driving an ablation tool inside with a steerable instrument assembly.
Figure 220B:
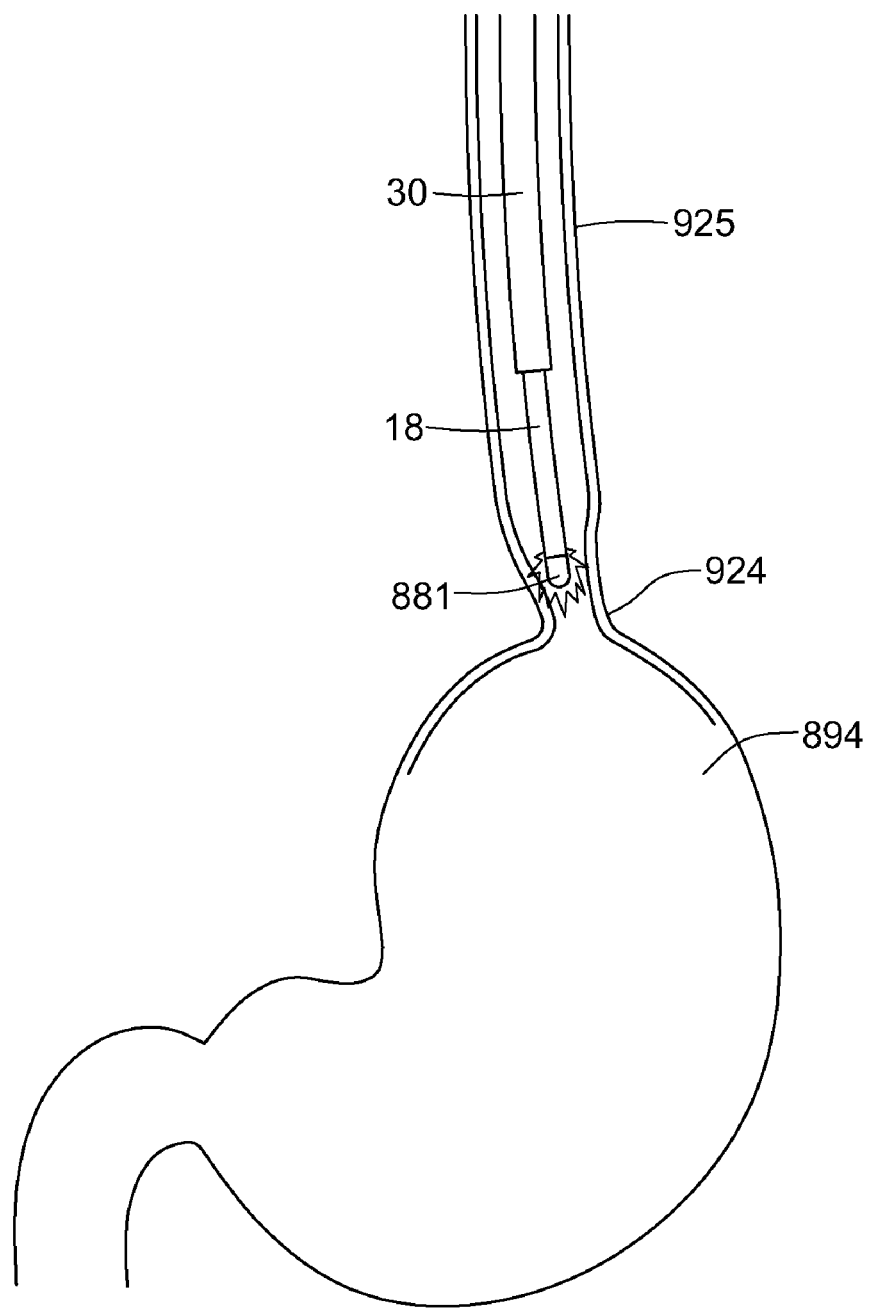
Figure 220C:
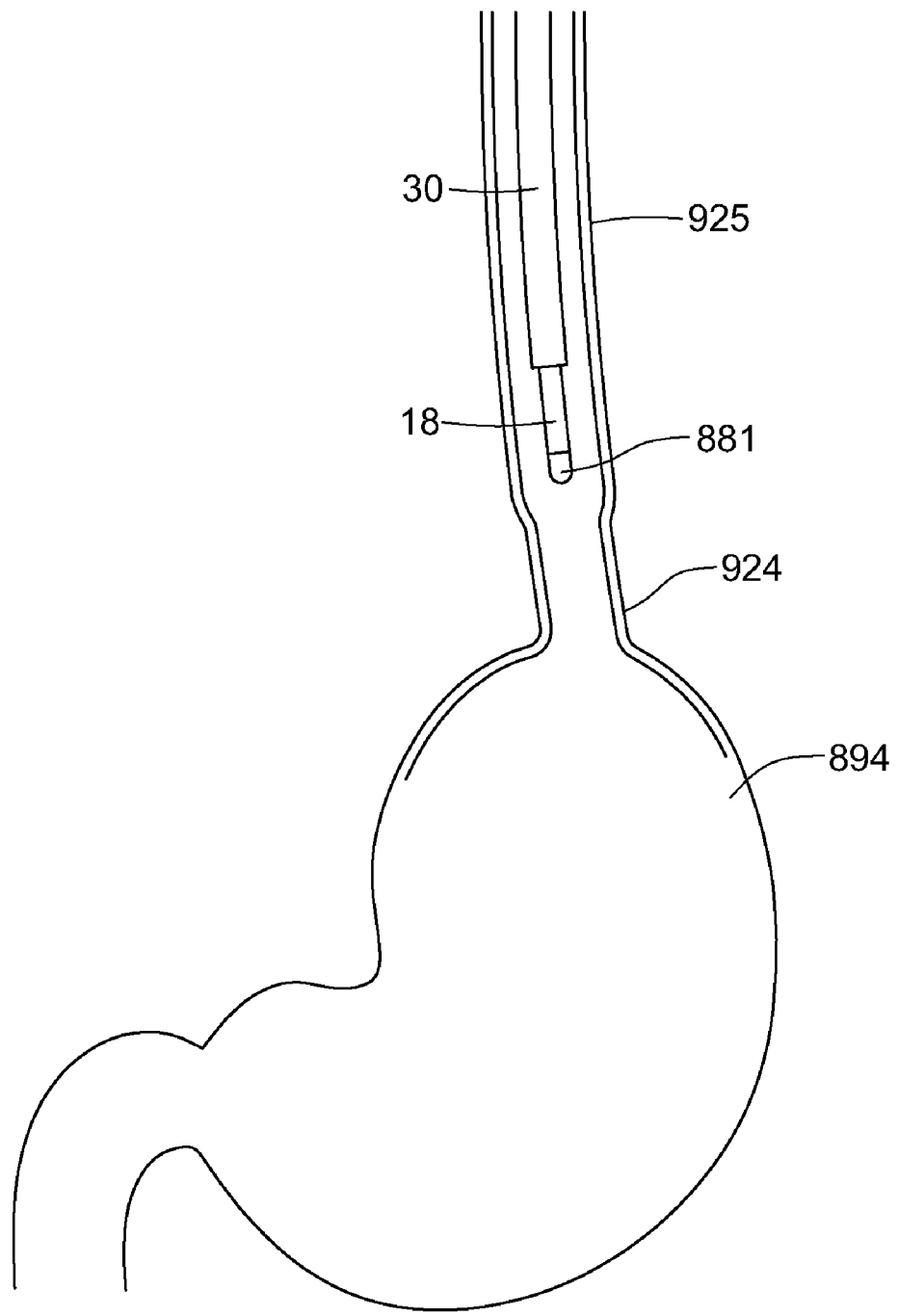

Upper Gastrointestinal Intervention:

From an endolumenal approach, the LES (924) may be dilated with a balloon (851) using steerable tool assemblies (30, 18) such as those in embodiments described herein. Referring to FIGS. 219A-C, a steerable instrument assembly comprising an expandable balloon (851) may be precisely located within the LES (924), expanded, and removed to at least transiently dilate or expand the LES (924). Referring to FIGS. 220A-C, an ablation tool (881) utilizing RF, laser, cryo, ultrasound, etc. may be coupled to a guide/sheath assembly (18, 30) and utilized to ablate the tissue comprising an overly tight LES (924) from the inside to result in a dilated LES. Ablation may be combined with dilation, as in an expandable balloon with ablative properties. In one embodiment the ablative tool (881) has circumferentially oriented ablation zones, as opposed to a discrete ablation zone at the distal tip of a conventional RF ablation catheter, to apply a more dispersed ablation to the tissue of the surrounding LES (924) during a particular bout of ablative action.

Figure 221A:
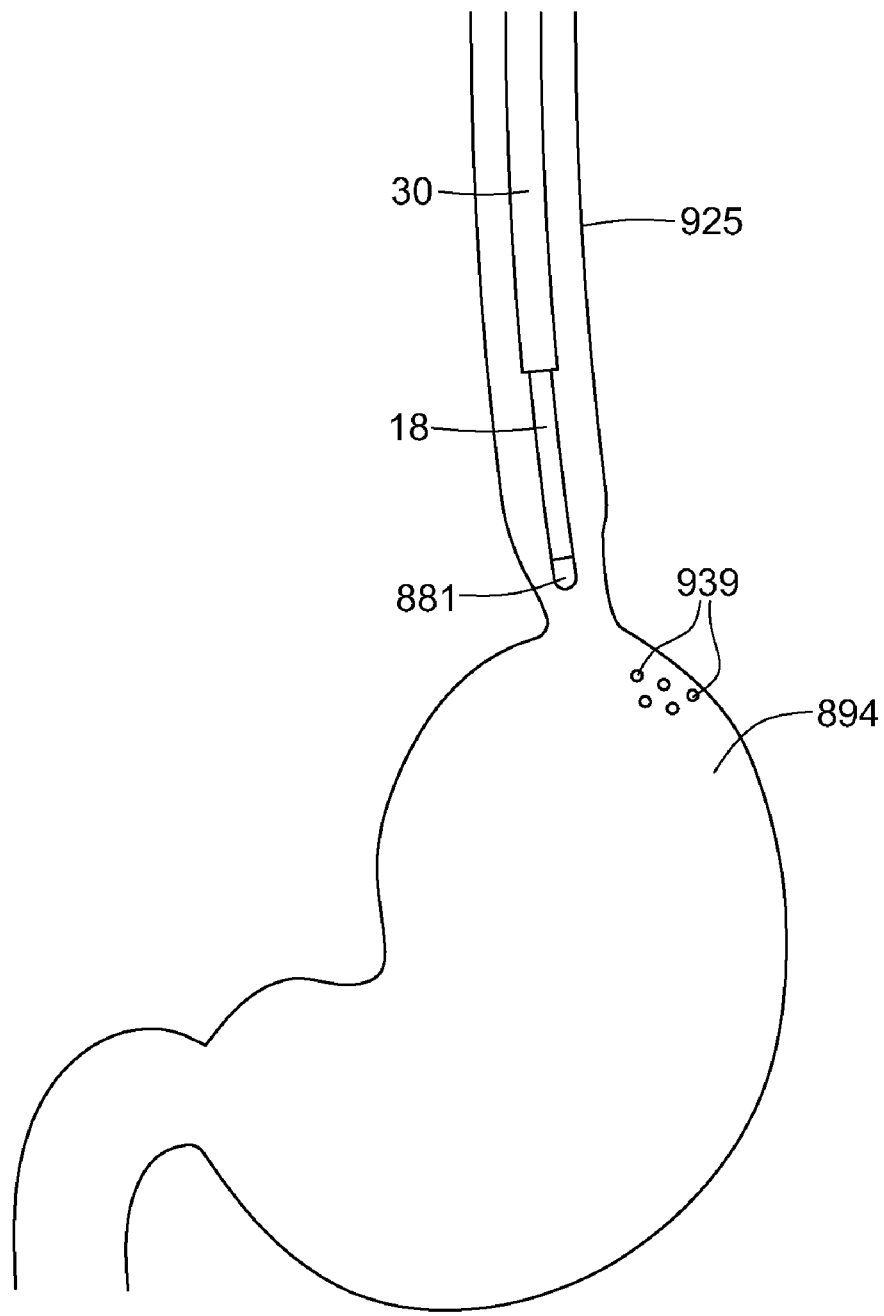
FIGS. 221A-221B illustrate one embodiment of a system and procedure for ablating Ghrelin producing cells by driving an ablative probe tool coupled to a steerable instrument assembly inside the stomach.
Figure 221B:
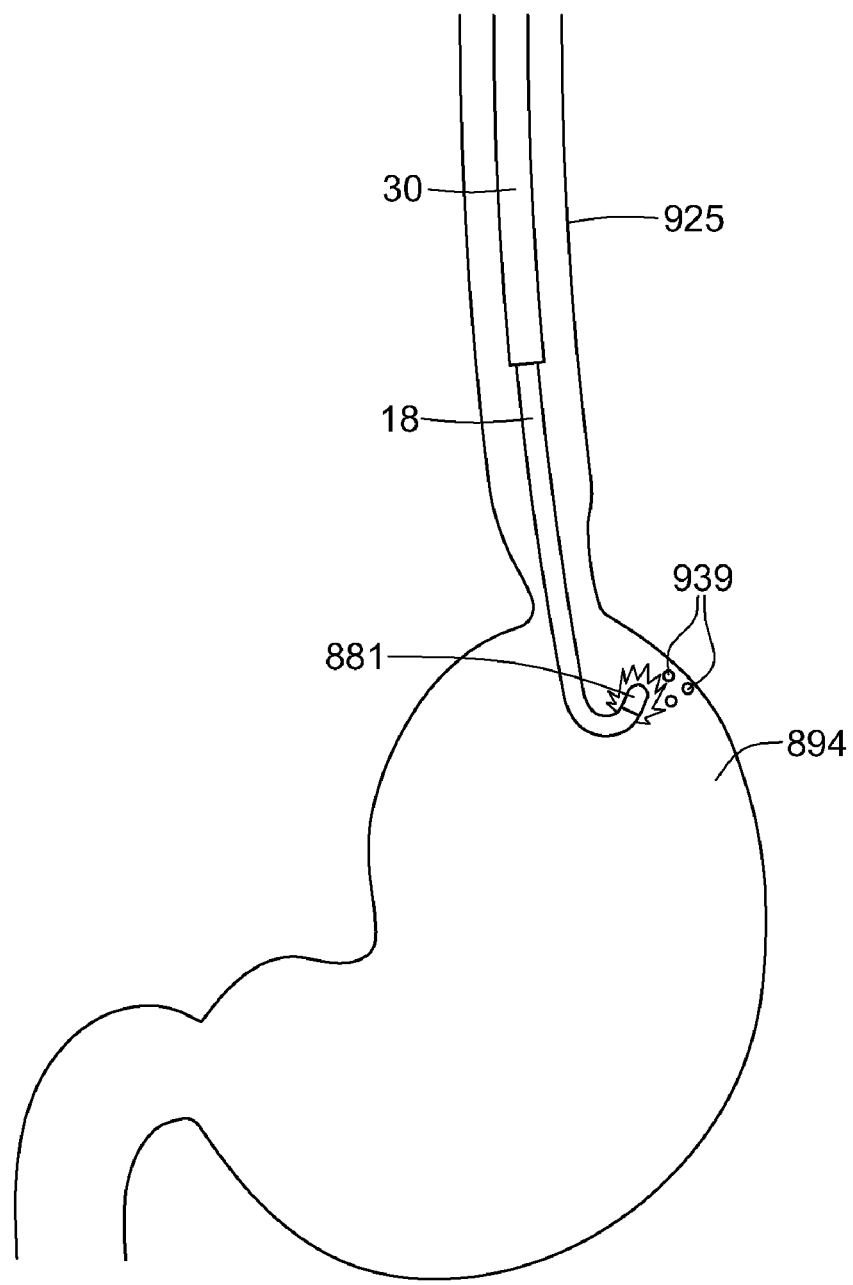

Referring to FIGS. 221A-B, in one embodiment, an ablative probe tool (881) coupled to the end of a steerable instrument assembly (30, 18) may be advanced and steered toward lesions of cells (939) known to produce the hormone "Ghrelin", which activates specialized neurons in the hypothalamus involved in weight regulation. Ablation of a portion of these cells using RF, cryo, laser, ultrasound, etc may be used to treat obesity through appetite suppression.

Figure 222A:
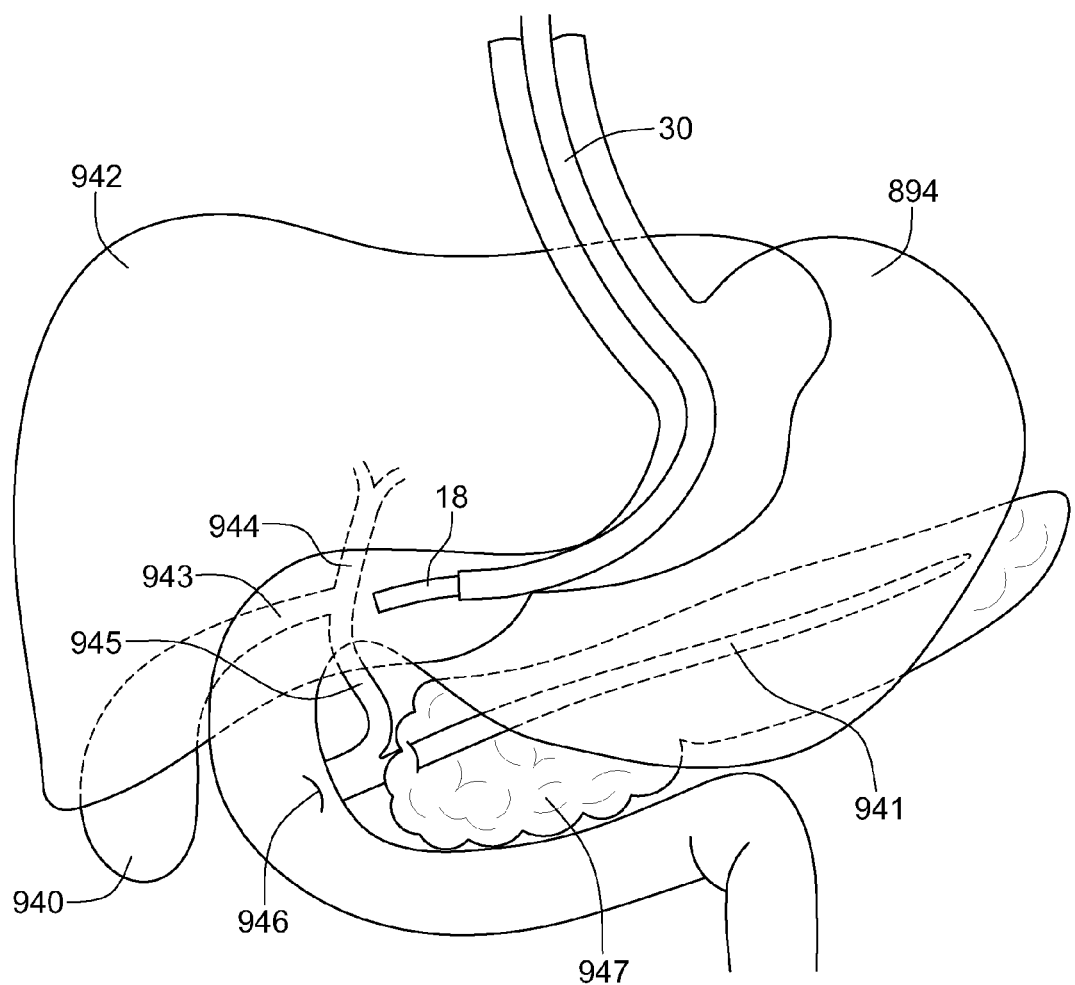
FIGS. 222A-222I illustrate embodiments of systems and procedures wherein an elongate steerable instrument assembly is used to navigate through the esophagus, stomach, and sphincter Oddi to access the pancreatic duct, common bile duct, cystic duct, gall bladder, hepatic ducts, and live.
Figure 222B:
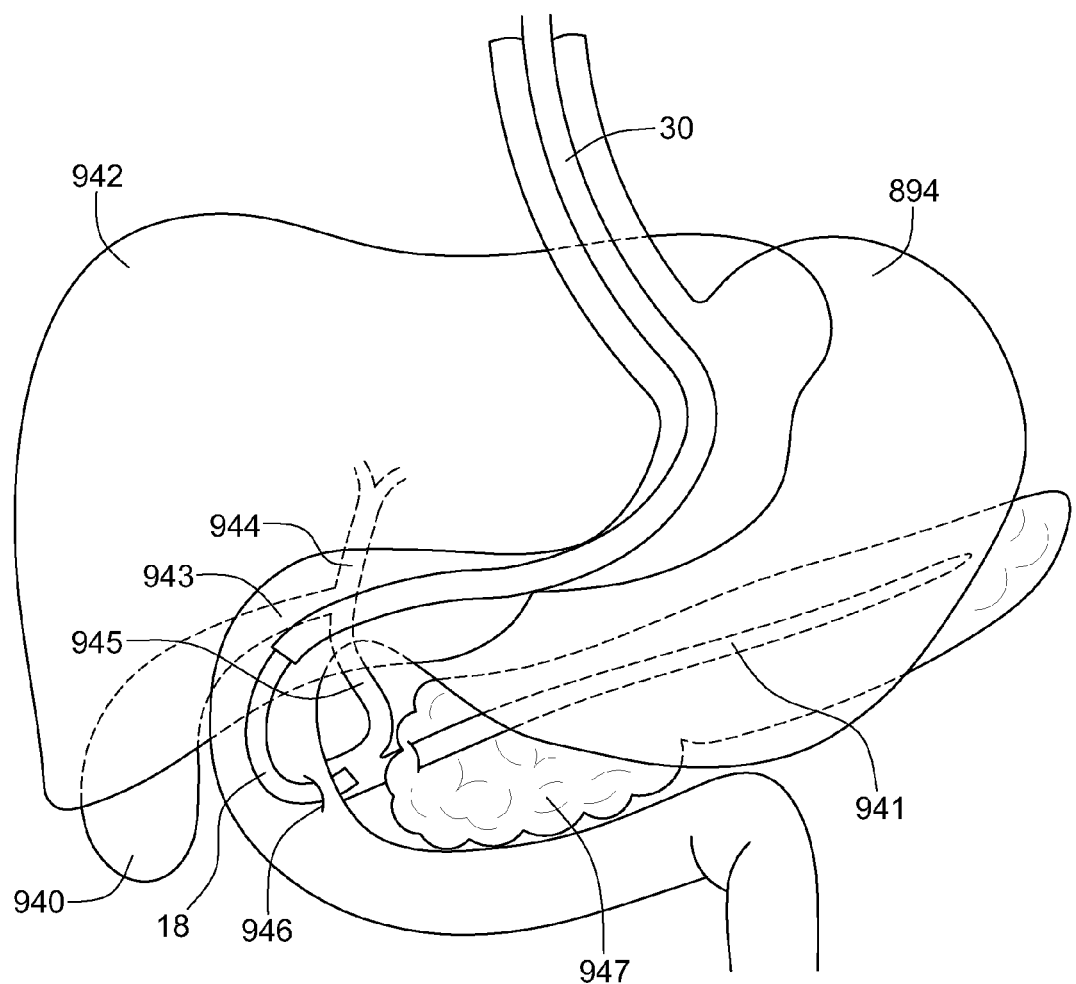
Figure 222C:
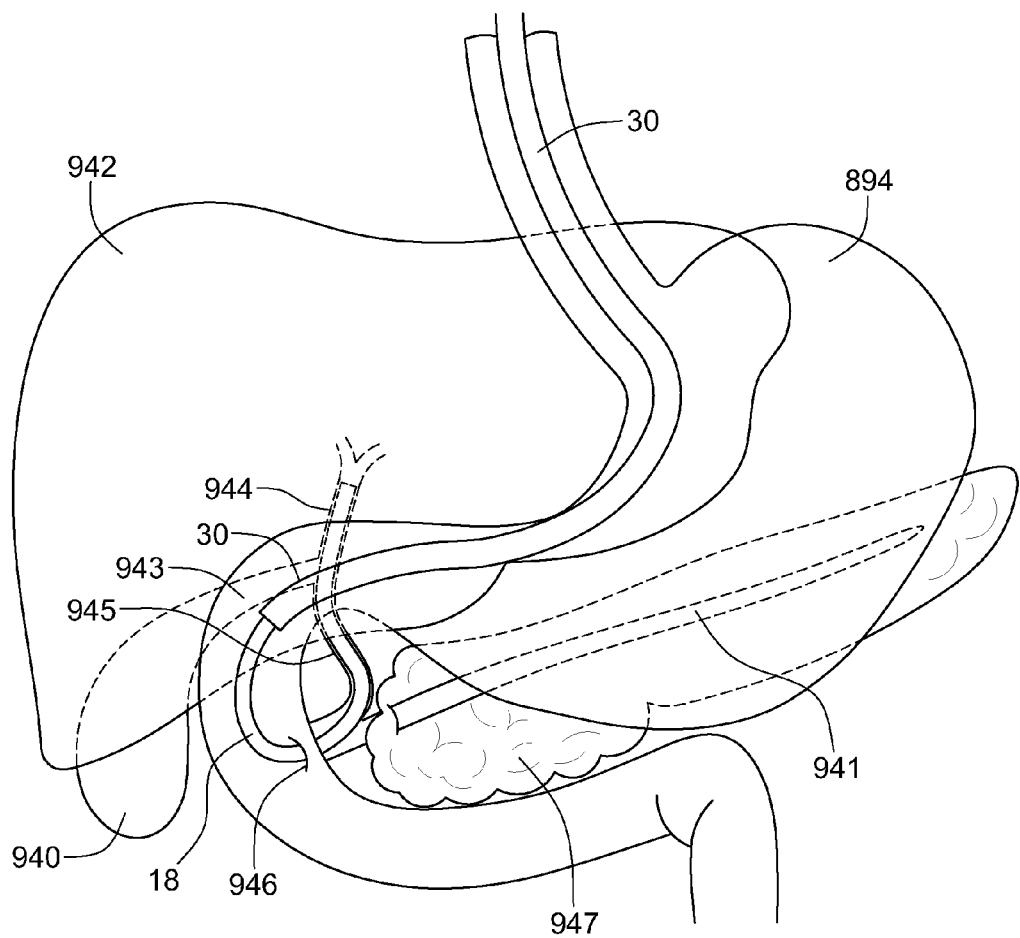
Figure 222D:
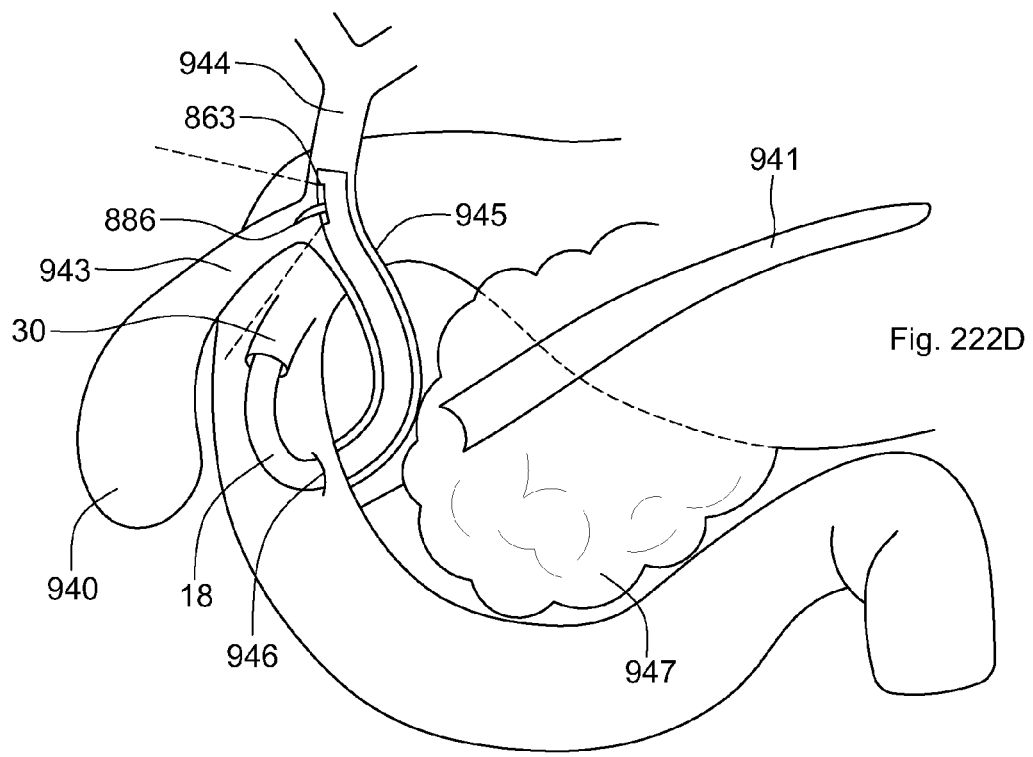
Figure 222E:
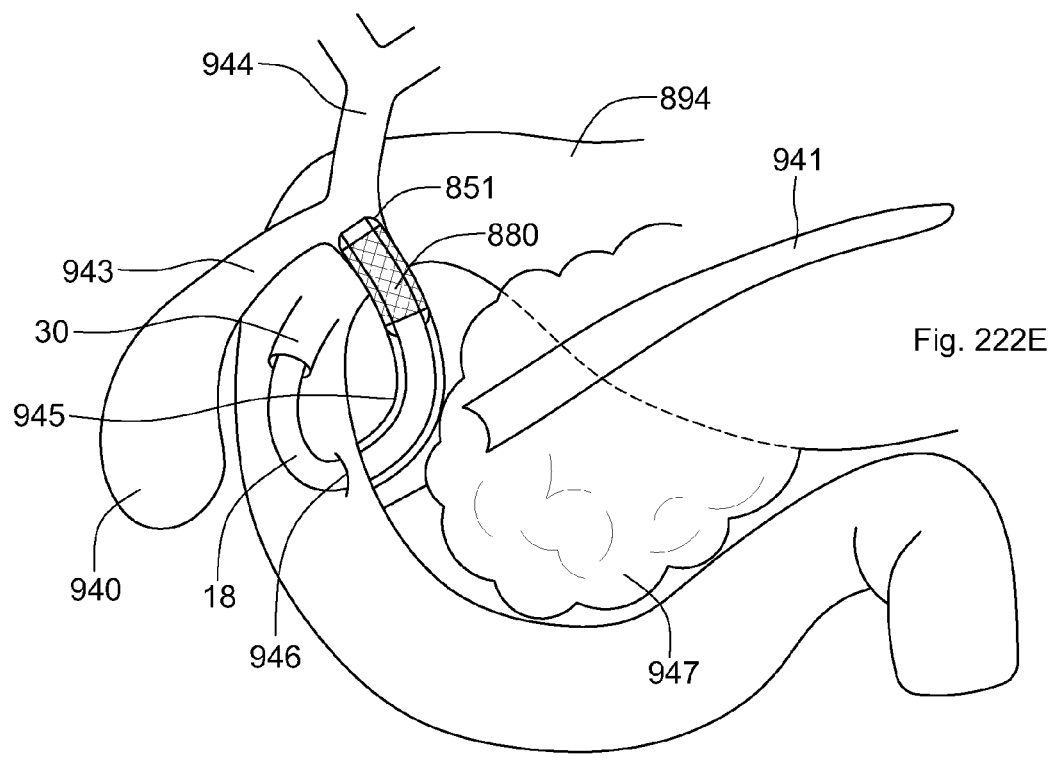
Figure 222F:
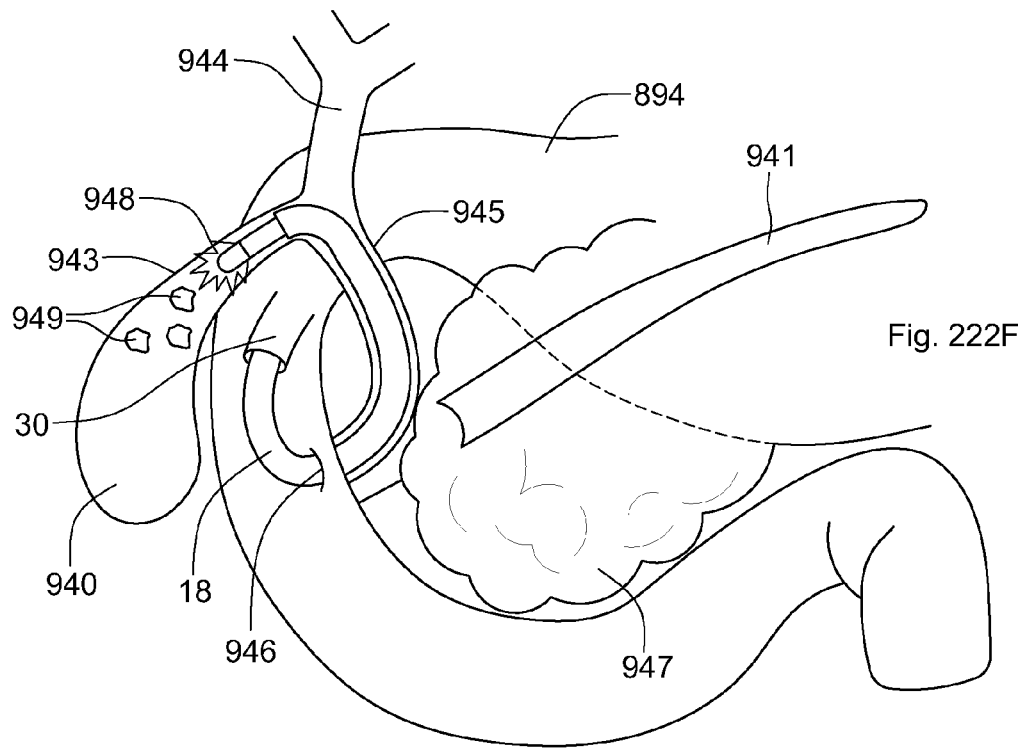
Figure 222G:
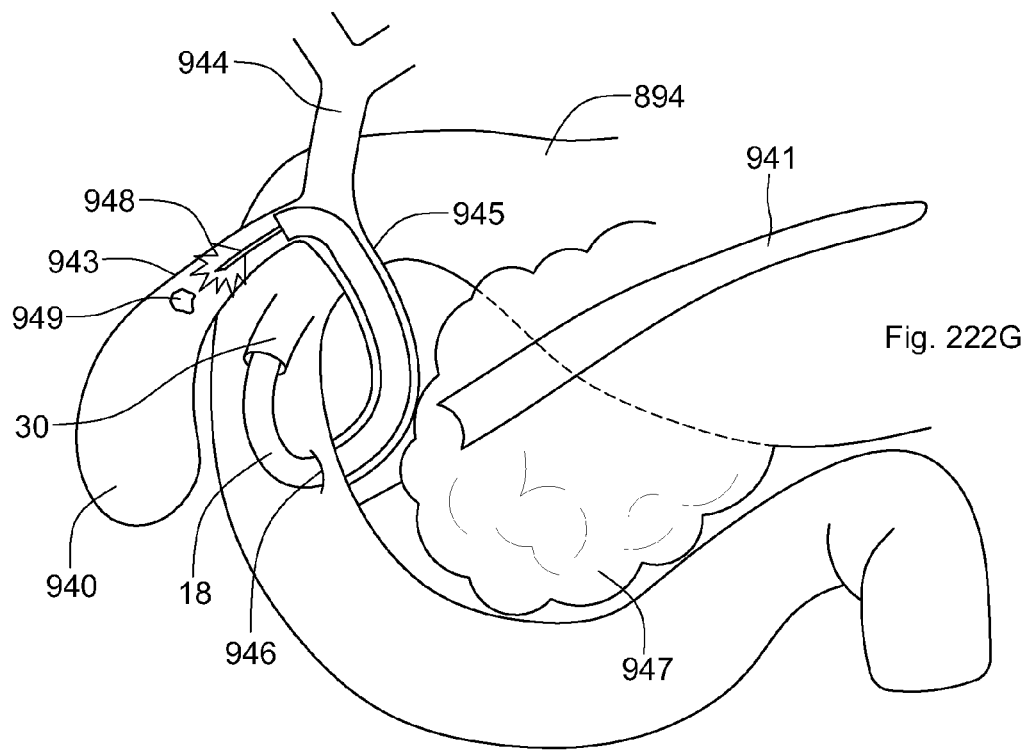
Figure 222H:
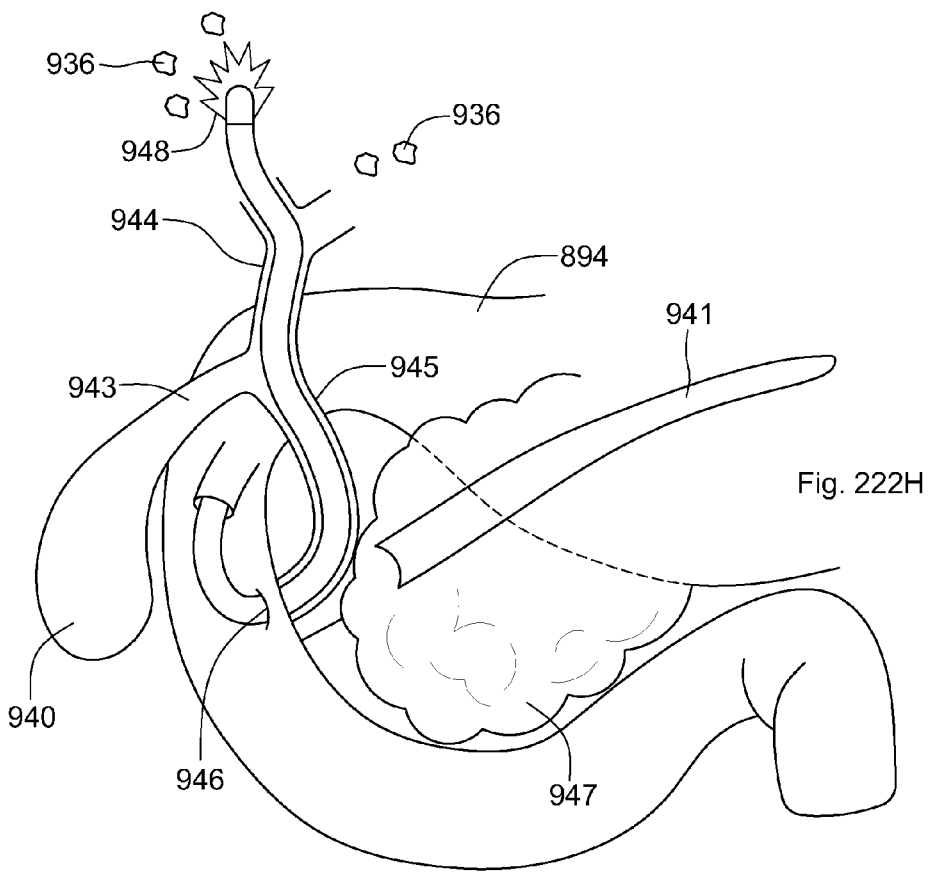

Referring to FIGS. 222A-I, an elongate steerable instrument assembly (30, 18) may be utilized to navigate through the esophagus (925), through the stomach (894), and through the sphincter of Oddi (946) to access the pancreatic duct (941), common bile duct (945), cystic duct (943), gall bladder (940), hepatic ducts (944), and liver (942). Referring to FIG. 222B, one embodiment of a steerable instrument assembly comprising a sheath instrument (30) and guide instrument (18) may be navigated into the duodenum, and the smaller guide instrument may be turned and advanced through the sphincter of Oddi (946). Referring to FIG. 222C, the steerable guide (18) instrument may be navigated into the common bile duct (945) and up into the hepatic ducts (944) to clear obstructions, vacuum out stones (949, 936), and destroy stones (949, 936), with energy and/or chemical treatments. Referring to FIG. 222D, a steerable guide instrument (18) comprising an ultrasound device (863), such as side-firing ultrasound array, and a retractable needle (886) may be utilized to cannulate and clear obstructions within the cystic duct (943) and gall bladder (940). Referring to FIG. 222E, a steerable guide instrument (18) may be utilized to deploy a self-expanding or expandable prosthesis (880), such as a stent or stent graft structure, within the subject duct system, such as in the common bile duct (945). Referring to FIGS. 222F-G, an ablation or lithotripsy tool (948), such as those utilizing RF, cryo, ultrasound, and/or laser, may be utilized to clear obstructions, such as stones (949, 936), from the cystic duct (943) and/or gall bladder (940). Similarly, obstructions in the hepatic duct system may be addressed, as depicted in FIG. 222H.

Figure 222I:
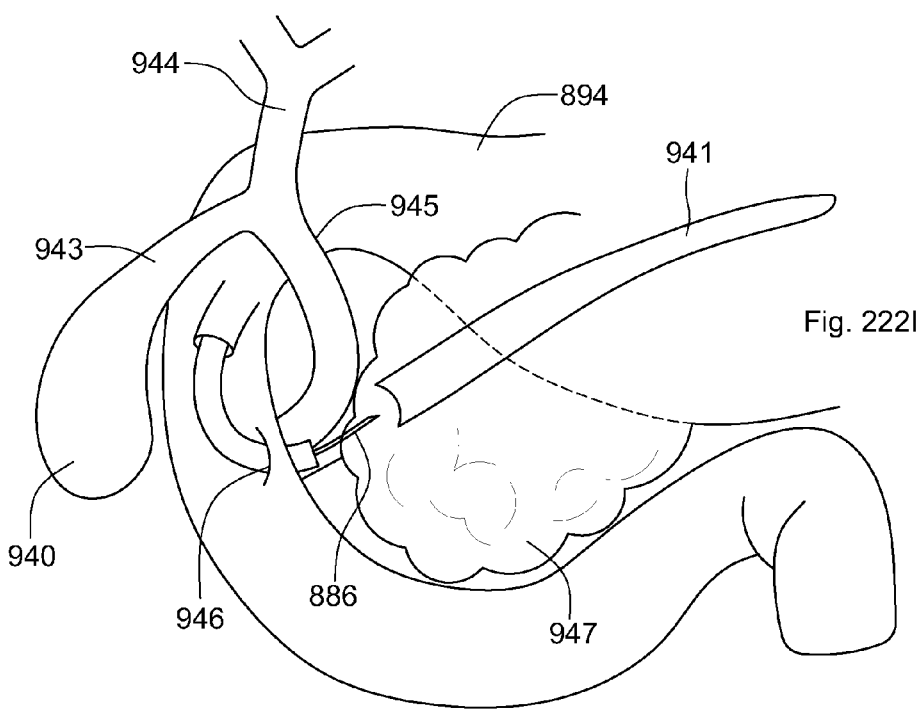

As shown in FIG. 222I, subsequent to cannulating the sphincter of Oddi (946), rather than turning up the common bile duct (945), the steerable instrument may be steered and advanced into the pancreatic duct (941), where it may be utilized to clear obstructions, such as stones, and may be utilized to biopsy, treat, and/or lyse the pancreatic (947) tissue utilizing, for example, a side-firing ultrasound array with a side-protruding retractable needle configuration.

Figure 223A:
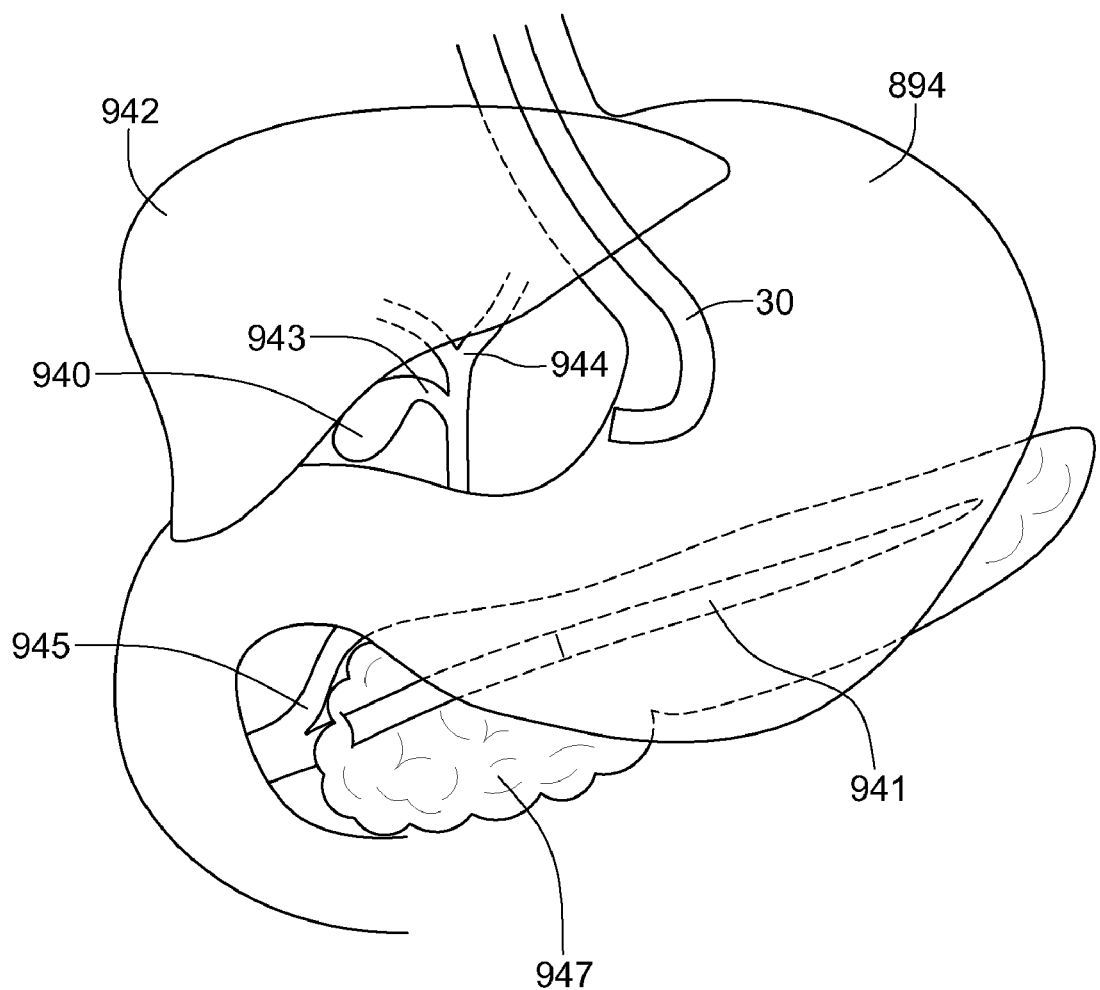
FIGS. 223A-223G illustrate one embodiment of a transgastric cholesectomy system and procedure utilizing a steerable instrument.
Figure 223B:
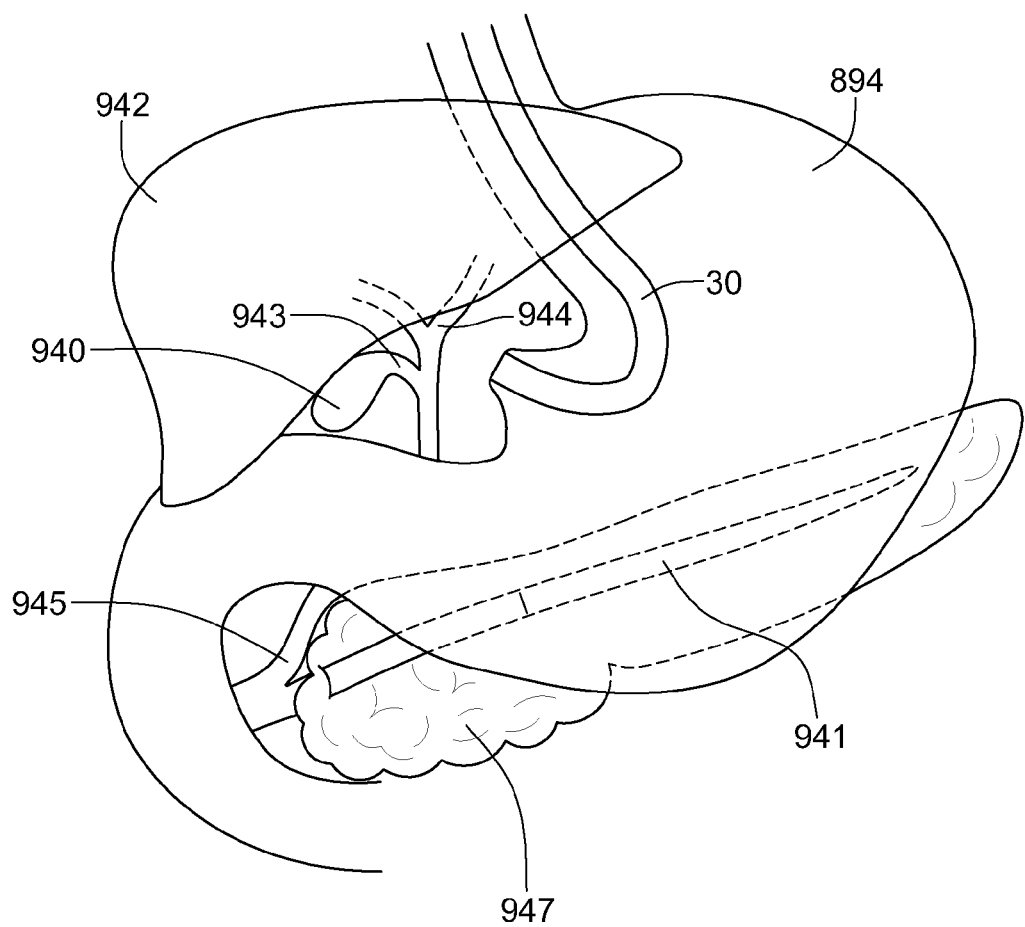
Figure 223C:
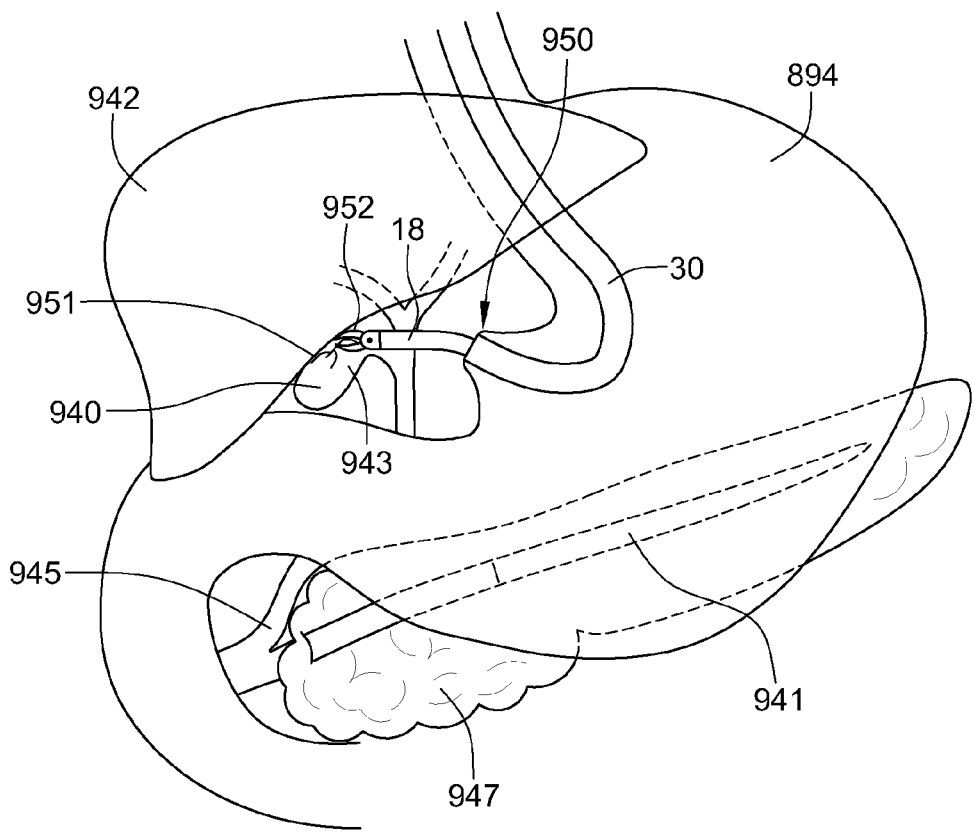
Figure 223D:
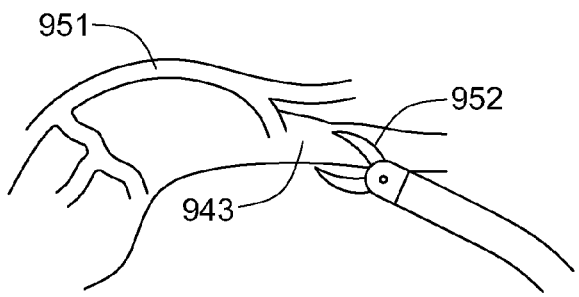
Figure 223E:
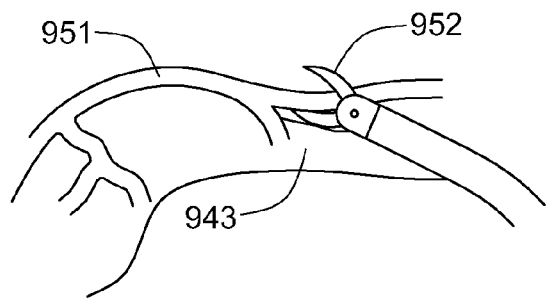
Figure 223F:
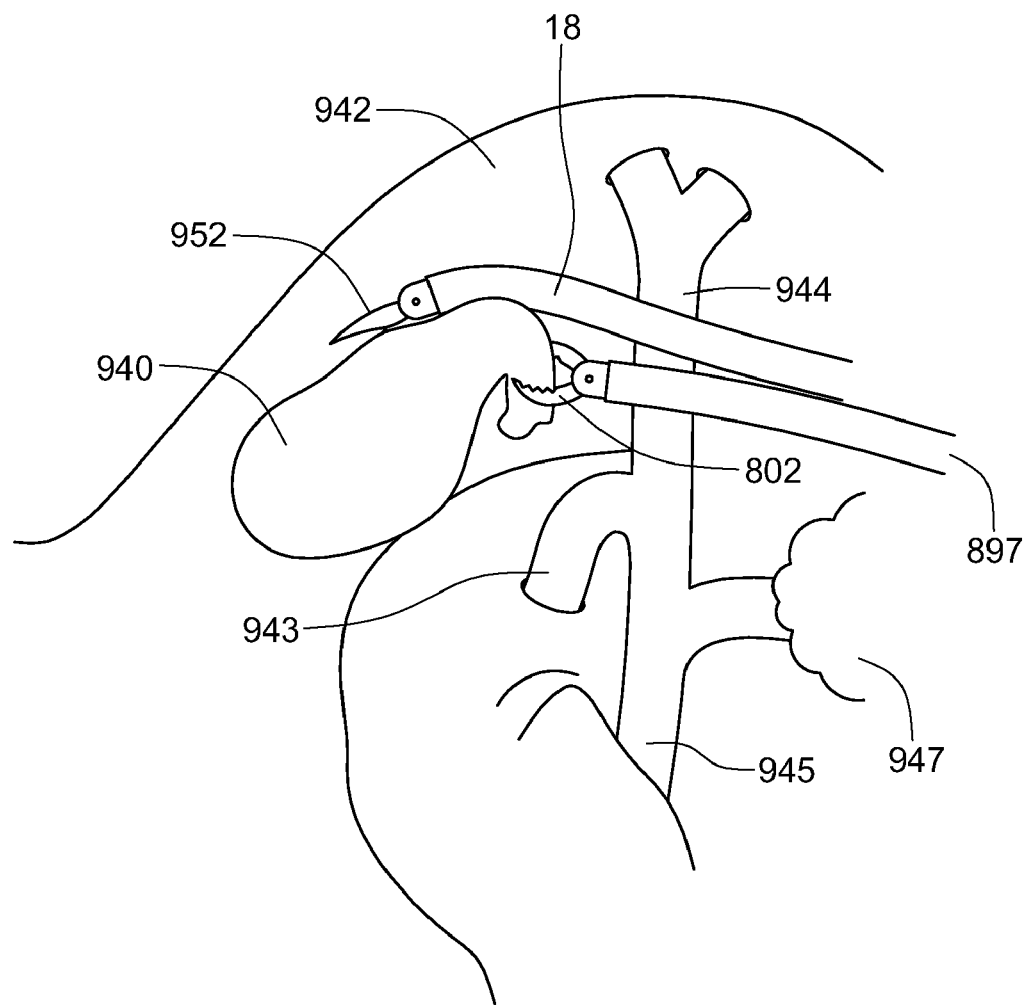
Figure 223G:
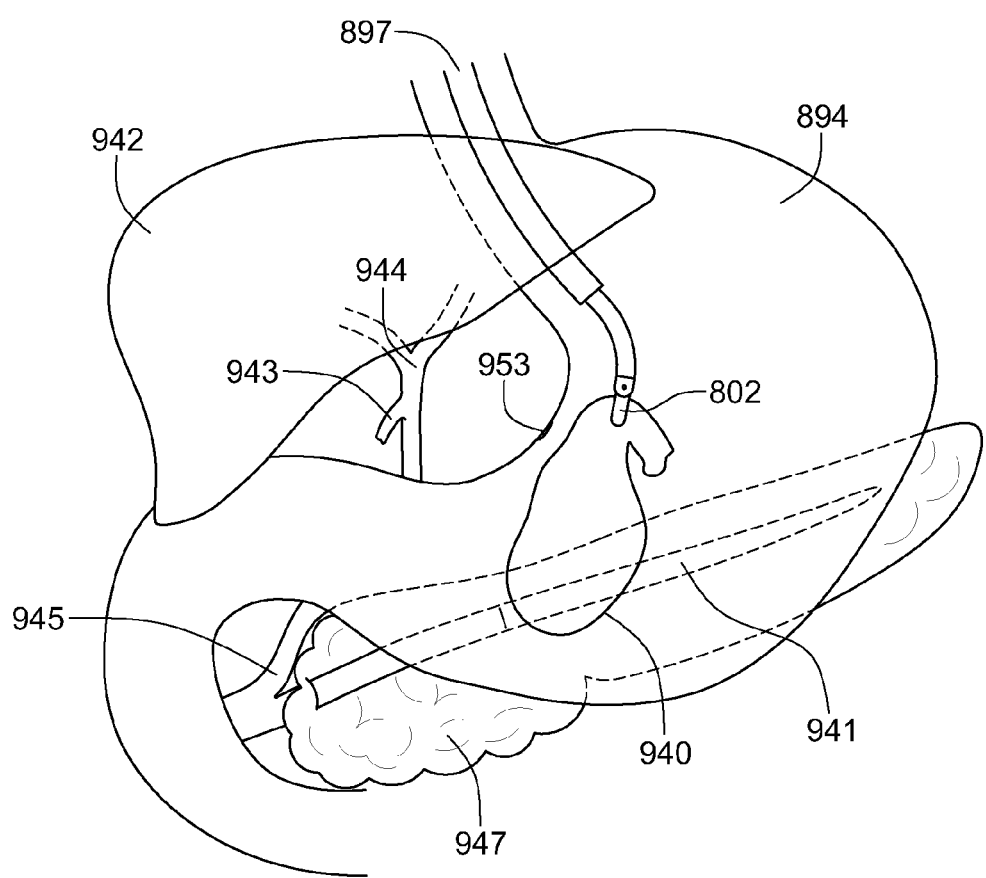

Referring to FIGS. 223A-G, a trans-gastric cholesectomy procedure using one embodiment of the invention is depicted. Referring to FIGS. 223A-B, a steerable instrument, such as a sheath (30) and/or guide (18) instrument, is navigated to the right wall of the stomach (994), which it is utilized to temporarily distend, as shown in FIG. 223B, a portion of the right stomach toward the gall bladder (940) to facilitate ultrasound imaging of the structures adjacent the distal end of the steerable instrument. The normal anatomic position of the gall bladder (940) and cystic duct (943) relative to the right stomach should create a beneficial field of view for ultrasound imaging, particularly with a portion of the stomach (894) distended over toward the region where the gall bladder (940) should be positioned. After confirming the location of the gall bladder (940) and related structures, and also potentially repositioning or re-vectoring the steerable instrument (30), a sterile portion of the instrument assembly is advanced across the gastric mucosa toward the cystic duct (943) and cystic artery (951), preferably along with an on-board image capturing means, to observe the distal end of the instrument assembly, as depicted in FIG. 223D-F.

Referring to FIG. 223D, according to one embodiment, a clip applier (not shown) may be utilized to ligate the cystic duct (943), after which a scissors or other cutting tool (952) may be utilized to sever the cystic duct. A cautery/cutting tool, such as a bipolary cautery scissors (952), may be utilized to isolate the gall bladder (940) from the cystic artery (951), as depicted in FIG. 223E. Subsequently, as depicted in FIG. 223F, a dissection and/or cautery tool (952) may be utilized to dissect the gall bladder (940) away from the liver (942) bed. Another sterile tool (897) may be advanced across the gastric mucosa to grasp the gall bladder (940) and prevent spillage of its contents, as depicted in FIG. 223F. Subsequent to separation of the gall bladder (940) from other tissue, it may be pulled through the gastric mucosa into the stomach (894) and removed through the mouth. The defect created in the gastric mucosa is closed (953) expediently using a suturing device or prosthetic quick-connect port hardware, either of which may be coupled to the distal end of a steerable instrument assembly for in-situ intervention as described herein. Transgastric access as described herein may also be utilized to access the peritoneum.

Figure 224A:
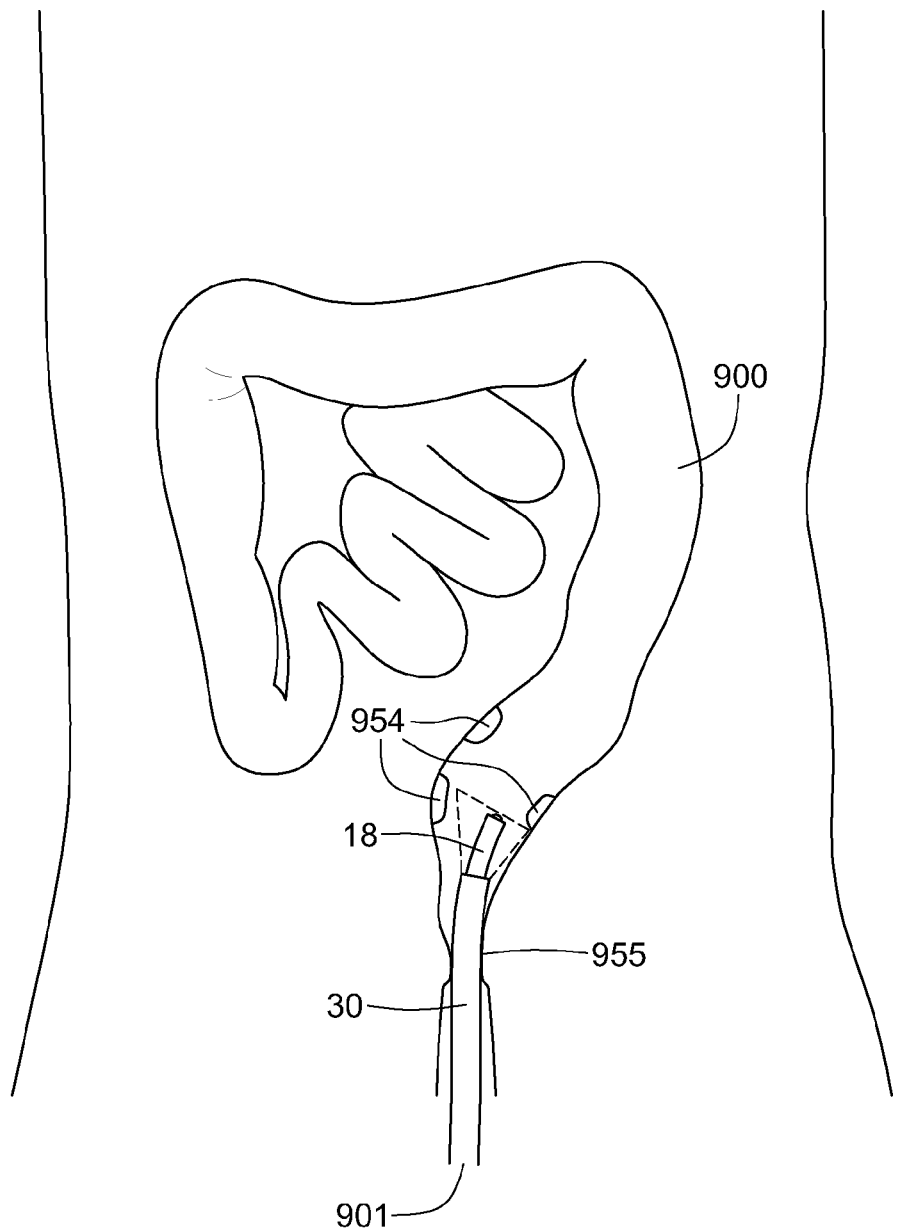
FIGS. 224A-224F illustrate one embodiment of a system and procedure using a steerable instrument assembly to navigate the colon and intervening to biopsy, lyse, or remove tissue.
Figure 224B:
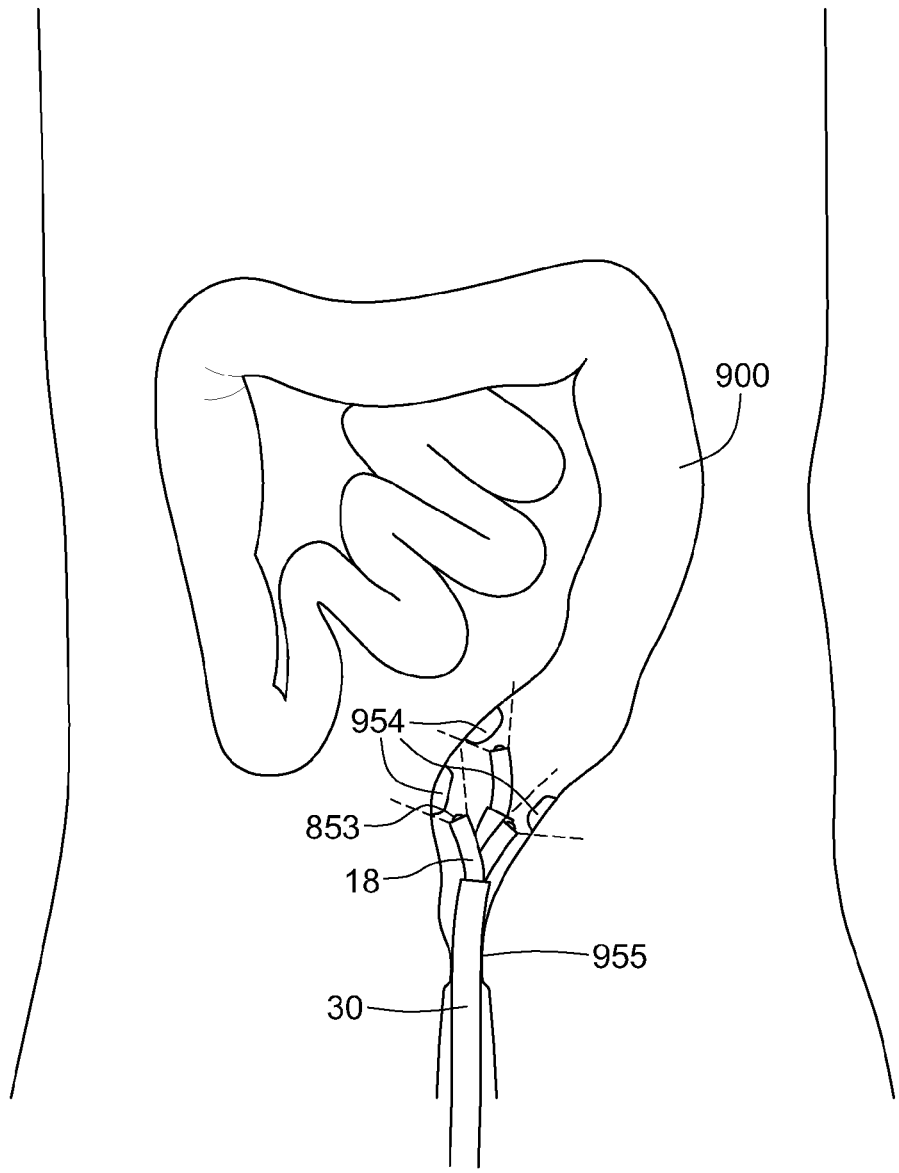
Figure 224C:
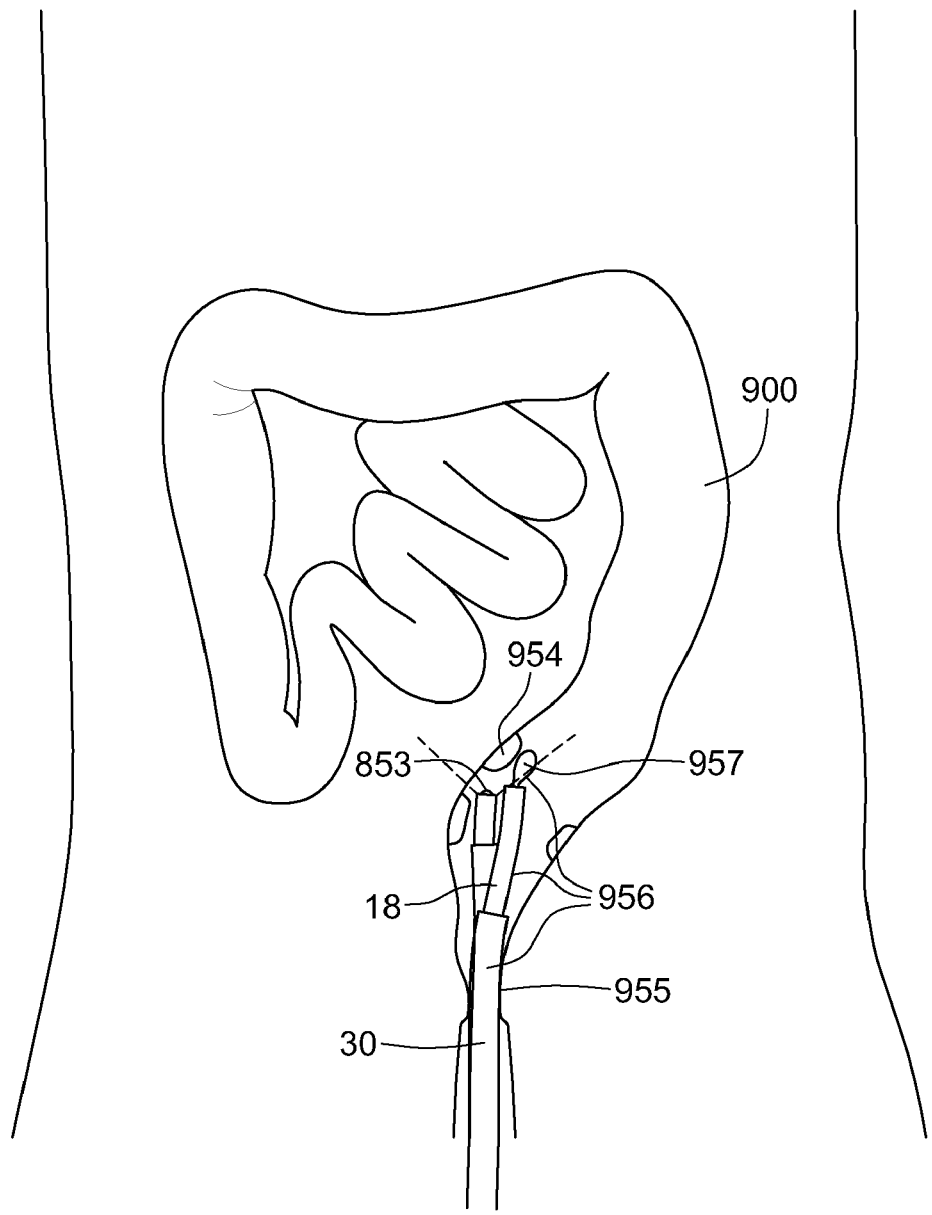
Figure 224D:
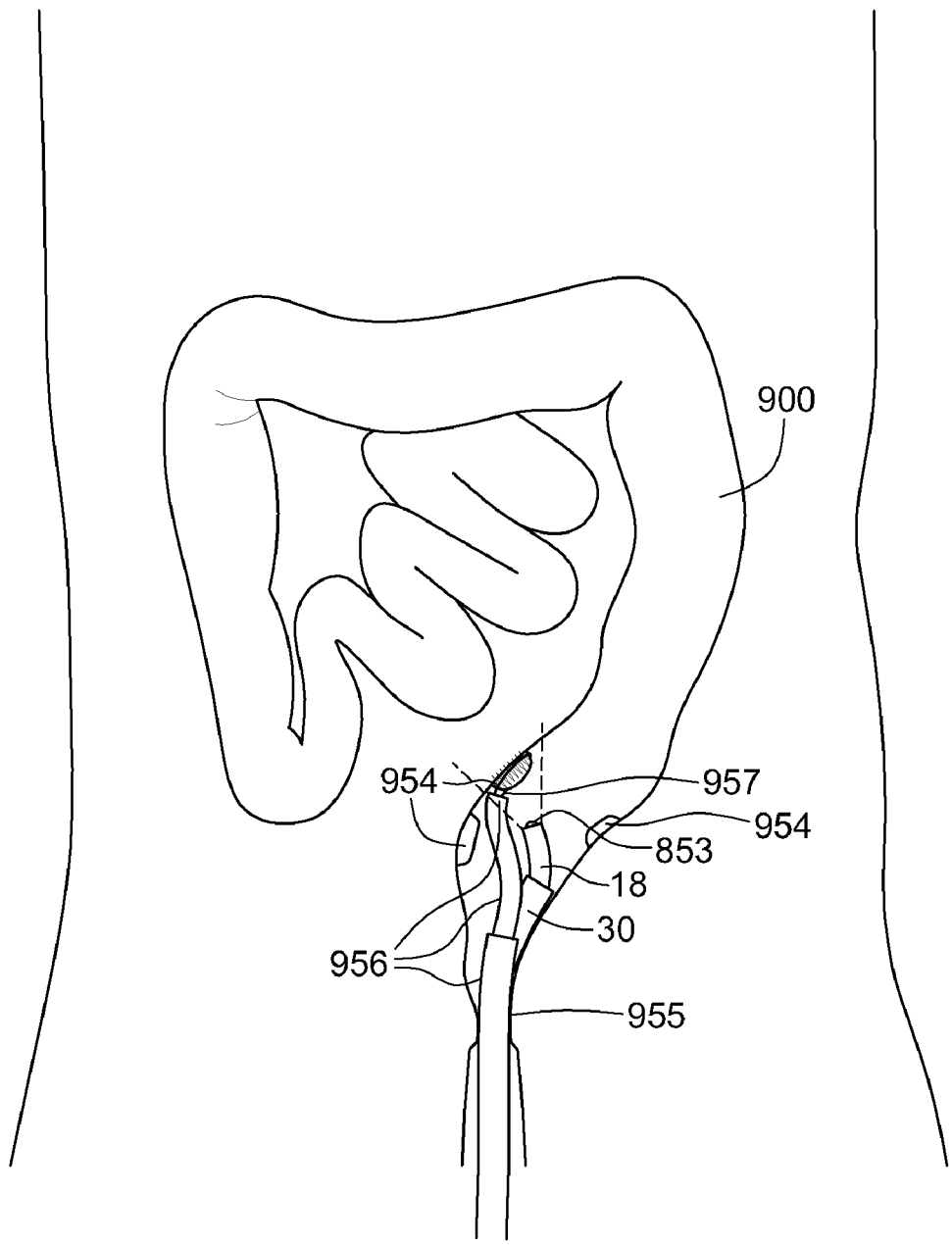
Figure 224E:
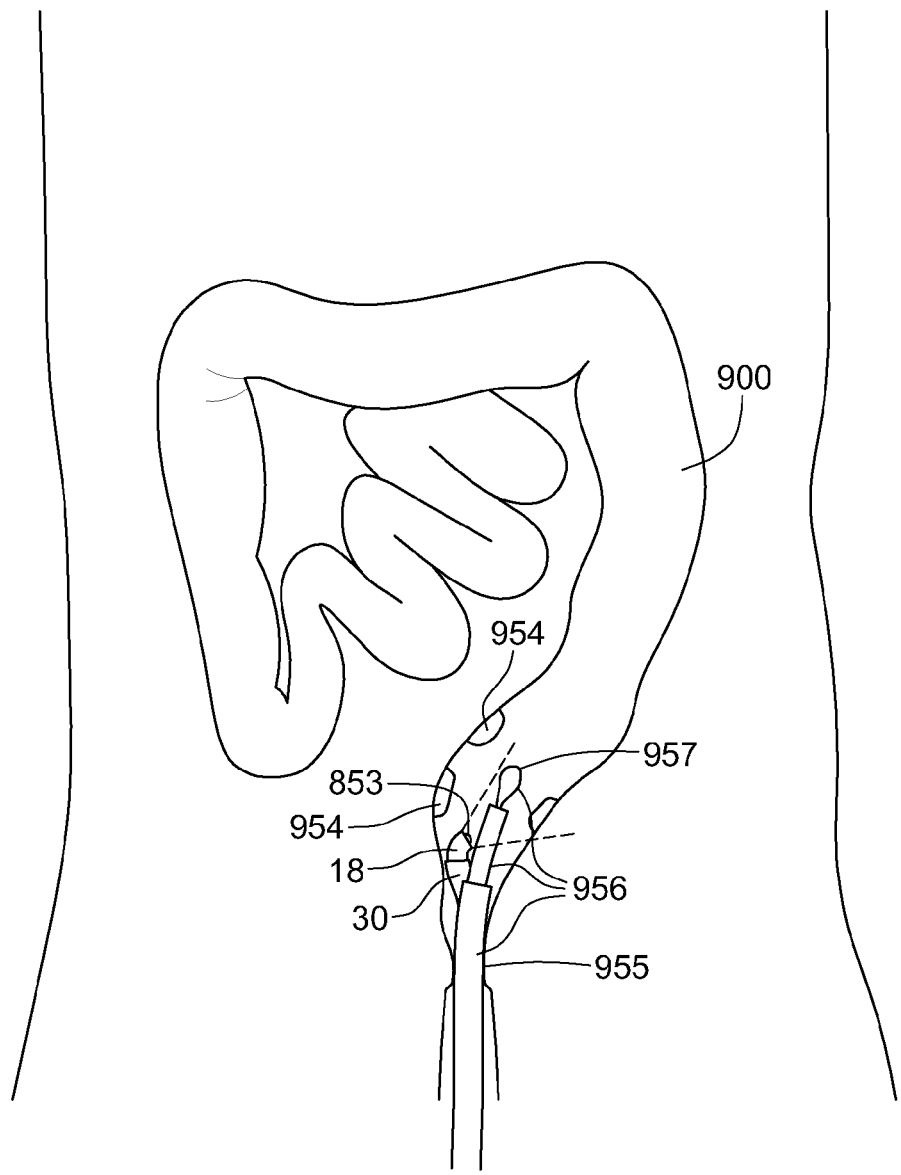
Figure 224F:
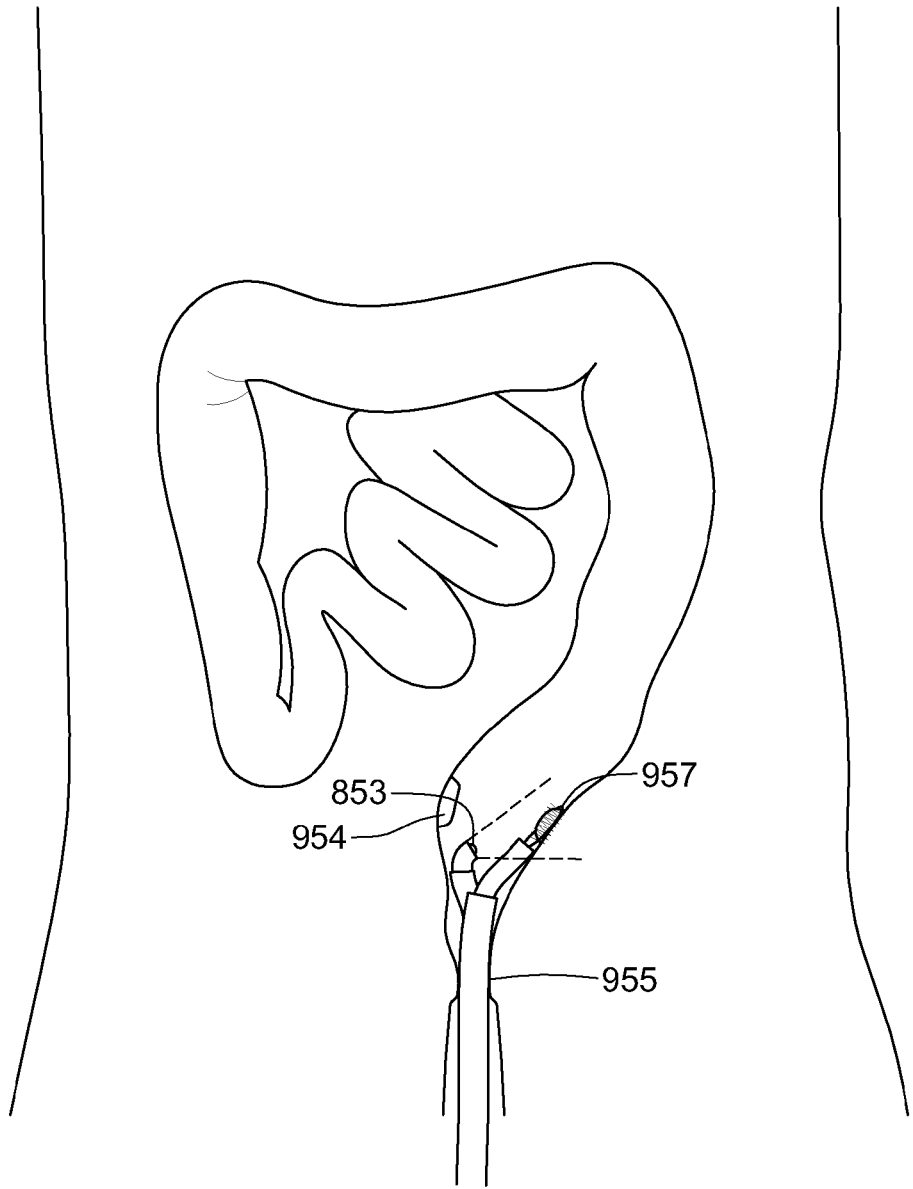

Lower Gastrointestinal Intervention:

Referring to FIGS. 224A-F, a steerable instrument assembly may be utilized to navigate past the rectum (955) and into the colon (900) and intervene to biopsy, lyse, and/or remove tissue defects or malformations (954), such as polyps. Referring to FIG. 224A, a steerable instrument assembly (901) is depicted steerably navigating the colon (900) with a forward-looking image capture device (853), such as a CCD or fiber camera. The high degree of steerability of the instrument assembly facilitates examination of tissue defects (954) in all directions, as depicted in FIG. 224B. Referring to FIG. 224C, the instrument assembly may comprise multiple instrument sub-assemblies, one of which may comprise a polyp-removing cautery snare device (957). As shown in FIGS. 224D and 224E, the cautery snare device (957) may be precisely navigated into position, then utilized to cauterize and remove a tissue defect (954) such as a polyp. Referring to FIG. 224F, the instrument assembly may then be redirected to another defect (954) where a similar process may be repeated. Alternatively, a biopsy needle (not shown) may be deployed from a steerable instrument assembly to precisely sample tissue defects in the colon.

Figure 225A:
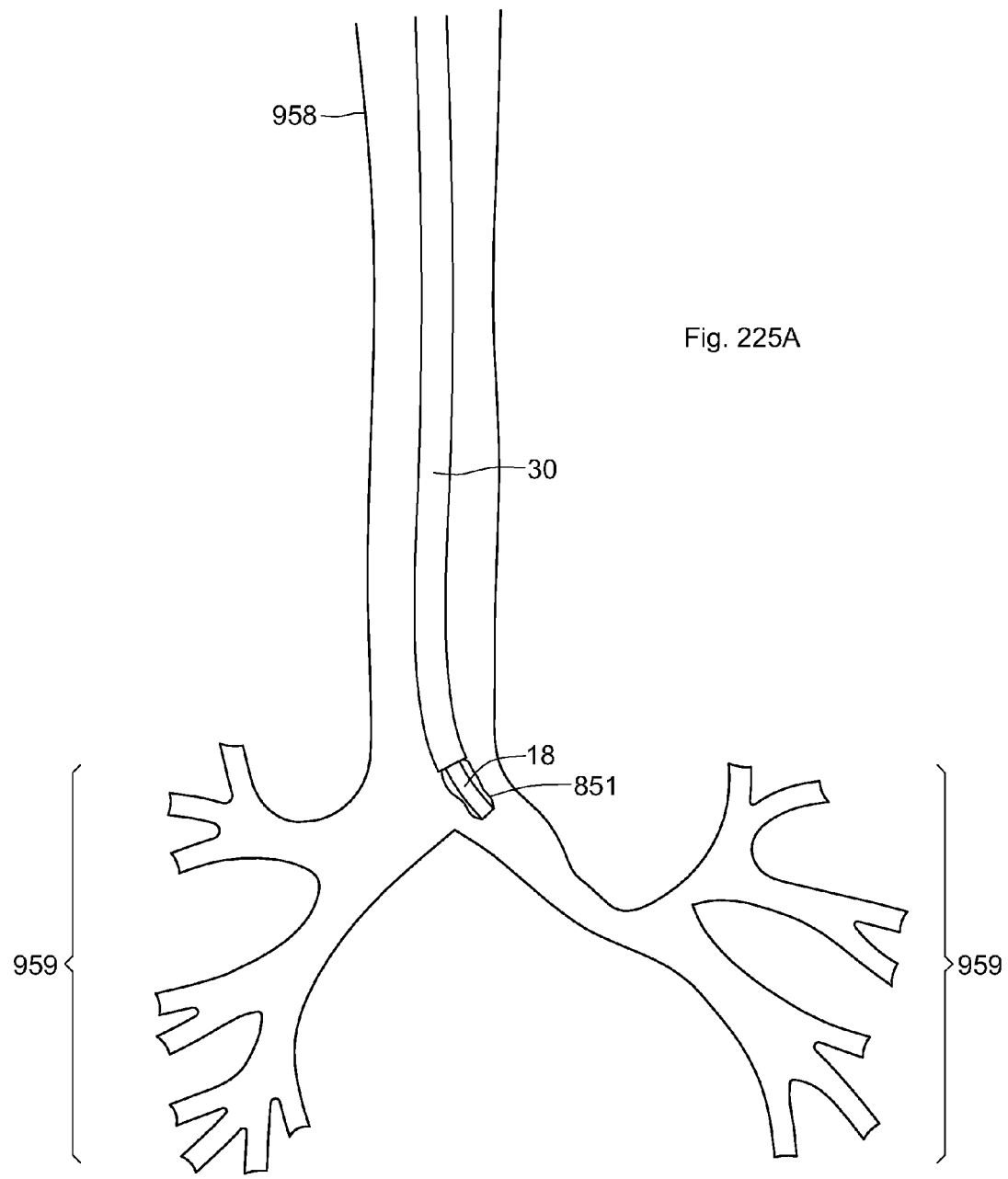
FIGS. 225A-225C illustrates one embodiment of a transbronchial intervention system and procedure wherein a steerable instrument assembly is advanced down the bronchi to deploy an expandable stent structure.
Figure 225B:
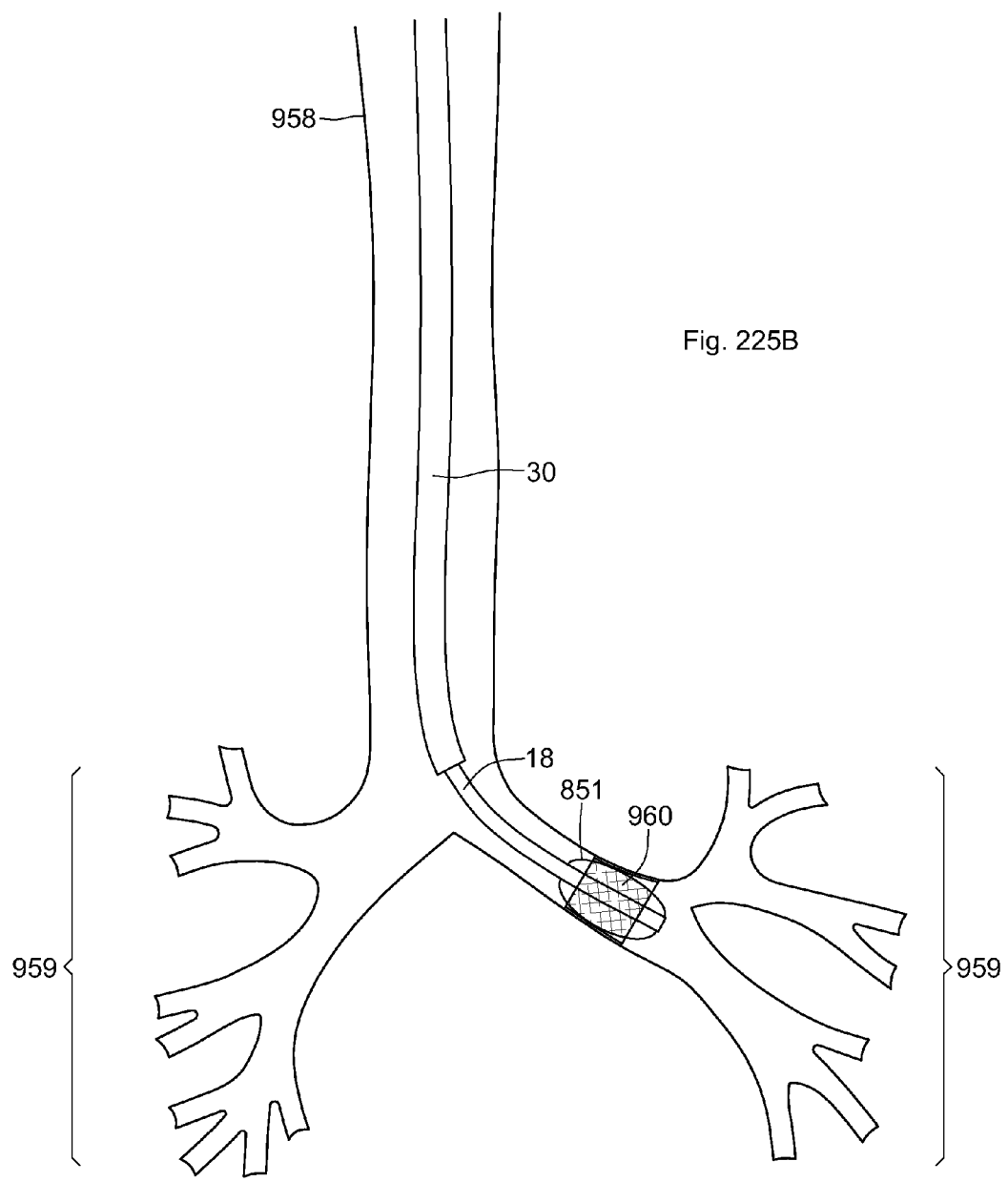
Figure 225C:
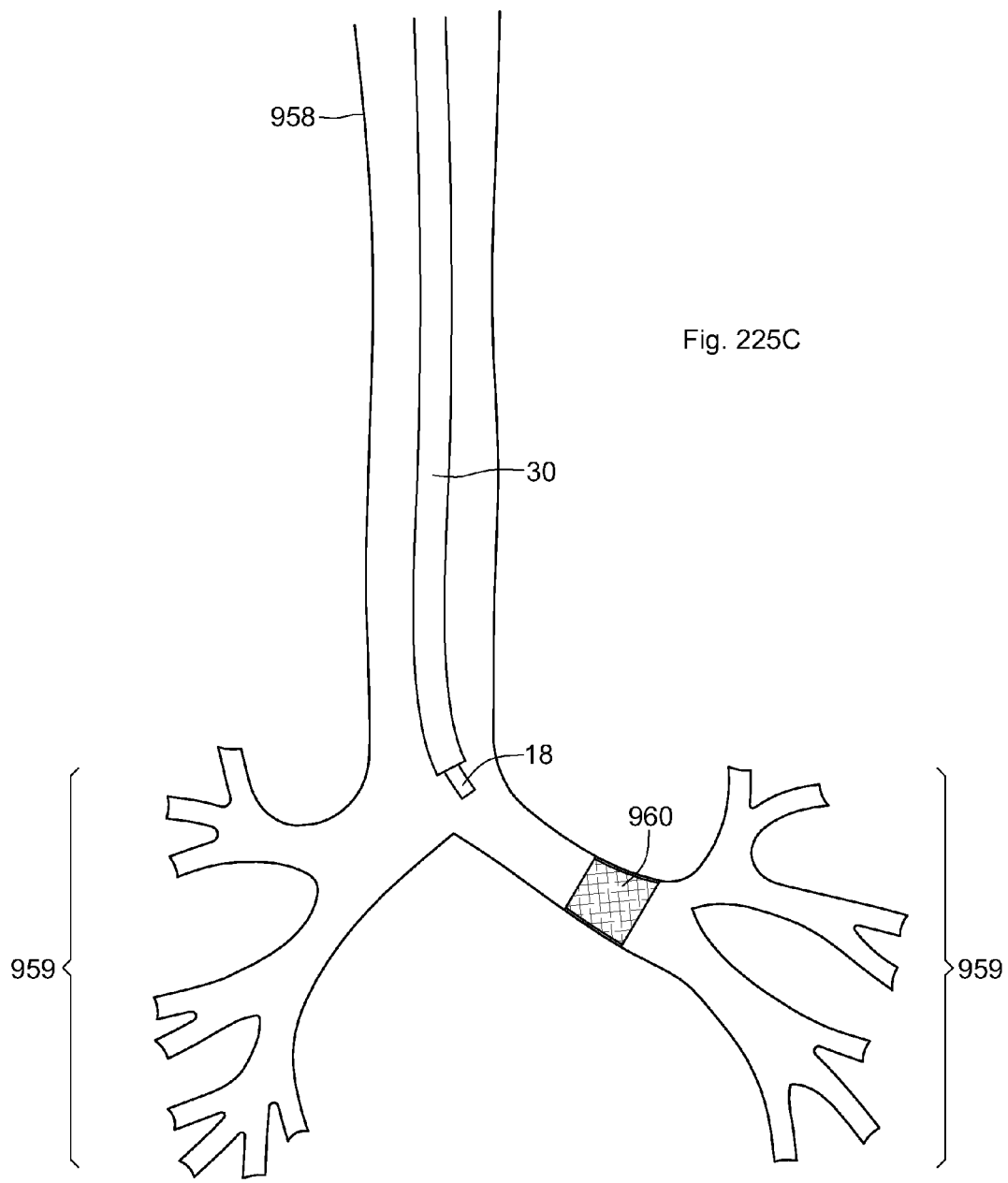
Figure 226A:
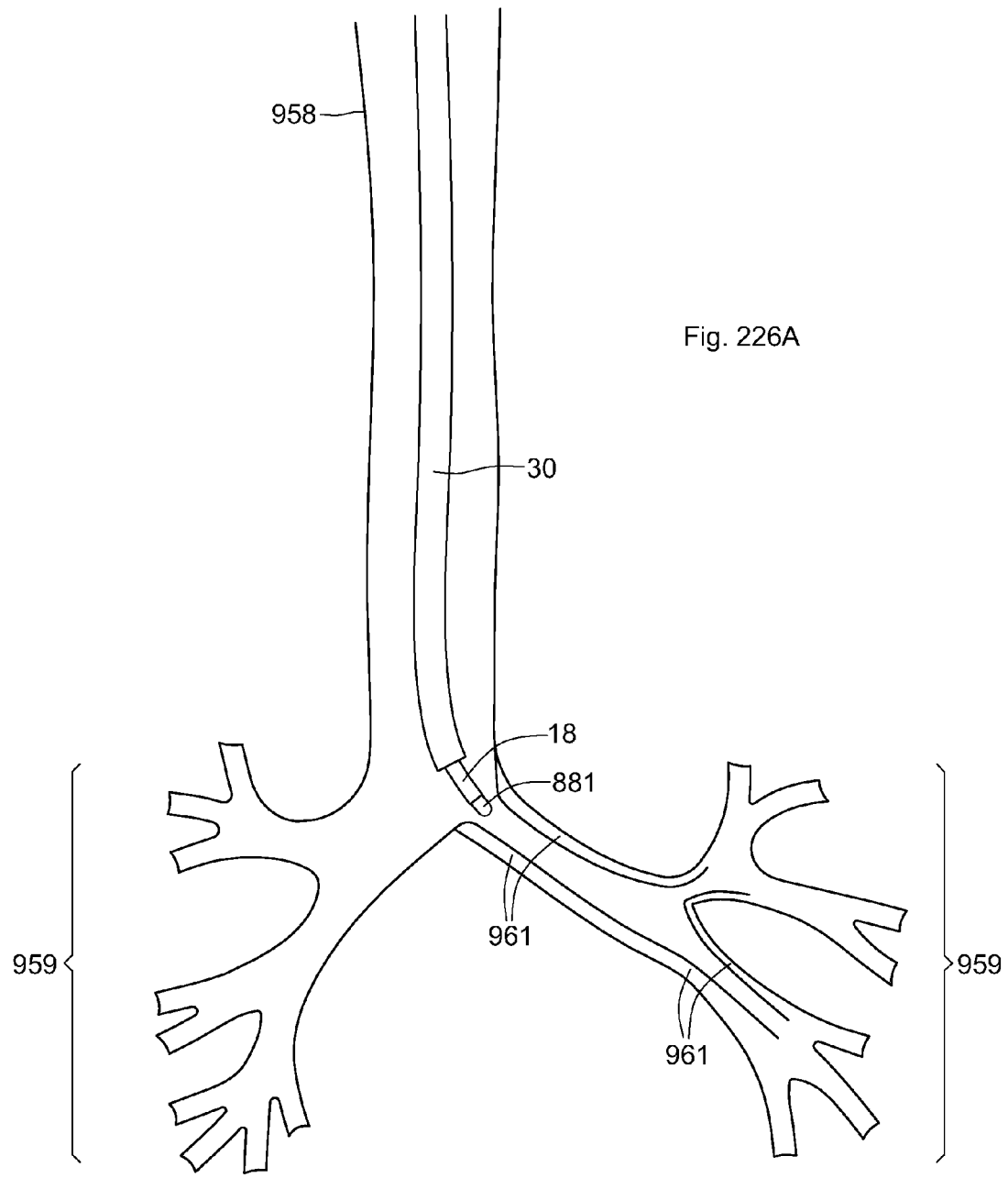
FIGS. 226A-226D illustrate another embodiment of a trans-bronchial intervention system and procedure wherein a steerable instrument assembly is advanced down the bronchi to perform ablation.
Figure 226B:
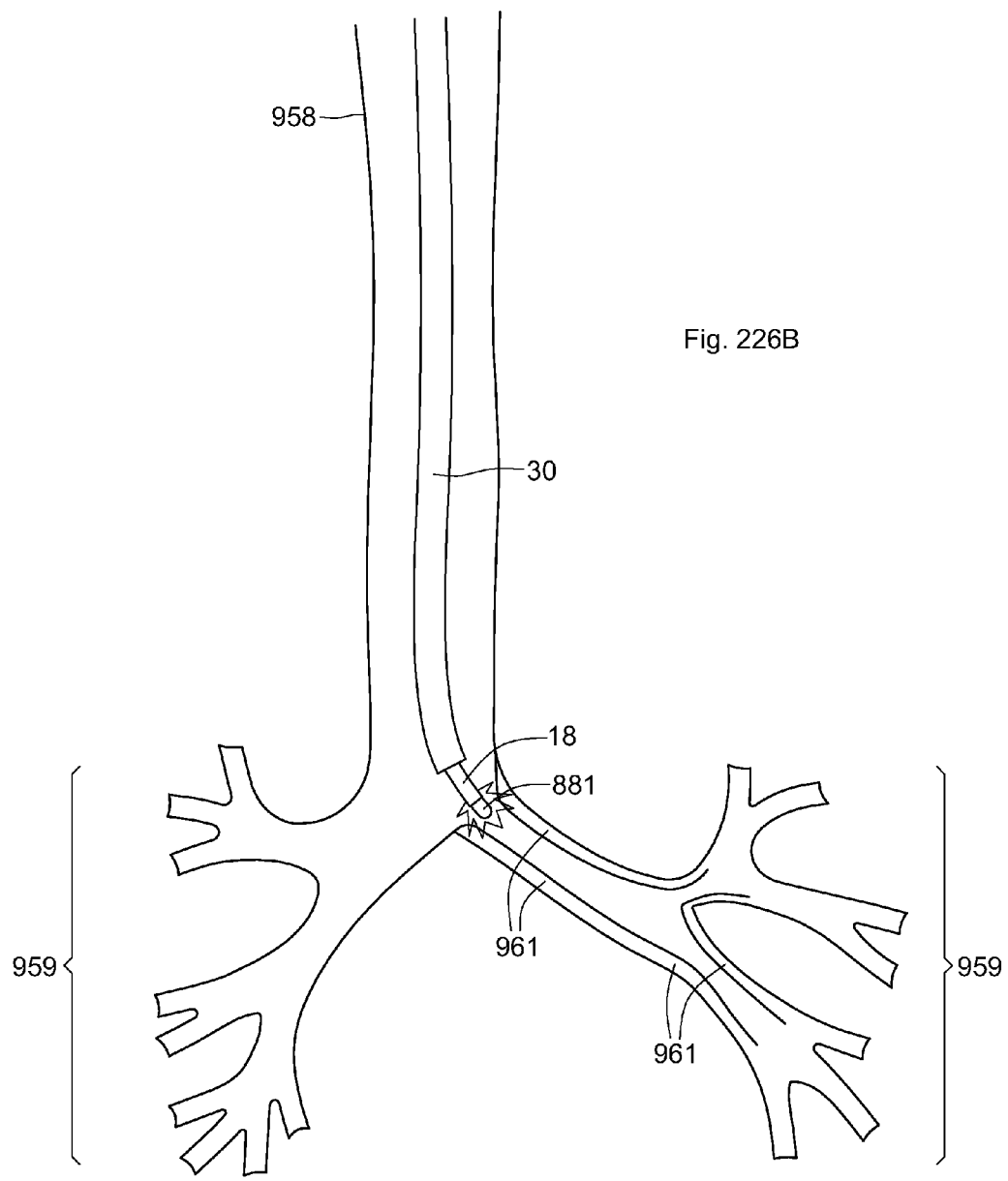
Figure 226C:
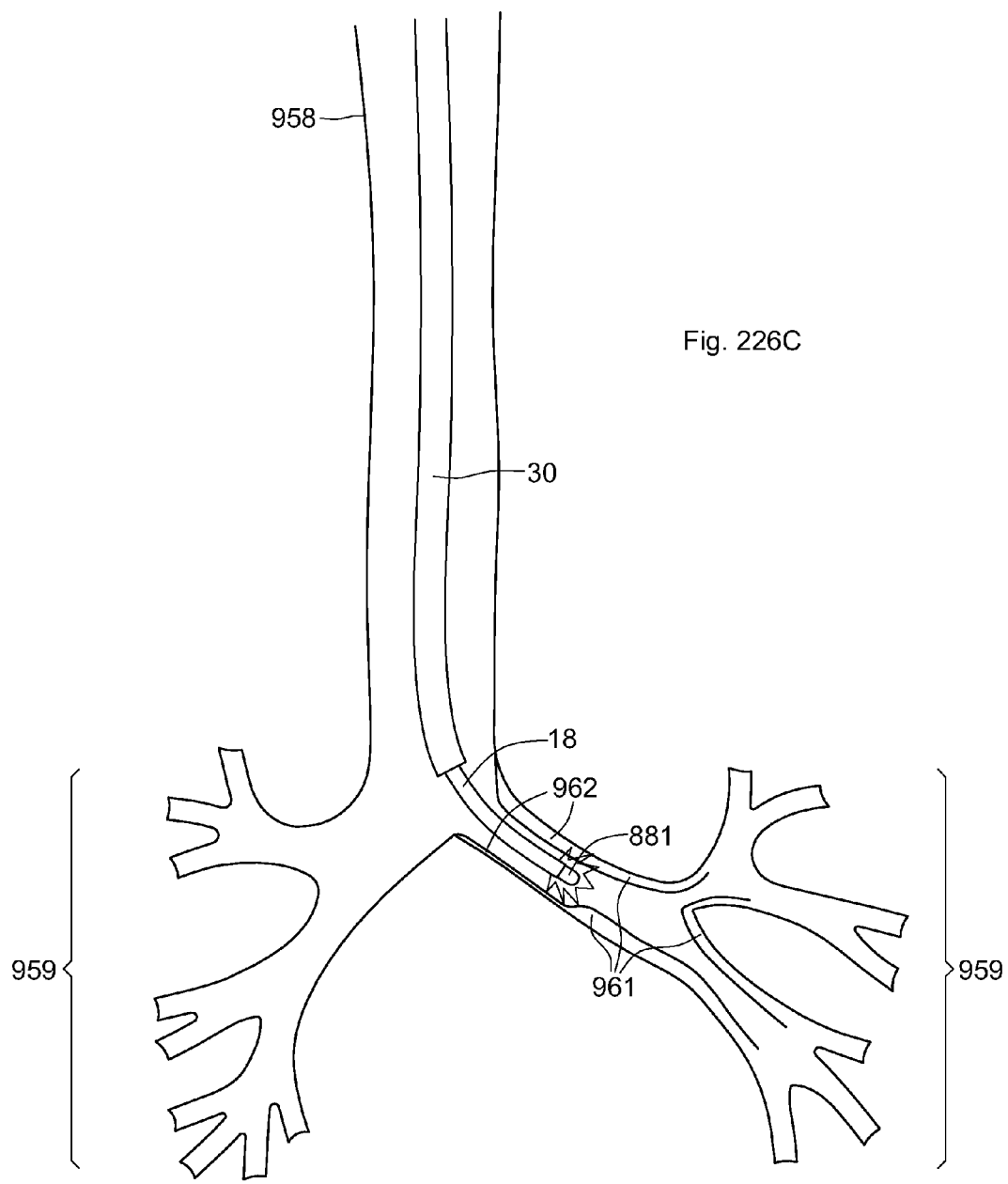
Figure 226D:
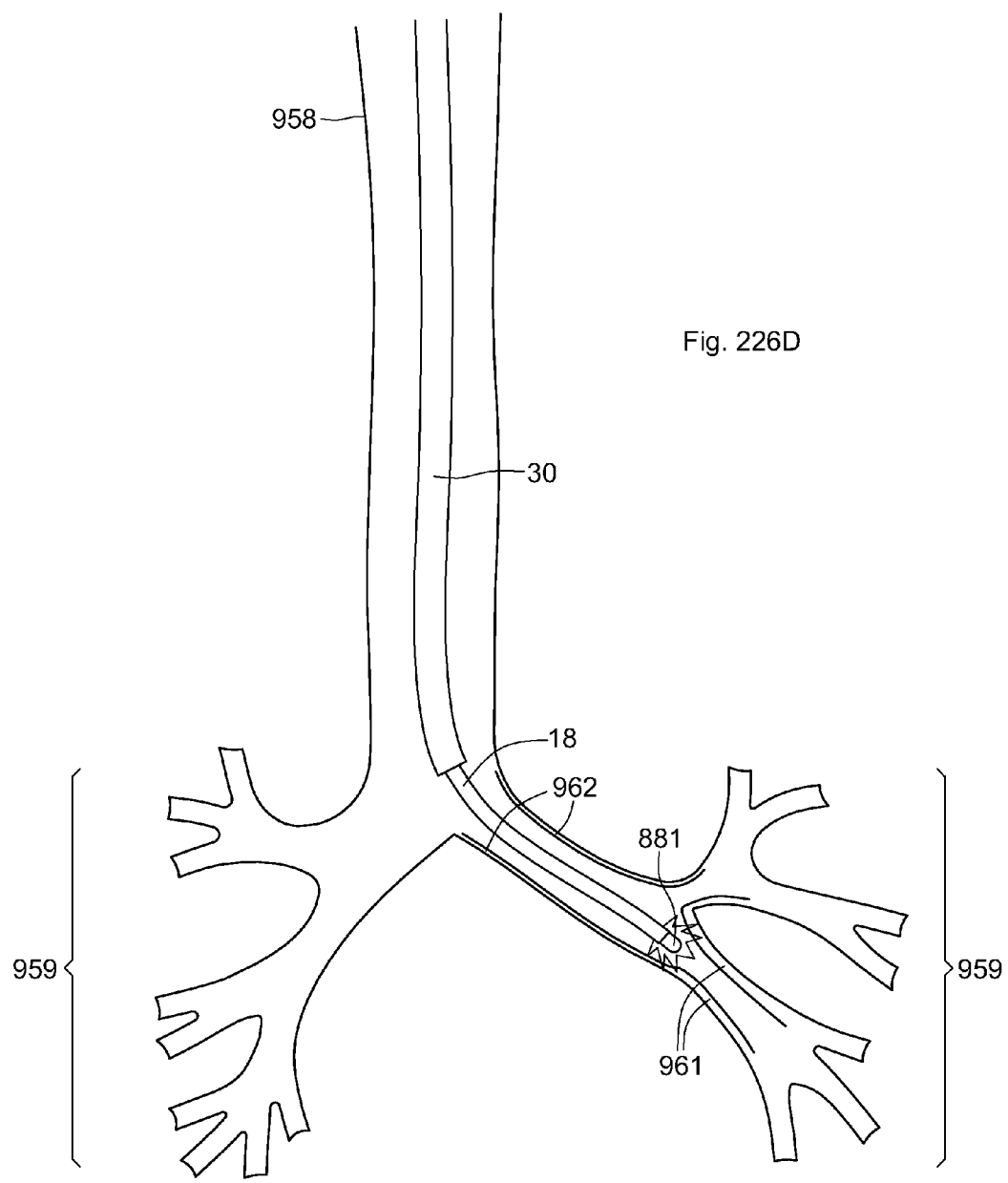

Trans-Bronchial Intervention:

Referring to FIGS. 225A-228D, one or more steerable instrument assemblies may be utilized to navigate, diagnose, and treat the trachea (958), bronchii (959), and lungs (964). Referring to FIGS. 225A-C, a steerable instrument assembly (30, 18) comprising an expandable balloon (851) may be steerably advanced down the bronchi (959) and utilized to deploy an expandable prosthesis (960), such as a stent structure which may be configured to house a one-way valve, in the case of a treatment for a disease such as emphysema wherein it may be desirable to decrease active lung volume, a drug-eluting polymer, etc. In another embodiment, a stent may be deployed to assist in maintaining patency of a particular section of airway. Referring to FIGS. 226A-D, certain bronchi (959) may be ablated (881) with cryo, RF, ultrasound, etc to prevent constriction (961) of smooth muscle in the walls of the bronchi which may be associated with asthma. The muscles themselves may be ablated (881), or the motor neurons leading to them may be ablated, to leave the airways more open (962).

Figure 227A:
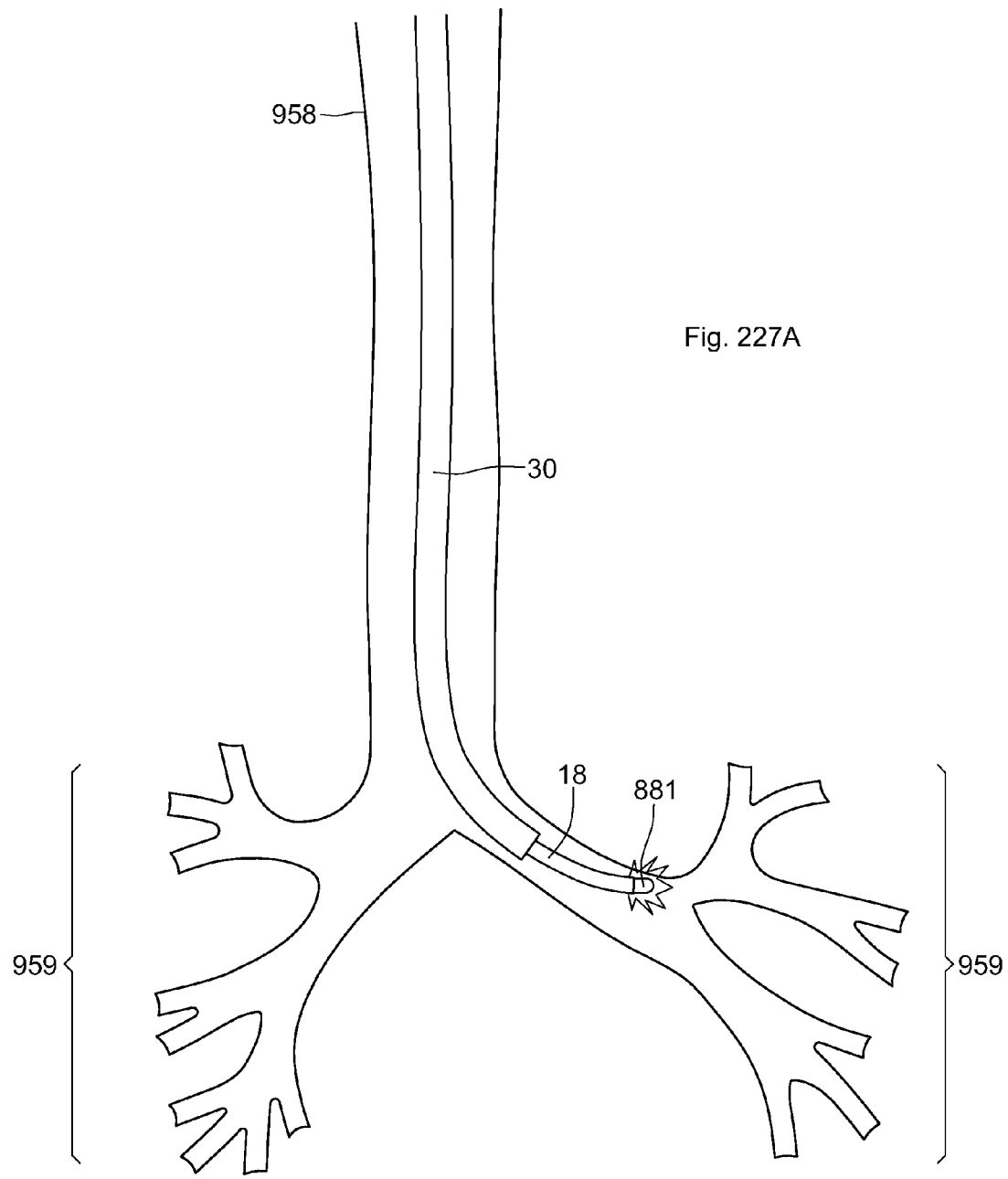
FIGS. 227A-227C illustrate yet another embodiment of a trans-bronchial intervention system and procedure wherein a steerable instrument assembly with an ablation tool is advanced down the bronchi to ablate to cause scarring.
Figure 227B:
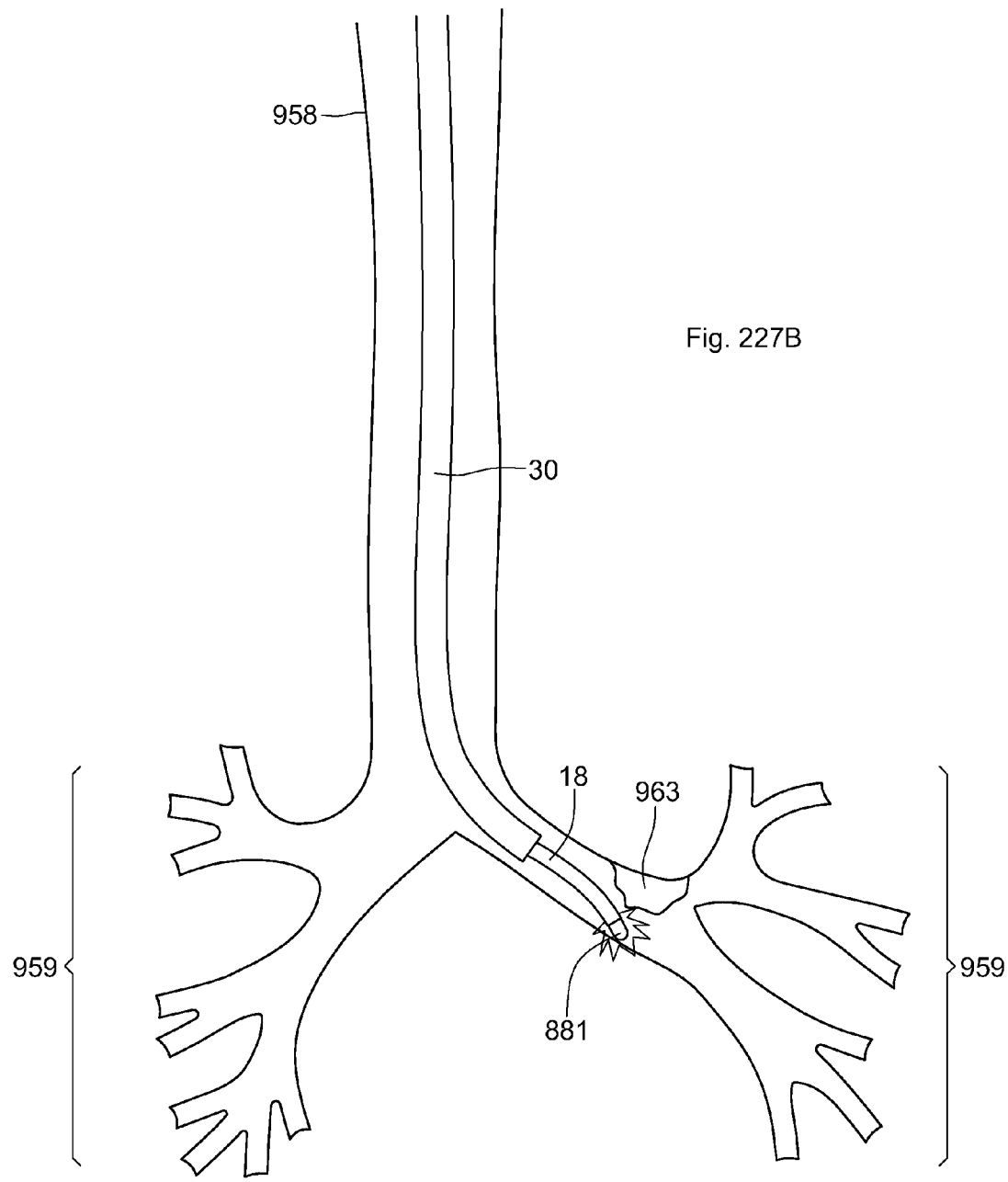
Figure 227C:
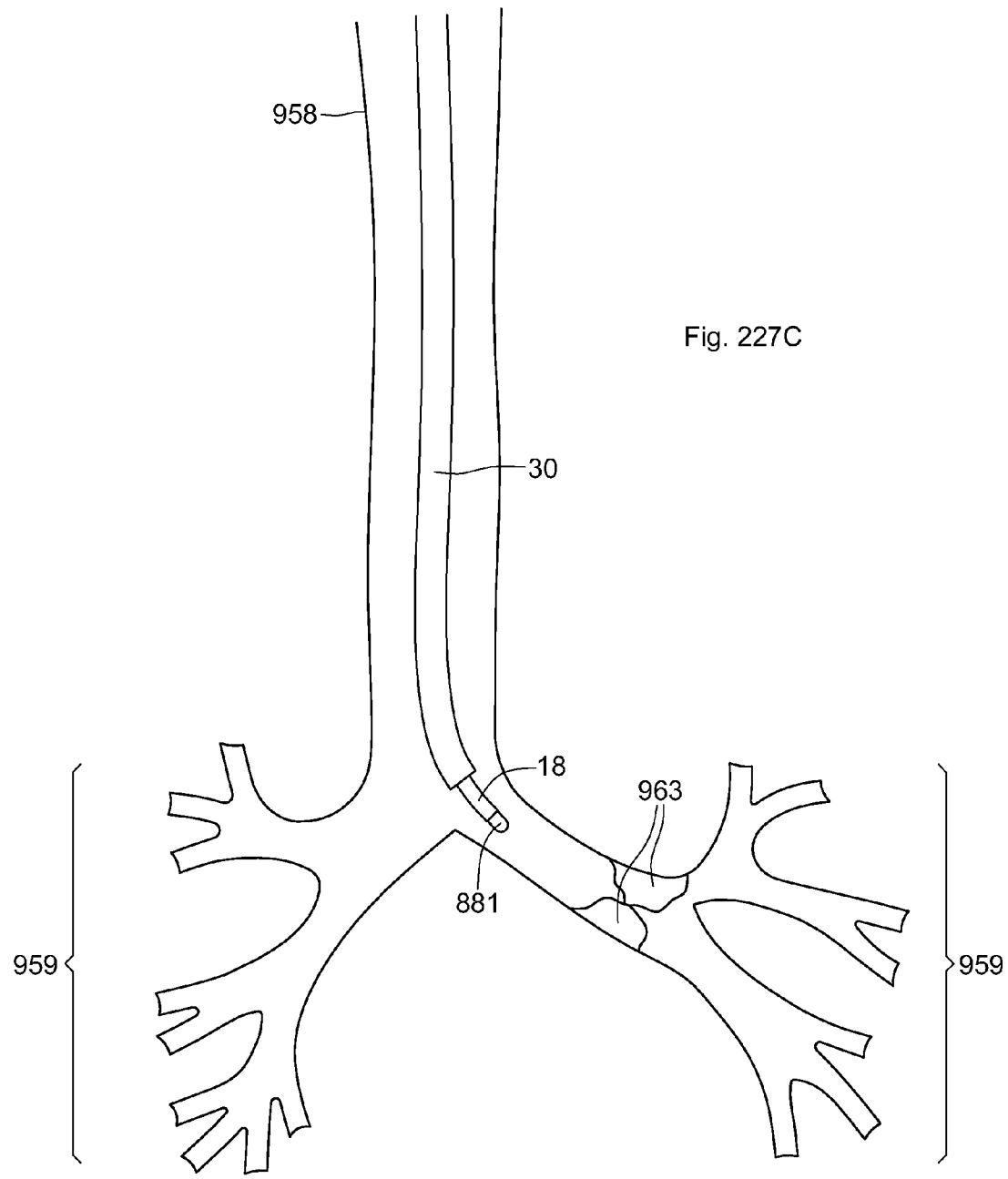
Figure 228A:
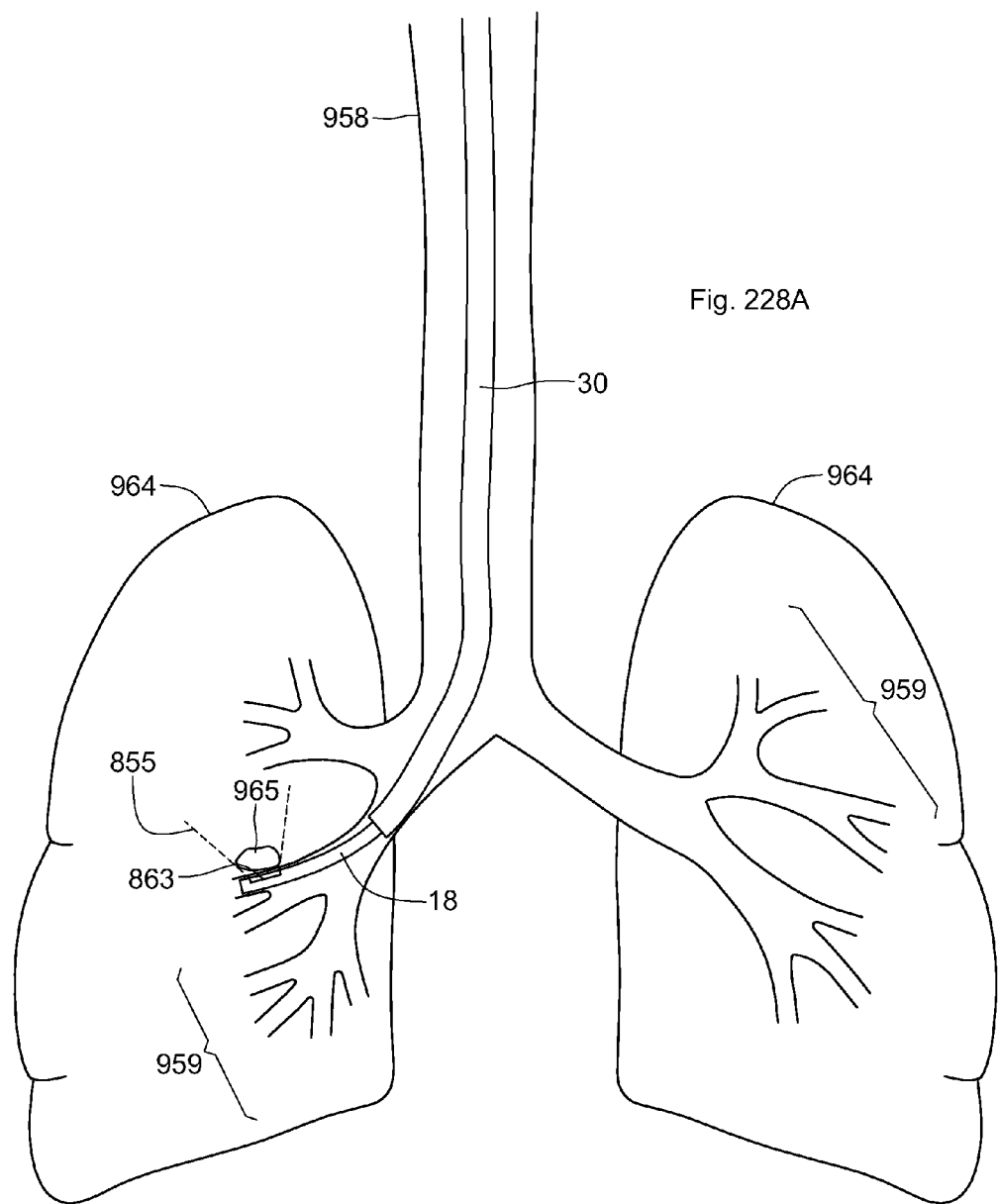
FIGS. 228A-228D illustrate another embodiment of a trans-bronchial intervention system and procedure wherein a steerable instrument assembly is used to position a side firing ultrasound array and a side protruding, retractable, needle electrode.
Figure 228B:
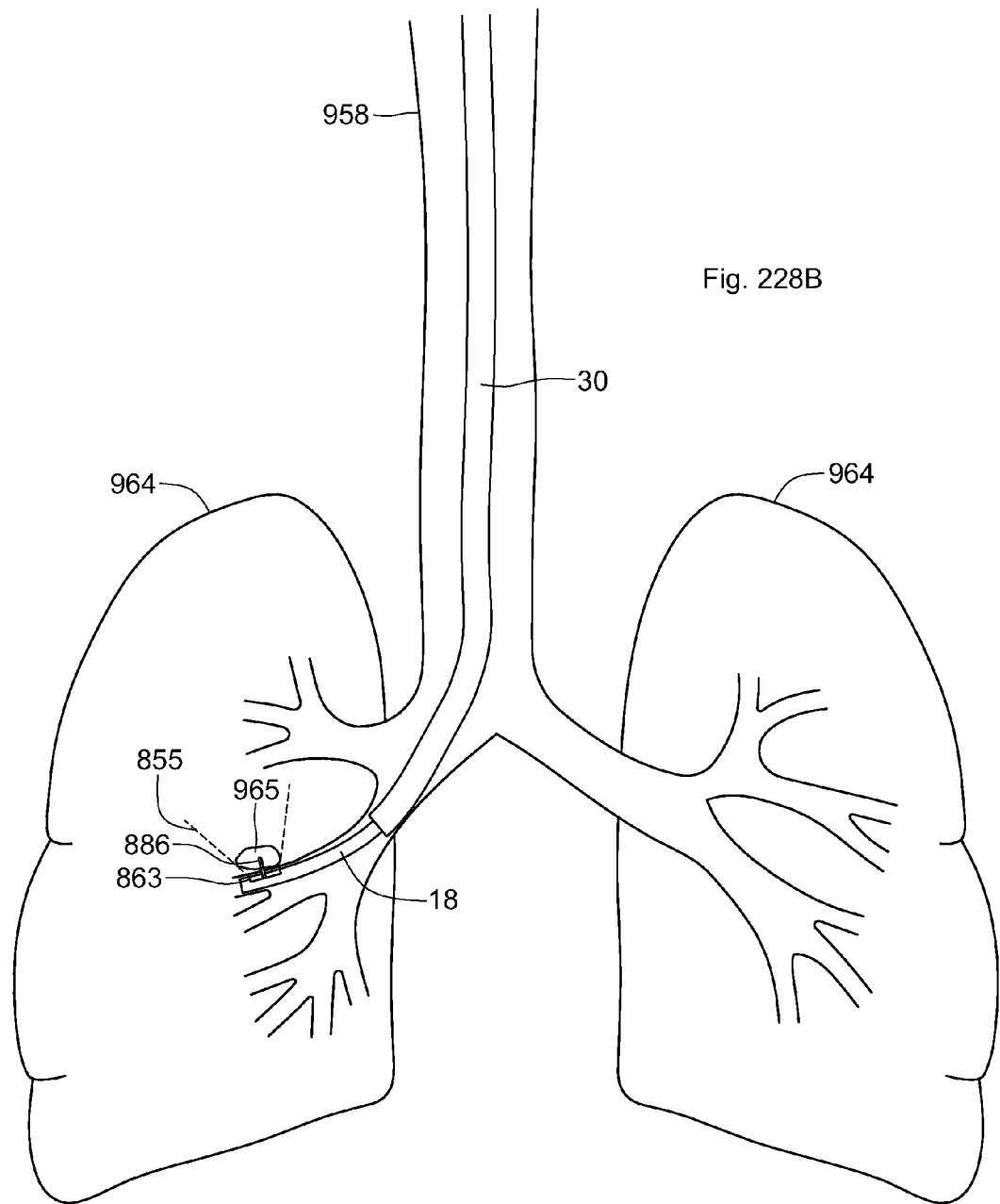
Figure 228C:
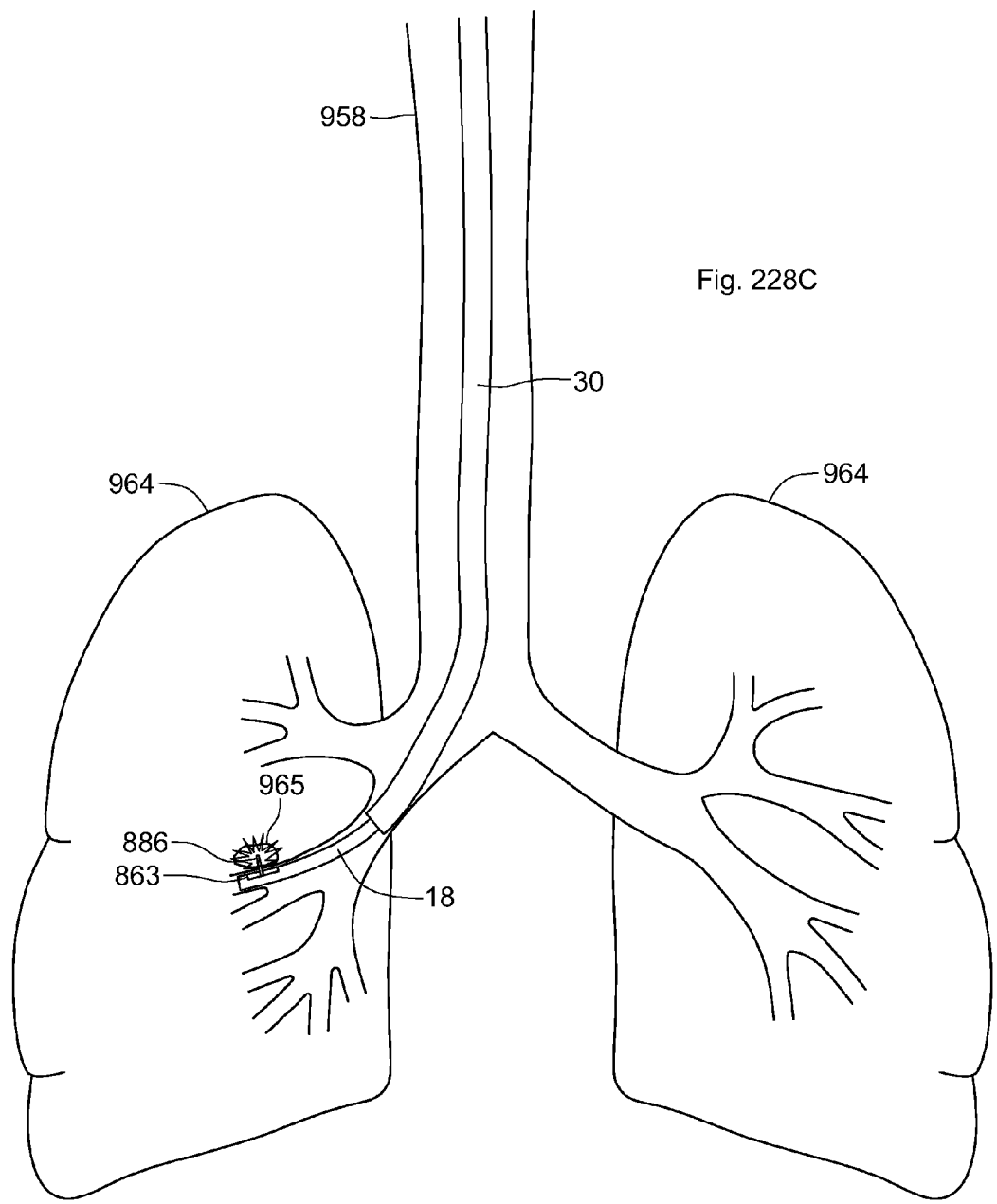
Figure 228D:
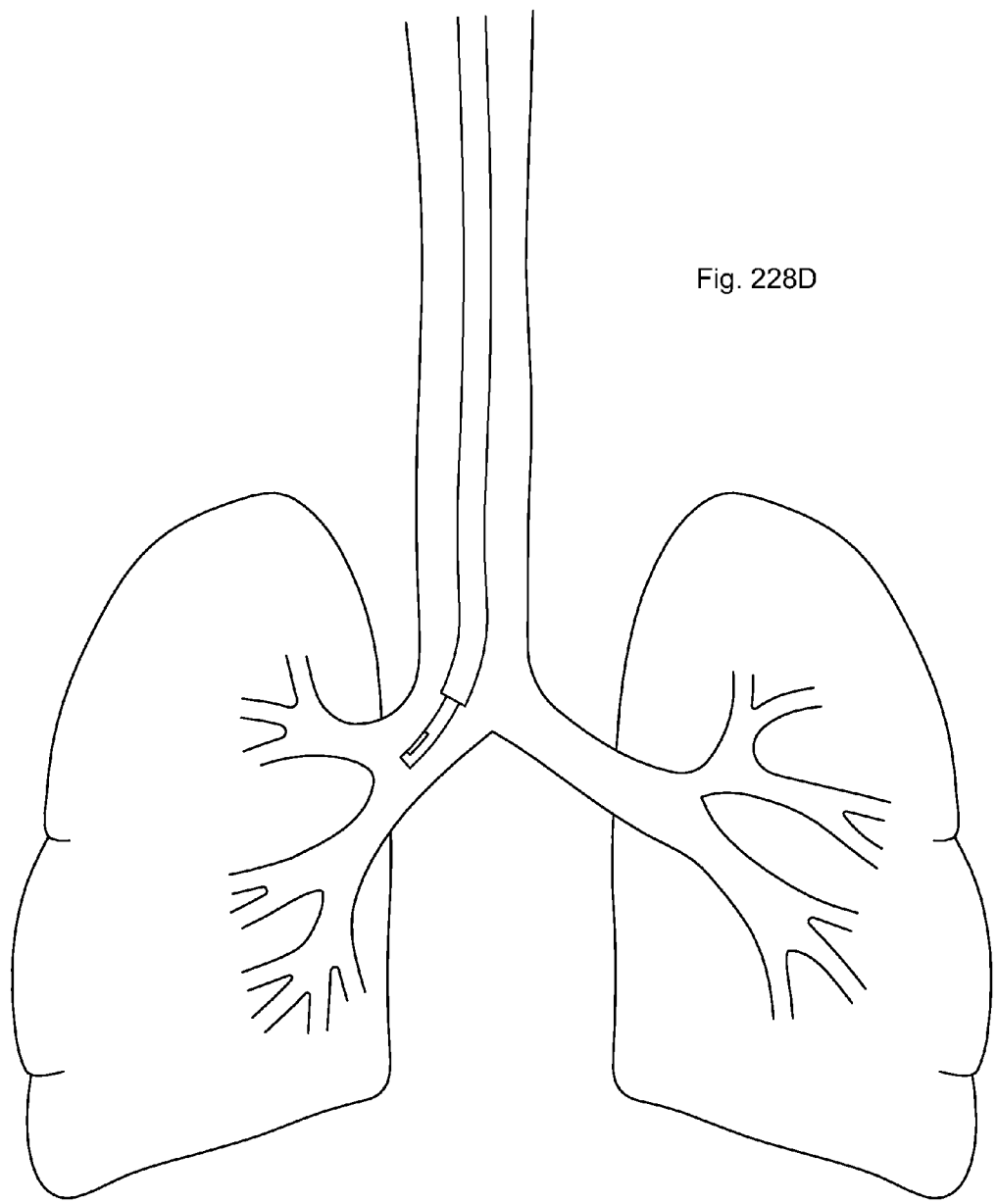

Referring to FIGS. 227A-C, an ablation tool (881) may be coupled to a steerable instrument assembly (18, 30) to navigate the bronchi (959) and ablate a specific location to cause a scarring (963) and eventual partial or total occlusion of an airway leading to lung volume which is not wanted, for reasons such as emphysema. Referring to FIGS. 228A-D, a steerable instrument may be utilized to position an ultrasound device (863), such as a side-firing ultrasound array, along with a side-protruding, retractable needle (866) which may also function as an electrode, to find, biopsy, inject, ablate (886), and/or lyse potential or known lesions (965), such as tumors, of the lung.

Arthroscopic Intervention:

Steerable tool assemblies according to some embodiments of the invention may be used to drive from side ports of a human knee synovial joint to posterior aspects of the same joint to facilitate precision passing of a needle and suture from anterior or side to posterior and thereby repair a meniscus tear with sutures. A distracted synovial joint (such as the hip joint) may be investigated with a small steerable instrument positioned at the end of a slender steerable instrument assembly configured to navigate a distracted and preferably irrigated joint space, such as that of the human hip.

Spinal Intervention:

The steerable platform provided by embodiments of the invention may also be utilized to steer/navigate to the intervertebral disk space, e.g., by driving around calcified tissue and nerves. A spinal tap may be conducted, and a very thin steerable device inserted and turned up the CSF channel into the subdural brain to vacuum out subdural hematomas, biopsy brain tissue, investigate, and otherwise navigate the brain region.

Thoracic Intervention:

Steerable instruments and instrument assemblies according to some embodiments of the invention may also be utilized for IMA takedown and cauterization of associated small vessels after dropping one lung (preferably the left), then a bypass may be conducted with a distal anastomoses of one or more IMAs. A mediastinoscopy may be conducted from a suprasternal access route. The epicardial space may be accessed from a subxiphoid access route for epicardial ablation or pacing lead placement. Lung wedge resection may be conducted from a transthoracic approach, preferably utilizing CT/MR data to assist in guidance to tissue defects such as tumors. Vagal nerve or splanchnic nerve pacing leads may be placed thoracoscopically with a high degree of precision. As described above, a Heller myotomy may be conducted from a trans-thoracic approach.

Nasopharynx Intervention:

As depicted in the embodiments of FIGS. 229A-F, the nasal/sinus passageways may be navigated, diagnosed, and treated utilizing a steerable instrument assembly (30, 18) according to certain embodiments of the invention. In one embodiment, the maxillary sinus may be navigated, irrigated, medicated with a steerable instrument having an overall cross sectional dimension less than about 2.5 mm to pass through the nasal passageway (967) and past the entry to the maxillary sinus. Further, this entry to the maxillary sinus may be increased with a burr, drilling, or other dilation tool (966) configured to at least partially resect calcified and associated soft tissue with high degrees of precision, as depicted in FIG. 229G. In other embodiments, the frontal, ethmoidal, and sphenoidal sinuses may be accessed, diagnosed, and treated.

Figure 229A:
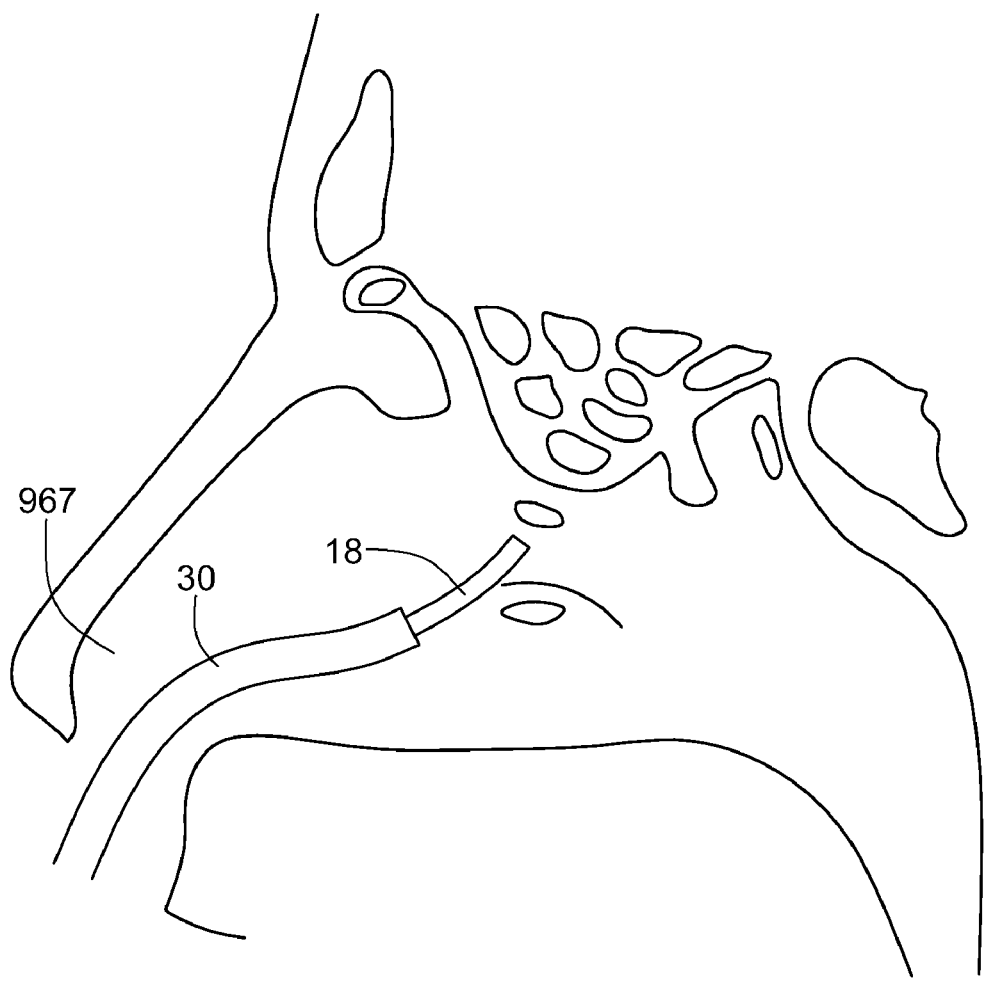
FIGS. 229A-229G illustrate various embodiment of Nasopharynx intervention systems and procedures wherein a steerable instrument is used to access and navigate the frontal, ethmoidal, or sphenoidal sinus via the nasal passage.
Figure 229B:
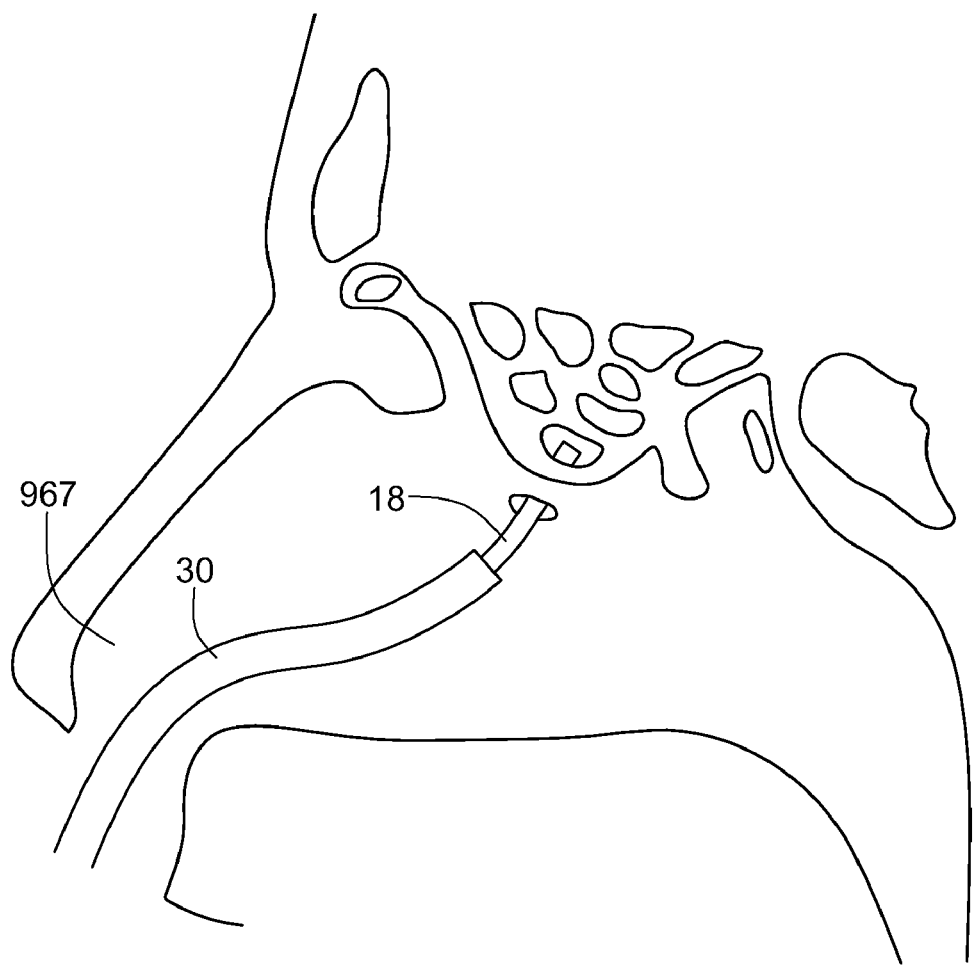
Figure 229C:
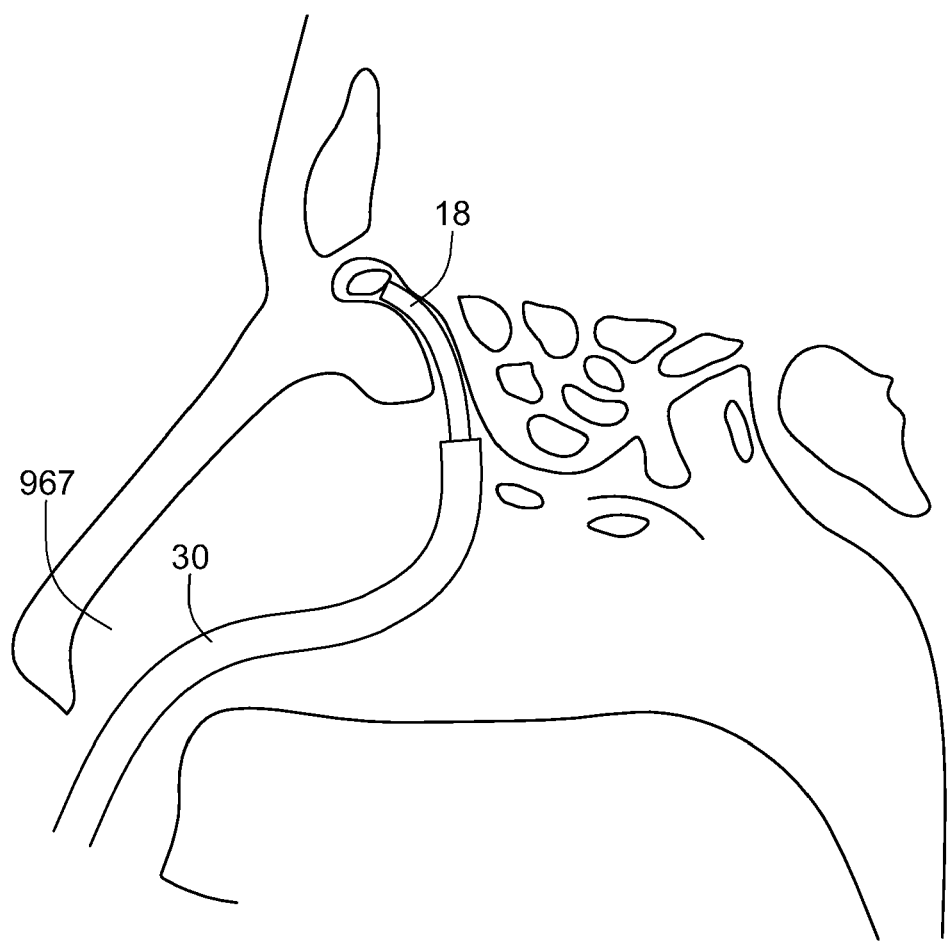
Figure 229D:
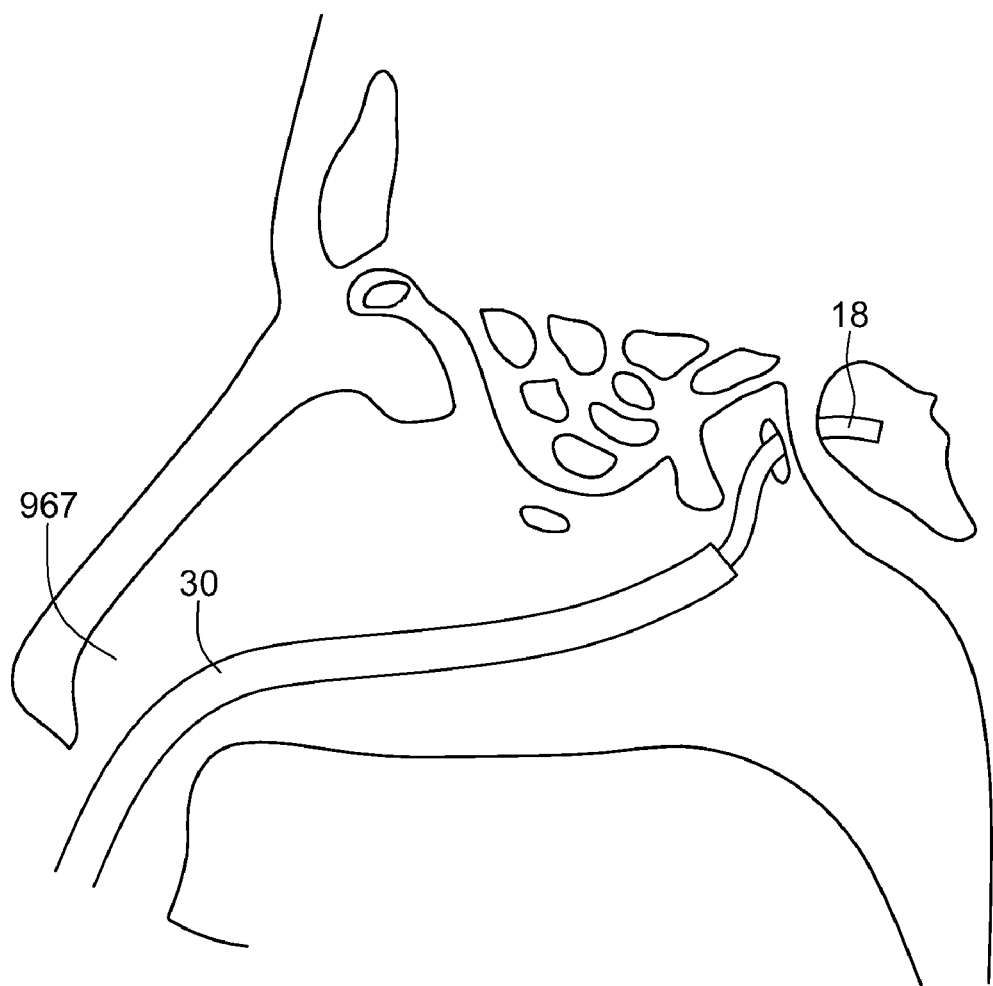
Figure 229E:
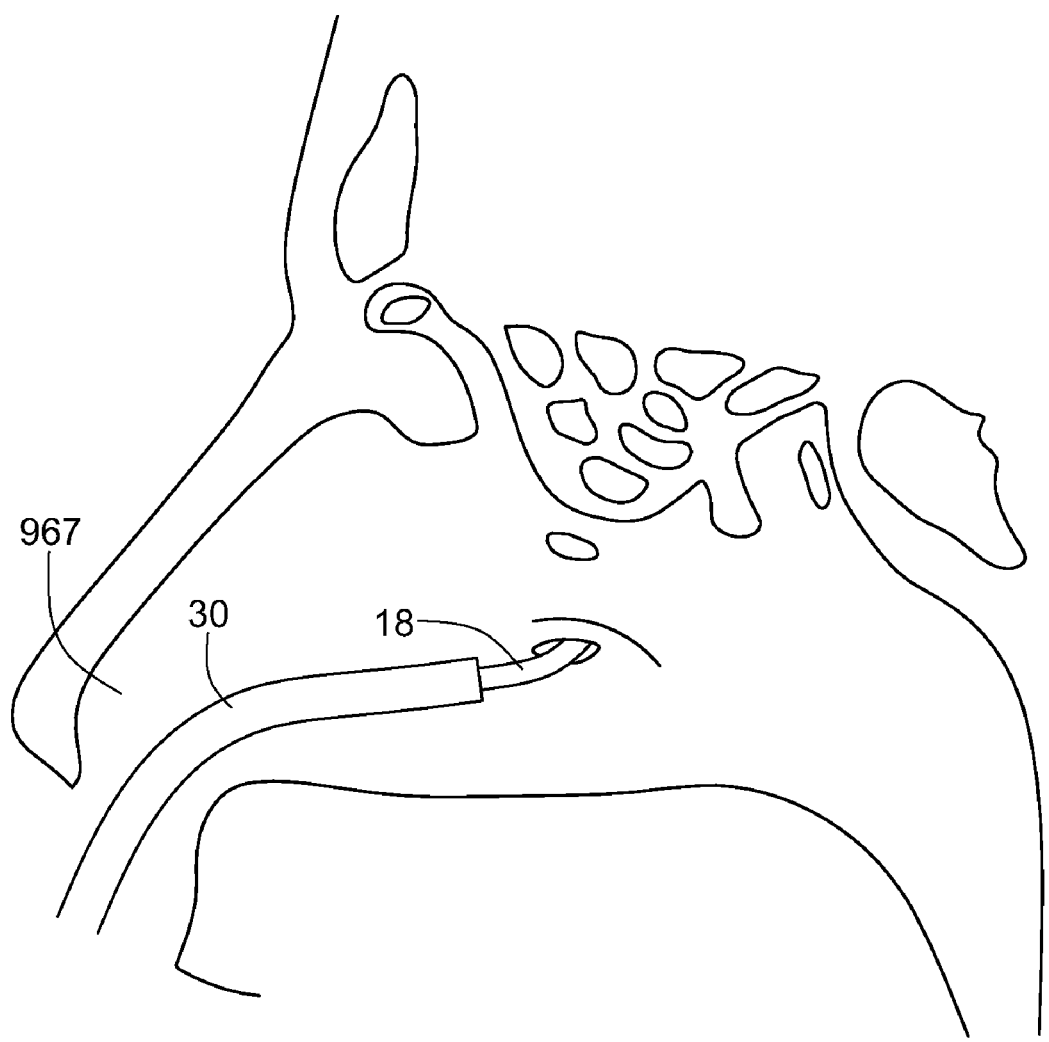
Figure 229F:
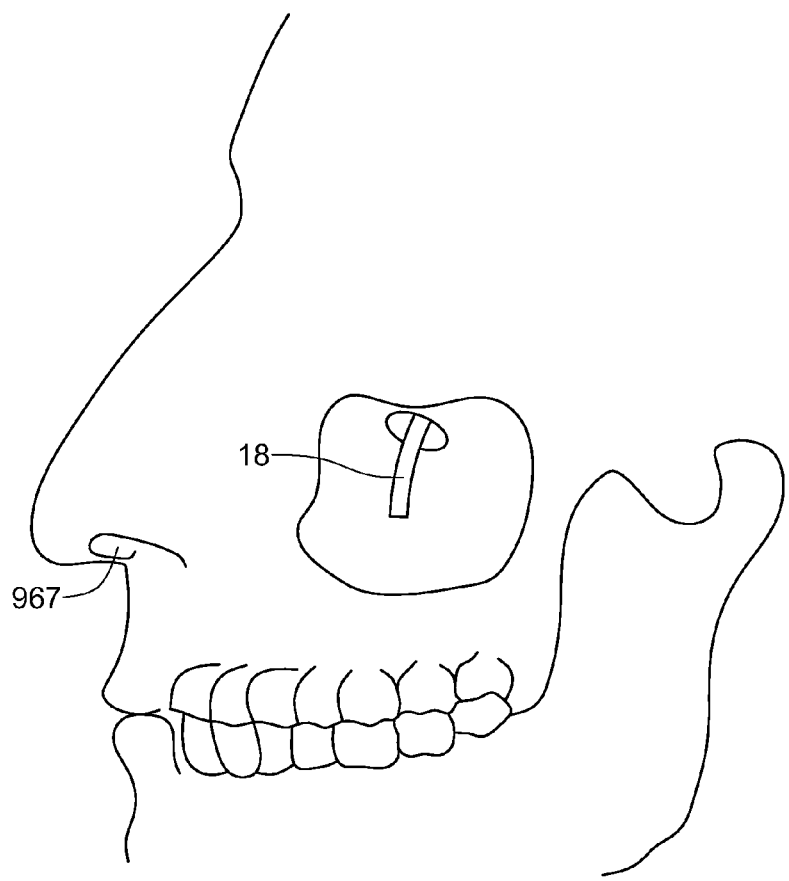
Figure 229G:
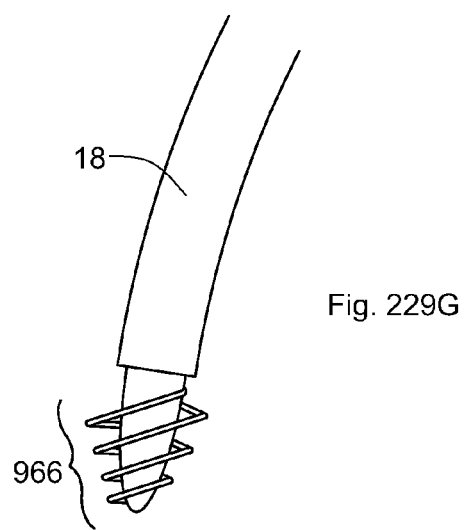

Referring to FIG. 229A, each of the frontal, ethmoidal, sphenoidal sinuses may be access via the nasal passage, as well as the ostium to the maxillary sinus. Referring to FIG. 229A, a steerable instrument navigates the ethmoidal spaces. Referring to FIG. 229C, a steerable instrument navigates the frontal sinus. Referring to FIG. 229D, a steerable instrument navigates the sphenoidal sinus. Referring to FIG. 229E, a steerable instrument is depicted entering the ostium into the maxillary sinus. Referring to FIG. 229F, the distal tip of the steerable instrument is depicted navigating down into the maxillary sinus. Referring to FIG. 229G, a burr distal tip (966) is depicted which may be utilized for enlarging the ostium to the maxillary sinus.

Figure 230A:
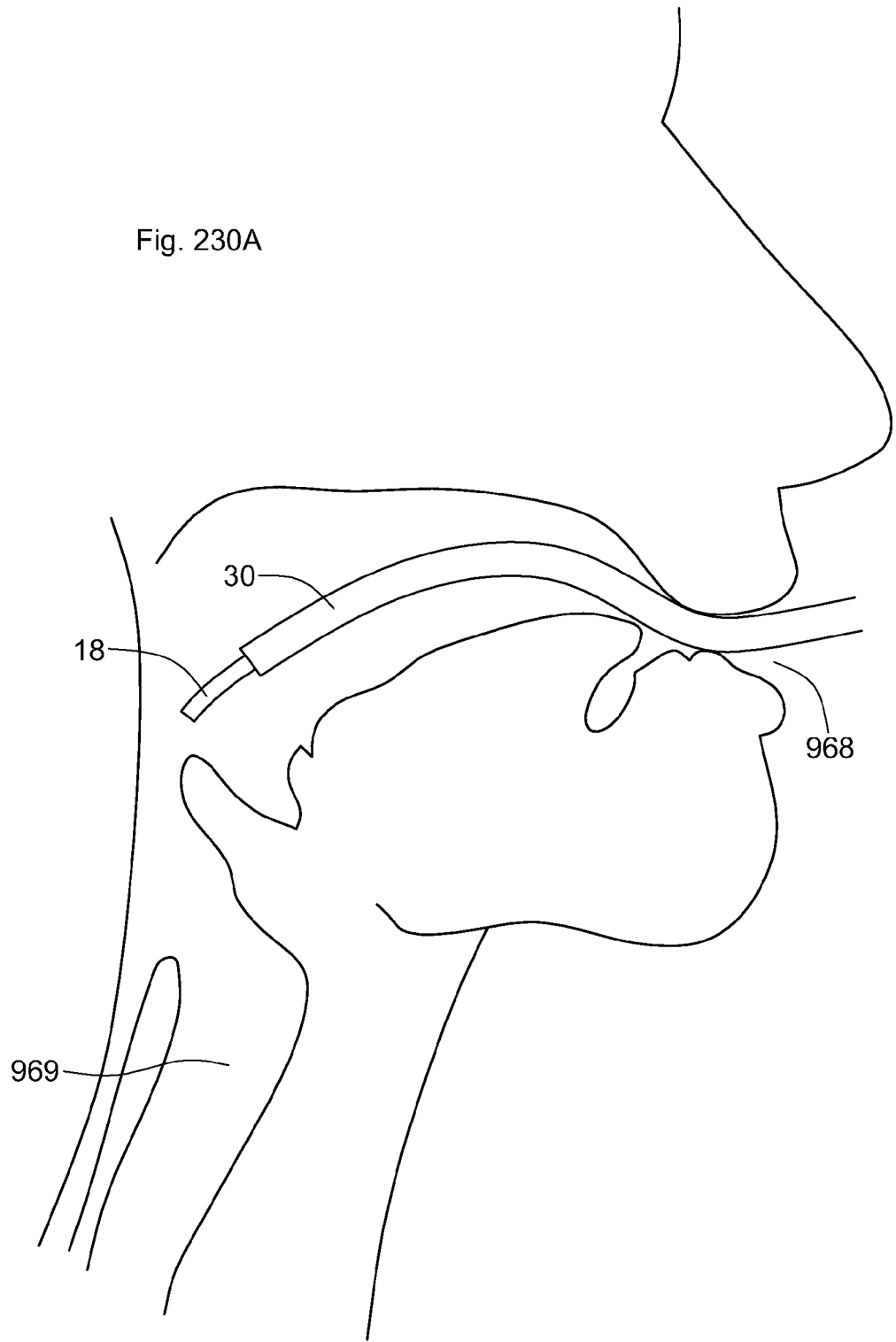
Figure 230B:
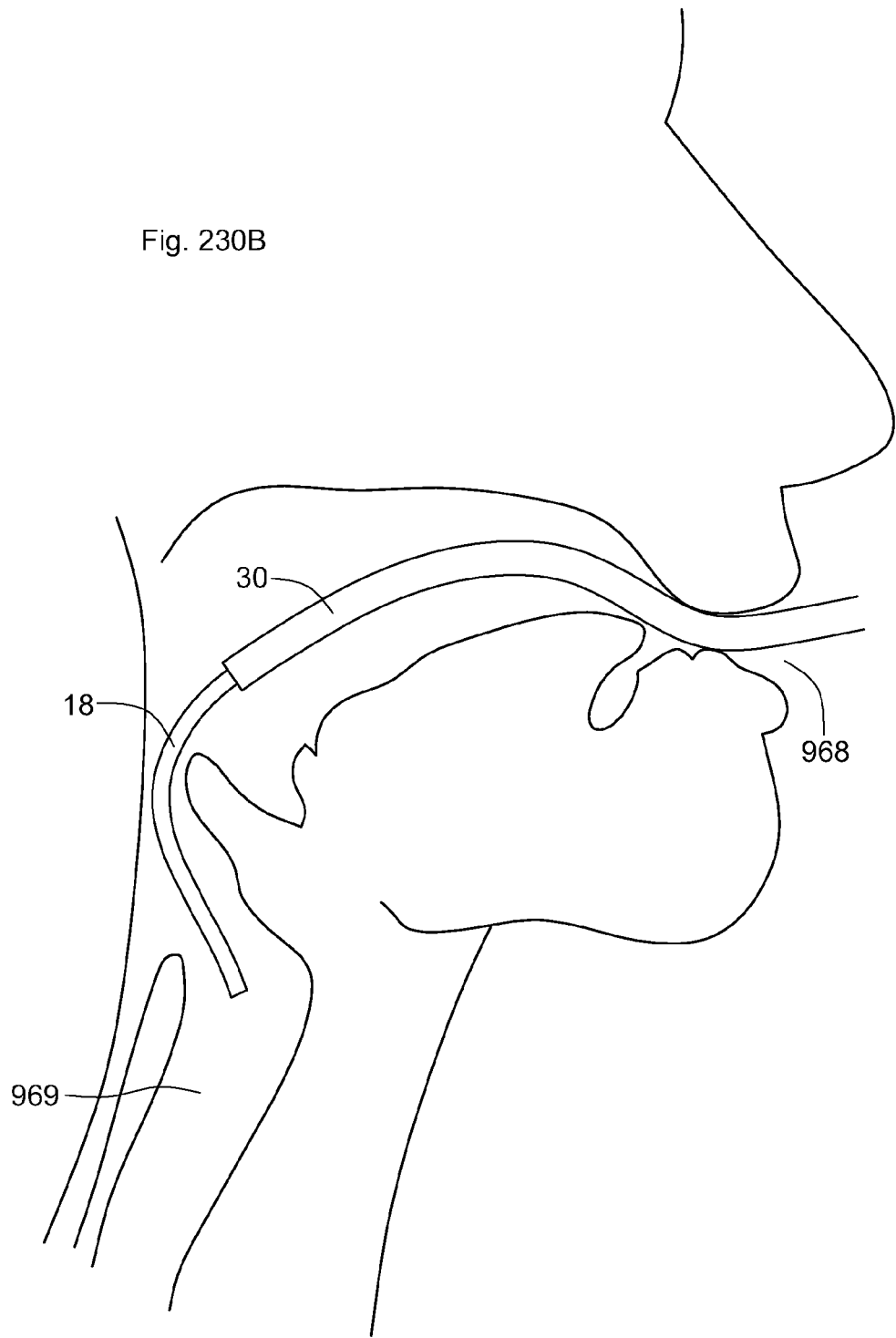

Larnyx Intervention:

The larynx may be biopsied, modified, ablated, etc using the flexible/steerable platform provided by some embodiments, through the mouth (968), in contrast to conventional rigid laryngoscopes. Referring to FIG. 230A, a steerable instrument assembly, preferably comprising an image capture device such as a direct visualization means, such as a CCD or fiber device, may be steerably and flexible navigated through the mouth (968), and turned down into the region of the larynx (969). Referring to FIG. 230B, depending upon the particular anatomy of the patient, significant turning and steerability may be required to navigate the distal end of a steerable instrument assembly to the larynx. FIGS. 230C-E depict various embodiments of tools which may be coupled to the distal end of a steerable instrument and utilized in the larynx.

Referring to FIG. 230C, according to one embodiment, an ultrasound device (863), such as a side firing ultrasound array, with a side protruding retractable needle (886) is depicted. The needle (886) may be configured to function as an ablation electrode in one embodiment. The ultrasound device (863) may be utilized to guide the needle into position within, against, or adjacent to a targeted tissue mass, such as a suspected tumor. The retractable needle may be utilized to biopsy, ablate (RF, cryo, laser, ultrasound, etc), lyse, inject, etc the targeted tissue mass. Referring to FIG. 230D, a more bluntly-shaped ablation tip (881) may optionally be utilized to ablate (RF, cryo, laser, etc) or lyse a targeted tissue mass, and potentially cause the targeted tissue mass (970) to scar down or shrink. Referring to FIG. 230E, a grasper (802) or other tool may be utilized to surgically intervene in the larynx (969) area to place a prosthesis, remove a mass or obstruction, or surgically modify targeted tissue to address clinical problems such as sleep apnea.

Figure 231A:
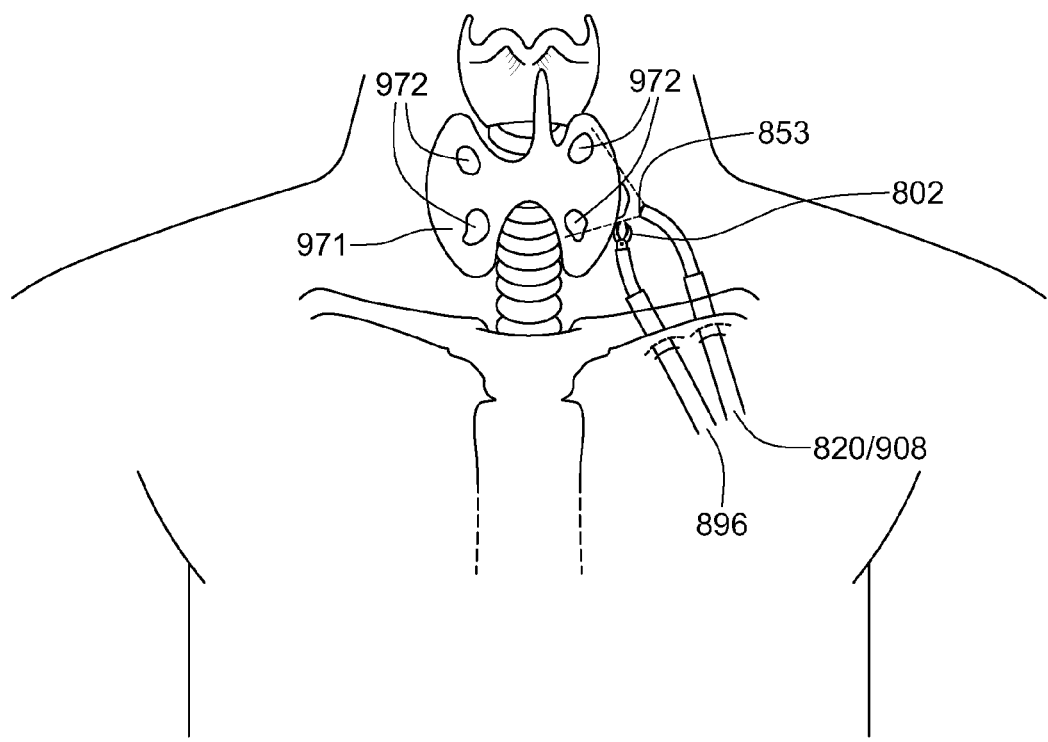
FIGS. 231A-231C illustrate embodiments of intervention systems and procedures for the thyroid and parathyroid.
Figure 231B:
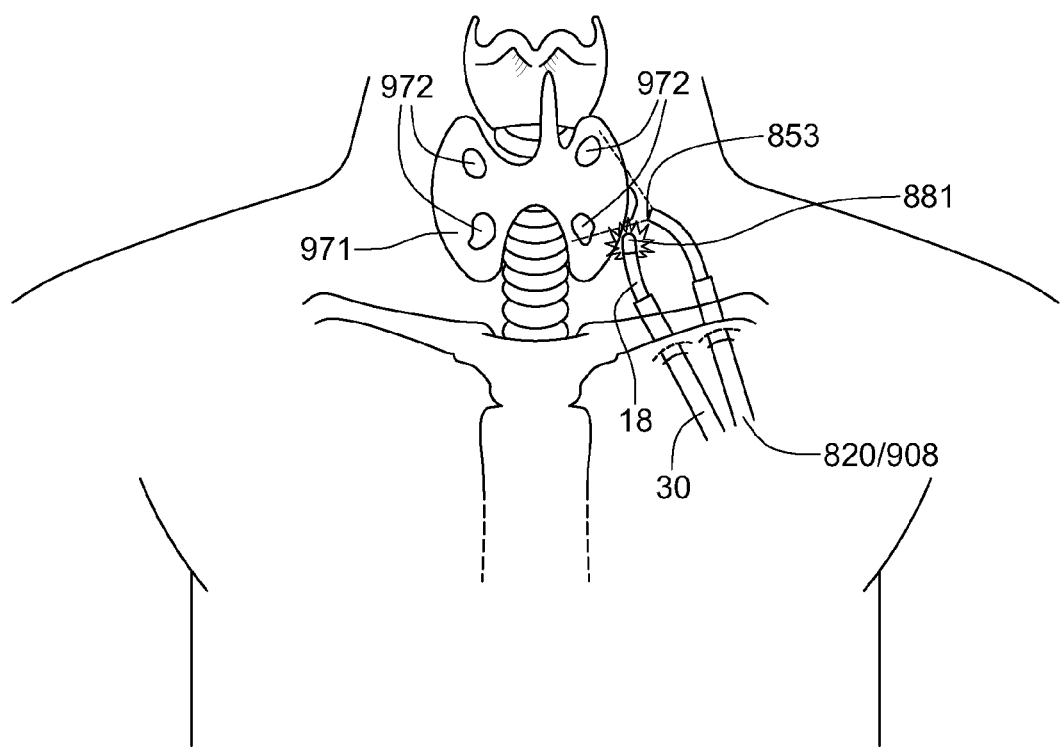
Figure 231C:
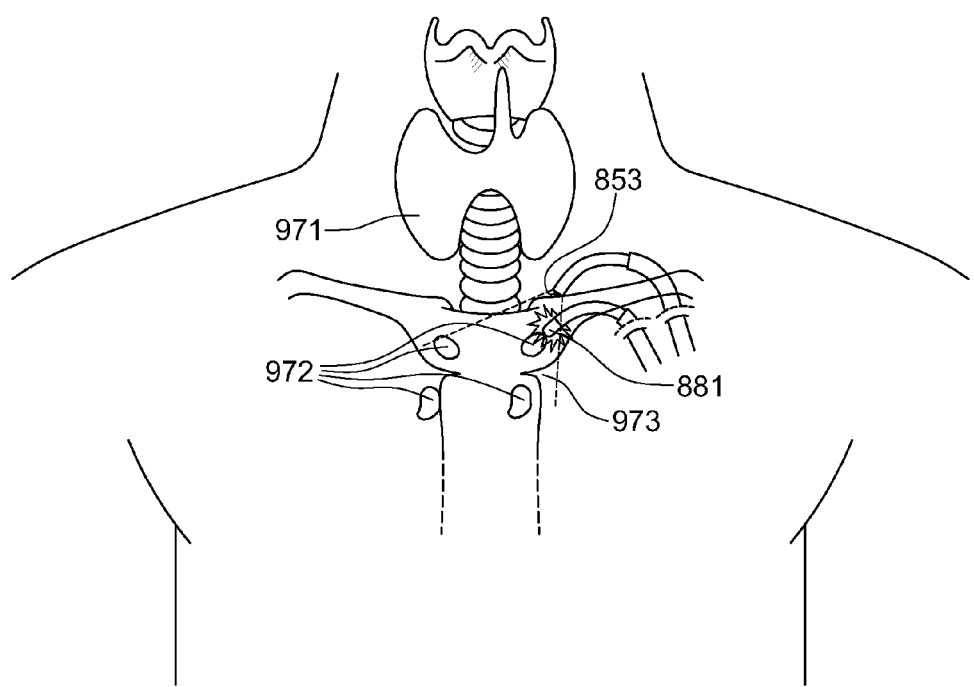

Thyroid/Parathyroid Intervention:

Referring to FIGS. 231A-C, one or more steerable instrument assemblies according to various embodiments may be navigated from a transcutaneous access point above the clavicle, to the region of the thyroid (971) and parathyroid (972). Once in the area of the thyroid (971), the steerable instruments (896, 820/901), preferably comprising an image capture device such as a direct visualization means such as a CCD or fiber device, may be utilized to examine the thyroid (971) and/or parathyroid (972), biopsy them, ablate them (RF, cryo, laser, ultrasound, etc) partially lyse them, inject them, or resect and remove a portion of either of them. Referring to FIG. 231A, with a forward-looking steerable endoscope (820, 901) focused upon the thyroid and/or parathyroid, one or more steerable instrument assemblies (896) constructed according to some embodiments, may be utilized to manipulate the thyroid and/or parathyroid. In one embodiment, a grasping and resection tool (802), such as a bipolar grasper or scissor, may be utilized to resect portions of the thyroid and/or parathyroid. Referring to FIG. 231B, an ablation tool (881—RF, cryo, laser, ultrasound, etc) may be utilized to destroy a portion of the thyroid and/or parathyroid in situ. Referring to FIG. 231C, should one or more of the nodes of the parathyroid (972) be un-locatable in the normal position adjacent the thyroid (971), the steerable instruments may be backed off and steered down into the mediastinal region (973) in hopes of locating the missing nodes of the parathyroid (972) in such location.

Figure 232A:
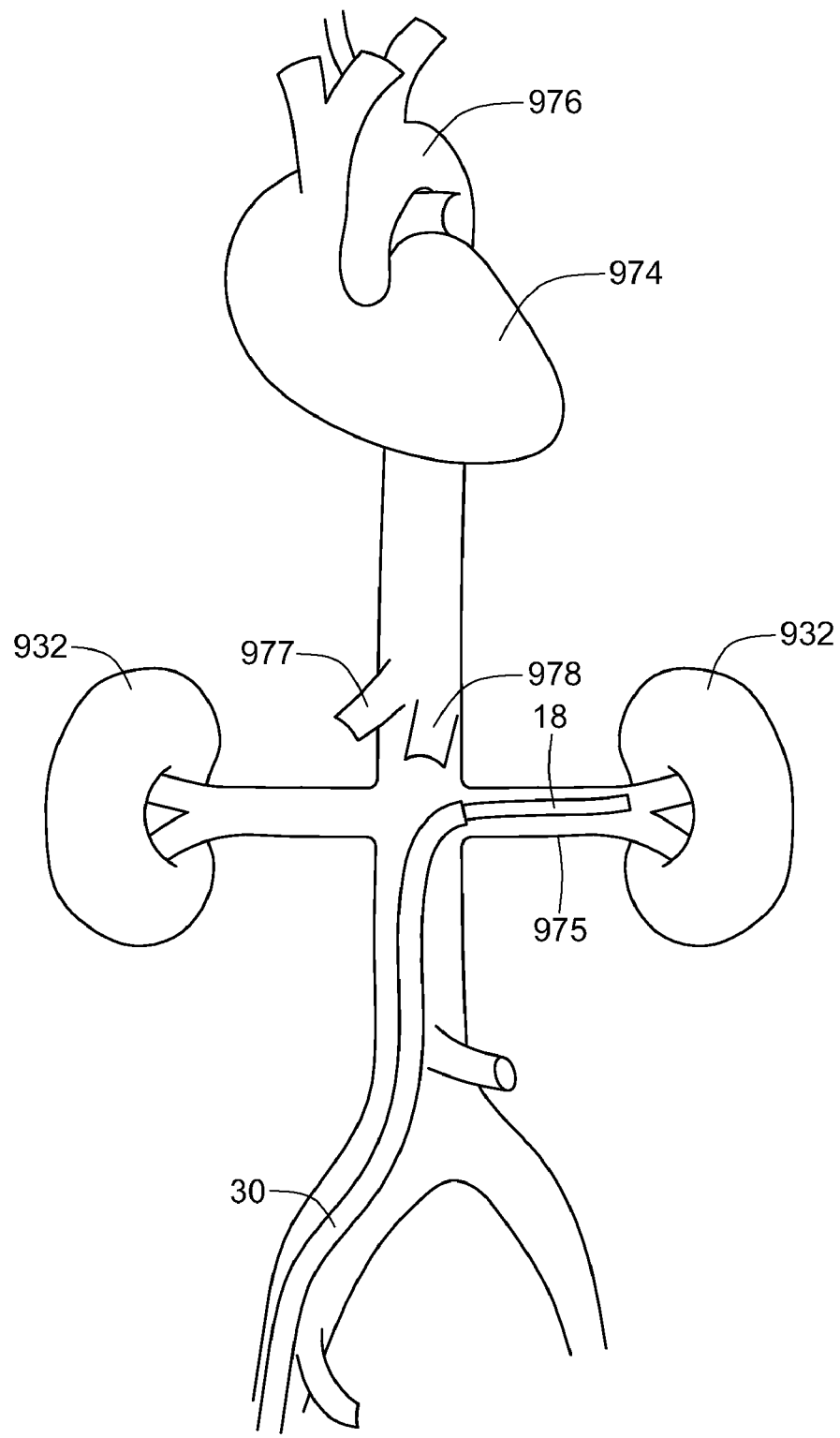
FIGS. 232A-232C illustrate embodiments of vascular intervention systems and procedures using a steerable instrument platform to navigate the ascending aorta.
Figure 232B:
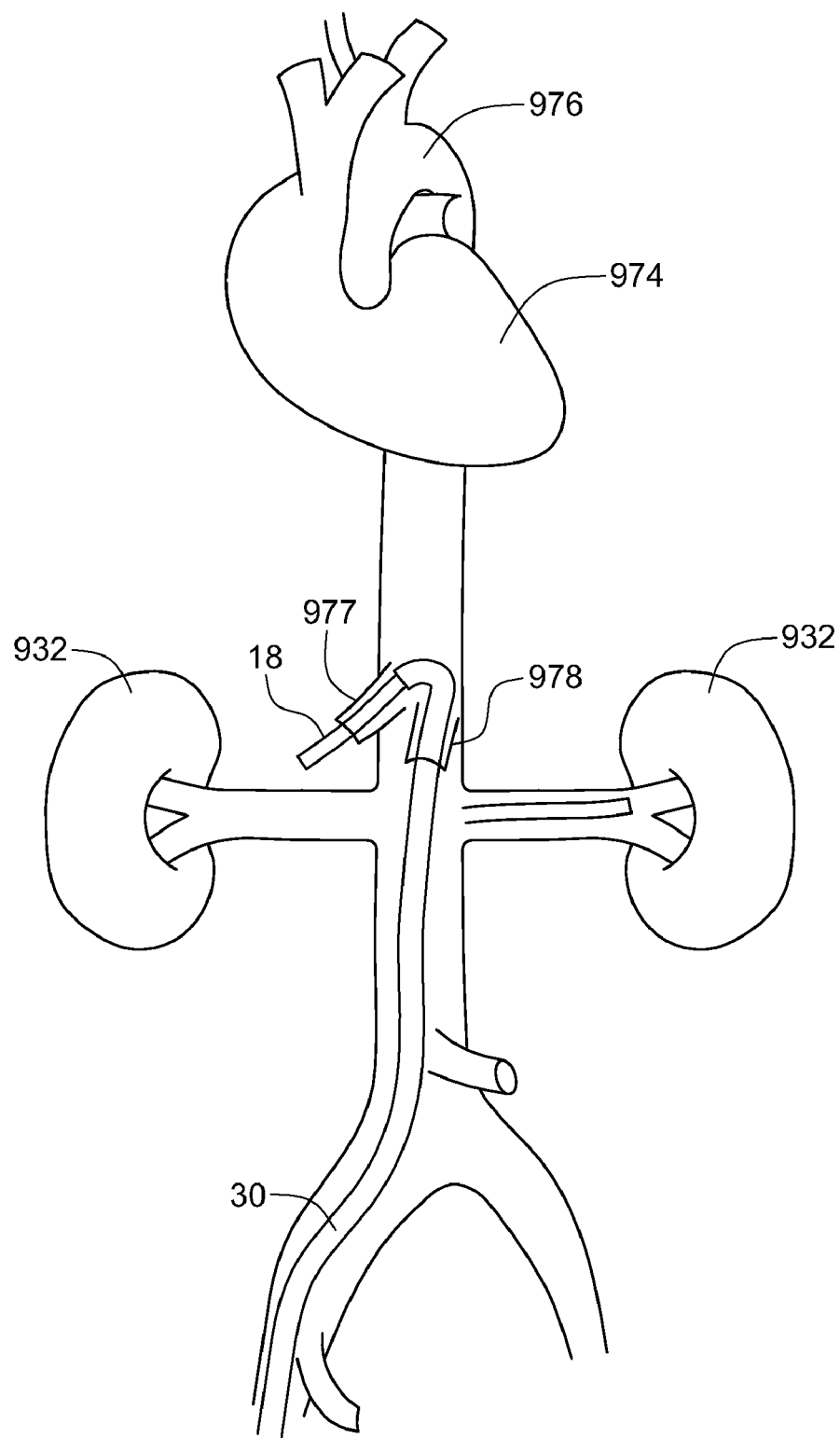
Figure 232C:
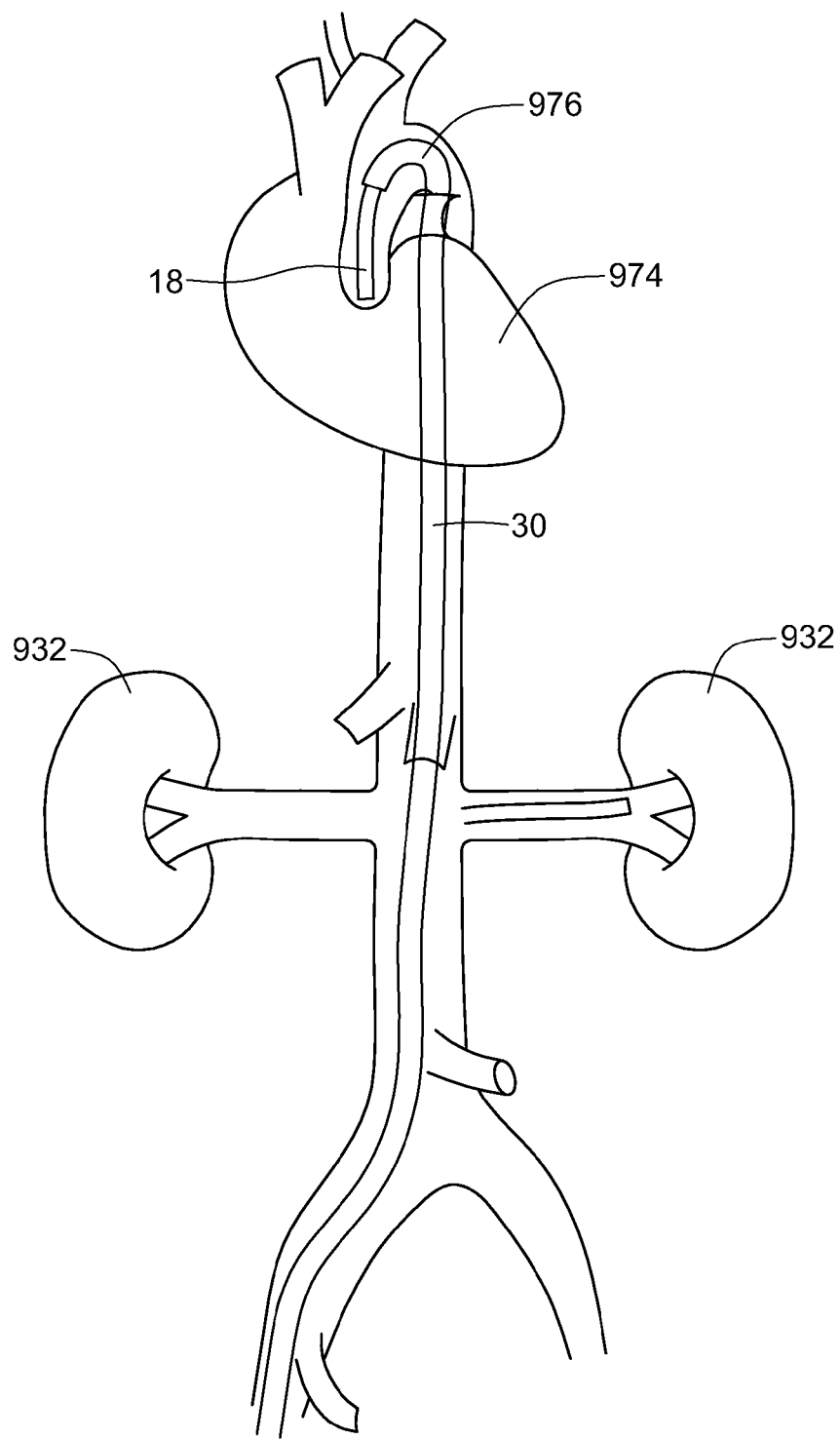

Vascular Intervention:

Expandable prostheses, such as stents and stentgrafts, may be deployed and locked into place with decreased risk of "endoleaks" by deploying small nitinol or stainless toggle bolt type staple clips tacked circumferentially around, and longitudinally down the long axis of, a stent or stent-graft from the inside out using the subject steerable instrument system of various embodiments of the invention. Referring to FIGS. 232A-C, the subject steerable instrument platform may be utilized throughout the ascending aorta to navigate, diagnose, treat, and intervene with distally-deployed tools such as clip or staple appliers, retractable needles, etc. Referring to FIG. 232A, a steerable guide (18) and sheath (30) assembly navigates the renal artery (975). Referring to FIG. 232B, a steerable instrument navigates the celiac trunk (977). Referring to FIG. 232C, a steerable instrument navigates the aortic arch (976) and may be utilized to enter the left ventricle of the heart (974) from a retrograde approach through the aortic outflow tract.

Figure 233A:
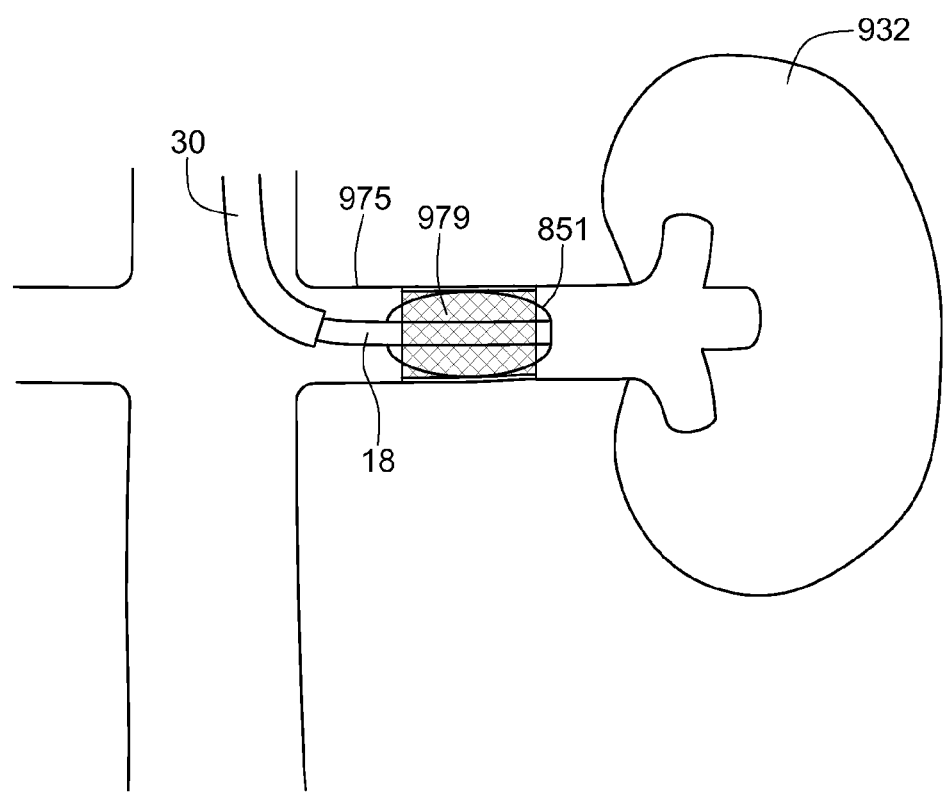
FIGS. 233A-233E illustrate various embodiments of renal artery intervention systems and procedures using a steerable instrument assembly.
Figure 233B:
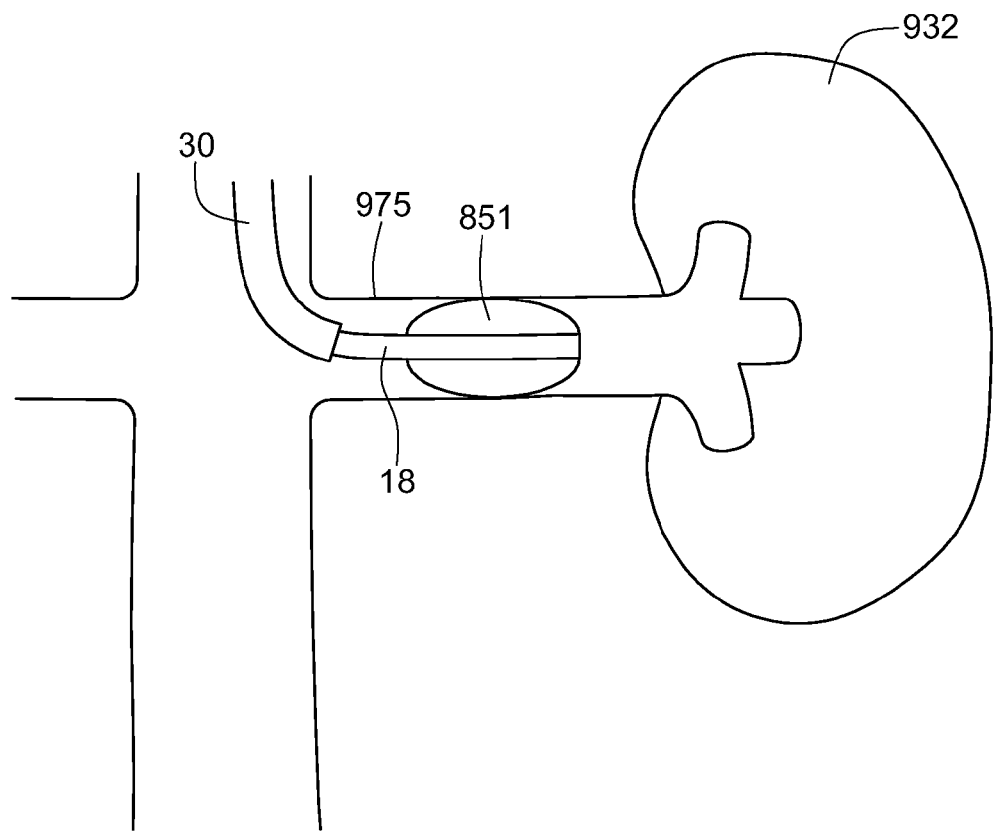
Figure 233C:
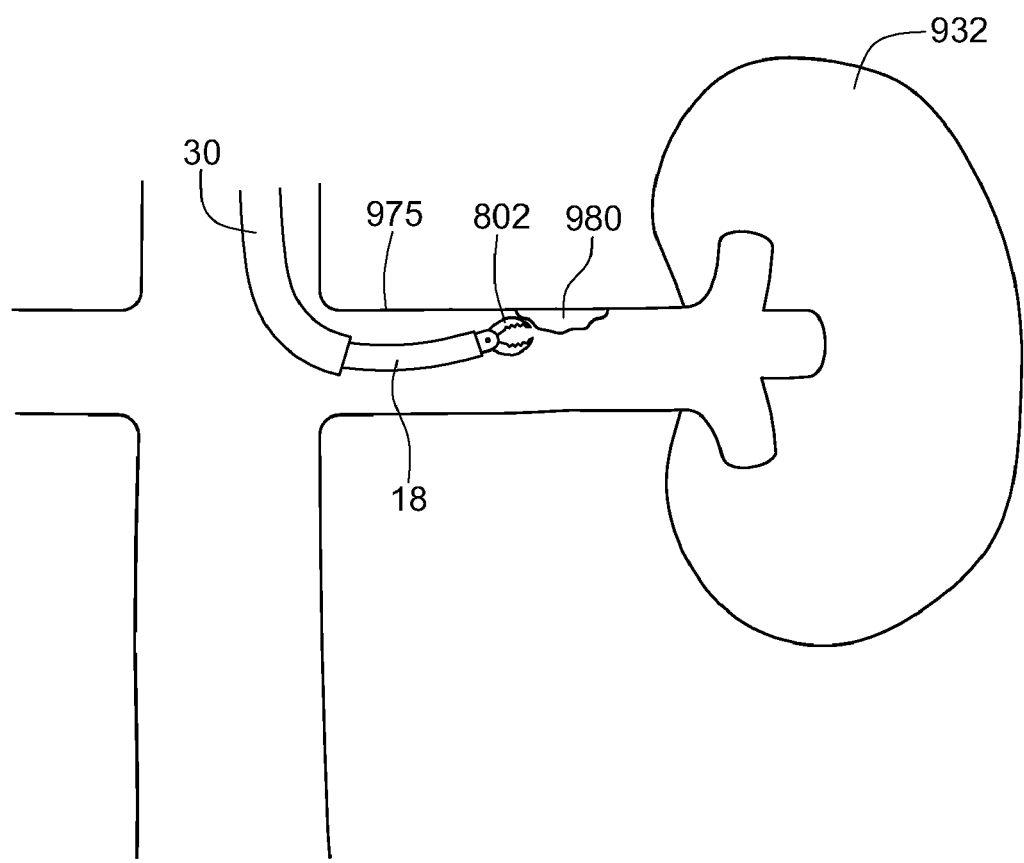
Figure 233D:
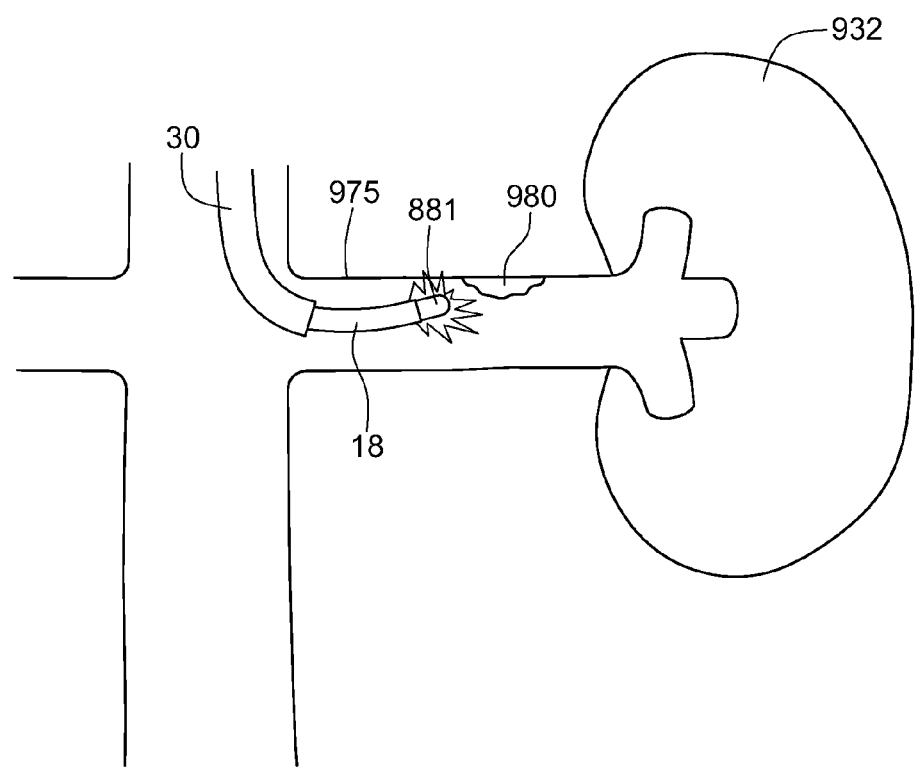
Figure 233E:
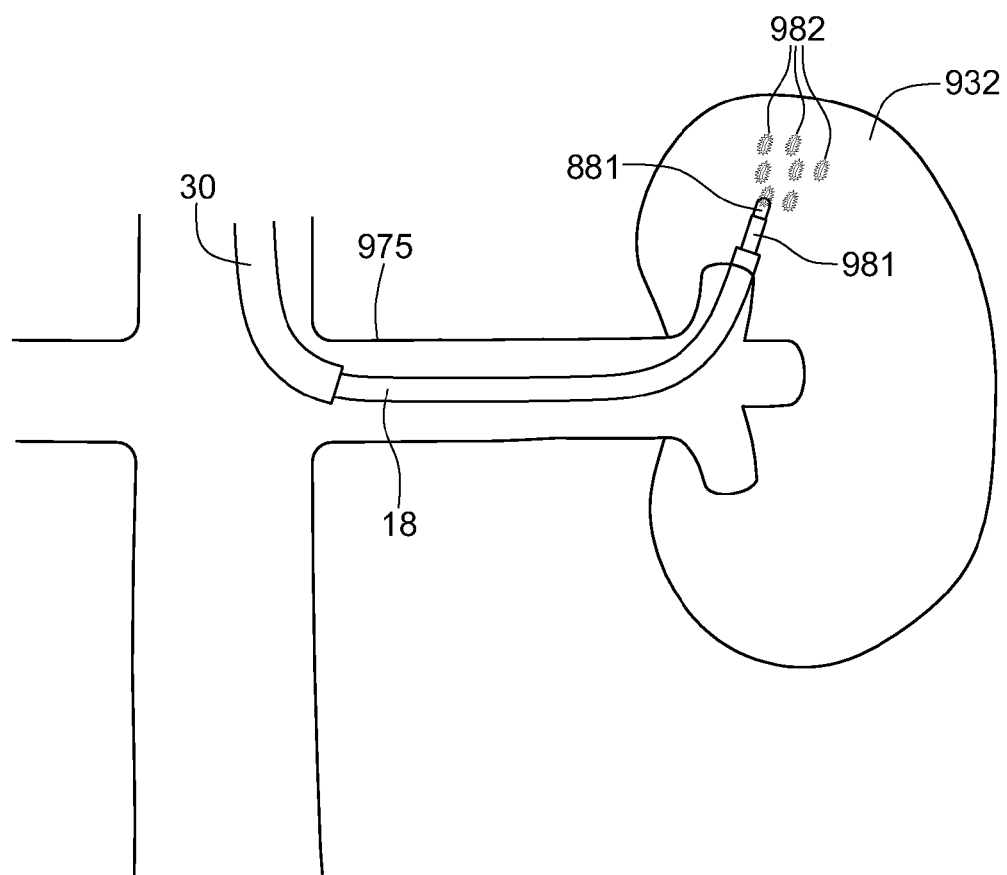

Referring to FIGS. 233A-E, renal artery (975) interventions are depicted. Referring to FIG. 233A, an expandable or self-expanding prosthesis (979), such as a stent or stent graft, may be deployed from an embodiment of the steerable instrument assembly, such as that depicted. The depicted instrument assembly may comprise an expandable balloon (851) and be observed in part with fluoroscopy. Referring to FIG. 233B, in another embodiment, a similar instrument assembly may be utilized to dilate a renal artery (975) lumen. Referring to FIG. 233C, a grasping (802) or cutting tool may be utilized to clear an obstruction (980) in the renal artery to ensure adequate perfusion of the kidneys (932). Referring to FIG. 233D, an ablation tool (881) distally carried by the guide instrument (18) may be utilized to ablate (RF, cryo, laser, ultrasound, etc) plaques or other obstructions (980) in the renal artery. Referring to FIG. 233E, a steerable instrument platform may be utilized to ablate (881) tissue lesions within the kidney (982) parenchyma, or deliver radioactive seeds to lesions within the parenchyma of the kidney (982) from a transvascular approach. Fluoroscopy may be utilized to observe placement of such seeds or other prostheses.

Figure 234A:
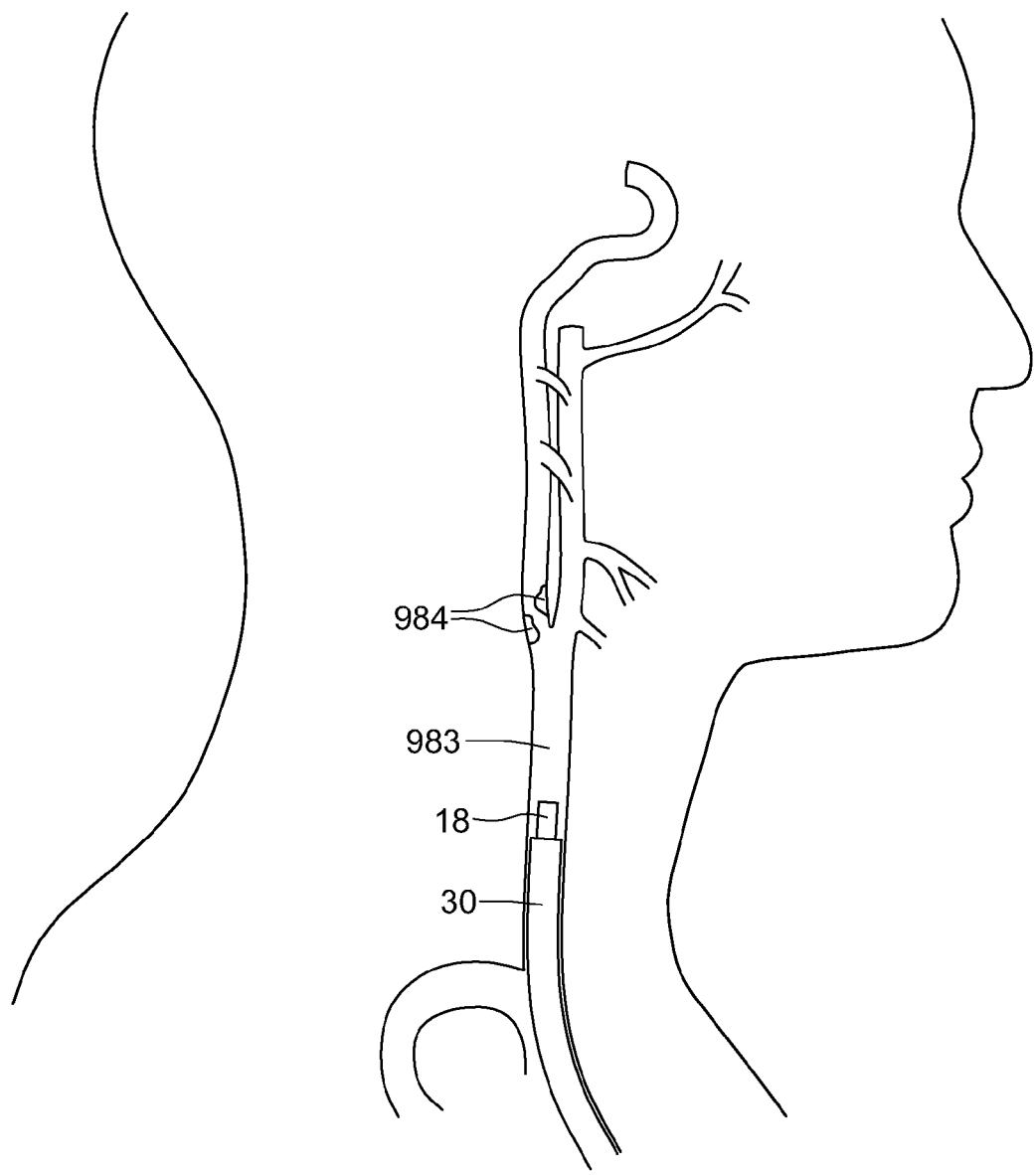
FIGS. 234A-234E illustrate one embodiment of a system and procedure for using a downsized steerable instrument assembly to navigate up into the carotid artery to perform a procedure.
Figure 234B:
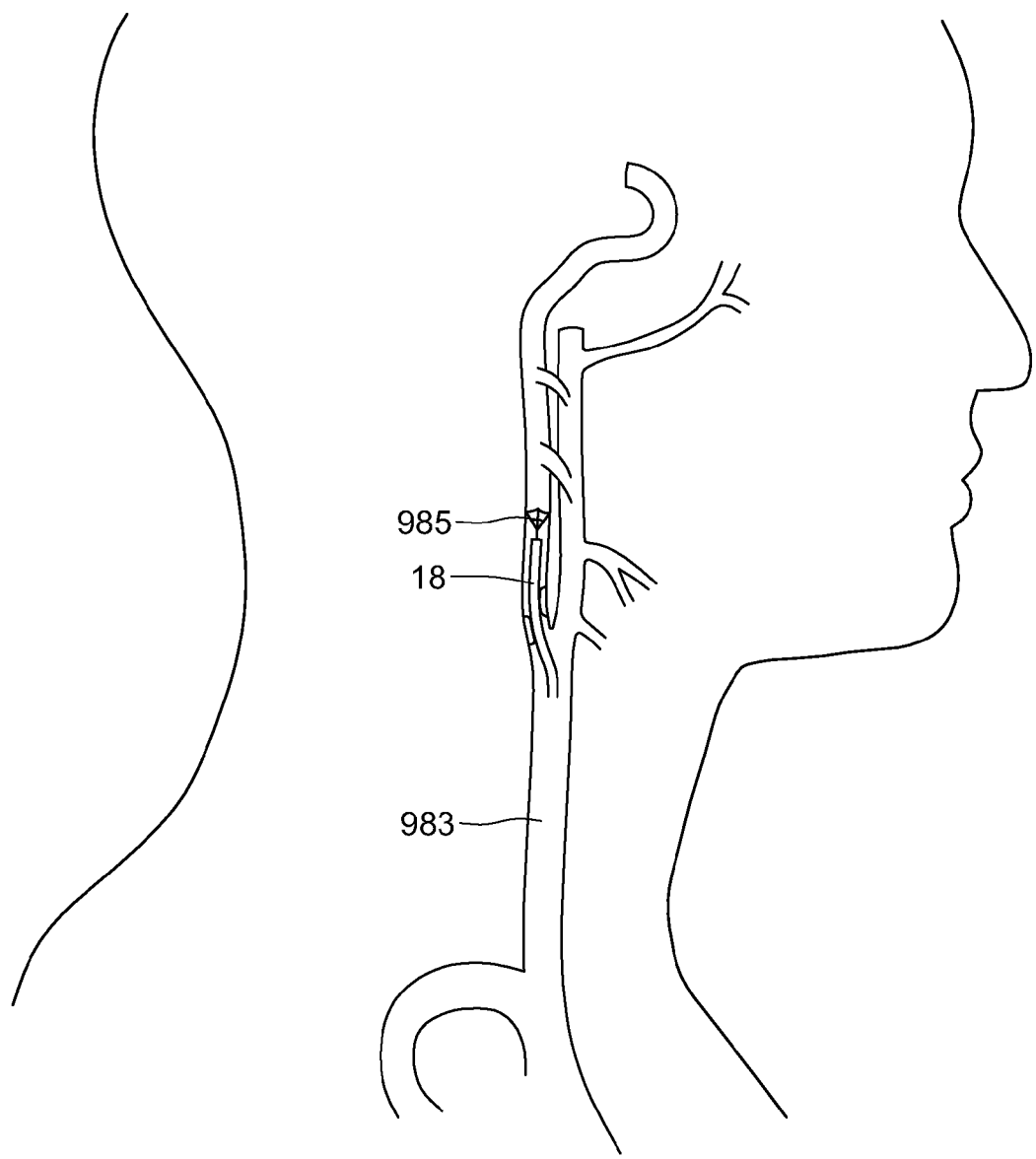
Figure 234C:
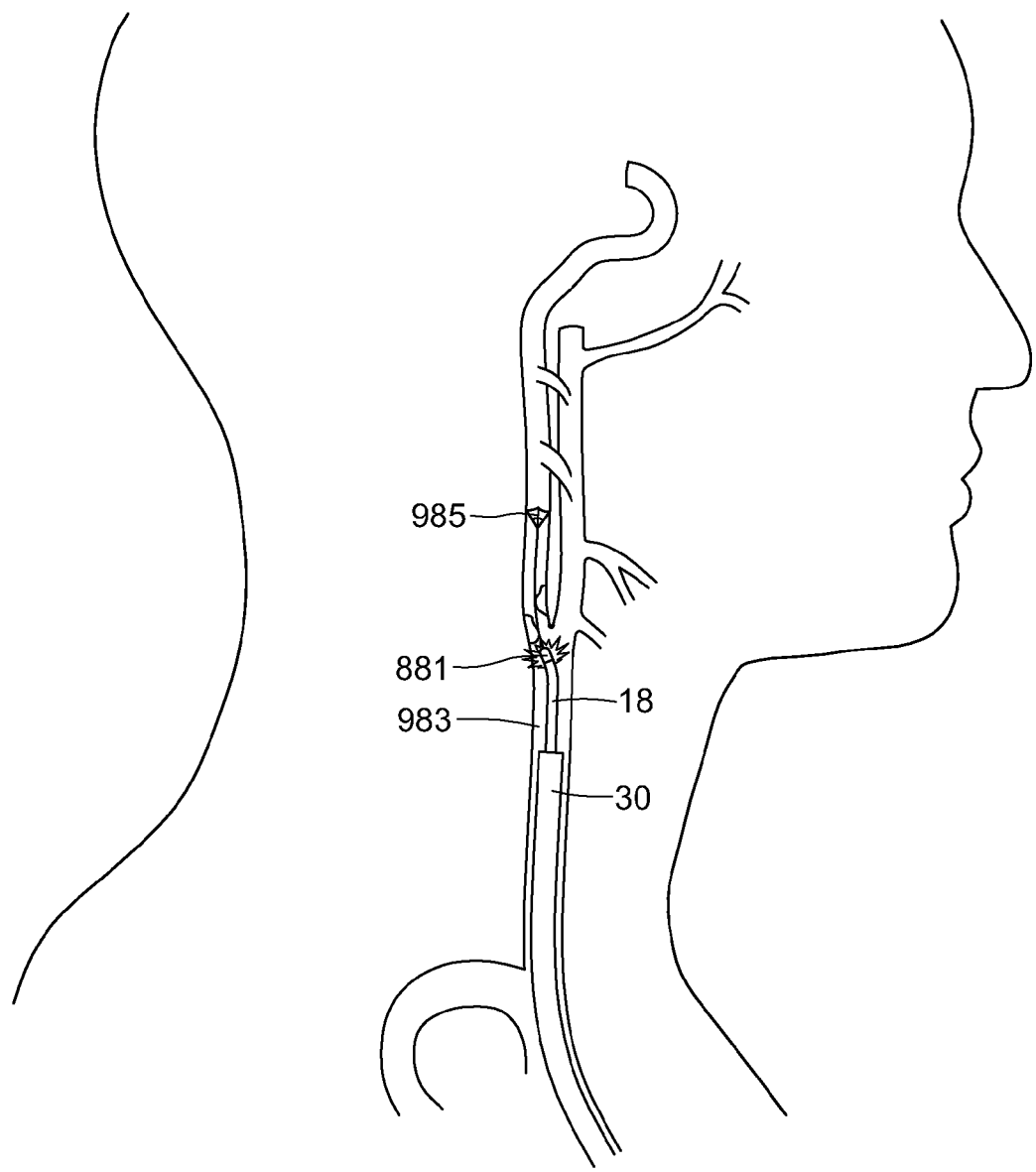
Figure 234D:
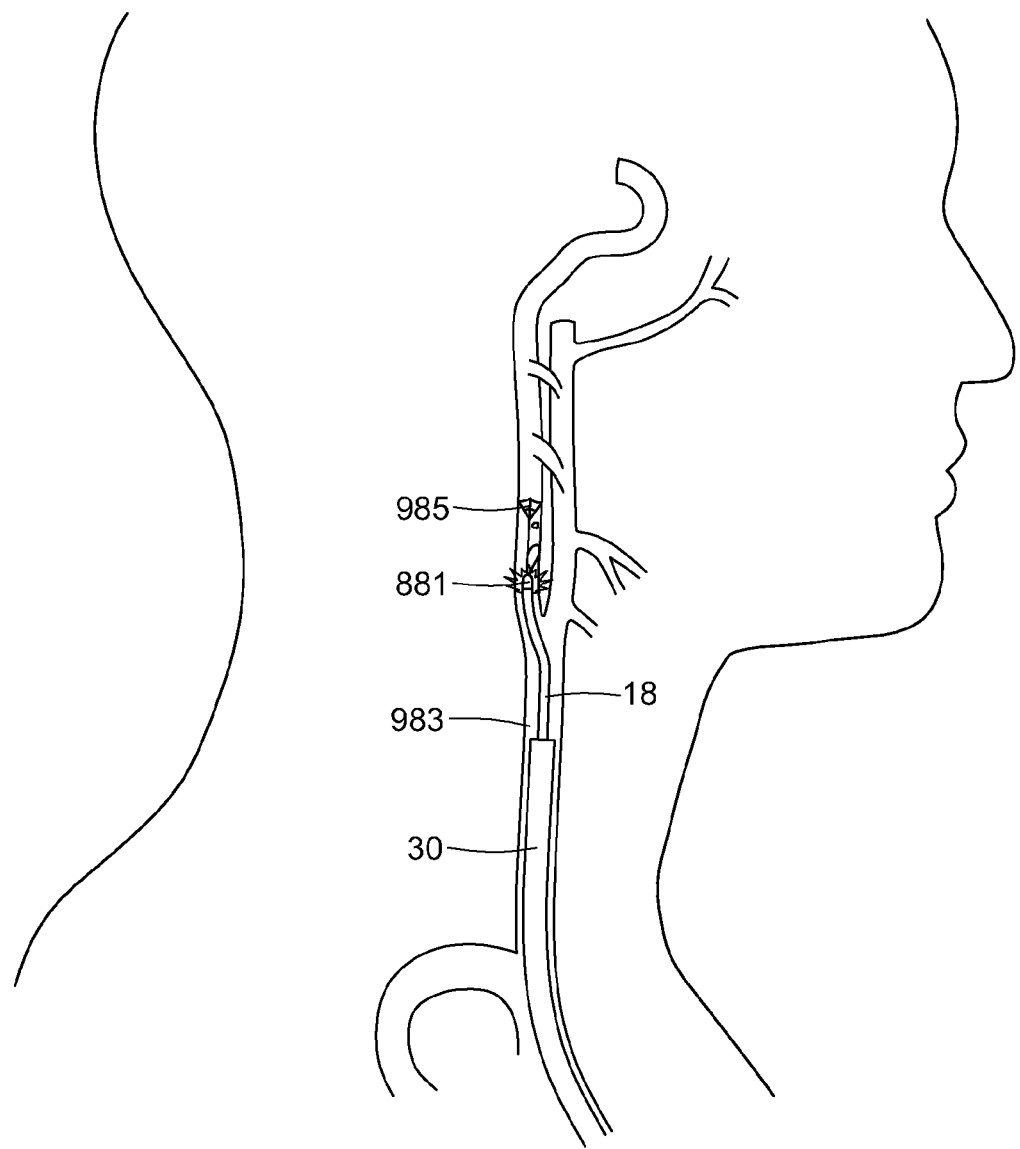
Figure 234E:
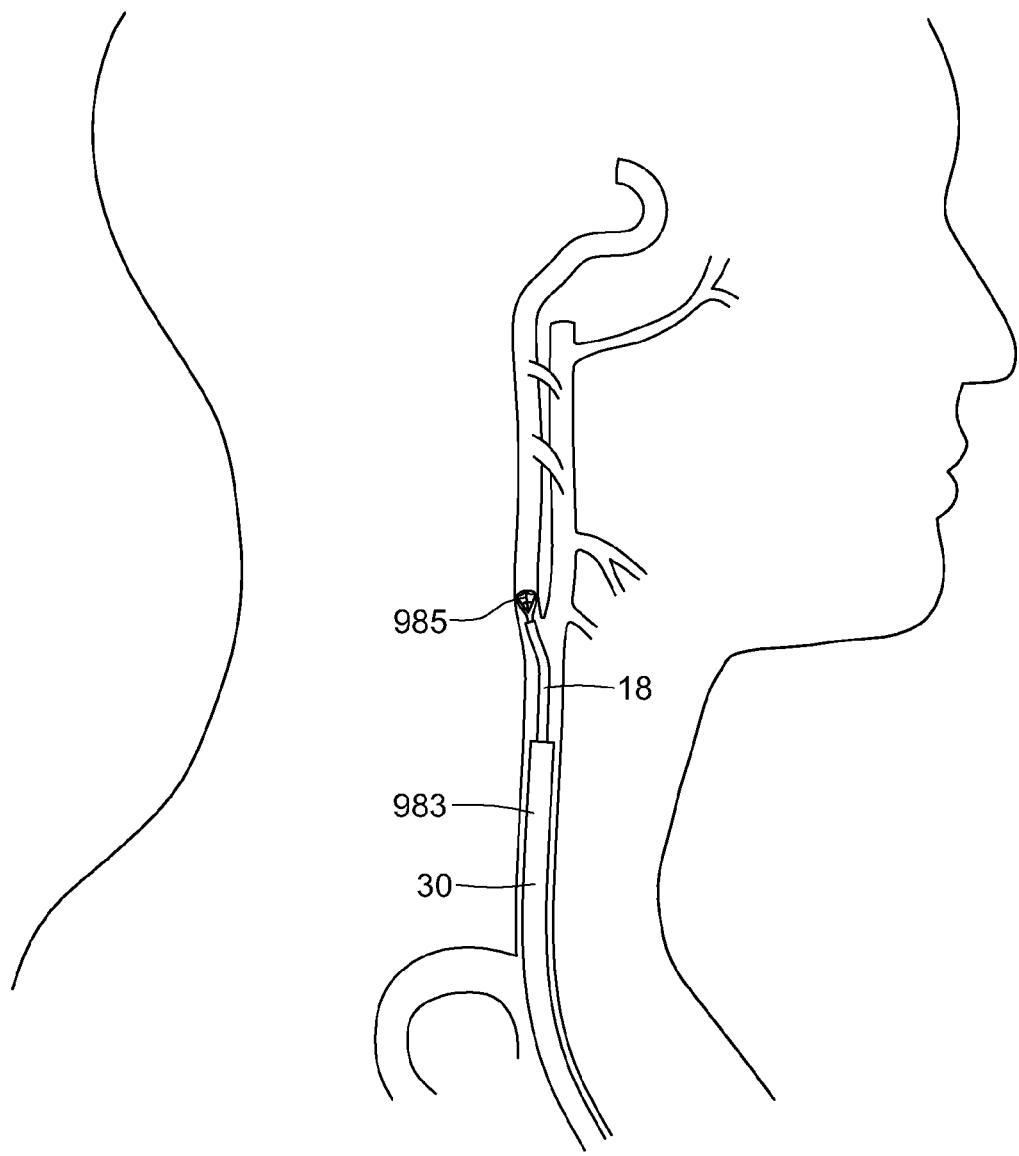
Figure 235A:
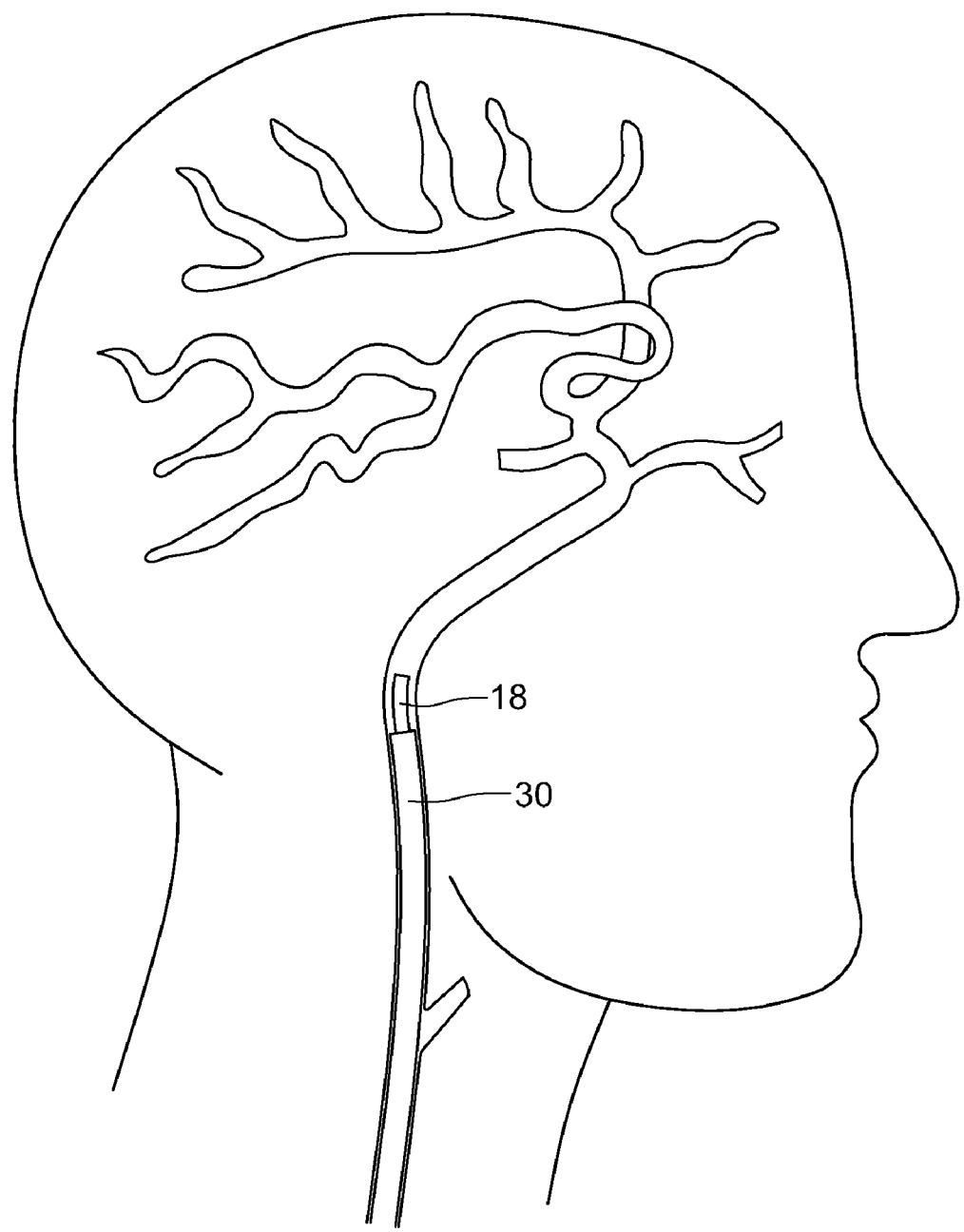
FIGS. 235A-235D illustrate one embodiment of a system and procedure for using a downsized steerable instrument assembly to navigate past the carotid arteries and up into the peripheral neurovascular to perform a procedure.
Figure 235B:
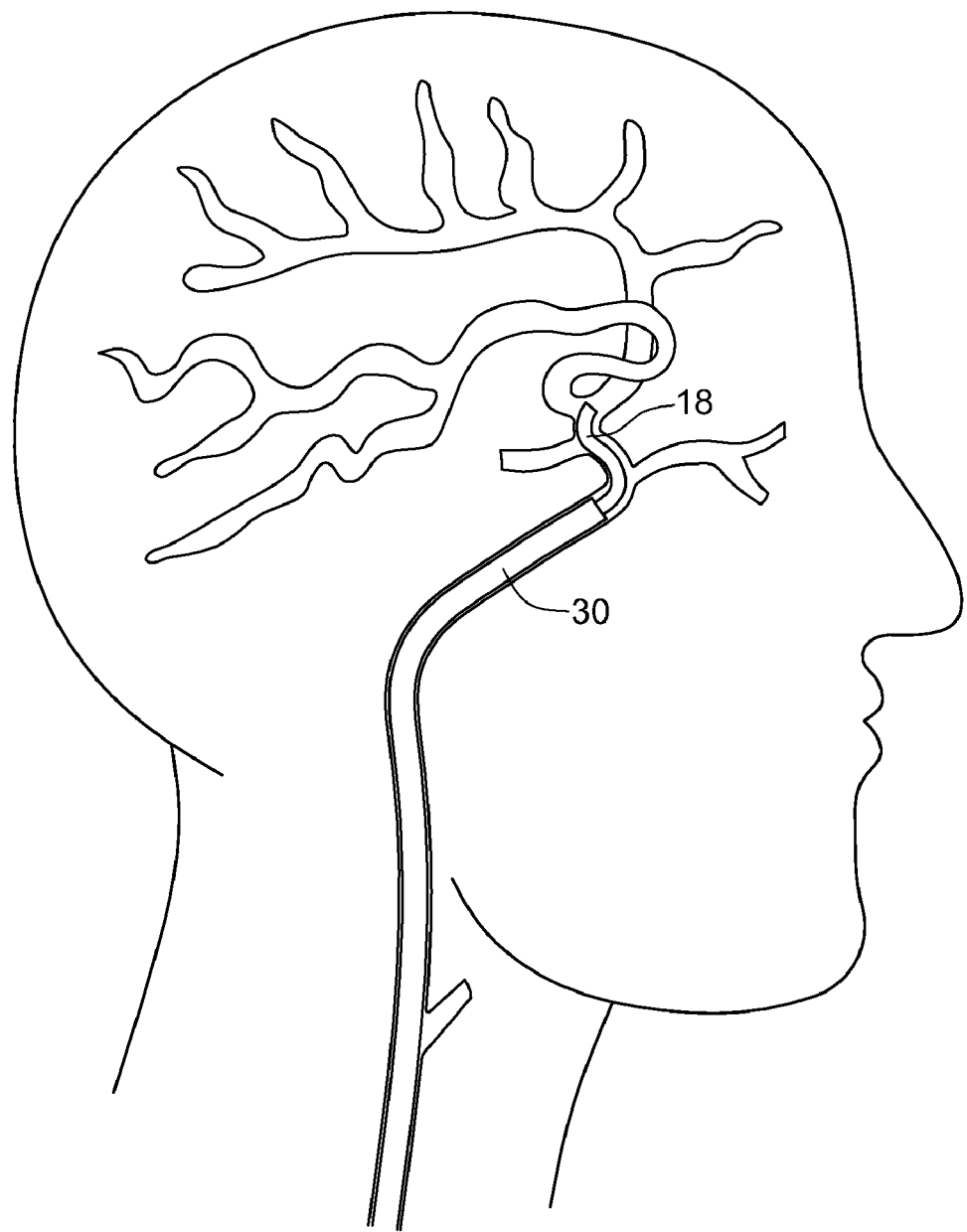
Figure 235C:
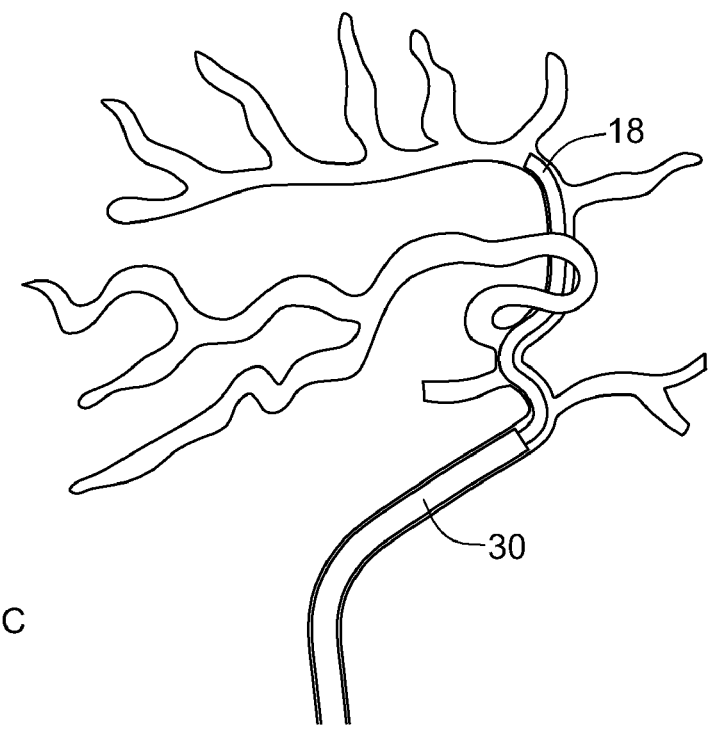
Figure 235D:
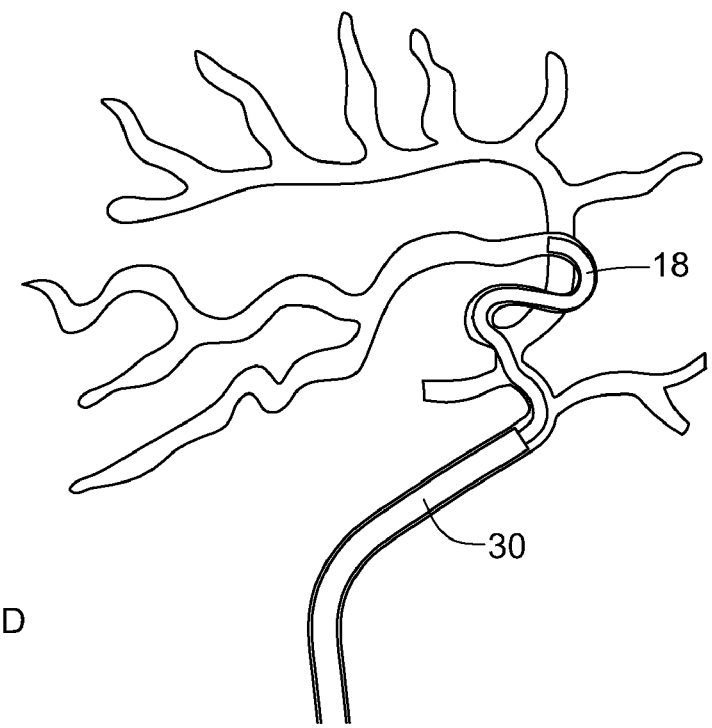

Referring to FIGS. 234A-E, a downsized steerable instrument assembly according to one embodiment may be navigated up into the carotid artery (983), and more particularly, may be utilized to navigate around plaques and other potentially unstable zones or structures (984), utilizing modern imaging modalities, such as CT and MR, along with the navigation capabilities of the subject system, to plan a path around key obstacles and electromechanically execute on such plan. For example, referring to FIGS. 234A-234E, a distal protection device (985) may be carefully deployed from a fairly distal position achieved by a steerable instrument platform (30, 18). Subsequently, as depicted in FIGS. 234C-D, ablation (881), obliteration, or plaque removal by RF, ultrasound, vacuum, grasper, cryo, laser, etc may be conducted with the distal protection device (985) safely in place. Later, as depicted in FIG. 234E, the distal protection device (985) may be retrieved.

Referring to FIGS. 235A-D, a downsized steerable instrument assembly (18, 30) according to another embodiment may be utilized to navigate past the carotid arteries and up into the peripheral neurovascular, all the way to the circle of Willis. Suction tools may be utilized to retrieve clots, aneurysm-filling devices, such as coils, may be placed with a high degree of precision, and brain tissue may be biopsied, ablated (RF, cryo, laser, ultrasound), injected, etc, among other things.

Other Interventions—Saphenous Vein Harvesting, Plastic Surgery:

The steerable instruments provided by embodiments of the invention can provide the equivalent of a Guidant "VasoView" procedure for harvesting the Saphenous vein, but significantly improved—because of the steerability of the subject instruments (they can make sharp turns immediately after a transcutaneous crossing—unlike the stiff, straight Vaso-View).

By way of non-limiting example, face lift dissection may be accomplished from behind the ears with this highly steerable platform configured to steer with precision around convex surfaces, such as the transcutaneous face. Similarly, the steerability of the subject platform may be utilized to facilitate liposuction of the front, side, and posterior pelvic region from one or more bikini area transcutaneous access ports, as well as breast implant dissection and placement from an umbilicus access port, and brow lift subcutaneous dissection from a more posterior position (back away from the hairline where the port or ports will be less visible subsequent to the intervention).

What is claimed is:

1. A robotic endoscopic instrument system, comprising:
a parent endoscopic instrument defining a working lumen and having a base removably coupled to an parent instrument interface of an instrument driver, the instrument driver comprising at least one motor operably coupled through the parent instrument interface to a control element extending thorough the parent endoscopic instrument, whereby movement of a distal bending portion of the parent endoscopic instrument may be controlled by selected operation of the motor; and
a guide-sheath instrument pair at least partially positioned in the working lumen of the parent endoscopic instrument, the guide-sheath instrument pair including
a sheath instrument defining a working lumen and having a base removably coupled to a sheath instrument interface located on a same or different instrument driver as the parent instrument interface, and
a guide instrument positioned in the sheath instrument lumen and comprising a base removably coupled to a guide instrument interface located on a same or different instrument driver as the respective parent instrument interface and sheath instrument interface, wherein the parent endoscopic instrument, sheath instrument and guide instrument are independently controllable by the respective same or different instrument drivers.

2. The system of claim 1, wherein the parent endoscopic instrument further comprises one or more image capture devices.

3. The system of claim 1, wherein the parent endoscopic instrument further comprises one or more imaging radiation sources.

4. The system of claim 1, wherein the parent endoscopic instrument further comprises an irrigation port.

5. The system of claim 1, further comprising a tool positioned in a working lumen of the guide instrument, wherein the tool may be actuated by an actuator operatively coupled to the guide instrument base.

6. The apparatus of claim 5, wherein the tool is selected from the group comprising an electrode, a grasper, a scissor, a needle, a collapsible basket, a cauterizing tool, a scalpel, an expandable balloon, a staple applier, a laser emitting element, an ultrasound transducer, and a cryogenic cooling element.

7. The apparatus of claim 5, wherein the tool can be actuated to mechanically manipulate internal body tissue at an interventional procedure site.

8. The apparatus of claim 1, further comprising a respective localization sensor coupled to one or more of the parent endoscopic instrument, sheath instrument and guide instrument.

9. The apparatus of claim 1, wherein the guide instrument interface is movable relative to the sheath instrument interface, such that the guide instrument is axially movable relative to the sheath instrument, whereby a distal end portion of the guide instrument may be extended out of, and retracted back into, a distal opening of the sheath instrument in communication with the sheath working lumen.

10. A robotic endoscopic instrument system, comprising:
a parent endoscopic instrument defining a plurality of working lumens and having a base removably coupled to an instrument interface of a parent instrument driver, the parent instrument driver comprising at least one motor operably coupled through the instrument interface to a control element extending thorough the parent endoscopic instrument, whereby movement of a distal bending portion of the parent endoscopic instrument may be controlled by selected operation of the motor;
a first guide-sheath instrument pair at least partially positioned in a first working lumen of the parent endoscopic instrument, the first guide-sheath instrument pair including
a first sheath instrument defining a working lumen and having a base removably coupled to a sheath instrument interface of a first guide-sheath instrument driver, and
a first guide instrument positioned in the first sheath instrument working lumen and comprising a base removably coupled to a guide instrument interface of the first guide-sheath instrument driver,
wherein the first sheath instrument and first guide instrument are independently controllable by the first guide-sheath instrument driver; and
a second guide-sheath instrument pair at least partially positioned in a second working lumen of the parent endoscopic instrument, the second guide-sheath instrument pair including
a second sheath instrument defining a working lumen and having a base removably coupled to a sheath instrument interface of a second guide-sheath instrument driver, and
a second guide instrument positioned in the second sheath instrument working lumen and comprising a base removably coupled to a guide instrument interface of the second guide-sheath instrument driver,
wherein the second sheath instrument and second guide instrument are independently controllable by the first guide-sheath instrument driver.

11. The system of claim 10, wherein the parent endoscopic instrument further comprises one or more image capture devices.

12. The system of claim 10, wherein the parent endoscopic instrument further comprises one or more imaging radiation sources.

13. The system of claim 10, wherein the parent endoscopic instrument further comprises an irrigation port.

14. The system of claim 10, further comprising a respective tool positioned in one or both of a working lumen of the first guide instrument and a working lumen of the second guide instrument, wherein the respective tools may be actuated by actuators operatively coupled to the respective first and second guide instrument bases.

15. The system of claim 14, wherein the respective tool or tools are selected from the group comprising an electrode, a grasper, a cauterizing tool, a scalpel, a scissor, a needle, a collapsible basket, an expandable balloon, a staple applier, a laser emitting element, an ultrasound transducer, and a cryogenic cooling element.

16. The system of claim 14, wherein the respective tool or tools can be actuated to mechanically manipulate internal body tissue at an interventional procedure site.

17. The system of claim 10, further comprising a respective localization sensor coupled to one or more of the parent endoscopic instrument, first sheath instrument, first guide instrument, second sheath instrument and second guide instrument.

18. The system of claim 10, wherein
the guide instrument interface of the first guide-sheath instrument driver is movable relative to the sheath instrument interface of the first guide-sheath instrument driver, such that the first guide instrument is axially movable relative to the first sheath instrument, whereby a distal end portion of the first guide instrument may be extended out of, and retracted back into, a distal opening of the first sheath instrument in communication with the first sheath working lumen, and
the guide instrument interface of the second guide-sheath instrument driver is movable relative to the sheath instrument interface of the second guide-sheath instrument driver, such that the second guide instrument is axially movable relative to the second sheath instrument, whereby a distal end portion of the second guide instrument may be extended out of, and retracted back into, a distal opening of the second sheath instrument in communication with the second sheath working lumen.

19. A robotic endoscopic instrument system, comprising:
a parent endoscopic instrument defining a plurality of working lumens and having a base removably coupled to an instrument interface of a parent instrument driver, the parent instrument driver comprising at least one motor operably coupled through the instrument interface to a control element extending thorough the parent endoscopic instrument, whereby movement of a distal bending portion of the parent endoscopic instrument may be controlled by selected operation of the motor;

a first guide-sheath-tool assembly at least partially positioned in a first working lumen of the parent endoscopic instrument, the first guide-sheath-tool assembly including
- a first sheath instrument defining a working lumen and having a base removably coupled to a sheath instrument interface of a first guide-sheath-tool instrument driver,
- a first guide instrument positioned in the first sheath instrument working lumen, the first guide instrument defining a working lumen and comprising a base removably coupled to a guide instrument interface of the first guide-sheath-tool instrument driver, and
- a first tool positioned in the working lumen of the first guide instrument, wherein the tool may be actuated by an actuator operatively coupled to the guide instrument base,
- wherein the first sheath instrument, first guide instrument and first tool are independently controllable by the first guide-sheath-tool instrument driver; and a second guide-sheath instrument pair at least partially positioned in a second working lumen of the parent endoscopic instrument, the second guide-sheath instrument pair including
- a second sheath instrument defining a working lumen and having a base removably coupled to a sheath instrument interface of a second guide-sheath-tool instrument driver, and
- a second guide instrument positioned in the second sheath instrument working lumen, the second guide instrument defining a working lumen and comprising a base removably coupled to a guide instrument interface of the second guide-sheath-tool instrument driver, and
- a second tool positioned in the working lumen of the second guide instrument, wherein the tool may be actuated by an actuator operatively coupled to the guide instrument base,
- wherein the second sheath instrument, second guide instrument and second tool are independently controllable by the second guide-sheath-tool instrument driver.

20. The system of claim 19, wherein the first tool and second tool are each selected from the group comprising an electrode, a grasper, a cauterizing tool, a scalpel, a scissor, a needle, a collapsible basket, an expandable balloon, a staple applier, a laser emitting element, an ultrasound transducer, and a cryogenic cooling element.

21. The system of claim 19, wherein one or both of the first and second tools can be actuated to mechanically manipulate internal body tissue at an interventional procedure site.

22. The system of claim 19, wherein
- the guide instrument interface of the first guide-sheath-tool instrument driver is movable relative to the sheath instrument interface of the first guide-sheath-tool instrument driver, such that the first guide instrument is axially movable relative to the first sheath instrument, whereby a distal end portion of the first tool extending out of the first guide instrument may be extended out of, and retracted back into, a distal opening of the first sheath instrument in communication with the first sheath working lumen, and
- the guide instrument interface of the second guide-sheath instrument driver is movable relative to the sheath instrument interface of the second guide-sheath instrument driver, such that the second guide instrument is axially movable relative to the second sheath instrument, whereby a distal end portion of the second tool extending out of the second guide instrument may be extended out of, and retracted back into, a distal opening of the second sheath instrument in communication with the second sheath working lumen.

\* \* \* \* \*